US011208650B2

(12) United States Patent
Freier

(10) Patent No.: US 11,208,650 B2
(45) Date of Patent: Dec. 28, 2021

(54) MODULATORS OF IRF5 EXPRESSION

(71) Applicant: Ionis Pharmaceuticals, Inc., Carlsbad, CA (US)

(72) Inventor: Susan M. Freier, San Diego, CA (US)

(73) Assignee: IONIS PHARMACEUTICALS, INC., Carlsbad, CA (US)

(*) Notice: Subject to any disclaimer, the term of this patent is extended or adjusted under 35 U.S.C. 154(b) by 89 days.

(21) Appl. No.: 16/684,988

(22) Filed: Nov. 15, 2019

(65) Prior Publication Data

US 2020/0208147 A1 Jul. 2, 2020

Related U.S. Application Data

(60) Provisional application No. 62/767,615, filed on Nov. 15, 2018.

(51) Int. Cl.
C12N 15/11 (2006.01)
A61P 1/04 (2006.01)

(52) U.S. Cl.
CPC .............. *C12N 15/11* (2013.01); *A61P 1/04* (2018.01); *C12N 2310/315* (2013.01); *C12N 2310/321* (2013.01); *C12N 2310/3231* (2013.01); *C12N 2310/3341* (2013.01)

(58) Field of Classification Search
None
See application file for complete search history.

(56) References Cited

U.S. PATENT DOCUMENTS

| 34,036 A | 12/1861 | McGeehan |
| 44,779 A | 10/1864 | Manishi et al. |
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |

(Continued)

FOREIGN PATENT DOCUMENTS

| WO | 9914226 A3 | 3/1999 |
| WO | 0063364 A2 | 10/2000 |

(Continued)

OTHER PUBLICATIONS

Bi, et al., "Loss of interferon regulatory factor 5 (IRF5) expression in human ductal carcinoma correlates with disease stage and contributes to metastasis", Breast Cancer Research, vol. 13: R111, (2011).
Boorsma, et al. "Macrophage Heterogeneity in Respiratory Diseases", Mediators of Inflammation, pp. 1-19, (2013).
Branch, et al., "A good antisense molecule is hard to find", TIBS, vol. 23, pp. 45-50, (1998).
Chin, Andrew, "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke, S.T., "Basic Principles of Antisense Therapeutics", Antisense Research and Application, Chapter 1, pp. 1-50, (1998).

(Continued)

*Primary Examiner* — Tracy Vivlemore
(74) *Attorney, Agent, or Firm* — Ice Miller LLP

(57) ABSTRACT

The present embodiments provide methods, compounds, and compositions useful for inhibiting IRF5 expression, which may be useful for treating, preventing, or ameliorating a disease associated with IRF5.

16 Claims, No Drawings
Specification includes a Sequence Listing.

(56) References Cited

U.S. PATENT DOCUMENTS

| | | |
|---|---|---|
| 5,457,187 A | 10/1995 | Gmeiner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,801,154 A | 9/1998 | Baracchini et al. |
| 5,808,027 A | 9/1998 | Cook et al. |
| 5,811,534 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'o et al. |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,673,661 B1 | 1/2004 | Liu et al. |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 7,015,315 B1 | 3/2006 | Cook et al. |
| 7,034,133 B2 | 4/2006 | Wengel et al. |
| 7,053,207 B2 | 5/2006 | Wengel |
| 7,101,993 B1 | 9/2006 | Cook et al. |
| 7,262,177 B2 | 8/2007 | Ts'O et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Seth et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Seth et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,148,074 B2 | 4/2012 | Behrens et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 9/2015 | Prakash et al. |
| 9,290,760 B2 | 3/2016 | Rajeev et al. |
| 2001/0053519 A1 | 12/2001 | Fodor et al. |
| 2003/0082807 A1 | 5/2003 | Wengel |
| 2003/0158403 A1 | 8/2003 | Manoharan et al. |
| 2003/0175906 A1 | 9/2003 | Manoharan et al. |
| 2003/0207841 A1 | 11/2003 | Kaneko et al. |
| 2003/0224377 A1 | 12/2003 | Wengel et al. |
| 2003/0228597 A1 | 12/2003 | Cowsert et al. |
| 2004/0143114 A1 | 7/2004 | Imanishi et al. |
| 2004/0171570 A1 | 9/2004 | Allerson et al. |
| 2004/0192918 A1 | 9/2004 | Imanishi et al. |
| 2005/0130923 A1 | 6/2005 | Bhat et al. |
| 2006/0148740 A1 | 7/2006 | Platenburg |
| 2007/0031844 A1 | 2/2007 | Khvorova et al. |
| 2007/0039072 A1 | 2/2007 | Khvorova et al. |
| 2008/0039618 A1 | 2/2008 | Allerson et al. |
| 2010/0190837 A1 | 7/2010 | Migawa et al. |
| 2010/0197762 A1 | 8/2010 | Swayze |
| 2011/0054005 A1 | 3/2011 | Naito et al. |
| 2011/0123520 A1 | 5/2011 | Manoharan et al. |
| 2013/0130378 A1 | 5/2013 | Manoharan et al. |
| 2013/0203836 A1 | 8/2013 | Rajeev et al. |
| 2014/0107330 A1 | 4/2014 | Freier et al. |

(56) References Cited

U.S. PATENT DOCUMENTS

| | | |
|---|---|---|
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275208 A1 | 10/2015 | Oestergaard et al. |
| 2015/0275212 A1 | 10/2015 | Albaek et al. |
| 2017/0081667 A1 | 3/2017 | Chen et al. |

FOREIGN PATENT DOCUMENTS

| | | |
|---|---|---|
| WO | 2004106356 A1 | 12/2004 |
| WO | 2006070860 A1 | 7/2006 |
| WO | 2007134181 A2 | 11/2007 |
| WO | 2008101157 A1 | 8/2008 |
| WO | 2012093258 A2 | 7/2012 |
| WO | 2015137459 A1 | 9/2015 |
| WO | 2017015555 A1 | 1/2017 |

OTHER PUBLICATIONS

Crooke, ST., "Antisense Drug Technology", Second Edition, CRC Press, Chapters 1-28, (2008).

Egli, et al., "Synthesis, improved antisense activity and structural rationale for the divergent RNA affinities of 3'-fluoro hexitol nucleic acid (FHNA and Ara-FHNA) modified oligonucleotides.", J Am Chem, vol. 133, No. 41, pp. 16642-16649, (2011).

Gautschi, et al., "Activity of a novel bcl-2/bcl-xLbispecific antisense oligonucleotide against tumors of diverse histologic origins", J. Natl. Cancer Inst., vol. 93, pp. 463-471, (2001).

Graham, et al., "A common haplotype of interferon regulatory factor 5 (IRF5) regulates splicing and expression and is associated with increased risk of systemic lupus erythematosus", Nat. Genet. vol. 38, pp. 550-555, (20016).

Graham, et al., "Three functional variants of IFN regulatory factor 5 (IRF5) define risk and protective haplotypes for human lupus" Proc. Natl. Acad. Sci. USA, vol. 104, pp. 6758-6763, (2007).

Hedl, et al., "IRF5 risk polymorphisms contribute to interindividual variance in pattern recognition receptor-mediated cytokine secretion in human monocyte-derived cells" J. Immunol., vol. 188, pp. 5348-5356, (2012).

Krausgruber, et al., "IRF5 is required for late-phase TNF secretion by human dendritic cells", Blood, vol. 115, No. 22, pp. 4421-4430, (2010).

Krausgruber, et al., "IRF5 promotes inflammatory macrophage polarization and TH1-TH17 responses", Nat. Immun., vol. 12, No. 3, pp. 231-236, (2011).

Kristjansdottir, et al., "Interferon regulatory factor 5 (IRF5) gene variants are associated with multiple sclerosis in three distinct populations", J. Med. Genet., vol. 45, pp. 362-369, (2008).

Li, et al., "IL-27/IFN-y Induce MyD88-Dependant Steroid-Resistant Airway Hyperresponsiveness by Inhibiting Glucocorticoid Signaling in Macrophages", J. Immunol., vol. 185, pp. 4401-4409, (2010).

Liu, et al., "Macrophage Polarization in Inflammatory Diseases", Int. J. Biol. Sci., vol. 10, pp. 520-529, (2014).

Maher, et al., "Comparative hybrid arrest by tandem antisense oligodeoxyribonucleotides or oligodeoxyribonucleoside methylpbosphonates in a cell-free system", Nucl. Acid. Res. vol. 16, No. 8, pp. 3341-3358, (1988).

Mori, et al., "Identification of the interferon regulatory factor 5 gene (IRF-5) as a direct target for p53", Oncogene, vol. 21, pp. 2914-2918 (2002).

New England Biolabs 1998/99 Catalog, Nucleic Acids, Linkers and Primers, (cover page and pp. 121 and 284).

Reynolds, et al., "Rational siRNA design for RNA interference", Nature Biotechnology, vol. 22, No. 3, pp. 326-330, (2004).

Sanghvi, Yogesh S., "Heterocyclic Base Modifications in Nucleic Acids and Their Applications in Antisense Oligonucleotides", Antisense Research and Applications, pp. 273-288, (1993).

Schoenemeyer et al., "The Interferon Regulatory Factor, IRF5, Is a Central Mediator of Toll-like Receptor 7 Signaling", J. Biol. Chem., vol. 280, No. 17, pp. 17005-17012, (2005).

Seth, et al., "Short Antisense Oligonucleotides with Novel 2'-4' Conformationaly Restricted Nucleoside Analogues Show Improved Potency Without Increased Toxicity in Animals.", J. Med. Chem., vol. 52, pp. 10-13, (2009).

Sweeney, Susan E., "Targeting interferon regulatory factors to inhibit activation of the type I IFN response: Implications for treatment of autoimmune disorders", Cell Immunol., vol. 271, No. 2, pp. 342-349, (2011).

Wang, et al., "Evidence of association between interferon regulatory factor 5 gene polymorphisms and asthma", Gene, vol. 504, pp. 220-225, (2012).

Woolf, et al., "Specificity of antisense oligonucleotides in vivo", PNAS, vol. 89, pp. 7305-7309, (1992).

Altschul, Stephen F. et al. "Basic Local Alignment Search Tool," Journal of Molecular Biology, vol. 215, issue 3 (Oct. 1990), pp. 403-410.

Zhang, J. et al. "PowerBLAST: a new network BLAST application for interactive or automated sequence analysis and annotation," Genome Research, vol. 7, issue 6 (Jun. 1997), pp. 649-656.

Frieden, Miriam et al. "Expanding the design horizon of antisense oligonucleotides with alpha-L-LNA," Nucleic Acids Research, vol. 31, issue 21 (Nov. 2003), pp. 6365-6372.

Wan, Brad W. et al. "Synthesis, biophysical properties and biological activity of second generation antisense oligonucleotides containing chiral phosphorothioate linkages," Nucleic Acids Research, vol. 42, issue 22 (Dec. 2014), pp. 13456-13468.

Wahlestedt, Claes et al. "Potent and nontoxic antisense oligonucleotides containing locked nucleic acids," Proceedings of the National Academy of Sciences of the United States of America (PNAS), vol. 97, No. 10 (May 2000), pp. 5633-5638.

Smith, Temple F. et al. "Comparison of Biosequences," Advances in Applied Mathematics, vol. 2 (1981), pp. 482-489.

Zhou, Chuanzheng et al. "Fine Tuning of Electrostatics around the Internucleotidic Phosphate through Incorporation of Modified 2',4'-Carbocyclic-LNAs and -ENAs Leads to Significant Modulation of Antisense Properties," Journal of Organic Chemistry, vol. 74, issue 1 (2009), pp. 118-134.

Freier, S. M. et al. "The ups and downs of nucleic acid duplex stability: structure-stability studies on chemically-modified DNA:RNA duplexes," Nucleic Acids Research, vol. 25, issue 22 (Nov. 1997), pp. 4429-4443.

Albaek, Nanna et al. "Analogues of a Locked Nucleic Acid with Three-Carbon 2',4'-Linkages: Synthesis by Ring-Closing Metathesis and Influence of Nucleic Acid Duplex Stability and Structure," Journal of Organic Chemistry, vol. 71, issue 20 (Jun. 2006), pp. 7731-7740.

Singh, Sanjay K. et al. "LNA (locked nucleic acids): synthesis and high-affinity nucleic acid recognition," Chemical Communications, (1998) pp. 455-456.

Singh, Sanjay K. et al. "Synthesis of 2'-Amino-LNA: A Novel Conformationally Restricted High-Affinity Oligonucleotide Analogue with a Handle," Journal of Organic Chemistry, vol. 63, issue 26 (Jul. 1998), pp. 10035-10039.

Srivastava, Puneetet et al. "Five-and six-membered conformationally locked 2',4'-carbocyclic ribo-Thymidines: Synthesis, structure, and biochemical studies," Journal of the American Chemical Society, vol. 129, issue 26 (Jun. 2007), pp. 8362-8379.

Koshkin, Alexei A. et al. "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," Tetrahedron, vol. 54, issue 14 (Apr. 1998), pp. 3607-3630.

Kumar, Ravindra et al. "The first analogues of LNA (Locked Nucleic Acids): Phosphorothioate-LNA and 2'-thio-LNA," Bioorganic & Medicinal Chemistry Letters, vol. 8, issue 16 (Aug. 1998), pp. 2219-2222.

Elayadi, Anissa N. et al. "Application of PNA and LNA oligomers to chemotherapy," Current Opinion in Investigational Drugs, vol. 2, issue 4, (2001), pp. 558-561.

(56) References Cited

OTHER PUBLICATIONS

Braasch Dwaine A. et al. "Locked nucleic acid (LNA): fine-tuning the recognition of DNA and RNA," Chemistry & Biology, vol. 8, issue 1 (Jan. 2001), pp. 1-7.

Ørum, Henrik et al. "Locked nucleic acids: A promising molecular family for gene-function analysis and antisense drug development," Current Opinion in Molecular Therapeutics, vol. 3, issue 3 (Jun. 2001), pp. 239-243.

Leumann, Christian J. "DNA Analogues: From Supramolecular Principles to Biological Properties," Bioorganic & Medicinal Chemistry, vol. 10, issue 4 (Apr. 2002), pp. 841-854.

Braasch Dwaine A. et al. "Novel antisense and peptide nucleic acid strategies for controlling gene expression," Biochemistry (American Chemical Society), vol. 41, No. 14 (Mar. 2002), pp. 4503-4510.

Kumar, Vipin et al. "Design, synthesis, biophysical and primer extension studies of novel acyclic butyl nucleic acid (BuNA)," Organic & Biomolecular Chemistry, vol. 11, issue 35 (Jul. 2013), pp. 5853-5865.

Crooke, Stanley T. "Antisense Drug Technology: Principles, Strategies, and Applications," CRC Press (Second Edition) (2008), pp. 163-166 and 442-443.

Oka, Natsuhisa et al. "An Oxazaphospholidine Approach for the Stereocontrolled Synthesis of Oligonucleoside Phosphorothioates," Journal of the American Chemical Society, vol. 125, issue 27 (Jun. 2003), pp. 8307-8317.

SEQUENCE LISTING

```
<160> NUMBER OF SEQ ID NOS: 1356

<210> SEQ ID NO 1
<211> LENGTH: 2955
<212> TYPE: DNA
<213> ORGANISM: Homo sapiens

<400> SEQUENCE: 1
gcagaaagcg gaactgagcc cgcgtgttct gaggccaggg cagggctgga gcgttctgaa     60
cacctccccg tcccagcccc tgggccaggc aagggccggc cttacctctc ctgggttggt    120
ggcagcagag ctgggctctg agggaggcct gcaatgtgag acagtagcag ctcagaggcg    180
gcactaggca ggtgcaaccc caaaagaccc ctctgccatg aaccagtcca tcccagtggc    240
tcccacccca ccccgccgcg tgcggctgaa gccctggctg gtggcccagg tgaacagctg    300
ccagtaccca gggcttcaat gggtcaacgg ggaaaagaaa ttattctgca tccctggag    360 gcatgccaca aggcatggtc ccagccagga cggagataac accatcttca aggcctgggc    420
caaggagaca gggaaataca ccgaaggcgt ggatgaagcc gatccggcca agtggaaggc    480
caacctgcgc tgtgccctta acaagagccg ggacttccgc ctcatctacg acgggccccg    540
ggacatgcca cctcagccct acaagatcta cgaggtctgc tccaatggcc ctgctcccac    600
agactcccag ccccctgagg attactcttt tggtgcagga gaggaggagg aagaagagga    660
agagctgcag aggatgttgc caagcctgag cctcacagag gatgtcaagt ggccgcccac    720
tctgcagccg cccactctgc ggccgcctac tctgcagccg cccactctgc agccgcccgt    780
ggtgctgggt cccctgctc cagacccag cccctggct cctcccctg caaccctgc    840 tggcttcagg gagcttctct ctgaggtcct ggagcctggg cccctgcctg ccagcctgcc    900
ccctgcaggc gaacagctcc tgccagacct gctgatcagc cccacatgc tgcctctgac    960 cgacctggag atcaagtttc agtaccgggg gcggccaccc cgggccctca ccatcagcaa   1020 ccccatggc tgccggctct tctacagcca gctggaggcc acccaggagc aggtggaact   1080
cttcggcccc ataagcctgg agcaagtgcg cttcccagc cctgaggaca tcccagtga   1140 caagcagcgc ttctacacga accagctgct ggatgtcctg gaccgcgggc tcatcctcca   1200
gctacagggc caggacccttt atgccatccg cctgtgtcag tgcaaggtgt tctgagcgg   1260 gccttgtgcc tcagcccatg actcatgccc caaccccatc cagcgggagg tcaagaccaa   1320
gcttttcagc ctggagcatt ttctcaatga gctcatcctg ttccaaaagg gccagaccaa   1380
```

```
caccccacca cccttcgaga tcttcttctg ctttggggaa gaatggcctg accgcaaacc    1440
ccgagagaag aagctcatta ctgtacaggt ggtgcctgta gcagctcgac tgctgctgga    1500
gatgttctca ggggagctat cttggtcagc tgatagtatc cggctacaga tctcaaaccc    1560
agacctcaaa gaccgcatgg tggagcaatt caaggagctc catcacatct ggcagtccca    1620
gcagcggttg cagcctgtgg cccaggcccc tcctggagca ggccttggtg ttggccaggg    1680
gccctggcct atgcacccag ctggcatgca ataacaaggc tgcagacggt gactggccct    1740
ggcttcctgg gtggcggtgc ggactgatgt ggagatgtga cagccccgat gagcacctgg    1800
ctggctgcag ggtcctacct ctgggtttcc tggaagtgga tttgggccaa gaaggagagg    1860
gagaaaggcc cgagcccctg ccttcccggg cctttctctc ctgggctgtc tctggtctgg    1920
tcagcctggc tctcgggaaa ttcagccatg agcagggaaa gaactctccc aaccctgggg    1980
cctagctgta taggaggaat tgcctaaggg tggcccactc ttgtgattgc cccatttcct    2040
ctggcaacaa aagccagagt gttgtgggcc aagtcccccc acagggcctc tgcagggcat    2100
ggccctgatt tccctggttt gagactcact tcctcatctc cctgtcctct gagataatat    2160
gagtgagcac ttaggtatca tatcagatgc tcaaggctgg cagctacccc cttcttgaga    2220
gtccaagaac ctggagcaga ataattttt atgtattttt ggattaatga atgttaaaaa    2280
cagactcagc tgtttctttc cttttactac taccagttgc tcccatgctg ctccaccagg    2340
ccctgtttcg gatgccaact ggcccactcc ccaagcactt gccccagct tgcgaccatt     2400 ggcactggga gggcctggct tctgggctga tgggtcagtt gggccttcat aaacactcac    2460
ctggctggct ttgccttcca ggaggaagct ggctgaagca agggtgtgga attttaaatg    2520
tgtgcacagt ctggaaaact gtcagaatca gttttcccat aaaagggtgg gctagcattg    2580
cagctgcatt tgggaccatt caaatctgtc actctcttgt gtatattcct gtgctattaa    2640
atatatcagg gcagtgcatg taaatcatcc tgatatattt aatatatta ttatattgtc     2700 ccccgaggtg gggacagtga gtgagttctc ttagtccccc cagagctggt tgttaaagag    2760
cctggcacct acccgctctc acttcatctg tgtcatctct gcacactcca gcccactttc    2820
tgccttcagc cattgagtgg aagctgcccc aggcccttac caggtgcaga tgcccaatct    2880
tgatgcccag ccatcagaac tgtgagccaa ataaaccttt ttctgtataa attacccaaa    2940
aaaaaaaaaa aaaaa                                                     2955
```

<210> SEQ ID NO 2
<211> LENGTH: 12896
<212> TYPE: DNA
<213> ORGANISM: Homo sapiens

<400> SEQUENCE: 2

```
gagagccacc ctcgccaggg gtgtaggcag gcgagaggag ggcctggagc tgtgggtcgg     60
ccacactgcg ccctcatttg tgtgcagccc cggaggacca gagtggggaa gcaccccacc    120
ctctcccagg gcccaactga gcactgcagc gggaggtacg gggttgtcaa atgacagttt    180
tgccattcca gattgccaaa agagccagtg gccagtctag ggcaccgcgc cgtctggcat    240
ctccctggag gccctgggcc tggcccgagg ctcagcccgg atctgcagtt gccaggtcag    300
tgcggggccc ggagtggatt cgcggggcgg ggcggggcac tgcccgcgcc cggagctcag    360
cagcagctgc ccaggggcgg gggcggcaag acgcggaagt gcccggcagg ttggcggacc    420
ggcgggaggc gcagcctggg cagagctcag cttggtcccg ccgccggcc ggtgctccct     480
```

-continued

| | |
|---|---|
| ggcgcagcca cgcaggcgca ccgcagacag gtgggtcccg gccgccgcgc tctcctctct | 540 |
| gcgtccgcgc ccggcgcgcc ccgagggtgg cgggagcggt gccggctact gcccccaagt | 600 |
| ctaggcctag actgggcccc gcgcccccca ggcacctgcg ggcggcggga tgaagactgg | 660 |
| agtagggcgg ggtccgcgtc cagctgcgcc tggaaagcga gctcgggggg gtgcctacag | 720 |
| cagggtgcgc ccggccggcc tgggacttcc aaagcgcctc ccacgccccg atcggtttgg | 780 |
| ggtgctggcg cccggggagc ccagtgaccc aggcggcgga gtgggcagcg ctgcgggggg | 840 |
| cgccggctct gctgctctcc ctccccctcg ccatcgccca gaatgggggt tcccgggagc | 900 |
| cccgctggag gctggcttgg accacagagg agcgaggccc gatccttact ttcgatgcac | 960 |
| tcgcccttgc tcttaccggg ccaccctcac cctttcggaa aagaggttga ggttaaagcg | 1020 |
| ttcatccccc gggatcttca ggccaatggc aggaactgtg caagagtttg ggggaagatg | 1080 |
| gtgtcaggta gaggctgcgt ccctgggctc gcggccggga atggcagact ctcgtccccc | 1140 |
| gagcagcgga aaaggatggg gcgcaatagt tcctgggctg gtttcctcag gtcctgtccc | 1200 |
| agaacttaag aaggcaacaa tgaagaggct aaacgtggag gaaaagtgag gctagcatgg | 1260 |
| ccgggatgcg tggggagatg gttgtctccg gaccccggga ggggcgggag cgggtacctg | 1320 |
| ggagcagagg ctggagtggg ggactttccc agcctcgcgg ccacgctgaa cacagcaggg | 1380 |
| cgaggaccgg ggtgctgctc ctccagcagc aggaggagag gtccagaggc cgactctgga | 1440 |
| ggtgggggtg gctccgcggg ctggcccagg gggtgtgccc cagcggagca cgcgggaggg | 1500 |
| gtgggggcgg aggggagggg ggagcagggg cggaggactg ggctgggcct gggctcctcg | 1560 |
| agggcccaga atggggataa gtgaccagaa ccagagaggg ctcggctgta tcgatgtagg | 1620 |
| aaactgtagc ccctcaggag gccctctggc aagacctccc cttcctgccc ccacccccag | 1680 |
| tagttatggg gcctggggtg ctggggctga ggggttccaa gagtcaaggg aagcactggg | 1740 |
| aaatcacccc tttttatcta aaggccctac tttgggggttt ttcccctgta ccctggtctt | 1800 |
| cccctacect gacectggga ggaagctgaa agaagcttct ttctgggcac cttttgcccc | 1860 |
| agagcctcag cctgtctgga ccaggtgggc agcagggccc agggtgtggg cagctgaccc | 1920 |
| ggaggggtgg gatttggggg tcagggcctg tacagggaac cccttgtcct ctccctgagc | 1980 |
| tgggtgtggg tttgcaagga gacatgtgac ccagaccaac cctgggagca gcagggcgcc | 2040 |
| tgctgtctgg ccactcttac taggactgct gtggcacttc ctcccctagt gggtccctgg | 2100 |
| tgcccatgaa ttgcagctcc tgggtggtgg tgggggcact gtctcctggg actccagcat | 2160 |
| ggccctgggg tgagctgtgg gcttacccca cctcagcagg tcctctaggg ctgcccactg | 2220 |
| gatgcttcgc tgcctcacac aattgtaggg acttcctcag gctgttggat ttccccacct | 2280 |
| tccgggctc aggtccattg acttaggtct agggctccat acatttcacc cagagactcc | 2340 |
| ggagcctggc aggcagacct gttctgacac cgaacttcca aagtcatggg ccttgattgg | 2400 |
| ggtggtctga attagaccta gccctttct gggcagaagg gagcttctag gaggatggat | 2460 |
| gctgttcggg ttagagctcg tgtggaccta gctgcaggca aaagccttga ggctgagtcc | 2520 |
| cttctgtggc atggtggaca gactctcgct catcacagcc gggcttgtca cgggagctcc | 2580 |
| tcctccacac ccctccctaa gctgcctgta tggacgcggc cctctgacac tgaggtcgga | 2640 |
| gttatcattt caaaaccttg ctctgtatta acagccgtg ttgggcaggg ccagactgct | 2700 |
| ggactgacag taggggcag gcagccggac cctctgagct ccccaacggc accagcgcct | 2760 |
| gcacggcctc agcccagggg gtcattaggg aagctctccc cgattctgtg cagacagagc | 2820 |
| ttcctctgtc caccccttgct cggccagaat tgtgtgccgc tggtgactgg caccctcta | 2880 |

```
ttctagggcc aaggcctctc aggggtctac agatacaact atgggtgggt gcacacccat    2940
gttataaacc acactaaatg cacaaaaact gtctgcaagt ttggggtgcg gggaacagct    3000
ctgggtggga ggttggaaat ttggtctggg ggacccactc ggctccctcc ctcagcccac    3060
agtgagtctg gtttctgagt tgtcccggtc tagccacttt cgtttccect ggggccgggt    3120 ggaggctggg gcagaaagcg gaactgagcc cgcgtgttct gaggccaggg cagggctgga    3180
gcgttctgaa cacctccccg tcccagcccc tgggccaggc aagggccggc cttacctctc    3240
ctgggttggt ggcagcagag ctgggctctg agggaggcct gcaatgtgag acagtagcag    3300
ctcagaggcg gcactaggca ggtgcaaccc caaaaggtac tgggcaggga atttcagggg    3360
aaactgaggc tccatgctgc aaggccaaag caggcccaga cacagggagt tcagctcgaa    3420
cgtttgctcc ttacttgctg accgacacat tcacttctga tgggctgtgc tgtgtaatga    3480
cccagtcctt tctgtcttcc acccaggggt ctcaagtgaa gggccaaggg catgggtaag    3540
gggaggagag ggacagaagg ggactcagga ctgtggagag tttccggttc tgggctggag    3600
agggagttgg gcaggtgaag gggaggaggc agggtccctc tggcctgact ccagggaggc    3660
agtgaagctg tggcctggga ggcggggctc gtgcccctgg gtaggtagca gttagagctg    3720
tggcttctgt ttcctgtagc cttcctaaca ggctccggca ggcgttaggg ccttcctaag    3780
tgctacccga atgcgtgtcc agtgggagga aagggggag gaccaagaac ctagatgaat    3840
ggccctagag aggtaacatc tgtttggtgc ctgctgtcat tggaggtggg ttgagttggt    3900
tgatgggatt tctctaaaga tattgagaaa ctgctttcct ctgagggcag gtgtccttgg    3960
gagctccaga tgagattctt gttgagggca tctccggagg gaactctcag gggatggagg    4020
gtgagaaaac ttgggcaggg aagaatcgaa ctagggtgt agactgagca ggaggctgtc    4080
ttcgggctga tcccacagag cgctcgctgt cccaggtagc cagcttgaga caagacagcc    4140
gggcttttgg tgtcaggcag tcactggctg tgggctgccc cccaagagca aggggtgggc    4200
ctaacctgtg gtgtgagtag tggaaggcgg ttctctggcc aacgggctgc ttgctgctgt    4260
tagcagttgg agaatggatg cctctgcccg gtaaagggca cctggggccg cgcccgcagc    4320
attcactaac tcgtaactct ccttcccttc ctccaaacac aaaattccat gacactagac    4380
aagaaagctg atgcttggaa aagagaattg gccttaaata cctagatgga ctggagagac    4440
catcctttgt ggtccatagc ttgacctctg agtaccctgt ccccatccac ctgcagacct    4500
gctgaggctc ccctctggct ttctcctgca gaccctctg ccatgaacca gtccatccca    4560
gtggctccca ccccacccg ccgcgtgcgc ctgaagccct ggctggtggc ccaggtgaac    4620
agctgccagt acccagggct tcaatgggtc aacgggaaa agaaattatt ctgcatcccc    4680
tggaggcatg ccacaaggca tggtcccagc caggacggga ataacaccat cttcaaggta    4740
agccccgggg aggaggttgg ctggacctcc agggcaccct gtccccagaa gaggagcgca    4800
cataacgcac acaggcagct cctcgaggct ggccacccgc ccagctacca tgctgctgct    4860
gatgccgggc ccggactaag gggatgcaga cgtagacaca gggtacacct ttttcctttt    4920
tttttttttt taagacagag tctcgctctg tagcccaggc tggagtgcag tggcacgatc    4980
tcagctcact gcaacctctg cctcctgggt tcaagcaatt ctcctgcctc agcctcctga    5040
gtagctggga ttacaggcat gagccaccac gcctggccta gggcacatct tttctaacct    5100
gcaccctaga gcatcgtggg gactgagggt ccccagaagg ccttcccata actcgtccta    5160
ctcacccttt gctcgtctca ctcctattac tcatgaggac ttgttcagtg cacgcatatg    5220
```

```
ctaaaggaag ccaacgatca tcatctttct aaaaatttta ttttttaaatt agtatatatt    5280
tatggggtac acagtggtga tttgataagc acagtgatca gatcaggtac ttagcatatc    5340
cataatctca aacatttgtc atttctttgt gttgggaaca aactatttttt aatataagat    5400
tcagatacat catcaatctt tcaattgttt aaattttcta atttttttta gagacagggc    5460
ctcacactgt tgaccagatt ccaatttttt tttttttttt tttttttttt ttgagacagg    5520
gtctcactct gtcacccagg ctggagtgca gtggcttgat ctcagctcac tgcagcctcg    5580
acctcccagg ctcaggtgag tctcccatct caacctcctt gagtagctgg gattacaggt    5640
gcctgccacc acaactggct aattttttgt acttttagta gagactttgc catgttgccc    5700
aggctggtct tgaactcctg gactcaagca atccacccac ctcagcctcc cagagtgctg    5760
ggattacagg tgtgagccac catgcccggc ccaatctttt tttttaattg atgtactaca    5820
actgtacata tatactcttt tttttttttt ttgagatgag ttgttgctct gttgcctagt    5880
gttgcaccat tggtgagcag tggtgcagtc atagcacaac ctccaactca gctcaagtga    5940
tcctccagtc tcagcttcct gagtagccgt gactacaggt gcatgccacc atgcccagct    6000
aattttttt tttttttttg agatggagtc ttgcttttttc accctagctg gagtgcaatg    6060
gcacaatctc agctcactgc aacctctgcc acctgggttc aagcaattct cctgcctcag    6120
cctcccgagt agctaggatt acaggcacct gccaccatgc ccggctaatt tttttttttt    6180
tttttttttt tttttttttt tttgtatttt tggtaaagac agggtttcac cctgttggcc    6240
aggctggtct tgaactcctg acctcatgat ccacctgcct tggcctccca agtgctggg    6300
attacaggcg tgagccaccg tgcccagcct aattttttga ttttgatatt tgtaaagatg    6360
aggtctcact tgttgcccca ggctggtctc aagctcatgg gctcaagtga tcctcccacc    6420
tcagcctcct gagtagctgg tatcacaggc gcaagccact gtgctctctc caataatctt    6480
aatgctagga tgtacctcgc ataatagttt ttgcttacat tttagttttt ttgcacatgt    6540
gtgtatatgg aatgcaaaat tggaatcaag tgaatatctt gatttatagc ctggattttt    6600
ttcacccaat atcaggatca gctttccttt ccaacatacg tccacatcac ttttcgtgac    6660
tgtagaattt ccactggaat ggtttagcac aatttggtca ctgagtcttg gttttagat    6720
acttgagatt gctttttaaaa cctgaactta aaaccacat tgtcatgtag gctgtcttaa    6780
tgcttccctt tttttcatcc tcaattattt tgggggttga tttcctagag ttgaaaattg    6840
ctgggtcaaa ggcaatgctt attttttaaa actttgggta catattttct tagttttgg    6900
gcttgatcct tacctttcca aaattctttt gctaatccat ttattttgta taggtaatac    6960
agtcacaaaa ttcaacatta aaaggcatag aatggtttag agcaaaaagt ctccctcctt    7020
ccctggttca tcaccaccca ctcccctccc tagcctttcc ctagaggcag ccgtgttgtc    7080
attttcttgt ttagccttcc tgagagattt ttatgcacat gtaagcaaat atggaactat    7140
cctttcctct acttttcata agaaatgcta gatatctgca tatttgtcta gacttaatac    7200
ttcttgacga ttgctacatg tcagcttata aacagtttcc tgcttttcct tttttgtgc    7260
tgcccagtat ttttcattca atgggttggc cgtaatttca ccagcccctc attgatggat    7320
gttgcattgg gtattttggg tcatcttta cacacagcac tgctgcgaat aactttgtgt    7380
gtgcaatatt ttgtgtgaat gcttctatga tatttaggat gaattcctag aaatcaaata    7440
gctgggttaa aaggtagaaa gaaatgttgg taaccctcac ctcacctaat tgccattcaa    7500
aataatacca acagctccag tgtctcgagc ctgtcctatg tgcaggttta gctctgagtg    7560
ctttacggac atcaactccc ctcatctttt ttgagatagg gtatcactct gtcgtccagg    7620
```

```
ctggagtgca gagcataatc atggctcact gcagccttga actccccagc tcaagcaatc    7680
ctctcacctc agcctcctga gtagctggga ccacaggcac ccaccactat gcccagctaa    7740 tttttttgtaa agacaggagt ctcgttatgt tgcctaggct ggactccaac tcctgggctc    7800
aagcagtcct cccaccttgg cctcccaaaa tgttgggatt acaggtgcga ccactgtgc    7860 ccagccaaca tcaacccctt gagtcttcgc tgccactcca tgaggtgggc aactgtgagg    7920
agatcaagac aaagggaggc agtgacatgg cctggcacac agctggcggg gggcacttcc    7980
agattcaaac ccagcctggc tccagggtgc tcacccttat cccgcacgct gtcctcctta    8040
gagatcacac tgtttcaccc tcccaggagc agggactatg gatgcatctc atagcccta    8100 gatttcatgt agcttgctgg cagcctgagg gctggggcag gactgtggca gactcccacg    8160
ctgcaaacca ggtctggggc tcagcgaggc tcagcctgta gccgaagttc tccccacaca    8220
gtagagtctc ctatgggaca ggaggcagac tgggctgtg gcagggatga ggttctctgt    8280
ggtcggctat ttcttcctgc cccaggcctg ggcaaggag acaggaaat acaccgaagg    8340 cgtggatgaa gccgatccgg ccaagtggaa ggccaacctg cgctgtgccc ttaacaagag    8400
ccgggacttc cgcctcatct acgacgggcc ccgggacatg ccacctcagc cctacaagat    8460
ctacgaggtc tgctccaatg gccctgctcc cacaggtatc aggcctagcc ctctgtgggc    8520
cacctgggag gctgtgcaat gtcctggccc ccagccatga gctcttgggt gcaggcaggc    8580
caagggcccc tctagcaggc agtggtccag gaaacgatgc gggggctccc gctaggtcat    8640
gacacccagg gcttccagga gtggctggga tgggtcactg gcatatcagg aatggcttgg    8700
cgtgcagtca gggacctggg tgcttcttcc ttaccattgc cctcgttttg gcttctggct    8760
ccagcctagg tctcatggcc catggagtcg gggaggtctt tcccaatcct ggtggctgtg    8820
ccctccacct cgccctgtgt tggggcagc tttggggaag gcagaagctg cataggagct    8880
acaggcagcc tctcagggga tcttgcttct cctccgacat tgactccttt actgccctgc    8940
ttttctctcc ctgctgtgca gactcccagc ccctgagga ttactctttt ggtgcaggag    9000
aggaggagga agaagaggaa gaggtgagtg tgggttgagg aggcaggtgg agccctggac    9060
gagctctctg ctgtccccat cggccttagg tttccgcagc cccactccca tggagccccg    9120
tggccctctc aatagttctc cttgtttctt ctcctgggat tctgaacgat aggagcacag    9180
tccccacctg ctccttccca gggcattgtc attaccctgt gtgtgtgacc cacgcagcag    9240
ttggggcttg gtaggtctga ctccctgcag aaggcaaatg aggaaagtga ggcaaagggc    9300
ttttctgacc tgcctgggat ggacgagctg ggaccggagg cagggtcttg cctgagctaa    9360
actgaggcta ggggagttgc ctcatagttc tcgcctgtta ttttccccagc cccaggtcag    9420 tggaataacc tgtcctcctt tctctcccat ctcttccctc ccttgctggt ggtgtccctt    9480
cagctgcaga ggatgttgcc aagcctgagc ctcacaggtg gggccgggag tggtggttg    9540 ggggtctagt atacagagaa gctataggta ccataggtac ctggaagggg gctgatggga    9600
ggctagggtg gcccagggct gggaggaggt gtgcctggga ggcagttcgt ggaggtggca    9660
ctgacagccg tccacacgca ctctctgtag atgcagtgca gtctggcccc cacatgacac    9720
cctattcttt actcaaagag gatgtcaagt ggccgcccac tctgcagccg cccactctgc    9780
ggccgcctac tctgcagccg cccactctgc agccgcccgt ggtgctgggt cccctgctc    9840 cagaccccag cccctggct cctccccctg gcaaccctgc tggcttcagg agcttctct    9900 ctgaggtcct ggagcctggg cccctgcctg ccagcctgcc cctgcaggc gaacagctcc    9960
```

-continued

```
tgccagacct gctgatcagc ccccacatgc tgcctcgtaa ggacccatgg ctgggcacgg    10020
ggaagcagtg ctgggggatt ggggtaggat tggcaaggag ggtggagggt gctggactcc    10080
cttgggtggg aaaagtggga gggcggatgg ggctgggcct ggccactggg ctgcagaatg    10140
gggaggcgtg gggctcaagg acgggatggg cctgccttct gccccacagt gaccgacctg    10200
gagatcaagt ttcagtaccg ggggcggcca ccccgggccc tcaccatcag caaccccat    10260 ggctgccggc tcttctacag ccagctggag gccacccagg agcaggtgga actcttcggc    10320
cccataagcc tggagcaagt gcgcttcccc agccctgagg acatcccag tgacaagcag     10380 cgcttctaca cgaaccagct gctggatgtc ctggaccgcg ggctcatcct ccagctacag    10440
ggccaggacc tttatgccat ccgcctgtgt cagtgcaagg tgttctggag cgggccttgt    10500
gcctcagccc atgactcatg ccccaacccc atccagcggg aggtcaagac caagcttttc    10560
agcctggagc atttctcaa tggtgagggc ccaaagctgt gatcctcctg gctgcctctt    10620
gcccagggca tggttccagc ctctgactag ggaccttgat tttgatgcag agctcatcct    10680
gttccaaaag ggccagacca acaccccacc acccttcgag atcttcttct gctttgggga    10740
agaatggcct gaccgcaaac cccgagagaa gaagctcatt actgtacagg tacatctccc    10800
ctatcccaaa gtcggccttg gcttgaaaac tggggaatcc tggggctagg cccttgcccc    10860
aggctggagg ctcagggctc cctgagcagt gtgaacttgg cggcagaga ccatcaaggc     10920 tcagagccga agaatgcggt ctattactca cccctgatgg ctgtcctcat gcacagctgg    10980
atctggcagc cctgccacag gtctccctgt ctcatctcct ctttgcctcc caggtggtgc    11040
ctgtagcagc tcgactgctg ctggagatgt tctcagggga gctatcttgg tcagctgata    11100
gtatccggct acagatctca aacccagacc tcaaagaccg catggtggag caattcaagg    11160
agctccatca catctggcag tcccagcagc ggttgcagcc tgtggcccag gcccctcctg    11220
gagcaggcct tggtgttggc caggggcct ggcctatgca cccagctggc atgcaataac     11280
aaggctgcag acggtgactg gccctggctt cctgggtggc ggtgcggact gatgtggaga    11340
tgtgacagcc ccgatgagca cctggctggc tgcagggtcc tacctctggg tttcctggaa    11400
gtggatttgg gccaagaagg agagggagaa aggcccgagc ccctgccttc ccgggccttt    11460
ctctcctggg ctgtctctgg tctggtcagc ctggctctcg ggaaattcag ccatgagcag    11520
ggaaagaact ctcccaaccc tggggcctag ctgtatagga ggaattgcct aagggtggcc    11580
cactcttgtg attgccccat ttcctctggc aacaaaagcc agagtgttgt gggccaagtc    11640
cccccacagg gcctctgcag ggcatggccc tgatttccct ggtttgagac tcacttcctc    11700
atctccctgt cctctgagat aatatgagtg agcacttagg tatcatatca gatgctcaag    11760
gctggcagct acccccttct tgagagtcca agaacctgga gcagaaataa tttttatgta    11820 ttttggatt aatgaatgtt aaaaacagac tcagctgttt ctttcctttt actactacca     11880
gttgctccca tgctgctcca ccaggccctg tttcggatgc caactggccc actcccaag    11940 cacttgcccc cagcttgcga ccattggcac tgggagggcc tggcttctgg gctgatgggt    12000
cagttgggcc ttcataaaca ctcacctggc tggctttgcc ttccaggagg aagctggctg    12060
aagcaagggt gtggaatttt aaatgtgtgc acagtctgga aaactgtcag atcagttttt    12120
cccataaaag ggtgggctag cattgcagct gcatttggga ccattcaaat ctgtcactct    12180
cttgtgtata ttcctgtgct attaaatata tcagggcagt gcatgtaaat catcctgata    12240
tatttaatat atttattata ttgtccccg aggtggggac agtgagtgag ttctcttagt     12300 cccccccagag ctggttgtta aagagcctgg cacctacccg ctctcacttc atctgtgtca   12360
```

-continued

| | | | |
|---|---|---|---|
| tctctgcaca | ctccagccca | ctttctgcct | tcagccattg agtggaagct gccccaggcc | 12420 |
| cttaccaggt | gcagatgccc | aatcttgatg | cccagccatc agaactgtga gccaaataaa | 12480 |
| ccttttctg | tataaattac | ccagcctcgg | gtcttcgttt acagcaacgc aaaatagatt | 12540 |
| aaaccccat | aaatgttcaa | ggatacctg | ccccacagcc tcgtccacag aatatattgt | 12600 |
| cactgtttgg | atttttgcca | acctgacagg | tgagatagta tctcagtgcc acttctcatt | 12660 |
| atcagcaagg | ctgagtagct | tttcacatgg | ttaagtggcc tgtacagatt ttttaaata | 12720 |
| attttagaat | ggttttagat | ttatggaaaa | gttcctaata gagttcctat ggacccacac | 12780 |
| tttctccaat | tgttaacatc | ttacattact | atggcacact tgtgacaata atgaaaccat | 12840 |
| gtggacaatt | actatgaact | caacttcttt | atttggattt catgagtttt tcggat | 12896 |

<210> SEQ ID NO 3
<211> LENGTH: 2910
<212> TYPE: DNA
<213> ORGANISM: Homo sapiens

<400> SEQUENCE: 3

| | | | |
|---|---|---|---|
| agtgcccggc | aggttggcgg | accggcggga | ggcgcagcct gggcagagct cagcttggtc | 60 |
| ccgccgcccg | gccggtgctc | cctggcgcag | ccacgcaggc gcaccgcaga cagacccctc | 120 |
| tgccatgaac | cagtccatcc | cagtggctcc | caccccaccc cgccgcgtgc ggctgaagcc | 180 |
| ctggctggtg | gcccaggtga | acagctgcca | gtacccaggg cttcaatggg tcaacgggga | 240 |
| aaagaaatta | ttctgcatcc | cctggaggca | tgccacaagg catggtccca gccaggacgg | 300 |
| agataacacc | atcttcaagg | cctgggccaa | ggagacaggg aaatacaccg aaggcgtgga | 360 |
| tgaagccgat | ccggccaagt | ggaaggccaa | cctgcgctgt gcccttaaca agagccggga | 420 |
| cttccgcctc | atctacgacg | gccccggga | catgccacct cagccctaca agatctacga | 480 |
| ggtctgctcc | aatggccctg | ctcccacaga | ctcccagccc cctgaggatt actcttttgg | 540 |
| tgcaggagag | gaggaggaag | aagaggaaga | gctgcagagg atgttgccaa gcctgagcct | 600 |
| cacagatgca | gtgcagtctg | gcccccacat | gacaccctat tctttactca aagaggatgt | 660 |
| caagtggccg | cccactctgc | agccgcccac | tctgcggccg cctactctgc agccgcccac | 720 |
| tctgcagccg | cccgtggtgc | tgggtccccc | tgctccagac cccagccccc tggctcctcc | 780 |
| ccctggcaac | cctgctggct | tcaggagct | tctctctgag gtcctggagc ctgggcccct | 840 |
| gcctgccagc | ctgccccctg | caggcgaaca | gctcctgcca gacctgctga tcagccccca | 900 |
| catgctgcct | ctgaccgacc | tggagatcaa | gtttcagtac cgggggcggc caccccgggc | 960 |
| cctcaccatc | agcaaccccc | atggctgccg | gctcttctac agccagctgg aggccaccca | 1020 |
| ggagcaggtg | gaactcttcg | gccccataag | cctggagcaa gtgcgcttcc ccagccctga | 1080 |
| ggacatcccc | agtgacaagc | agcgcttcta | cacgaaccag ctgctggatg tcctggaccg | 1140 |
| cgggctcatc | ctccagctac | agggccagga | ccttttatgcc atccgcctgt gtcagtgcaa | 1200 |
| ggtgttctgg | agcgggcctt | gtgcctcagc | ccatgactca tgcccaacc ccatccagcg | 1260 |
| ggaggtcaag | accaagcttt | tcagcctgga | gcattttctc aatgagctca tcctgttcca | 1320 |
| aaagggccag | accaacaccc | caccacccctt | cgagatcttc ttctgctttg gggaagaatg | 1380 |
| gcctgaccgc | aaaccccgag | agaagaagct | cattactgta caggtggtgc tgtagcagc | 1440 |
| tcgactgctg | ctggagatgt | tctcagggga | gctatcttgg tcagctgata gtatccggct | 1500 |
| acagatctca | aacccagacc | tcaaagaccg | catggtggag caattcaagg agctccatca | 1560 |

| | |
|---|---|
| catctggcag tcccagcagc ggttgcagcc tgtggcccag gccctcctg gagcaggcct | 1620 |
| tggtgttggc caggggccct ggcctatgca cccagctggc atgcaataac aaggctgcag | 1680 |
| acggtgactg gccctggctt cctgggtggc ggtgcggact gatgtggaga tgtgacagcc | 1740 |
| ccgatgagca cctggctggc tgcagggtcc tacctctggg tttcctggaa gtggatttgg | 1800 |
| gccaagaagg agagggagaa aggcccgagc ccctgccttc ccgggccttt ctctcctggg | 1860 |
| ctgtctctgg tctggtcagc ctggctctcg ggaaattcag ccatgagcag ggaaagaact | 1920 |
| ctcccaaccc tggggcctag ctgtatagga ggaattgcct aagggtggcc cactcttgtg | 1980 |
| attgccccat ttcctctggc aacaaaagcc agagtgttgt gggccaagtc ccccacagg | 2040 |
| gcctctgcag ggcatggccc tgatttccct ggtttgagac tcacttcctc atctccctgt | 2100 |
| cctctgagat aatatgagtg agcacttagg tatcatatca gatgctcaag ctggcagct | 2160 |
| acccccttct tgagagtcca agaacctgga gcagaaataa ttttatgta ttttggatt | 2220 |
| aatgaatgtt aaaaacagac tcagctgttt ctttccttt actactacca gttgctccca | 2280 |
| tgctgctcca ccaggccctg tttcggatgc caactggccc actccccaag cacttgcccc | 2340 |
| cagcttgcga ccattggcac tgggagggcc tggcttctgg gctgatgggt cagttgggcc | 2400 |
| ttcataaaca ctcacctggc tggctttgcc ttccaggagg aagctggctg aagcaagggt | 2460 |
| gtggaatttt aaatgtgtgc acagtctgga aaactgtcag aatcagtttt cccataaaag | 2520 |
| ggtgggctag cattgcagct gcatttggga ccattcaaat ctgtcactct cttgtgtata | 2580 |
| ttcctgtgct attaaatata tcagggcagt gcatgtaaat catcctgata tatttaatat | 2640 |
| atttattata ttgtcccccg aggtggggac agtgagtgag ttctcttagt cccccagag | 2700 |
| ctggttgtta aagagcctgg cacctacccg ctctcacttc atctgtgtca tctctgcaca | 2760 |
| ctccagccca ctttctgcct tcagccattg agtggaagct gccccaggcc cttaccaggt | 2820 |
| gcagatgccc aatcttgatg cccagccatc agaactgtga gccaaataaa cctttttctg | 2880 |
| tataaattac ccaaaaaaaa aaaaaaaaa | 2910 |

<210> SEQ ID NO 4
<211> LENGTH: 2187
<212> TYPE: DNA
<213> ORGANISM: Homo sapiens

<400> SEQUENCE: 4

| | |
|---|---|
| gcggcgggag gcgcagcctg ggcagagctc agcttggtcc cgccgcccgg ccggtgctcc | 60 |
| ctggcgcagc cacgcaggcg caccgcagac agacccctct gccatgaacc agtccatccc | 120 |
| agtggctccc acccaccccc gccgcgtgcg gctgaagccc tggctggtgg cccaggtgaa | 180 |
| cagctgccag tacccagggc ttcaatgggt caacggggaa aagaaattat tctgcatccc | 240 |
| ctggaggcat gccacaaggc atggtcccag ccaggacgga gataacacca tcttcaaggc | 300 |
| ctgggccaag gagacaggga atacaccga aggcgtggat gaagccgatc cggccaagtg | 360 |
| gaaggccaac ctgcgctgtg cccttaacaa gagccgggac ttccgcctca tctacgacgg | 420 |
| gcccgggac atgccaccctc agccctacaa gatctacgag gtctgctcca atggccctgc | 480 |
| tcccacagac tccagccccc tgaggatta ctcttttggt gcaggagagg aggaggaaga | 540 |
| agaggaagag ctgcagagga tgttgccaag cctgagcctc acagatgcag tgcagtctgg | 600 |
| cccccacatg acaccctatt ctttactcaa agaggatgtc aagtggccgc ccactctgca | 660 |
| gccgccact ctgcagccgc ccgtggtgct gggtccccct gctccagacc ccagccccct | 720 |
| ggctcctccc cctggcaacc tgctggctt cagggagctt ctctctgagg tcctggagcc | 780 |

```
tgggcccctg cctgccagcc tgcccctgc aggcgaacag ctcctgccag acctgctgat    840 cagccccac atgctgcctc tgaccgacct ggagatcaag tttcagtacc ggggcggcc      900 accccgggcc ctcaccatca gcaaccccca tggctgccgg ctcttctaca gccagctgga    960
ggccacccag gagcaggtgg aactcttcgg ccccataagc ctggagcaag tgcgcttccc   1020
cagccctgag gacatcccca gtgacaagca gcgcttctac acgaaccagc tgctggatgt   1080
cctggaccgc gggctcatcc tccagctaca gggccaggac ctttatgcca tccgcctgtg   1140
tcagtgcaag gtgttctgga gcgggccttg tgcctcagcc catgactcat gccccaaccc   1200
catccagcgg gaggtcaaga ccaagctttt cagcctggag cattttctca atgagctcat   1260
cctgttccaa aagggccaga ccaacacccc accacccttc gagatcttct tctgctttgg   1320
ggaagaatgg cctgaccgca aaccccgaga agaagaagctc attactgtac aggtggtgcc   1380
tgtagcagct cgactgctgc tggagatgtt ctcaggggag ctatcttggt cagctgatag   1440
tatccggcta cagatctcaa acccagacct caaagaccgc atggtggagc aattcaagga   1500
gctccatcac atctggcagt cccagcagcg gttgcagcct gtggcccagg cccctcctgg   1560
agcaggcctt ggtgttggcc aggggccctg gcctatgcac ccagctggca tgcaataaca   1620
aggctgcaga cggtgactgg ccctggcttc ctgggtggcg gtgcggactg atgtggagat   1680
gtgacagccc cgatgagcac ctggctggct gcagggtcct acctctgggt ttcctggaag   1740
tggatttggg ccaagaagga gagggagaaa ggcccgagcc cctgccttcc cgggcctttc   1800
tctcctgggc tgtctctggt ctggtcagcc tggctctcgg gaaattcagc catgagcagg   1860
gaaagaactc tcccaaccct ggggcctagc tgtataggag gaattgccta agggtggccc   1920
actcttgtga ttgccccatt tcctctggca acaaaagcca gagtgttgtg gccaagtcc    1980 ccccacaggg cctctgcagg gcatggccct gatttccctg gtttgagact cacttcctca   2040 tctcctgtc ctctgagata atatgagtga gcacttaggt atcatatcag atgctcaagg   2100
ctggcagcta ccccctttctt gagagtccaa gaacctggag cagaaataat ttttatgtat   2160
ttttggatta ataaatgtta aaaacag                                        2187
```

<210> SEQ ID NO 5
<211> LENGTH: 556
<212> TYPE: DNA
<213> ORGANISM: Homo sapiens

<400> SEQUENCE: 5

```
gcagaaagcg gaactgagcc cgcgtgttct gaggccaggg cagggctgga gcgttctgaa     60
cacctccccg tcccagcccc tgggccaggc aagggccggc cttacctctc ctgggttggt    120
ggcagcagag ctgggctctg agggaggcct gcaatgtgag acagtagcag ctcagaggcg    180
gcactaggca ggtgcaaccc caaaagaccc ctctgccatg aaccagtcca tcccagtggc    240
tcccacccca ccccgccgcg tgcggctgaa gccctggctg gtggcccagg tgaacagctg    300
ccagtaccca gggcttcaat gggtcaacgg ggaaaagaaa ttattctgca tcccctggag    360
gcatgccaca aggcatggtc ccagccagga cggagataac accatcttca aggcctgggc    420
caaggagaca gggaaataca ccgaaggcgt ggatgaagcc gatccggcca gtggaaggc    480 caacctgcgc tgtgccctta acaagagccg ggacttccgc ctcatctacg acgggccccg    540
ggacatgcca cctcag                                                    556
```

<210> SEQ ID NO 6

<211> LENGTH: 2862
<212> TYPE: DNA
<213> ORGANISM: Homo sapiens

<400> SEQUENCE: 6

```
agtgcccggc aggttggcgg accggcggga ggcgcagcct gggcagagct cagcttggtc      60
ccgccgcccg gccggtgctc cctggcgcag ccacgcaggc gcaccgcaga cagacccctc     120
tgccatgaac cagtccatcc cagtggctcc caccccaccc cgccgcgtgc ggctgaagcc     180
ctggctggtg gcccaggtga acagctgcca gtacccaggg cttcaatggg tcaacgggga     240
aaagaaatta ttctgcatcc cctggaggca tgccacaagg catggtccca gccaggacgg     300
agataacacc atcttcaagg cctgggccaa ggagacaggg aaatacaccg aaggcgtgga     360
tgaagccgat ccggccaagt ggaaggccaa cctgcgctgt gcccttaaca agagccggga     420
cttccgcctc atctacgacg ggccccggga catgccacct cagccctaca agatctacga     480
ggtctgctcc aatggccctg ctcccacaga ctcccagccc cctgaggatt actcttttgg     540
tgcaggagag gaggaggaag aagaggaaga gctgcagagg atgttgccaa gcctgagcct     600
cacagaggat gtcaagtggc cgcccactct gcagccgccc actctgcggc cgcctactct     660
gcagccgccc actctgcagc cgcccgtggt gctgggtccc cctgctccag accccagccc     720
cctggctcct cccccctggca acctgctgg cttcagggag cttctctctg aggtcctgga     780
gcctgggccc ctgcctgcca gcctgccccc tgcaggcgaa cagctcctgc cagacctgct     840
gatcagcccc cacatgctgc ctctgaccga cctggagatc aagtttcagt accggggcg     900
gccaccccgg gccctcacca tcagcaaccc ccatggctgc cggctcttct acagccagct     960
ggaggccacc caggagcagg tggaactctt cggccccata agcctggagc aagtgcgctt    1020
ccccagccct gaggacatcc ccagtgacaa gcagcgcttc tacacgaacc agctgctgga    1080
tgtcctggac cgcgggctca tcctccagct acagggccag gacctttatg ccatccgcct    1140
gtgtcagtgc aaggtgttct ggagcgggcc ttgtgcctca gcccatgact catgccccaa    1200
ccccatccag cgggaggtca agaccaagct tttcagcctg gagcattttc tcaatgagct    1260
catcctgttc caaaagggcc agaccaacac cccaccaccc ttcgagatct tcttctgctt    1320
tgggaagaa tggcctgacc gcaaaccccg agagaagaag ctcattactg tacaggtggt    1380
gcctgtagca gctcgactgc tgctggagat gttctcaggg gagctatctt ggtcagctga    1440
tagtatccgg ctacagatct caaacccaga cctcaaagac cgcatggtgg agcaattcaa    1500
ggagctccat cacatctggc agtcccagca gcggttgcag cctgtggccc aggcccctcc    1560
tggagcaggc cttggtgttg ccaggggcc ctggcctatg cacccagctg gcatgcaata    1620
acaaggctgc agacggtgac tggccctggc ttcctgggtg gcggtgcgga ctgatgtgga    1680
gatgtgacag cccccgatgag cacctggctg gctgcagggt cctacctctg ggtttcctgg    1740
aagtggattt gggccaagaa ggagagggag aaaggcccga gccctgcct tcccgggcct    1800
ttctctcctg ggctgtctct ggtctggtca gcctggctct cgggaaattc agccatgagc    1860
agggaaagaa ctctcccaac cctggggcct agctgtatag gaggaattgc ctaagggtgg    1920
cccactcttg tgattgcccc atttcctctg gcaacaaaag ccagagtgtt gtgggccaag    1980
tcccccaca gggcctctgc agggcatggc cctgatttcc ctggtttgag actcacttcc    2040
tcatctccct gtcctctgag ataatatgag tgagcactta ggtatcatat cagatgctca    2100
aggctggcag ctaccccctt cttgagagtc caagaacctg gagcagaaat aattttatg    2160
tatttttgga ttaatgaatg ttaaaaacag actcagctgt ttctttcctt ttactactac    2220
```

```
cagttgctcc catgctgctc caccaggccc tgtttcggat gccaactggc ccactcccca    2280
agcacttgcc cccagcttgc gaccattggc actgggaggg cctggcttct gggctgatgg    2340
gtcagttggg ccttcataaa cactcacctg gctggctttg ccttccagga ggaagctggc    2400
tgaagcaagg gtgtggaatt ttaaatgtgt gcacagtctg gaaaactgtc agaatcagtt    2460
ttcccataaa agggtgggct agcattgcag ctgcatttgg gaccattcaa atctgtcact    2520
ctcttgtgta tattcctgtg ctattaaata tatcagggca gtgcatgtaa atcatcctga    2580
tatatttaat atatttatta tattgtcccc cgaggtgggg acagtgagtg agttctctta    2640 gtcccccag agctggttgt taaagagcct ggcacctacc cgctctcact tcatctgtgt    2700
catctctgca cactccagcc cactttctgc cttcagccat tgagtggaag ctgccccagg    2760
cccttaccag gtgcagatgc ccaatcttga tgcccagcca tcagaactgt gagccaaata    2820 aaccttttt c tgtataaatt acccaaaaaa aaaaaaaaa aa                        2862
```

```
<210> SEQ ID NO 7
<211> LENGTH: 2604
<212> TYPE: DNA
<213> ORGANISM: Homo sapiens

<400> SEQUENCE: 7
```

```
agtgcccggc aggttggcgg accggcggga ggcgcagcct gggcagagct cagcttggtc      60
ccgccgcccg gccggtgctc cctggcgcag ccacgcaggc gcaccgcaga cagacccctc     120
tgccatgaac cagtccatcc cagtggctcc caccccaccc cgccgcgtgc ggctgaagcc     180
ctggctggtg gccaggtga  acagctgcca gtacccaggg cttcaatggg tcaacgggga     240
aaagaaatta ttctgcatcc cctggaggca tgccacaagg catggtccca gccaggacgg     300
agataacacc atcttcaagg cctgggccaa ggagacaggg aaatacaccg aaggcgtgga     360
tgaagccgat ccggccaagt ggaaggccaa cctgcgctgt gcccttaaca agagccggga     420
cttccgcctc atctacgacg ggccccggga catgccacct cagccctaca agatctacga     480
ggtctgctcc aatggccctg ctcccacaga ctcccagccc cctgaggatt actcttttgg     540
tgcaggagag gaggaggaag aagaggaaga gctgcagagg atgttgccaa gcctgagcct     600
cacagtgacc gacctggaga tcaagttttca gtaccggggg cggccacccc gggccctcac     660
catcagcaac cccatggct  gccggctctt ctacagccag ctggaggcca cccaggagca     720
ggtggaactc ttcggcccca taagcctgga gcaagtgcgc ttccccagcc ctgaggacat     780
ccccagtgac aagcagcgct tctacacgaa ccagctgctg gatgtcctgg accgcgggct     840
catcctccag ctacagggcc aggaccttta tgccatccgc ctgtgtcagt gcaaggtgtt     900
ctggagcggg ccttgtgcct cagcccatga ctcatgcccc aacccccatcc agcgggaggt     960 caagaccaag ctttttcagcc tggagcattt tctcaatgag ctcatcctgt tccaaaaggg    1020
ccagaccaac accccaccac ccttcgagat cttcttctgc tttggggaag aatggcctga    1080
ccgcaaaccc cgagagaaga agctcattac tgtacaggtg gtgcctgtag cagctcgact    1140
gctgctggag atgttctcag gggagctatc ttggtcagct gatagtatcc ggctacagat    1200
ctcaaaccca gacctcaaag accgcatggt ggagcaattc aaggagctcc atcacatctg    1260
gcagtcccag cagcggttgc agcctgtggc ccaggcccct cctggagcag gccttggtgt    1320
tggccagggg ccctggccta tgcacccagc tggcatgcaa taacaaggct gcagacggtg    1380
actggccctg gcttcctggg tggcggtgcg gactgatgtg gagatgtgac agccccgatg    1440
```

| | |
|---|---|
| agcacctggc tggctgcagg gtcctacctc tgggtttcct ggaagtggat ttgggccaag | 1500 |
| aaggagaggg agaaaggccc gagccctgc cttcccgggc cttctctcc tgggctgtct | 1560 |
| ctggtctggt cagcctggct ctcgggaaat tcagccatga gcagggaaag aactctccca | 1620 |
| accctggggc ctagctgtat aggaggaatt gcctaagggt ggcccactct tgtgattgcc | 1680 |
| ccatttcctc tggcaacaaa agccagagtg ttgtgggcca agtcccccca cagggcctct | 1740 |
| gcagggcatg gccctgattt ccctggtttg agactcactt cctcatctcc ctgtcctctg | 1800 |
| agataatatg agtgagcact taggtatcat atcagatgct caaggctggc agctaccccc | 1860 |
| ttcttgagag tccaagaacc tggagcagaa ataattttta tgtattttg gattaatgaa | 1920 |
| tgttaaaaac agactcagct gtttctttcc ttttactact accagttgct cccatgctgc | 1980 |
| tccaccaggc cctgtttcgg atgccaactg gcccactccc caagcacttg ccccagctt | 2040 |
| gcgaccattg gcactgggag ggcctggctt ctgggctgat gggtcagttg ggccttcata | 2100 |
| aacactcacc tggctggctt tgccttccag gaggaagctg gctgaagcaa gggtgtggaa | 2160 |
| ttttaaatgt gtgcacagtc tggaaaactg tcagaatcag ttttcccata aaagggtggg | 2220 |
| ctagcattgc agctgcattt gggaccattc aaatctgtca ctctcttgtg tatattcctg | 2280 |
| tgctattaaa tatatcaggg cagtgcatgt aaatcatcct gatatattta atatatttat | 2340 |
| tatattgtcc cccgaggtgg ggacagtgag tgagttctct tagtcccccc agagctggtt | 2400 |
| gttaaagagc ctggcaccta cccgctctca cttcatctgt gtcatctctg cacactccag | 2460 |
| cccactttct gccttcagcc attgagtgga agctgcccca ggcccttacc aggtgcagat | 2520 |
| gcccaatctt gatgcccagc catcagaact gtgagccaaa taaaccttt tctgtataaa | 2580 |
| ttacccaaaa aaaaaaaaaa aaaa | 2604 |

<210> SEQ ID NO 8
<211> LENGTH: 2778
<212> TYPE: DNA
<213> ORGANISM: Homo sapiens

<400> SEQUENCE: 8

| | |
|---|---|
| gtccagctgc gcctggaaag cgagctcgga cccctctgcc atgaaccagt ccatcccagt | 60 |
| ggctcccacc ccaccccgcc gcgtgcggct gaagccctgg ctggtggccc aggtgaacag | 120 |
| ctgccagtac ccagggcttc aatgggtcaa cggggaaaag aaattattct gcatcccctg | 180 |
| gaggcatgcc acaaggcatg gtcccagcca ggacggagat aacaccatct tcaaggcctg | 240 |
| ggccaaggag acagggaaat acaccgaagg cgtggatgaa gccgatccgg ccaagtggaa | 300 |
| ggccaacctg cgctgtgccc ttaacaagag ccgggacttc cgcctcatct acgacgggcc | 360 |
| ccgggacatg ccacctcagc cctacaagat ctacgaggtc tgctccaatg ccctgctcc | 420 |
| cacagactcc cagcccctg aggattactc ttttggtgca ggagaggagg aggaagaaga | 480 |
| ggaagagctg cagaggatgt tgccaagcct gagcctcaca gaggatgtca gtgggccgcc | 540 |
| cactctgcag ccgccactc tgcggccgcc tactctgcag ccgccactc tgcagccgcc | 600 |
| cgtggtgctg ggtccccctg ctccagaccc cagccccctg gctcctcccc ctggcaaccc | 660 |
| tgctggcttc agggagcttc tctctgaggt cctggagcct gggcccctgc tgccagcct | 720 |
| gccccctgca ggcgaacagc tcctgccaga cctgctgatc agcccccaca tgctgcctct | 780 |
| gaccgacctg gagatcaagt ttcagtaccg ggggcggcca cccgggccc tcaccatcag | 840 |
| caaccccat ggctgccggc tcttctacag ccagctggag gccacccagg agcaggtgga | 900 |
| actcttcggc cccataagcc tggagcaagt gcgcttcccc agccctgagg acatccccag | 960 |

| | |
|---|---|
| tgacaagcag cgcttctaca cgaaccagct gctggatgtc ctggaccgcg ggctcatcct | 1020 |
| ccagctacag ggccaggacc tttatgccat ccgcctgtgt cagtgcaagg tgttctggag | 1080 |
| cgggccttgt gcctcagccc atgactcatg ccccaacccc atccagcggg aggtcaagac | 1140 |
| caagcttttc agcctggagc attttctcaa tgagctcatc ctgttccaaa agggccagac | 1200 |
| caacacccca ccaccttcg agatcttctt ctgctttggg aagaatggc ctgaccgcaa | 1260 |
| accccgagag aagaagctca ttactgtaca ggtggtgcct gtagcagctc gactgctgct | 1320 |
| ggagatgttc tcaggggagc tatcttggtc agctgatagt atccggctac agatctcaaa | 1380 |
| cccagacctc aaagaccgca tggtggagca attcaaggag ctccatcaca tctggcagtc | 1440 |
| ccagcagcgg ttgcagcctg tggcccaggc ccctcctgga gcaggccttg tgttggcca | 1500 |
| ggggccctgg cctatgcacc cagctggcat gcaataacaa ggctgcagac ggtgactggc | 1560 |
| cctggcttcc tgggtggcgg tgcggactga tgtggagatg tgacagcccc gatgagcacc | 1620 |
| tggctggctg cagggtccta cctctggtt tcctggaagt ggatttgggc caagaaggag | 1680 |
| agggagaaag gcccgagccc ctgccttccc gggcctttct ctcctgggct gtctctggtc | 1740 |
| tggtcagcct ggctctcggg aaattcagcc atgagcaggg aaagaactct cccaaccctg | 1800 |
| gggcctagct gtataggagg aattgcctaa gggtggccca ctcttgtgat tgccccattt | 1860 |
| cctctggcaa caaaagccag agtgttgtgg gccaagtccc cccacagggc ctctgcaggg | 1920 |
| catggccctg atttccctgg tttgagactc acttcctcat ctccctgtcc tctgagataa | 1980 |
| tatgagtgag cacttaggta tcatatcaga tgctcaaggc tggcagctac ccccttcttg | 2040 |
| agagtccaag aacctggagc agaaataatt tttatgtatt tttggattaa tgaatgttaa | 2100 |
| aaacagactc agctgtttct ttcctttac tactaccagt tgctcccatg ctgctccacc | 2160 |
| aggccctgtt tcggatgcca actggcccac tccccaagca cttcccca gcttgcgacc | 2220 |
| attggcactg ggagggcctg gcttctgggc tgatgggtca gttgggcctt cataaacact | 2280 |
| cacctggctg gctttgcctt ccaggaggaa gctggctgaa gcaagggtgt ggaattttaa | 2340 |
| atgtgtgcac agtctggaaa actgtcagaa tcagttttcc cataaaaggg tgggctagca | 2400 |
| ttgcagctgc atttgggacc attcaaatct gtcactctct tgtgtatatt cctgtgctat | 2460 |
| taaatatatc agggcagtgc atgtaaatca tcctgatata tttaatatat ttattatatt | 2520 |
| gtccccgag gtgggacag tgagtgagtt ctcttagtcc ccccagagct ggttgttaaa | 2580 |
| gagcctggca cctacccgct ctcacttcat ctgtgtcatc tctgcacact ccagcccact | 2640 |
| ttctgccttc agccattgag tggaagctgc cccaggccct taccaggtgc agatgcccaa | 2700 |
| tcttgatgcc cagccatcag aactgtgagc caaataaacc tttttctgta taaattaccc | 2760 |
| aaaaaaaaaa aaaaaaaa | 2778 |

<210> SEQ ID NO 9
<211> LENGTH: 18000
<212> TYPE: DNA
<213> ORGANISM: Homo sapiens

<400> SEQUENCE: 9

| | |
|---|---|
| ccctcctccc ccctgctccc caccccagcc acccccactct acactcgctc acacagcgta | 60 |
| gcttctactc gagtcagggg agggtgcctc ctaccacacc ctcagtctgt gatattccag | 120 |
| ccaggggaaa tggggaagg ggccatctca ctgtggggag tgggggccc ggacagacct | 180 |
| ccctgtcccc accgcctcct ggcccatcaa ggggaaatgg gagtgctcac acaagggccg | 240 |

```
ggtgtggctt cacttcccct ctacttgccc ttccacccccc aggatggcac tgggaggcca    300
agggatccca gatcctggaa acactggagt gctgctctct gtccttcctt tctcctgggc    360
catgtctctg gccccagatg attcttggct caggttcttt cagttgaggg aagtcaggat    420
ctgagccaag ctgagcccct gcatagcctc tatcccggga gccccatatc aatgctgccg    480
gcttggtaac atcatccccc ttttagagac gaggaaatga gatttgaggt cctacttaag    540
gccacttggc tggaatacag caaagccagg tgcaagcccc ttctctgcac gcagcccgtg    600
ctgcttcttg aggttcagag gctctaagga aggggcctca cctgagcaag atggacagtg    660 ggaaggggc agagggcaga attctagggt ctcacggtcc ctcagaatgg gtgaggagta    720
tttgataaca aagaaggct cttcttagct attgctccag atacgaccag catagaatat    780
ttttctatta agcataactg acctccagtg aaaaaggttc cattttgtg gggagccact    840 tttgaaatag caatttcatt ttattattat tattttgaga taagatctca cttctacgcc    900
caggctggag tgcggtggtg tgcctcctgg gttcaagcaa ttctcccacc tcagcctccc    960
aagtaggtgg aactataggt gtgtgtcacc acgccaggct aattttttgta ttttttgtag   1020 agacaaggtt ttgccatatt gcccaggctg gtctcgaact cttggactca agtgatctgc   1080
ctgccttagc ctctcaaagt gttgggatta caaatgtgag ccaccgtgcc tggcctagca   1140
atttcatttt taaagaaaga aatataaaac gatctaccca ttcacatttt ccccatccat   1200
actttaaatt ttaaaatat gaataatga aatactcagc agatacaaat aataaaatac   1260
ttatatataa tgatatttcg acttcatatt agggcttcaa aggtcaggaa agagggagag   1320
atacagaaga gaaaaaaaaa aaacgttaac acatgagtgt cttttttttaa cttgttaaag   1380 gtaaagttca acccaggaga agggaggga gggaaggtca aagttctgat tcatcaacaa   1440
atactacttt atttgttaaa aatacaaggc tctgcttggc gcagtggctc ccgcctgtaa   1500
tcccagcact ttgggaggcc aaggcgggtg gatcgcctga ggtcaggagc tcgagaccag   1560
cctggccaac atggtgaaac cccgtctcta cttgggaggc tgaggcagga gaatcgcttg   1620
aactggggag gcagaggttg cagtgagctg agatcgcact gctgcactcc agcccgggtg   1680
acagagcaag actccatatc aaaaaataaa ataaaataaa atgaacaatg aaaagacagg   1740
agggaggttc ctgagtaagc tgattcgagt ggaaatcaga catcaaaatt gaaacccgct   1800
gaattttcca aaaagccaga tgctcataga actgaagctt gagacactta catcagtaca   1860
cctgctgcct gttgaccaat tcctcttcct tgtccctcct gttttccttc cctgctatat   1920
aagcccctaa ctttagtcaa ggggagggat ggattggagg tttgtctccc ctctcaacag   1980
ctcactggct gatgtcaccg gaataaagtc ttccctggca atactcgctg tctcagtgat   2040
aggctttctg tgcggtgagc agccagacct ggaccaaacc cctggcaatc cataacaaaa   2100
tcataagcaa aatcaaccag gaagctattt gcaccctgga accccacctg ggaggggaag   2160
tcaaggcaga cttccagag aaggcgatgc tgaaaatttc agaaacagaa attttgaaga   2220
gcaagagtta ccaagcgaag aacattccat gagaaggaac aggaggtgtg tgaaggtgga   2280
ggttctgggg tgaggttctt tatggaatcg aaaacggttc agaaccacag gtcgacggtc   2340
aaggtagtag tgagaggagg tgggacaggc gaccacgccg ctgcccctgg gatgactgga   2400
aggcgactta ggggagctgg ggcgagacag gtgcagggtt tgaggatgag aaaggcacag   2460
agtgactaga ggattcccgc ctgcaagcac atctggaagg ggtgtctgga tcctgggggc   2520
agcgactgtg ttctagggcg agagccaccc tcgccagggg tgtaggcagg cgagaggagg   2580
gcctggagct gtgggtcggc cacactgcgc cctcatttgt gtgcagcccc ggaggaccag   2640
```

```
agtggggaag cacccaccc tctcccaggg cccaactgag cactgcagcg ggaggtacgg    2700
ggttgtcaaa tgacagtttt gccattccag attgccaaaa gagccagtgg ccagtctagg    2760
gcaccgcgcc gtctggcatc tccctggagg ccctgggcct ggcccgaggc tcagcccgga    2820
tctgcagttg ccaggtcagt gcggggcccg gagtggattc gcggggcggg gcggggcact    2880
gcccgcgccc ggagctcagc agcagctgcc caggggcggg ggcggcaaga cgcggaagtg    2940
cccggcaggt tggcggaccg gcgggaggcg cagcctgggc agagctcagc ttggtcccgc    3000
cgcccggccg gtgctccctg gcgcagccac gcaggcgcac cgcagacagg tgggtcccgg    3060
ccgccgcgct ctcctctctg cgtccgcgcc cggcgcgccc cgagggtggc gggagcggtg    3120
ccggctactg cccccaagtc taggcctaga ctgggccccg cgcccccag gcacctgcgg    3180
gcggcgggat gaagactgga gtagggcggg gtccgcgtcc agctgcgcct ggaaagcgag    3240
ctcgggtggg tgcctacagc agggtgcgcc cggccggcct gggacttcca aagcgcctcc    3300
cacgccccga tcggtttggg gtgctggcgc ccggggagcc cagtgaccca ggcggcggag    3360
tgggcagcgc tgcgggggc gccggctctg ctgctctccc tcccctcgc catcgcccag     3420
aatgggggtt cccgggagcc ccgctggagg ctggcttgga ccacagagga gcgaggcccg    3480
atccttactt tcgatgcact cgcccttgct cttaccgggc caccctcacc ctttcggaaa    3540
agaggttgag gttaaagcgt tcatcccccg ggatcttcag gccaatggca ggaactgtgc    3600
aagagtttgg gggaagatgg tgtcaggtag aggctgcgtc cctgggctcg cggccgggaa    3660
tggcagactc tcgtcccccg agcagcggaa aaggatgggg cgcaatagtt cctgggctgg    3720
tttcctcagg tcctgtccca gaacttaaga aggcaacaat gaagaggcta aacgtggagg    3780
aaaagtgagg ctagcatggc cgggatgcgt ggggagatgg ttgtctccgg accccgggag    3840
gggcgggagc gggtacctgg gagcagaggc tggagtgggg gactttccca gcctcgcggc    3900
cacgctgaac acagcagggc gaggaccggg gtgctgctcc tccagcagca ggaggagagg    3960
tccagaggcc gactctggag gtgggggtgg ctccgcgggc tggcccaggg ggtgtgcccc    4020
agcggagcac gcgggagggg tggggcgga gggaggggg gagcaggggc ggaggactgg     4080
gctgggcctg ggctcctcga gggcccagaa tggggataag tgaccagaac cagagagggc    4140
tcggctgtat cgatgtagga aactgtagcc cctcaggagg ccctctggca agacctcccc    4200
ttcctgcccc caccccagt agttatgggg cctggggtgc tggggctgag gggttccaag    4260
agtcaaggga agcactggga aatcacccct tttatctaa aggccctact ttggggtttt    4320
tcccctgtac cctggtcttc ccctaccctg accctgggag gaagctgaaa gaagcttctt    4380
tctgggcacc ttttgcccca gagcctcagc ctgtctggac caggtgggca gcagggccca    4440
gggtgtgggc agctgacccg gaggggtggg atttgggggt cagggcctgt acagggaacc    4500
ccttgtcctc tccctgagct gggtgtgggt ttgcaaggag acatgtgacc cagaccaacc    4560
ctgggagcag cagggcgcct gctgtctggc cactcttact aggactgctg tggcacttcc    4620
tcccctagtg ggtccctggt gcccatgaat tgcagctcct gggtggtggt ggggcactg    4680
tctcctggga ctccagcatg gcctgggt gagctgtggg cttacccac ctcagcaggt     4740
cctctagggc tgcccactgg atgcttcgct gcctcacaca attgtaggga cttcctcagg    4800
ctgttggatt tccccacctt ccggggctca ggtccattga cttaggtcta gggctccata    4860
catttcaccc agagactccg gagcctggca ggcagacctg ttctgacacc gaacttccaa    4920
agtcatgggc cttgattggg gtggtctgaa ttagacctag ccctttctg gcagaagg      4980
```

```
agcttctagg aggatggatg ctgttcgggt tagagctcgt gtggacctag ctgcaggcaa    5040
aagccttgag gctgagtccc ttctgtggca tggtggacag actctcgctc atcacagccg    5100
ggcttgtcac gggagctcct cctccacacc cctccctaag ctgcctgtat ggacgcggcc    5160
ctctgacact gaggtcggag ttatcatttc aaaaccttgc tctgtattaa acagccgtgt    5220
tgggcagggc cagactgctg gactgacagt aggggggcagg cagccggacc ctctgagctc    5280
cccaacggca ccagcgcctg cacggcctca gcccaggggg tcattaggga agctctcccc    5340
gattctgtgc agacagagct tcctctgtcc accctttgctc ggccagaatt gtgtgccgct    5400
ggtgactggc acccctctat tctagggcca aggcctctca ggggtctaca gatacaacta    5460
tgggtgggtg cacacccatg ttataaacca cactaaatgc acaaaactg tctgcaagtt     5520 tggggtgcgg ggaacagctc tgggtgggag gttggaaatt tggtctgggg acccactcg    5580 gctccctccc tcagcccaca gtgagtctgg tttctgagtt gtcccggtct agccactttc    5640
gtttcccctg gggccgggtg gaggctgggg cagaaagcgg aactgagccc gcgtgttctg    5700
aggccagggc agggctggag cgttctgaac acctccccgt cccagcccct gggccaggca    5760
agggccggcc ttacctctcc tgggttggtg gcagcagagc tgggctctga gggaggcctg    5820
caatgtgaga cagtagcagc tcagaggcgg cactaggcag gtgcaacccc aaaaggtact    5880
gggcagggaa tttcagggga aactgaggct ccatgctgca aggccaaagc aggcccagac    5940
acagggagtt cagctcgaac gtttgctcct tacttgctga ccgacacatt cacttctgat    6000
gggctgtgct gtgtaatgac ccagtccttt ctgtcttcca cccaggggtc tcaagtgaag    6060
ggccaagggc atgggtaagg ggaggagagg gacagaaggg gactcaggac tgtggagagt    6120
ttccggttct gggctggaga gggagttggg caggtgaagg ggaggaggca gggtccctct    6180
ggcctgactc cagggaggca gtgaagctgt ggcctgggag gcggggctcg tgcccctggg    6240
taggtagcag ttagagctgt ggcttctgtt tcctgtagcc ttcctaacag gctccggcag    6300
gcgttagggc cttcctaagt gctacccgaa tgcgtgtcca gtgggaggag aaggggggagg    6360 accaagaacc tagatgaatg ccctagaga ggtaacatct gtttggtgcc tgctgtcatt     6420
ggaggtgggt tgagttggtt gatgggatt ctctaaagat attgagaaac tgctttcctc     6480
tgagggcagg tgtccttggg agctccagat gagattcttg ttgagggcat ctccggaggg    6540
aactctcagg ggatggaggg tgagaaaact tgggcaggga agaatcgaac tagggggtgta    6600 gactgagcag gaggctgtct tcgggctgat cccacagagc gctcgctgtc ccaggtagcc    6660
agcttgagac aagacagccg ggcttttggt gtcaggcagt cactggctgt gggctgcccc    6720
ccaagagcaa ggggtgggcc taacctgtgg tgtgagtagt ggaaggcggt tctctggcca    6780
acgggctgct tgctgctgtt agcagttgga gaatggatgc ctctgcccgg taaagggcac    6840
ctggggccgc gcccgcagca ttcactaact cgtaactctc cttcccttcc tccaaacaca    6900
aaattccatg acactagaca agaaagctga tgcttggaaa agagaattgg ccttaaatac    6960
ctagatggac tggagagacc atcctttgtg gtccatagct tgacctctga gtaccctgtc    7020
cccatccacc tgcagacctg ctgaggctcc cctctggctt tctcctgcag acccctctgc    7080
catgaaccag tccatcccag tggctcccac cccaccccgc cgcgtgcggc tgaagccctg    7140
gctggtggcc caggtgaaca gctgccagta cccagggctt caatgggtca acggggaaaa    7200
gaaattattc tgcatcccct ggaggcatgc cacaaggcat ggtccagcc aggacggaga     7260 taacaccatc ttcaaggtaa gcccgggga ggaggttggc tggacctcca gggcaccctg     7320
tccccagaag aggagcgcac ataacgcaca caggcagctc ctcgaggctg ccacccgcc     7380
```

```
cagctaccat gctgctgctg atgccgggcc cggactaagg ggatgcagac gtagacacag   7440
ggtacacctt tttccttttt tttttttttt aagacagagt ctcgctctgt agcccaggct   7500
ggagtgcagt ggcacgatct cagctcactg caacctctgc ctcctgggtt caagcaattc   7560
tcctgcctca gcctcctgag tagctgggat tacaggcatg agccaccacg cctggcctag   7620
ggcacatctt ttctaacctg caccctagag catcgtgggg actgagggtc cccagaaggc   7680
cttcccataa ctcgtcctac tcacccttttg ctcgtctcac tcctattact catgaggact   7740
tgttcagtgc acgcatatgc taaaggaagc aacgatcat catctttcta aaaattttat   7800
ttttaaatta gtatatattt atggggtaca cagtggtgat tgataagca cagtgatcag   7860 atcaggtact tagcatatcc ataatctcaa acatttgtca tttctttgtg ttgggaacaa   7920
actattttta atataagatt cagatacatc atcaatcttt caattgttta aattttctaa   7980 tttttttttag agacagggcc tcacactgtt gaccagattc caattttttt tttttttttt   8040
tttttttttt tgagacaggg tctcactctg tcacccaggc tggagtgcag tggcttgatc   8100
tcagctcact gcagcctcga cctcccaggc tcaggtgagt ctcccatctc aacctccttg   8160
agtagctggg attacaggtg cctgccacca caactggcta attttttgta cttttagtag   8220
agactttgcc atgttgccca ggctggtctt gaactcctgg actcaagcaa tccacccacc   8280
tcagcctccc agagtgctgg gattacaggt gtgagccacc atgcccggcc caatcttttt   8340
ttttaattga tgtactacaa ctgtacatat atactctttt ttttttttttt tgagatgagt   8400 tgttgctctg ttgcctagtg ttgcaccatt ggtgagcagt ggtgcagtca tagcacaacc   8460
tccaactcag ctcaagtgat cctccagtct cagcttcctg agtagccgtg actacaggtg   8520
catgccacca tgcccagcta atttttttttt tttttttga gatggagtct tgcttttttca   8580 ccctagctgg agtgcaatgg cacaatctca gctcactgca acctctgcca cctgggttca   8640
agcaattctc ctgcctcagc ctcccgagta gctaggatta caggcacctg ccaccatgcc   8700
cggctaattt ttttttttttt ttttttttttt tttttttttt ttgtattttt ggtaaagaca   8760
gggtttcacc ctgttggcca ggctggtctt gaactcctga cctcatgatc cacctgcctt   8820
ggcctcccaa agtgctggga ttacaggcgt gagccaccgt gcccagccta atttttttgat   8880 tttgatattt gtaaagatga ggtctcactt tgttgcccag gctggtctca agctcatggg   8940
ctcaagtgat cctcccacct cagcctcctg agtagctggt atcacaggcg caagccactg   9000
tgctctctcc aataatctta atgctaggat gtacctcgca taatagtttt tgcttacatt   9060
ttagtttttt tgcacatgtg tgtatatgga atgcaaaatt ggaatcaagt gaatatcttg   9120
atttatagcc tggattttttt tcacccaata tcaggatcag ctttccttttc caacatacgt   9180 ccacatcact tttcgtgact gtagaatttc cactggaatg gttagcaca atttggtcac   9240 tgagtcttgg ttttttagata cttgagattg cttttaaaac ctgaacttaa aaaccacatt   9300
gtcatgtagg ctgtcttaat gcttcccttt ttttcatcct caattatttt ggggggttgat   9360 ttcctagagt tgaaaattgc tgggtcaaag gcaatgctta tttttttaaaa ctttgggtac   9420 atattttctt agttttttggg cttgatccctt acctttccaa aattcttttg ctaatccatt   9480
tattttgtat aggtaataca gtcacaaaat tcaacattaa aaggcataga atggtttaga   9540
gcaaaaagtc tccctccttc cctggttcat caccacccac tcccctccct agcctttccc   9600
tagaggcagc cgtgttgtca ttttcttgtt tagccttcct gagagatttt tatgcacatg   9660
taagcaaata tggaactatc ctttcctcta cttttcataa gaaatgctag atatctgcat   9720
```

```
atttgtctag acttaatact tcttgacgat tgctacatgt cagcttataa acagtttcct    9780
gcttttcttt ttttgtgct gcccagtatt tttcattcaa tgggttggcc gtaatttcac    9840
cagcccctca ttgatggatg ttgcattggg tattttgggt catcttttac acacagcact   9900
gctgcgaata actttgtgtg tgcaatattt tgtgtgaatg cttctatgat atttaggatg    9960
aattcctaga aatcaaatag ctgggttaaa aggtagaaag aaatgttggt aaccctcacc  10020
tcacctaatt gccattcaaa ataataccaa cagctccagt gtctcgagcc tgtcctatgt  10080
gcaggtttag ctctgagtgc tttacggaca tcaactcccc tcatctttt tgagataggg    10140
tatcactctg tcgtccaggc tggagtgcag agcataatca tggctcactg cagccttgaa  10200
ctccccagct caagcaatcc tctcacctca gcctcctgag tagctgggac cacaggcacc  10260
caccactatg cccagctaat ttttttgtaaa gacaggagtc tcgttatgtt gcctaggctg  10320
gactccaact cctgggctca agcagtcctc ccaccttggc ctcccaaaat gttgggatta  10380
caggtgcgag ccactgtgcc cagccaacat caacccttg agtcttcgct gccactccat   10440
gaggtgggca actgtgagga gatcaagaca aagggaggca gtgacatggc ctggcacaca  10500
gctggcgggg ggcacttcca gattcaaacc cagcctggct ccagggtgct cacccttatc  10560
ccgcacgctg tcctccttag agatcacact gtttcaccct cccaggagca gggactatgg  10620
atgcatctca tagcccctag atttcatgta gcttgctggc agcctgaggg ctggggcagg  10680
actgtgcag actcccacgc tgcaaaccag gtctggggct cagcgaggct cagcctgtag   10740
ccgaagttct ccccacacag tagagtctcc tatgggacag gaggcagact ggggctgtgg  10800
cagggatgag gttctctgtg tcggctatt tcttcctgcc ccaggcctgg gccaaggaga   10860
cagggaaata caccgaaggc gtggatgaag ccgatccggc caagtggaag gccaacctgc  10920
gctgtgccct taacaagagc cgggacttcc gcctcatcta cgacgggccc cgggacatgc  10980
cacctcagcc ctacaagatc tacgaggtct gctccaatgg ccctgctccc acaggtatca  11040
ggcctagccc tctgtgggcc acctgggagg ctgtgcaatg tcctggcccc cagccatgag  11100
ctcttgggtg caggcaggcc aagggcccct ctagcaggca gtggtccagg aaacgatgcg  11160
ggggctcccg ctaggtcatg cacccaggg cttccaggag tggctgggat gggtcactgg   11220
catatcagga atggcttggc gtgcagtcag ggacctgggt gcttcttcct taccattgcc  11280
ctcgttttgg cttctggctc cagcctaggt ctcatggccc atggagtcgg ggaggtcttt  11340
cccaatcctg gtggctgtgc cctccacctc gccctgtgtt gggggcagct ttggggaagg  11400
cagaagctgc ataggagcta caggcagcct ctcaggggat cttgcttctc ctccgacatt  11460
gactccttta ctgccctgct tttctctccc tgctgtgcag actcccagcc ccctgaggat  11520
tactcttttg gtgcaggaga ggaggaggaa gaagaggaag aggtgagtgt gggttgagga  11580
ggcaggtgga gccctggacg agctctctgc tgtccccatc ggccttaggt ttccgcagcc  11640
ccactcccat ggagcccgt ggccctctca atagttctcc ttgtttcttc tcctgggatt   11700
ctgaacgata ggagcacagt ccccacctgc tccttcccag gcattgtca ttaccctgtg    11760
tgtgtgaccc acgcagcagt gggcttgg taggtctgac tccctgcaga aggcaaatga    11820
ggaaagtgag gcaaagggct tttctgacct gcctgggatg gacgagctgg gaccggaggc  11880
agggtcttgc ctgagctaaa ctgaggctag gggagttgcc tcatagttct cgcctgttat  11940
ttccccagcc ccaggtcagt ggaataacct gtcctccttt ctctcccatc tcttccctcc  12000
cttgctggtg tgtccccttc agctgcagag gatgttgcca agcctgagcc tcacaggtgg  12060
ggccgggagg tggtggttgg gggtctagta tacagagaag ctataggtac cataggtacc  12120
```

```
tggaaggggg ctgatgggag gctagggtgg cccagggctg ggaggaggtg tgcctgggag    12180
gcagttcgtg gaggtggcac tgacagccgt ccacacgcac tctctgtaga tgcagtgcag    12240
tctggccccc acatgacacc ctattcttta ctcaaagagg atgtcaagtg gccgcccact    12300
ctgcagccgc ccactctgcg gccgcctact ctgcagccgc ccactctgca gccgcccgtg    12360
gtgctgggtc cccctgctcc agacccccagc cccctggctc ctcccccctgg caaccctgct   12420
```

```
ggcttcaggg agcttctctc tgaggtcctg gagcctgggc cctgcctgc cagcctgccc      12480 cctgcaggcg aacagctcct gccagacctg ctgatcagcc cccacatgct gcctcgtaag    12540
gacccatggc tgggcacggg gaagcagtgc tggggggattg gggtaggatt ggcaaggagg   12600
gtggagggtg ctggactccc ttgggtggga aaagtgggag ggcggatggg gctgggcctg    12660
gccactgggc tgcagaatgg ggaggcgtgg ggctcaagga cgggatgggc ctgccttctg    12720
ccccacagtg accgacctgg agatcaagtt tcagtaccgg gggcggccac cccgggccct    12780
caccatcagc aaccccatg gctgccggct cttctacagc cagctggagg ccacccagga    12840
gcaggtggaa ctcttcggcc cataagcct ggagcaagtg cgcttcccca gccctgagga    12900
catccccagt gacaagcagc gcttctacac gaaccagctg ctggatgtcc tggaccgcgg    12960
gctcatcctc cagctacagg gccaggacct ttatgccatc cgcctgtgtc agtgcaaggt    13020
gttctggagc gggccttgtg cctcagccca tgactcatgc cccaacccca tccagcggga    13080
ggtcaagacc aagcttttca gcctggagca ttttctcaat ggtgagggcc aaagctgtg    13140 atcctcctgg ctgcctcttg cccagggcat ggttccagcc tctgactagg gaccttgatt   13200
ttgatgcaga gctcatcctg ttccaaaagg gccagaccaa caccccacca cccttcgaga    13260
tcttcttctg ctttggggaa gaatggcctg accgcaaacc ccgagagaag aagctcatta    13320
ctgtacaggt acatctcccc tatcccaaag tcggccttgg cttgaaaact ggggaatcct    13380
ggggctaggc ccttgcccca ggctggagc tcagggctcc ctgagcagtg tgaacttggc     13440
ggccagagac catcaaggct cagagccgga gaatgcggtc tattactcac ccctgatggc    13500
tgtcctcatg cacagctgga tctggcagcc ctgccacagg tctccctgtc tcatctcctc    13560
tttgcctccc aggtggtgcc tgtagcagct cgactgctgc tggagatgtt ctcagggag    13620 ctatcttggt cagctgatag tatccggcta cagatctcaa acccagacct caaagaccgc    13680
atggtggagc aattcaagga gctccatcac atctggcagt cccagcagcg gttgcagcct    13740
gtggcccagg cccctcctgg agcaggcctt ggtgttggcc aggggccctg gcctatgcac   13800
ccagctggca tgcaataaca aggctgcaga cggtgactgg ccctggcttc ctgggtggcg    13860
gtgcggactg atgtggagat gtgacagccc cgatgagcac ctggctggct gcagggtcct    13920
acctctgggt ttcctggaag tggatttggg ccaagaagga gagggagaaa ggcccgagcc    13980
cctgccttcc cgggcctttc tctcctgggc tgtctctggt ctggtcagcc tggctctcgg    14040
gaaattcagc catgagcagg gaaagaactc tcccaaccct ggggcctagc tgtataggag    14100
gaattgccta agggtggccc actcttgtga ttgccccatt tcctctggca acaaaagcca    14160
gagtgttgtg ggccaagtcc ccccacaggg cctctgcagg gcatggccct gatttccctg    14220
gtttgagact cacttcctca tctccctgtc ctctgagata atatgagtga gcacttaggt    14280
atcatatcag atgctcaagg ctggcagcta ccccttctt gagagtccaa gaacctggag    14340
cagaaataat ttttatgtat ttttggatta atgaatgtta aaaacagact cagctgtttc     14400 tttccttta ctactaccag ttgctcccat gctgctccac caggccctgt ttcggatgcc      14460
```

```
aactggccca ctccccaagc acttgccccc agcttgcgac cattggcact gggagggcct    14520
ggcttctggg ctgatgggtc agttgggcct tcataaacac tcacctggct ggctttgcct    14580
tccaggagga agctggctga agcaagggtg tggaatttta aatgtgtgca cagtctggaa    14640
aactgtcaga atcagttttc ccataaaagg gtgggctagc attgcagctg catttgggac    14700
cattcaaatc tgtcactctc ttgtgtatat tcctgtgcta ttaaatatat cagggcagtg    14760
catgtaaatc atcctgatat atttaatata tttattatat tgtcccccga ggtgggggaca   14820
gtgagtgagt tctcttagtc cccccagagc tggttgttaa agagcctggc acctacccgc    14880
tctcacttca tctgtgtcat ctctgcacac tccagcccac tttctgcctt cagccattga    14940
gtggaagctg ccccaggccc ttaccaggtg cagatgccca atcttgatgc ccagccatca    15000
gaactgtgag ccaaataaac cttttttctgt ataaattacc cagcctcggg tcttcgttta   15060
cagcaacgca aaatagatta aaccccccata aatgttcaag gataccttgc cccacagcct   15120
cgtccacaga atatattgtc actgtttgga tttttgccaa cctgacaggt gagatagtat    15180
ctcagtgcca cttctcatta tcagcaaggc tgagtagctt ttcacatggt taagtggcct    15240
gtacagattt ttttaaataa ttttagaatg gttttagatt tatggaaaag ttcctaatag    15300
agttcctatg gacccacact ttctccaatt gttaacatct tacattacta tggcacactt    15360
gtgacaataa tgaaaccatg tggacaatta ctatgaactc aacttcttta tttggatttc    15420
atgagttttt cggatatcct ttttctgttc caggatacta tccaagatat cacattacat    15480
tcacttgtca catctcctta gactcctctg gtctatgaca gtttcttaga ctttccttgt    15540
tgttggtctt gatggttttg aggaatactg gccattttttt aaagcatgtc ccccagtttg   15600
ggcttatctg atgtatttct catttgtttt tagagatagg gtctttgtgt tgcccaggct    15660
ggagtgccat ggtgcaacct tgaactcctg ggctcagatg atcctcccac gtagctggga    15720
ctacgggtgc acaccaccac acctggcttt tttttttttga gacctggtct caatatattg   15780
cccaggctgg tctcaaactc ctggcctcaa gtgatcttcc caccgtggcc tcccaaacag    15840
ctgagattac aggtgtgaac cactgtgccc cgcctgtttc tcatggtttt tgtatggaag    15900
accacagagg tgaagcatca ttcccactac atcatatcaa gggtgcatac tattaacctg    15960
atttatcact gtttctgact gaggtagtga taggttcctc tatcatagtt actcttcatc    16020
ctccctgatc tatatgtaca caggtaccgt ggttttagta ttattcacct gcatcctctt    16080
aaacttcacc aactagagta cagtgattac gtagtgctcc ttttgtctta gttttcaatc    16140
atttacaaag gtgtgcacct ttttcttcac aggcctgtgc agttctactc cctcttgcaa    16200
ttgtcaatgt tttgagatta ggagaaggga gatgtcacat atctggtttc cagcttcttc    16260
caaaaaactg gcaaatatga aaacactgtc atacattcct caaaggcaaa aatcagctgg    16320
aactctggat gggggaatgtt ctcccagttc aatacggtcc tctcctggcc tgcttccttt   16380
cactgctctc cgtgtcccta agggcatttg agtttgcaac ccttgatgaa tggtggagca    16440
gggagactga gtgtagatga attggggaag cttggaaggg ccaggtgccc ctcgcgacca    16500
cgagtgggct gacttcccca gtactgctag cagttgagta actgccaaaa atcttccctg    16560
aatttgtatt aattggtttc ctaaaactaa aatgaaaaca gcaatgaaaa cctggctgtc    16620
acttacagat ctctgtgttg tagtagccag ctgtggatga acagtatcca gaagtgacag    16680
atgtaacaaa ctccagaggt aaaggcaggc cagtgtgagg tacaattcac tgctcccaag    16740
ccaggctagg gctccccttg gtaatagctt ttggctgctc tggtgccctg tgctggagct    16800
taagttggaa cccacaggac cttgatgccc acatcctggg gatgaatgca tcccttttagc   16860
```

```
cccagcagtt tctctcccttt ctttcaagct ccttgtcccc accaagttca tccttataac   16920
caactaaata taccctttttt aagactctca gctctttgac ataaagaacc taccctggcc   16980
gggtgcagtg gctcacgcct gtagtcccag cactttggga ggccgaggtg ggcagatcac   17040
gaggtcagga gttcgagacc agcctggcca acatggtgaa accccatctc tactaaaaat   17100
acaaatatta gctggtcatg gtggtgggtg cctgtaatcc tagctgctca ggaggctgag   17160
gcaggagaat cgctggaccc catcagacag aggttgcagt gagctgaaat cccaccattg   17220
cactccagcc tgggcaacag agcaaggctc cctctcaaaa aaaaaaaac aaaaaaacaa    17280 aacaaaacaa aacaaaacaa aaggaaaaaa agaaaaaacg taccctttttc agtctctgta   17340 gagtagaaga tatcaatggc ttttcccatt tttgctgaaa gagcattctt ggaaggcaat   17400
gttctcattt gctggtaatc tatcccaaag aatcaggcac atcttgttgc aaaatcttga   17460
acctttaagg tctcttggtt ttggctttca tcttatgatt cacttaaatc agggccacac   17520
aaggtagaca tttaaataaa ctcatgaatg ttgatgccat tcaaaagcac agtttccttt   17580
atgtcttagg tgtgcattct cagttactgt tctttataac aattcccttc agatacataa   17640
ggattacaag ttactgtgtt ttagtacagt cttgctggaa atagccccaa tgctgatgat   17700
ctgtgttcca cataatcatg gccaacattt catggctaat cctatcacgg aacagacaat   17760
tctgtgggga gatgacttag gcaagttcag gtgcagttag ctgacctgcc cacatggacg   17820
ggagatactc atcctatttc tactagacaa tgccatgcag aaacacagca tctccattag   17880
gtgagctgat cctgaacagt tcctttttaa attaaaatct agatgggcat ccttgctctg   17940
ccgaaagttt cagagcagcc cttttcaaata atctgtaagg cttaagtaag cagtgaggtt   18000
```

<210> SEQ ID NO 10

<400> SEQUENCE: 10

000

<210> SEQ ID NO 11
<211> LENGTH: 22
<212> TYPE: DNA
<213> ORGANISM: Artificial sequence
<220> FEATURE:
<223> OTHER INFORMATION: Primer

<400> SEQUENCE: 11
gccaaggaga cagggaaata ca                                              22

<210> SEQ ID NO 12
<211> LENGTH: 19
<212> TYPE: DNA
<213> ORGANISM: Artificial sequence
<220> FEATURE:
<223> OTHER INFORMATION: Primer

<400> SEQUENCE: 12
gcaggttggc cttccactt                                                  19

<210> SEQ ID NO 13
<211> LENGTH: 23
<212> TYPE: DNA
<213> ORGANISM: Artificial sequence
<220> FEATURE:
<223> OTHER INFORMATION: Probe

<400> SEQUENCE: 13
cgaaggcgtg gatgaagccg atc    23

<210> SEQ ID NO 14
<211> LENGTH: 23
<212> TYPE: DNA
<213> ORGANISM: Artificial sequence
<220> FEATURE:
<223> OTHER INFORMATION: Primer

<400> SEQUENCE: 14
ttcgagatct tcttctgctt tgg    23

<210> SEQ ID NO 15
<211> LENGTH: 25
<212> TYPE: DNA
<213> ORGANISM: Artificial sequence
<220> FEATURE:
<223> OTHER INFORMATION: Primer

<400> SEQUENCE: 15
gcaccacctg tacagtaatg agctt    25

<210> SEQ ID NO 16
<211> LENGTH: 23
<212> TYPE: DNA
<213> ORGANISM: Artificial sequence
<220> FEATURE:
<223> OTHER INFORMATION: Probe

<400> SEQUENCE: 16
cctgaccgca aaccccgaga gaa    23

<210> SEQ ID NO 17
<211> LENGTH: 19
<212> TYPE: DNA
<213> ORGANISM: Artificial sequence
<220> FEATURE:
<223> OTHER INFORMATION: Primer

<400> SEQUENCE: 17
ccacctcagc cctacaaga    19

<210> SEQ ID NO 18
<211> LENGTH: 18
<212> TYPE: DNA
<213> ORGANISM: Artificial sequence
<220> FEATURE:
<223> OTHER INFORMATION: Primer

<400> SEQUENCE: 18
tcaggcttgg caacatcc    18

<210> SEQ ID NO 19
<211> LENGTH: 21
<212> TYPE: DNA
<213> ORGANISM: Artificial sequence
<220> FEATURE:
<223> OTHER INFORMATION: Probe

<400> SEQUENCE: 19
cctgctccca cagactccca g    21

<210> SEQ ID NO 20

<400> SEQUENCE: 20

000

<210> SEQ ID NO 21
<400> SEQUENCE: 21
000

<210> SEQ ID NO 22
<400> SEQUENCE: 22
000

<210> SEQ ID NO 23
<400> SEQUENCE: 23
000

<210> SEQ ID NO 24
<400> SEQUENCE: 24
000

<210> SEQ ID NO 25
<400> SEQUENCE: 25
000

<210> SEQ ID NO 26
<400> SEQUENCE: 26
000

<210> SEQ ID NO 27
<400> SEQUENCE: 27
000

<210> SEQ ID NO 28
<400> SEQUENCE: 28
000

<210> SEQ ID NO 29
<400> SEQUENCE: 29
000

<210> SEQ ID NO 30
<400> SEQUENCE: 30
000

<210> SEQ ID NO 31
<400> SEQUENCE: 31
000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
tcccatttca ggagacctgg    20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
gctgattaga gagaggtccc    20

<210> SEQ ID NO 37
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 37
ggttcatggc agaggg    16

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 38
tgggatggac tggttc    16

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 39
gcactgacac aggcgg                                                    16

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 40
ccgccaacct gccggg                                                    16

<210> SEQ ID NO 41
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 41
gtccgccaac ctgccg                                                    16

<210> SEQ ID NO 42
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 42
gccggtccgc caacct                                                    16

<210> SEQ ID NO 43
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 43
ccgccggtcc gccaac                                                    16

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 44
tcccgccggt ccgcca                                                    16

<210> SEQ ID NO 45
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 45
cctcccgccg gtccgc                                                    16

<210> SEQ ID NO 46
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 46
cgcctcccgc cggtcc                                               16

<210> SEQ ID NO 47
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 47
tgcgcctccc gccggt                                               16

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 48
ctctgcccag gctgcg                                               16

<210> SEQ ID NO 49
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 49
ccaagctgag ctctgc                                               16

<210> SEQ ID NO 50
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 50
gaccaagctg agctct                                               16

<210> SEQ ID NO 51
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 51
cgggaccaag ctgagc                                               16

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
ggcgggacca agctga                                               16

<210> SEQ ID NO 53
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 53
ggcggcggga ccaagc                                                      16

<210> SEQ ID NO 54
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 54
caccggccgg gcggcg                                                      16

<210> SEQ ID NO 55
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 55
agcaccggcc gggcgg                                                      16

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
ggagcaccgg ccgggc                                                      16

<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 57
cagggagcac cggccg                                                      16

<210> SEQ ID NO 58
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 58
gccagggagc accggc                                                      16

<210> SEQ ID NO 59
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 59
gcgccaggga gcaccg                                               16

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
ctgcgccagg gagcac                                               16

<210> SEQ ID NO 61
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 61
ggctgcgcca gggagc                                               16

<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 62
gtggctgcgc caggga                                               16

<210> SEQ ID NO 63
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 63
tctgcggtgc gcctgc                                               16

<210> SEQ ID NO 64
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 64
tgtctgcggt gcgcct                                               16

<210> SEQ ID NO 65
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 65
tggttcatgg cagagg                                               16

```
<210> SEQ ID NO 66
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 66
ctggttcatg gcagag                                                  16

<210> SEQ ID NO 67
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 67
gactggttca tggcag                                                  16

<210> SEQ ID NO 68
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 68
ggactggttc atggca                                                  16

<210> SEQ ID NO 69
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 69
atggactggt tcatgg                                                  16

<210> SEQ ID NO 70
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 70
gatggactgg ttcatg                                                  16

<210> SEQ ID NO 71
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 71
ggatggactg gttcat                                                  16

<210> SEQ ID NO 72
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 72
gggatggact ggttca                                                    16

<210> SEQ ID NO 73
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 73
cactgggatg gactgg                                                    16

<210> SEQ ID NO 74
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 74
gccactggga tggact                                                    16

<210> SEQ ID NO 75
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 75
gagccactgg gatgga                                                    16

<210> SEQ ID NO 76
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 76
cagccgcacg cggcgg                                                    16

<210> SEQ ID NO 77
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 77
ttcagccgca cgcggc                                                    16

<210> SEQ ID NO 78
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 78
gcttcagccg cacgcg                                                    16

<210> SEQ ID NO 79
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 79
gggcttcagc cgcacg                                                     16

<210> SEQ ID NO 80
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 80
agctgttcac ctgggc                                                     16

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
gcagctgttc acctgg                                                     16

<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 82
tggcagctgt tcacct                                                     16

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
actggcagct gttcac                                                     16

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
gtactggcag ctgttc                                                     16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
```

```
gggtactggc agctgt                                                      16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
ctgggtactg gcagct                                                      16

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
ccctgggtac tggcag                                                      16

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 88
agccctgggt actggc                                                      16

<210> SEQ ID NO 89
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
gaagccctgg gtactg                                                      16

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
ttgaagccct gggtac                                                      16

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 91
cattgaagcc ctgggt                                                      16

<210> SEQ ID NO 92
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 92
cccattgaag ccctgg                                                16

<210> SEQ ID NO 93
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 93
gacccattga agccct                                                16

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
ttgacccatt gaagcc                                                16

<210> SEQ ID NO 95
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 95
cgttgaccca ttgaag                                                16

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
cccgttgacc cattga                                                16

<210> SEQ ID NO 97
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 97
tccccgttga cccatt                                                16

<210> SEQ ID NO 98
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 98
tttccccgtt gaccca                                                16
```

<210> SEQ ID NO 99
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 99
cttttccccg ttgacc                                               16

<210> SEQ ID NO 100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 100
ttcttttccc cgttga                                               16

<210> SEQ ID NO 101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 101
atttcttttc cccgtt                                               16

<210> SEQ ID NO 102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 102
taatttcttt tccccg                                               16

<210> SEQ ID NO 103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 103
ttgtggcatg cctcca                                               16

<210> SEQ ID NO 104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 104
ccttgtggca tgcctc                                               16

<210> SEQ ID NO 105
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 105
tgccttgtgg catgcc                                                    16

<210> SEQ ID NO 106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 106
catgccttgt ggcatg                                                    16

<210> SEQ ID NO 107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 107
accatgcctt gtggca                                                    16

<210> SEQ ID NO 108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 108
ggaccatgcc ttgtgg                                                    16

<210> SEQ ID NO 109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 109
tgggaccatg ccttgt                                                    16

<210> SEQ ID NO 110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 110
ggctgggacc atgcct                                                    16

<210> SEQ ID NO 111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 111
cgtcctggct gggacc                                                    16

<210> SEQ ID NO 112
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 112
ctccgtcctg gctggg                                                  16

<210> SEQ ID NO 113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 113
gttatctccg tcctgg                                                  16

<210> SEQ ID NO 114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 114
tctccgtcct ggctgg                                                  16

<210> SEQ ID NO 115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 115
atctccgtcc tggctg                                                  16

<210> SEQ ID NO 116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 116
tatctccgtc ctggct                                                  16

<210> SEQ ID NO 117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 117
ttatctccgt cctggc                                                  16

<210> SEQ ID NO 118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 118
```
tgttatctcc gtcctg                                                      16

<210> SEQ ID NO 119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 119
gtgttatctc cgtcct                                                      16

<210> SEQ ID NO 120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 120
ggtgttatct ccgtcc                                                      16

<210> SEQ ID NO 121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 121
tggtgttatc tccgtc                                                      16

<210> SEQ ID NO 122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 122
atggtgttat ctccgt                                                      16

<210> SEQ ID NO 123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 123
agatggtgtt atctcc                                                      16

<210> SEQ ID NO 124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 124
gaagatggtg ttatct                                                      16

<210> SEQ ID NO 125
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 125
ttgaagatgg tgttat                                                    16

<210> SEQ ID NO 126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 126
ccttgaagat ggtgtt                                                    16

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 127
ggccttgaag atggtg                                                    16

<210> SEQ ID NO 128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 128
cttgttaagg gcacag                                                    16

<210> SEQ ID NO 129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 129
tcttgttaag ggcaca                                                    16

<210> SEQ ID NO 130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 130
ctcttgttaa gggcac                                                    16

<210> SEQ ID NO 131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 131
ggctcttgtt aagggc                                                    16
```

<210> SEQ ID NO 132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 132
ccggctcttg ttaagg                                                         16

<210> SEQ ID NO 133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 133
tcccggctct tgttaa                                                         16

<210> SEQ ID NO 134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 134
agtcccggct cttgtt                                                         16

<210> SEQ ID NO 135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 135
gaagtcccgg ctcttg                                                         16

<210> SEQ ID NO 136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 136
cggaagtccc ggctct                                                         16

<210> SEQ ID NO 137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 137
ggcggaagtc ccggct                                                         16

<210> SEQ ID NO 138
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 138
gaggcggaag tcccgg                                                         16

<210> SEQ ID NO 139
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 139
atgaggcgga agtccc                                                         16

<210> SEQ ID NO 140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 140
agatgaggcg gaagtc                                                         16

<210> SEQ ID NO 141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 141
gtagatgagg cggaag                                                         16

<210> SEQ ID NO 142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 142
aggtggcatg tcccgg                                                         16

<210> SEQ ID NO 143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 143
tgaggtggca tgtccc                                                         16

<210> SEQ ID NO 144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 144
gctgaggtgg catgtc                                                         16

<210> SEQ ID NO 145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 145
gggctgaggt ggcatg                                                       16

<210> SEQ ID NO 146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 146
tagggctgag gtggca                                                       16

<210> SEQ ID NO 147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 147
atcttgtagg gctgag                                                       16

<210> SEQ ID NO 148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 148
agatcttgta gggctg                                                       16

<210> SEQ ID NO 149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 149
gtagatcttg tagggc                                                       16

<210> SEQ ID NO 150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 150
cattggagca gacctc                                                       16

<210> SEQ ID NO 151
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 151
gccattggag cagacc                                                         16

<210> SEQ ID NO 152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 152
gggccattgg agcaga                                                         16

<210> SEQ ID NO 153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 153
cagggccatt ggagca                                                         16

<210> SEQ ID NO 154
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 154
agcagggcca ttggag                                                         16

<210> SEQ ID NO 155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 155
ggagcagggc cattgg                                                         16

<210> SEQ ID NO 156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 156
gagtctgtgg gagcag                                                         16

<210> SEQ ID NO 157
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 157
aagagtaatc ctcagg                                                         16

<210> SEQ ID NO 158
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 158
aaaagagtaa tcctca                                                    16

<210> SEQ ID NO 159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 159
ccaaaagagt aatcct                                                    16

<210> SEQ ID NO 160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 160
caccaaaaga gtaatc                                                    16

<210> SEQ ID NO 161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 161
ctcctataca gctagg                                                    16

<210> SEQ ID NO 162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 162
cttaggcaat tcctcc                                                    16

<210> SEQ ID NO 163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 163
ctaagtgctc actcat                                                    16

<210> SEQ ID NO 164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 164
```
agccttgagc atctga                                                          16

<210> SEQ ID NO 165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 165
gccagccttg agcatc                                                          16

<210> SEQ ID NO 166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 166
tatacagcta ggcccc                                                          16

<210> SEQ ID NO 167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 167
ctatacagct aggccc                                                          16

<210> SEQ ID NO 168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 168
cctatacagc taggcc                                                          16

<210> SEQ ID NO 169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 169
tcctatacag ctaggc                                                          16

<210> SEQ ID NO 170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 170
cctcctatac agctag                                                          16

<210> SEQ ID NO 171
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 171
tcctcctata cagcta                                                     16

<210> SEQ ID NO 172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 172
ttcctcctat acagct                                                     16

<210> SEQ ID NO 173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 173
attcctccta tacagc                                                     16

<210> SEQ ID NO 174
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 174
aattcctcct atacag                                                     16

<210> SEQ ID NO 175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 175
gcaattcctc ctatac                                                     16

<210> SEQ ID NO 176
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 176
ggcaattcct cctata                                                     16

<210> SEQ ID NO 177
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 177
ttaggcaatt cctcct                                                     16
```

<210> SEQ ID NO 178
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 178
ccttaggcaa ttcctc                                                    16

<210> SEQ ID NO 179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 179
cccttaggca attcct                                                    16

<210> SEQ ID NO 180
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 180
acccttaggc aattcc                                                    16

<210> SEQ ID NO 181
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 181
ccacccttag gcaatt                                                    16

<210> SEQ ID NO 182
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 182
ggccacccTt aggcaa                                                    16

<210> SEQ ID NO 183
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 183
gtgggccacc cttagg                                                    16

<210> SEQ ID NO 184
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 184
agagtgggcc accctt                                                       16

<210> SEQ ID NO 185
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 185
caagagtggg ccaccc                                                       16

<210> SEQ ID NO 186
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 186
cacaagagtg ggccac                                                       16

<210> SEQ ID NO 187
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 187
atcacaagag tgggcc                                                       16

<210> SEQ ID NO 188
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 188
caatcacaag agtggg                                                       16

<210> SEQ ID NO 189
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 189
ggcaatcaca agagtg                                                       16

<210> SEQ ID NO 190
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 190
gttgccagag gaaatg                                                       16

<210> SEQ ID NO 191

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 191
ttgttgccag aggaaa                                                  16

<210> SEQ ID NO 192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 192
ttttgttgcc agagga                                                  16

<210> SEQ ID NO 193
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 193
ggcttttgtt gccaga                                                  16

<210> SEQ ID NO 194
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 194
acactctggc ttttgt                                                  16

<210> SEQ ID NO 195
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 195
caacactctg gctttt                                                  16

<210> SEQ ID NO 196
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 196
cacaacactc tggctt                                                  16

<210> SEQ ID NO 197
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 197
```
acttggccca caacac 16

<210> SEQ ID NO 198
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 198
ggacttggcc cacaac 16

<210> SEQ ID NO 199
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 199
catgccctgc agaggc 16

<210> SEQ ID NO 200
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 200
aatcagggcc atgccc 16

<210> SEQ ID NO 201
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 201
gaaatcaggg ccatgc 16

<210> SEQ ID NO 202
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 202
caaaccaggg aaatca 16

<210> SEQ ID NO 203
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 203
ctcaaaccag ggaaat 16

<210> SEQ ID NO 204
<211> LENGTH: 16
<212> TYPE: DNA

<210> SEQ ID NO 204
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 204
gtctcaaacc agggaa                                                      16

<210> SEQ ID NO 205
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 205
gagtctcaaa ccaggg                                                      16

<210> SEQ ID NO 206
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 206
gtgagtctca aaccag                                                      16

<210> SEQ ID NO 207
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 207
gaagtgagtc tcaaac                                                      16

<210> SEQ ID NO 208
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 208
aggaagtgag tctcaa                                                      16

<210> SEQ ID NO 209
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 209
tgaggaagtg agtctc                                                      16

<210> SEQ ID NO 210
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 210
tatctcagag gacagg                                                      16

<210> SEQ ID NO 211
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 211
attatctcag aggaca                                                    16

<210> SEQ ID NO 212
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 212
atattatctc agagga                                                    16

<210> SEQ ID NO 213
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 213
ctcatattat ctcaga                                                    16

<210> SEQ ID NO 214
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 214
ctcactcata ttatct                                                    16

<210> SEQ ID NO 215
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 215
tgctcactca tattat                                                    16

<210> SEQ ID NO 216
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 216
gtgctcactc atatta                                                    16

<210> SEQ ID NO 217
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 217
agtgctcact catatt                                              16

<210> SEQ ID NO 218
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 218
aagtgctcac tcatat                                              16

<210> SEQ ID NO 219
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 219
taagtgctca ctcata                                              16

<210> SEQ ID NO 220
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 220
cctaagtgct cactca                                              16

<210> SEQ ID NO 221
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 221
acctaagtgc tcactc                                              16

<210> SEQ ID NO 222
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 222
tacctaagtg ctcact                                              16

<210> SEQ ID NO 223
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 223
atacctaagt gctcac                                              16

```
<210> SEQ ID NO 224
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 224
gatacctaag tgctca                                                   16

<210> SEQ ID NO 225
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 225
atgataccta agtgct                                                   16

<210> SEQ ID NO 226
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 226
atatgatacc taagtg                                                   16

<210> SEQ ID NO 227
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 227
tgatatgata cctaag                                                   16

<210> SEQ ID NO 228
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 228
tctgatatga taccta                                                   16

<210> SEQ ID NO 229
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 229
catctgatat gatacc                                                   16

<210> SEQ ID NO 230
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 230
agcatctgat atgata                                              16

<210> SEQ ID NO 231
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 231
tgagcatctg atatga                                              16

<210> SEQ ID NO 232
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 232
ttgagcatct gatatg                                              16

<210> SEQ ID NO 233
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 233
cttgagcatc tgatat                                              16

<210> SEQ ID NO 234
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 234
ccttgagcat ctgata                                              16

<210> SEQ ID NO 235
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 235
gccttgagca tctgat                                              16

<210> SEQ ID NO 236
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 236
ccagccttga gcatct                                              16

<210> SEQ ID NO 237
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 237
tgccagcctt gagcat                                               16

<210> SEQ ID NO 238
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 238
tgaggctcag gcttgg                                               16

<210> SEQ ID NO 239
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 239
cggctgcaga gtgggc                                               16

<210> SEQ ID NO 240
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 240
ggcggctgca gagtgg                                               16

<210> SEQ ID NO 241
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 241
gggcggctgc agagtg                                               16

<210> SEQ ID NO 242
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 242
gtgggcggct gcagag                                               16

<210> SEQ ID NO 243
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 243
```

-continued agtgggcggc tgcaga                                              16

<210> SEQ ID NO 244
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 244
gagtgggcgg ctgcag                                              16

<210> SEQ ID NO 245
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 245
cagagtgggc ggctgc                                              16

<210> SEQ ID NO 246
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 246
gcagagtggg cggctg                                              16

<210> SEQ ID NO 247
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 247
tgcaccaaaa gagtaa                                              16

<210> SEQ ID NO 248
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 248
cctgcaccaa aagagt                                              16

<210> SEQ ID NO 249
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 249
ctcctgcacc aaaaga                                              16

<210> SEQ ID NO 250
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 250
ctctcctgca ccaaaa                                                    16

<210> SEQ ID NO 251
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 251
aacatcctct gcagct                                                    16

<210> SEQ ID NO 252
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 252
ggcaacatcc tctgca                                                    16

<210> SEQ ID NO 253
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 253
ttggcaacat cctctg                                                    16

<210> SEQ ID NO 254
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 254
gcttggcaac atcctc                                                    16

<210> SEQ ID NO 255
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 255
aggcttggca acatcc                                                    16

<210> SEQ ID NO 256
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 256
ctcaggcttg gcaaca                                                    16

<210> SEQ ID NO 257
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 257
aggctcaggc ttggca                                                  16

<210> SEQ ID NO 258
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 258
gtgaggctca ggcttg                                                  16

<210> SEQ ID NO 259
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 259
tgtgaggctc aggctt                                                  16

<210> SEQ ID NO 260
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 260
tctgtgaggc tcaggc                                                  16

<210> SEQ ID NO 261
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 261
cagactgcac tgcatc                                                  16

<210> SEQ ID NO 262
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 262
gccagactgc actgca                                                  16

<210> SEQ ID NO 263
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 263
gggccagact gcactg                                                        16

<210> SEQ ID NO 264
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 264
aatagggtgt catgtg                                                        16

<210> SEQ ID NO 265
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 265
agaatagggt gtcatg                                                        16

<210> SEQ ID NO 266
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 266
aaagaatagg gtgtca                                                        16

<210> SEQ ID NO 267
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 267
gtaaagaata gggtgt                                                        16

<210> SEQ ID NO 268
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 268
gagtaaagaa tagggt                                                        16

<210> SEQ ID NO 269
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 269
ttgagtaaag aatagg                                                        16

<210> SEQ ID NO 270
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 270
ctttgagtaa agaata                                                    16

<210> SEQ ID NO 271
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 271
ctctttgagt aaagaa                                                    16

<210> SEQ ID NO 272
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 272
tcctctttga gtaaag                                                    16

<210> SEQ ID NO 273
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 273
catcctcttt gagtaa                                                    16

<210> SEQ ID NO 274
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 274
gacatcctct ttgagt                                                    16

<210> SEQ ID NO 275
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 275
ttgacatcct ctttga                                                    16

<210> SEQ ID NO 276
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 276
```
acttgacatc ctcttt				16

<210> SEQ ID NO 277
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 277
ggccacttga catcct				16

<210> SEQ ID NO 278
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 278
gcggccactt gacatc				16

<210> SEQ ID NO 279
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 279
gggcggccac ttgaca				16

<210> SEQ ID NO 280
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 280
gtgggcggcc acttga				16

<210> SEQ ID NO 281
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 281
gagtgggcgg ccactt				16

<210> SEQ ID NO 282
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 282
cagagtgggc ggccac				16

<210> SEQ ID NO 283
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 283
tgcagagtgg gcggcc                                                     16

<210> SEQ ID NO 284
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 284
cgcagagtgg gcggct                                                     16

<210> SEQ ID NO 285
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 285
ccgcagagtg ggcggc                                                     16

<210> SEQ ID NO 286
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 286
gcggccgcag agtggg                                                     16

<210> SEQ ID NO 287
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 287
aggcggccgc agagtg                                                     16

<210> SEQ ID NO 288
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 288
gtaggcggcc gcagag                                                     16

<210> SEQ ID NO 289
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 289
gagtaggcgg ccgcag                                                     16
```

<210> SEQ ID NO 290
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 290
cagagtaggc ggccgc                                              16

<210> SEQ ID NO 291
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 291
tgcagagtag gcggcc                                              16

<210> SEQ ID NO 292
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 292
gctgcagagt aggcgg                                              16

<210> SEQ ID NO 293
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 293
cggctgcaga gtaggc                                              16

<210> SEQ ID NO 294
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 294
ggcggctgca gagtag                                              16

<210> SEQ ID NO 295
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 295
tgcagagtgg gcggct                                              16

<210> SEQ ID NO 296
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 296
cgggcggctg cagagt                                                       16

<210> SEQ ID NO 297
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 297
acgggcggct gcagag                                                       16

<210> SEQ ID NO 298
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 298
ccacgggcgg ctgcag                                                       16

<210> SEQ ID NO 299
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 299
accacgggcg gctgca                                                       16

<210> SEQ ID NO 300
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 300
caccacgggc ggctgc                                                       16

<210> SEQ ID NO 301
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 301
agcaccacgg gcggct                                                       16

<210> SEQ ID NO 302
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 302
ccagcaccac gggcgg                                                       16

```
<210> SEQ ID NO 303
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 303
acccagcacc acgggc                                                      16

<210> SEQ ID NO 304
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 304
ggacccagca ccacgg                                                      16

<210> SEQ ID NO 305
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 305
agccagcagg gttgcc                                                      16

<210> SEQ ID NO 306
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 306
gaagccagca gggttg                                                      16

<210> SEQ ID NO 307
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 307
ctgaagccag cagggt                                                      16

<210> SEQ ID NO 308
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 308
agagaagctc cctgaa                                                      16

<210> SEQ ID NO 309
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 309
tcagagagaa gctccc                                                        16

<210> SEQ ID NO 310
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 310
aagcgcactt gctcca                                                        16

<210> SEQ ID NO 311
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 311
gtctggcagg agctgt                                                        16

<210> SEQ ID NO 312
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 312
gcgcacttgc tccagg                                                        16

<210> SEQ ID NO 313
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 313
ggatgagccc gcggtc                                                        16

<210> SEQ ID NO 314
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 314
gacctcagag agaagc                                                        16

<210> SEQ ID NO 315
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 315
aggctccagg acctca                                                        16

<210> SEQ ID NO 316
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 316
gctgttcgcc tgcagg                                                  16

<210> SEQ ID NO 317
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 317
gagctgttcg cctgca                                                  16

<210> SEQ ID NO 318
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 318
aggagctgtt cgcctg                                                  16

<210> SEQ ID NO 319
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 319
gcaggagctg ttcgcc                                                  16

<210> SEQ ID NO 320
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 320
ggcaggagct gttcgc                                                  16

<210> SEQ ID NO 321
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 321
tggcaggagc tgttcg                                                  16

<210> SEQ ID NO 322
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 322
```

| | |
|---|---|
| ctggcaggag ctgttc | 16 |

<210> SEQ ID NO 323
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 323

| | |
|---|---|
| tctggcagga gctgtt | 16 |

<210> SEQ ID NO 324
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 324

| | |
|---|---|
| ggtctggcag gagctg | 16 |

<210> SEQ ID NO 325
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 325

| | |
|---|---|
| aggtctggca ggagct | 16 |

<210> SEQ ID NO 326
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 326

| | |
|---|---|
| caggtctggc aggagc | 16 |

<210> SEQ ID NO 327
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 327

| | |
|---|---|
| agcaggtctg gcagga | 16 |

<210> SEQ ID NO 328
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 328

| | |
|---|---|
| gatcagcagg tctggc | 16 |

<210> SEQ ID NO 329
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 329
ctgatcagca ggtctg                                                    16

<210> SEQ ID NO 330
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 330
ggctgatcag caggtc                                                    16

<210> SEQ ID NO 331
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 331
gtcagaggca gcatgt                                                    16

<210> SEQ ID NO 332
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 332
cggtcagagg cagcat                                                    16

<210> SEQ ID NO 333
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 333
gtcggtcaga ggcagc                                                    16

<210> SEQ ID NO 334
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 334
caggtcggtc agaggc                                                    16

<210> SEQ ID NO 335
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 335
tccaggtcgg tcagag                                                    16
```

<210> SEQ ID NO 336
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 336
tgatggtgag ggcccg                                           16

<210> SEQ ID NO 337
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 337
gctgatggtg agggcc                                           16

<210> SEQ ID NO 338
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 338
ttgctgatgg tgaggg                                           16

<210> SEQ ID NO 339
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 339
gagccggcag ccatgg                                           16

<210> SEQ ID NO 340
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 340
ctgtagaaga gccggc                                           16

<210> SEQ ID NO 341
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 341
ggctgtagaa gagccg                                           16

<210> SEQ ID NO 342
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 342
ctggctgtag aagagc                                                      16

<210> SEQ ID NO 343
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 343
agctggctgt agaaga                                                      16

<210> SEQ ID NO 344
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 344
ccagctggct gtagaa                                                      16

<210> SEQ ID NO 345
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 345
agagttccac ctgctc                                                      16

<210> SEQ ID NO 346
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 346
gaagagttcc acctgc                                                      16

<210> SEQ ID NO 347
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 347
gccgaagagt tccacc                                                      16

<210> SEQ ID NO 348
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 348
gggccgaaga gttcca                                                      16

<210> SEQ ID NO 349
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 349
cttgctccag gcttat                                               16

<210> SEQ ID NO 350
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 350
cacttgctcc aggctt                                               16

<210> SEQ ID NO 351
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 351
gcacttgctc caggct                                               16

<210> SEQ ID NO 352
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 352
cgcacttgct ccaggc                                               16

<210> SEQ ID NO 353
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 353
agcgcacttg ctccag                                               16

<210> SEQ ID NO 354
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 354
gaagcgcact tgctcc                                               16

<210> SEQ ID NO 355
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 355
```
ggaagcgcac ttgctc                                                   16

<210> SEQ ID NO 356
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 356
gggaagcgca cttgct                                                   16

<210> SEQ ID NO 357
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 357
gatgtcctca gggctg                                                   16

<210> SEQ ID NO 358
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 358
cgctgcttgt cactgg                                                   16

<210> SEQ ID NO 359
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 359
acatccagca gctggt                                                   16

<210> SEQ ID NO 360
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 360
ggacatccag cagctg                                                   16

<210> SEQ ID NO 361
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 361
cggtccagga catcca                                                   16

<210> SEQ ID NO 362
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 362
cgcggtccag gacatc                                                       16

<210> SEQ ID NO 363
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 363
cccgcggtcc aggaca                                                       16

<210> SEQ ID NO 364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 364
agcccgcggt ccagga                                                       16

<210> SEQ ID NO 365
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 365
gagcccgcgg tccagg                                                       16

<210> SEQ ID NO 366
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 366
atgagcccgc ggtcca                                                       16

<210> SEQ ID NO 367
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 367
gatgagcccg cggtcc                                                       16

<210> SEQ ID NO 368
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 368
aggatgagcc cgcggt                                                       16
```

<210> SEQ ID NO 369
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 369
gaggatgagc ccgcgg					16

<210> SEQ ID NO 370
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 370
ggaggatgag cccgcg					16

<210> SEQ ID NO 371
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 371
tggaggatga gcccgc					16

<210> SEQ ID NO 372
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 372
ctggaggatg agcccg					16

<210> SEQ ID NO 373
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 373
agctggagga tgagcc					16

<210> SEQ ID NO 374
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 374
gtagctggag gatgag					16

<210> SEQ ID NO 375
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 375
ctgtagctgg aggatg                                                    16

<210> SEQ ID NO 376
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 376
ccctgtagct ggagga                                                    16

<210> SEQ ID NO 377
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 377
ggccctgtag ctggag                                                    16

<210> SEQ ID NO 378
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 378
ctggccctgt agctgg                                                    16

<210> SEQ ID NO 379
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 379
gtcctggccc tgtagc                                                    16

<210> SEQ ID NO 380
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 380
aggtcctggc cctgta                                                    16

<210> SEQ ID NO 381
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 381
aaaggtcctg gccctg                                                    16

<210> SEQ ID NO 382
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 382
ataaaggtcc tggccc                                                       16

<210> SEQ ID NO 383
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 383
gcataaaggt cctggc                                                       16

<210> SEQ ID NO 384
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 384
tggcataaag gtcctg                                                       16

<210> SEQ ID NO 385
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 385
gatggcataa aggtcc                                                       16

<210> SEQ ID NO 386
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 386
cggatggcat aaaggt                                                       16

<210> SEQ ID NO 387
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 387
cactgacaca ggcgga                                                       16

<210> SEQ ID NO 388
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 388
tgcactgaca caggcg                                                    16

<210> SEQ ID NO 389
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 389
ctccagaaca ccttgc                                                    16

<210> SEQ ID NO 390
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 390
catgagtcat gggctg                                                    16

<210> SEQ ID NO 391
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 391
tcttgacctc ccgctg                                                    16

<210> SEQ ID NO 392
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 392
aagcttggtc ttgacc                                                    16

<210> SEQ ID NO 393
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 393
ggtctggccc ttttgg                                                    16

<210> SEQ ID NO 394
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 394
ggcggatggc ataaag                                                    16

<210> SEQ ID NO 395
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 395
gacacaggcg gatggc                                                      16

<210> SEQ ID NO 396
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 396
tgacacaggc ggatgg                                                      16

<210> SEQ ID NO 397
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 397
actgacacag gcggat                                                      16

<210> SEQ ID NO 398
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 398
ttgcactgac acaggc                                                      16

<210> SEQ ID NO 399
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 399
cttgcactga cacagg                                                      16

<210> SEQ ID NO 400
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 400
ccttgcactg acacag                                                      16

<210> SEQ ID NO 401
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 401
```
accttgcact gacaca         16

<210> SEQ ID NO 402
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 402
caccttgcac tgacac         16

<210> SEQ ID NO 403
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 403
gaacaccttg cactga         16

<210> SEQ ID NO 404
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 404
agaacacctt gcactg         16

<210> SEQ ID NO 405
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 405
cagaacacct tgcact         16

<210> SEQ ID NO 406
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 406
ccagaacacc ttgcac         16

<210> SEQ ID NO 407
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 407
tccagaacac cttgca         16

<210> SEQ ID NO 408
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 408
gctccagaac accttg                                                      16

<210> SEQ ID NO 409
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 409
cgctccagaa cacctt                                                      16

<210> SEQ ID NO 410
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 410
ccgctccaga acacct                                                      16

<210> SEQ ID NO 411
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 411
cccgctccag aacacc                                                      16

<210> SEQ ID NO 412
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 412
gcccgctcca gaacac                                                      16

<210> SEQ ID NO 413
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 413
aggcccgctc cagaac                                                      16

<210> SEQ ID NO 414
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 414
caaggcccgc tccaga                                                      16
```

```
<210> SEQ ID NO 415
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 415
cacaaggccc gctcca                                                       16

<210> SEQ ID NO 416
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 416
ggcacaaggc ccgctc                                                       16

<210> SEQ ID NO 417
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 417
gaggcacaag gcccgc                                                       16

<210> SEQ ID NO 418
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 418
ctgaggcaca aggccc                                                       16

<210> SEQ ID NO 419
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 419
atgggctgag gcacaa                                                       16

<210> SEQ ID NO 420
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 420
gtcatgggct gaggca                                                       16

<210> SEQ ID NO 421
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 421
agtcatgggc tgaggc                                                    16

<210> SEQ ID NO 422
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 422
gagtcatggg ctgagg                                                    16

<210> SEQ ID NO 423
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 423
tgagtcatgg gctgag                                                    16

<210> SEQ ID NO 424
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 424
atgagtcatg ggctga                                                    16

<210> SEQ ID NO 425
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 425
gcatgagtca tgggct                                                    16

<210> SEQ ID NO 426
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 426
ggcatgagtc atgggc                                                    16

<210> SEQ ID NO 427
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 427
acctcccgct ggatgg                                                    16

<210> SEQ ID NO 428
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 428
gacctcccgc tggatg                                               16

<210> SEQ ID NO 429
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 429
tgacctcccg ctggat                                               16

<210> SEQ ID NO 430
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 430
ttgacctccc gctgga                                               16

<210> SEQ ID NO 431
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 431
cttgacctcc cgctgg                                               16

<210> SEQ ID NO 432
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 432
gtcttgacct cccgct                                               16

<210> SEQ ID NO 433
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 433
ggtcttgacc tcccgc                                               16

<210> SEQ ID NO 434
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 434
```
cttggtcttg acctcc                                              16

<210> SEQ ID NO 435
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 435
gcttggtctt gacctc                                              16

<210> SEQ ID NO 436
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 436
agcttggtct tgacct                                              16

<210> SEQ ID NO 437
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 437
aaagcttggt cttgac                                              16

<210> SEQ ID NO 438
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 438
aaaagcttgg tcttga                                              16

<210> SEQ ID NO 439
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 439
gaaaagcttg gtcttg                                              16

<210> SEQ ID NO 440
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 440
tgaaaagctt ggtctt                                              16

<210> SEQ ID NO 441
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 441
ctgaaaagct tggtct                                                   16

<210> SEQ ID NO 442
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 442
ggctgaaaag cttggt                                                   16

<210> SEQ ID NO 443
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 443
caggctgaaa agcttg                                                   16

<210> SEQ ID NO 444
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 444
tccaggctga aaagct                                                   16

<210> SEQ ID NO 445
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 445
tgagctcatt gagaaa                                                   16

<210> SEQ ID NO 446
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 446
gatgagctca ttgaga                                                   16

<210> SEQ ID NO 447
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 447
aggatgagct cattga                                                   16
```

<210> SEQ ID NO 448
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 448
acaggatgag ctcatt                                                        16

<210> SEQ ID NO 449
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 449
gaacaggatg agctca                                                        16

<210> SEQ ID NO 450
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 450
tggaacagga tgagct                                                        16

<210> SEQ ID NO 451
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 451 ggccctttg gaacag                                                         16

<210> SEQ ID NO 452
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 452
tggccctttt ggaaca                                                        16

<210> SEQ ID NO 453
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 453
ctggcccttt tggaac                                                        16

<210> SEQ ID NO 454
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 454
tctggccctt ttggaa                                                          16

<210> SEQ ID NO 455
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 455
gtctggccct tttgga                                                          16

<210> SEQ ID NO 456
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 456
tggtctggcc cttttg                                                          16

<210> SEQ ID NO 457
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 457
ttggtctggc cctttt                                                          16

<210> SEQ ID NO 458
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 458
gttggtctgg ccctttt                                                         16

<210> SEQ ID NO 459
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 459
tgttggtctg gccctt                                                          16

<210> SEQ ID NO 460
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 460
gtgttggtct ggccct                                                          16

```
<210> SEQ ID NO 461
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 461
atctcgaagg gtggtg                                                    16

<210> SEQ ID NO 462
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 462
aagatctcga agggtg                                                    16

<210> SEQ ID NO 463
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 463
aagaagatct cgaagg                                                    16

<210> SEQ ID NO 464
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 464
gatagctccc ctgaga                                                    16

<210> SEQ ID NO 465
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 465
gaccaagata gctccc                                                    16

<210> SEQ ID NO 466
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 466
agccggatac tatcag                                                    16

<210> SEQ ID NO 467
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 467
atctgtagcc ggatac                                                    16

<210> SEQ ID NO 468
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 468
gcggtctttg aggtct                                                    16

<210> SEQ ID NO 469
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 469
agaagaagat ctcgaa                                                    16

<210> SEQ ID NO 470
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 470
gcagaagaag atctcg                                                    16

<210> SEQ ID NO 471
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 471
cggtcaggcc attctt                                                    16

<210> SEQ ID NO 472
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 472
tgcggtcagg ccattc                                                    16

<210> SEQ ID NO 473
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 473
tttgcggtca ggccat                                                    16

<210> SEQ ID NO 474
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 474
gggtttgcgg tcaggc                                               16

<210> SEQ ID NO 475
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 475
gagcttcttc tctcgg                                               16

<210> SEQ ID NO 476
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 476
atgagcttct tctctc                                               16

<210> SEQ ID NO 477
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 477
taatgagctt cttctc                                               16

<210> SEQ ID NO 478
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 478
agtaatgagc ttcttc                                               16

<210> SEQ ID NO 479
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 479
acagtaatga gcttct                                               16

<210> SEQ ID NO 480
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 480
```
gtacagtaat gagctt                                                              16

<210> SEQ ID NO 481
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 481
ctgtacagta atgagc                                                              16

<210> SEQ ID NO 482
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 482
acctgtacag taatga                                                              16

<210> SEQ ID NO 483
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 483
ccacctgtac agtaat                                                              16

<210> SEQ ID NO 484
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 484
caccacctgt acagta                                                              16

<210> SEQ ID NO 485
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 485
ggcaccacct gtacag                                                              16

<210> SEQ ID NO 486
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 486
caggcaccac ctgtac                                                              16

<210> SEQ ID NO 487
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 487
tacaggcacc acctgt                                                   16

<210> SEQ ID NO 488
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 488
gctacaggca ccacct                                                   16

<210> SEQ ID NO 489
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 489
ctgctacagg caccac                                                   16

<210> SEQ ID NO 490
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 490
agctgctaca ggcacc                                                   16

<210> SEQ ID NO 491
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 491
cgagctgcta caggca                                                   16

<210> SEQ ID NO 492
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 492
gtcgagctgc tacagg                                                   16

<210> SEQ ID NO 493
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 493
cagtcgagct gctaca                                                   16
```

```
<210> SEQ ID NO 494
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 494
agcagtcgag ctgcta                                                   16

<210> SEQ ID NO 495
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 495
gcagcagtcg agctgc                                                   16

<210> SEQ ID NO 496
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 496
cagcagcagt cgagct                                                   16

<210> SEQ ID NO 497
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 497
tccagcagca gtcgag                                                   16

<210> SEQ ID NO 498
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 498
tctccagcag cagtcg                                                   16

<210> SEQ ID NO 499
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 499
catctccagc agcagt                                                   16

<210> SEQ ID NO 500
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 500
gaacatctcc agcagc                                                         16

<210> SEQ ID NO 501
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 501
tgagaacatc tccagc                                                         16

<210> SEQ ID NO 502
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 502
cctgagaaca tctcca                                                         16

<210> SEQ ID NO 503
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 503
cccctgagaa catctc                                                         16

<210> SEQ ID NO 504
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 504
ctcccctgag aacatc                                                         16

<210> SEQ ID NO 505
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 505
gctcccctga gaacat                                                         16

<210> SEQ ID NO 506
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 506
agctcccctg agaaca                                                         16

<210> SEQ ID NO 507
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 507
tagctcccct gagaac                                              16

<210> SEQ ID NO 508
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 508
atagctcccc tgagaa                                              16

<210> SEQ ID NO 509
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 509
agatagctcc cctgag                                              16

<210> SEQ ID NO 510
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 510
aagatagctc ccctga                                              16

<210> SEQ ID NO 511
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 511
caagatagct cccctg                                              16

<210> SEQ ID NO 512
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 512
ccaagatagc tcccct                                              16

<210> SEQ ID NO 513
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 513
```
accaagatag ctcccc                                                  16

<210> SEQ ID NO 514
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 514
tgaccaagat agctcc                                                  16

<210> SEQ ID NO 515
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 515
ctgaccaaga tagctc                                                  16

<210> SEQ ID NO 516
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 516
gctgaccaag atagct                                                  16

<210> SEQ ID NO 517
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 517
agctgaccaa gatagc                                                  16

<210> SEQ ID NO 518
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 518
cagctgacca agatag                                                  16

<210> SEQ ID NO 519
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 519
atcagctgac caagat                                                  16

<210> SEQ ID NO 520
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 520
ctatcagctg accaag                                                     16

<210> SEQ ID NO 521
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 521
tactatcagc tgacca                                                     16

<210> SEQ ID NO 522
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 522
gatactatca gctgac                                                     16

<210> SEQ ID NO 523
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 523
ggatactatc agctga                                                     16

<210> SEQ ID NO 524
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 524
cggatactat cagctg                                                     16

<210> SEQ ID NO 525
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 525
ccggatacta tcagct                                                     16

<210> SEQ ID NO 526
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 526
gccggatact atcagc                                                     16
```

```
<210> SEQ ID NO 527
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 527
tagccggata ctatca                                                    16

<210> SEQ ID NO 528
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 528
gtagccggat actatc                                                    16

<210> SEQ ID NO 529
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 529
tgtagccgga tactat                                                    16

<210> SEQ ID NO 530
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 530
ctgtagccgg atacta                                                    16

<210> SEQ ID NO 531
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 531
tctgtagccg gatact                                                    16

<210> SEQ ID NO 532
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 532
gatctgtagc cggata                                                    16

<210> SEQ ID NO 533
<211> LENGTH: 16
<212> TYPE: DNA
<213> ORGANISM: Artificial sequence
<220> FEATURE:
```

<223> OTHER INFORMATION: Synthetic oligonucleotide

<400> SEQUENCE: 533
agatctgtag ccggat                                                        16

<210> SEQ ID NO 534
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 534
gtttgagatc tgtagc                                                        16

<210> SEQ ID NO 535
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 535
ctttgaggtc tgggtt                                                        16

<210> SEQ ID NO 536
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 536
tctttgaggt ctgggt                                                        16

<210> SEQ ID NO 537
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 537
gtctttgagg tctggg                                                        16

<210> SEQ ID NO 538
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 538
ggtctttgag gtctgg                                                        16

<210> SEQ ID NO 539
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 539
cggtctttga ggtctg                                                        16

```
<210> SEQ ID NO 540
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 540
tgcggtcttt gaggtc                                                     16

<210> SEQ ID NO 541
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 541
accgctgctg ggactg                                                     16

<210> SEQ ID NO 542
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 542
atgcggtctt tgaggt                                                     16

<210> SEQ ID NO 543
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 543
catgcggtct ttgagg                                                     16

<210> SEQ ID NO 544
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 544
ccatgcggtc tttgag                                                     16

<210> SEQ ID NO 545
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 545
accatgcggt ctttga                                                     16

<210> SEQ ID NO 546
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 546
ccaccatgcg gtcttt                                                      16

<210> SEQ ID NO 547
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 547
ctccaccatg cggtct                                                      16

<210> SEQ ID NO 548
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 548
tgctccacca tgcggt                                                      16

<210> SEQ ID NO 549
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 549
attgctccac catgcg                                                      16

<210> SEQ ID NO 550
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 550
gaattgctcc accatg                                                      16

<210> SEQ ID NO 551
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 551
ttgaattgct ccacca                                                      16

<210> SEQ ID NO 552
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 552
ccttgaattg ctccac                                                      16

<210> SEQ ID NO 553
<211> LENGTH: 16
```

<212> TYPE: DNA
<213> ORGANISM: Artificial sequence
<220> FEATURE:
<223> OTHER INFORMATION: Synthetic oligonucleotide

<400> SEQUENCE: 553
ctccttgaat tgctcc                                            16

<210> SEQ ID NO 554
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 554
agctccttga attgct                                            16

<210> SEQ ID NO 555
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 555
ggagctcctt gaattg                                            16

<210> SEQ ID NO 556
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 556
atggagctcc ttgaat                                            16

<210> SEQ ID NO 557
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 557
tgatggagct ccttga                                            16

<210> SEQ ID NO 558
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 558
tgtgatggag ctcctt                                            16

<210> SEQ ID NO 559
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 559
gatgtgatgg agctcc 16

<210> SEQ ID NO 560
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 560
cagatgtgat ggagct 16

<210> SEQ ID NO 561
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 561
ctgccagatg tgatgg 16

<210> SEQ ID NO 562
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 562
gactgccaga tgtgat 16

<210> SEQ ID NO 563
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 563
gggactgcca gatgtg 16

<210> SEQ ID NO 564
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 564
ctgggactgc cagatg 16

<210> SEQ ID NO 565
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 565
tgctgggact gccaga 16

<210> SEQ ID NO 566
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 566
ctgctgggac tgccag                                                    16

<210> SEQ ID NO 567
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 567
gctgctggga ctgcca                                                    16

<210> SEQ ID NO 568
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 568
ccgctgctgg gactgc                                                    16

<210> SEQ ID NO 569
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 569
aaccgctgct gggact                                                    16

<210> SEQ ID NO 570
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 570
gcaaccgctg ctggga                                                    16

<210> SEQ ID NO 571
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 571
ctgcaaccgc tgctgg                                                    16

<210> SEQ ID NO 572
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 572
ggctgcaacc gctgct                                                    16
```

```
<210> SEQ ID NO 573
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 573
cacaggctgc aaccgc                                                    16

<210> SEQ ID NO 574
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 574
gccacaggct gcaacc                                                    16

<210> SEQ ID NO 575
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 575
gggccacagg ctgcaa                                                    16

<210> SEQ ID NO 576
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 576
aggcctgctc caggag                                                    16

<210> SEQ ID NO 577
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 577
accaaggcct gctcca                                                    16

<210> SEQ ID NO 578
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 578
acaccaaggc ctgctc                                                    16

<210> SEQ ID NO 579
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 579
ccaacaccaa ggcctg                                                   16

<210> SEQ ID NO 580
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 580
ggccaacacc aaggcc                                                   16

<210> SEQ ID NO 581
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 581
ctggccaaca ccaagg                                                   16

<210> SEQ ID NO 582
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 582
cccctggcca acacca                                                   16

<210> SEQ ID NO 583
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 583
ggcccctggc caacac                                                   16

<210> SEQ ID NO 584
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 584
agggcccctg gccaac                                                   16

<210> SEQ ID NO 585
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 585
taggccaggg cccctg                                                   16

<210> SEQ ID NO 586

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 586
cataggccag ggcccc                                                      16

<210> SEQ ID NO 587
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 587
tgcataggcc agggcc                                                      16

<210> SEQ ID NO 588
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 588
ggtgcatagg ccaggg                                                      16

<210> SEQ ID NO 589
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 589
tgggtgcata ggccag                                                      16

<210> SEQ ID NO 590
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 590
agctgggtgc ataggc                                                      16

<210> SEQ ID NO 591
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 591
gccagctggg tgcata                                                      16

<210> SEQ ID NO 592
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 592
```
catgccagct gggtgc                                                        16

<210> SEQ ID NO 593
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 593
tgcatgccag ctgggt                                                        16

<210> SEQ ID NO 594
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 594
attgcatgcc agctgg                                                        16

<210> SEQ ID NO 595
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 595
ttattgcatg ccagct                                                        16

<210> SEQ ID NO 596
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 596
tgttattgca tgccag                                                        16

<210> SEQ ID NO 597
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 597
cttgttattg catgcc                                                        16

<210> SEQ ID NO 598
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 598
gccttgttat tgcatg                                                        16

<210> SEQ ID NO 599
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 599
cagccttgtt attgca					16

<210> SEQ ID NO 600
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 600
tgcagccttg ttattg					16

<210> SEQ ID NO 601
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 601
tctgcagcct tgttat					16

<210> SEQ ID NO 602
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 602
cgtctgcagc cttgtt					16

<210> SEQ ID NO 603
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 603
accgtctgca gccttg					16

<210> SEQ ID NO 604
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 604
tcaccgtctg cagcct					16

<210> SEQ ID NO 605
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 605
agtcaccgtc tgcagc					16

<210> SEQ ID NO 606
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 606
ccagtcaccg tctgca                                                   16

<210> SEQ ID NO 607
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 607
ggccagtcac cgtctg                                                   16

<210> SEQ ID NO 608
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 608
agggccagtc accgtc                                                   16

<210> SEQ ID NO 609
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 609
ccagggccag tcaccg                                                   16

<210> SEQ ID NO 610
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 610
gaagccaggg ccagtc                                                   16

<210> SEQ ID NO 611
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 611
ccgccaccca ggaagc                                                   16

<210> SEQ ID NO 612
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 612
caccgccacc caggaa                                                          16

<210> SEQ ID NO 613
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 613
cgcaccgcca cccagg                                                          16

<210> SEQ ID NO 614
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 614
tccgcaccgc caccca                                                          16

<210> SEQ ID NO 615
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 615
gtccgcaccg ccaccc                                                          16

<210> SEQ ID NO 616
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 616
agtccgcacc gccacc                                                          16

<210> SEQ ID NO 617
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 617
cagtccgcac cgccac                                                          16

<210> SEQ ID NO 618
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 618
atcagtccgc accgcc                                                          16

```
<210> SEQ ID NO 619
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 619
tcacatctcc acatca                                                         16

<210> SEQ ID NO 620
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 620
agaccagaga cagccc                                                         16

<210> SEQ ID NO 621
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 621
ggctgaccag accaga                                                         16

<210> SEQ ID NO 622
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 622
gagttctttc cctgct                                                         16

<210> SEQ ID NO 623
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 623
tcagtccgca ccgcca                                                         16

<210> SEQ ID NO 624
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 624
catcagtccg caccgc                                                         16

<210> SEQ ID NO 625
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 625
acatcagtcc gcaccg                                                        16

<210> SEQ ID NO 626
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 626
cacatcagtc cgcacc                                                        16

<210> SEQ ID NO 627
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 627
ccacatcagt ccgcac                                                        16

<210> SEQ ID NO 628
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 628
tccacatcag tccgca                                                        16

<210> SEQ ID NO 629
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 629
tctccacatc agtccg                                                        16

<210> SEQ ID NO 630
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 630
atctccacat cagtcc                                                        16

<210> SEQ ID NO 631
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 631
catctccaca tcagtc                                                        16

<210> SEQ ID NO 632
<211> LENGTH: 16
```

<212> TYPE: DNA
<213> ORGANISM: Artificial sequence
<220> FEATURE:
<223> OTHER INFORMATION: Synthetic oligonucleotide

<400> SEQUENCE: 632
acatctccac atcagt                                                         16

<210> SEQ ID NO 633
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 633
cacatctcca catcag                                                         16

<210> SEQ ID NO 634
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 634
gtcacatctc cacatc                                                         16

<210> SEQ ID NO 635
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 635
tgtcacatct ccacat                                                         16

<210> SEQ ID NO 636
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 636
ctgtcacatc tccaca                                                         16

<210> SEQ ID NO 637
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 637
gctgtcacat ctccac                                                         16

<210> SEQ ID NO 638
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 638

```
ggctgtcaca tctcca                                                    16

<210> SEQ ID NO 639
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 639
gccaggtgct catcgg                                                    16

<210> SEQ ID NO 640
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 640
cagccaggtg ctcatc                                                    16

<210> SEQ ID NO 641
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 641
gccagccagg tgctca                                                    16

<210> SEQ ID NO 642
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 642
gtaggaccct gcagcc                                                    16

<210> SEQ ID NO 643
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 643
aggtaggacc ctgcag                                                    16

<210> SEQ ID NO 644
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 644
agaggtagga ccctgc                                                    16

<210> SEQ ID NO 645
<211> LENGTH: 16
<212> TYPE: DNA
<213> ORGANISM: Artificial sequence
```

<220> FEATURE:
<223> OTHER INFORMATION: Synthetic oligonucleotide

<400> SEQUENCE: 645
cccagaggta ggaccc                                                        16

<210> SEQ ID NO 646
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 646
aacccagagg taggac                                                        16

<210> SEQ ID NO 647
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 647
gaaacccaga ggtagg                                                        16

<210> SEQ ID NO 648
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 648
tccacttcca ggaaac                                                        16

<210> SEQ ID NO 649
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 649
ggcccaaatc cacttc                                                        16

<210> SEQ ID NO 650
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 650
ttggcccaaa tccact                                                        16

<210> SEQ ID NO 651
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 651
tcttggccca aatcca                                                        16

<210> SEQ ID NO 652
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 652
cttcttggcc caaatc                                                   16

<210> SEQ ID NO 653
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 653
tccttcttgg cccaaa                                                   16

<210> SEQ ID NO 654
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 654
ctcgggcctt tctccc                                                   16

<210> SEQ ID NO 655
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 655
ggctcgggcc tttctc                                                   16

<210> SEQ ID NO 656
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 656
agagaaaggc ccggga                                                   16

<210> SEQ ID NO 657
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 657
ggagagaaag gcccgg                                                   16

<210> SEQ ID NO 658
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 658
agagacagcc caggag                                                    16

<210> SEQ ID NO 659
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 659
accagagaca gcccag                                                    16

<210> SEQ ID NO 660
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 660
gaccagagac agccca                                                    16

<210> SEQ ID NO 661
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 661
cagaccagag acagcc                                                    16

<210> SEQ ID NO 662
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 662
ccagaccaga gacagc                                                    16

<210> SEQ ID NO 663
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 663
accagaccag agacag                                                    16

<210> SEQ ID NO 664
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 664
gaccagacca gagaca                                                    16

<210> SEQ ID NO 665
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 665
tgaccagacc agagac                                               16

<210> SEQ ID NO 666
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 666
gctgaccaga ccagag                                               16

<210> SEQ ID NO 667
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 667
aggctgacca gaccag                                               16

<210> SEQ ID NO 668
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 668
agccaggctg accaga                                               16

<210> SEQ ID NO 669
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 669
gagagccagg ctgacc                                               16

<210> SEQ ID NO 670
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 670
tcccgagagc caggct                                               16

<210> SEQ ID NO 671
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 671
```
tttcccgaga gccagg                                            16

<210> SEQ ID NO 672
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 672
gaatttcccg agagcc                                            16

<210> SEQ ID NO 673
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 673
ctgaatttcc cgagag                                            16

<210> SEQ ID NO 674
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 674
ggctgaattt cccgag                                            16

<210> SEQ ID NO 675
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 675
atggctgaat ttcccg                                            16

<210> SEQ ID NO 676
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 676
tcatggctga atttcc                                            16

<210> SEQ ID NO 677
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 677
gctcatggct gaattt                                            16

<210> SEQ ID NO 678
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 678
ctgctcatgg ctgaat                                                       16

<210> SEQ ID NO 679
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 679
ccctgctcat ggctga                                                       16

<210> SEQ ID NO 680
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 680 cttttccctgc tcatgg                                                      16

<210> SEQ ID NO 681
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 681
tctttccctg ctcatg                                                       16

<210> SEQ ID NO 682
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 682
ttctttccct gctcat                                                       16

<210> SEQ ID NO 683
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 683
gttctttccc tgctca                                                       16

<210> SEQ ID NO 684
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 684
agttctttcc ctgctc                                                       16
```

<210> SEQ ID NO 685
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 685
agagttcttt ccctgc                                              16

<210> SEQ ID NO 686
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 686
gagagttctt tccctg                                              16

<210> SEQ ID NO 687
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 687
ggagagttct ttccct                                              16

<210> SEQ ID NO 688
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 688
gggagagttc tttccc                                              16

<210> SEQ ID NO 689
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 689
tgggagagtt ctttcc                                              16

<210> SEQ ID NO 690
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 690
gttgggagag ttcttt                                              16

<210> SEQ ID NO 691
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 691
ctaggcccca gggttg                                                       16

<210> SEQ ID NO 692
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 692
agctaggccc cagggt                                                       16

<210> SEQ ID NO 693
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 693
acagctaggc cccagg                                                       16

<210> SEQ ID NO 694
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 694
atacagctag gcccca                                                       16

<210> SEQ ID NO 695
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 695
gttcttggac tctcaa                                                       16

<210> SEQ ID NO 696
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 696
atttctgctc caggtt                                                       16

<210> SEQ ID NO 697
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 697
agctgccagc cttgag                                                       16

```
<210> SEQ ID NO 698
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 698
tagctgccag ccttga                                                    16

<210> SEQ ID NO 699
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 699
gtagctgcca gccttg                                                    16

<210> SEQ ID NO 700
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 700
gggtagctgc cagcct                                                    16

<210> SEQ ID NO 701
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 701
tggactctca agaagg                                                    16

<210> SEQ ID NO 702
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 702
ttggactctc aagaag                                                    16

<210> SEQ ID NO 703
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 703
cttggactct caagaa                                                    16

<210> SEQ ID NO 704
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 704
tcttggactc tcaaga                                                       16

<210> SEQ ID NO 705
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 705
ttcttggact ctcaag                                                       16

<210> SEQ ID NO 706
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 706
ggttcttgga ctctca                                                       16

<210> SEQ ID NO 707
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 707
aggttcttgg actctc                                                       16

<210> SEQ ID NO 708
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 708
caggttcttg gactct                                                       16

<210> SEQ ID NO 709
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 709
ccaggttctt ggactc                                                       16

<210> SEQ ID NO 710
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 710
tccaggttct tggact                                                       16

<210> SEQ ID NO 711
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 711
gctccaggtt cttgga                                                  16

<210> SEQ ID NO 712
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 712
tgctccaggt tcttgg                                                  16

<210> SEQ ID NO 713
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 713
ctgctccagg ttcttg                                                  16

<210> SEQ ID NO 714
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 714
tctgctccag gttctt                                                  16

<210> SEQ ID NO 715
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 715
ttctgctcca ggttct                                                  16

<210> SEQ ID NO 716
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 716
tttctgctcc aggttc                                                  16

<210> SEQ ID NO 717
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 717
```
tatttctgct ccaggt                                                     16

<210> SEQ ID NO 718
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 718
ttatttctgc tccagg                                                     16

<210> SEQ ID NO 719
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 719
attatttctg ctccag                                                     16

<210> SEQ ID NO 720
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 720
aattatttct gctcca                                                     16

<210> SEQ ID NO 721
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 721
aacattcatt aatcca                                                     16

<210> SEQ ID NO 722
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 722
acagctgagt ctgttt                                                     16

<210> SEQ ID NO 723
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 723
tggtagtagt aaaagg                                                     16

<210> SEQ ID NO 724
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 724
tgggagcaac tggtag                                               16

<210> SEQ ID NO 725
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 725
ggtggagcag catggg                                               16

<210> SEQ ID NO 726
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 726
ccgaaacagg gcctgg                                               16

<210> SEQ ID NO 727
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 727
cagttggcat ccgaaa                                               16

<210> SEQ ID NO 728
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 728
aatggtcgca agctgg                                               16

<210> SEQ ID NO 729
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 729
tcccagtgcc aatggt                                               16

<210> SEQ ID NO 730
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 730
catcagccca gaagcc                                               16
```

<210> SEQ ID NO 731
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 731
ccaactgacc catcag                                                       16

<210> SEQ ID NO 732
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 732
ttatgaaggc ccaact                                                       16

<210> SEQ ID NO 733
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 733
aggtgagtgt ttatga                                                       16

<210> SEQ ID NO 734
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 734
aaagccagcc aggtga                                                       16

<210> SEQ ID NO 735
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 735
ttgcttcagc cagctt                                                       16

<210> SEQ ID NO 736
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 736
ttccacaccc ttgctt                                                       16

<210> SEQ ID NO 737
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 737
actgtgcaca cattta                                                    16

<210> SEQ ID NO 738
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 738
agttttccag actgtg                                                    16

<210> SEQ ID NO 739
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 739
ctgattctga cagttt                                                    16

<210> SEQ ID NO 740
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 740
ttatgggaaa actgat                                                    16

<210> SEQ ID NO 741
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 741
gcccaccctt ttatgg                                                    16

<210> SEQ ID NO 742
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 742
tgcaatgcta gcccac                                                    16

<210> SEQ ID NO 743
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 743
caaatgcagc tgcaat                                                    16

<210> SEQ ID NO 744
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 744
ttgaatggtc ccaaat                                              16

<210> SEQ ID NO 745
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 745
gagtgacaga tttgaa                                              16

<210> SEQ ID NO 746
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 746
agcacaggaa tataca                                              16

<210> SEQ ID NO 747
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 747
gccctgatat atttaa                                              16

<210> SEQ ID NO 748
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 748
tacatgcact gccctg                                              16

<210> SEQ ID NO 749
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 749
caggatgatt tacatg                                              16

<210> SEQ ID NO 750
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 750
```
actgtcccca cctcgg                                              16

<210> SEQ ID NO 751
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 751
actaagagaa ctcact                                              16

<210> SEQ ID NO 752
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 752
ggctctttaa caacca                                              16

<210> SEQ ID NO 753
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 753
gcgggtaggt gccagg                                              16

<210> SEQ ID NO 754
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 754
tgaagtgaga gcgggt                                              16

<210> SEQ ID NO 755
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 755
gtgcagagat gacaca                                              16

<210> SEQ ID NO 756
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 756
tgggctggag tgtgca                                              16

<210> SEQ ID NO 757
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 757
caatggctga aggcag                                                       16

<210> SEQ ID NO 758
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 758
gctgggcatc aagatt                                                       16

<210> SEQ ID NO 759
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 759
gttctgatgg ctgggc                                                       16

<210> SEQ ID NO 760
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 760
ctggaatggc aaaact                                                       16

<210> SEQ ID NO 761
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 761
gccactggct cttttg                                                       16

<210> SEQ ID NO 762
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 762
ccctagactg gccact                                                       16

<210> SEQ ID NO 763
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 763
acggcgcggt gccta                                                        16
```

```
<210> SEQ ID NO 764
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 764
agcctcgggc caggcc                                                   16

<210> SEQ ID NO 765
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 765
atccgggctg agcctc                                                   16

<210> SEQ ID NO 766
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 766
ccccgcactg acctgg                                                   16

<210> SEQ ID NO 767
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 767
ccactccggg ccccgc                                                   16

<210> SEQ ID NO 768
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 768
ccccgcgaat ccactc                                                   16

<210> SEQ ID NO 769
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 769
cgcccctggg cagctg                                                   16

<210> SEQ ID NO 770
<211> LENGTH: 16
<212> TYPE: DNA
<213> ORGANISM: Artificial sequence
<220> FEATURE:
```

<223> OTHER INFORMATION: Synthetic oligonucleotide

<400> SEQUENCE: 770
gagatgccag acggcg                                                             16

<210> SEQ ID NO 771
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 771
tgagctccgg gcgcgg                                                             16

<210> SEQ ID NO 772
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 772
gacccacctg tctgcg                                                             16

<210> SEQ ID NO 773
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 773
cggcggccgg gaccca                                                             16

<210> SEQ ID NO 774
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 774
cggacgcaga gaggag                                                             16

<210> SEQ ID NO 775
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 775
ctcccgccac cctcgg                                                             16

<210> SEQ ID NO 776
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 776
gccggcaccg ctcccg                                                             16

```
<210> SEQ ID NO 777
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 777
taggcctaga cttggg                                                   16

<210> SEQ ID NO 778
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 778
tcccgccgcc cgcagg                                                   16

<210> SEQ ID NO 779
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 779
ccagtcttca tcccgc                                                   16

<210> SEQ ID NO 780
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 780
cccgccctac tccagt                                                   16

<210> SEQ ID NO 781
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 781
ctcgctttcc aggcgc                                                   16

<210> SEQ ID NO 782
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 782
cccccccgag ctcgct                                                   16

<210> SEQ ID NO 783
<211> LENGTH: 16
<212> TYPE: DNA
<213> ORGANISM: Artificial sequence
<220> FEATURE:
<223> OTHER INFORMATION: Synthetic oligonucleotide
```

-continued

<400> SEQUENCE: 783
gctgtaggca cccccc                                              16

<210> SEQ ID NO 784
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 784
tggaagtccc aggccg                                              16

<210> SEQ ID NO 785
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 785
ccccaaaccg atcggg                                              16

<210> SEQ ID NO 786
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 786
ccgcctgggt cactgg                                              16

<210> SEQ ID NO 787
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 787
gcccactccg ccgcct                                              16

<210> SEQ ID NO 788
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 788
ctgggcgatg gcgagg                                              16

<210> SEQ ID NO 789
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 789 aaccccatt ctgggc                                               16

<210> SEQ ID NO 790
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 790
ggctcccggg aacccc                                                   16

<210> SEQ ID NO 791
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 791
tgtggtccaa gccagc                                                   16

<210> SEQ ID NO 792
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 792
aggatcgggc ctcgct                                                   16

<210> SEQ ID NO 793
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 793
atcgaaagta aggatc                                                   16

<210> SEQ ID NO 794
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 794
gagcaagggc gagtgc                                                   16

<210> SEQ ID NO 795
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 795
ggcccggtaa gagcaa                                                   16

<210> SEQ ID NO 796
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 796
```

```
tttccgaaag ggtgag                                                 16

<210> SEQ ID NO 797
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 797
gcctgaagat cccggg                                                 16

<210> SEQ ID NO 798
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 798
cctgccattg gcctga                                                 16

<210> SEQ ID NO 799
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 799
cccaaactct tgcaca                                                 16

<210> SEQ ID NO 800
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 800
acctgacacc atcttc                                                 16

<210> SEQ ID NO 801
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 801
acgcagcctc tacctg                                                 16

<210> SEQ ID NO 802
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 802
cgagcccagg gacgca                                                 16

<210> SEQ ID NO 803
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 803
attcccggcc gcgagc                                                    16

<210> SEQ ID NO 804
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 804
agagtctgcc attccc                                                    16

<210> SEQ ID NO 805
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 805
gaactattgc gcccca                                                    16

<210> SEQ ID NO 806
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 806
accagcccag gaacta                                                    16

<210> SEQ ID NO 807
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 807
acctgaggaa accagc                                                    16

<210> SEQ ID NO 808
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 808
gttctgggac aggacc                                                    16

<210> SEQ ID NO 809
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 809
cctcttcatt gttgcc                                                    16
```

```
<210> SEQ ID NO 810
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 810
catgctagcc tcactt                                                       16

<210> SEQ ID NO 811
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 811
aaccatctcc ccacgc                                                       16

<210> SEQ ID NO 812
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 812
gtccggagac aaccat                                                       16

<210> SEQ ID NO 813
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 813
tcccaggtac ccgctc                                                       16

<210> SEQ ID NO 814
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 814
agtcccccac tccagc                                                       16

<210> SEQ ID NO 815
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 815
cgaggctggg aaagtc                                                       16

<210> SEQ ID NO 816
<211> LENGTH: 16
<212> TYPE: DNA
<213> ORGANISM: Artificial sequence
<220> FEATURE:
<223> OTHER INFORMATION: Synthetic oligonucleotide
```

-continued

```
<400> SEQUENCE: 816
cctcgccctg ctgtgt                                               16

<210> SEQ ID NO 817
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 817
gcaccccggt cctcgc                                               16

<210> SEQ ID NO 818
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 818
attctgggcc ctcgag                                               16

<210> SEQ ID NO 819
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 819
ctggttctgg tcactt                                               16

<210> SEQ ID NO 820
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 820
gccgagccct ctctgg                                               16

<210> SEQ ID NO 821
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 821
catcgataca gccgag                                               16

<210> SEQ ID NO 822
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 822
cttgccagag ggcctc                                               16

<210> SEQ ID NO 823
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 823
ccccataact actggg                                                    16

<210> SEQ ID NO 824
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 824
gaacccctca gcccca                                                    16

<210> SEQ ID NO 825
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 825
ttgactcttg gaaccc                                                    16

<210> SEQ ID NO 826
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 826
agtgcttccc ttgact                                                    16

<210> SEQ ID NO 827
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 827
ctttagataa aaaggg                                                    16

<210> SEQ ID NO 828
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 828
aaagtagggc ctttag                                                    16

<210> SEQ ID NO 829
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 829
```
gcccagaaag aagctt        16

<210> SEQ ID NO 830
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 830
ggtccagaca ggctga        16

<210> SEQ ID NO 831
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 831
ctccgggtca gctgcc        16

<210> SEQ ID NO 832
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 832
aatcccaccc ctccgg        16

<210> SEQ ID NO 833
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 833
ccctgtacag gccctg        16

<210> SEQ ID NO 834
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 834
acatgtctcc ttgcaa        16

<210> SEQ ID NO 835
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 835
ggtctgggtc acatgt        16

<210> SEQ ID NO 836
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 836
gccagacagc aggcgc                                                    16

<210> SEQ ID NO 837
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 837
tagtaagagt ggccag                                                    16

<210> SEQ ID NO 838
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 838
cacagcagtc ctagta                                                    16

<210> SEQ ID NO 839
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 839
gaggaagtgc cacagc                                                    16

<210> SEQ ID NO 840
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 840
tgcaattcat gggcac                                                    16

<210> SEQ ID NO 841
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 841
acccaggagc tgcaat                                                    16

<210> SEQ ID NO 842
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 842
agacagtgcc cccacc                                                    16

<210> SEQ ID NO 843
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 843
taagcccaca gctcac                                                    16

<210> SEQ ID NO 844
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 844
gacctgctga ggtggg                                                    16

<210> SEQ ID NO 845
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 845
ggcgcaccct gctgta                                                    16

<210> SEQ ID NO 846
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 846 tcactttcc tccacg                                                     16

<210> SEQ ID NO 847
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 847
gggccagccc gcggag                                                    16

<210> SEQ ID NO 848
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 848
cagtttccta catcga                                                    16

<210> SEQ ID NO 849
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 849
tcgggtagca cttagg 16

<210> SEQ ID NO 850
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 850
agtgggcagc cctaga 16

<210> SEQ ID NO 851
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 851
tgtgaggcag cgaagc 16

<210> SEQ ID NO 852
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 852
cctacaattg tgtgag 16

<210> SEQ ID NO 853
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 853
gaaatccaac agcctg 16

<210> SEQ ID NO 854
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 854
agccccggaa ggtggg 16

<210> SEQ ID NO 855
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 855
aatggacctg agcccc 16

```
<210> SEQ ID NO 856
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 856
tggagcccta gaccta                                                       16

<210> SEQ ID NO 857
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 857
gtgaaatgta tggagc                                                       16

<210> SEQ ID NO 858
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 858
gagtctctgg gtgaaa                                                       16

<210> SEQ ID NO 859
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 859
ccaggctccg gagtct                                                       16

<210> SEQ ID NO 860
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 860
tggaagttcg gtgtca                                                       16

<210> SEQ ID NO 861
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 861
gcccatgact ttggaa                                                       16

<210> SEQ ID NO 862
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 862
cccaatcaag gcccat                                                       16

<210> SEQ ID NO 863
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 863
taggtctaat tcagac                                                       16

<210> SEQ ID NO 864
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 864
agaaaagggc taggtc                                                       16

<210> SEQ ID NO 865
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 865
tccatcctcc tagaag                                                       16

<210> SEQ ID NO 866
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 866
ccgaacagca tccatc                                                       16

<210> SEQ ID NO 867
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 867
gagctctaac ccgaac                                                       16

<210> SEQ ID NO 868
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 868
agggactcag cctcaa                                                       16

<210> SEQ ID NO 869
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 869
atgccacaga agggac                                                   16

<210> SEQ ID NO 870
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 870
tctgtccacc atgcca                                                   16

<210> SEQ ID NO 871
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 871
atgagcgaga gtctgt                                                   16

<210> SEQ ID NO 872
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 872
gtgtcagagg gccgcg                                                   16

<210> SEQ ID NO 873
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 873
tccgacctca gtgtca                                                   16

<210> SEQ ID NO 874
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 874
aaatgataac tccgac                                                   16

<210> SEQ ID NO 875
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 875
```
gtttaataca gagcaa                                                   16

<210> SEQ ID NO 876
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 876
caacacggct gtttaa                                                   16

<210> SEQ ID NO 877
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 877
ctgtcagtcc agcagt                                                   16

<210> SEQ ID NO 878
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 878
tgcctgcccc ctactg                                                   16

<210> SEQ ID NO 879
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 879
gaggccgtgc aggcgc                                                   16

<210> SEQ ID NO 880
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 880
gaccccctgg gctgag                                                   16

<210> SEQ ID NO 881
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 881
cttccctaat gacccc                                                   16

<210> SEQ ID NO 882
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 882
tctgcacaga atcggg                                                      16

<210> SEQ ID NO 883
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 883
caagggtgga cagagg                                                      16

<210> SEQ ID NO 884
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 884
tctggccgag caaggg                                                      16

<210> SEQ ID NO 885
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 885
ggcacacaat tctggc                                                      16

<210> SEQ ID NO 886
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 886
gccctagaat agaggg                                                      16

<210> SEQ ID NO 887
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 887
agaggccttg gccta                                                       16

<210> SEQ ID NO 888
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 888
acccatagtt gtatct                                                      16
```

```
<210> SEQ ID NO 889
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 889
ggtttataac atgggt                                                       16

<210> SEQ ID NO 890
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 890
gcaccccaaa cttgca                                                       16

<210> SEQ ID NO 891
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 891
gctgttcccc gcaccc                                                       16

<210> SEQ ID NO 892
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 892
tcccacccag agctgt                                                       16

<210> SEQ ID NO 893
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 893
ccccagacca aatttc                                                       16

<210> SEQ ID NO 894
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 894
cgagtgggtc ccccag                                                       16

<210> SEQ ID NO 895
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 895
actcactgtg ggctga                                              16

<210> SEQ ID NO 896
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 896
ggctagaccg ggacaa                                              16

<210> SEQ ID NO 897
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 897
aaacgaaagt ggctag                                              16

<210> SEQ ID NO 898
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 898
tccacccggc cccagg                                              16

<210> SEQ ID NO 899
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 899
cccagtacct tttggg                                              16

<210> SEQ ID NO 900
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 900
aaattccctg cccagt                                              16

<210> SEQ ID NO 901
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 901
tggccttgca gcatgg                                              16

<210> SEQ ID NO 902
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 902
gtctgggcct gctttg                                                     16

<210> SEQ ID NO 903
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 903
aactccctgt gtctgg                                                     16

<210> SEQ ID NO 904
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 904
catcagaagt gaatgt                                                     16

<210> SEQ ID NO 905
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 905
acagcacagc ccatca                                                     16

<210> SEQ ID NO 906
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 906
gggtcattac acagca                                                     16

<210> SEQ ID NO 907
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 907
gcccttcact tgagac                                                     16

<210> SEQ ID NO 908
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 908
```
catgcccttg gccctt 16

<210> SEQ ID NO 909
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 909
ctccccttac ccatgc 16

<210> SEQ ID NO 910
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 910
gtcctgagtc cccttc 16

<210> SEQ ID NO 911
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 911
aactctccac agtcct 16

<210> SEQ ID NO 912
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 912
aggccagagg gaccct 16

<210> SEQ ID NO 913
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 913
actgcctccc tggagt 16

<210> SEQ ID NO 914
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 914
tgctacctac ccaggg 16

<210> SEQ ID NO 915
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 915
cagctctaac tgctac                                                    16

<210> SEQ ID NO 916
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 916
gaaggctaca ggaaac                                                    16

<210> SEQ ID NO 917
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 917
agcctgttag gaaggc                                                    16

<210> SEQ ID NO 918
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 918
cgcctgccgg agcctg                                                    16

<210> SEQ ID NO 919
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 919
aggaaggccc taacgc                                                    16

<210> SEQ ID NO 920
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 920
cgaagcatcc agtggg                                                    16

<210> SEQ ID NO 921
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 921
aggtccacac gagctc                                                    16
```

<210> SEQ ID NO 922
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 922
caggcagctt agggag                                                    16

<210> SEQ ID NO 923
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 923
catttagtgt ggttta                                                    16

<210> SEQ ID NO 924
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 924
gcatggagcc tcagtt                                                    16

<210> SEQ ID NO 925
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 925
tgagacccct gggtgg                                                    16

<210> SEQ ID NO 926
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 926
gcattcgggt agcact                                                    16

<210> SEQ ID NO 927
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 927
atcaccactg tgtacc                                                    16

<210> SEQ ID NO 928
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 928
ttcgggtagc acttag                                                     16

<210> SEQ ID NO 929
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 929
attcgggtag cactta                                                     16

<210> SEQ ID NO 930
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 930
cattcgggta gcactt                                                     16

<210> SEQ ID NO 931
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 931
cgcattcggg tagcac                                                     16

<210> SEQ ID NO 932
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 932
acgcattcgg gtagca                                                     16

<210> SEQ ID NO 933
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 933
cacgcattcg ggtagc                                                     16

<210> SEQ ID NO 934
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 934
acacgcattc gggtag                                                     16

```
<210> SEQ ID NO 935
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 935
gacacgcatt cgggta                                               16

<210> SEQ ID NO 936
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 936
ccactgtgta ccccat                                               16

<210> SEQ ID NO 937
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 937
accactgtgt accccca                                              16

<210> SEQ ID NO 938
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 938
caccactgtg taccccca                                             16

<210> SEQ ID NO 939
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 939
tcaccactgt gtaccc                                               16

<210> SEQ ID NO 940
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 940
aatcaccact gtgtac                                               16

<210> SEQ ID NO 941
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 941
aaatcaccac tgtgta                                                   16

<210> SEQ ID NO 942
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 942
caaatcacca ctgtgt                                                   16

<210> SEQ ID NO 943
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 943
tcaaatcacc actgtg                                                   16

<210> SEQ ID NO 944
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 944
atcaaatcac cactgt                                                   16

<210> SEQ ID NO 945
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 945
cttggtcctc cccctt                                                   16

<210> SEQ ID NO 946
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 946
catctaggtt cttggt                                                   16

<210> SEQ ID NO 947
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 947
ctctagggcc attcat                                                   16

<210> SEQ ID NO 948
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 948
gcaccaaaca gatgtt                                              16

<210> SEQ ID NO 949
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 949
accaactcaa cccacc                                              16

<210> SEQ ID NO 950
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 950
aatcccatca accaac                                              16

<210> SEQ ID NO 951
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 951
tctttagaga aatccc                                              16

<210> SEQ ID NO 952
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 952
aaggacacct gccctc                                              16

<210> SEQ ID NO 953
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 953
ctggagctcc caagga                                              16

<210> SEQ ID NO 954
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 954
```
aagaatctca tctgga                                              16

<210> SEQ ID NO 955
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 955
tgccctcaac aagaat                                              16

<210> SEQ ID NO 956
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 956
ctgagagttc cctccg                                              16

<210> SEQ ID NO 957
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 957
ctcctgctca gtctac                                              16

<210> SEQ ID NO 958
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 958
ctgggacagc gagcgc                                              16

<210> SEQ ID NO 959
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 959
tcttgtctca agctgg                                              16

<210> SEQ ID NO 960
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 960
tgacaccaaa agcccg                                              16

<210> SEQ ID NO 961
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 961
agtgactgcc tgacac                                                      16

<210> SEQ ID NO 962
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 962
gcccacccct tgctct                                                      16

<210> SEQ ID NO 963
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 963
ctactcacac cacagg                                                      16

<210> SEQ ID NO 964
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 964
ccgccttcca ctactc                                                      16

<210> SEQ ID NO 965
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 965
ggccagagaa ccgcct                                                      16

<210> SEQ ID NO 966
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 966
cagcaagcag cccgtt                                                      16

<210> SEQ ID NO 967
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 967
ctgctaacag cagcaa                                                      16
```

```
<210> SEQ ID NO 968
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 968
cattctccaa ctgcta                                                     16

<210> SEQ ID NO 969
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 969
gcagaggcat ccattc                                                     16

<210> SEQ ID NO 970
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 970
ccccaggtgc cctta                                                      16

<210> SEQ ID NO 971
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 971
ctgcgggcgc ggcccc                                                     16

<210> SEQ ID NO 972
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 972
gagttacgag ttagtg                                                     16

<210> SEQ ID NO 973
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 973
tcatggaatt ttgtgt                                                     16

<210> SEQ ID NO 974
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 974
ttgtctagtg tcatgg                                                     16

<210> SEQ ID NO 975
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 975
gcatcagctt tcttgt                                                     16

<210> SEQ ID NO 976
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 976
taaggccaat tctctt                                                     16

<210> SEQ ID NO 977
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 977
atctaggtat ttaagg                                                     16

<210> SEQ ID NO 978
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 978
tctccagtcc atctag                                                     16

<210> SEQ ID NO 979
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 979
aaggatggtc tctcca                                                     16

<210> SEQ ID NO 980
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 980
ctcagaggtc aagcta                                                     16

<210> SEQ ID NO 981
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 981
ggtctgcagg tggatg                                                    16

<210> SEQ ID NO 982
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 982
gggcttacct tgaaga                                                    16

<210> SEQ ID NO 983
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 983
caacctcctc cccggg                                                    16

<210> SEQ ID NO 984
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 984
gaggtccagc caacct                                                    16

<210> SEQ ID NO 985
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 985
ttatgtgcgc tcctct                                                    16

<210> SEQ ID NO 986
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 986
gagctgcctg tgtgcg                                                    16

<210> SEQ ID NO 987
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 987
```

```
ccagcctcga ggagct                                                   16

<210> SEQ ID NO 988
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 988
ccggcatcag cagcag                                                   16

<210> SEQ ID NO 989
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 989
aaaggtgtac cctgtg                                                   16

<210> SEQ ID NO 990
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 990
aagatgtgcc ctaggc                                                   16

<210> SEQ ID NO 991
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 991
gcaggttaga aaagat                                                   16

<210> SEQ ID NO 992
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 992
gctctagggt gcaggt                                                   16

<210> SEQ ID NO 993
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 993
tccccacgat gctcta                                                   16

<210> SEQ ID NO 994
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 994
cgagttatgg gaaggc                                                    16

<210> SEQ ID NO 995
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 995
aggagtgaga cgagca                                                    16

<210> SEQ ID NO 996
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 996
aacaagtcct catgag                                                    16

<210> SEQ ID NO 997
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 997
tcctttagca tatgcg                                                    16

<210> SEQ ID NO 998
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 998
gatgttacct ctctag                                                    16

<210> SEQ ID NO 999
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 999
agttttctca ccctcc                                                    16

<210> SEQ ID NO 1000
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1000
gtctacaccc ctagtt                                                    16
```

<210> SEQ ID NO 1001
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1001
cacaggttag gcccac                                                    16

<210> SEQ ID NO 1002
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1002
ggacagggta ctcaga                                                    16

<210> SEQ ID NO 1003
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1003
gcattccata tacaca                                                    16

<210> SEQ ID NO 1004
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1004 tgcctttta tgttga                                                     16

<210> SEQ ID NO 1005
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1005
ctagacaaat atgcag                                                    16

<210> SEQ ID NO 1006
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1006
cattccatat acacac                                                    16

<210> SEQ ID NO 1007
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1007
tgcattccat atacac                                                        16

<210> SEQ ID NO 1008
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1008
ttgcattcca tataca                                                        16

<210> SEQ ID NO 1009
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1009
tttgcattcc atatac                                                        16

<210> SEQ ID NO 1010
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1010
ttttgcattc catata                                                        16

<210> SEQ ID NO 1011
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1011
attttgcatt ccatat                                                        16

<210> SEQ ID NO 1012
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1012
cttttaatgt tgaatt                                                        16

<210> SEQ ID NO 1013
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1013
ccttttaatg ttgaat                                                        16

```
<210> SEQ ID NO 1014
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1014
gccttttaat gttgaa                                                   16

<210> SEQ ID NO 1015
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1015
atgcctttta atgttg                                                   16

<210> SEQ ID NO 1016
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1016
tatgcctttt aatgtt                                                   16

<210> SEQ ID NO 1017
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1017
ctatgccttt taatgt                                                   16

<210> SEQ ID NO 1018
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1018
tctatgcctt ttaatg                                                   16

<210> SEQ ID NO 1019
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1019
caaatatgca gatatc                                                   16

<210> SEQ ID NO 1020
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1020
gacaaatatg cagata                                              16

<210> SEQ ID NO 1021
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1021
agacaaatat gcagat                                              16

<210> SEQ ID NO 1022
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1022
tagacaaata tgcaga                                              16

<210> SEQ ID NO 1023
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1023
tctagacaaa tatgca                                              16

<210> SEQ ID NO 1024
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1024
gtctagacaa atatgc                                              16

<210> SEQ ID NO 1025
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1025
agtctagaca aatatg                                              16

<210> SEQ ID NO 1026
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1026
aagtctagac aaatat                                              16

<210> SEQ ID NO 1027
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1027
taagtctaga caaata                                                    16

<210> SEQ ID NO 1028
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1028
tatcaaatca ccactg                                                    16

<210> SEQ ID NO 1029
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1029
tcactgtgct tatcaa                                                    16

<210> SEQ ID NO 1030
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1030
tacctgatct gatcac                                                    16

<210> SEQ ID NO 1031
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1031
gatatgctaa gtacct                                                    16

<210> SEQ ID NO 1032
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1032
gtttgttccc aacaca                                                    16

<210> SEQ ID NO 1033
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1033
```

-continued gtatctgaat cttata						16

<210> SEQ ID NO 1034
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1034
gattgatgat gtatct						16

<210> SEQ ID NO 1035
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1035
acaattgaaa gattga						16

<210> SEQ ID NO 1036
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1036
atctggtcaa cagtgt						16

<210> SEQ ID NO 1037
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1037
caaggaggtt gagatg						16

<210> SEQ ID NO 1038
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1038
gtagtacatc aattaa						16

<210> SEQ ID NO 1039
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1039
atgtacagtt gtagta						16

<210> SEQ ID NO 1040
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1040
aacactaggc aacaga                                                       16

<210> SEQ ID NO 1041
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1041
ccaatggtgc aacact                                                       16

<210> SEQ ID NO 1042
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1042
ccactgctca ccaatg                                                       16

<210> SEQ ID NO 1043
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1043
tggaggttgt gctatg                                                       16

<210> SEQ ID NO 1044
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1044
ttgagctgag ttggag                                                       16

<210> SEQ ID NO 1045
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1045
acatcctagc attaag                                                       16

<210> SEQ ID NO 1046
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1046
aaactattat gcgagg                                                       16
```

```
<210> SEQ ID NO 1047
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1047
tccaattttg cattcc                                              16

<210> SEQ ID NO 1048
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1048
ttcacttgat tccaat                                              16

<210> SEQ ID NO 1049
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1049
aaggaaagct gatcct                                              16

<210> SEQ ID NO 1050
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1050
gtatgttgga aaggaa                                              16

<210> SEQ ID NO 1051
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1051
aaaagtgatg tggacg                                              16

<210> SEQ ID NO 1052
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1052
cattccagtg gaaatt                                              16

<210> SEQ ID NO 1053
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1053
aattgtgcta aaccat                                               16

<210> SEQ ID NO 1054
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1054
tcagtgacca aattgt                                               16

<210> SEQ ID NO 1055
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1055
caagtatcta aaaacc                                               16

<210> SEQ ID NO 1056
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1056
catgacaatg tggttt                                               16

<210> SEQ ID NO 1057
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1057
agacagccta catgac                                               16

<210> SEQ ID NO 1058
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1058
ggaagcatta agacag                                               16

<210> SEQ ID NO 1059
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1059
cccaaaataa ttgagg                                               16

<210> SEQ ID NO 1060
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1060
ggaaatcaac ccccaa                                                     16

<210> SEQ ID NO 1061
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1061
ttgcctttga cccagc                                                     16

<210> SEQ ID NO 1062
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1062
gcccaaaaac taagaa                                                     16

<210> SEQ ID NO 1063
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1063
taaggatcaa gcccaa                                                     16

<210> SEQ ID NO 1064
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1064
ctgtattacc tataca                                                     16

<210> SEQ ID NO 1065
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1065
gaattttgtg actgta                                                     16

<210> SEQ ID NO 1066
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1066
```
accattctat gcctttt 16

<210> SEQ ID NO 1067
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1067 gagactttt gctcta 16

<210> SEQ ID NO 1068
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1068
gtgatgaacc agggaa 16

<210> SEQ ID NO 1069
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1069
ggaaaggcta gggagg 16

<210> SEQ ID NO 1070
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1070
acggctgcct ctaggg 16

<210> SEQ ID NO 1071
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1071
aggatagttc catatt 16

<210> SEQ ID NO 1072
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1072
tatgaaaagt agagga 16

<210> SEQ ID NO 1073
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1073
ctagcatttc ttatga                                                     16

<210> SEQ ID NO 1074
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1074
tattaagtct agacaa                                                     16

<210> SEQ ID NO 1075
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1075
cgtcaagaag tattaa                                                     16

<210> SEQ ID NO 1076
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1076
tgacatgtag caatcg                                                     16

<210> SEQ ID NO 1077
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1077
ttggagagag cacagt                                                     16

<210> SEQ ID NO 1078
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1078
aattctacag tcacga                                                     16

<210> SEQ ID NO 1079
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1079
catgtgcata aaaatc                                                     16
```

<210> SEQ ID NO 1080
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1080
agaagcattc acacaa                                                   16

<210> SEQ ID NO 1081
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1081
gcattcacac aaaata                                                   16

<210> SEQ ID NO 1082
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1082
agcattcaca caaaat                                                   16

<210> SEQ ID NO 1083
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1083
aagcattcac acaaaa                                                   16

<210> SEQ ID NO 1084
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1084
gaagcattca cacaaa                                                   16

<210> SEQ ID NO 1085
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1085
tagaagcatt cacaca                                                   16

<210> SEQ ID NO 1086
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1086
atagaagcat tcacac    16

<210> SEQ ID NO 1087
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1087
catagaagca ttcaca    16

<210> SEQ ID NO 1088
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1088
tcatagaagc attcac    16

<210> SEQ ID NO 1089
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1089
atcatagaag cattca    16

<210> SEQ ID NO 1090
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1090
gtttataagc tgacat    16

<210> SEQ ID NO 1091
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1091
gcaggaaact gtttat    16

<210> SEQ ID NO 1092
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1092
actgggcagc acaaaa    16

```
<210> SEQ ID NO 1093
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1093
acccattgaa tgaaaa                                            16

<210> SEQ ID NO 1094
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1094
attacggcca acccat                                            16

<210> SEQ ID NO 1095
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1095
ggctggtgaa attacg                                            16

<210> SEQ ID NO 1096
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1096
catccatcaa tgaggg                                            16

<210> SEQ ID NO 1097
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1097
cccaatgcaa catcca                                            16

<210> SEQ ID NO 1098
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1098
tgacccaaaa taccca                                            16

<210> SEQ ID NO 1099
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1099
gtgtaaaaga tgaccc                                                        16

<210> SEQ ID NO 1100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1100
agcagtgctg tgtgta                                                        16

<210> SEQ ID NO 1101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1101
attgcacaca caaagt                                                        16

<210> SEQ ID NO 1102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1102
tatcatagaa gcattc                                                        16

<210> SEQ ID NO 1103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1103
ctatttgatt tctagg                                                        16

<210> SEQ ID NO 1104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1104
ttttaaccca gctatt                                                        16

<210> SEQ ID NO 1105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1105
ggttaccaac atttct                                                        16

<210> SEQ ID NO 1106
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1106
gtgaggtgag ggttac                                                    16

<210> SEQ ID NO 1107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1107
acactggagc tgttgg                                                    16

<210> SEQ ID NO 1108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1108
acaggctcga gacact                                                    16

<210> SEQ ID NO 1109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1109
tgcacatagg acaggc                                                    16

<210> SEQ ID NO 1110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1110
taaagcactc agagct                                                    16

<210> SEQ ID NO 1111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1111
ttgatgtccg taaagc                                                    16

<210> SEQ ID NO 1112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1112
```
agcgaagact caaggg                                                           16

<210> SEQ ID NO 1113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1113
catggagtgg cagcga                                                           16

<210> SEQ ID NO 1114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1114
agttgcccac ctcatg                                                           16

<210> SEQ ID NO 1115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1115
atctcctcac agttgc                                                           16

<210> SEQ ID NO 1116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1116
cctttgtctt gatctc                                                           16

<210> SEQ ID NO 1117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1117
gccatgtcac tgcctc                                                           16

<210> SEQ ID NO 1118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1118
cgccagctgt gtgcca                                                           16

<210> SEQ ID NO 1119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1119
tggaagtgcc ccccgc                                                    16

<210> SEQ ID NO 1120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1120
ggtttgaatc tggaag                                                    16

<210> SEQ ID NO 1121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1121
ggtgagcacc ctggag                                                    16

<210> SEQ ID NO 1122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1122
tctaaggagg acagcg                                                    16

<210> SEQ ID NO 1123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1123
gtgaaacagt gtgatc                                                    16

<210> SEQ ID NO 1124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1124
atagtccctg ctcctg                                                    16

<210> SEQ ID NO 1125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1125
gtgggagtct gccaca                                                    16

<210> SEQ ID NO 1126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1126
gacctggttt gcagcg                                                         16

<210> SEQ ID NO 1127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1127
cgctgagccc cagacc                                                         16

<210> SEQ ID NO 1128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1128
ggctgagcct cgctga                                                         16

<210> SEQ ID NO 1129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1129
aacttcggct acaggc                                                         16

<210> SEQ ID NO 1130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1130
gactctactg tgtggg                                                         16

<210> SEQ ID NO 1131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1131
cacagagaac ctcatc                                                         16

<210> SEQ ID NO 1132
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1132
aatagccgac cacaga                                                    16

<210> SEQ ID NO 1133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1133
gcctgatacc tgtggg                                                    16

<210> SEQ ID NO 1134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1134
attgcacagc ctccca                                                    16

<210> SEQ ID NO 1135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1135
acccaagagc tcatgg                                                    16

<210> SEQ ID NO 1136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1136
cttggcctgc ctgcac                                                    16

<210> SEQ ID NO 1137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1137
ttcctggacc actgcc                                                    16

<210> SEQ ID NO 1138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1138
gcgggagccc ccgcat                                                    16

<210> SEQ ID NO 1139
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1139
gccctgggtg tcatga                                                   16

<210> SEQ ID NO 1140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1140
cactcctgga agccct                                                   16

<210> SEQ ID NO 1141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1141
gacccatccc agccac                                                   16

<210> SEQ ID NO 1142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1142
atatgccagt gaccca                                                   16

<210> SEQ ID NO 1143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1143
gccattcctg atatgc                                                   16

<210> SEQ ID NO 1144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1144
tgcacgccaa gccatt                                                   16

<210> SEQ ID NO 1145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1145
```
gaagcaccca ggtccc                                         16

<210> SEQ ID NO 1146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1146
atggtaagga agaagc                                         16

<210> SEQ ID NO 1147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1147
aacgagggca atggta                                         16

<210> SEQ ID NO 1148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1148
ccatgagacc taggct                                         16

<210> SEQ ID NO 1149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1149
actccatggg ccatga                                         16

<210> SEQ ID NO 1150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1150
ggattgggaa agacct                                         16

<210> SEQ ID NO 1151
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1151
cgaggtggag ggcaca                                         16

<210> SEQ ID NO 1152
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1152
caacacaggg cgaggt                                                      16

<210> SEQ ID NO 1153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1153
tatgcagctt ctgcct                                                      16

<210> SEQ ID NO 1154
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1154
tggcaattag gtgagg                                                      16

<210> SEQ ID NO 1155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1155
caagctacat gaaatc                                                      16

<210> SEQ ID NO 1156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1156
tcatgaccta gcggga                                                      16

<210> SEQ ID NO 1157
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1157
cagtttagct caggca                                                      16

<210> SEQ ID NO 1158
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1158
tagctcaggc aagacc                                                      16

<210> SEQ ID NO 1159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1159
ttagctcagg caagac                                                      16

<210> SEQ ID NO 1160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1160
tttagctcag gcaaga                                                      16

<210> SEQ ID NO 1161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1161
gtttagctca ggcaag                                                      16

<210> SEQ ID NO 1162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1162
agtttagctc aggcaa                                                      16

<210> SEQ ID NO 1163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1163
gcctcagttt agctca                                                      16

<210> SEQ ID NO 1164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1164
agcctcagtt tagctc                                                      16

<210> SEQ ID NO 1165
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 1165
ctgtagctcc tatgca                                                     16

<210> SEQ ID NO 1166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1166
agaagcaaga tcccct                                                     16

<210> SEQ ID NO 1167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1167
atgtcggagg agaagc                                                     16

<210> SEQ ID NO 1168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1168
aaaggagtca atgtcg                                                     16

<210> SEQ ID NO 1169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1169
gcagggcagt aaagga                                                     16

<210> SEQ ID NO 1170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1170
gtctgcacag caggga                                                     16

<210> SEQ ID NO 1171
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1171
aacccacact cacctc                                                     16
```

```
<210> SEQ ID NO 1172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1172
cgtccagggc tccacc                                                  16

<210> SEQ ID NO 1173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1173
gacagcagag agctcg                                                  16

<210> SEQ ID NO 1174
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1174
gcggaaacct aaggcc                                                  16

<210> SEQ ID NO 1175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1175
attgagaggg ccacgg                                                  16

<210> SEQ ID NO 1176
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1176
gaaacaagga gaacta                                                  16

<210> SEQ ID NO 1177
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1177
ttcagaatcc caggag                                                  16

<210> SEQ ID NO 1178
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1178
gactgtgctc ctatcg                                                   16

<210> SEQ ID NO 1179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1179
gacaatgccc tgggaa                                                   16

<210> SEQ ID NO 1180
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1180
acagggtaat gacaat                                                   16

<210> SEQ ID NO 1181
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1181
cgtgggtcac acacac                                                   16

<210> SEQ ID NO 1182
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1182
agccccaact gctgcg                                                   16

<210> SEQ ID NO 1183
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1183
ggagtcagac ctacca                                                   16

<210> SEQ ID NO 1184
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1184
ccttctgcag ggagtc                                                   16

<210> SEQ ID NO 1185
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1185
gccctttgcc tcactt                                                       16

<210> SEQ ID NO 1186
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1186
ctccggtccc agctcg                                                       16

<210> SEQ ID NO 1187
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1187
aagaccctgc ctccgg                                                       16

<210> SEQ ID NO 1188
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1188
tagcctcagt ttagct                                                       16

<210> SEQ ID NO 1189
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1189
gaactatgag gcaact                                                       16

<210> SEQ ID NO 1190
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1190
taacaggcga gaacta                                                       16

<210> SEQ ID NO 1191
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1191
```
gaaaggagga caggtt                                                  16

<210> SEQ ID NO 1192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1192
tgaagggaca ccacca                                                  16

<210> SEQ ID NO 1193
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1193
tagaccccca accacc                                                  16

<210> SEQ ID NO 1194
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1194
cctatagctt ctctgt                                                  16

<210> SEQ ID NO 1195
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1195
aggtacctat ggtacc                                                  16

<210> SEQ ID NO 1196
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1196
agcccccttc caggta                                                  16

<210> SEQ ID NO 1197
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1197
tagcctccca tcagcc                                                  16

<210> SEQ ID NO 1198
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1198
cctgggccac cctagc                                                   16

<210> SEQ ID NO 1199
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1199
cgaactgcct cccagg                                                   16

<210> SEQ ID NO 1200
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1200
tgccacctcc acgaac                                                   16

<210> SEQ ID NO 1201
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1201
cggctgtcag tgccac                                                   16

<210> SEQ ID NO 1202
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1202
cactgcatct acagag                                                   16

<210> SEQ ID NO 1203
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1203
cagccatggg tcctta                                                   16

<210> SEQ ID NO 1204
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1204
ttccccgtgc ccagcc                                                   16
```

```
<210> SEQ ID NO 1205
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1205 aatccccag cactgc                                                    16

<210> SEQ ID NO 1206
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1206
ttgccaatcc taccc                                                    16

<210> SEQ ID NO 1207
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1207
cacccaaggg agtcca                                                   16

<210> SEQ ID NO 1208
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1208
agccccatcc gccctc                                                   16

<210> SEQ ID NO 1209
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1209
ggcccatccc gtcctt                                                   16

<210> SEQ ID NO 1210
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1210
ggtcggtcac tgtggg                                                   16

<210> SEQ ID NO 1211
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1211
ctttgggccc tcacca                                                      16

<210> SEQ ID NO 1212
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1212
aggatcacag ctttgg                                                      16

<210> SEQ ID NO 1213
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1213
atgccctggg caagag                                                      16

<210> SEQ ID NO 1214
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1214
aggctggaac catgcc                                                      16

<210> SEQ ID NO 1215
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1215
ccctagtcag aggctg                                                      16

<210> SEQ ID NO 1216
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1216
aaatcaaggt ccctag                                                      16

<210> SEQ ID NO 1217
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1217
gctctgcatc aaaatc                                                      16

<210> SEQ ID NO 1218
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1218
atgtacctgt acagta                                                      16

<210> SEQ ID NO 1219
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1219
ccgactttgg gatagg                                                      16

<210> SEQ ID NO 1220
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1220
caagccaagg ccgact                                                      16

<210> SEQ ID NO 1221
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1221
ccccagtttt caagcc                                                      16

<210> SEQ ID NO 1222
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1222
tagccccagg attccc                                                      16

<210> SEQ ID NO 1223
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1223
aagttcacac tgctca                                                      16

<210> SEQ ID NO 1224
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1224
```
cggctctgag ccttga                                                        16

<210> SEQ ID NO 1225
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1225
agtaatagac cgcatt                                                        16

<210> SEQ ID NO 1226
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1226
aggacagcca tcaggg                                                        16

<210> SEQ ID NO 1227
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1227
gctgtgcatg aggaca                                                        16

<210> SEQ ID NO 1228
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1228
gccagatcca gctgtg                                                        16

<210> SEQ ID NO 1229
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1229
accacctggg aggcaa                                                        16

<210> SEQ ID NO 1230
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1230
tcccctgaga ggctgc                                                        16

<210> SEQ ID NO 1231
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1231
ctctgtatac tagacc                                                    16

<210> SEQ ID NO 1232
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1232
acgcctcccc attctg                                                    16

<210> SEQ ID NO 1233
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1233
ctctggccgc caagtt                                                    16

<210> SEQ ID NO 1234
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1234
tctgtctgcg gtgcgc                                                    16

<210> SEQ ID NO 1235
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1235
ggtctgtctg cggtgc                                                    16

<210> SEQ ID NO 1236
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1236
gcatctgtga ggctca                                                    16

<210> SEQ ID NO 1237
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1237
ctgcatctgt gaggct                                                    16
```

<210> SEQ ID NO 1238
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1238
cactgcatct gtgagg                                                       16

<210> SEQ ID NO 1239
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1239
tgcactgcat ctgtga                                                       16

<210> SEQ ID NO 1240
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1240
actgcactgc atctgt                                                       16

<210> SEQ ID NO 1241
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1241
caattttgca ttccat                                                       16

<210> SEQ ID NO 1242
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1242
ccaattttgc attcca                                                       16

<210> SEQ ID NO 1243
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1243
aattttgcat tccata                                                       16

<210> SEQ ID NO 1244
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1244
ttccaatttt gcattc                                                        16

<210> SEQ ID NO 1245
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1245
attccaattt tgcatt                                                        16

<210> SEQ ID NO 1246
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1246
tgattccaat tttgca                                                        16

<210> SEQ ID NO 1247
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1247
cttgattcca attttg                                                        16

<210> SEQ ID NO 1248
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1248
cacttgattc caattt                                                        16

<210> SEQ ID NO 1249
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1249
aagggcacag cgcagg                                                        16

<210> SEQ ID NO 1250
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1250
gggcacagcg caggtt                                                        16

```
<210> SEQ ID NO 1251
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1251
agggcacagc gcaggt                                                       16

<210> SEQ ID NO 1252
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1252
taagggcaca gcgcag                                                       16

<210> SEQ ID NO 1253
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1253
ttaagggcac agcgca                                                       16

<210> SEQ ID NO 1254
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1254
ggtgtatttc cctgtc                                                       16

<210> SEQ ID NO 1255
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1255
ttctgcaggg agtcag                                                       16

<210> SEQ ID NO 1256
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1256
cttctgcagg gagtca                                                       16

<210> SEQ ID NO 1257
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1257
gggagtcaga cctacc                                               16

<210> SEQ ID NO 1258
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1258
cagggagtca gaccta                                               16

<210> SEQ ID NO 1259
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1259
tgcagggagt cagacc                                               16

<210> SEQ ID NO 1260
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1260
tctgcaggga gtcaga                                               16

<210> SEQ ID NO 1261
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1261
gccttctgca gggagt                                               16

<210> SEQ ID NO 1262
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1262
tgccttctgc agggag                                               16

<210> SEQ ID NO 1263
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1263
ttgccttctg caggga                                               16

<210> SEQ ID NO 1264
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1264
atttgccttc tgcagg                                                    16

<210> SEQ ID NO 1265
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1265
tcatttgcct tctgca                                                    16

<210> SEQ ID NO 1266
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1266
gagtgagacg agcaaa                                                    16

<210> SEQ ID NO 1267
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1267
ggaagtgagt ctcaaa                                                    16

<210> SEQ ID NO 1268
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1268
ggagtgagac gagcaa                                                    16

<210> SEQ ID NO 1269
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1269
gaggaagtga gtctca                                                    16

<210> SEQ ID NO 1270
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1270
```
ctgatatgat acctaa					16

<210> SEQ ID NO 1271
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1271
atctgatatg atacct					16

<210> SEQ ID NO 1272
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1272
acgagttatg ggaagg					16

<210> SEQ ID NO 1273
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1273
ggacgagtta tgggaa					16

<210> SEQ ID NO 1274
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1274
taggacgagt tatggg					16

<210> SEQ ID NO 1275
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1275
agtaggacga gttatg					16

<210> SEQ ID NO 1276
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1276
tgagtaggac gagtta					16

<210> SEQ ID NO 1277
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1277
ggtgagtagg acgagt                                                    16

<210> SEQ ID NO 1278
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1278
agggtgagta ggacga                                                    16

<210> SEQ ID NO 1279
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1279
aaagggtgag taggac                                                    16

<210> SEQ ID NO 1280
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1280
gcaaagggtg agtagg                                                    16

<210> SEQ ID NO 1281
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1281
gagcaaaggg tgagta                                                    16

<210> SEQ ID NO 1282
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1282
acgagcaaag ggtgag                                                    16

<210> SEQ ID NO 1283
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1283
agacgagcaa agggtg                                                    16
```

```
<210> SEQ ID NO 1284
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1284
gagacgagca aagggt                                                    16

<210> SEQ ID NO 1285
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1285
tgagacgagc aaaggg                                                    16

<210> SEQ ID NO 1286
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1286
gtgagacgag caaagg                                                    16

<210> SEQ ID NO 1287
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1287
agtgagacga gcaaag                                                    16

<210> SEQ ID NO 1288
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1288
taggagtgag acgagc                                                    16

<210> SEQ ID NO 1289
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1289
ataggagtga gacgag                                                    16

<210> SEQ ID NO 1290
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1290
aataggagtg agacga                                                        16

<210> SEQ ID NO 1291
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1291
taataggagt gagacg                                                        16

<210> SEQ ID NO 1292
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1292
gtaataggag tgagac                                                        16

<210> SEQ ID NO 1293
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1293
gagtaatagg agtgag                                                        16

<210> SEQ ID NO 1294
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1294
atgagtaata ggagtg                                                        16

<210> SEQ ID NO 1295
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1295
tcatgagtaa taggag                                                        16

<210> SEQ ID NO 1296
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1296
cctcatgagt aatagg                                                        16

<210> SEQ ID NO 1297
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1297
ctgacacagg cggatg                                                    16

<210> SEQ ID NO 1298
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1298
cattctatgc ctttta                                                    16

<210> SEQ ID NO 1299
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1299
ccattctatg cctttt                                                    16

<210> SEQ ID NO 1300
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1300
aaccattcta tgcctt                                                    16

<210> SEQ ID NO 1301
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1301
aaaccattct atgcct                                                    16

<210> SEQ ID NO 1302
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1302
taaaccattc tatgcc                                                    16

<210> SEQ ID NO 1303
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1303
```
ctaaaccatt ctatgc                                                  16

<210> SEQ ID NO 1304
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1304
ctctaaacca ttctat                                                  16

<210> SEQ ID NO 1305
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1305
tgctctaaac cattct                                                  16

<210> SEQ ID NO 1306
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1306
tttgctctaa accatt                                                  16

<210> SEQ ID NO 1307
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1307 cttttttgctc taaacc                                                 16

<210> SEQ ID NO 1308
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1308 agacttttg ctctaa                                                   16

<210> SEQ ID NO 1309
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1309
actgtattac ctatac                                                  16

<210> SEQ ID NO 1310
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1310
gactgtatta cctata 16

<210> SEQ ID NO 1311
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1311
tgactgtatt acctat 16

<210> SEQ ID NO 1312
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1312
gtgactgtat taccta 16

<210> SEQ ID NO 1313
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1313
tgtgactgta ttacct 16

<210> SEQ ID NO 1314
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1314
ttgtgactgt attacc 16

<210> SEQ ID NO 1315
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1315
tttgtgactg tattac 16

<210> SEQ ID NO 1316
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1316
ttttgtgact gtatta 16

<210> SEQ ID NO 1317
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1317
attttgtgac tgtatt                                                         16

<210> SEQ ID NO 1318
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1318
aattttgtga ctgtat                                                         16

<210> SEQ ID NO 1319
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1319
tgaattttgt gactgt                                                         16

<210> SEQ ID NO 1320
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1320
ttgaattttg tgactg                                                         16

<210> SEQ ID NO 1321
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1321
gttgaatttt gtgact                                                         16

<210> SEQ ID NO 1322
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1322
tgttgaattt tgtgac                                                         16

<210> SEQ ID NO 1323
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 1323
caatgcaaca tccatc                                                    16

<210> SEQ ID NO 1324
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1324
gtgtatttcc ctgtct                                                    16

<210> SEQ ID NO 1325
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1325
ccaatgcaac atccat                                                    16

<210> SEQ ID NO 1326
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1326
cggtgtattt ccctgt                                                    16

<210> SEQ ID NO 1327
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1327
acatccatca atgagg                                                    16

<210> SEQ ID NO 1328
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1328
caacatccat caatga                                                    16

<210> SEQ ID NO 1329
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1329
tgcaacatcc atcaat                                                    16
```

```
<210> SEQ ID NO 1330
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1330
atgcaacatc catcaa                                                       16

<210> SEQ ID NO 1331
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1331
aatgcaacat ccatca                                                       16

<210> SEQ ID NO 1332
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1332
acccaatgca acatcc                                                       16

<210> SEQ ID NO 1333
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1333
tacccaatgc aacatc                                                       16

<210> SEQ ID NO 1334
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1334
atacccaatg caacat                                                       16

<210> SEQ ID NO 1335
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1335
gatggtgtta tctccg                                                       16

<210> SEQ ID NO 1336
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1336
tgagtctcaa accagg                                                    16

<210> SEQ ID NO 1337
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1337
aagatggtgt tatctc                                                    16

<210> SEQ ID NO 1338
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1338
agtgagtctc aaacca                                                    16

<210> SEQ ID NO 1339
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1339
gtctagtgtc atggaa                                                    16

<210> SEQ ID NO 1340
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1340
tgtctagtgt catgga                                                    16

<210> SEQ ID NO 1341
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1341
gtcatggaat tttgtg                                                    16

<210> SEQ ID NO 1342
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1342
gtgtcatgga attttg                                                    16

<210> SEQ ID NO 1343
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1343
tagtgtcatg gaattt                                                    16

<210> SEQ ID NO 1344
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1344
ctagtgtcat ggaatt                                                    16

<210> SEQ ID NO 1345
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1345
tctagtgtca tggaat                                                    16

<210> SEQ ID NO 1346
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1346
cttgtctagt gtcatg                                                    16

<210> SEQ ID NO 1347
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1347
tcttgtctag tgtcat                                                    16

<210> SEQ ID NO 1348
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1348
ttcttgtcta gtgtca                                                    16

<210> SEQ ID NO 1349
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1349
```
tttcttgtct agtgtc                                                       16

<210> SEQ ID NO 1350
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1350
ctttcttgtc tagtgt                                                       16

<210> SEQ ID NO 1351
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1351
agctttcttg tctagt                                                       16

<210> SEQ ID NO 1352
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1352
tcagctttct tgtcta                                                       16

<210> SEQ ID NO 1353
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1353
catcagcttt cttgtc                                                       16

<210> SEQ ID NO 1354
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: bases at these positions are RNA
<220> FEATURE:
<221> NAME/KEY: misc_feature
<222> LOCATION: (4)..(7)
<223> OTHER INFORMATION: bases at these positions are RNA
<220> FEATURE:
<221> NAME/KEY: misc_feature
<222> LOCATION: (9)..(10)
<223> OTHER INFORMATION: bases at these positions are RNA
<220> FEATURE:
<221> NAME/KEY: misc_feature
<222> LOCATION: (12)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 1354

```
tctgauatga taccta                                                      16

<210> SEQ ID NO 1355
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (3)..(6)
<223> OTHER INFORMATION: bases at these positions are RNA
<220> FEATURE:
<221> NAME/KEY: misc_feature
<222> LOCATION: (8)..(9)
<223> OTHER INFORMATION: bases at these positions are RNA
<220> FEATURE:
<221> NAME/KEY: misc_feature
<222> LOCATION: (11)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 1355
ctgauatgat acctaa                                                      16

<210> SEQ ID NO 1356
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: bases at these positions are RNA
<220> FEATURE:
<221> NAME/KEY: misc_feature
<222> LOCATION: (4)..(7)
<223> OTHER INFORMATION: bases at these positions are RNA
<220> FEATURE:
<221> NAME/KEY: misc_feature
<222> LOCATION: (9)..(9)
<223> OTHER INFORMATION: bases at these positions are RNA
<220> FEATURE:
<221> NAME/KEY: misc_feature
<222> LOCATION: (11)..(12)
<223> OTHER INFORMATION: bases at these positions are RNA
<220> FEATURE:
<221> NAME/KEY: misc_feature
<222> LOCATION: (14)..(16)
<223> OTHER INFORMATION: bases at these positions are RNA

<400> SEQUENCE: 1356
tgtcuagtgt catgga                                                      16
```

MODULATORS OF IRF5 EXPRESSION

CROSS-REFERENCE TO RELATED APPLICATION

The present application claims priority to U.S. Provisional Patent Application No. 62/767,615, filed Nov. 15, 2018, the disclosure of which is incorporated herein by reference in its entirety.

SEQUENCE LISTING

The present application is being filed along with a Sequence Listing in electronic format. The Sequence Listing is provided as a file entitled BIOL0341USLSEQ_ST25.txt created Nov. 5, 2018, which is 324 kb in size. The information in the electronic format of the sequence listing is incorporated herein by reference in its entirety.

FIELD

The present embodiments provide methods, compounds, and compositions useful for inhibiting Interferon Regulatory Factor 5 (IRF5; Humirf5) expression, and in certain instances, reducing the amount of IRF5 protein in a cell or animal, which can be useful for treating, preventing, or ameliorating a disease associated with IRF5.

BACKGROUND

Interferon Regulatory Factor 5 or IRF5 is an important regulator of inflammation and autoimmunity. There is a large body of evidence that links IRF5 risk alleles, which are associated with high expression, to the risk of autoimmune diseases, such as systemic lupus erythematosus, rheumatoid arthritis, systemic sclerosis, inflammatory bowel disease, and multiple sclerosis (Hedl and Abhaham, J. Immunol., 2012, 188: 5348-5356; Kristjansdottir et al., J. Med. Genet. 2008, 45: 362-369; Graham et al., Nature Genet. 2006, 38: 550-555; Graham et al., PNAS, 2007, 104: 6758-6763).

The current standard of medical care for Crohn's disease and ulcerative colitis, the two major forms of inflammatory bowel disease in humans, involves treatment with anti-inflammatory agents, corticosteroids, immunomodulators, including azathioprine, or its active metabolite 6-mercaptopurine, methotrexate, biologic agents, including tumor necrosis factor antagonist therapies, anti-integrin therapies, and anti-interleukin (IL) 12/23 therapy. It is an object herein to provide compounds and compositions of high efficacy and tolerability for the treatment of diseases disclosed herein.

SUMMARY

Certain embodiments provided herein are compounds and methods for reducing the amount or activity of IRF5 mRNA, and in certain embodiments, reducing the amount of IRF5 protein in a cell or individual. In certain embodiments, the individual has a gastrointestinal disease. In certain embodiments, the individual has an inflammatory bowel disease. In certain embodiments, the disease is Crohn's disease. In certain embodiments, the disease is inflammatory bowel disease (IBD). In certain embodiments, the disease is ulcerative colitis. In certain embodiments, the disease is systemic lupus erythematosus (SLE). In certain embodiments, the disease is rheumatoid arthritis. In certain embodiments, the disease is primary biliary cirrhosis. In certain embodiments, the disease is systemic sclerosis. In certain embodiments, the disease is Sjogren's syndrome. In certain embodiments, the disease is multiple sclerosis. In certain embodiments, the disease is scleroderma. In certain embodiments, the disease is interstitial lung disease (SSc-ILD). In certain embodiments, the disease is polycystic kidney disease (PKD). In certain embodiments, the disease is chronic kidney disease (CKD). In certain embodiments, the disease is NASH. In certain embodiments, the disease is liver fibrosis. In certain embodiments, the disease is asthma. In certain embodiments, the disease is severe asthma. Certain compounds provided herein are directed to compounds and compositions that reduce inflammation in an animal.

Certain embodiments provided herein are directed to potent and tolerable compounds and compositions useful for inhibiting IRF5 expression, which can be useful for treating, preventing, ameliorating, or slowing progression of an inflammatory disease. Certain embodiments provided herein are directed to compounds and compositions that are more potent or have greater therapeutic value than compounds publicly disclosed.

DETAILED DESCRIPTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Compounds described by ION number indicate a combination of nucleobase sequence, chemical modification, and motif.

DEFINITIONS

Unless otherwise indicated, the following terms have the following meanings:

"2'-deoxyfuranosyl sugar moiety" or "2'-deoxyfuranosyl sugar" means a furanosyl sugar moiety having two hydrogens at the 2'-position. 2'-deoxyfuranosyl sugar moieties may be unmodified or modified and may be substituted at positions other than the 2'-position or unsubstituted. A β-D-2'-deoxyribosyl sugar moiety in the context of an oligonucleotide is an unsubstituted, unmodified 2'-deoxyfuranosyl and is found in naturally occurring deoxyribonucleic acids (DNA).

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE) refers to a 2'-O (CH$_2$)$_2$—OCH$_3$) in the place of the 2'—OH group of a ribosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"3' target site" refers to the nucleotide of a target nucleic acid which is complementary to the 3'-most nucleotide of a particular compound.

"5' target site" refers to the nucleotide of a target nucleic acid which is complementary to the 5'-most nucleotide of a particular compound.

"5-methylcytosine" means a cytosine with a methyl group attached to the 5 position.

"About" means within ±10% of a value. For example, if it is stated, "the compounds affected about 70% inhibition of PNPLA3", it is implied that PNPLA3 levels are inhibited within a range of 60% and 80%.

"Administration" or "administering" refers to routes of introducing a compound or composition provided herein to an individual to perform its intended function. An example of a route of administration that can be used includes, but is not limited to parenteral administration, such as subcutaneous, intravenous, or intramuscular injection or infusion.

"Administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel or sequentially.

"Amelioration" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable and/or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an oligonucleotide and optionally one or more additional features, such as a conjugate group or terminal group. Examples of antisense compounds include single-stranded and double-stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cell-targeting moiety" means a conjugate group or portion of a conjugate group that is capable of binding to a particular cell type or particular cell types.

"cEt" or "constrained ethyl" means a ribosyl bicyclic sugar moiety wherein the second ring of the bicyclic sugar is formed via a bridge connecting the 4'-carbon and the 2'-carbon, wherein the bridge has the formula: 4'-CH (CH$_3$)—O-2', and wherein the methyl group of the bridge is in the S configuration.

"cEt nucleoside" means a nucleoside comprising a cEt modified sugar moiety.

"Chemical modification" in a compound describes the substitutions or changes through chemical reaction, of any of the units in the compound relative to the original state of such unit. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine ($^mC$) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Conjugate group" means a group of atoms that is attached to an oligonucleotide. Conjugate groups include a conjugate moiety and a conjugate linker that attaches the conjugate moiety to the oligonucleotide.

"Conjugate linker" means a group of atoms comprising at least one bond that connects a conjugate moiety to an oligonucleotide.

"Conjugate moiety" means a group of atoms that is attached to an oligonucleotide via a conjugate linker.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Designing" or "Designed to" refer to the process of designing a compound that specifically hybridizes with a selected nucleic acid molecule.

"Diluent" means an ingredient in a composition that lacks pharmacological activity, but is pharmaceutically necessary or desirable. For example, the diluent in an injected composition can be a liquid, e.g. saline solution.

"Differently modified" means chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Dose" means a specified quantity of a compound or pharmaceutical agent provided in a single administration, or in a specified time period. In certain embodiments, a dose may be administered in two or more boluses, tablets, or injections. For example, in certain embodiments, where subcutaneous administration is desired, the desired dose may require a volume not easily accommodated by a single injection. In such embodiments, two or more injections may be used to achieve the desired dose. In certain embodiments, a dose may be administered in two or more injections to minimize injection site reaction in an individual. In other embodiments, the compound or pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Double-stranded antisense compound" means an antisense compound comprising two oligomeric compounds that are complementary to each other and form a duplex, and wherein one of the two said oligomeric compounds comprises an oligonucleotide.

"Effective amount" means the amount of compound sufficient to effectuate a desired physiological outcome in an individual in need of the compound. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to, the products of transcription and translation.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means the annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

"Immediately adjacent" means there are no intervening elements between the immediately adjacent elements of the same kind (e.g. no intervening nucleobases between the immediately adjacent nucleobases).

"Individual" means a human or non-human animal selected for treatment or therapy.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage. Non-phosphate linkages are referred to herein as modified internucleoside linkages.

"IRF5" means any nucleic acid or protein of IRF5. "IRF5 nucleic acid" means any nucleic acid encoding IRF5. For example, in certain embodiments, an IRF5 nucleic acid includes a DNA sequence encoding IRF5, an RNA sequence transcribed from DNA encoding IRF5 (including genomic DNA comprising introns and exons), and an mRNA sequence encoding IRF5. "IRF5 mRNA" means an mRNA encoding a IRF5 protein. The target may be referred to in either upper or lower case.

"IRF5 specific inhibitor" refers to any agent capable of specifically inhibiting IRF5 RNA and/or IRF5 protein expression or activity at the molecular level. For example, IRF5 specific inhibitors include nucleic acids (including antisense compounds), peptides, antibodies, small molecules, and other agents capable of inhibiting the expression of IRF5 RNA and/or IRF5 protein.

"Lengthened oligonucleotides" are those that have one or more additional nucleosides relative to an oligonucleotide disclosed herein, e.g. a parent oligonucleotide.

"Linked nucleosides" means adjacent nucleosides linked together by an internucleoside linkage.

"Linker-nucleoside" means a nucleoside that links an oligonucleotide to a conjugate moiety. Linker-nucleosides are located within the conjugate linker of a compound. Linker-nucleosides are not considered part of the oligonucleotide portion of a compound even if they are contiguous with the oligonucleotide.

"Mismatch" or "non-complementary" means a nucleobase of a first oligonucleotide that is not complementary to the corresponding nucleobase of a second oligonucleotide or target nucleic acid when the first and second oligonucleotides are aligned. For example, nucleobases including but not limited to a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modulating" refers to changing or adjusting a feature in a cell, tissue, organ or organism. For example, modulating IRF5 RNA can mean to increase or decrease the level of IRF5 RNA and/or IRF5 protein in a cell, tissue, organ or organism. A "modulator" effects the change in the cell, tissue, organ or organism. For example, an IRF5 compound can be a modulator that decreases the amount of IRF5 RNA and/or IRF5 protein in a cell, tissue, organ or organism.

"MOE" means methoxyethyl.

"Monomer" refers to a single unit of an oligomer. Monomers include, but are not limited to, nucleosides and nucleotides.

"Motif" means the pattern of unmodified and/or modified sugar moieties, nucleobases, and/or internucleoside linkages, in an oligonucleotide.

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Oligomeric compound" means a compound comprising a single oligonucleotide and, optionally, one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified. "Unmodified oligonucleotide" means an oligonucleotide that does not comprise any sugar, nucleobase, or internucleoside modification.

"Parent oligonucleotide" means an oligonucleotide whose sequence is used as the basis of design for more oligonucleotides of similar sequence but with different lengths, motifs, and/or chemistries. The newly designed oligonucleotides may have the same or overlapping sequence as the parent oligonucleotide.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutically acceptable carrier or diluent" means any substance suitable for use in administering to an individual. For example, a pharmaceutically acceptable carrier can be a sterile aqueous solution, such as PBS or water-for-injection.

"Pharmaceutically acceptable salts" means physiologically and pharmaceutically acceptable salts of compounds, such as oligomeric compounds or oligonucleotides, i.e., salts that retain the desired biological activity of the parent compound and do not impart undesired toxicological effects thereto.

"Pharmaceutical agent" means a compound that provides a therapeutic benefit when administered to an individual.

"Pharmaceutical composition" means a mixture of substances suitable for administering to an individual. For example, a pharmaceutical composition may comprise one or more compounds or salt thereof and a sterile aqueous solution.

"Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Prevent" refers to delaying or forestalling the onset, development or progression of a disease, disorder, or condition for a period of time from minutes to indefinitely.

"Prodrug" means a compound in a form outside the body which, when administered to an individual, is metabolized to another form within the body or cells thereof. In certain embodiments, the metabolized form is the active, or more active, form of the compound (e.g., drug). Typically conversion of a prodrug within the body is facilitated by the action of an enzyme(s) (e.g., endogenous or viral enzyme) or chemical(s) present in cells or tissues, and/or by physiologic conditions.

"Reduce" means to bring down to a smaller extent, size, amount, or number.

"RefSeq No." is a unique combination of letters and numbers assigned to a sequence to indicate the sequence is for a particular target transcript (e.g., target gene). Such sequence and information about the target gene (collectively, the gene record) can be found in a genetic sequence database. Genetic sequence databases include the NCBI Reference Sequence database, GenBank, the European Nucleotide Archive, and the DNA Data Bank of Japan (the latter three forming the International Nucleotide Sequence Database Collaboration or INSDC).

"Region" is defined as a portion of the target nucleic acid having at least one identifiable structure, function, or characteristic.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double-stranded siRNA, single-stranded RNA (ssRNA), and microRNA, including microRNA mimics.

"Segments" are defined as smaller or sub-portions of regions within a nucleic acid.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded" in reference to a compound means the compound has only one oligonucleotide.

"Self-complementary" means an oligonucleotide that at least partially hybridizes to itself. A compound consisting of one oligonucleotide, wherein the oligonucleotide of the compound is self-complementary, is a single-stranded compound. A single-stranded compound may be capable of binding to a complementary compound to form a duplex.

"Sites" are defined as unique nucleobase positions within a target nucleic acid.

"Specifically hybridizable" refers to an oligonucleotide having a sufficient degree of complementarity between the oligonucleotide and a target nucleic acid to induce a desired effect, while exhibiting minimal or no effects on non-target nucleic acids. In certain embodiments, specific hybridization occurs under physiological conditions.

"Specifically inhibit" with reference to a target nucleic acid means to reduce or block expression of the target nucleic acid while exhibiting fewer, minimal, or no effects on non-target nucleic acids. Reduction does not necessarily indicate a total elimination of the target nucleic acid's expression.

"Standard cell assay" means assay(s) described in the Examples and reasonable variations thereof.

"Standard in vivo experiment" means the procedure(s) described in the Example(s) and reasonable variations thereof.

"Stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

"Sugar moiety" means an unmodified sugar moiety or a modified sugar moiety. As used herein, "unmodified sugar moiety" means a β-D-ribosyl moiety, as found in naturally occurring RNA, or a β-D-2'-deoxyribosyl sugar moiety as found in naturally occurring DNA. As used herein, "modified sugar moiety" or "modified sugar" means a sugar surrogate or a furanosyl sugar moiety other than a β-D-ribosyl or a β-D-2'-deoxyribosyl. Modified furanosyl sugar moieties may be modified or substituted at a certain position(s) of the sugar moiety, substituted, or unsubstituted, and they may or may not have a stereoconfiguration other than β-D-ribosyl. Modified furanosyl sugar moieties include bicyclic sugars and non-bicyclic sugars.

"Sugar surrogate" means a modified sugar moiety that does not comprise a furanosyl or tetrahydrofuranyl ring (is not a "furanosyl sugar moiety") and that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

"Synergy" or "synergize" refers to an effect of a combination that is greater than additive of the effects of each component alone at the same doses.

"Target gene" refers to a gene encoding a target.

"Targeting" means the specific hybridization of a compound to a target nucleic acid in order to induce a desired effect.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"Target segment" means the sequence of nucleotides of a target nucleic acid to which a compound is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

"Therapeutically effective amount" means an amount of a compound, pharmaceutical agent, or composition that provides a therapeutic benefit to an individual.

"Treat" refers to administering a compound or pharmaceutical composition to an animal in order to effect an alteration or improvement of a disease, disorder, or condition in the animal.

CERTAIN EMBODIMENTS

Certain embodiments provide methods, compounds and compositions for inhibiting Interferon Regulatory Factor 5 (IRF5) expression.

Certain embodiments provide compounds targeted to an IRF5 nucleic acid. In certain embodiments, the IRF5 nucleic acid has the sequence set forth in RefSeq or GENBANK Accession No. U51127.1 (incorporated by reference, disclosed herein as SEQ ID NO: 4); GENBANK Accession No. NT_007933.14 truncated from nucleotides 53761170 to 53774065 (incorporated by reference, disclosed herein as SEQ ID NO: 2); GENBANK Accession No. DC427600.1 (incorporated by reference, disclosed herein as SEQ ID NO: 5); GENBANK Accession No. NM_001098627.3 (incorporated by reference, disclosed herein as SEQ ID NO: 1); GENBANK Accession No. NM_001098629.2 (incorporated by reference, disclosed herein as SEQ ID NO: 3); GENBANK Accession No. NM_001098630.2 (incorporated by reference, disclosed herein as SEQ ID NO: 6); GENBANK Accession No. NM_001242452.2 (incorporated by reference, disclosed herein as SEQ ID NO: 7); GENBANK Accession No. NM_032643.4 (incorporated by reference, disclosed herein as SEQ ID NO: 8); and GENBANK Accession No. NC_000007.14 truncated from nucleotides 128935001 to 128953000 (incorporated by reference, disclosed herein as SEQ ID NO: 9). In certain embodiments, the compound is an antisense compound or oligomeric compound. In certain embodiments, the compound is single-stranded. In certain embodiments, the compound is double-stranded.

In certain embodiments, the compound comprises a modified oligonucleotide 16 linked nucleosides in length. In certain embodiments, the compound is an antisense compound or oligomeric compound.

Certain embodiments provide a compound comprising a modified oligonucleotide 12 to 30 linked nucleosides in length and having a nucleobase sequence comprising the nucleobase sequence of any one of SEQ ID NOs: 37-1356. In certain embodiments, the compound is an antisense compound or oligomeric compound. In certain embodiments, the compound is single-stranded. In certain embodiments, the compound is double-stranded. In certain embodiments, the modified oligonucleotide is 16 to 30 linked nucleosides in length.

Certain embodiments provide a compound comprising a modified oligonucleotide consisting of the nucleobase sequence of any one of SEQ ID NOs: 37-1356. In certain embodiments, the compound is an antisense compound or oligomeric compound. In certain embodiments, the compound is single-stranded. In certain embodiments, the compound is double-stranded.

Certain embodiments provide a compound comprising a modified oligonucleotide 12 to 30 linked nucleosides in length and complementary within nucleobases 4366-4381, 5141-5156, 5140-5160, 5179-5194, 11544-11559, 11542-11596, 11736-11751, 11737-11752, 11720-11790, or 11794-11809 of SEQ ID NO: 2, wherein said modified oligonucleotide is at least 85%, at least 90%, at least 95%, or 100% complementary to SEQ ID NO: 2. In certain embodiments, the compound is an antisense compound or oligomeric compound. In certain embodiments, the compound is single-stranded. In certain embodiments, the compound is double-stranded. In certain embodiments, the modified oligonucleotide is 16 to 30 linked nucleosides in length.

In certain embodiments, compounds target nucleotides 11737-11752 of an IRF5 nucleic acid. In certain embodiments, compounds target within nucleotides 4366-4381, 5141-5156, 5140-5160, 5179-5194, 11544-11559, 11542-11596, 11736-11751, 11737-11752, 11720-11790, or 11794-11809 of an IRF5 nucleic acid having the nucleobase sequence of SEQ ID NO: 2. In certain embodiments, compounds have at least an 8, 9, 10, 11, 12, 13, 14, 15, or 16 contiguous nucleobase portion complementary to an equal length portion within nucleotides 4366-4381, 5141-5156, 5140-5160, 5179-5194, 11544-11559, 11542-11596, 11736-11751, 11737-11752, 11720-11790, or 11794-11809 of an IRF5 nucleic acid having the nucleobase sequence of SEQ ID NO: 2. In certain embodiments, these compounds are antisense compounds, oligomeric compounds, or oligonucleotides.

In certain embodiments, a compound comprises a modified oligonucleotide 12 to 30 linked nucleosides in length and having a nucleobase sequence comprising at least an 8, 9, 10, 11, 12, 13, 14, 15, or 16 contiguous nucleobase portion any one of SEQ ID NOs: 168, 228, 717, 1340, 1270, 1272, and 1294. In certain embodiments, the modified oligonucleotide is 16 to 30 linked nucleosides in length.

In certain embodiments, a compound comprises a modified oligonucleotide 12 to 30 linked nucleosides in length and having a nucleobase sequence comprising any one of SEQ ID NOs: 228, 168, 717, 1340, 1270, 1272, and 1294. In certain embodiments, the modified oligonucleotide is 16 to 30 linked nucleosides in length.

In certain embodiments, a compound comprises a modified oligonucleotide having a nucleobase sequence consisting of any one of SEQ ID NOs: 228, 168, 717, 1340, 1270, 1272, and 1294.

In certain embodiments, compounds targeted to IRF5 are ION 729018, 728958, 785525, 785674, 785675, 786503, 786524, and 786548. Out of over 1,320 compounds that were screened as described in the Examples section below, ION 729018, 728958, 785525, 785674, 785675, 786503, 786524, and 786548 emerged as the top lead compounds. In particular, ION 729018 exhibited significant efficacy and tolerability out of over 1,320 compounds.

In certain embodiments, any of the foregoing modified oligonucleotides comprises at least one modified internucleoside linkage, at least one modified sugar, and/or at least one modified nucleobase.

In certain embodiments, any of the foregoing modified oligonucleotides comprises at least one modified sugar. In certain embodiments, at least one modified sugar comprises a 2'-O-methoxyethyl group. In certain embodiments, at least one modified sugar is a bicyclic sugar, such as a 4'-CH (CH3)-O-2' group, a 4'-CH2-O-2' group, or a 4'-(CH2)2-O-2' group.

In certain embodiments, the modified oligonucleotide comprises at least one modified internucleoside linkage, such as a phosphorothioate internucleoside linkage.

In certain embodiments, any of the foregoing modified oligonucleotides comprises at least one modified nucleobase, such as 5-methylcytosine.

In certain embodiments, any of the foregoing modified oligonucleotides comprises:
  a gap segment consisting of linked deoxynucleosides;
  a 5' wing segment consisting of linked nucleosides; and
  a 3' wing segment consisting of linked nucleosides;
wherein the gap segment is positioned between the 5' wing segment and the 3' wing segment and wherein each nucleoside of each wing segment comprises a modified sugar. In certain embodiments, the modified oligonucleotide is 12 to 30 linked nucleosides in length having a nucleobase sequence comprising the sequence recited in any one of SEQ ID NOs: 228, 168, 717, 1340, 1270, 1272, and 1294. In certain embodiments, the modified oligonucleotide is 16 to 30 linked nucleosides in length having a nucleobase sequence comprising the sequence recited in any one of SEQ ID NOs: 228, 168, 717, 1340, 1270, 1272, and 1294. In certain embodiments, the modified oligonucleotide is 16 linked nucleosides in length having a nucleobase sequence consisting of the sequence recited in any one of SEQ ID NOs: 228, 168, 717, 1340, 1270, 1272, and 1294.

In certain embodiments, a compound comprises or consists of a modified oligonucleotide 12-30 linked nucleobases in length having a nucleobase sequence comprising the sequence recited in any one of SEQ ID NOs: 228, 168, 1270, 1272, and 1294, wherein the modified oligonucleotide comprises
  a gap segment consisting of ten linked deoxynucleosides;
  a 5' wing segment consisting of three linked nucleosides; and
  a 3' wing segment consisting of three linked nucleosides;
wherein the gap segment is positioned between the 5' wing segment and the 3' wing segment, wherein each nucleoside of each wing segment comprises a cEt sugar; wherein each internucleoside linkage is a phosphorothioate linkage and wherein each cytosine is a 5-methylcytosine. In certain embodiments, the modified oligonucleotide consists of 16-30 linked nucleosides. In certain embodiments, the modified oligonucleotide consists of 16 linked nucleosides.

In certain embodiments, a compound consists of a modified oligonucleotide 16 linked nucleobases in length having a nucleobase sequence consists of the sequence recited in SEQ ID NO: 228, wherein the modified oligonucleotide comprises
  a gap segment consisting of ten linked deoxynucleosides;
  a 5' wing segment consisting of three linked nucleosides; and
  a 3' wing segment consisting of three linked nucleosides;
wherein the gap segment is positioned between the 5' wing segment and the 3' wing segment, wherein each nucleoside of each wing segment comprises a cEt sugar; wherein each internucleoside linkage is a phosphorothioate linkage and wherein each cytosine is a 5-methylcytosine.

In certain embodiments, a compound comprises or consists of a modified oligonucleotide 12-30 linked nucleobases in length having a nucleobase sequence comprising the sequence recited in any one of SEQ ID NOs: 717, wherein the modified oligonucleotide comprises
  a gap segment consisting of ten linked deoxynucleosides;
  a 5' wing segment consisting of two linked nucleosides; and
  a 3' wing segment consisting of four linked nucleosides;
wherein the gap segment is positioned between the 5' wing segment and the 3' wing segment, wherein each of the nucleosides in the 5' wing segment comprises a cEt sugar (kk); wherein the nucleosides of the 3' wing segment comprise from 5' to 3' direction of a cEt sugar, a 2'-MOE sugar, a cEt sugar, and a 2'-MOE sugar (keke); wherein each internucleoside linkage is a phosphorothioate linkage and wherein each cytosine is a 5-methylcytosine. In certain embodiments, the modified oligonucleotide consists of 16-30 linked nucleosides. In certain embodiments, the modified oligonucleotide consists of 16 linked nucleosides.

In certain embodiments, a compound comprises or consists of a modified oligonucleotide 12-30 linked nucleobases in length having a nucleobase sequence comprising the sequence recited in any one of SEQ ID NOs: 717 and 1340, wherein the modified oligonucleotide comprises
  a gap segment consisting of nine linked deoxynucleosides;
  a 5' wing segment consisting of two linked nucleosides; and
  a 3' wing segment consisting of five linked nucleosides;
wherein the gap segment is positioned between the 5' wing segment and the 3' wing segment, wherein each of the nucleosides in the 5' wing segment comprises a cEt sugar (kk); wherein the nucleosides of the 3' wing segment from 5' to 3' direction comprise a 2'-MOE sugar, a 2'-MOE sugar, a 2'-MOE sugar, a cEt sugar and a cEt sugar (eeekk); wherein each internucleoside linkage is a phosphorothioate linkage and wherein each cytosine is a 5-methylcytosine. In certain embodiments, the modified oligonucleotide consists of 16-30 linked nucleosides. In certain embodiments, the modified oligonucleotide consists of 16 linked nucleosides.
In certain embodiments, a compound comprises or consists of ION 729018 or salt thereof, having the following chemical structure:
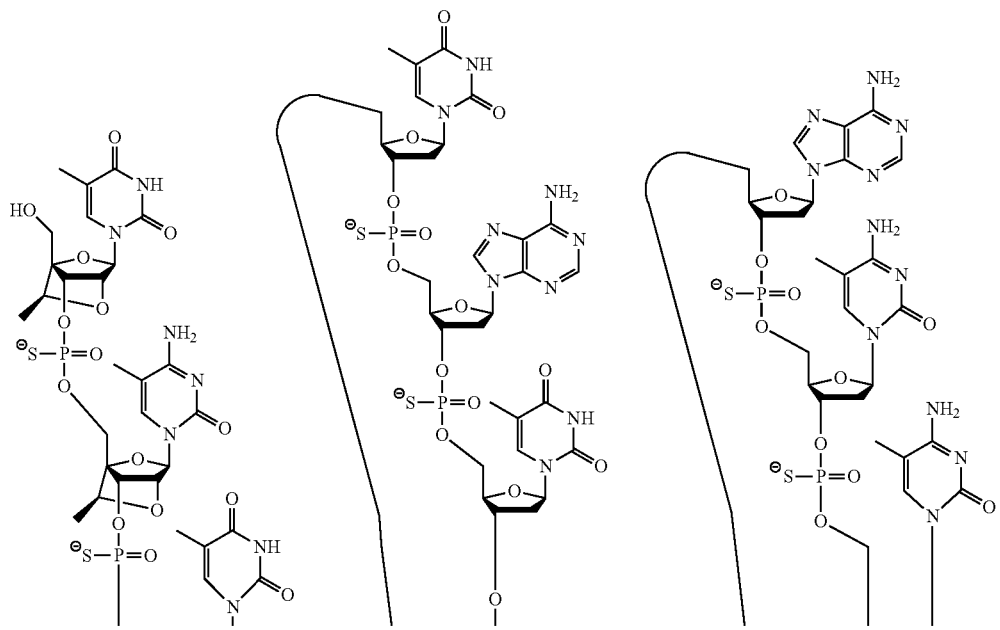
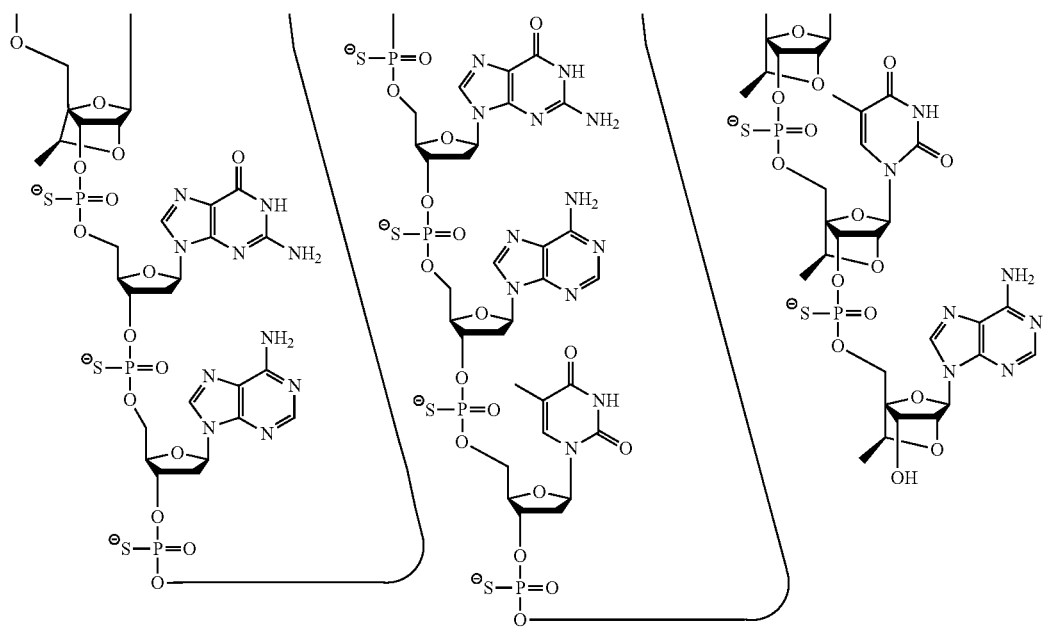

In certain embodiments, a compound comprises or consists of the sodium salt of ION 729018, having the following chemical structure:

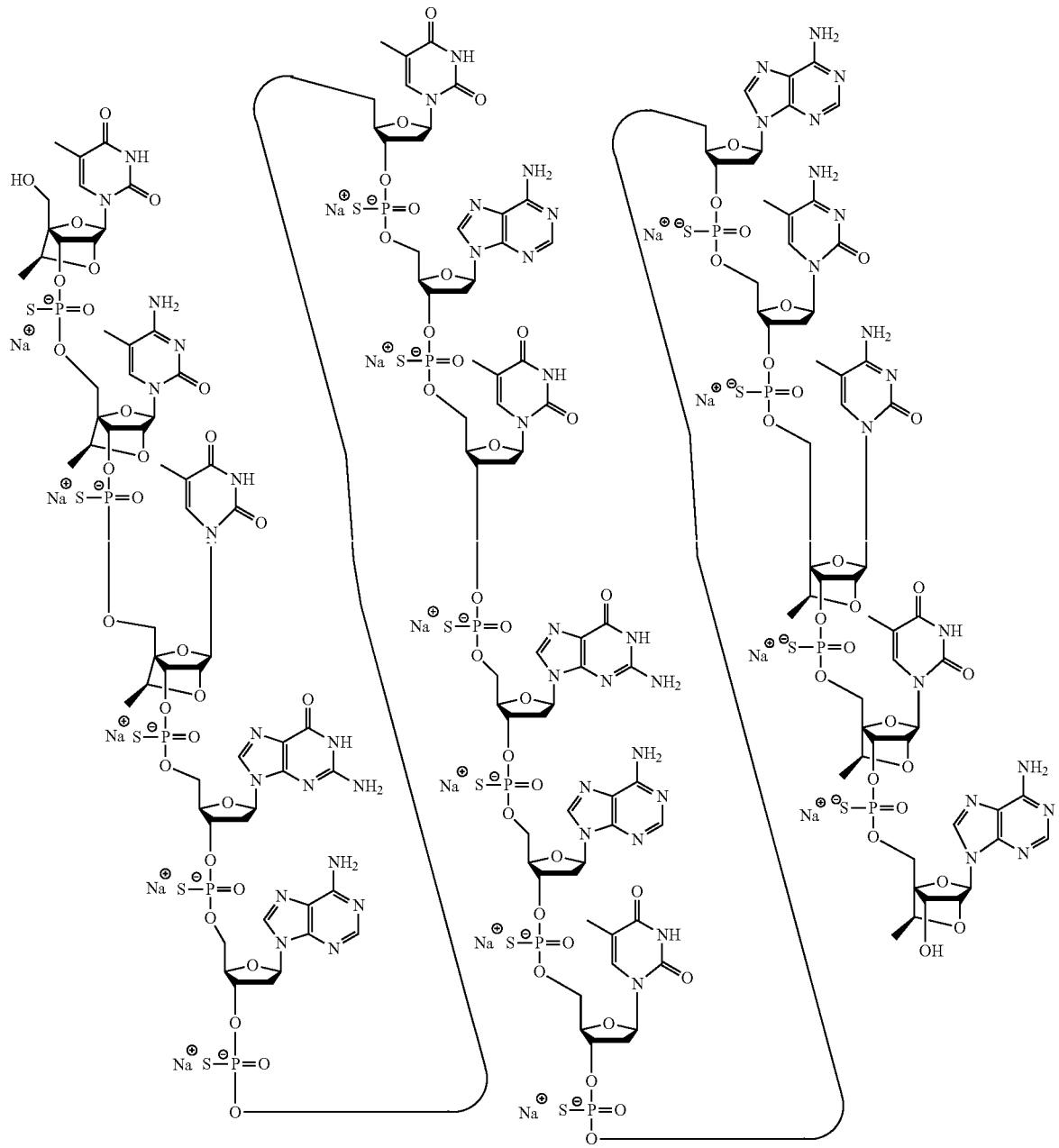

In any of the foregoing embodiments, the compound or oligonucleotide can be at least 85%, at least 90%, at least 95%, at least 98%, at least 99%, or 100% complementary to a nucleic acid encoding IRF5.

In any of the foregoing embodiments, the compound can be single-stranded. In certain embodiments, the compound comprises deoxyribonucleotides. In certain embodiments, the compound is double-stranded. In certain embodiments, the compound is double-stranded and comprises ribonucleotides. In any of the foregoing embodiments, the compound can be an antisense compound or oligomeric compound.

In any of the foregoing embodiments, the compound can be 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides in length. In certain embodiments, the compound comprises or consists of an oligonucleotide.

In certain embodiments, compounds or compositions provided herein comprise a pharmaceutically acceptable salt of the modified oligonucleotide. In certain embodiments, the salt is a sodium salt. In certain embodiments, the salt is a potassium salt.

In certain embodiments, the compounds or compositions as described herein are active by virtue of having at least one of an in vitro $IC_{50}$ of less than 2 µM, less than 1.5 µM, less than 1 µM, less than 0.9 µM, less than 0.8 µM, less than 0.7 µM, less than 0.6 µM, less than 0.5 µM, less than 0.4 µM, less than 0.3 µM, less than 0.2 µM, less than 0.1 µM, less than 0.05 µM, less than 0.04 µM, less than 0.03 µM, less than 0.02 µM, or less than 0.01 µM.

In certain embodiments, the compounds or compositions as described herein are highly tolerable as demonstrated by having at least one of an increase in alanine transaminase (ALT) or aspartate transaminase (AST) value of no more than 4 fold, 3 fold, or 2 fold over control animals, or an increase in liver, spleen, or kidney weight of no more than 30%, 20%, 15%, 12%, 10%, 5%, or 2% compared to control animals. In certain embodiments, the compounds or compositions as described herein are highly tolerable as demonstrated by having no increase of ALT or AST over control animals. In certain embodiments, the compounds or compositions as described herein are highly tolerable as demonstrated by having no increase in liver, spleen, or kidney weight over control animals.

Certain embodiments provide a composition comprising the compound of any of the aforementioned embodiments or any pharmaceutically acceptable salt thereof and at least one of a pharmaceutically acceptable carrier or diluent. In certain embodiments, the composition has a viscosity less than about 40 centipoise (cP), less than about 30 centipose (cP), less than about 20 centipose (cP), less than about 15 centipose (cP), or less than about 10 centipoise (cP). In certain embodiments, the composition having any of the aforementioned viscosities comprises a compound provided herein at a concentration of about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL. In certain embodiments, the composition having any of the aforementioned viscosities and/or compound concentrations has a temperature of room temperature, or about 20° C., about 21° C., about 22° C., about 23° C., about 24° C., about 25° C., about 26° C., about 27° C., about 28° C., about 29° C., or about 30° C.

Certain Indications

Certain embodiments provided herein relate to methods of inhibiting IRF5 expression, which can be useful for treating, preventing, or ameliorating a disease associated with IRF5 in an individual, by administration of a compound that targets IRF5. In certain embodiments, the compound can be a IRF5 specific inhibitor. In certain embodiments, the compound can be an antisense compound, an oligomeric compound, or an oligonucleotide targeted to IRF5.

Examples of diseases associated with IRF5 treatable, preventable, and/or ameliorable with the methods provided herein include inflammatory bowel disease (IBD), ulcerative colitis, Crohn's disease, systemic lupus erythematosus (SLE), rheumatoid arthritis, primary biliary cirrhosis, systemic sclerosis, Sjogren's syndrome, multiple sclerosis, scleroderma, interstitial lung disease (SSc-ILD), polycystic kidney disease (PKD), chronic kidney disease (CKD), NASH, liver fibrosis, asthma, and severe asthma. Certain compounds provided herein are directed to compounds and compositions that reduce inflammation, cirrhosis, fibrosis, proteinuria, joint inflammation, autoantibody production, inflammatory cell infiltration, collagen deposits, or inflammatory cytokine production in an individual. Certain compounds provided herein are directed to compounds and compositions that reduce inflammation in the gastrointestinal tract, diarrhea, pain, fatigue, abdominal cramping, blood in the stool, intestinal inflammation, disruption of the epithelial barrier of the gastrointestinal tract, dysbiosis, increased bowel frequency, tenesmus or painful spasms of the anal sphincter, constipation, or unintended weight loss in an individual, comprising administering a compound targeted to IRF5 to the individual, thereby reducing or inhibiting reduces inflammation in the gastrointestinal tract, diarrhea, pain, fatigue, abdominal cramping, blood in the stool, intestinal inflammation, disruption of the epithelial barrier of the gastrointestinal tract, dysbiosis, increased bowel frequency, tenesmus or painful spasms of the anal sphincter, constipation, or unintended weight loss in an individual.

In certain embodiments, a method of treating, preventing, or ameliorating a disease associated with IRF5 in an individual comprises administering to the individual a compound comprising a IRF5 specific inhibitor, thereby treating, preventing, or ameliorating the disease. In certain embodiments, the individual is identified as having, or at risk of having, a disease associated with IRF5. In certain embodiments, the disease is an inflammatory disease. In certain embodiments, the disease is an gastrointestinal disease. In certain embodiments, the gastrointestinal disease is ulcerative colitis or Crohn's disease. In certain embodiments, the compound comprises an antisense compound targeted to IRF5. In certain embodiments, the compound comprises an oligonucleotide targeted to IRF5. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 37-1356. In certain embodiments, a compound comprises a modified oligonucleotide 12 to 30 linked nucleosides in length and having a nucleobase sequence comprising the nucleobase sequence of any one of SEQ ID NOs: 37-1356. In certain embodiments, a compound comprises a modified oligonucleotide consisting of the nucleobase sequence of any one of SEQ ID NOs: 37-1356. In certain embodiments, a compound comprises a modified oligonucleotide 16 to 30 linked nucleosides in length having a nucleobase sequence comprising any one of SEQ ID NOs: 228, 168, 717, 1340, 1270, 1272, and 1294. In certain embodiments, a compound comprises a modified oligonucleotide having a nucleobase sequence consisting of any one of SEQ ID NOs: 228, 168, 717, 1340, 1270, 1272, and 1294. In certain embodiments, the compound is ION 729018, 728958, 785525, 785674, 785675, 786503, 786524, or 786548. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound improves, preserves, or prevents inflammation, cirrhosis, fibrosis, proteinuria, joint inflammation, autoantibody production, inflammatory cell infiltration, collagen deposits, or inflammatory cytokine production in an animal.

In certain embodiments, a method of treating, preventing, or ameliorating inflammation, cirrhosis, fibrosis, proteinuria, joint inflammation, autoantibody production, inflammatory cell infiltration, collagen deposits, or inflammatory cytokine production in an animal comprises administering to the individual a compound comprising a IRF5 specific inhibitor, thereby treating, preventing, or ameliorating inflammation, cirrhosis, fibrosis, proteinuria, joint inflammation, autoantibody production, inflammatory cell infiltration, collagen deposits, or inflammatory cytokine production. In certain embodiments, a method of treating, preventing, or ameliorating inflammation in the gastrointestinal tract, diarrhea, pain, fatigue, abdominal cramping, blood in the stool, intestinal inflammation, disruption of the epithelial barrier of the gastrointestinal tract, dysbiosis, increased bowel frequency, tenesmus or painful spasms of the anal sphincter, constipation, or unintended weight loss in an individual, comprising administering a compound targeted to IRF5 to the individual, thereby reducing or inhibiting reduces inflammation in the gastrointestinal tract, diarrhea, pain, fatigue, abdominal cramping, blood in the stool, intestinal inflammation, disruption of the epithelial barrier of the gastrointestinal tract, dysbiosis, increased bowel frequency, tenesmus or painful spasms of the anal sphincter, constipation, or unintended weight loss. In certain embodiments, the compound comprises an antisense compound targeted to IRF5. In certain embodiments, the compound comprises an oligonucleotide targeted to IRF5. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 37-1356. In certain embodiments, a compound comprises a modified oligonucleotide 12 to 30 linked nucleosides in length and having a nucleobase sequence comprising the nucleobase sequence of any one of SEQ ID NOs: 37-1356. In certain embodiments, a compound comprises a modified oligonucleotide consisting of the nucleobase sequence of any one of SEQ ID NOs: 37-1356. In certain embodiments, a compound comprises a modified oligonucleotide 16 to 30 linked nucleosides in length having a nucleobase sequence comprising any one of SEQ ID NOs: 228, 168, 717, 1340, 1270, 1272, and 1294. In certain embodiments, a compound comprises a modified oligonucleotide having a nucleobase sequence consisting of any one of SEQ ID NOs: 228, 168, 717, 1340, 1270, 1272, and 1294. In certain embodiments, the compound is ION 729018, 728958, 785525, 785674, 785675, 786503, 786524, or 786548. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound improves, preserves, or prevents inflammation, cirrhosis, fibrosis, proteinuria, joint inflammation, autoantibody production, inflammatory cell infiltration, collagen deposits, or inflammatory cytokine production. In certain embodiments, administering the compound improves, preserves, or prevents inflammation in the gastrointestinal tract, diarrhea, pain, fatigue, abdominal cramping, blood in the stool, intestinal inflammation, disruption of the epithelial barrier of the gastrointestinal tract, dysbiosis, increased bowel frequency, tenesmus or painful spasms of the anal sphincter, constipation, or unintended weight loss in an individual. In certain embodiments, the individual is identified as having, or at risk of having, a disease associated with IRF5.

In certain embodiments, a method of inhibiting expression of IRF5 in an individual having, or at risk of having, a disease associated with IRF5 comprises administering to the individual a compound comprising a IRF5 specific inhibitor, thereby inhibiting expression of IRF5 in the individual. In certain embodiments, administering the compound inhibits expression of IRF5 in the gastrointestinal tract. In certain embodiments, administering the compound inhibits expression of IRF5 in the liver. In certain embodiments, administering the compound inhibits expression of IRF5 in the lungs. In certain embodiments, administering the compound inhibits expression of IRF5 in the kidneys. In certain embodiments, administering the compound inhibits expression of IRF5 in the joints. In certain embodiments, the disease is an inflammatory disease. In certain embodiments, the disease is a gastrointestinal disease. In certain embodiments, the gastrointestinal disease is ulcerative colitis or Crohn's disease. In certain embodiments, the individual has, or is at risk of having, inflammatory bowel disease (IBD), systemic lupus erythematosus (SLE), rheumatoid arthritis, primary biliary cirrhosis, systemic sclerosis, Sjogren's syndrome, multiple sclerosis, scleroderma, interstitial lung disease (SSc-ILD), polycystic kidney disease (PKD), chronic kidney disease (CKD), NASH, liver fibrosis, asthma, or severe asthma. In certain embodiments, the individual has, or is at risk of having, inflammation, cirrhosis, fibrosis, proteinuria, joint inflammation, autoantibody production, inflammatory cell infiltration, collagen deposits, or inflammatory cytokine production. In certain embodiments, the individual has, or is at risk of having, inflammation in the gastrointestinal tract, diarrhea, pain, fatigue, abdominal cramping, blood in the stool, intestinal inflammation, disruption of the epithelial barrier of the gastrointestinal tract, dysbiosis, increased bowel frequency, tenesmus or painful spasms of the anal sphincter, constipation, or unintended weight loss. In certain embodiments, the compound comprises an antisense compound targeted to IRF5. In certain embodiments, the compound comprises an oligonucleotide targeted to IRF5. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 37-1356. In certain embodiments, a compound comprises a modified oligonucleotide 12 to 30 linked nucleosides in length and having a nucleobase sequence comprising the nucleobase sequence of any one of SEQ ID NOs: 37-1356. In certain embodiments, a compound comprises a modified oligonucleotide consisting of the nucleobase sequence of any one of SEQ ID NOs: 37-1356. In certain embodiments, a compound comprises a modified oligonucleotide 16 to 30 linked nucleosides in length having a nucleobase sequence comprising any one of SEQ ID NOs: 228, 168, 717, 1340, 1270, 1272, and 1294. In certain embodiments, a compound comprises a modified oligonucleotide having a nucleobase sequence consisting of any one of SEQ ID NOs: 228, 168, 717, 1340, 1270, 1272, and 1294. In certain embodiments, the compound is ION 729018, 728958, 785525, 785674, 785675, 786503, 786524, or 786548. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound improves, preserves, or prevents inflammation, cirrhosis, fibrosis, proteinuria, joint inflammation, autoantibody production, inflammatory cell infiltration, collagen deposits, or inflammatory cytokine production. In certain embodiments, administering the compound improves, preserves, or prevents inflammation in the gastrointestinal tract, diarrhea, pain, fatigue, abdominal cramping, blood in the stool, intestinal inflammation, disruption of the epithelial barrier of the gastrointestinal tract, dysbiosis, increased bowel frequency, tenesmus or painful spasms of the anal sphincter, constipation, or unintended weight loss.

In certain embodiments, a method of inhibiting expression of IRF5 in a cell comprises contacting the cell with a compound comprising a IRF5 specific inhibitor, thereby inhibiting expression of IRF5 in the cell. In certain embodiments, the cell is a gastrointestinal tract cell. In certain embodiments, the cell is a liver cell. In certain embodiments, the cell is a kidney cell. In certain embodiments, the cell is a lung cell. In certain embodiments, the cell is in the gastrointestinal tract, the lungs, the liver, the kidney, or any other organ. In certain embodiments, the cell is in the gastrointestinal tract of an individual who has, or is at risk of having, inflammation in the gastrointestinal tract, diarrhea, pain, fatigue, abdominal cramping, blood in the stool, intestinal inflammation, disruption of the epithelial barrier of the gastrointestinal tract, dysbiosis, increased bowel frequency, tenesmus or painful spasms of the anal sphincter, constipation, or unintended weight loss. In certain embodiments, the compound comprises an antisense compound targeted to IRF5. In certain embodiments, the compound comprises an oligonucleotide targeted to IRF5. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 37-1356. In certain embodiments, a compound comprises a modified oligonucleotide 12 to 30 linked nucleosides in length and having a nucleobase sequence comprising the nucleobase sequence of any one of SEQ ID NOs: 37-1356. In certain embodiments, a compound comprises a modified oligonucleotide consisting of the nucleobase sequence of any one of SEQ ID NOs: 37-1356. In certain embodiments, a compound comprises a modified oligonucleotide 16 to 30 linked nucleosides in length having a nucleobase sequence comprising any one of SEQ ID NOs: 228, 168, 717, 1340, 1270, 1272, and 1294. In certain embodiments, a compound comprises a modified oligonucleotide having a nucleobase sequence consisting of any one of SEQ ID NOs: 228, 168, 717, 1340, 1270, 1272, and 1294. In certain embodiments, the compound is ION 729018, 728958, 785525, 785674, 785675, 786503, 786524, or 786548. In any of the foregoing embodiments, the compound can be single-stranded or double-stranded. In any of the foregoing embodiments, the compound can be an antisense compound or oligomeric compound.

In certain embodiments, a method of reducing or inhibiting inflammation, cirrhosis, fibrosis, proteinuria, joint inflammation, autoantibody production, inflammatory cell infiltration, collagen deposits, or inflammatory cytokine production in an individual having, or at risk of having, a disease associated with IRF5 comprises administering to the individual a compound comprising a IRF5 specific inhibitor, thereby reducing or inhibiting inflammation, cirrhosis, fibrosis, proteinuria, joint inflammation, autoantibody production, inflammatory cell infiltration, collagen deposits, or inflammatory cytokine production in the individual. In certain embodiments, a method of reducing or inhibiting inflammation in the gastrointestinal tract, diarrhea, pain, fatigue, abdominal cramping, blood in the stool, intestinal inflammation, disruption of the epithelial barrier of the gastrointestinal tract, dysbiosis, increased bowel frequency, tenesmus or painful spasms of the anal sphincter, constipation, or unintended weight loss in an individual having, or at risk of having, a disease associated with IRF5 comprises administering to the individual a compound comprising a IRF5 specific inhibitor, thereby reducing or inhibiting inflammation in the gastrointestinal tract, diarrhea, pain, fatigue, abdominal cramping, blood in the stool, intestinal inflammation, disruption of the epithelial barrier of the gastrointestinal tract, dysbiosis, increased bowel frequency, tenesmus or painful spasms of the anal sphincter, constipation, or unintended weight loss in the individual. In certain embodiments, the individual has, or is at risk of having, inflammatory bowel disease (IBD), systemic lupus erythematosus (SLE), rheumatoid arthritis, primary biliary cirrhosis, systemic sclerosis, Sjogren's syndrome, multiple sclerosis, scleroderma, interstitial lung disease (SSc-ILD), polycystic kidney disease (PKD), chronic kidney disease (CKD), NASH, liver fibrosis, asthma, or severe asthma. In certain embodiments, the compound comprises an antisense compound targeted to IRF5. In certain embodiments, the compound comprises an oligonucleotide targeted to IRF5. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 37-1356. In certain embodiments, a compound comprises a modified oligonucleotide 12 to 30 linked nucleosides in length and having a nucleobase sequence comprising the nucleobase sequence of any one of SEQ ID NOs: 37-1356. In certain embodiments, a compound comprises a modified oligonucleotide consisting of the nucleobase sequence of any one of SEQ ID NOs: 37-1356. In certain embodiments, a compound comprises a modified oligonucleotide 16 to 30 linked nucleosides in length having a nucleobase sequence comprising any one of SEQ ID NOs: 228, 168, 717, 1340, 1270, 1272, and 1294. In certain embodiments, a compound comprises a modified oligonucleotide having a nucleobase sequence consisting of any one of SEQ ID NOs: 228, 168, 717, 1340, 1270, 1272, and 1294. In certain embodiments, the compound is ION 729018, 728958, 785525, 785674, 785675, 786503, 786524, or 786548. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, the individual is identified as having, or at risk of having, a disease associated with IRF5.

Certain embodiments are drawn to a compound comprising a IRF5 specific inhibitor for use in treating a disease associated with IRF5. In certain embodiments, the disease is inflammatory bowel disease (IBD), systemic lupus erythematosus (SLE), rheumatoid arthritis, primary biliary cirrhosis, systemic sclerosis, Sjogren's syndrome, multiple sclerosis, scleroderma, interstitial lung disease (SSc-ILD), polycystic kidney disease (PKD), chronic kidney disease (CKD), NASH, liver fibrosis, asthma, or severe asthma. In certain embodiments, the compound comprises an antisense compound targeted to IRF5. In certain embodiments, the compound comprises an oligonucleotide targeted to IRF5. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 37-1356. In certain embodiments, a compound comprises a modified oligonucleotide 12 to 30 linked nucleosides in length and having a nucleobase sequence comprising the nucleobase sequence of any one of SEQ ID NOs: 37-1356. In certain embodiments, a compound comprises a modified oligonucleotide consisting of the nucleobase sequence of any one of SEQ ID NOs: 37-1356. In certain embodiments, a compound comprises a modified oligonucleotide 16 to 30 linked nucleosides in length having a nucleobase sequence comprising any one of SEQ ID NOs: 228, 168, 717, 1340, 1270, 1272, and 1294. In certain embodiments, a compound comprises a modified oligonucleotide having a nucleobase sequence consisting of any one of SEQ ID NOs: 228, 168, 717, 1340, 1270, 1272, and 1294. In certain embodiments, the compound is ION 729018, 728958, 785525, 785674, 785675, 786503, 786524, or 786548. In any of the foregoing embodiments, the compound can be single-stranded or double-stranded. In any of the foregoing embodiments, the compound can be an antisense compound or oligomeric compound. In certain embodiments, the compound is administered to the individual parenterally.

Certain embodiments are drawn to a compound comprising an IRF5 specific inhibitor for use in reducing or inhibiting inflammation, cirrhosis, fibrosis, proteinuria, joint inflammation, autoantibody production, inflammatory cell infiltration, collagen deposits, or inflammatory cytokine production in an individual having, or at risk of having, inflammatory bowel disease (IBD), systemic lupus erythematosus (SLE), rheumatoid arthritis, primary biliary cirrhosis, systemic sclerosis, Sjogren's syndrome, multiple sclerosis, scleroderma, interstitial lung disease (SSc-ILD), polycystic kidney disease (PKD), chronic kidney disease (CKD), NASH, liver fibrosis, asthma, or severe asthma. In certain embodiments, the IRF5 specific inhibitor for use reduces or inhibits inflammation in the gastrointestinal tract, diarrhea, pain, fatigue, abdominal cramping, blood in the stool, intestinal inflammation, disruption of the epithelial barrier of the gastrointestinal tract, dysbiosis, increased bowel frequency, tenesmus or painful spasms of the anal sphincter, constipation, or unintended weight loss in an individual. In certain embodiments, the compound comprises an antisense compound targeted to IRF5. In certain embodiments, the compound comprises an oligonucleotide targeted to IRF5. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 37-1356. In certain embodiments, a compound comprises a modified oligonucleotide 12 to 30 linked nucleosides in length and having a nucleobase sequence comprising the nucleobase sequence of any one of SEQ ID NOs: 37-1356. In certain embodiments, a compound comprises a modified oligonucleotide consisting of the nucleobase sequence of any one of SEQ ID NOs: 37-1356. In certain embodiments, a compound comprises a modified oligonucleotide 16 to 30 linked nucleosides in length having a nucleobase sequence comprising any one of SEQ ID NOs: 228, 168, 717, 1340, 1270, 1272, and 1294. In certain embodiments, a compound comprises a modified oligonucleotide having a nucleobase sequence consisting of any one of SEQ ID NOs: 228, 168, 717, 1340, 1270, 1272, and 1294. In certain embodiments, the compound is ION 729018, 728958, 785525, 785674, 785675, 786503, 786524, or 786548. In any of the foregoing embodiments, the compound can be single-stranded or double-stranded. In any of the foregoing embodiments, the compound can be an antisense compound or oligomeric compound.

Certain embodiments are drawn to the use of a compound comprising a IRF5 specific inhibitor for the manufacture or preparation of a medicament for treating a disease associated with IRF5. Certain embodiments are drawn to the use of a compound comprising a IRF5 specific inhibitor for the preparation of a medicament for treating a disease associated with IRF5. In certain embodiments, the disease is an inflammatory disease. In certain embodiments, the disease is a gastrointestinal disease. In certain embodiments, the gastrointestinal disease is ulcerative colitis or Crohn's disease. In certain embodiments, the disease is inflammatory bowel disease (IBD), systemic lupus erythematosus (SLE), rheumatoid arthritis, primary biliary cirrhosis, systemic sclerosis, Sjogren's syndrome, multiple sclerosis, scleroderma, interstitial lung disease (SSc-ILD), polycystic kidney disease (PKD), chronic kidney disease (CKD), NASH, liver fibrosis, asthma, or severe asthma. In certain embodiments, the compound comprises an antisense compound targeted to IRF5. In certain embodiments, the compound comprises an oligonucleotide targeted to IRF5. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 37-1356. In certain embodiments, a compound comprises a modified oligonucleotide 12 to 30 linked nucleosides in length and having a nucleobase sequence comprising the nucleobase sequence of any one of SEQ ID NOs: 37-1356. In certain embodiments, a compound comprises a modified oligonucleotide consisting of the nucleobase sequence of any one of SEQ ID NOs: 37-1356. In certain embodiments, a compound comprises a modified oligonucleotide 16 to 30 linked nucleosides in length having a nucleobase sequence comprising any one of SEQ ID NOs: 228, 168, 717, 1340, 1270, 1272, and 1294. In certain embodiments, a compound comprises a modified oligonucleotide having a nucleobase sequence consisting of any one of SEQ ID NOs: 228, 168, 717, 1340, 1270, 1272, and 1294. In certain embodiments, the compound is ION 729018, 728958, 785525, 785674, 785675, 786503, 786524, or 786548. In any of the foregoing embodiments, the compound can be single-stranded or double-stranded. In any of the foregoing embodiments, the compound can be an antisense compound or oligomeric compound.

Certain embodiments are drawn to the use of a compound comprising a IRF5 specific inhibitor for the manufacture or preparation of a medicament for reducing or inhibiting inflammation, cirrhosis, fibrosis, proteinuria, joint inflammation, autoantibody production, inflammatory cell infiltration, collagen deposits, or inflammatory cytokine production in an individual having, or at risk of having, a disease associated with IRF5. In certain embodiments, the IRF5 specific inhibitor for the manufacture or preparation of the medicament reduces or inhibits inflammation in the gastrointestinal tract, diarrhea, pain, fatigue, abdominal cramping, blood in the stool, intestinal inflammation, disruption of the epithelial barrier of the gastrointestinal tract, dysbiosis, increased bowel frequency, tenesmus or painful spasms of the anal sphincter, constipation, or unintended weight loss in an individual. In certain embodiments, the disease is inflammatory bowel disease (IBD), systemic lupus erythematosus (SLE), rheumatoid arthritis, primary biliary cirrhosis, systemic sclerosis, Sjogren's syndrome, multiple sclerosis, scleroderma, interstitial lung disease (SSc-ILD), polycystic kidney disease (PKD), chronic kidney disease (CKD), NASH, liver fibrosis, asthma, or severe asthma. Certain embodiments are drawn to use of a compound comprising a IRF5 specific inhibitor for the preparation of a medicament for treating a disease associated with IRF5. In certain embodiments, the disease is inflammatory bowel disease (IBD), systemic lupus erythematosus (SLE), rheumatoid arthritis, primary biliary cirrhosis, systemic sclerosis, Sjogren's syndrome, multiple sclerosis, scleroderma, interstitial lung disease (SSc-ILD), polycystic kidney disease (PKD), chronic kidney disease (CKD), NASH, liver fibrosis, asthma, or severe asthma. In certain embodiments, the compound comprises an antisense compound targeted to IRF5. In certain embodiments, the compound comprises an oligonucleotide targeted to IRF5. In certain embodiments, a compound comprises a modified oligonucleotide 12 to 30 linked nucleosides in length and having a nucleobase sequence comprising at least 8 contiguous nucleobases of any of the nucleobase sequences of SEQ ID NOs: 37-1356. In certain embodiments, a compound comprises a modified oligonucleotide 12 to 30 linked nucleosides in length and having a nucleobase sequence comprising the nucleobase sequence of any one of SEQ ID NOs: 37-1356. In certain embodiments, a compound comprises a modified oligonucleotide consisting of the nucleobase sequence of any one of SEQ ID NOs: 37-1356. In certain embodiments, a compound comprises a modified oligonucleotide 16 to 30 linked nucleosides in length having a nucleobase sequence comprising any one of SEQ ID NOs: 228, 168, 717, 1340, 1270, 1272, and 1294. In certain embodiments, a compound comprises a modified oligonucleotide having a nucleobase sequence consisting of any one of SEQ ID NOs: 228, 168, 717, 1340, 1270, 1272, and 1294. In certain embodiments, the compound is ION 729018, 728958, 785525, 785674, 785675, 786503, 786524, or 786548. In any of the foregoing embodiments, the compound can be single-stranded or double-stranded. In any of the foregoing embodiments, the compound can be an antisense compound or oligomeric compound.

In any of the foregoing methods or uses, the compound can be targeted to IRF5. In certain embodiments, the compound comprises or consists of a modified oligonucleotide, for example, a modified oligonucleotide 8 to 80 linked nucleosides in length, 10 to 30 linked nucleosides in length, 12 to 30 linked nucleosides in length, or 20 linked nucleosides in length. In certain embodiments, the modified oligonucleotide is at least 80%, at least 85%, at least 90%, at least 95% or 100% complementary to any of the nucleobase sequences recited in SEQ ID NOs: 37-1356. In certain embodiments, the modified oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl modified sugar, and the modified nucleobase is a 5-methylcytosine. In certain embodiments, the modified oligonucleotide comprises a gap segment consisting of linked deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing embodiments, the modified oligonucleotide is 12 to 30, 15 to 30, 15 to 25, 15 to 24, 16 to 24, 17 to 24, 18 to 24, 19 to 24, 20 to 24, 19 to 22, 20 to 22, 16 to 20, or 16 or 20 linked nucleosides in length. In certain embodiments, the modified oligonucleotide is at least 80%, at least 85%, at least 90%, at least 95% or 100% complementary to any of the nucleobase sequences recited in SEQ ID NOs: 37-1356.

In certain embodiments, a compound comprises or consists of a modified oligonucleotide 12-30 linked nucleobases in length having a nucleobase sequence comprising the sequence recited in any one of SEQ ID NOs: 228, 168, 1270, 1272, and 1294, wherein the modified oligonucleotide comprises a gap segment consisting of ten linked deoxynucleosides;
a 5' wing segment consisting of three linked nucleosides; and
a 3' wing segment consisting of three linked nucleosides; wherein the gap segment is positioned between the 5' wing segment and the 3' wing segment, wherein each nucleoside of each wing segment comprises a cEt sugar; wherein each internucleoside linkage is a phosphorothioate linkage and wherein each cytosine is a 5-methylcytosine. In certain embodiments, the modified oligonucleotide consists of 16-30 linked nucleosides. In certain embodiments, the modified oligonucleotide consists of 16 linked nucleosides.

In certain embodiments, a compound consists of a modified oligonucleotide 16 linked nucleobases in length having a nucleobase sequence consists of the sequence recited in SEQ ID NO: 228, wherein the modified oligonucleotide comprises a gap segment consisting of ten linked deoxynucleosides;
a 5' wing segment consisting of three linked nucleosides; and
a 3' wing segment consisting of three linked nucleosides; wherein the gap segment is positioned between the 5' wing segment and the 3' wing segment, wherein each nucleoside of each wing segment comprises a cEt sugar; wherein each internucleoside linkage is a phosphorothioate linkage and wherein each cytosine is a 5-methylcytosine.

In certain embodiments, a compound comprises or consists of a modified oligonucleotide 12-30 linked nucleobases in length having a nucleobase sequence comprising the sequence recited in any one of SEQ ID NOs: 717, wherein the modified oligonucleotide comprises a gap segment consisting of ten linked deoxynucleosides;
a 5' wing segment consisting of two linked nucleosides; and
a 3' wing segment consisting of four linked nucleosides; wherein the gap segment is positioned between the 5' wing segment and the 3' wing segment, wherein each of the nucleosides in the 5' wing segment comprises a cEt sugar (kk); wherein the nucleosides of the 3' wing segment comprise from 5' to 3' direction of a cEt sugar, a 2'-MOE sugar, a cEt sugar, and a 2'-MOE sugar (keke); wherein each internucleoside linkage is a phosphorothioate linkage and wherein each cytosine is a 5-methylcytosine. In certain embodiments, the modified oligonucleotide consists of 16-30 linked nucleosides. In certain embodiments, the modified oligonucleotide consists of 16 linked nucleosides.

In certain embodiments, a compound comprises or consists of a modified oligonucleotide 12-30 linked nucleobases in length having a nucleobase sequence comprising the sequence recited in any one of SEQ ID NOs: 717 and 1340, wherein the modified oligonucleotide comprises a gap segment consisting of nine linked deoxynucleosides;
a 5' wing segment consisting of two linked nucleosides; and
a 3' wing segment consisting of five linked nucleosides; wherein the gap segment is positioned between the 5' wing segment and the 3' wing segment, wherein each of the nucleosides in the 5' wing segment comprises a cEt sugar (kk); wherein the nucleosides of the 3' wing segment from 5' to 3' direction comprise a 2'-MOE sugar, a 2'-MOE sugar, a 2'-MOE sugar, a cEt sugar and a cEt sugar (eeekk); wherein each internucleoside linkage is a phosphorothioate linkage and wherein each cytosine is a 5-methylcytosine. In certain embodiments, the modified oligonucleotide consists of 16-30 linked nucleosides. In certain embodiments, the modified oligonucleotide consists of 16 linked nucleosides.

In certain embodiments, a compound comprises or consists of ION 729018 or salt thereof, having the following chemical structure:

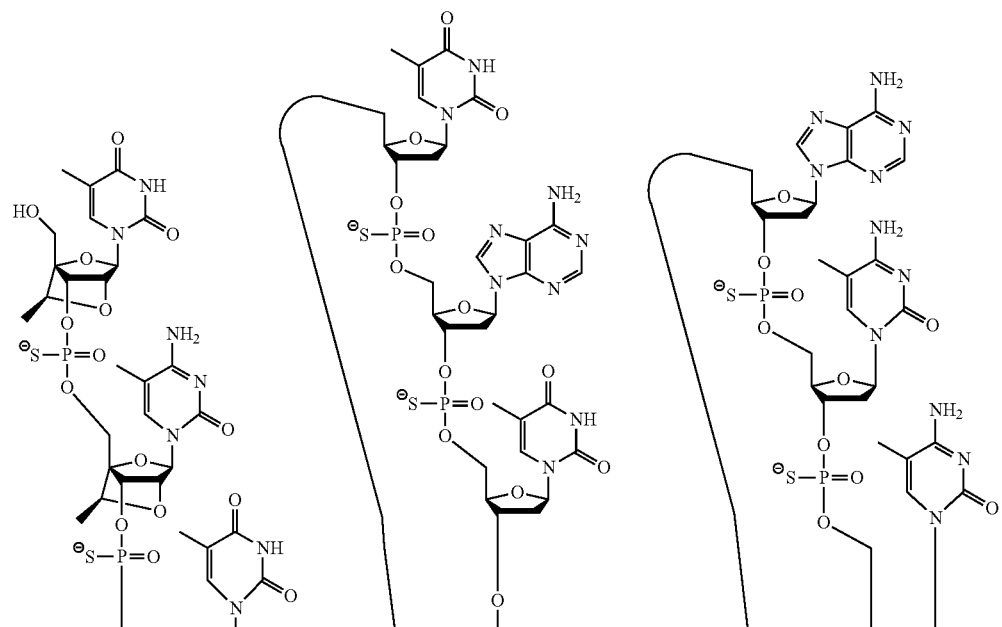
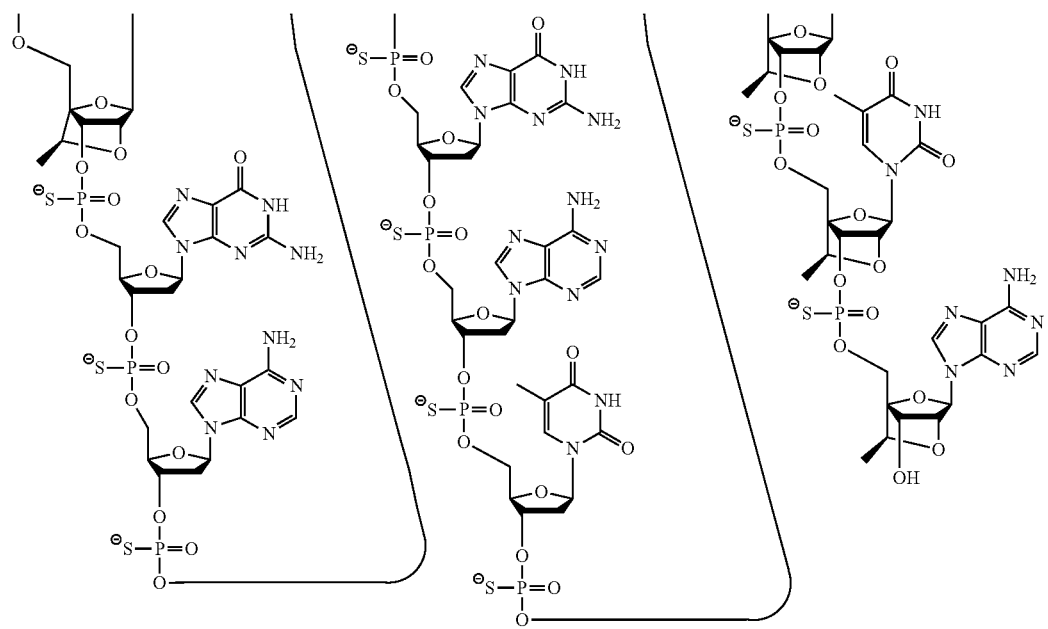

In certain embodiments, a compound comprises or consists of the sodium salt of ION 729018, having the following chemical structure:

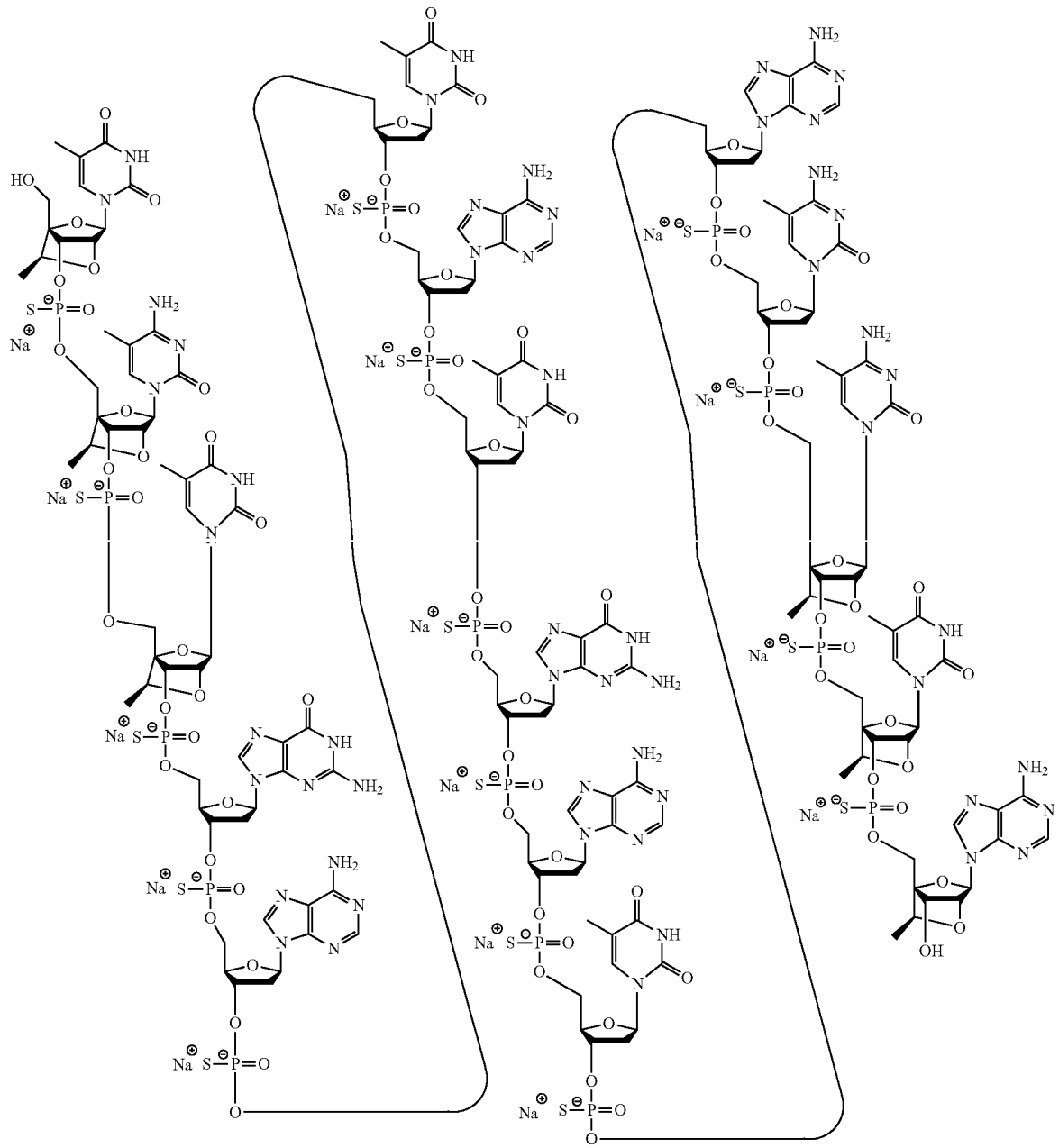

In any of the foregoing methods or uses, the compound can be administered parenterally. For example, in certain embodiments the compound can be administered through injection or infusion. Parenteral administration includes subcutaneous administration, intravenous administration, intramuscular administration, intraarterial administration, intraperitoneal administration, or intracranial administration, e.g. intrathecal or intracerebroventricular administration.

Certain Compounds

In certain embodiments, compounds described herein can be antisense compounds. In certain embodiments, the antisense compound comprises or consists of an oligomeric compound. In certain embodiments, the oligomeric compound comprises a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide and optionally a conjugate group. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, compounds are double-stranded. Such double-stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, compound comprises a conjugate group. In certain embodiments, one of the modified oligonucleotides is conjugated. In certain embodiments, both the modified oligonucleotides are conjugated. In certain embodiments, the first modified oligonucleotide is conjugated. In certain embodiments, the second modified oligonucleotide is conjugated. In certain embodiments, the first modified oligonucleotide is 16-30 linked nucleosides in length and the second modified oligonucleotide is 16-30 linked nucleosides in length. In certain embodiments, one of the modified oligonucleotides has a nucleobase sequence comprising at least 8 contiguous nucleobases of any of SEQ ID NOs: 37-1356.

In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of a modified oligonucleotide and optionally a conjugate group. The oligonucleotide of the second oligomeric compound of such a double-stranded antisense compound may be modified or unmodified. Either or both oligomeric compounds of a double-stranded antisense compound may comprise a conjugate group. The oligomeric compounds of double-stranded antisense compounds may include non-complementary overhanging nucleosides.

Examples of single-stranded and double-stranded compounds include, but are not limited to, oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 12 to 30 linked subunits in length. In certain embodiments, a compound described herein comprises an oligonucleotide 12 to 22 linked subunits in length. In certain embodiments, compound described herein comprises an oligonucleotide 14 to 30 linked subunits in length. In certain embodiments, compound described herein comprises an oligonucleotide 14 to 20 linked subunits in length. In certain embodiments, a compound described herein comprises an oligonucleotide 15 to 30 linked subunits in length. In certain embodiments, a compound described herein comprises an oligonucleotide 15 to 20 linked subunits in length. In certain embodiments, a compound described herein comprises an oligonucleotide 16 to 30 linked subunits in length. In certain embodiments, a compound described herein comprises an oligonucleotide 16 to 20 linked subunits in length. In certain embodiments, a compound described herein comprises an oligonucleotide 17 to 30 linked subunits in length. In certain embodiments, a compound described herein comprises an oligonucleotide 17 to 20 linked subunits in length. In certain embodiments, a compound described herein comprises an oligonucleotide 18 to 30 linked subunits in length. In certain embodiments, a compound described herein comprises an oligonucleotide 18 to 20 linked subunits in length. In certain embodiments, a compound described herein comprises an oligonucleotide 20 to 30 linked subunits in length. In other words, such oligonucleotides are 12 to 30 linked subunits, 14 to 30 linked subunits, 14 to 20 linked subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, or 20 to 30 subunits in length, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, or 30 linked subunits in length, or a range defined by any two of the above values. In some embodiments the linked subunits are nucleotides, nucleosides, or nucleobases.

In certain embodiments, the compound may further comprise additional features or elements, such as a conjugate group, that are attached to the oligonucleotide. In certain embodiments, such compounds are antisense compounds. In certain embodiments, such compounds are oligomeric compounds. In embodiments where a conjugate group comprises a nucleoside (i.e. a nucleoside that links the conjugate group to the oligonucleotide), the nucleoside of the conjugate group is not counted in the length of the oligonucleotide.

In certain embodiments, compounds may be shortened or truncated. For example, a single subunit may be deleted from the 5' end (5' truncation), or alternatively from the 3' end (3' truncation). A shortened or truncated compound targeted to a IRF5 nucleic acid may have two subunits deleted from the 5' end, or alternatively, may have two subunits deleted from the 3' end of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively, to the 3' end (3' addition) of the compound. Alternatively, the added subunits may be dispersed throughout the compound.

It is possible to increase or decrease the length of a compound, such as an oligonucleotide, and/or introduce mismatch bases without eliminating activity (Woolf et al. *Proc. Natl. Acad. Sci. USA* 1992, 89:7305-7309; Gautschi et al. *J. Natl. Cancer Inst.* March 2001, 93:463-471; Maher and Dolnick *Nuc. Acid. Res.* 1998, 16:3341-3358). However, seemingly small changes in oligonucleotide sequence, chemistry and motif can make large differences in one or more of the many properties required for clinical development (Seth et al. *J. Med. Chem.* 2009, 52, 10; Egli et al. *J. Am. Chem. Soc.* 2011, 133, 16642).

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence-specific RNAi, for example, short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term "RNAi" is meant to be equivalent to other terms used to describe sequence-specific RNA interference, such as post transcriptional gene silencing, translational inhibition, or epigenetics.

In certain embodiments, a compound described herein can comprise any of the oligonucleotide sequences targeted to IRF5 described herein. In certain embodiments, the compound can be double-stranded. In certain embodiments, the compound comprises a first strand comprising at least an 8, 9, 10, 11, 12, 13, 14, 15, or 16 contiguous nucleobase portion of any one of SEQ ID NOs: 37-1356 and a second strand. In certain embodiments, the compound comprises a first strand comprising the nucleobase sequence of any one of SEQ ID NOs: 37-1356 and a second strand. In certain embodiments, the compound comprises ribonucleotides in which the first strand has uracil (U) in place of thymine (T) in any one of SEQ ID NOs: 37-1356. In certain embodiments, the compound comprises (i) a first strand comprising a nucleobase sequence complementary to the site on IRF5 to which any of SEQ ID NOs: 37-1356 is targeted, and (ii) a second strand. In certain embodiments, the compound comprises one or more modified nucleotides in which the 2' position of the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains one or two capped strands, as disclosed, for example, by WO 00/63364, filed Apr. 19, 2000.

In certain embodiments, the first strand of the compound is an siRNA guide strand and the second strand of the compound is an siRNA passenger strand. In certain embodiments, the second strand of the compound is complementary to the first strand. In certain embodiments, each strand of the compound is 16, 17, 18, 19, 20, 21, 22, or 23 linked nucleosides in length. In certain embodiments, the first or second strand of the compound can comprise a conjugate group.

In certain embodiments, a compound described herein can comprise any of the oligonucleotide sequences targeted to IRF5 described herein. In certain embodiments, the compound is single stranded. In certain embodiments, such a compound is a single-stranded RNAi (ssRNAi) compound. In certain embodiments, the compound comprises at least an 8, 9, 10, 11, 12, 13, 14, 15, or 16 contiguous nucleobase portion of any one of SEQ ID NOs: 37-1356. In certain embodiments, the compound comprises the nucleobase sequence of any one of SEQ ID NOs: 37-1356. In certain embodiments, the compound comprises ribonucleotides in which uracil (U) is in place of thymine (T) in any one of SEQ ID NOs: 37-1356. In certain embodiments, the compound comprises a nucleobase sequence complementary to the site on IRF5 to which any of SEQ ID NOs: 37-1356 is targeted. In certain embodiments, the compound comprises one or more modified nucleotides in which the 2' position in the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains a capped strand, as disclosed, for example, by WO 00/63364, filed Apr. 19, 2000. In certain embodiments, the compound consists of 16, 17, 18, 19, 20, 21, 22, or 23 linked nucleosides. In certain embodiments, the compound can comprise a conjugate group.

Certain Mechanisms

In certain embodiments, compounds described herein comprise or consist of modified oligonucleotides. In certain embodiments, compounds described herein are antisense compounds. In certain embodiments, compounds comprise oligomeric compounds. In certain embodiments, compounds described herein are capable of hybridizing to a target nucleic acid, resulting in at least one antisense activity. In certain embodiments, compounds described herein selectively affect one or more target nucleic acid. Such compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

Nucleotide sequences that encode IRF5 include, without limitation, the following: RefSeq or GENBANK Accession No. U51127.1 (incorporated by reference, disclosed herein as SEQ ID NO: 4); GENBANK Accession No. NT_007933.14 truncated from nucleotides 53761170 to 53774065 (incorporated by reference, disclosed herein as SEQ ID NO: 2); GENBANK Accession No. DC427600.1 (incorporated by reference, disclosed herein as SEQ ID NO: 5); GENBANK Accession No. NM_001098627.3 (incorporated by reference, disclosed herein as SEQ ID NO: 1); GENBANK Accession No. NM_001098629.2 (incorporated by reference, disclosed herein as SEQ ID NO: 3); GENBANK Accession No. NM_001098630.2 (incorporated by reference, disclosed herein as SEQ ID NO: 6); GENBANK Accession No. NM_001242452.2 (incorporated by reference, disclosed herein as SEQ ID NO: 7); GENBANK Accession No. NM_032643.4 (incorporated by reference, disclosed herein as SEQ ID NO: 8); and GENBANK Accession No. NC_000007.14 truncated from nucleotides 128935001 to 128953000 (incorporated by reference, disclosed herein as SEQ ID NO: 9).

Hybridization

In some embodiments, hybridization occurs between a compound disclosed herein and a IRF5 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a IRF5 nucleic acid.

Complementarity

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine (mC) and guanine (G), unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a IRF5 nucleic acid may be tolerated provided that the compound remains able to specifically hybridize to a target nucleic acid. Moreover, a compound may hybridize over one or more segments of a IRF5 nucleic acid such that intervening or adjacent segments are not involved in the hybridization event (e.g., a loop structure, mismatch or hairpin structure).

In certain embodiments, the compounds provided herein, or a specified portion thereof are at least, or are up to 70%, 80%, 85%, 86%, 87%, 88%, 89%, 90%, 91%, 92%, 93%, 94%, 95%, 96%, 97%, 98%, 99%, or 100% complementary to a IRF5 nucleic acid, a target region, target segment, or specified portion thereof. In certain embodiments, the compounds provided herein, or a specified portion thereof, are 70% to 75%, 75% to 80%, 80% to 85%, 85% to 90%, 90% to 95%, 95% to 100%, or any number in between these ranges, complementary to a IRF5 nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid. Percent complementarity of a compound with a region of a target nucleic acid can be determined routinely using BLAST programs (basic local alignment search tools) and PowerBLAST programs known in the art (Altschul et al., *J. Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e. 100% complementary) to a target nucleic acid, or specified portion thereof. For example, a compound may be fully complementary to a IRF5 nucleic acid, or a target region, or a target segment or target sequence thereof. As used herein, "fully complementary" means each nucleobase of a compound is complementary to the corresponding nucleobase of a target nucleic acid. For example, a 20 nucleobase compound is fully complementary to a target sequence that is 400 nucleobases long, so long as there is a corresponding 20 nucleobase portion of the target nucleic acid that is fully complementary to the compound. "Fully complementary" can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments, selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e. linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a IRF5 nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a IRF5 nucleic acid, or specified portion thereof.

In certain embodiments, compounds described herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of a compound. In certain embodiments, the compounds, are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 17, 18, 19, 20, or more nucleobase portion of a target segment, or a range defined by any two of these values.

Identity

The compounds provided herein may also have a defined percent identity to a particular nucleotide sequence, SEQ ID NO, or compound represented by a specific ION number, or portion thereof. In certain embodiments, compounds described herein are antisense compounds or oligomeric compounds. In certain embodiments, compounds described herein are modified oligonucleotides. As used herein, a compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of a compound is calculated according to the number of bases that have identical base pairing relative to the sequence to which it is being compared.

In certain embodiments, compounds described herein, or portions thereof, are, or are at least, 70%, 75%, 80%, 85%, 90%, 91%, 92%, 93%, 94%, 95%, 96%, 97%, 98%, 99% or 100% identical to one or more of the compounds or SEQ ID NOs, or a portion thereof, disclosed herein. In certain embodiments, compounds described herein are about 70%, 75%, 80%, 85%, 90%, 91%, 92%, 93%, 94%, 95%, 96%, 97%, 98%, or 99% identical, or any percentage between such values, to a particular nucleotide sequence, SEQ ID NO, or compound represented by a specific ION number, or portion thereof, in which the compounds comprise an oligonucleotide having one or more mismatched nucleobases. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

In certain embodiments, compounds described herein comprise or consist of antisense compounds. In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, compounds described herein comprise or consist of oligonucleotides. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Certain Modified Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Modified Nucleosides

Modified nucleosides comprise a modified sugar moiety or a modified nucleobase or both a modified sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified furanosyl sugar moieties comprising one or more acyclic substituent, including, but not limited, to substituents at the 2', 4', and/or 5' positions. In certain embodiments, the furanosyl sugar moiety is a ribosyl sugar moiety. In certain embodiments, one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for linearly non-bicyclic modified sugar moieties include, but are not limited to, alkoxy (e.g., methoxy), alkyl, and those described in Manoharan et al., WO 2015/106128. Examples of 5'-substituent groups suitable for non-bicyclic modified sugar moieties include, but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted nucleoside or 2'-non-bicyclic modified nucleoside comprises a sugar moiety comprising a linear 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a linear 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a linear 2'-substituent group selected from: F, OCH$_3$, and OCH$_2$CH$_2$OCH$_3$.

Nucleosides comprising modified sugar moieties, such as non-bicyclic modified sugar moieties, are referred to by the position(s) of the substitution(s) on the sugar moiety of the nucleoside. For example, nucleosides comprising 2'-substituted or 2'-modified sugar moieties are referred to as 2'-substituted nucleosides or 2'-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. In certain such embodiments, the furanose ring is a ribose ring. Examples of such 4' to 2' bridging sugar substituents include, but are not limited to: 4'-CH$_2$-2', 4'-(CH$_2$)$_2$-2', 4'-(CH$_2$)$_3$-2', 4'-CH$_2$—O-2'

("LNA"), 4'-CH₂—S-2', 4'-(CH₂)₂—O-2' ("ENA"), 4'-CH (CH₃)—O-2' (referred to as "constrained ethyl" or "cEt" when in the S configuration), 4'-CH₂—O—CH₂-2', 4'-CH₂—N(R)-2', 4'-CH(CH₂OCH₃)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH₃)(CH₃)—O-2' and analogs thereof (see, e.g., Seth et al., U.S. Pat. No. 8,278,283), 4'-CH₂—N(OCH₃)-2' and analogs thereof (see, e.g., Prakash et al., U.S. Pat. No. 8,278,425), 4'-CH₂—O—N(CH₃)-2' (see, e.g., Allerson et al., U.S. Pat. No. 7,696,345 and Allerson et al., U.S. Pat. No. 8,124,745), 4'-CH₂—C(H) (CH₃)-2' (see, e.g., Zhou, et al., *J. Org. Chem.*, 2009, 74, 118-134), 4'-CH₂—C(=CH₂)-2' and analogs thereof (see e.g., Seth et al., U.S. Pat. No. 8,278,426), 4'-C(R$_a$R$_b$)—N (R)—O-2', 4'-C(R$_a$R$_b$)—O—N(R)-2', 4'-CH₂—O—N(R)-2', and 4'-CH₂—N(R)—O-2', wherein each R, R$_a$, and R$_b$ is, independently, H, a protecting group, or C₁-C₁₂ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)₂—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C₁-C₁₂ alkyl, substituted C₁-C₁₂ alkyl, C₂-C₁₂ alkenyl, substituted C₂-C₁₂ alkenyl, C₂-C₁₂ alkynyl, substituted C₂-C₁₂ alkynyl, C₅-C₂₀ aryl, substituted C₅-C₂₀ aryl, heterocycle radical, substituted heterocycle radical, heteroaryl, substituted heteroaryl, C₅-C₇ alicyclic radical, substituted C₅-C₇ alicyclic radical, halogen, OJ₁, NJ₁J₂, SJ₁, N₃, COOJ₁, acyl (C(=O)—H), substituted acyl, CN, sulfonyl (S(=O)₂-J₁), or sulfoxyl (S(=O)-J₁); and each J₁ and J₂ is, independently, H, C₁-C₁₂ alkyl, substituted C₁-C₁₂ alkyl, C₂-C₁₂ alkenyl, substituted C₂-C₁₂ alkenyl, C₂-C₁₂ alkynyl, substituted C₂-C₁₂ alkynyl, C₅-C₂₀ aryl, substituted C₅-C₂₀ aryl, acyl (C(=O)—H), substituted acyl, a heterocycle radical, a substituted heterocycle radical, C₁-C₁₂ aminoalkyl, substituted C₁-C₁₂ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Wahlestedt et al., *Proc. Natl. Acad. Sci. U S. A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129, 8362-8379; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. RE44,779; Wengel et al., U.S. Pat. No. 6,794,499, Wengel et al., U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; Allerson et al., US2008/0039618; and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

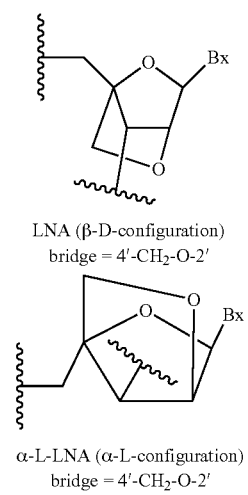

LNA (β-D-configuration)
bridge = 4'-CH₂-O-2'

α-L-LNA (α-L-configuration)
bridge = 4'-CH₂-O-2'

α-L-methyleneoxy (4'-CH₂—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include, but are not limited to, hexitol nucleic acid ("HNA"), anitol nucleic acid ("ANA"), manitol nucleic acid ("MNA") (see e.g., Leumann, C J. *Bioorg. & Med. Chem.* 2002, 10, 841-854), fluoro HNA:

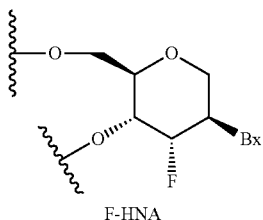

F-HNA ("F-HNA", see e.g., Swayze et al., U.S. Pat. No. 8,088,904; Swayze et al., U.S. Pat. No. 8,440,803; and Swayze et al., U.S. Pat. No. 9,005,906) F-HNA can also be referred to as a F-THP or 3'-fluoro tetrahydropyran, and nucleosides comprising additional modified THP compounds having the formula:

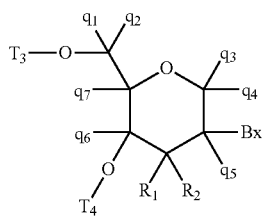

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

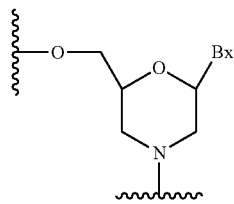

In certain embodiments, morpholinos may be modified, for example, by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include, but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., US2013/130378.

Many other bicyclic and tricyclic sugar and sugar surrogate ring systems are known in the art that can be used in modified nucleosides.

2. Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds.

In certain embodiments, compounds described herein comprise modified oligonucleotides. In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleosides that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (C≡C—$CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly, 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one, and 9-(2-aminoethoxy)-1,3-diazaphenoxazine-2-one (G-clamp). Modified nucleobases may also include those in which the purine or pyrimidine base is replaced with other heterocycles, for example, 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases, as well as other modified nucleobases include without limitation, Manoharan et al., US2003/0158403, Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

In certain embodiments, compounds targeted to a IRF5 nucleic acid comprise one or more modified nucleobases. In certain embodiments, the modified nucleobase is 5-methylcytosine. In certain embodiments, each cytosine is a 5-methylcytosine.

Modified Internucleoside Linkages

The naturally occurring internucleoside linkage of RNA and DNA is a 3' to 5' phosphodiester linkage. In certain embodiments, compounds described herein having one or more modified, i.e. non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

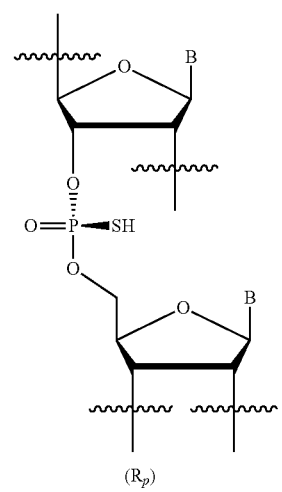

(Rp)

-continued

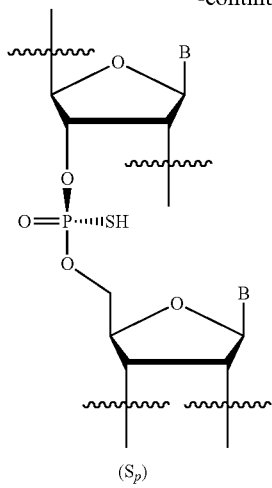

(S_p)

Unless otherwise indicated, chiral internucleoside linkages of modified oligonucleotides described herein can be stereorandom or in a particular stereochemical configuration.

In certain embodiments, compounds targeted to a IRF5 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include, but are not limited to, phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS-P=S"). Representative non-phosphorus containing internucleoside linking groups include, but are not limited to, methylenemethylimino (—CH$_2$—N(CH$_3$)—O—CH$_2$), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include, but are not limited to, alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See, for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments, the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and, if it does have a gapped nucleoside motif, the wing and gap lengths may or may not be the same.

In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, oligonucleotides having a gapmer nucleoside motif comprise a linkage motif comprising all phosphorothioate linkages except for one or two methylphosphonate linkages. In certain embodiments, one methylphosphonate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments, it is desirable to decrease the number of phosphorothioate internucleoside linkages while retaining nuclease resistance. In certain embodiments, it is desirable to increase the number of phosphodiester internucleoside linkages while retaining nuclease resistance.

3. Certain Motifs

In certain embodiments, compounds described herein comprise oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleosides comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

a. Certain Sugar Motifs

In certain embodiments, compounds described herein comprise oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include, but are not limited to, any of the sugar modifications discussed herein.

In certain embodiments, modified oligonucleotides comprise or consist of a region having a gapmer motif, which comprises two external regions or "wings" and a central or internal region or "gap". The three regions of a gapmer motif (the 5'-wing, the gap, and the 3'-wing) form a contiguous sequence of nucleosides, wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleosides having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiments, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified oligonucleotide comprises the same 2'-modification.

b. Certain Nucleobase Motifs

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments, the block is within 3 nucleosides of the 3'-end of the oligonucleotide. In certain embodiments, the block is at the 5'-end of the oligonucleotide. In certain embodiments, the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

c. Certain Internucleoside Linkage Motifs

In certain embodiments, compounds described herein comprise oligonucleotides. In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

4. Certain Modified Oligonucleotides

In certain embodiments, compounds described herein comprise modified oligonucleotides. In certain embodiments, the above modifications (sugar, nucleobase, internucleoside linkage) are incorporated into a modified oligonucleotide. In certain embodiments, modified oligonucleotides are characterized by their modification, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such gapmer oligonucleotides may comprise one or more modified nucleobases independent of the gapmer pattern of the sugar modifications. Furthermore, in certain instances, an oligonucleotide is described by an overall length or range and by lengths or length ranges of two or more regions (e.g., a regions of nucleosides having specified sugar modifications). In such circumstances, it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide will be 22, which exceeds the upper limit of the overall length of the modified oligonucleotide (20). Herein, if a description of an oligonucleotide is silent with respect to one or more parameters, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

Certain Conjugated Compounds

In certain embodiments, the compounds described herein comprise or consist of an oligonucleotide (modified or unmodified) and, optionally, one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

In certain embodiments, the oligonucleotide is modified. In certain embodiments, the oligonucleotide of a compound has a nucleobase sequence that is complementary to a target nucleic acid. In certain embodiments, oligonucleotides are complementary to a messenger RNA (mRNA). In certain embodiments, oligonucleotides are complementary to a pre-mRNA. In certain embodiments, oligonucleotides are complementary to a sense transcript.

Examples of terminal groups include but are not limited to conjugate groups, capping groups, phosphate moieties, protecting groups, modified or unmodified nucleosides, and two or more nucleosides that are independently modified or unmodified.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Certain embodiments provide pharmaceutical compositions comprising one or more compounds or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compounds and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

A compound described herein targeted to IRF5 nucleic acid can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a compound targeted to IRF5 nucleic acid and a pharmaceutically acceptable diluent. In certain embodiments, the pharmaceutically acceptable diluent is water. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound.

In certain embodiments, the compounds or compositions further comprise a pharmaceutically acceptable carrier or diluent.

Certain Selected Compounds

Approximately 1,320 newly designed compounds of various lengths, chemistries, and motifs were tested for their effect on human IRF5 mRNA in vitro in several cell types (Examples 1 and 2). Of 1,320 compounds tested for potency at a single dose in vitro, over 110 selected compounds were tested for dose dependent inhibition in THP-1 cells, as well as in KARPAS-229 cells (Example 3).

These oligonucleotides were then tested for tolerability in preclinical rodent models (Examples 4 and 5). Body weights and organ weights, liver function markers (such as alanine transaminase, aspartate transaminase and bilirubin), hematology markers (such as hemoglobin and hematocrit levels, as well as individual blood cell counts), and kidney function markers (such as BUN and creatinine) were measured. Of the over 110 compounds tested by dose response assays, 53 compounds were further screened for tolerability in a CD-1 mouse model. Nineteen oligonucleotides were further screened in the Sprague-Dawley rat model.

Twelve compounds were then selected and tested in a mouse xenograft model, where the mice were inoculated with human non-Hodgkin's Large Cell Lymphoma (KARPAS-229) cells and treated with the compounds (Example 6). The efficacy and tolerability of the compounds were then tested. Eight compounds were then selected to be tested for efficacy at two separate doses in an IRF5 transgenic mouse model (Example 7).

IONs 729018, 728958, 785525, 785674, 785675, 786503, 786524, and 786548 were tested for tolerability in cynomolgus monkeys (Example 8). Treatment with the compounds was well tolerated in the monkeys, in particular, treatment with ION 729018. Further analysis was done with these compounds, including measuring for viscosity, evaluation of proinflammatory effects, and dose-dependent inhibition confirmation assays.

Modified oligonucleotides with different chemistry modifications were also designed overlapping the target regions of three compounds, IONs 729018, 786503, and 785675 (Example 13). These newly designed compounds along with the three parent oligonucleotides were tested in a multi-dose assay. Many of the newly designed compounds demonstrated strong efficacy in inhibiting IRF5.

Accordingly, provided herein are compounds with any one or more of the improved properties. In certain embodiments, the compounds as described herein are potent and tolerable.

EXAMPLES

The Examples below describe the screening process to identify lead compounds targeted to IRF5. ION 728958, 729018, 785525, 785674, 785675, 786503, 786524, and 786548 resulted in high potency and tolerability. For instance, ION 729018 exhibited high potency and tolerability.

Non-Limiting Disclosure and Incorporation by Reference

Although the sequence listing accompanying this filing identifies each sequence as either "RNA" or "DNA" as required, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to, those in the sequence listing, are intended to encompass nucleic acids containing any combination of natural or modified RNA and/or DNA, including, but not limited to, such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and compounds having other modified nucleobases, such as "AT$^m$CGAUCG," wherein $^m$C indicates a cytosine base comprising a methyl group at the 5-position.

Certain compounds described herein (e.g. modified oligonucleotides) have one or more asymmetric centers and thus give rise to enantiomers, diastereomers, and other stereoisomeric configurations that may be defined, in terms of absolute stereochemistry, as (R) or (S), as α or β, such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms. Likewise, all tautomeric forms of the compounds provided herein are included unless otherwise indicated. Unless otherwise indicated, oligomeric compounds and modified oligonucleotides described herein are intended to include corresponding salt forms.

Compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S.

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human IRF5 in THP-1 Cells by cEt Gapmers

Modified oligonucleotides were designed to target an IRF5 nucleic acid and were tested for their effect on IRF5 RNA levels in vitro. The modified oligonucleotides were tested in a series of experiments that had similar culture conditions. The results for each experiment are presented in separate tables shown below.

The newly designed modified oligonucleotides in the Tables below were designed as 3-10-3 cEt gapmers. The gapmers are 16 nucleosides in length, wherein the central gap segment comprises of ten 2'-deoxynucleosides and is flanked by wing segments on the 5' direction and the 3' direction comprising three nucleosides each. Each nucleoside in the 5' wing segment and each nucleoside in the 3' wing segment has a cEt sugar modification. The internucleoside linkages throughout each gapmer are phosphorothioate (P=S) linkages. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted in the human gene sequence. Most of the modified oligonucleotide listed in the Tables below are targeted to either human IRF5 mRNA, designated herein as SEQ ID NO: 1 (GENBANK Accession No. NM_001098627.3) or to human IRF5 genomic sequence, designated herein as SEQ ID NO: 2 (GENBANK Accession No. NT_007933.14 truncated from nucleotides 53761170 to 53774065). In addition, a small number of modified oligonucleotides are targeted to IRF5 mRNA designated herein as SEQ ID No: 3 (GENBANK Accession No. NM_001098629.1). 'N/A' indicates that the modified oligonucleotide does not target that gene sequence with 100% complementarity.

Cultured THP-1 cells at a density of 30,000 cells per well were transfected using electroporation with 2,000 nM of modified oligonucleotide. After a treatment period of approximately 24 hours, RNA was isolated from the cells and IRF5 RNA levels were measured by quantitative real-time RTPCR. Human primer probe set HTS4167 (forward sequence GCCAAGGAGACAGGGAAATACA, designated herein as SEQ ID NO: 11; reverse sequence GCAGGTTGGCCTTCCACTT; designated herein as SEQ ID NO: 12; probe sequence CGAAGGCGTGGATGAAGCCGATC, designated herein as SEQ ID NO: 13) was used to measure RNA levels. IRF5 RNA levels were adjusted according to total RNA content, as measured by RIBOGREEN®. Results are presented as percent inhibition of IRF5 relative to untreated control cells. As used herein, a value of '0' indicates that treatment with the modified oligonucleotide did not inhibit IRF5 mRNA levels. 'N.D.' indicates that the % inhibition is not defined for that modified oligonucleotide in that experiment. Activity of that modified oligonucleotide may be defined in a different experiment.

TABLE 1

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665773 | N/A | N/A | 4534 | 4549 | GGTTCATGGCAGAGGG | 46 | 37 |
| 665775 | N/A | N/A | 4545 | 4560 | TGGGATGGACTGGTTC | 35 | 38 |

TABLE 1-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665893 | 1228 | 1243 | 10461 | 10476 | GCACTGACACAGGCGG | 70 | 39 |
| 728374 | N/A | N/A | 402 | 417 | CCGCCAACCTGCCGGG | 3 | 40 |
| 728375 | N/A | N/A | 404 | 419 | GTCCGCCAACCTGCCG | 0 | 41 |
| 728376 | N/A | N/A | 408 | 423 | GCCGGTCCGCCAACCT | 12 | 42 |
| 728377 | N/A | N/A | 410 | 425 | CCGCCGGTCCGCCAAC | 0 | 43 |
| 728378 | N/A | N/A | 412 | 427 | TCCCGCCGGTCCGCCA | 7 | 44 |
| 728379 | N/A | N/A | 414 | 429 | CCTCCCGCCGGTCCGC | 7 | 45 |
| 728380 | N/A | N/A | 416 | 431 | CGCCTCCCGCCGGTCC | 18 | 46 |
| 728381 | N/A | N/A | 418 | 433 | TGCGCCTCCCGCCGGT | 9 | 47 |
| 728382 | N/A | N/A | 430 | 445 | CTCTGCCCAGGCTGCG | 17 | 48 |
| 728383 | N/A | N/A | 440 | 455 | CCAAGCTGAGCTCTGC | 29 | 49 |
| 728384 | N/A | N/A | 442 | 457 | GACCAAGCTGAGCTCT | 22 | 50 |
| 728385 | N/A | N/A | 445 | 460 | CGGGACCAAGCTGAGC | 17 | 51 |
| 728386 | N/A | N/A | 447 | 462 | GGCGGGACCAAGCTGA | 0 | 52 |
| 728387 | N/A | N/A | 450 | 465 | GGCGGCGGGACCAAGC | 6 | 53 |
| 728388 | N/A | N/A | 459 | 474 | CACCGGCCGGGCGGCG | 0 | 54 |
| 728389 | N/A | N/A | 461 | 476 | AGCACCGGCCGGGCGG | 0 | 55 |
| 728390 | N/A | N/A | 463 | 478 | GGAGCACCGGCCGGGC | 9 | 56 |
| 728391 | N/A | N/A | 466 | 481 | CAGGGAGCACCGGCCG | 15 | 57 |
| 728392 | N/A | N/A | 468 | 483 | GCCAGGGAGCACCGGC | 0 | 58 |
| 728393 | N/A | N/A | 470 | 485 | GCGCCAGGGAGCACCG | 4 | 59 |
| 728394 | N/A | N/A | 472 | 487 | CTGCGCCAGGGAGCAC | 4 | 60 |
| 728395 | N/A | N/A | 474 | 489 | GGCTGCGCCAGGGAGC | N.D. | 61 |
| 728396 | N/A | N/A | 476 | 491 | GTGGCTGCGCCAGGGA | 8 | 62 |
| 728397 | N/A | N/A | 492 | 507 | TCTGCGGTGCGCCTGC | 25 | 63 |
| 728398 | N/A | N/A | 494 | 509 | TGTCTGCGGTGCGCCT | 31 | 64 |
| 728401 | 210 | 225 | 4535 | 4550 | TGGTTCATGGCAGAGG | 50 | 65 |
| 728402 | 211 | 226 | 4536 | 4551 | CTGGTTCATGGCAGAG | 44 | 66 |
| 728403 | 213 | 228 | 4538 | 4553 | GACTGGTTCATGGCAG | 25 | 67 |
| 728404 | 214 | 229 | 4539 | 4554 | GGACTGGTTCATGGCA | 32 | 68 |
| 728405 | 216 | 231 | 4541 | 4556 | ATGGACTGGTTCATGG | 49 | 69 |
| 728406 | 217 | 232 | 4542 | 4557 | GATGGACTGGTTCATG | 42 | 70 |
| 728407 | 218 | 233 | 4543 | 4558 | GGATGGACTGGTTCAT | 47 | 71 |
| 728408 | 219 | 234 | 4544 | 4559 | GGGATGGACTGGTTCA | 53 | 72 |
| 728409 | 223 | 238 | 4548 | 4563 | CACTGGGATGGACTGG | 40 | 73 |
| 728410 | 225 | 240 | 4550 | 4565 | GCCACTGGGATGGACT | 16 | 74 |

TABLE 1-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728411 | 227 | 242 | 4552 | 4567 | GAGCCACTGGGATGGA | 40 | 75 |
| 728412 | 253 | 268 | 4578 | 4593 | CAGCCGCACGCGGCGG | 6 | 76 |
| 728413 | 255 | 270 | 4580 | 4595 | TTCAGCCGCACGCGGC | 44 | 77 |
| 728414 | 257 | 272 | 4582 | 4597 | GCTTCAGCCGCACGCG | 27 | 78 |
| 728415 | 259 | 274 | 4584 | 4599 | GGGCTTCAGCCGCACG | 8 | 79 |
| 728416 | 284 | 299 | 4609 | 4624 | AGCTGTTCACCTGGGC | 5 | 80 |
| 728417 | 286 | 301 | 4611 | 4626 | GCAGCTGTTCACCTGG | 3 | 81 |
| 728418 | 288 | 303 | 4613 | 4628 | TGGCAGCTGTTCACCT | 0 | 82 |
| 728419 | 290 | 305 | 4615 | 4630 | ACTGGCAGCTGTTCAC | 5 | 83 |
| 728420 | 292 | 307 | 4617 | 4632 | GTACTGGCAGCTGTTC | 0 | 84 |
| 728421 | 294 | 309 | 4619 | 4634 | GGGTACTGGCAGCTGT | 9 | 85 |
| 728422 | 296 | 311 | 4621 | 4636 | CTGGGTACTGGCAGCT | 0 | 86 |
| 728423 | 298 | 313 | 4623 | 4638 | CCCTGGGTACTGGCAG | 24 | 87 |
| 728424 | 300 | 315 | 4625 | 4640 | AGCCCTGGGTACTGGC | 0 | 88 |
| 728425 | 302 | 317 | 4627 | 4642 | GAAGCCCTGGGTACTG | 0 | 89 |
| 728426 | 304 | 319 | 4629 | 4644 | TTGAAGCCCTGGGTAC | 11 | 90 |
| 728427 | 306 | 321 | 4631 | 4646 | CATTGAAGCCCTGGGT | 13 | 91 |
| 728428 | 308 | 323 | 4633 | 4648 | CCCATTGAAGCCCTGG | 15 | 92 |
| 728429 | 310 | 325 | 4635 | 4650 | GACCCATTGAAGCCCT | 14 | 93 |
| 728430 | 312 | 327 | 4637 | 4652 | TTGACCCATTGAAGCC | 11 | 94 |
| 728431 | 314 | 329 | 4639 | 4654 | CGTTGACCCATTGAAG | 0 | 95 |
| 728432 | 316 | 331 | 4641 | 4656 | CCCGTTGACCCATTGA | 25 | 96 |
| 728433 | 318 | 333 | 4643 | 4658 | TCCCCGTTGACCCATT | 6 | 97 |
| 728434 | 320 | 335 | 4645 | 4660 | TTTCCCCGTTGACCCA | 20 | 98 |
| 728435 | 322 | 337 | 4647 | 4662 | CTTTTCCCCGTTGACC | 12 | 99 |
| 728436 | 324 | 339 | 4649 | 4664 | TTCTTTTCCCCGTTGA | 13 | 100 |
| 728437 | 326 | 341 | 4651 | 4666 | ATTTCTTTTCCCCGTT | 7 | 101 |
| 728438 | 328 | 343 | 4653 | 4668 | TAATTTCTTTTCCCCG | 19 | 102 |
| 728439 | 356 | 371 | 4681 | 4696 | TTGTGGCATGCCTCCA | 25 | 103 |
| 728440 | 358 | 373 | 4683 | 4698 | CCTTGTGGCATGCCTC | 31 | 104 |
| 728441 | 360 | 375 | 4685 | 4700 | TGCCTTGTGGCATGCC | 7 | 105 |
| 728442 | 362 | 377 | 4687 | 4702 | CATGCCTTGTGGCATG | 5 | 106 |
| 728443 | 364 | 379 | 4689 | 4704 | ACCATGCCTTGTGGCA | 5 | 107 |
| 728444 | 366 | 381 | 4691 | 4706 | GGACCATGCCTTGTGG | 6 | 108 |
| 728445 | 368 | 383 | 4693 | 4708 | TGGGACCATGCCTTGT | 10 | 109 |
| 728446 | 371 | 386 | 4696 | 4711 | GGCTGGGACCATGCCT | 0 | 110 |

TABLE 1-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728447 | 377 | 392 | 4702 | 4717 | CGTCCTGGCTGGGACC | 2 | 111 |
| 728448 | 380 | 395 | 4705 | 4720 | CTCCGTCCTGGCTGGG | 18 | 112 |

TABLE 2

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665795 | 385 | 400 | 4710 | 4725 | GTTATCTCCGTCCTGG | 58 | 113 |
| 665893 | 1228 | 1243 | 10461 | 10476 | GCACTGACACAGGCGG | 75 | 39 |
| 728449 | 381 | 396 | 4706 | 4721 | TCTCCGTCCTGGCTGG | 2 | 114 |
| 728450 | 382 | 397 | 4707 | 4722 | ATCTCCGTCCTGGCTG | 3 | 115 |
| 728451 | 383 | 398 | 4708 | 4723 | TATCTCCGTCCTGGCT | 0 | 116 |
| 728452 | 384 | 399 | 4709 | 4724 | TTATCTCCGTCCTGGC | 11 | 117 |
| 728453 | 386 | 401 | 4711 | 4726 | TGTTATCTCCGTCCTG | 14 | 118 |
| 728454 | 387 | 402 | 4712 | 4727 | GTGTTATCTCCGTCCT | 27 | 119 |
| 728455 | 388 | 403 | 4713 | 4728 | GGTGTTATCTCCGTCC | 18 | 120 |
| 728456 | 389 | 404 | 4714 | 4729 | TGGTGTTATCTCCGTC | 31 | 121 |
| 728457 | 390 | 405 | 4715 | 4730 | ATGGTGTTATCTCCGT | 17 | 122 |
| 728458 | 392 | 407 | 4717 | 4732 | AGATGGTGTTATCTCC | 50 | 123 |
| 728459 | 394 | 409 | 4719 | 4734 | GAAGATGGTGTTATCT | 14 | 124 |
| 728460 | 396 | 411 | 4721 | 4736 | TTGAAGATGGTGTTAT | 15 | 125 |
| 728461 | 398 | 413 | 4723 | 4738 | CCTTGAAGATGGTGTT | 29 | 126 |
| 728462 | 400 | 415 | N/A | N/A | GGCCTTGAAGATGGTG | 4 | 127 |
| 728492 | 490 | 505 | 8383 | 8398 | CTTGTTAAGGGCACAG | 26 | 128 |
| 728493 | 491 | 506 | 8384 | 8399 | TCTTGTTAAGGGCACA | 30 | 129 |
| 728494 | 492 | 507 | 8385 | 8400 | CTCTTGTTAAGGGCAC | 45 | 130 |
| 728495 | 494 | 509 | 8387 | 8402 | GGCTCTTGTTAAGGGC | 17 | 131 |
| 728496 | 496 | 511 | 8389 | 8404 | CCGGCTCTTGTTAAGG | 5 | 132 |
| 728497 | 498 | 513 | 8391 | 8406 | TCCCGGCTCTTGTTAA | 14 | 133 |
| 728498 | 500 | 515 | 8393 | 8408 | AGTCCCGGCTCTTGTT | 57 | 134 |
| 728499 | 502 | 517 | 8395 | 8410 | GAAGTCCCGGCTCTTG | 45 | 135 |
| 728500 | 504 | 519 | 8397 | 8412 | CGGAAGTCCCGGCTCT | 43 | 136 |
| 728501 | 506 | 521 | 8399 | 8414 | GGCGGAAGTCCCGGCT | 13 | 137 |
| 728502 | 508 | 523 | 8401 | 8416 | GAGGCGGAAGTCCCGG | 35 | 138 |

TABLE 2-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728503 | 510 | 525 | 8403 | 8418 | ATGAGGCGGAAGTCCC | 23 | 139 |
| 728504 | 512 | 527 | 8405 | 8420 | AGATGAGGCGGAAGTC | 21 | 140 |
| 728505 | 514 | 529 | 8407 | 8422 | GTAGATGAGGCGGAAG | 29 | 141 |
| 728506 | 538 | 553 | 8431 | 8446 | AGGTGGCATGTCCCGG | 41 | 142 |
| 728507 | 540 | 555 | 8433 | 8448 | TGAGGTGGCATGTCCC | 40 | 143 |
| 728508 | 542 | 557 | 8435 | 8450 | GCTGAGGTGGCATGTC | 33 | 144 |
| 728509 | 544 | 559 | 8437 | 8452 | GGGCTGAGGTGGCATG | 44 | 145 |
| 728510 | 546 | 561 | 8439 | 8454 | TAGGGCTGAGGTGGCA | 41 | 146 |
| 728511 | 552 | 567 | 8445 | 8460 | ATCTTGTAGGGCTGAG | 29 | 147 |
| 728512 | 554 | 569 | 8447 | 8462 | AGATCTTGTAGGGCTG | 45 | 148 |
| 728513 | 556 | 571 | 8449 | 8464 | GTAGATCTTGTAGGGC | 36 | 149 |
| 728514 | 572 | 587 | 8465 | 8480 | CATTGGAGCAGACCTC | 0 | 150 |
| 728515 | 574 | 589 | 8467 | 8482 | GCCATTGGAGCAGACC | 13 | 151 |
| 728516 | 576 | 591 | 8469 | 8484 | GGGCCATTGGAGCAGA | 15 | 152 |
| 728517 | 578 | 593 | 8471 | 8486 | CAGGGCCATTGGAGCA | 15 | 153 |
| 728518 | 580 | 595 | 8473 | 8488 | AGCAGGGCCATTGGAG | 13 | 154 |
| 728519 | 582 | 597 | 8475 | 8490 | GGAGCAGGGCCATTGG | 24 | 155 |
| 728520 | 591 | 606 | N/A | N/A | GAGTCTGTGGGAGCAG | 35 | 156 |
| 728521 | 614 | 629 | 8973 | 8988 | AAGAGTAATCCTCAGG | 22 | 157 |
| 728522 | 616 | 631 | 8975 | 8990 | AAAAGAGTAATCCTCA | 0 | 158 |
| 728523 | 618 | 633 | 8977 | 8992 | CCAAAAGAGTAATCCT | 6 | 159 |
| 728524 | 620 | 635 | 8979 | 8994 | CACCAAAAGAGTAATC | 1 | 160 |

TABLE 3

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665893 | 1228 | 1243 | 10461 | 10476 | GCACTGACACAGGCGG | 75 | 39 |
| 665985 | 1981 | 1996 | 11546 | 11561 | CTCCTATACAGCTAGG | 49 | 161 |
| 665987 | 1993 | 2008 | 11558 | 11573 | CTTAGGCAATTCCTCC | 50 | 162 |
| 666005 | 2159 | 2174 | 11724 | 11739 | CTAAGTGCTCACTCAT | 64 | 163 |
| 666007 | 2183 | 2198 | 11748 | 11763 | AGCCTTGAGCATCTGA | 63 | 164 |
| 666009 | 2186 | 2201 | 11751 | 11766 | GCCAGCCTTGAGCATC | 50 | 165 |
| 728956 | 1977 | 1992 | 11542 | 11557 | TATACAGCTAGGCCCC | 32 | 166 |
| 728957 | 1978 | 1993 | 11543 | 11558 | CTATACAGCTAGGCCC | 43 | 167 |

TABLE 3-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728958 | 1979 | 1994 | 11544 | 11559 | CCTATACAGCTAGGCC | 68 | 168 |
| 728959 | 1980 | 1995 | 11545 | 11560 | TCCTATACAGCTAGGC | 39 | 169 |
| 728960 | 1982 | 1997 | 11547 | 11562 | CCTCCTATACAGCTAG | 48 | 170 |
| 728961 | 1983 | 1998 | 11548 | 11563 | TCCTCCTATACAGCTA | 46 | 171 |
| 728962 | 1984 | 1999 | 11549 | 11564 | TTCCTCCTATACAGCT | 60 | 172 |
| 728963 | 1985 | 2000 | 11550 | 11565 | ATTCCTCCTATACAGC | 35 | 173 |
| 728964 | 1986 | 2001 | 11551 | 11566 | AATTCCTCCTATACAG | 28 | 174 |
| 728965 | 1988 | 2003 | 11553 | 11568 | GCAATTCCTCCTATAC | 61 | 175 |
| 728966 | 1989 | 2004 | 11554 | 11569 | GGCAATTCCTCCTATA | 60 | 176 |
| 728967 | 1992 | 2007 | 11557 | 11572 | TTAGGCAATTCCTCCT | 51 | 177 |
| 728968 | 1994 | 2009 | 11559 | 11574 | CCTTAGGCAATTCCTC | 64 | 178 |
| 728969 | 1995 | 2010 | 11560 | 11575 | CCCTTAGGCAATTCCT | 68 | 179 |
| 728970 | 1996 | 2011 | 11561 | 11576 | ACCCTTAGGCAATTCC | 77 | 180 |
| 728971 | 1998 | 2013 | 11563 | 11578 | CCACCCTTAGGCAATT | 46 | 181 |
| 728972 | 2000 | 2015 | 11565 | 11580 | GGCCACCCTTAGGCAA | 62 | 182 |
| 728973 | 2003 | 2018 | 11568 | 11583 | GTGGGCCACCCTTAGG | 58 | 183 |
| 728974 | 2006 | 2021 | 11571 | 11586 | AGAGTGGGCCACCCTT | 33 | 184 |
| 728975 | 2008 | 2023 | 11573 | 11588 | CAAGAGTGGGCCACCC | 45 | 185 |
| 728976 | 2010 | 2025 | 11575 | 11590 | CACAAGAGTGGGCCAC | 37 | 186 |
| 728977 | 2012 | 2027 | 11577 | 11592 | ATCACAAGAGTGGGCC | 52 | 187 |
| 728978 | 2014 | 2029 | 11579 | 11594 | CAATCACAAGAGTGGG | 59 | 188 |
| 728979 | 2016 | 2031 | 11581 | 11596 | GGCAATCACAAGAGTG | 47 | 189 |
| 728980 | 2033 | 2048 | 11598 | 11613 | GTTGCCAGAGGAAATG | 13 | 190 |
| 728981 | 2035 | 2050 | 11600 | 11615 | TTGTTGCCAGAGGAAA | 15 | 191 |
| 728982 | 2037 | 2052 | 11602 | 11617 | TTTTGTTGCCAGAGGA | 19 | 192 |
| 728983 | 2040 | 2055 | 11605 | 11620 | GGCTTTTGTTGCCAGA | 17 | 193 |
| 728984 | 2047 | 2062 | 11612 | 11627 | ACACTCTGGCTTTTGT | 11 | 194 |
| 728985 | 2049 | 2064 | 11614 | 11629 | CAACACTCTGGCTTTT | 0 | 195 |
| 728986 | 2051 | 2066 | 11616 | 11631 | CACAACACTCTGGCTT | 44 | 196 |
| 728987 | 2059 | 2074 | 11624 | 11639 | ACTTGGCCCACAACAC | 9 | 197 |
| 728988 | 2061 | 2076 | 11626 | 11641 | GGACTTGGCCCACAAC | 29 | 198 |
| 728989 | 2086 | 2101 | 11651 | 11666 | CATGCCCTGCAGAGGC | 44 | 199 |
| 728990 | 2095 | 2110 | 11660 | 11675 | AATCAGGGCCATGCCC | 0 | 200 |
| 728991 | 2097 | 2112 | 11662 | 11677 | GAAATCAGGGCCATGC | 9 | 201 |
| 728992 | 2106 | 2121 | 11671 | 11686 | CAAACCAGGGAAATCA | 26 | 202 |
| 728993 | 2108 | 2123 | 11673 | 11688 | CTCAAACCAGGGAAAT | 51 | 203 |

TABLE 3-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728994 | 2110 | 2125 | 11675 | 11690 | GTCTCAAACCAGGGAA | 63 | 204 |
| 728995 | 2112 | 2127 | 11677 | 11692 | GAGTCTCAAACCAGGG | 61 | 205 |
| 728996 | 2114 | 2129 | 11679 | 11694 | GTGAGTCTCAAACCAG | 71 | 206 |
| 728997 | 2117 | 2132 | 11682 | 11697 | GAAGTGAGTCTCAAAC | 58 | 207 |
| 728998 | 2119 | 2134 | 11684 | 11699 | AGGAAGTGAGTCTCAA | 68 | 208 |
| 728999 | 2121 | 2136 | 11686 | 11701 | TGAGGAAGTGAGTCTC | 20 | 209 |
| 729000 | 2141 | 2156 | 11706 | 11721 | TATCTCAGAGGACAGG | 63 | 210 |
| 729001 | 2143 | 2158 | 11708 | 11723 | ATTATCTCAGAGGACA | 67 | 211 |
| 729002 | 2145 | 2160 | 11710 | 11725 | ATATTATCTCAGAGGA | 61 | 212 |
| 729003 | 2148 | 2163 | 11713 | 11728 | CTCATATTATCTCAGA | 64 | 213 |
| 729004 | 2152 | 2167 | 11717 | 11732 | CTCACTCATATTATCT | 50 | 214 |
| 729005 | 2154 | 2169 | 11719 | 11734 | TGCTCACTCATATTAT | 20 | 215 |
| 729006 | 2155 | 2170 | 11720 | 11735 | GTGCTCACTCATATTA | 53 | 216 |
| 729007 | 2156 | 2171 | 11721 | 11736 | AGTGCTCACTCATATT | 38 | 217 |
| 729008 | 2157 | 2172 | 11722 | 11737 | AAGTGCTCACTCATAT | 44 | 218 |
| 729009 | 2158 | 2173 | 11723 | 11738 | TAAGTGCTCACTCATA | 45 | 219 |
| 729010 | 2160 | 2175 | 11725 | 11740 | CCTAAGTGCTCACTCA | 63 | 220 |
| 729011 | 2161 | 2176 | 11726 | 11741 | ACCTAAGTGCTCACTC | 64 | 221 |
| 729012 | 2162 | 2177 | 11727 | 11742 | TACCTAAGTGCTCACT | 34 | 222 |
| 729013 | 2163 | 2178 | 11728 | 11743 | ATACCTAAGTGCTCAC | 56 | 223 |
| 729014 | 2164 | 2179 | 11729 | 11744 | GATACCTAAGTGCTCA | 60 | 224 |
| 729015 | 2166 | 2181 | 11731 | 11746 | ATGATACCTAAGTGCT | 57 | 225 |
| 729016 | 2168 | 2183 | 11733 | 11748 | ATATGATACCTAAGTG | 53 | 226 |
| 729017 | 2170 | 2185 | 11735 | 11750 | TGATATGATACCTAAG | 46 | 227 |
| <u>729018</u> | <u>2172</u> | <u>2187</u> | <u>11737</u> | <u>11752</u> | <u>TCTGATATGATACCTA</u> | <u>71</u> | <u>228</u> |
| 729019 | 2174 | 2189 | 11739 | 11754 | CATCTGATATGATACC | 63 | 229 |
| 729020 | 2176 | 2191 | 11741 | 11756 | AGCATCTGATATGATA | 65 | 230 |
| 729021 | 2178 | 2193 | 11743 | 11758 | TGAGCATCTGATATGA | 60 | 231 |
| 729022 | 2179 | 2194 | 11744 | 11759 | TTGAGCATCTGATATG | 37 | 232 |
| 729023 | 2180 | 2195 | 11745 | 11760 | CTTGAGCATCTGATAT | 36 | 233 |
| 729024 | 2181 | 2196 | 11746 | 11761 | CCTTGAGCATCTGATA | 56 | 234 |
| 729025 | 2182 | 2197 | 11747 | 11762 | GCCTTGAGCATCTGAT | 54 | 235 |
| 729026 | 2185 | 2200 | 11750 | 11765 | CCAGCCTTGAGCATCT | 51 | 236 |
| 729027 | 2187 | 2202 | 11752 | 11767 | TGCCAGCCTTGAGCAT | 14 | 237 |

TABLE 4

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665830 | 680 | 695 | 9499 | 9514 | TGAGGCTCAGGCTTGG | 65 | 238 |
| 665840 | 715 | 730 | 9755 | 9770 | CGGCTGCAGAGTGGGC | 43 | 239 |
|  | 760 | 775 | 9800 | 9815 |  |  |  |
| 665842 | 717 | 732 | 9757 | 9772 | GGCGGCTGCAGAGTGG | 43 | 240 |
|  | 762 | 777 | 9802 | 9817 |  |  |  |
| 665843 | 718 | 733 | 9758 | 9773 | GGGCGGCTGCAGAGTG | 53 | 241 |
|  | 763 | 778 | 9803 | 9818 |  |  |  |
| 665845 | 720 | 735 | 9760 | 9775 | GTGGGCGGCTGCAGAG | 43 | 242 |
|  | 750 | 765 | 9790 | 9805 |  |  |  |
| 665846 | 721 | 736 | 9761 | 9776 | AGTGGGCGGCTGCAGA | 28 | 243 |
|  | 751 | 766 | 9791 | 9806 |  |  |  |
| 665847 | 722 | 737 | 9762 | 9777 | GAGTGGGCGGCTGCAG | 24 | 244 |
|  | 752 | 767 | 9792 | 9807 |  |  |  |
| 665848 | 724 | 739 | 9764 | 9779 | CAGAGTGGGCGGCTGC | 40 | 245 |
|  | 754 | 769 | 9794 | 9809 |  |  |  |
| 665853 | 725 | 740 | 9765 | 9780 | GCAGAGTGGGCGGCTG | 11 | 246 |
|  | 755 | 770 | 9795 | 9810 |  |  |  |
| 665893 | 1228 | 1243 | 10461 | 10476 | GCACTGACACAGGCGG | 72 | 39 |
| 728525 | 622 | 637 | 8981 | 8996 | TGCACCAAAAGAGTAA | 22 | 247 |
| 728526 | 624 | 639 | 8983 | 8998 | CCTGCACCAAAAGAGT | 31 | 248 |
| 728527 | 626 | 641 | 8985 | 9000 | CTCCTGCACCAAAAGA | 39 | 249 |
| 728528 | 628 | 643 | 8987 | 9002 | CTCTCCTGCACCAAAA | 31 | 250 |
| 728529 | 663 | 678 | 9482 | 9497 | AACATCCTCTGCAGCT | 29 | 251 |
| 728530 | 666 | 681 | 9485 | 9500 | GGCAACATCCTCTGCA | 36 | 252 |
| 728531 | 668 | 683 | 9487 | 9502 | TTGGCAACATCCTCTG | 45 | 253 |
| 728532 | 670 | 685 | 9489 | 9504 | GCTTGGCAACATCCTC | 53 | 254 |
| 728533 | 672 | 687 | 9491 | 9506 | AGGCTTGGCAACATCC | 66 | 255 |
| 728534 | 675 | 690 | 9494 | 9509 | CTCAGGCTTGGCAACA | 42 | 256 |
| 728535 | 678 | 693 | 9497 | 9512 | AGGCTCAGGCTTGGCA | 60 | 257 |
| 728536 | 681 | 696 | 9500 | 9515 | GTGAGGCTCAGGCTTG | 44 | 258 |
| 728537 | 682 | 697 | 9501 | 9516 | TGTGAGGCTCAGGCTT | 34 | 259 |
| 728538 | 684 | 699 | N/A | N/A | TCTGTGAGGCTCAGGC | 41 | 260 |
| 728544 | N/A | N/A | 9690 | 9705 | CAGACTGCACTGCATC | 29 | 261 |
| 728545 | N/A | N/A | 9692 | 9707 | GCCAGACTGCACTGCA | 8 | 262 |
| 728546 | N/A | N/A | 9694 | 9709 | GGGCCAGACTGCACTG | 28 | 263 |
| 728547 | N/A | N/A | 9711 | 9726 | AATAGGGTGTCATGTG | 6 | 264 |
| 728548 | N/A | N/A | 9713 | 9728 | AGAATAGGGTGTCATG | 0 | 265 |
| 728549 | N/A | N/A | 9715 | 9730 | AAAGAATAGGGTGTCA | 17 | 266 |
| 728550 | N/A | N/A | 9717 | 9732 | GTAAAGAATAGGGTGT | 14 | 267 |
| 728551 | N/A | N/A | 9719 | 9734 | GAGTAAAGAATAGGGT | 24 | 268 |

TABLE 4-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728552 | N/A | N/A | 9721 | 9736 | TTGAGTAAAGAATAGG | 12 | 269 |
| 728553 | N/A | N/A | 9723 | 9738 | CTTTGAGTAAAGAATA | 8 | 270 |
| 728554 | N/A | N/A | 9725 | 9740 | CTCTTTGAGTAAAGAA | 0 | 271 |
| 728555 | N/A | N/A | 9727 | 9742 | TCCTCTTTGAGTAAAG | 14 | 272 |
| 728556 | N/A | N/A | 9729 | 9744 | CATCCTCTTTGAGTAA | 21 | 273 |
| 728557 | N/A | N/A | 9731 | 9746 | GACATCCTCTTTGAGT | 11 | 274 |
| 728558 | N/A | N/A | 9733 | 9748 | TTGACATCCTCTTTGA | 32 | 275 |
| 728559 | N/A | N/A | 9735 | 9750 | ACTTGACATCCTCTTT | 16 | 276 |
| 728560 | 699 | 714 | 9739 | 9754 | GGCCACTTGACATCCT | 6 | 277 |
| 728561 | 701 | 716 | 9741 | 9756 | GCGGCCACTTGACATC | 31 | 278 |
| 728562 | 703 | 718 | 9743 | 9758 | GGGCGGCCACTTGACA | 13 | 279 |
| 728563 | 705 | 720 | 9745 | 9760 | GTGGGCGGCCACTTGA | 40 | 280 |
| 728564 | 707 | 722 | 9747 | 9762 | GAGTGGGCGGCCACTT | 12 | 281 |
| 728565 | 709 | 724 | 9749 | 9764 | CAGAGTGGGCGGCCAC | 38 | 282 |
| 728566 | 711 | 726 | 9751 | 9766 | TGCAGAGTGGGCGGCC | 21 | 283 |
| 728567 | 726 | 741 | 9766 | 9781 | CGCAGAGTGGGCGGCT | 18 | 284 |
| 728568 | 727 | 742 | 9767 | 9782 | CCGCAGAGTGGGCGGC | 17 | 285 |
| 728569 | 731 | 746 | 9771 | 9786 | GCGGCCGCAGAGTGGG | 4 | 286 |
| 728570 | 733 | 748 | 9773 | 9788 | AGGCGGCCGCAGAGTG | 20 | 287 |
| 728571 | 735 | 750 | 9775 | 9790 | GTAGGCGGCCGCAGAG | 14 | 288 |
| 728572 | 737 | 752 | 9777 | 9792 | GAGTAGGCGGCCGCAG | 11 | 289 |
| 728573 | 739 | 754 | 9779 | 9794 | CAGAGTAGGCGGCCGC | 25 | 290 |
| 728574 | 741 | 756 | 9781 | 9796 | TGCAGAGTAGGCGGCC | 12 | 291 |
| 728575 | 743 | 758 | 9783 | 9798 | GCTGCAGAGTAGGCGG | 44 | 292 |
| 728576 | 745 | 760 | 9785 | 9800 | CGGCTGCAGAGTAGGC | 37 | 293 |
| 728577 | 747 | 762 | 9787 | 9802 | GGCGGCTGCAGAGTAG | 45 | 294 |
| 728578 | 756 | 771 | 9796 | 9811 | TGCAGAGTGGGCGGCT | 9 | 295 |
| 728579 | 764 | 779 | 9804 | 9819 | CGGGCGGCTGCAGAGT | 61 | 296 |
| 728580 | 765 | 780 | 9805 | 9820 | ACGGGCGGCTGCAGAG | 28 | 297 |
| 728581 | 767 | 782 | 9807 | 9822 | CCACGGGCGGCTGCAG | 17 | 298 |
| 728582 | 768 | 783 | 9808 | 9823 | ACCACGGGCGGCTGCA | 29 | 299 |
| 728583 | 769 | 784 | 9809 | 9824 | CACCACGGGCGGCTGC | 26 | 300 |
| 728584 | 771 | 786 | 9811 | 9826 | AGCACCACGGGCGGCT | 7 | 301 |
| 728585 | 773 | 788 | 9813 | 9828 | CCAGCACCACGGGCGG | 41 | 302 |
| 728586 | 775 | 790 | 9815 | 9830 | ACCCAGCACCACGGGC | 19 | 303 |
| 728587 | 777 | 792 | 9817 | 9832 | GGACCCAGCACCACGG | 41 | 304 |

TABLE 4-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728588 | 830 | 845 | 9870 | 9885 | AGCCAGCAGGGTTGCC | 26 | 305 |
| 728589 | 832 | 847 | 9872 | 9887 | GAAGCCAGCAGGGTTG | 16 | 306 |
| 728590 | 834 | 849 | 9874 | 9889 | CTGAAGCCAGCAGGGT | 26 | 307 |
| 728591 | 845 | 860 | 9885 | 9900 | AGAGAAGCTCCCTGAA | 8 | 308 |
| 728592 | 849 | 864 | 9889 | 9904 | TCAGAGAGAAGCTCCC | 3 | 309 |

TABLE 5

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 642685 | 1098 | 1113 | 10331 | 10346 | AAGCGCACTTGCTCCA | 33 | 310 |
| 665862 | 913 | 928 | 9953 | 9968 | GTCTGGCAGGAGCTGT | 51 | 311 |
| 665878 | 1096 | 1111 | 10329 | 10344 | GCGCACTTGCTCCAGG | 58 | 312 |
| 665884 | 1181 | 1196 | 10414 | 10429 | GGATGAGCCCGCGGTC | 56 | 313 |
| 665893 | 1228 | 1243 | 10461 | 10476 | GCACTGACACAGGCGG | 76 | 39 |
| 728593 | 853 | 868 | 9893 | 9908 | GACCTCAGAGAGAAGC | 10 | 314 |
| 728594 | 862 | 877 | 9902 | 9917 | AGGCTCCAGGACCTCA | 7 | 315 |
| 728595 | 902 | 917 | 9942 | 9957 | GCTGTTCGCCTGCAGG | 59 | 316 |
| 728596 | 904 | 919 | 9944 | 9959 | GAGCTGTTCGCCTGCA | 14 | 317 |
| 728597 | 906 | 921 | 9946 | 9961 | AGGAGCTGTTCGCCTG | 4 | 318 |
| 728598 | 908 | 923 | 9948 | 9963 | GCAGGAGCTGTTCGCC | 44 | 319 |
| 728599 | 909 | 924 | 9949 | 9964 | GGCAGGAGCTGTTCGC | 30 | 320 |
| 728600 | 910 | 925 | 9950 | 9965 | TGGCAGGAGCTGTTCG | 15 | 321 |
| 728601 | 911 | 926 | 9951 | 9966 | CTGGCAGGAGCTGTTC | 34 | 322 |
| 728602 | 912 | 927 | 9952 | 9967 | TCTGGCAGGAGCTGTT | 33 | 323 |
| 728603 | 914 | 929 | 9954 | 9969 | GGTCTGGCAGGAGCTG | 49 | 324 |
| 728604 | 915 | 930 | 9955 | 9970 | AGGTCTGGCAGGAGCT | 60 | 325 |
| 728605 | 916 | 931 | 9956 | 9971 | CAGGTCTGGCAGGAGC | 53 | 326 |
| 728606 | 918 | 933 | 9958 | 9973 | AGCAGGTCTGGCAGGA | 35 | 327 |
| 728607 | 922 | 937 | 9962 | 9977 | GATCAGCAGGTCTGGC | 17 | 328 |
| 728608 | 924 | 939 | 9964 | 9979 | CTGATCAGCAGGTCTG | 34 | 329 |
| 728609 | 926 | 941 | 9966 | 9981 | GGCTGATCAGCAGGTC | 38 | 330 |
| 728610 | 945 | 960 | N/A | N/A | GTCAGAGGCAGCATGT | 24 | 331 |
| 728611 | 947 | 962 | N/A | N/A | CGGTCAGAGGCAGCAT | 54 | 332 |
| 728612 | 949 | 964 | N/A | N/A | GTCGGTCAGAGGCAGC | 44 | 333 |

TABLE 5-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728613 | 952 | 967 | N/A | N/A | CAGGTCGGTCAGAGGC | 47 | 334 |
| 728614 | 954 | 969 | N/A | N/A | TCCAGGTCGGTCAGAG | 24 | 335 |
| 728615 | 1001 | 1016 | 10234 | 10249 | TGATGGTGAGGGCCCG | 18 | 336 |
| 728616 | 1003 | 1018 | 10236 | 10251 | GCTGATGGTGAGGGCC | 14 | 337 |
| 728617 | 1005 | 1020 | 10238 | 10253 | TTGCTGATGGTGAGGG | 37 | 338 |
| 728618 | 1024 | 1039 | 10257 | 10272 | GAGCCGGCAGCCATGG | 13 | 339 |
| 728619 | 1032 | 1047 | 10265 | 10280 | CTGTAGAAGAGCCGGC | 0 | 340 |
| 728620 | 1034 | 1049 | 10267 | 10282 | GGCTGTAGAAGAGCCG | 0 | 341 |
| 728621 | 1036 | 1051 | 10269 | 10284 | CTGGCTGTAGAAGAGC | 21 | 342 |
| 728622 | 1038 | 1053 | 10271 | 10286 | AGCTGGCTGTAGAAGA | 9 | 343 |
| 728623 | 1040 | 1055 | 10273 | 10288 | CCAGCTGGCTGTAGAA | 5 | 344 |
| 728624 | 1067 | 1082 | 10300 | 10315 | AGAGTTCCACCTGCTC | 23 | 345 |
| 728625 | 1069 | 1084 | 10302 | 10317 | GAAGAGTTCCACCTGC | 14 | 346 |
| 728626 | 1072 | 1087 | 10305 | 10320 | GCCGAAGAGTTCCACC | 22 | 347 |
| 728627 | 1074 | 1089 | 10307 | 10322 | GGGCCGAAGAGTTCCA | 13 | 348 |
| 728628 | 1091 | 1106 | 10324 | 10339 | CTTGCTCCAGGCTTAT | 24 | 349 |
| 728629 | 1093 | 1108 | 10326 | 10341 | CACTTGCTCCAGGCTT | 46 | 350 |
| 728630 | 1094 | 1109 | 10327 | 10342 | GCACTTGCTCCAGGCT | 66 | 351 |
| 728631 | 1095 | 1110 | 10328 | 10343 | CGCACTTGCTCCAGGC | 62 | 352 |
| 728632 | 1097 | 1112 | 10330 | 10345 | AGCGCACTTGCTCCAG | 55 | 353 |
| 728633 | 1099 | 1114 | 10332 | 10347 | GAAGCGCACTTGCTCC | 43 | 354 |
| 728634 | 1100 | 1115 | 10333 | 10348 | GGAAGCGCACTTGCTC | 57 | 355 |
| 728635 | 1101 | 1116 | 10334 | 10349 | GGGAAGCGCACTTGCT | 59 | 356 |
| 728636 | 1117 | 1132 | 10350 | 10365 | GATGTCCTCAGGGCTG | 22 | 357 |
| 728637 | 1134 | 1149 | 10367 | 10382 | CGCTGCTTGTCACTGG | 67 | 358 |
| 728638 | 1161 | 1176 | 10394 | 10409 | ACATCCAGCAGCTGGT | 0 | 359 |
| 728639 | 1163 | 1178 | 10396 | 10411 | GGACATCCAGCAGCTG | 8 | 360 |
| 728640 | 1170 | 1185 | 10403 | 10418 | CGGTCCAGGACATCCA | 32 | 361 |
| 728641 | 1172 | 1187 | 10405 | 10420 | CGCGGTCCAGGACATC | 47 | 362 |
| 728642 | 1174 | 1189 | 10407 | 10422 | CCCGCGGTCCAGGACA | 11 | 363 |
| 728643 | 1176 | 1191 | 10409 | 10424 | AGCCCGCGGTCCAGGA | 20 | 364 |
| 728644 | 1177 | 1192 | 10410 | 10425 | GAGCCCGCGGTCCAGG | 48 | 365 |
| 728645 | 1179 | 1194 | 10412 | 10427 | ATGAGCCCGCGGTCCA | 44 | 366 |
| 728646 | 1180 | 1195 | 10413 | 10428 | GATGAGCCCGCGGTCC | 59 | 367 |
| 728647 | 1182 | 1197 | 10415 | 10430 | AGGATGAGCCCGCGGT | 49 | 368 |
| 728648 | 1183 | 1198 | 10416 | 10431 | GAGGATGAGCCCGCGG | 36 | 369 |

TABLE 5-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728649 | 1184 | 1199 | 10417 | 10432 | GGAGGATGAGCCCGCG | 14 | 370 |
| 728650 | 1185 | 1200 | 10418 | 10433 | TGGAGGATGAGCCCGC | 27 | 371 |
| 728651 | 1186 | 1201 | 10419 | 10434 | CTGGAGGATGAGCCCG | 17 | 372 |
| 728652 | 1188 | 1203 | 10421 | 10436 | AGCTGGAGGATGAGCC | 0 | 373 |
| 728653 | 1190 | 1205 | 10423 | 10438 | GTAGCTGGAGGATGAG | 13 | 374 |
| 728654 | 1192 | 1207 | 10425 | 10440 | CTGTAGCTGGAGGATG | 3 | 375 |
| 728655 | 1194 | 1209 | 10427 | 10442 | CCCTGTAGCTGGAGGA | 4 | 376 |
| 728656 | 1196 | 1211 | 10429 | 10444 | GGCCCTGTAGCTGGAG | 24 | 377 |
| 728657 | 1198 | 1213 | 10431 | 10446 | CTGGCCCTGTAGCTGG | 9 | 378 |
| 728658 | 1201 | 1216 | 10434 | 10449 | GTCCTGGCCCTGTAGC | 25 | 379 |
| 728659 | 1203 | 1218 | 10436 | 10451 | AGGTCCTGGCCCTGTA | 43 | 380 |
| 728660 | 1205 | 1220 | 10438 | 10453 | AAAGGTCCTGGCCCTG | 23 | 381 |
| 728661 | 1207 | 1222 | 10440 | 10455 | ATAAAGGTCCTGGCCC | 10 | 382 |
| 728662 | 1209 | 1224 | 10442 | 10457 | GCATAAAGGTCCTGGC | 31 | 383 |
| 728663 | 1211 | 1226 | 10444 | 10459 | TGGCATAAAGGTCCTG | 46 | 384 |
| 728664 | 1213 | 1228 | 10446 | 10461 | GATGGCATAAAGGTCC | 42 | 385 |
| 728665 | 1215 | 1230 | 10448 | 10463 | CGGATGGCATAAAGGT | 39 | 386 |

TABLE 6

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665892 | 1227 | 1242 | 10460 | 10475 | CACTGACACAGGCGGA | 68 | 387 |
| 665893 | 1228 | 1243 | 10461 | 10476 | GCACTGACACAGGCGG | 65 | 39 |
| 665894 | 1229 | 1244 | 10462 | 10477 | TGCACTGACACAGGCG | 42 | 388 |
| 665895 | 1242 | 1257 | 10475 | 10490 | CTCCAGAACACCTTGC | 44 | 389 |
| 665900 | 1272 | 1287 | 10505 | 10520 | CATGAGTCATGGGCTG | 54 | 390 |
| 665902 | 1301 | 1316 | 10534 | 10549 | TCTTGACCTCCCGCTG | 37 | 391 |
| 665903 | 1309 | 1324 | 10542 | 10557 | AAGCTTGGTCTTGACC | 49 | 392 |
| 665908 | 1363 | 1378 | 10684 | 10699 | GGTCTGGCCCTTTTGG | 66 | 393 |
| 728666 | 1217 | 1232 | 10450 | 10465 | GGCGGATGGCATAAAG | 32 | 394 |
| 728667 | 1223 | 1238 | 10456 | 10471 | GACACAGGCGGATGGC | 49 | 395 |
| 728668 | 1224 | 1239 | 10457 | 10472 | TGACACAGGCGGATGG | 27 | 396 |
| 728669 | 1226 | 1241 | 10459 | 10474 | ACTGACACAGGCGGAT | 51 | 397 |

TABLE 6-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728670 | 1230 | 1245 | 10463 | 10478 | TTGCACTGACACAGGC | 68 | 398 |
| 728671 | 1231 | 1246 | 10464 | 10479 | CTTGCACTGACACAGG | 42 | 399 |
| 728672 | 1232 | 1247 | 10465 | 10480 | CCTTGCACTGACACAG | 56 | 400 |
| 728673 | 1233 | 1248 | 10466 | 10481 | ACCTTGCACTGACACA | 60 | 401 |
| 728674 | 1234 | 1249 | 10467 | 10482 | CACCTTGCACTGACAC | 57 | 402 |
| 728675 | 1237 | 1252 | 10470 | 10485 | GAACACCTTGCACTGA | 34 | 403 |
| 728676 | 1238 | 1253 | 10471 | 10486 | AGAACACCTTGCACTG | 39 | 404 |
| 728677 | 1239 | 1254 | 10472 | 10487 | CAGAACACCTTGCACT | 25 | 405 |
| 728678 | 1240 | 1255 | 10473 | 10488 | CCAGAACACCTTGCAC | 30 | 406 |
| 728679 | 1241 | 1256 | 10474 | 10489 | TCCAGAACACCTTGCA | 39 | 407 |
| 728680 | 1243 | 1258 | 10476 | 10491 | GCTCCAGAACACCTTG | 39 | 408 |
| 728681 | 1244 | 1259 | 10477 | 10492 | CGCTCCAGAACACCTT | 59 | 409 |
| 728682 | 1245 | 1260 | 10478 | 10493 | CCGCTCCAGAACACCT | 37 | 410 |
| 728683 | 1246 | 1261 | 10479 | 10494 | CCCGCTCCAGAACACC | 41 | 411 |
| 728684 | 1247 | 1262 | 10480 | 10495 | GCCCGCTCCAGAACAC | 19 | 412 |
| 728685 | 1249 | 1264 | 10482 | 10497 | AGGCCCGCTCCAGAAC | 24 | 413 |
| 728686 | 1251 | 1266 | 10484 | 10499 | CAAGGCCCGCTCCAGA | 28 | 414 |
| 728687 | 1253 | 1268 | 10486 | 10501 | CACAAGGCCCGCTCCA | 16 | 415 |
| 728688 | 1255 | 1270 | 10488 | 10503 | GGCACAAGGCCCGCTC | 12 | 416 |
| 728689 | 1257 | 1272 | 10490 | 10505 | GAGGCACAAGGCCCGC | 17 | 417 |
| 728690 | 1259 | 1274 | 10492 | 10507 | CTGAGGCACAAGGCCC | 13 | 418 |
| 728691 | 1264 | 1279 | 10497 | 10512 | ATGGGCTGAGGCACAA | 42 | 419 |
| 728692 | 1267 | 1282 | 10500 | 10515 | GTCATGGGCTGAGGCA | 51 | 420 |
| 728693 | 1268 | 1283 | 10501 | 10516 | AGTCATGGGCTGAGGC | 52 | 421 |
| 728694 | 1269 | 1284 | 10502 | 10517 | GAGTCATGGGCTGAGG | 59 | 422 |
| 728695 | 1270 | 1285 | 10503 | 10518 | TGAGTCATGGGCTGAG | 67 | 423 |
| 728696 | 1271 | 1286 | 10504 | 10519 | ATGAGTCATGGGCTGA | 75 | 424 |
| 728697 | 1273 | 1288 | 10506 | 10521 | GCATGAGTCATGGGCT | 23 | 425 |
| 728698 | 1274 | 1289 | 10507 | 10522 | GGCATGAGTCATGGGC | 47 | 426 |
| 728699 | 1296 | 1311 | 10529 | 10544 | ACCTCCCGCTGGATGG | 45 | 427 |
| 728700 | 1297 | 1312 | 10530 | 10545 | GACCTCCCGCTGGATG | 38 | 428 |
| 728701 | 1298 | 1313 | 10531 | 10546 | TGACCTCCCGCTGGAT | 53 | 429 |
| 728702 | 1299 | 1314 | 10532 | 10547 | TTGACCTCCCGCTGGA | 38 | 430 |
| 728703 | 1300 | 1315 | 10533 | 10548 | CTTGACCTCCCGCTGG | 33 | 431 |
| 728704 | 1302 | 1317 | 10535 | 10550 | GTCTTGACCTCCCGCT | 56 | 432 |
| 728705 | 1303 | 1318 | 10536 | 10551 | GGTCTTGACCTCCCGC | 71 | 433 |

TABLE 6-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
| --- | --- | --- | --- | --- | --- | --- | --- |
| 728706 | 1306 | 1321 | 10539 | 10554 | CTTGGTCTTGACCTCC | 73 | 434 |
| 728707 | 1307 | 1322 | 10540 | 10555 | GCTTGGTCTTGACCTC | 79 | 435 |
| 728708 | 1308 | 1323 | 10541 | 10556 | AGCTTGGTCTTGACCT | 79 | 436 |
| 728709 | 1310 | 1325 | 10543 | 10558 | AAAGCTTGGTCTTGAC | 46 | 437 |
| 728710 | 1311 | 1326 | 10544 | 10559 | AAAAGCTTGGTCTTGA | 29 | 438 |
| 728711 | 1312 | 1327 | 10545 | 10560 | GAAAAGCTTGGTCTTG | 24 | 439 |
| 728712 | 1313 | 1328 | 10546 | 10561 | TGAAAAGCTTGGTCTT | 11 | 440 |
| 728713 | 1314 | 1329 | 10547 | 10562 | CTGAAAAGCTTGGTCT | 13 | 441 |
| 728714 | 1316 | 1331 | 10549 | 10564 | GGCTGAAAAGCTTGGT | 11 | 442 |
| 728715 | 1318 | 1333 | 10551 | 10566 | CAGGCTGAAAAGCTTG | 1 | 443 |
| 728716 | 1320 | 1335 | 10553 | 10568 | TCCAGGCTGAAAAGCT | 5 | 444 |
| 728717 | 1340 | 1355 | N/A | N/A | TGAGCTCATTGAGAAA | 10 | 445 |
| 728718 | 1342 | 1357 | N/A | N/A | GATGAGCTCATTGAGA | 33 | 446 |
| 728719 | 1344 | 1359 | N/A | N/A | AGGATGAGCTCATTGA | 55 | 447 |
| 728720 | 1346 | 1361 | N/A | N/A | ACAGGATGAGCTCATT | 41 | 448 |
| 728721 | 1348 | 1363 | N/A | N/A | GAACAGGATGAGCTCA | 45 | 449 |
| 728722 | 1350 | 1365 | 10671 | 10686 | TGGAACAGGATGAGCT | 47 | 450 |
| 728723 | 1358 | 1373 | 10679 | 10694 | GGCCCTTTTGGAACAG | 29 | 451 |
| 728724 | 1359 | 1374 | 10680 | 10695 | TGGCCCTTTTGGAACA | 34 | 452 |
| 728725 | 1360 | 1375 | 10681 | 10696 | CTGGCCCTTTTGGAAC | 20 | 453 |
| 728726 | 1361 | 1376 | 10682 | 10697 | TCTGGCCCTTTTGGAA | 14 | 454 |
| 728727 | 1362 | 1377 | 10683 | 10698 | GTCTGGCCCTTTTGGA | 33 | 455 |
| 728728 | 1364 | 1379 | 10685 | 10700 | TGGTCTGGCCCTTTTG | 56 | 456 |
| 728729 | 1365 | 1380 | 10686 | 10701 | TTGGTCTGGCCCTTTT | 54 | 457 |
| 728730 | 1366 | 1381 | 10687 | 10702 | GTTGGTCTGGCCCTTT | 53 | 458 |
| 728731 | 1367 | 1382 | 10688 | 10703 | TGTTGGTCTGGCCCTT | 50 | 459 |
| 728732 | 1368 | 1383 | 10689 | 10704 | GTGTTGGTCTGGCCCT | 47 | 460 |
| 728733 | 1386 | 1401 | 10707 | 10722 | ATCTCGAAGGGTGGTG | 40 | 461 |
| 728734 | 1389 | 1404 | 10710 | 10725 | AAGATCTCGAAGGGTG | 52 | 462 |
| 728735 | 1392 | 1407 | 10713 | 10728 | AAGAAGATCTCGAAGG | 28 | 463 |

TABLE 7

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665893 | 1228 | 1243 | 10461 | 10476 | GCACTGACACAGGCGG | 73 | 39 |
| 665925 | 1506 | 1521 | 11071 | 11086 | GATAGCTCCCCTGAGA | 29 | 464 |
| 665926 | 1512 | 1527 | 11077 | 11092 | GACCAAGATAGCTCCC | 50 | 465 |
| 665929 | 1530 | 1545 | 11095 | 11110 | AGCCGGATACTATCAG | 49 | 466 |
| 665930 | 1536 | 1551 | 11101 | 11116 | ATCTGTAGCCGGATAC | 39 | 467 |
| 665933 | 1561 | 1576 | 11126 | 11141 | GCGGTCTTTGAGGTCT | 62 | 468 |
| 728736 | 1394 | 1409 | 10715 | 10730 | AGAAGAAGATCTCGAA | 13 | 469 |
| 728737 | 1396 | 1411 | 10717 | 10732 | GCAGAAGAAGATCTCG | 45 | 470 |
| 728738 | 1419 | 1434 | 10740 | 10755 | CGGTCAGGCCATTCTT | 52 | 471 |
| 728739 | 1421 | 1436 | 10742 | 10757 | TGCGGTCAGGCCATTC | 68 | 472 |
| 728740 | 1423 | 1438 | 10744 | 10759 | TTTGCGGTCAGGCCAT | 37 | 473 |
| 728741 | 1426 | 1441 | 10747 | 10762 | GGGTTTGCGGTCAGGC | 71 | 474 |
| 728742 | 1441 | 1456 | 10762 | 10777 | GAGCTTCTTCTCTCGG | 22 | 475 |
| 728743 | 1443 | 1458 | 10764 | 10779 | ATGAGCTTCTTCTCTC | 0 | 476 |
| 728744 | 1445 | 1460 | 10766 | 10781 | TAATGAGCTTCTTCTC | 14 | 477 |
| 728745 | 1447 | 1462 | 10768 | 10783 | AGTAATGAGCTTCTTC | 36 | 478 |
| 728746 | 1449 | 1464 | 10770 | 10785 | ACAGTAATGAGCTTCT | 30 | 479 |
| 728747 | 1451 | 1466 | 10772 | 10787 | GTACAGTAATGAGCTT | 26 | 480 |
| 728748 | 1453 | 1468 | 10774 | 10789 | CTGTACAGTAATGAGC | 37 | 481 |
| 728749 | 1455 | 1470 | 10776 | 10791 | ACCTGTACAGTAATGA | 28 | 482 |
| 728750 | 1457 | 1472 | N/A | N/A | CCACCTGTACAGTAAT | 27 | 483 |
| 728751 | 1459 | 1474 | N/A | N/A | CACCACCTGTACAGTA | 42 | 484 |
| 728752 | 1461 | 1476 | N/A | N/A | GGCACCACCTGTACAG | 27 | 485 |
| 728753 | 1463 | 1478 | N/A | N/A | CAGGCACCACCTGTAC | 53 | 486 |
| 728754 | 1465 | 1480 | N/A | N/A | TACAGGCACCACCTGT | 0 | 487 |
| 728755 | 1467 | 1482 | 11032 | 11047 | GCTACAGGCACCACCT | 37 | 488 |
| 728756 | 1469 | 1484 | 11034 | 11049 | CTGCTACAGGCACCAC | 53 | 489 |
| 728757 | 1471 | 1486 | 11036 | 11051 | AGCTGCTACAGGCACC | 41 | 490 |
| 728758 | 1473 | 1488 | 11038 | 11053 | CGAGCTGCTACAGGCA | 54 | 491 |
| 728759 | 1475 | 1490 | 11040 | 11055 | GTCGAGCTGCTACAGG | 63 | 492 |
| 728760 | 1477 | 1492 | 11042 | 11057 | CAGTCGAGCTGCTACA | 34 | 493 |
| 728761 | 1479 | 1494 | 11044 | 11059 | AGCAGTCGAGCTGCTA | 3 | 494 |
| 728762 | 1481 | 1496 | 11046 | 11061 | GCAGCAGTCGAGCTGC | 13 | 495 |
| 728763 | 1483 | 1498 | 11048 | 11063 | CAGCAGCAGTCGAGCT | 16 | 496 |
| 728764 | 1485 | 1500 | 11050 | 11065 | TCCAGCAGCAGTCGAG | 23 | 497 |
| 728765 | 1487 | 1502 | 11052 | 11067 | TCTCCAGCAGCAGTCG | 30 | 498 |

TABLE 7-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728766 | 1489 | 1504 | 11054 | 11069 | CATCTCCAGCAGCAGT | 31 | 499 |
| 728767 | 1492 | 1507 | 11057 | 11072 | GAACATCTCCAGCAGC | 47 | 500 |
| 728768 | 1495 | 1510 | 11060 | 11075 | TGAGAACATCTCCAGC | 33 | 501 |
| 728769 | 1497 | 1512 | 11062 | 11077 | CCTGAGAACATCTCCA | 60 | 502 |
| 728770 | 1499 | 1514 | 11064 | 11079 | CCCCTGAGAACATCTC | 43 | 503 |
| 728771 | 1501 | 1516 | 11066 | 11081 | CTCCCCTGAGAACATC | 42 | 504 |
| 728772 | 1502 | 1517 | 11067 | 11082 | GCTCCCCTGAGAACAT | 55 | 505 |
| 728773 | 1503 | 1518 | 11068 | 11083 | AGCTCCCCTGAGAACA | 54 | 506 |
| 728774 | 1504 | 1519 | 11069 | 11084 | TAGCTCCCCTGAGAAC | 29 | 507 |
| 728775 | 1505 | 1520 | 11070 | 11085 | ATAGCTCCCCTGAGAA | 15 | 508 |
| 728776 | 1507 | 1522 | 11072 | 11087 | AGATAGCTCCCCTGAG | 42 | 509 |
| 728777 | 1508 | 1523 | 11073 | 11088 | AAGATAGCTCCCCTGA | 52 | 510 |
| 728778 | 1509 | 1524 | 11074 | 11089 | CAAGATAGCTCCCCTG | 64 | 511 |
| 728779 | 1510 | 1525 | 11075 | 11090 | CCAAGATAGCTCCCCT | 50 | 512 |
| 728780 | 1511 | 1526 | 11076 | 11091 | ACCAAGATAGCTCCCC | 21 | 513 |
| 728781 | 1513 | 1528 | 11078 | 11093 | TGACCAAGATAGCTCC | 43 | 514 |
| 728782 | 1514 | 1529 | 11079 | 11094 | CTGACCAAGATAGCTC | 51 | 515 |
| 728783 | 1515 | 1530 | 11080 | 11095 | GCTGACCAAGATAGCT | 23 | 516 |
| 728784 | 1516 | 1531 | 11081 | 11096 | AGCTGACCAAGATAGC | 31 | 517 |
| 728785 | 1517 | 1532 | 11082 | 11097 | CAGCTGACCAAGATAG | 34 | 518 |
| 728786 | 1519 | 1534 | 11084 | 11099 | ATCAGCTGACCAAGAT | 28 | 519 |
| 728787 | 1521 | 1536 | 11086 | 11101 | CTATCAGCTGACCAAG | 48 | 520 |
| 728788 | 1523 | 1538 | 11088 | 11103 | TACTATCAGCTGACCA | 49 | 521 |
| 728789 | 1525 | 1540 | 11090 | 11105 | GATACTATCAGCTGAC | 58 | 522 |
| 728790 | 1526 | 1541 | 11091 | 11106 | GGATACTATCAGCTGA | 51 | 523 |
| 728791 | 1527 | 1542 | 11092 | 11107 | CGGATACTATCAGCTG | 55 | 524 |
| 728792 | 1528 | 1543 | 11093 | 11108 | CCGGATACTATCAGCT | 41 | 525 |
| 728793 | 1529 | 1544 | 11094 | 11109 | GCCGGATACTATCAGC | 68 | 526 |
| 728794 | 1531 | 1546 | 11096 | 11111 | TAGCCGGATACTATCA | 40 | 527 |
| 728795 | 1532 | 1547 | 11097 | 11112 | GTAGCCGGATACTATC | 48 | 528 |
| 728796 | 1533 | 1548 | 11098 | 11113 | TGTAGCCGGATACTAT | 34 | 529 |
| 728797 | 1534 | 1549 | 11099 | 11114 | CTGTAGCCGGATACTA | 52 | 530 |
| 728798 | 1535 | 1550 | 11100 | 11115 | TCTGTAGCCGGATACT | 53 | 531 |
| 728799 | 1537 | 1552 | 11102 | 11117 | GATCTGTAGCCGGATA | 46 | 532 |
| 728800 | 1538 | 1553 | 11103 | 11118 | AGATCTGTAGCCGGAT | 67 | 533 |
| 728801 | 1543 | 1558 | 11108 | 11123 | GTTTGAGATCTGTAGC | 55 | 534 |

TABLE 7-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728802 | 1556 | 1571 | 11121 | 11136 | CTTTGAGGTCTGGGTT | 63 | 535 |
| 728803 | 1557 | 1572 | 11122 | 11137 | TCTTTGAGGTCTGGGT | 55 | 536 |
| 728804 | 1558 | 1573 | 11123 | 11138 | GTCTTTGAGGTCTGGG | 61 | 537 |
| 728805 | 1559 | 1574 | 11124 | 11139 | GGTCTTTGAGGTCTGG | 58 | 538 |
| 728806 | 1560 | 1575 | 11125 | 11140 | CGGTCTTTGAGGTCTG | 74 | 539 |
| 728807 | 1562 | 1577 | 11127 | 11142 | TGCGGTCTTTGAGGTC | 58 | 540 |

TABLE 8

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665893 | 1228 | 1243 | 10461 | 10476 | GCACTGACACAGGCGG | 72 | 39 |
| 665933 | 1561 | 1576 | 11126 | 11141 | GCGGTCTTTGAGGTCT | 62 | 468 |
| 665942 | 1613 | 1628 | 11178 | 11193 | ACCGCTGCTGGGACTG | 40 | 541 |
| 728808 | 1563 | 1578 | 11128 | 11143 | ATGCGGTCTTTGAGGT | 37 | 542 |
| 728809 | 1564 | 1579 | 11129 | 11144 | CATGCGGTCTTTGAGG | 17 | 543 |
| 728810 | 1565 | 1580 | 11130 | 11145 | CCATGCGGTCTTTGAG | 43 | 544 |
| 728811 | 1566 | 1581 | 11131 | 11146 | ACCATGCGGTCTTTGA | 26 | 545 |
| 728812 | 1568 | 1583 | 11133 | 11148 | CCACCATGCGGTCTTT | 9 | 546 |
| 728813 | 1570 | 1585 | 11135 | 11150 | CTCCACCATGCGGTCT | 22 | 547 |
| 728814 | 1572 | 1587 | 11137 | 11152 | TGCTCCACCATGCGGT | 23 | 548 |
| 728815 | 1574 | 1589 | 11139 | 11154 | ATTGCTCCACCATGCG | 0 | 549 |
| 728816 | 1576 | 1591 | 11141 | 11156 | GAATTGCTCCACCATG | 0 | 550 |
| 728817 | 1578 | 1593 | 11143 | 11158 | TTGAATTGCTCCACCA | 0 | 551 |
| 728818 | 1580 | 1595 | 11145 | 11160 | CCTTGAATTGCTCCAC | 0 | 552 |
| 728819 | 1582 | 1597 | 11147 | 11162 | CTCCTTGAATTGCTCC | 0 | 553 |
| 728820 | 1584 | 1599 | 11149 | 11164 | AGCTCCTTGAATTGCT | 0 | 554 |
| 728821 | 1586 | 1601 | 11151 | 11166 | GGAGCTCCTTGAATTG | 0 | 555 |
| 728822 | 1588 | 1603 | 11153 | 11168 | ATGGAGCTCCTTGAAT | 2 | 556 |
| 728823 | 1590 | 1605 | 11155 | 11170 | TGATGGAGCTCCTTGA | 0 | 557 |
| 728824 | 1592 | 1607 | 11157 | 11172 | TGTGATGGAGCTCCTT | 0 | 558 |
| 728825 | 1594 | 1609 | 11159 | 11174 | GATGTGATGGAGCTCC | 30 | 559 |
| 728826 | 1596 | 1611 | 11161 | 11176 | CAGATGTGATGGAGCT | 27 | 560 |
| 728827 | 1600 | 1615 | 11165 | 11180 | CTGCCAGATGTGATGG | 7 | 561 |
| 728828 | 1602 | 1617 | 11167 | 11182 | GACTGCCAGATGTGAT | 0 | 562 |

TABLE 8-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728829 | 1604 | 1619 | 11169 | 11184 | GGGACTGCCAGATGTG | 31 | 563 |
| 728830 | 1606 | 1621 | 11171 | 11186 | CTGGGACTGCCAGATG | 40 | 564 |
| 728831 | 1608 | 1623 | 11173 | 11188 | TGCTGGGACTGCCAGA | 24 | 565 |
| 728832 | 1609 | 1624 | 11174 | 11189 | CTGCTGGGACTGCCAG | 19 | 566 |
| 728833 | 1610 | 1625 | 11175 | 11190 | GCTGCTGGGACTGCCA | 24 | 567 |
| 728834 | 1612 | 1627 | 11177 | 11192 | CCGCTGCTGGGACTGC | 37 | 568 |
| 728835 | 1614 | 1629 | 11179 | 11194 | AACCGCTGCTGGGACT | 19 | 569 |
| 728836 | 1616 | 1631 | 11181 | 11196 | GCAACCGCTGCTGGGA | 38 | 570 |
| 728837 | 1618 | 1633 | 11183 | 11198 | CTGCAACCGCTGCTGG | 26 | 571 |
| 728838 | 1620 | 1635 | 11185 | 11200 | GGCTGCAACCGCTGCT | 2 | 572 |
| 728839 | 1624 | 1639 | 11189 | 11204 | CACAGGCTGCAACCGC | 26 | 573 |
| 728840 | 1626 | 1641 | 11191 | 11206 | GCCACAGGCTGCAACC | 21 | 574 |
| 728841 | 1628 | 1643 | 11193 | 11208 | GGGCCACAGGCTGCAA | 37 | 575 |
| 728842 | 1650 | 1665 | 11215 | 11230 | AGGCCTGCTCCAGGAG | 0 | 576 |
| 728843 | 1654 | 1669 | 11219 | 11234 | ACCAAGGCCTGCTCCA | 30 | 577 |
| 728844 | 1656 | 1671 | 11221 | 11236 | ACACCAAGGCCTGCTC | 41 | 578 |
| 728845 | 1659 | 1674 | 11224 | 11239 | CCAACACCAAGGCCTG | 8 | 579 |
| 728846 | 1661 | 1676 | 11226 | 11241 | GGCCAACACCAAGGCC | 0 | 580 |
| 728847 | 1663 | 1678 | 11228 | 11243 | CTGGCCAACACCAAGG | 18 | 581 |
| 728848 | 1666 | 1681 | 11231 | 11246 | CCCCTGGCCAACACCA | 0 | 582 |
| 728849 | 1668 | 1683 | 11233 | 11248 | GGCCCCTGGCCAACAC | 0 | 583 |
| 728850 | 1670 | 1685 | 11235 | 11250 | AGGGCCCCTGGCCAAC | 21 | 584 |
| 728851 | 1676 | 1691 | 11241 | 11256 | TAGGCCAGGGCCCCTG | 0 | 585 |
| 728852 | 1678 | 1693 | 11243 | 11258 | CATAGGCCAGGGCCCC | 0 | 586 |
| 728853 | 1680 | 1695 | 11245 | 11260 | TGCATAGGCCAGGGCC | 0 | 587 |
| 728854 | 1682 | 1697 | 11247 | 11262 | GGTGCATAGGCCAGGG | 0 | 588 |
| 728855 | 1684 | 1699 | 11249 | 11264 | TGGGTGCATAGGCCAG | 0 | 589 |
| 728856 | 1687 | 1702 | 11252 | 11267 | AGCTGGGTGCATAGGC | 0 | 590 |
| 728857 | 1690 | 1705 | 11255 | 11270 | GCCAGCTGGGTGCATA | 15 | 591 |
| 728858 | 1693 | 1708 | 11258 | 11273 | CATGCCAGCTGGGTGC | 28 | 592 |
| 728859 | 1695 | 1710 | 11260 | 11275 | TGCATGCCAGCTGGGT | 32 | 593 |
| 728860 | 1697 | 1712 | 11262 | 11277 | ATTGCATGCCAGCTGG | 34 | 594 |
| 728861 | 1699 | 1714 | 11264 | 11279 | TTATTGCATGCCAGCT | 19 | 595 |
| 728862 | 1701 | 1716 | 11266 | 11281 | TGTTATTGCATGCCAG | 35 | 596 |
| 728863 | 1703 | 1718 | 11268 | 11283 | CTTGTTATTGCATGCC | 51 | 597 |
| 728864 | 1705 | 1720 | 11270 | 11285 | GCCTTGTTATTGCATG | 16 | 598 |

TABLE 8-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728865 | 1707 | 1722 | 11272 | 11287 | CAGCCTTGTTATTGCA | 3 | 599 |
| 728866 | 1709 | 1724 | 11274 | 11289 | TGCAGCCTTGTTATTG | 0 | 600 |
| 728867 | 1711 | 1726 | 11276 | 11291 | TCTGCAGCCTTGTTAT | 0 | 601 |
| 728868 | 1713 | 1728 | 11278 | 11293 | CGTCTGCAGCCTTGTT | 43 | 602 |
| 728869 | 1715 | 1730 | 11280 | 11295 | ACCGTCTGCAGCCTTG | 51 | 603 |
| 728870 | 1717 | 1732 | 11282 | 11297 | TCACCGTCTGCAGCCT | 14 | 604 |
| 728871 | 1719 | 1734 | 11284 | 11299 | AGTCACCGTCTGCAGC | 36 | 605 |
| 728872 | 1721 | 1736 | 11286 | 11301 | CCAGTCACCGTCTGCA | 57 | 606 |
| 728873 | 1723 | 1738 | 11288 | 11303 | GGCCAGTCACCGTCTG | 6 | 607 |
| 728874 | 1725 | 1740 | 11290 | 11305 | AGGGCCAGTCACCGTC | 28 | 608 |
| 728875 | 1727 | 1742 | 11292 | 11307 | CCAGGGCCAGTCACCG | 30 | 609 |
| 728876 | 1731 | 1746 | 11296 | 11311 | GAAGCCAGGGCCAGTC | 30 | 610 |
| 728877 | 1742 | 1757 | 11307 | 11322 | CCGCCACCCAGGAAGC | 30 | 611 |
| 728878 | 1744 | 1759 | 11309 | 11324 | CACCGCCACCCAGGAA | 9 | 612 |
| 728879 | 1746 | 1761 | 11311 | 11326 | CGCACCGCCACCCAGG | 46 | 613 |
| 728880 | 1748 | 1763 | 11313 | 11328 | TCCGCACCGCCACCCA | 29 | 614 |
| 728881 | 1749 | 1764 | 11314 | 11329 | GTCCGCACCGCCACCC | 30 | 615 |
| 728882 | 1750 | 1765 | 11315 | 11330 | AGTCCGCACCGCCACC | 27 | 616 |
| 728883 | 1751 | 1766 | 11316 | 11331 | CAGTCCGCACCGCCAC | 56 | 617 |

TABLE 9

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665893 | 1228 | 1243 | 10461 | 10476 | GCACTGACACAGGCGG | 74 | 39 |
| 665933 | 1561 | 1576 | 11126 | 11141 | GCGGTCTTTGAGGTCT | 60 | 468 |
| 665962 | 1753 | 1768 | 11318 | 11333 | ATCAGTCCGCACCGCC | 53 | 618 |
| 665964 | 1765 | 1780 | 11330 | 11345 | TCACATCTCCACATCA | 36 | 619 |
| 665973 | 1903 | 1918 | 11468 | 11483 | AGACCAGAGACAGCCC | 30 | 620 |
| 665975 | 1911 | 1926 | 11476 | 11491 | GGCTGACCAGACCAGA | 40 | 621 |
| 665981 | 1951 | 1966 | 11516 | 11531 | GAGTTCTTTCCCTGCT | 41 | 622 |
| 728884 | 1752 | 1767 | 11317 | 11332 | TCAGTCCGCACCGCCA | 46 | 623 |
| 728885 | 1754 | 1769 | 11319 | 11334 | CATCAGTCCGCACCGC | 23 | 624 |
| 728886 | 1755 | 1770 | 11320 | 11335 | ACATCAGTCCGCACCG | 48 | 625 |

TABLE 9-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728887 | 1756 | 1771 | 11321 | 11336 | CACATCAGTCCGCACC | 57 | 626 |
| 728888 | 1757 | 1772 | 11322 | 11337 | CCACATCAGTCCGCAC | 37 | 627 |
| 728889 | 1758 | 1773 | 11323 | 11338 | TCCACATCAGTCCGCA | 24 | 628 |
| 728890 | 1760 | 1775 | 11325 | 11340 | TCTCCACATCAGTCCG | 33 | 629 |
| 728891 | 1761 | 1776 | 11326 | 11341 | ATCTCCACATCAGTCC | 56 | 630 |
| 728892 | 1762 | 1777 | 11327 | 11342 | CATCTCCACATCAGTC | 37 | 631 |
| 728893 | 1763 | 1778 | 11328 | 11343 | ACATCTCCACATCAGT | 56 | 632 |
| 728894 | 1764 | 1779 | 11329 | 11344 | CACATCTCCACATCAG | 65 | 633 |
| 728895 | 1766 | 1781 | 11331 | 11346 | GTCACATCTCCACATC | 47 | 634 |
| 728896 | 1767 | 1782 | 11332 | 11347 | TGTCACATCTCCACAT | 21 | 635 |
| 728897 | 1768 | 1783 | 11333 | 11348 | CTGTCACATCTCCACA | 46 | 636 |
| 728898 | 1769 | 1784 | 11334 | 11349 | GCTGTCACATCTCCAC | 73 | 637 |
| 728899 | 1770 | 1785 | 11335 | 11350 | GGCTGTCACATCTCCA | 64 | 638 |
| 728900 | 1786 | 1801 | 11351 | 11366 | GCCAGGTGCTCATCGG | 37 | 639 |
| 728901 | 1788 | 1803 | 11353 | 11368 | CAGCCAGGTGCTCATC | 37 | 640 |
| 728902 | 1790 | 1805 | 11355 | 11370 | GCCAGCCAGGTGCTCA | 42 | 641 |
| 728903 | 1803 | 1818 | 11368 | 11383 | GTAGGACCCTGCAGCC | 31 | 642 |
| 728904 | 1805 | 1820 | 11370 | 11385 | AGGTAGGACCCTGCAG | 6 | 643 |
| 728905 | 1807 | 1822 | 11372 | 11387 | AGAGGTAGGACCCTGC | 60 | 644 |
| 728906 | 1810 | 1825 | 11375 | 11390 | CCCAGAGGTAGGACCC | 42 | 645 |
| 728907 | 1812 | 1827 | 11377 | 11392 | AACCCAGAGGTAGGAC | 32 | 646 |
| 728908 | 1814 | 1829 | 11379 | 11394 | GAAACCCAGAGGTAGG | 44 | 647 |
| 728909 | 1825 | 1840 | 11390 | 11405 | TCCACTTCCAGGAAAC | 25 | 648 |
| 728910 | 1833 | 1848 | 11398 | 11413 | GGCCCAAATCCACTTC | 11 | 649 |
| 728911 | 1835 | 1850 | 11400 | 11415 | TTGGCCCAAATCCACT | 9 | 650 |
| 728912 | 1837 | 1852 | 11402 | 11417 | TCTTGGCCCAAATCCA | 22 | 651 |
| 728913 | 1839 | 1854 | 11404 | 11419 | CTTCTTGGCCCAAATC | 15 | 652 |
| 728914 | 1841 | 1856 | 11406 | 11421 | TCCTTCTTGGCCCAAA | 31 | 653 |
| 728915 | 1859 | 1874 | 11424 | 11439 | CTCGGGCCTTTCTCCC | 2 | 654 |
| 728916 | 1861 | 1876 | 11426 | 11441 | GGCTCGGGCCTTTCTC | 10 | 655 |
| 728917 | 1884 | 1899 | 11449 | 11464 | AGAGAAAGGCCCGGGA | 0 | 656 |
| 728918 | 1886 | 1901 | 11451 | 11466 | GGAGAGAAAGGCCCGG | 0 | 657 |
| 728919 | 1898 | 1913 | 11463 | 11478 | AGAGACAGCCCAGGAG | 13 | 658 |
| 728920 | 1901 | 1916 | 11466 | 11481 | ACCAGAGACAGCCCAG | 52 | 659 |
| 728921 | 1902 | 1917 | 11467 | 11482 | GACCAGAGACAGCCCA | 42 | 660 |
| 728922 | 1904 | 1919 | 11469 | 11484 | CAGACCAGAGACAGCC | 38 | 661 |

TABLE 9-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 728923 | 1905 | 1920 | 11470 | 11485 | CCAGACCAGAGACAGC | 17 | 662 |
| 728924 | 1906 | 1921 | 11471 | 11486 | ACCAGACCAGAGACAG | 30 | 663 |
| 728925 | 1907 | 1922 | 11472 | 11487 | GACCAGACCAGAGACA | 14 | 664 |
| 728926 | 1908 | 1923 | 11473 | 11488 | TGACCAGACCAGAGAC | 7 | 665 |
| 728927 | 1910 | 1925 | 11475 | 11490 | GCTGACCAGACCAGAG | 26 | 666 |
| 728928 | 1912 | 1927 | 11477 | 11492 | AGGCTGACCAGACCAG | 14 | 667 |
| 728929 | 1916 | 1931 | 11481 | 11496 | AGCCAGGCTGACCAGA | 13 | 668 |
| 728930 | 1919 | 1934 | 11484 | 11499 | GAGAGCCAGGCTGACC | 26 | 669 |
| 728931 | 1923 | 1938 | 11488 | 11503 | TCCCGAGAGCCAGGCT | 26 | 670 |
| 728932 | 1925 | 1940 | 11490 | 11505 | TTTCCCGAGAGCCAGG | 26 | 671 |
| 728933 | 1928 | 1943 | 11493 | 11508 | GAATTTCCCGAGAGCC | 34 | 672 |
| 728934 | 1930 | 1945 | 11495 | 11510 | CTGAATTTCCCGAGAG | 33 | 673 |
| 728935 | 1932 | 1947 | 11497 | 11512 | GGCTGAATTTCCCGAG | 39 | 674 |
| 728936 | 1934 | 1949 | 11499 | 11514 | ATGGCTGAATTTCCCG | 39 | 675 |
| 728937 | 1936 | 1951 | 11501 | 11516 | TCATGGCTGAATTTCC | 36 | 676 |
| 728938 | 1938 | 1953 | 11503 | 11518 | GCTCATGGCTGAATTT | 30 | 677 |
| 728939 | 1940 | 1955 | 11505 | 11520 | CTGCTCATGGCTGAAT | 40 | 678 |
| 728940 | 1942 | 1957 | 11507 | 11522 | CCCTGCTCATGGCTGA | 51 | 679 |
| 728941 | 1946 | 1961 | 11511 | 11526 | CTTTCCCTGCTCATGG | 45 | 680 |
| 728942 | 1947 | 1962 | 11512 | 11527 | TCTTTCCCTGCTCATG | 54 | 681 |
| 728943 | 1948 | 1963 | 11513 | 11528 | TTCTTTCCCTGCTCAT | 16 | 682 |
| 728944 | 1949 | 1964 | 11514 | 11529 | GTTCTTTCCCTGCTCA | 56 | 683 |
| 728945 | 1950 | 1965 | 11515 | 11530 | AGTTCTTTCCCTGCTC | 56 | 684 |
| 728946 | 1952 | 1967 | 11517 | 11532 | AGAGTTCTTTCCCTGC | 56 | 685 |
| 728947 | 1953 | 1968 | 11518 | 11533 | GAGAGTTCTTTCCCTG | 54 | 686 |
| 728948 | 1954 | 1969 | 11519 | 11534 | GGAGAGTTCTTTCCCT | 32 | 687 |
| 728949 | 1955 | 1970 | 11520 | 11535 | GGGAGAGTTCTTTCCC | 1 | 688 |
| 728950 | 1956 | 1971 | 11521 | 11536 | TGGGAGAGTTCTTTCC | 24 | 689 |
| 728951 | 1958 | 1973 | 11523 | 11538 | GTTGGGAGAGTTCTTT | 29 | 690 |
| 728952 | 1970 | 1985 | 11535 | 11550 | CTAGGCCCCAGGGTTG | 35 | 691 |
| 728953 | 1972 | 1987 | 11537 | 11552 | AGCTAGGCCCCAGGGT | 23 | 692 |
| 728954 | 1974 | 1989 | 11539 | 11554 | ACAGCTAGGCCCCAGG | 64 | 693 |
| 728955 | 1976 | 1991 | 11541 | 11556 | ATACAGCTAGGCCCCA | 14 | 694 |

TABLE 10

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665893 | 1228 | 1243 | 10461 | 10476 | GCACTGACACAGGCGG | 73 | 39 |
| 665933 | 1561 | 1576 | 11126 | 11141 | GCGGTCTTTGAGGTCT | 69 | 468 |
| 666013 | 2215 | 2230 | 11780 | 11795 | GTTCTTGGACTCTCAA | 65 | 695 |
| 666015 | 2228 | 2243 | 11793 | 11808 | ATTTCTGCTCCAGGTT | 54 | 696 |
| 729028 | 2190 | 2205 | 11755 | 11770 | AGCTGCCAGCCTTGAG | 50 | 697 |
| 729029 | 2191 | 2206 | 11756 | 11771 | TAGCTGCCAGCCTTGA | 57 | 698 |
| 729030 | 2192 | 2207 | 11757 | 11772 | GTAGCTGCCAGCCTTG | 65 | 699 |
| 729031 | 2194 | 2209 | 11759 | 11774 | GGGTAGCTGCCAGCCT | 41 | 700 |
| 729032 | 2210 | 2225 | 11775 | 11790 | TGGACTCTCAAGAAGG | 55 | 701 |
| 729033 | 2211 | 2226 | 11776 | 11791 | TTGGACTCTCAAGAAG | 37 | 702 |
| 729034 | 2212 | 2227 | 11777 | 11792 | CTTGGACTCTCAAGAA | 38 | 703 |
| 729035 | 2213 | 2228 | 11778 | 11793 | TCTTGGACTCTCAAGA | 0 | 704 |
| 729036 | 2214 | 2229 | 11779 | 11794 | TTCTTGGACTCTCAAG | 55 | 705 |
| 729037 | 2216 | 2231 | 11781 | 11796 | GGTTCTTGGACTCTCA | 80 | 706 |
| 729038 | 2217 | 2232 | 11782 | 11797 | AGGTTCTTGGACTCTC | 85 | 707 |
| 729039 | 2218 | 2233 | 11783 | 11798 | CAGGTTCTTGGACTCT | 74 | 708 |
| 729040 | 2219 | 2234 | 11784 | 11799 | CCAGGTTCTTGGACTC | 67 | 709 |
| 729041 | 2220 | 2235 | 11785 | 11800 | TCCAGGTTCTTGGACT | 39 | 710 |
| 729042 | 2222 | 2237 | 11787 | 11802 | GCTCCAGGTTCTTGGA | 11 | 711 |
| 729043 | 2223 | 2238 | 11788 | 11803 | TGCTCCAGGTTCTTGG | 44 | 712 |
| 729044 | 2224 | 2239 | 11789 | 11804 | CTGCTCCAGGTTCTTG | 62 | 713 |
| 729045 | 2225 | 2240 | 11790 | 11805 | TCTGCTCCAGGTTCTT | 60 | 714 |
| 729046 | 2226 | 2241 | 11791 | 11806 | TTCTGCTCCAGGTTCT | 54 | 715 |
| 729047 | 2227 | 2242 | 11792 | 11807 | TTTCTGCTCCAGGTTC | 63 | 716 |
| 729048 | 2229 | 2244 | 11794 | 11809 | TATTTCTGCTCCAGGT | 63 | 717 |
| 729049 | 2230 | 2245 | 11795 | 11810 | TTATTTCTGCTCCAGG | 76 | 718 |
| 729050 | 2231 | 2246 | 11796 | 11811 | ATTATTTCTGCTCCAG | 76 | 719 |
| 729051 | 2232 | 2247 | 11797 | 11812 | AATTATTTCTGCTCCA | 58 | 720 |
| 729052 | 2260 | 2275 | 11825 | 11840 | AACATTCATTAATCCA | 55 | 721 |
| 729053 | 2278 | 2293 | 11843 | 11858 | ACAGCTGAGTCTGTTT | 26 | 722 |
| 729055 | 2300 | 2315 | 11865 | 11880 | TGGTAGTAGTAAAAGG | 24 | 723 |
| 729060 | 2310 | 2325 | 11875 | 11890 | TGGGAGCAACTGGTAG | 33 | 724 |
| 729064 | 2322 | 2337 | 11887 | 11902 | GGTGGAGCAGCATGGG | 14 | 725 |
| 729067 | 2336 | 2351 | 11901 | 11916 | CCGAAACAGGGCCTGG | 33 | 726 |
| 729072 | 2346 | 2361 | 11911 | 11926 | CAGTTGGCATCCGAAA | 8 | 727 |
| 729077 | 2385 | 2400 | 11950 | 11965 | AATGGTCGCAAGCTGG | 26 | 728 |

TABLE 10-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 729082 | 2395 | 2410 | 11960 | 11975 | TCCCAGTGCCAATGGT | 5 | 729 |
| 729086 | 2417 | 2432 | 11982 | 11997 | CATCAGCCCAGAAGCC | 12 | 730 |
| 729090 | 2427 | 2442 | 11992 | 12007 | CCAACTGACCCATCAG | 8 | 731 |
| 729095 | 2437 | 2452 | 12002 | 12017 | TTATGAAGGCCCAACT | 0 | 732 |
| 729100 | 2447 | 2462 | 12012 | 12027 | AGGTGAGTGTTTATGA | 33 | 733 |
| 729105 | 2457 | 2472 | 12022 | 12037 | AAAGCCAGCCAGGTGA | 30 | 734 |
| 729106 | 2486 | 2501 | 12051 | 12066 | TTGCTTCAGCCAGCTT | 15 | 735 |
| 729110 | 2496 | 2511 | 12061 | 12076 | TTCCACACCCTTGCTT | 11 | 736 |
| 729112 | 2515 | 2530 | 12080 | 12095 | ACTGTGCACACATTTA | 53 | 737 |
| 729116 | 2525 | 2540 | 12090 | 12105 | AGTTTTCCAGACTGTG | 28 | 738 |
| 729120 | 2536 | 2551 | 12101 | 12116 | CTGATTCTGACAGTTT | 0 | 739 |
| 729123 | 2547 | 2562 | 12112 | 12127 | TTATGGGAAAACTGAT | 0 | 740 |
| 729125 | 2557 | 2572 | 12122 | 12137 | GCCCACCCTTTTATGG | 0 | 741 |
| 729129 | 2567 | 2582 | 12132 | 12147 | TGCAATGCTAGCCCAC | 54 | 742 |
| 729134 | 2577 | 2592 | 12142 | 12157 | CAAATGCAGCTGCAAT | 27 | 743 |
| 729139 | 2588 | 2603 | 12153 | 12168 | TTGAATGGTCCCAAAT | 22 | 744 |
| 729144 | 2599 | 2614 | 12164 | 12179 | GAGTGACAGATTTGAA | 55 | 745 |
| 729146 | 2620 | 2635 | 12185 | 12200 | AGCACAGGAATATACA | 36 | 746 |
| 729150 | 2637 | 2652 | 12202 | 12217 | GCCCTGATATATTTAA | 0 | 747 |
| 729155 | 2647 | 2662 | 12212 | 12227 | TACATGCACTGCCCTG | 31 | 748 |
| 729160 | 2657 | 2672 | 12222 | 12237 | CAGGATGATTTACATG | 5 | 749 |
| 729164 | 2703 | 2718 | 12268 | 12283 | ACTGTCCCCACCTCGG | 10 | 750 |
| 729165 | 2720 | 2735 | 12285 | 12300 | ACTAAGAGAACTCACT | 31 | 751 |
| 729167 | 2747 | 2762 | 12312 | 12327 | GGCTCTTTAACAACCA | 20 | 752 |
| 729170 | 2761 | 2776 | 12326 | 12341 | GCGGGTAGGTGCCAGG | 40 | 753 |
| 729175 | 2771 | 2786 | 12336 | 12351 | TGAAGTGAGAGCGGGT | 45 | 754 |
| 729180 | 2789 | 2804 | 12354 | 12369 | GTGCAGAGATGACACA | 0 | 755 |
| 729182 | 2800 | 2815 | 12365 | 12380 | TGGGCTGGAGTGTGCA | 30 | 756 |
| 729185 | 2820 | 2835 | 12385 | 12400 | CAATGGCTGAAGGCAG | 14 | 757 |
| 729190 | 2876 | 2891 | 12441 | 12456 | GCTGGGCATCAAGATT | 7 | 758 |
| 729194 | 2885 | 2900 | 12450 | 12465 | GTTCTGATGGCTGGGC | 50 | 759 |
| 729251 | N/A | N/A | 176 | 191 | CTGGAATGGCAAAACT | 12 | 760 |
| 729252 | N/A | N/A | 197 | 212 | GCCACTGGCTCTTTTG | 0 | 761 |
| 729253 | N/A | N/A | 207 | 222 | CCCTAGACTGGCCACT | 1 | 762 |
| 729254 | N/A | N/A | 218 | 233 | ACGGCGCGGTGCCCTA | 10 | 763 |
| 729255 | N/A | N/A | 257 | 272 | AGCCTCGGGCCAGGCC | 12 | 764 |

TABLE 10-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 729256 | N/A | N/A | 267 | 282 | ATCCGGGCTGAGCCTC | 8 | 765 |
| 729257 | N/A | N/A | 292 | 307 | CCCCGCACTGACCTGG | 43 | 766 |
| 729258 | N/A | N/A | 302 | 317 | CCACTCCGGGCCCCGC | 0 | 767 |
| 729259 | N/A | N/A | 312 | 327 | CCCCGCGAATCCACTC | 0 | 768 |
| 729260 | N/A | N/A | 364 | 379 | CGCCCCTGGGCAGCTG | 0 | 769 |
| 729635 | N/A | N/A | 228 | 243 | GAGATGCCAGACGGCG | 0 | 770 |
| 729636 | N/A | N/A | 344 | 359 | TGAGCTCCGGGCGCGG | 5 | 771 |

TABLE 11

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665893 | 1228 | 1243 | 10461 | 10476 | GCACTGACACAGGCGG | 74 | 39 |
| 665933 | 1561 | 1576 | 11126 | 11141 | GCGGTCTTTGAGGTCT | 57 | 468 |
| 729261 | N/A | N/A | 502 | 517 | GACCCACCTGTCTGCG | 7 | 772 |
| 729262 | N/A | N/A | 512 | 527 | CGGCGGCCGGGACCCA | 18 | 773 |
| 729263 | N/A | N/A | 532 | 547 | CGGACGCAGAGAGGAG | 20 | 774 |
| 729264 | N/A | N/A | 561 | 576 | CTCCCGCCACCCTCGG | 9 | 775 |
| 729265 | N/A | N/A | 571 | 586 | GCCGGCACCGCTCCCG | 0 | 776 |
| 729266 | N/A | N/A | 594 | 609 | TAGGCCTAGACTTGGG | 26 | 777 |
| 729267 | N/A | N/A | 635 | 650 | TCCCGCCGCCCGCAGG | 10 | 778 |
| 729268 | N/A | N/A | 645 | 660 | CCAGTCTTCATCCCGC | 33 | 779 |
| 729269 | N/A | N/A | 656 | 671 | CCCGCCCTACTCCAGT | 26 | 780 |
| 729270 | N/A | N/A | 686 | 701 | CTCGCTTTCCAGGCGC | 4 | 781 |
| 729271 | N/A | N/A | 696 | 711 | CCCCCCCGAGCTCGCT | 8 | 782 |
| 729272 | N/A | N/A | 706 | 721 | GCTGTAGGCACCCCCC | 19 | 783 |
| 729273 | N/A | N/A | 736 | 751 | TGGAAGTCCCAGGCCG | 21 | 784 |
| 729274 | N/A | N/A | 767 | 782 | CCCCAAACCGATCGGG | 0 | 785 |
| 729275 | N/A | N/A | 801 | 816 | CCGCCTGGGTCACTGG | 11 | 786 |
| 729276 | N/A | N/A | 811 | 826 | GCCCACTCCGCCGCCT | 0 | 787 |
| 729277 | N/A | N/A | 866 | 881 | CTGGGCGATGGCGAGG | 10 | 788 |
| 729278 | N/A | N/A | 876 | 891 | AACCCCCATTCTGGGC | 6 | 789 |
| 729279 | N/A | N/A | 886 | 901 | GGCTCCCGGGAACCCC | 11 | 790 |
| 729280 | N/A | N/A | 911 | 926 | TGTGGTCCAAGCCAGC | 29 | 791 |
| 729281 | N/A | N/A | 931 | 946 | AGGATCGGGCCTCGCT | 30 | 792 |

TABLE 11-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 729282 | N/A | N/A | 941 | 956 | ATCGAAAGTAAGGATC | 17 | 793 |
| 729283 | N/A | N/A | 957 | 972 | GAGCAAGGGCGAGTGC | 29 | 794 |
| 729284 | N/A | N/A | 967 | 982 | GGCCCGGTAAGAGCAA | 6 | 795 |
| 729285 | N/A | N/A | 986 | 1001 | TTTCCGAAAGGGTGAG | 32 | 796 |
| 729286 | N/A | N/A | 1028 | 1043 | GCCTGAAGATCCCGGG | 14 | 797 |
| 729287 | N/A | N/A | 1038 | 1053 | CCTGCCATTGGCCTGA | 14 | 798 |
| 729288 | N/A | N/A | 1057 | 1072 | CCCAAACTCTTGCACA | 25 | 799 |
| 729289 | N/A | N/A | 1074 | 1089 | ACCTGACACCATCTTC | 9 | 800 |
| 729290 | N/A | N/A | 1085 | 1100 | ACGCAGCCTCTACCTG | 0 | 801 |
| 729291 | N/A | N/A | 1096 | 1111 | CGAGCCCAGGGACGCA | 16 | 802 |
| 729292 | N/A | N/A | 1107 | 1122 | ATTCCCGGCCGCGAGC | 19 | 803 |
| 729293 | N/A | N/A | 1117 | 1132 | AGAGTCTGCCATTCCC | 44 | 804 |
| 729294 | N/A | N/A | 1157 | 1172 | GAACTATTGCGCCCCA | 35 | 805 |
| 729295 | N/A | N/A | 1167 | 1182 | ACCAGCCCAGGAACTA | 15 | 806 |
| 729296 | N/A | N/A | 1177 | 1192 | ACCTGAGGAAACCAGC | 15 | 807 |
| 729297 | N/A | N/A | 1190 | 1205 | GTTCTGGGACAGGACC | 19 | 808 |
| 729298 | N/A | N/A | 1213 | 1228 | CCTCTTCATTGTTGCC | 42 | 809 |
| 729299 | N/A | N/A | 1244 | 1259 | CATGCTAGCCTCACTT | 23 | 810 |
| 729300 | N/A | N/A | 1268 | 1283 | AACCATCTCCCCACGC | 21 | 811 |
| 729301 | N/A | N/A | 1278 | 1293 | GTCCGGAGACAACCAT | 13 | 812 |
| 729302 | N/A | N/A | 1308 | 1323 | TCCCAGGTACCCGCTC | 7 | 813 |
| 729303 | N/A | N/A | 1330 | 1345 | AGTCCCCCACTCCAGC | 23 | 814 |
| 729304 | N/A | N/A | 1342 | 1357 | CGAGGCTGGGAAAGTC | 18 | 815 |
| 729305 | N/A | N/A | 1370 | 1385 | CCTCGCCCTGCTGTGT | 18 | 816 |
| 729306 | N/A | N/A | 1380 | 1395 | GCACCCCGGTCCTCGC | 27 | 817 |
| 729307 | N/A | N/A | 1557 | 1572 | ATTCTGGGCCCTCGAG | 3 | 818 |
| 729308 | N/A | N/A | 1579 | 1594 | CTGGTTCTGGTCACTT | 41 | 819 |
| 729309 | N/A | N/A | 1591 | 1606 | GCCGAGCCCTCTCTGG | 13 | 820 |
| 729310 | N/A | N/A | 1601 | 1616 | CATCGATACAGCCGAG | 42 | 821 |
| 729311 | N/A | N/A | 1638 | 1653 | CTTGCCAGAGGGCCTC | 40 | 822 |
| 729312 | N/A | N/A | 1676 | 1691 | CCCCATAACTACTGGG | 20 | 823 |
| 729313 | N/A | N/A | 1702 | 1717 | GAACCCCTCAGCCCCA | 8 | 824 |
| 729314 | N/A | N/A | 1712 | 1727 | TTGACTCTTGGAACCC | 40 | 825 |
| 729315 | N/A | N/A | 1722 | 1737 | AGTGCTTCCCTTGACT | 20 | 826 |
| 729316 | N/A | N/A | 1748 | 1763 | CTTTAGATAAAAAGGG | 12 | 827 |
| 729317 | N/A | N/A | 1758 | 1773 | AAAGTAGGGCCTTTAG | 27 | 828 |

TABLE 11-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 729318 | N/A | N/A | 1833 | 1848 | GCCCAGAAAGAAGCTT | 5 | 829 |
| 729319 | N/A | N/A | 1867 | 1882 | GGTCCAGACAGGCTGA | 15 | 830 |
| 729320 | N/A | N/A | 1909 | 1924 | CTCCGGGTCAGCTGCC | 25 | 831 |
| 729321 | N/A | N/A | 1919 | 1934 | AATCCCACCCCTCCGG | 8 | 832 |
| 729322 | N/A | N/A | 1942 | 1957 | CCCTGTACAGGCCCTG | 1 | 833 |
| 729323 | N/A | N/A | 1992 | 2007 | ACATGTCTCCTTGCAA | 6 | 834 |
| 729324 | N/A | N/A | 2002 | 2017 | GGTCTGGGTCACATGT | 33 | 835 |
| 729325 | N/A | N/A | 2036 | 2051 | GCCAGACAGCAGGCGC | 11 | 836 |
| 729326 | N/A | N/A | 2047 | 2062 | TAGTAAGAGTGGCCAG | 16 | 837 |
| 729327 | N/A | N/A | 2058 | 2073 | CACAGCAGTCCTAGTA | 9 | 838 |
| 729328 | N/A | N/A | 2068 | 2083 | GAGGAAGTGCCACAGC | 17 | 839 |
| 729329 | N/A | N/A | 2100 | 2115 | TGCAATTCATGGGCAC | 18 | 840 |
| 729330 | N/A | N/A | 2110 | 2125 | ACCCAGGAGCTGCAAT | 4 | 841 |
| 729331 | N/A | N/A | 2129 | 2144 | AGACAGTGCCCCCACC | 5 | 842 |
| 729332 | N/A | N/A | 2170 | 2185 | TAAGCCCACAGCTCAC | 0 | 843 |
| 729333 | N/A | N/A | 2187 | 2202 | GACCTGCTGAGGTGGG | 15 | 844 |
| 729637 | N/A | N/A | 716 | 731 | GGCGCACCCTGCTGTA | 17 | 845 |
| 729638 | N/A | N/A | 1234 | 1249 | TCACTTTTCCTCCACG | 38 | 846 |
| 729639 | N/A | N/A | 1452 | 1467 | GGGCCAGCCCGCGGAG | 15 | 847 |
| 729640 | N/A | N/A | 1611 | 1626 | CAGTTTCCTACATCGA | 22 | 848 |

TABLE 12

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665893 | 1228 | 1243 | 10461 | 10476 | GCACTGACACAGGCGG | 73 | 39 |
| 665933 | 1561 | 1576 | 11126 | 11141 | GCGGTCTTTGAGGTCT | 63 | 468 |
| 729195 | N/A | N/A | 3775 | 3790 | TCGGGTAGCACTTAGG | 53 | 849 |
| 729334 | N/A | N/A | 2204 | 2219 | AGTGGGCAGCCCTAGA | 12 | 850 |
| 729335 | N/A | N/A | 2224 | 2239 | TGTGAGGCAGCGAAGC | 32 | 851 |
| 729336 | N/A | N/A | 2234 | 2249 | CCTACAATTGTGTGAG | 10 | 852 |
| 729337 | N/A | N/A | 2258 | 2273 | GAAATCCAACAGCCTG | 25 | 853 |
| 729338 | N/A | N/A | 2274 | 2289 | AGCCCCGGAAGGTGGG | 11 | 854 |
| 729339 | N/A | N/A | 2284 | 2299 | AATGGACCTGAGCCCC | 25 | 855 |

TABLE 12-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 729340 | N/A | N/A | 2304 | 2319 | TGGAGCCCTAGACCTA | 13 | 856 |
| 729341 | N/A | N/A | 2314 | 2329 | GTGAAATGTATGGAGC | 20 | 857 |
| 729342 | N/A | N/A | 2324 | 2339 | GAGTCTCTGGGTGAAA | 16 | 858 |
| 729343 | N/A | N/A | 2334 | 2349 | CCAGGCTCCGGAGTCT | 0 | 859 |
| 729344 | N/A | N/A | 2365 | 2380 | TGGAAGTTCGGTGTCA | 27 | 860 |
| 729345 | N/A | N/A | 2376 | 2391 | GCCCATGACTTTGGAA | 8 | 861 |
| 729346 | N/A | N/A | 2386 | 2401 | CCCAATCAAGGCCCAT | 16 | 862 |
| 729347 | N/A | N/A | 2405 | 2420 | TAGGTCTAATTCAGAC | 6 | 863 |
| 729348 | N/A | N/A | 2415 | 2430 | AGAAAAGGGCTAGGTC | 0 | 864 |
| 729349 | N/A | N/A | 2444 | 2459 | TCCATCCTCCTAGAAG | 0 | 865 |
| 729350 | N/A | N/A | 2454 | 2469 | CCGAACAGCATCCATC | 3 | 866 |
| 729351 | N/A | N/A | 2464 | 2479 | GAGCTCTAACCCGAAC | 0 | 867 |
| 729352 | N/A | N/A | 2507 | 2522 | AGGGACTCAGCCTCAA | 18 | 868 |
| 729353 | N/A | N/A | 2517 | 2532 | ATGCCACAGAAGGGAC | 15 | 869 |
| 729354 | N/A | N/A | 2527 | 2542 | TCTGTCCACCATGCCA | 6 | 870 |
| 729355 | N/A | N/A | 2538 | 2553 | ATGAGCGAGAGTCTGT | 25 | 871 |
| 729356 | N/A | N/A | 2615 | 2630 | GTGTCAGAGGGCCGCG | 28 | 872 |
| 729357 | N/A | N/A | 2625 | 2640 | TCCGACCTCAGTGTCA | 20 | 873 |
| 729358 | N/A | N/A | 2635 | 2650 | AAATGATAACTCCGAC | 27 | 874 |
| 729359 | N/A | N/A | 2658 | 2673 | GTTTAATACAGAGCAA | 36 | 875 |
| 729360 | N/A | N/A | 2668 | 2683 | CAACACGGCTGTTTAA | 0 | 876 |
| 729361 | N/A | N/A | 2695 | 2710 | CTGTCAGTCCAGCAGT | 29 | 877 |
| 729362 | N/A | N/A | 2708 | 2723 | TGCCTGCCCCCTACTG | 5 | 878 |
| 729363 | N/A | N/A | 2755 | 2770 | GAGGCCGTGCAGGCGC | 23 | 879 |
| 729364 | N/A | N/A | 2768 | 2783 | GACCCCCTGGGCTGAG | 17 | 880 |
| 729365 | N/A | N/A | 2778 | 2793 | CTTCCCTAATGACCCC | 19 | 881 |
| 729366 | N/A | N/A | 2799 | 2814 | TCTGCACAGAATCGGG | 18 | 882 |
| 729367 | N/A | N/A | 2823 | 2838 | CAAGGGTGGACAGAGG | 14 | 883 |
| 729368 | N/A | N/A | 2833 | 2848 | TCTGGCCGAGCAAGGG | 24 | 884 |
| 729369 | N/A | N/A | 2843 | 2858 | GGCACACAATTCTGGC | 3 | 885 |
| 729370 | N/A | N/A | 2874 | 2889 | GCCCTAGAATAGAGGG | 9 | 886 |
| 729371 | N/A | N/A | 2884 | 2899 | AGAGGCCTTGGCCCTA | 5 | 887 |
| 729372 | N/A | N/A | 2911 | 2926 | ACCCATAGTTGTATCT | 13 | 888 |
| 729373 | N/A | N/A | 2935 | 2950 | GGTTTATAACATGGGT | 11 | 889 |
| 729374 | N/A | N/A | 2974 | 2989 | GCACCCCAAACTTGCA | 11 | 890 |
| 729375 | N/A | N/A | 2984 | 2999 | GCTGTTCCCCGCACCC | 17 | 891 |

TABLE 12-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 729376 | N/A | N/A | 2995 | 3010 | TCCCACCCAGAGCTGT | 7 | 892 |
| 729377 | N/A | N/A | 3016 | 3031 | CCCCAGACCAAATTTC | 0 | 893 |
| 729378 | N/A | N/A | 3026 | 3041 | CGAGTGGGTCCCCCAG | 17 | 894 |
| 729379 | N/A | N/A | 3052 | 3067 | ACTCACTGTGGGCTGA | 22 | 895 |
| 729380 | N/A | N/A | 3080 | 3095 | GGCTAGACCGGGACAA | 29 | 896 |
| 729381 | N/A | N/A | 3090 | 3105 | AAACGAAAGTGGCTAG | 11 | 897 |
| 729382 | N/A | N/A | 3108 | 3123 | TCCACCCGGCCCCAGG | 3 | 898 |
| 729383 | N/A | N/A | 3329 | 3344 | CCCAGTACCTTTTGGG | 0 | 899 |
| 729384 | N/A | N/A | 3339 | 3354 | AAATTCCCTGCCCAGT | 6 | 900 |
| 729385 | N/A | N/A | 3372 | 3387 | TGGCCTTGCAGCATGG | 27 | 901 |
| 729386 | N/A | N/A | 3386 | 3401 | GTCTGGGCCTGCTTTG | 23 | 902 |
| 729387 | N/A | N/A | 3396 | 3411 | AACTCCCTGTGTCTGG | 18 | 903 |
| 729388 | N/A | N/A | 3447 | 3462 | CATCAGAAGTGAATGT | 8 | 904 |
| 729389 | N/A | N/A | 3458 | 3473 | ACAGCACAGCCCATCA | 14 | 905 |
| 729390 | N/A | N/A | 3468 | 3483 | GGGTCATTACACAGCA | 23 | 906 |
| 729391 | N/A | N/A | 3509 | 3524 | GCCCTTCACTTGAGAC | 13 | 907 |
| 729392 | N/A | N/A | 3519 | 3534 | CATGCCCTTGGCCCTT | 8 | 908 |
| 729393 | N/A | N/A | 3530 | 3545 | CTCCCCTTACCCATGC | 0 | 909 |
| 729394 | N/A | N/A | 3556 | 3571 | GTCCTGAGTCCCCTTC | 0 | 910 |
| 729395 | N/A | N/A | 3567 | 3582 | AACTCTCCACAGTCCT | 10 | 911 |
| 729396 | N/A | N/A | 3631 | 3646 | AGGCCAGAGGGACCCT | 0 | 912 |
| 729397 | N/A | N/A | 3648 | 3663 | ACTGCCTCCCTGGAGT | 0 | 913 |
| 729398 | N/A | N/A | 3695 | 3710 | TGCTACCTACCCAGGG | 2 | 914 |
| 729399 | N/A | N/A | 3705 | 3720 | CAGCTCTAACTGCTAC | 0 | 915 |
| 729400 | N/A | N/A | 3729 | 3744 | GAAGGCTACAGGAAAC | 0 | 916 |
| 729401 | N/A | N/A | 3739 | 3754 | AGCCTGTTAGGAAGGC | 0 | 917 |
| 729402 | N/A | N/A | 3749 | 3764 | CGCCTGCCGGAGCCTG | 18 | 918 |
| 729403 | N/A | N/A | 3762 | 3777 | AGGAAGGCCCTAACGC | 0 | 919 |
| 729641 | N/A | N/A | 2214 | 2229 | CGAAGCATCCAGTGGG | 20 | 920 |
| 729642 | N/A | N/A | 2474 | 2489 | AGGTCCACACGAGCTC | 30 | 921 |
| 729643 | N/A | N/A | 2593 | 2608 | CAGGCAGCTTAGGGAG | 1 | 922 |
| 729644 | N/A | N/A | 2945 | 2960 | CATTTAGTGTGGTTTA | 28 | 923 |
| 729645 | N/A | N/A | 3362 | 3377 | GCATGGAGCCTCAGTT | 33 | 924 |
| 729646 | N/A | N/A | 3499 | 3514 | TGAGACCCCTGGGTGG | 21 | 925 |

TABLE 13

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665893 | 1228 | 1243 | 10461 | 10476 | GCACTGACACAGGCGG | 83 | 39 |
| 665933 | 1561 | 1576 | 11126 | 11141 | GCGGTCTTTGAGGTCT | 59 | 468 |
| 666150 | N/A | N/A | 3779 | 3794 | GCATTCGGGTAGCACT | 46 | 926 |
| 666168 | N/A | N/A | 5286 | 5301 | ATCACCACTGTGTACC | 62 | 927 |
| 729196 | N/A | N/A | 3776 | 3791 | TTCGGGTAGCACTTAG | 49 | 928 |
| 729197 | N/A | N/A | 3777 | 3792 | ATTCGGGTAGCACTTA | 36 | 929 |
| 729198 | N/A | N/A | 3778 | 3793 | CATTCGGGTAGCACTT | 33 | 930 |
| 729199 | N/A | N/A | 3780 | 3795 | CGCATTCGGGTAGCAC | 46 | 931 |
| 729200 | N/A | N/A | 3781 | 3796 | ACGCATTCGGGTAGCA | 40 | 932 |
| 729201 | N/A | N/A | 3782 | 3797 | CACGCATTCGGGTAGC | 59 | 933 |
| 729202 | N/A | N/A | 3783 | 3798 | ACACGCATTCGGGTAG | 36 | 934 |
| 729203 | N/A | N/A | 3784 | 3799 | GACACGCATTCGGGTA | 35 | 935 |
| 729204 | N/A | N/A | 5282 | 5297 | CCACTGTGTACCCCAT | 50 | 936 |
| 729205 | N/A | N/A | 5283 | 5298 | ACCACTGTGTACCCCA | 72 | 937 |
| 729206 | N/A | N/A | 5284 | 5299 | CACCACTGTGTACCCC | 71 | 938 |
| 729207 | N/A | N/A | 5285 | 5300 | TCACCACTGTGTACCC | 57 | 939 |
| 729208 | N/A | N/A | 5287 | 5302 | AATCACCACTGTGTAC | 20 | 940 |
| 729209 | N/A | N/A | 5288 | 5303 | AAATCACCACTGTGTA | 32 | 941 |
| 729210 | N/A | N/A | 5289 | 5304 | CAAATCACCACTGTGT | 12 | 942 |
| 729211 | N/A | N/A | 5290 | 5305 | TCAAATCACCACTGTG | 44 | 943 |
| 729212 | N/A | N/A | 5291 | 5306 | ATCAAATCACCACTGT | 42 | 944 |
| 729404 | N/A | N/A | 3812 | 3827 | CTTGGTCCTCCCCCTT | 21 | 945 |
| 729405 | N/A | N/A | 3822 | 3837 | CATCTAGGTTCTTGGT | 27 | 946 |
| 729406 | N/A | N/A | 3835 | 3850 | CTCTAGGGCCATTCAT | 19 | 947 |
| 729407 | N/A | N/A | 3855 | 3870 | GCACCAAACAGATGTT | 19 | 948 |
| 729408 | N/A | N/A | 3885 | 3900 | ACCAACTCAACCCACC | 13 | 949 |
| 729409 | N/A | N/A | 3895 | 3910 | AATCCCATCAACCAAC | 15 | 950 |
| 729410 | N/A | N/A | 3905 | 3920 | TCTTTAGAGAAATCCC | 38 | 951 |
| 729411 | N/A | N/A | 3943 | 3958 | AAGGACACCTGCCCTC | 6 | 952 |
| 729412 | N/A | N/A | 3954 | 3969 | CTGGAGCTCCCAAGGA | 17 | 953 |
| 729413 | N/A | N/A | 3965 | 3980 | AAGAATCTCATCTGGA | 4 | 954 |
| 729414 | N/A | N/A | 3975 | 3990 | TGCCCTCAACAAGAAT | 0 | 955 |
| 729415 | N/A | N/A | 3995 | 4010 | CTGAGAGTTCCCTCCG | 22 | 956 |
| 729416 | N/A | N/A | 4059 | 4074 | CTCCTGCTCAGTCTAC | 21 | 957 |
| 729417 | N/A | N/A | 4100 | 4115 | CTGGGACAGCGAGCGC | 47 | 958 |
| 729418 | N/A | N/A | 4120 | 4135 | TCTTGTCTCAAGCTGG | 32 | 959 |

TABLE 13-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 729419 | N/A | N/A | 4140 | 4155 | TGACACCAAAAGCCCG | 37 | 960 |
| 729420 | N/A | N/A | 4150 | 4165 | AGTGACTGCCTGACAC | 11 | 961 |
| 729421 | N/A | N/A | 4185 | 4200 | GCCCACCCCTTGCTCT | 11 | 962 |
| 729422 | N/A | N/A | 4205 | 4220 | CTACTCACACCACAGG | 38 | 963 |
| 729423 | N/A | N/A | 4215 | 4230 | CCGCCTTCCACTACTC | 26 | 964 |
| 729424 | N/A | N/A | 4225 | 4240 | GGCCAGAGAACCGCCT | 14 | 965 |
| 729425 | N/A | N/A | 4241 | 4256 | CAGCAAGCAGCCCGTT | 21 | 966 |
| 729426 | N/A | N/A | 4251 | 4266 | CTGCTAACAGCAGCAA | 10 | 967 |
| 729427 | N/A | N/A | 4261 | 4276 | CATTCTCCAACTGCTA | 43 | 968 |
| 729428 | N/A | N/A | 4272 | 4287 | GCAGAGGCATCCATTC | 19 | 969 |
| 729429 | N/A | N/A | 4292 | 4307 | CCCCAGGTGCCCTTTA | 7 | 970 |
| 729430 | N/A | N/A | 4304 | 4319 | CTGCGGGCGCGGCCCC | 22 | 971 |
| 729431 | N/A | N/A | 4324 | 4339 | GAGTTACGAGTTAGTG | 49 | 972 |
| 729432 | N/A | N/A | 4357 | 4372 | TCATGGAATTTTGTGT | 31 | 973 |
| 729433 | N/A | N/A | 4367 | 4382 | TTGTCTAGTGTCATGG | 64 | 974 |
| 729434 | N/A | N/A | 4379 | 4394 | GCATCAGCTTTCTTGT | 39 | 975 |
| 729435 | N/A | N/A | 4401 | 4416 | TAAGGCCAATTCTCTT | 19 | 976 |
| 729436 | N/A | N/A | 4412 | 4427 | ATCTAGGTATTTAAGG | 19 | 977 |
| 729437 | N/A | N/A | 4422 | 4437 | TCTCCAGTCCATCTAG | 15 | 978 |
| 729438 | N/A | N/A | 4432 | 4447 | AAGGATGGTCTCTCCA | 14 | 979 |
| 729439 | N/A | N/A | 4457 | 4472 | CTCAGAGGTCAAGCTA | 30 | 980 |
| 729440 | N/A | N/A | 4484 | 4499 | GGTCTGCAGGTGGATG | 26 | 981 |
| 729441 | N/A | N/A | 4730 | 4745 | GGGCTTACCTTGAAGA | 20 | 982 |
| 729442 | N/A | N/A | 4744 | 4759 | CAACCTCCTCCCCGGG | 12 | 983 |
| 729443 | N/A | N/A | 4754 | 4769 | GAGGTCCAGCCAACCT | 1 | 984 |
| 729444 | N/A | N/A | 4790 | 4805 | TTATGTGCGCTCCTCT | 26 | 985 |
| 729445 | N/A | N/A | 4806 | 4821 | GAGCTGCCTGTGTGCG | 31 | 986 |
| 729446 | N/A | N/A | 4817 | 4832 | CCAGCCTCGAGGAGCT | 4 | 987 |
| 729447 | N/A | N/A | 4853 | 4868 | CCGGCATCAGCAGCAG | 57 | 988 |
| 729448 | N/A | N/A | 4897 | 4912 | AAAGGTGTACCCTGTG | 36 | 989 |
| 729449 | N/A | N/A | 5076 | 5091 | AAGATGTGCCCTAGGC | 35 | 990 |
| 729450 | N/A | N/A | 5087 | 5102 | GCAGGTTAGAAAAGAT | 16 | 991 |
| 729451 | N/A | N/A | 5097 | 5112 | GCTCTAGGGTGCAGGT | 49 | 992 |
| 729452 | N/A | N/A | 5107 | 5122 | TCCCCACGATGCTCTA | 14 | 993 |
| 729453 | N/A | N/A | 5140 | 5155 | CGAGTTATGGGAAGGC | 66 | 994 |
| 729454 | N/A | N/A | 5170 | 5185 | AGGAGTGAGACGAGCA | 75 | 995 |

TABLE 13-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
| --- | --- | --- | --- | --- | --- | --- | --- |
| 729455 | N/A | N/A | 5190 | 5205 | AACAAGTCCTCATGAG | 19 | 996 |
| 729456 | N/A | N/A | 5213 | 5228 | TCCTTTAGCATATGCG | 67 | 997 |
| 729647 | N/A | N/A | 3845 | 3860 | GATGTTACCTCTCTAG | 38 | 998 |
| 729648 | N/A | N/A | 4016 | 4031 | AGTTTTCTCACCCTCC | 49 | 999 |
| 729649 | N/A | N/A | 4049 | 4064 | GTCTACACCCCTAGTT | 24 | 1000 |
| 729650 | N/A | N/A | 4195 | 4210 | CACAGGTTAGGCCCAC | 44 | 1001 |
| 729651 | N/A | N/A | 4467 | 4482 | GGACAGGGTACTCAGA | 26 | 1002 |

TABLE 14

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
| --- | --- | --- | --- | --- | --- | --- | --- |
| 665893 | 1228 | 1243 | 10461 | 10476 | GCACTGACACAGGCGG | 23 | 39 |
| 665933 | 1561 | 1576 | 11126 | 11141 | GCGGTCTTTGAGGTCT | 46 | 468 |
| 666178 | N/A | N/A | 6540 | 6555 | GCATTCCATATACACA | 51 | 1003 |
| 666184 | N/A | N/A | 6972 | 6987 | TGCCTTTTAATGTTGA | 36 | 1004 |
| 666187 | N/A | N/A | 7176 | 7191 | CTAGACAAATATGCAG | 29 | 1005 |
| 729213 | N/A | N/A | 6539 | 6554 | CATTCCATATACACAC | 71 | 1006 |
| 729214 | N/A | N/A | 6541 | 6556 | TGCATTCCATATACAC | 28 | 1007 |
| 729215 | N/A | N/A | 6542 | 6557 | TTGCATTCCATATACA | 27 | 1008 |
| 729216 | N/A | N/A | 6543 | 6558 | TTTGCATTCCATATAC | 3 | 1009 |
| 729217 | N/A | N/A | 6544 | 6559 | TTTTGCATTCCATATA | 19 | 1010 |
| 729218 | N/A | N/A | 6545 | 6560 | ATTTTGCATTCCATAT | 20 | 1011 |
| 729219 | N/A | N/A | 6969 | 6984 | CTTTTAATGTTGAATT | 0 | 1012 |
| 729220 | N/A | N/A | 6970 | 6985 | CCTTTTAATGTTGAAT | 0 | 1013 |
| 729221 | N/A | N/A | 6971 | 6986 | GCCTTTTAATGTTGAA | 50 | 1014 |
| 729222 | N/A | N/A | 6973 | 6988 | ATGCCTTTTAATGTTG | 0 | 1015 |
| 729223 | N/A | N/A | 6974 | 6989 | TATGCCTTTTAATGTT | 10 | 1016 |
| 729224 | N/A | N/A | 6975 | 6990 | CTATGCCTTTTAATGT | 0 | 1017 |
| 729225 | N/A | N/A | 6976 | 6991 | TCTATGCCTTTTAATG | 13 | 1018 |
| 729226 | N/A | N/A | 7171 | 7186 | CAAATATGCAGATATC | 3 | 1019 |
| 729227 | N/A | N/A | 7173 | 7188 | GACAAATATGCAGATA | 0 | 1020 |
| 729228 | N/A | N/A | 7174 | 7189 | AGACAAATATGCAGAT | 1 | 1021 |
| 729229 | N/A | N/A | 7175 | 7190 | TAGACAAATATGCAGA | 27 | 1022 |
| 729230 | N/A | N/A | 7177 | 7192 | TCTAGACAAATATGCA | 18 | 1023 |

TABLE 14-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 729231 | N/A | N/A | 7178 | 7193 | GTCTAGACAAATATGC | 0 | 1024 |
| 729232 | N/A | N/A | 7179 | 7194 | AGTCTAGACAAATATG | 12 | 1025 |
| 729233 | N/A | N/A | 7180 | 7195 | AAGTCTAGACAAATAT | 0 | 1026 |
| 729234 | N/A | N/A | 7181 | 7196 | TAAGTCTAGACAAATA | 0 | 1027 |
| 729457 | N/A | N/A | 5292 | 5307 | TATCAAATCACCACTG | 0 | 1028 |
| 729458 | N/A | N/A | 5302 | 5317 | TCACTGTGCTTATCAA | 22 | 1029 |
| 729459 | N/A | N/A | 5314 | 5329 | TACCTGATCTGATCAC | 0 | 1030 |
| 729460 | N/A | N/A | 5325 | 5340 | GATATGCTAAGTACCT | 43 | 1031 |
| 729461 | N/A | N/A | 5368 | 5383 | GTTTGTTCCCAACACA | 34 | 1032 |
| 729462 | N/A | N/A | 5393 | 5408 | GTATCTGAATCTTATA | 22 | 1033 |
| 729463 | N/A | N/A | 5403 | 5418 | GATTGATGATGTATCT | 0 | 1034 |
| 729464 | N/A | N/A | 5413 | 5428 | ACAATTGAAAGATTGA | 0 | 1035 |
| 729465 | N/A | N/A | 5464 | 5479 | ATCTGGTCAACAGTGT | 21 | 1036 |
| 729466 | N/A | N/A | 5606 | 5621 | CAAGGAGGTTGAGATG | 0 | 1037 |
| 729467 | N/A | N/A | 5804 | 5819 | GTAGTACATCAATTAA | 0 | 1038 |
| 729468 | N/A | N/A | 5814 | 5829 | ATGTACAGTTGTAGTA | 0 | 1039 |
| 729469 | N/A | N/A | 5868 | 5883 | AACACTAGGCAACAGA | 0 | 1040 |
| 729470 | N/A | N/A | 5878 | 5893 | CCAATGGTGCAACACT | 0 | 1041 |
| 729471 | N/A | N/A | 5888 | 5903 | CCACTGCTCACCAATG | 0 | 1042 |
| 729472 | N/A | N/A | 5910 | 5925 | TGGAGGTTGTGCTATG | 0 | 1043 |
| 729473 | N/A | N/A | 5921 | 5936 | TTGAGCTGAGTTGGAG | 0 | 1044 |
| 729474 | N/A | N/A | 6478 | 6493 | ACATCCTAGCATTAAG | 0 | 1045 |
| 729475 | N/A | N/A | 6495 | 6510 | AAACTATTATGCGAGG | 55 | 1046 |
| 729476 | N/A | N/A | 6549 | 6564 | TCCAATTTTGCATTCC | 64 | 1047 |
| 729477 | N/A | N/A | 6559 | 6574 | TTCACTTGATTCCAAT | 14 | 1048 |
| 729478 | N/A | N/A | 6614 | 6629 | AAGGAAAGCTGATCCT | 0 | 1049 |
| 729479 | N/A | N/A | 6624 | 6639 | GTATGTTGGAAAGGAA | 19 | 1050 |
| 729480 | N/A | N/A | 6639 | 6654 | AAAAGTGATGTGGACG | 23 | 1051 |
| 729481 | N/A | N/A | 6666 | 6681 | CATTCCAGTGGAAATT | 2 | 1052 |
| 729482 | N/A | N/A | 6679 | 6694 | AATTGTGCTAAACCAT | 10 | 1053 |
| 729483 | N/A | N/A | 6689 | 6704 | TCAGTGACCAAATTGT | 30 | 1054 |
| 729484 | N/A | N/A | 6710 | 6725 | CAAGTATCTAAAAACC | 0 | 1055 |
| 729485 | N/A | N/A | 6752 | 6767 | CATGACAATGTGGTTT | 37 | 1056 |
| 729486 | N/A | N/A | 6762 | 6777 | AGACAGCCTACATGAC | 23 | 1057 |
| 729487 | N/A | N/A | 6772 | 6787 | GGAAGCATTAAGACAG | 6 | 1058 |
| 729488 | N/A | N/A | 6799 | 6814 | CCCAAAATAATTGAGG | 0 | 1059 |

TABLE 14-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 729489 | N/A | N/A | 6810 | 6825 | GGAAATCAACCCCCAA | 21 | 1060 |
| 729490 | N/A | N/A | 6840 | 6855 | TTGCCTTTGACCCAGC | 34 | 1061 |
| 729491 | N/A | N/A | 6887 | 6902 | GCCCAAAAACTAAGAA | 0 | 1062 |
| 729492 | N/A | N/A | 6897 | 6912 | TAAGGATCAAGCCCAA | 26 | 1063 |
| 729493 | N/A | N/A | 6947 | 6962 | CTGTATTACCTATACA | 0 | 1064 |
| 729494 | N/A | N/A | 6958 | 6973 | GAATTTTGTGACTGTA | 56 | 1065 |
| 729495 | N/A | N/A | 6981 | 6996 | ACCATTCTATGCCTTT | 53 | 1066 |
| 729496 | N/A | N/A | 6998 | 7013 | GAGACTTTTGCTCTA | 0 | 1067 |
| 729497 | N/A | N/A | 7019 | 7034 | GTGATGAACCAGGGAA | 44 | 1068 |
| 729498 | N/A | N/A | 7045 | 7060 | GGAAAGGCTAGGGAGG | 1 | 1069 |
| 729499 | N/A | N/A | 7059 | 7074 | ACGGCTGCCTCTAGGG | 9 | 1070 |
| 729500 | N/A | N/A | 7128 | 7143 | AGGATAGTTCCATATT | 15 | 1071 |
| 729501 | N/A | N/A | 7145 | 7160 | TATGAAAAGTAGAGGA | 0 | 1072 |
| 729502 | N/A | N/A | 7156 | 7171 | CTAGCATTTCTTATGA | 2 | 1073 |
| 729503 | N/A | N/A | 7184 | 7199 | TATTAAGTCTAGACAA | 0 | 1074 |
| 729504 | N/A | N/A | 7194 | 7209 | CGTCAAGAAGTATTAA | 0 | 1075 |
| 729505 | N/A | N/A | 7208 | 7223 | TGACATGTAGCAATCG | 28 | 1076 |
| 729652 | N/A | N/A | 6458 | 6473 | TTGGAGAGAGCACAGT | 11 | 1077 |
| 729653 | N/A | N/A | 6654 | 6669 | AATTCTACAGTCACGA | 26 | 1078 |
| 729654 | N/A | N/A | 7106 | 7121 | CATGTGCATAAAAATC | 0 | 1079 |

TABLE 15

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665893 | 1228 | 1243 | 10461 | 10476 | GCACTGACACAGGCGG | 78 | 39 |
| 665933 | 1561 | 1576 | 11126 | 11141 | GCGGTCTTTGAGGTCT | 58 | 468 |
| 666188 | N/A | N/A | 7391 | 7406 | AGAAGCATTCACACAA | 41 | 1080 |
| 729235 | N/A | N/A | 7387 | 7402 | GCATTCACACAAAATA | 52 | 1081 |
| 729236 | N/A | N/A | 7388 | 7403 | AGCATTCACACAAAAT | 54 | 1082 |
| 729237 | N/A | N/A | 7389 | 7404 | AAGCATTCACACAAAA | 27 | 1083 |
| 729238 | N/A | N/A | 7390 | 7405 | GAAGCATTCACACAAA | 39 | 1084 |
| 729239 | N/A | N/A | 7392 | 7407 | TAGAAGCATTCACACA | 41 | 1085 |
| 729240 | N/A | N/A | 7393 | 7408 | ATAGAAGCATTCACAC | 22 | 1086 |

TABLE 15-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 729241 | N/A | N/A | 7394 | 7409 | CATAGAAGCATTCACA | 46 | 1087 |
| 729242 | N/A | N/A | 7395 | 7410 | TCATAGAAGCATTCAC | 50 | 1088 |
| 729243 | N/A | N/A | 7396 | 7411 | ATCATAGAAGCATTCA | 59 | 1089 |
| 729506 | N/A | N/A | 7218 | 7233 | GTTTATAAGCTGACAT | 39 | 1090 |
| 729507 | N/A | N/A | 7228 | 7243 | GCAGGAAACTGTTTAT | 55 | 1091 |
| 729508 | N/A | N/A | 7253 | 7268 | ACTGGGCAGCACAAAA | 25 | 1092 |
| 729509 | N/A | N/A | 7271 | 7286 | ACCCATTGAATGAAAA | 23 | 1093 |
| 729510 | N/A | N/A | 7281 | 7296 | ATTACGGCCAACCCAT | 0 | 1094 |
| 729511 | N/A | N/A | 7291 | 7306 | GGCTGGTGAAATTACG | 10 | 1095 |
| 729512 | N/A | N/A | 7306 | 7321 | CATCCATCAATGAGGG | 51 | 1096 |
| 729513 | N/A | N/A | 7316 | 7331 | CCCAATGCAACATCCA | 69 | 1097 |
| 729514 | N/A | N/A | 7328 | 7343 | TGACCCAAAATACCCA | 44 | 1098 |
| 729515 | N/A | N/A | 7338 | 7353 | GTGTAAAAGATGACCC | 37 | 1099 |
| 729516 | N/A | N/A | 7349 | 7364 | AGCAGTGCTGTGTGTA | 48 | 1100 |
| 729517 | N/A | N/A | 7372 | 7387 | ATTGCACACACAAAGT | 10 | 1101 |
| 729518 | N/A | N/A | 7397 | 7412 | TATCATAGAAGCATTC | 24 | 1102 |
| 729519 | N/A | N/A | 7426 | 7441 | CTATTTGATTTCTAGG | 18 | 1103 |
| 729520 | N/A | N/A | 7437 | 7452 | TTTTAACCCAGCTATT | 6 | 1104 |
| 729521 | N/A | N/A | 7460 | 7475 | GGTTACCAACATTTCT | 42 | 1105 |
| 729522 | N/A | N/A | 7470 | 7485 | GTGAGGTGAGGGTTAC | 38 | 1106 |
| 729523 | N/A | N/A | 7508 | 7523 | ACACTGGAGCTGTTGG | 51 | 1107 |
| 729524 | N/A | N/A | 7519 | 7534 | ACAGGCTCGAGACACT | 31 | 1108 |
| 729525 | N/A | N/A | 7529 | 7544 | TGCACATAGGACAGGC | 22 | 1109 |
| 729526 | N/A | N/A | 7550 | 7565 | TAAAGCACTCAGAGCT | 16 | 1110 |
| 729527 | N/A | N/A | 7560 | 7575 | TTGATGTCCGTAAAGC | 53 | 1111 |
| 729528 | N/A | N/A | 7876 | 7891 | AGCGAAGACTCAAGGG | 48 | 1112 |
| 729529 | N/A | N/A | 7887 | 7902 | CATGGAGTGGCAGCGA | 42 | 1113 |
| 729530 | N/A | N/A | 7899 | 7914 | AGTTGCCCACCTCATG | 22 | 1114 |
| 729531 | N/A | N/A | 7909 | 7924 | ATCTCCTCACAGTTGC | 28 | 1115 |
| 729532 | N/A | N/A | 7920 | 7935 | CCTTTGTCTTGATCTC | 48 | 1116 |
| 729533 | N/A | N/A | 7936 | 7951 | GCCATGTCACTGCCTC | 30 | 1117 |
| 729534 | N/A | N/A | 7953 | 7968 | CGCCAGCTGTGTGCCA | 28 | 1118 |
| 729535 | N/A | N/A | 7966 | 7981 | TGGAAGTGCCCCCCGC | 34 | 1119 |
| 729536 | N/A | N/A | 7976 | 7991 | GGTTTGAATCTGGAAG | 31 | 1120 |
| 729537 | N/A | N/A | 8000 | 8015 | GGTGAGCACCCTGGAG | 30 | 1121 |
| 729538 | N/A | N/A | 8027 | 8042 | TCTAAGGAGGACAGCG | 35 | 1122 |

TABLE 15-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 729539 | N/A | N/A | 8043 | 8058 | GTGAAACAGTGTGATC | 40 | 1123 |
| 729540 | N/A | N/A | 8064 | 8079 | ATAGTCCCTGCTCCTG | 49 | 1124 |
| 729541 | N/A | N/A | 8144 | 8159 | GTGGGAGTCTGCCACA | 6 | 1125 |
| 729542 | N/A | N/A | 8159 | 8174 | GACCTGGTTTGCAGCG | 34 | 1126 |
| 729543 | N/A | N/A | 8171 | 8186 | CGCTGAGCCCCAGACC | 0 | 1127 |
| 729544 | N/A | N/A | 8181 | 8196 | GGCTGAGCCTCGCTGA | 22 | 1128 |
| 729545 | N/A | N/A | 8194 | 8209 | AACTTCGGCTACAGGC | 39 | 1129 |
| 729546 | N/A | N/A | 8213 | 8228 | GACTCTACTGTGTGGG | 38 | 1130 |
| 729547 | N/A | N/A | 8266 | 8281 | CACAGAGAACCTCATC | 11 | 1131 |
| 729548 | N/A | N/A | 8276 | 8291 | AATAGCCGACCACAGA | 10 | 1132 |
| 729549 | N/A | N/A | 8489 | 8504 | GCCTGATACCTGTGGG | 3 | 1133 |
| 729550 | N/A | N/A | 8525 | 8540 | ATTGCACAGCCTCCCA | 8 | 1134 |
| 729551 | N/A | N/A | 8555 | 8570 | ACCCAAGAGCTCATGG | 6 | 1135 |
| 729552 | N/A | N/A | 8569 | 8584 | CTTGGCCTGCCTGCAC | 10 | 1136 |
| 729553 | N/A | N/A | 8598 | 8613 | TTCCTGGACCACTGCC | 15 | 1137 |
| 729554 | N/A | N/A | 8617 | 8632 | GCGGGAGCCCCCGCAT | 22 | 1138 |
| 729555 | N/A | N/A | 8637 | 8652 | GCCCTGGGTGTCATGA | 17 | 1139 |
| 729556 | N/A | N/A | 8648 | 8663 | CACTCCTGGAAGCCCT | 0 | 1140 |
| 729557 | N/A | N/A | 8661 | 8676 | GACCCATCCCAGCCAC | 7 | 1141 |
| 729558 | N/A | N/A | 8671 | 8686 | ATATGCCAGTGACCCA | 15 | 1142 |
| 729559 | N/A | N/A | 8681 | 8696 | GCCATTCCTGATATGC | 28 | 1143 |
| 729560 | N/A | N/A | 8691 | 8706 | TGCACGCCAAGCCATT | 28 | 1144 |
| 729561 | N/A | N/A | 8711 | 8726 | GAAGCACCCAGGTCCC | 24 | 1145 |
| 729562 | N/A | N/A | 8722 | 8737 | ATGGTAAGGAAGAAGC | 18 | 1146 |
| 729563 | N/A | N/A | 8732 | 8747 | AACGAGGGCAATGGTA | 11 | 1147 |
| 729564 | N/A | N/A | 8763 | 8778 | CCATGAGACCTAGGCT | 3 | 1148 |
| 729565 | N/A | N/A | 8773 | 8788 | ACTCCATGGGCCATGA | 3 | 1149 |
| 729566 | N/A | N/A | 8794 | 8809 | GGATTGGGAAAGACCT | 15 | 1150 |
| 729567 | N/A | N/A | 8817 | 8832 | CGAGGTGGAGGGCACA | 11 | 1151 |
| 729568 | N/A | N/A | 8827 | 8842 | CAACACAGGGCGAGGT | 8 | 1152 |
| 729569 | N/A | N/A | 8859 | 8874 | TATGCAGCTTCTGCCT | 3 | 1153 |
| 729655 | N/A | N/A | 7480 | 7495 | TGGCAATTAGGTGAGG | 48 | 1154 |
| 729656 | N/A | N/A | 8101 | 8116 | CAAGCTACATGAAATC | 11 | 1155 |
| 729657 | N/A | N/A | 8627 | 8642 | TCATGACCTAGCGGGA | 11 | 1156 |

TABLE 16

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 665893 | 1228 | 1243 | 10461 | 10476 | GCACTGACACAGGCGG | 83 | 39 |
| 665933 | 1561 | 1576 | 11126 | 11141 | GCGGTCTTTGAGGTCT | 64 | 468 |
| 666208 | N/A | N/A | 9349 | 9364 | CAGTTTAGCTCAGGCA | 69 | 1157 |
| 729244 | N/A | N/A | 9344 | 9359 | TAGCTCAGGCAAGACC | 32 | 1158 |
| 729245 | N/A | N/A | 9345 | 9360 | TTAGCTCAGGCAAGAC | 17 | 1159 |
| 729246 | N/A | N/A | 9346 | 9361 | TTTAGCTCAGGCAAGA | 23 | 1160 |
| 729247 | N/A | N/A | 9347 | 9362 | GTTTAGCTCAGGCAAG | 24 | 1161 |
| 729248 | N/A | N/A | 9348 | 9363 | AGTTTAGCTCAGGCAA | 47 | 1162 |
| 729249 | N/A | N/A | 9353 | 9368 | GCCTCAGTTTAGCTCA | 23 | 1163 |
| 729250 | N/A | N/A | 9354 | 9369 | AGCCTCAGTTTAGCTC | 9 | 1164 |
| 729570 | N/A | N/A | 8869 | 8884 | CTGTAGCTCCTATGCA | 14 | 1165 |
| 729571 | N/A | N/A | 8895 | 8910 | AGAAGCAAGATCCCCT | 2 | 1166 |
| 729572 | N/A | N/A | 8905 | 8920 | ATGTCGGAGGAGAAGC | 0 | 1167 |
| 729573 | N/A | N/A | 8915 | 8930 | AAAGGAGTCAATGTCG | 0 | 1168 |
| 729574 | N/A | N/A | 8925 | 8940 | GCAGGGCAGTAAAGGA | 12 | 1169 |
| 729575 | N/A | N/A | 8948 | 8963 | GTCTGCACAGCAGGGA | 24 | 1170 |
| 729576 | N/A | N/A | 9021 | 9036 | AACCCACACTCACCTC | 25 | 1171 |
| 729577 | N/A | N/A | 9046 | 9061 | CGTCCAGGGCTCCACC | 13 | 1172 |
| 729578 | N/A | N/A | 9060 | 9075 | GACAGCAGAGAGCTCG | 9 | 1173 |
| 729579 | N/A | N/A | 9082 | 9097 | GCGGAAACCTAAGGCC | 12 | 1174 |
| 729580 | N/A | N/A | 9118 | 9133 | ATTGAGAGGGCCACGG | 27 | 1175 |
| 729581 | N/A | N/A | 9133 | 9148 | GAAACAAGGAGAACTA | 29 | 1176 |
| 729582 | N/A | N/A | 9151 | 9166 | TTCAGAATCCCAGGAG | 21 | 1177 |
| 729583 | N/A | N/A | 9167 | 9182 | GACTGTGCTCCTATCG | 27 | 1178 |
| 729584 | N/A | N/A | 9195 | 9210 | GACAATGCCCTGGGAA | 55 | 1179 |
| 729585 | N/A | N/A | 9205 | 9220 | ACAGGGTAATGACAAT | 28 | 1180 |
| 729586 | N/A | N/A | 9219 | 9234 | CGTGGGTCACACACAC | 39 | 1181 |
| 729587 | N/A | N/A | 9233 | 9248 | AGCCCCAACTGCTGCG | 25 | 1182 |
| 729588 | N/A | N/A | 9249 | 9264 | GGAGTCAGACCTACCA | 18 | 1183 |
| 729589 | N/A | N/A | 9259 | 9274 | CCTTCTGCAGGGAGTC | 73 | 1184 |
| 729590 | N/A | N/A | 9285 | 9300 | GCCCTTTGCCTCACTT | 17 | 1185 |
| 729591 | N/A | N/A | 9324 | 9339 | CTCCGGTCCCAGCTCG | 6 | 1186 |
| 729592 | N/A | N/A | 9334 | 9349 | AAGACCCTGCCTCCGG | 23 | 1187 |
| 729593 | N/A | N/A | 9355 | 9370 | TAGCCTCAGTTTAGCT | 0 | 1188 |
| 729594 | N/A | N/A | 9375 | 9390 | GAACTATGAGGCAACT | 10 | 1189 |
| 729595 | N/A | N/A | 9385 | 9400 | TAACAGGCGAGAACTA | 9 | 1190 |

TABLE 16-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 729596 | N/A | N/A | 9427 | 9442 | GAAAGGAGGACAGGTT | 0 | 1191 |
| 729597 | N/A | N/A | 9467 | 9482 | TGAAGGGACACCACCA | 31 | 1192 |
| 729598 | N/A | N/A | 9533 | 9548 | TAGACCCCAACCACC | 5 | 1193 |
| 729599 | N/A | N/A | 9553 | 9568 | CCTATAGCTTCTCTGT | 51 | 1194 |
| 729600 | N/A | N/A | 9567 | 9582 | AGGTACCTATGGTACC | 9 | 1195 |
| 729601 | N/A | N/A | 9578 | 9593 | AGCCCCCTTCCAGGTA | 28 | 1196 |
| 729602 | N/A | N/A | 9590 | 9605 | TAGCCTCCCATCAGCC | 11 | 1197 |
| 729603 | N/A | N/A | 9602 | 9617 | CCTGGGCCACCCTAGC | 11 | 1198 |
| 729604 | N/A | N/A | 9634 | 9649 | CGAACTGCCTCCCAGG | 7 | 1199 |
| 729605 | N/A | N/A | 9645 | 9660 | TGCCACCTCCACGAAC | 39 | 1200 |
| 729606 | N/A | N/A | 9655 | 9670 | CGGCTGTCAGTGCCAC | 17 | 1201 |
| 729607 | N/A | N/A | 9683 | 9698 | CACTGCATCTACAGAG | 17 | 1202 |
| 729608 | N/A | N/A | 9998 | 10013 | CAGCCATGGGTCCTTA | 18 | 1203 |
| 729609 | N/A | N/A | 10009 | 10024 | TTCCCCGTGCCCAGCC | 0 | 1204 |
| 729610 | N/A | N/A | 10025 | 10040 | AATCCCCCAGCACTGC | 22 | 1205 |
| 729611 | N/A | N/A | 10041 | 10056 | TTGCCAATCCTACCCC | 31 | 1206 |
| 729612 | N/A | N/A | 10073 | 10088 | CACCCAAGGGAGTCCA | 22 | 1207 |
| 729613 | N/A | N/A | 10099 | 10114 | AGCCCCATCCGCCCTC | 3 | 1208 |
| 729614 | N/A | N/A | 10157 | 10172 | GGCCCATCCCGTCCTT | 0 | 1209 |
| 729615 | N/A | N/A | 10183 | 10198 | GGTCGGTCACTGTGGG | 8 | 1210 |
| 729616 | N/A | N/A | 10581 | 10596 | CTTTGGGCCCTCACCA | 0 | 1211 |
| 729617 | N/A | N/A | 10591 | 10606 | AGGATCACAGCTTTGG | 12 | 1212 |
| 729618 | N/A | N/A | 10616 | 10631 | ATGCCCTGGGCAAGAG | 8 | 1213 |
| 729619 | N/A | N/A | 10627 | 10642 | AGGCTGGAACCATGCC | 0 | 1214 |
| 729620 | N/A | N/A | 10637 | 10652 | CCCTAGTCAGAGGCTG | 11 | 1215 |
| 729621 | N/A | N/A | 10647 | 10662 | AAATCAAGGTCCCTAG | 2 | 1216 |
| 729622 | N/A | N/A | 10658 | 10673 | GCTCTGCATCAAAATC | 7 | 1217 |
| 729623 | N/A | N/A | 10780 | 10795 | ATGTACCTGTACAGTA | 14 | 1218 |
| 729624 | N/A | N/A | 10800 | 10815 | CCGACTTTGGGATAGG | 15 | 1219 |
| 729625 | N/A | N/A | 10810 | 10825 | CAAGCCAAGGCCGACT | 36 | 1220 |
| 729626 | N/A | N/A | 10820 | 10835 | CCCCAGTTTTCAAGCC | 13 | 1221 |
| 729627 | N/A | N/A | 10833 | 10848 | TAGCCCCAGGATTCCC | 5 | 1222 |
| 729628 | N/A | N/A | 10883 | 10898 | AAGTTCACACTGCTCA | 38 | 1223 |
| 729629 | N/A | N/A | 10914 | 10929 | CGGCTCTGAGCCTTGA | 0 | 1224 |
| 729630 | N/A | N/A | 10933 | 10948 | AGTAATAGACCGCATT | 21 | 1225 |
| 729631 | N/A | N/A | 10952 | 10967 | AGGACAGCCATCAGGG | 8 | 1226 |

TABLE 16-continued

Inhibition of IRF5 RNA by 3-10-3 cEt gapmers targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | IRF5 (% Inhibition) | SEQ ID NO |
|---|---|---|---|---|---|---|---|
| 729632 | N/A | N/A | 10962 | 10977 | GCTGTGCATGAGGACA | 17 | 1227 |
| 729633 | N/A | N/A | 10972 | 10987 | GCCAGATCCAGCTGTG | 0 | 1228 |
| 729634 | N/A | N/A | 11023 | 11038 | ACCACCTGGGAGGCAA | 16 | 1229 |
| 729658 | N/A | N/A | 8885 | 8900 | TCCCCTGAGAGGCTGC | 20 | 1230 |
| 729659 | N/A | N/A | 9543 | 9558 | CTCTGTATACTAGACC | 64 | 1231 |
| 729660 | N/A | N/A | 10134 | 10149 | ACGCCTCCCCATTCTG | 6 | 1232 |
| 729661 | N/A | N/A | 10894 | 10909 | CTCTGGCCGCCAAGTT | 5 | 1233 |

TABLE 17

Inhibition of IRF5 RNA by 3-10-3 cEt gapmers targeting SEQ ID NO: 3

| Compound Number | SEQ ID NO: 3 Start Site | SEQ ID NO: 3 Stop Site | Sequence (5' to 3') | IRF5 (% Inhibition) | SEQ ID NO |
|---|---|---|---|---|---|
| 728399 | 96 | 111 | TCTGTCTGCGGTGCGC | 26 | 1234 |
| 728400 | 98 | 113 | GGTCTGTCTGCGGTGC | 23 | 1235 |
| 728539 | 591 | 606 | GCATCTGTGAGGCTCA | 21 | 1236 |
| 728540 | 593 | 608 | CTGCATCTGTGAGGCT | 30 | 1237 |
| 728541 | 595 | 610 | CACTGCATCTGTGAGG | 8 | 1238 |
| 728542 | 597 | 612 | TGCACTGCATCTGTGA | 20 | 1239 |
| 728543 | 599 | 614 | ACTGCACTGCATCTGT | 12 | 1240 |

Example 2: Antisense Inhibition of Human IRF5 in KARPAS-229 Cells by Modified Oligonucleotides In the second stage of the screening, modified oligonucleotides were designed to sites adjacent to the most active leads/sites from the first stage of screening described above. Briefly, active leads from the first phase of the screening were microwalked until previously tested or rejected sites were approximately reached. Several different chemistry modifications were tested, which are specified in the Chemistry Notation column of the tables below, wherein the notation "d" refers to a 2'-deoxyribose sugar, the notation "s" refers to a phosphorothioate internucleoside linkage, the notation "k" refers to a cEt modified sugar, and the notation "$^{m}$C" refers to a 5-methyl cytosine.

Cultured KARPAS-229 cells at a density of 10,000 cells per well were treated using free uptake with 4,000 nM of modified oligonucleotide. After a treatment period of approximately 48 hours, RNA was isolated from the cells and IRF5 mRNA levels were measured by quantitative real-time RTPCR. Human primer probe set RTS4524 (forward sequence TTCGAGATCTTCTTCTGCTTTGG, designated herein as SEQ ID NO: 14; reverse sequence GCACCACCTGTACAGTAATGAGCTT; designated herein as SEQ ID NO: 15; probe sequence CCTGACCGCAAACCCCGAGAGAA, designated herein as SEQ ID NO: 16) was used to measure mRNA levels. IRF5 mRNA levels were adjusted according to total RNA content, as measured by RIBOGREEN®. Results are presented as percent inhibition of IRF5 relative to untreated control cells. As used herein, a value of '0' indicates that treatment with the modified oligonucleotide did not inhibit IRF5 mRNA levels. 'N/A' indicates that the modified oligonucleotide does not target that gene sequence with 100% complementarity.

TABLE 18

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 666178 | N/A | N/A | 6540 | 6555 | GCATTCCATATACACA | $G_{ks}{}^mC_{ks}A_{ks}T_{ds}T_{ds}{}^mC_{ds}{}^mC_{ds}A_{ds}T_{ds}A_{ds}T_{ds}A_{ds}{}^mC_{ds}A_{ks}{}^mC_{ks}A_k$ | 21 | 1003 |
| 728708 | 1308 | 1323 | 10541 | 10556 | AGCTTGGTCTTGACCT | $A_{ks}G_{ks}{}^mC_{ks}T_{ds}T_{ds}G_{ds}G_{ds}T_{ds}{}^mC_{ds}T_{ds}T_{ds}G_{ds}A_{ds}{}^mC_{ks}{}^mC_{ks}T_k$ | 48 | 436 |
| 728894 | 1764 | 1779 | 11329 | 11344 | CACATCTCCACATCAG | ${}^mC_{ks}A_{ks}{}^mC_{ks}A_{ds}T_{ds}{}^mC_{ds}T_{ds}{}^mC_{ds}{}^mC_{ds}A_{ds}C_{ds}A_{ds}T_{ds}{}^mC_{ks}A_{ks}G_k$ | 45 | 633 |
| 729213 | N/A | N/A | 6539 | 6554 | CATTCCATATACACAC | ${}^mC_{ks}A_{ks}T_{ks}T_{ds}{}^mC_{ds}{}^mC_{ds}A_{ds}T_{ds}A_{ds}T_{ds}A_{ds}{}^mC_{ds}A_{ds}{}^mC_{ks}A_{ks}{}^mC_k$ | 28 | 1006 |
| 729476 | N/A | N/A | 6549 | 6564 | TCCAATTTTGCATTCC | $T_{ks}{}^mC_{ks}{}^mC_{ks}A_{ds}A_{ds}T_{ds}T_{ds}T_{ds}T_{ds}G_{ds}{}^mC_{ds}A_{ds}T_{ds}T_{ks}{}^mC_{ks}{}^mC_k$ | 79 | 1047 |
| 785370 | 1762 | 1777 | 11327 | 11342 | CATCTCCACATCAGTC | ${}^mC_{ks}A_{ds}T_{ds}{}^mC_{ds}T_{ds}{}^mC_{ds}{}^mC_{ds}A_{ds}{}^mC_{ds}A_{ds}T_{ds}{}^mC_{ks}A_{es}G_{ks}T_{es}{}^mC_k$ | 25 | 631 |
| 785371 | 1764 | 1779 | 11329 | 11344 | CACATCTCCACATCAG | ${}^mC_{ks}A_{ds}{}^mC_{ds}A_{ds}T_{ds}{}^mC_{ds}T_{ds}{}^mC_{ds}{}^mC_{ds}A_{ds}C_{ds}A_{ds}T_{es}{}^mC_{ks}A_{es}G_k$ | 15 | 633 |
| 785392 | N/A | N/A | 6539 | 6554 | CATTCCATATACACAC | ${}^mC_{ks}A_{ds}T_{ds}T_{ds}{}^mC_{ds}{}^mC_{ds}A_{ds}T_{ds}A_{ds}T_{ds}A_{ds}{}^mC_{ks}A_{es}{}^mC_{ks}A_{es}{}^mC_k$ | 31 | 1006 |
| 785393 | N/A | N/A | 6540 | 6555 | GCATTCCATATACACA | $G_{ks}{}^mC_{ds}A_{ds}T_{ds}T_{ds}{}^mC_{ds}{}^mC_{ds}A_{ds}T_{ds}A_{ds}T_{ds}A_{ks}{}^mC_{es}A_{ks}{}^mC_{es}A_k$ | 39 | 1003 |
| 785394 | N/A | N/A | 6547 | 6562 | CAATTTTGCATTCCAT | ${}^mC_{ks}A_{ds}A_{ds}T_{ds}T_{ds}T_{ds}T_{ds}G_{ds}{}^mC_{ds}A_{ds}T_{ds}T_{ks}{}^mC_{es}{}^mC_{ks}A_{es}T_k$ | 21 | 1241 |
| 785395 | N/A | N/A | 6549 | 6564 | TCCAATTTTGCATTCC | $T_{ks}{}^mC_{ds}{}^mC_{ds}A_{ds}A_{ds}T_{ds}T_{ds}T_{ds}T_{ds}G_{ds}{}^mC_{ds}A_{ks}T_{es}T_{ks}{}^mC_{es}{}^mC_k$ | 37 | 1047 |
| 785425 | 1762 | 1777 | 11327 | 11342 | CATCTCCACATCAGTC | ${}^mC_{ks}A_{ds}T_{ds}{}^mC_{ds}T_{ds}{}^mC_{ds}{}^mC_{ds}A_{ds}{}^mC_{ds}A_{ds}T_{ds}{}^mC_{ks}A_{es}G_{es}T_{ks}{}^mC_e$ | 32 | 631 |
| 785426 | 1764 | 1779 | 11329 | 11344 | CACATCTCCACATCAG | ${}^mC_{ks}A_{ds}{}^mC_{ds}A_{ds}T_{ds}{}^mC_{ds}T_{ds}{}^mC_{ds}{}^mC_{ds}A_{ds}C_{ds}A_{ds}{}^mC_{ks}A_{es}T_{ks}{}^mC_{es}A_{ks}G_e$ | 2 | 633 |
| 785447 | N/A | N/A | 6539 | 6554 | CATTCCATATACACAC | ${}^mC_{ks}A_{ds}T_{ds}T_{ds}{}^mC_{ds}{}^mC_{ds}A_{ds}T_{ds}A_{ds}T_{ds}A_{ds}T_{ks}{}^mC_{es}A_{ks}{}^mC_{es}A_{ks}{}^mC_e$ | 7 | 1006 |
| 785448 | N/A | N/A | 6540 | 6555 | GCATTCCATATACACA | $G_{ks}{}^mC_{ds}A_{ds}T_{ds}T_{ds}{}^mC_{ds}{}^mC_{ds}A_{ds}T_{ds}A_{ds}T_{ks}A_{es}{}^mC_{ks}A_{es}{}^mC_{ks}A_e$ | 34 | 1003 |
| 785449 | N/A | N/A | 6547 | 6562 | CAATTTTGCATTCCAT | ${}^mC_{ks}A_{ds}A_{ds}T_{ds}T_{ds}T_{ds}T_{ds}G_{ds}{}^mC_{ds}A_{ds}T_{ks}T_{es}{}^mC_{ks}{}^mC_{es}A_{ks}T_e$ | 19 | 1241 |
| 785450 | N/A | N/A | 6549 | 6564 | TCCAATTTTGCATTCC | $T_{ks}{}^mC_{ds}{}^mC_{ds}A_{ds}A_{ds}T_{ds}T_{ds}T_{ds}T_{ds}G_{ds}{}^mC_{ks}A_{es}T_{ks}T_{es}{}^mC_{ks}{}^mC_e$ | 6 | 1047 |
| 785471 | 1764 | 1779 | 11329 | 11344 | CACATCTCCACATCAG | ${}^mC_{ks}A_{es}{}^mC_{ks}A_{ds}T_{ds}{}^mC_{ds}T_{ds}{}^mC_{ds}{}^mC_{ds}A_{ds}C_{ds}A_{ds}T_{es}{}^mC_{es}A_{ks}G_k$ | 26 | 633 |

TABLE 18-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785483 | N/A | N/A | 6539 | 6554 | CATTCCATATACACAC | $^mC_{ks}A_{es}T_{ks}T_{ds}{}^mC_{ds}{}^mC_{ds}A_{ds}T_{ds}A_{ds}T_{ds}A_{ds}{}^mC_{ds}A_{es}{}^mC_{es}A_{ks}{}^mC_k$ | 24 | 1006 |
| 785484 | N/A | N/A | 6540 | 6555 | GCATTCCATATACACA | $G_{ks}{}^mC_{es}A_{ks}T_{ds}T_{ds}{}^mC_{ds}{}^mC_{ds}A_{ds}T_{ds}A_{ds}T_{ds}A_{ds}{}^mC_{es}A_{es}{}^mC_{ks}A_k$ | 48 | 1003 |
| 785485 | N/A | N/A | 6549 | 6564 | TCCAATTTTGCATTCC | $T_{ks}{}^mC_{es}{}^mC_{ks}A_{ds}A_{ds}T_{ds}T_{ds}T_{ds}T_{ds}G_{ds}{}^mC_{ds}A_{ds}T_{es}T_{es}{}^mC_{ks}{}^mC_k$ | 76 | 1047 |
| 785513 | 1763 | 1778 | 11328 | 11343 | ACATCTCCACATCAGT | $A_{ks}{}^mC_{ks}A_{ds}T_{ds}{}^mC_{ds}T_{ds}{}^mC_{ds}{}^mC_{ds}A_{ds}{}^mC_{ds}A_{ds}T_{ds}{}^mC_{ks}A_{es}G_{ks}T_e$ | 36 | 632 |
| 785514 | 1764 | 1779 | 11329 | 11344 | CACATCTCCACATCAG | $^mC_{ks}A_{ks}{}^mC_{ds}A_{ds}T_{ds}{}^mC_{ds}T_{ds}{}^mC_{ds}{}^mC_{ds}A_{ds}{}^mC_{ds}A_{ds}T_{ks}{}^mC_{es}A_{ks}G_e$ | 23 | 633 |
| 785535 | N/A | N/A | 6539 | 6554 | CATTCCATATACACAC | $^mC_{ks}A_{ks}T_{ds}T_{ds}{}^mC_{ds}{}^mC_{ds}A_{ds}T_{ds}A_{ds}T_{ds}A_{ds}{}^mC_{ds}A_{ks}{}^mC_{es}A_{ks}{}^mC_e$ | 30 | 1006 |
| 785536 | N/A | N/A | 6540 | 6555 | GCATTCCATATACACA | $G_{ks}{}^mC_{ks}A_{ds}T_{ds}T_{ds}{}^mC_{ds}{}^mC_{ds}A_{ds}T_{ds}A_{ds}T_{ds}A_{ds}{}^mC_{ks}A_{es}{}^mC_{ks}A_e$ | 37 | 1003 |
| 785537 | N/A | N/A | 6548 | 6563 | CCAATTTTGCATTCCA | $^mC_{ks}{}^mC_{ks}A_{ds}A_{ds}T_{ds}T_{ds}T_{ds}T_{ds}G_{ds}{}^mC_{ds}A_{ds}T_{ds}T_{ks}{}^mC_{es}{}^mC_{ks}A_e$ | 57 | 1242 |
| 785538 | N/A | N/A | 6549 | 6564 | TCCAATTTTGCATTCC | $T_{ks}{}^mC_{ks}{}^mC_{ds}A_{ds}A_{ds}T_{ds}T_{ds}T_{ds}T_{ds}G_{ds}{}^mC_{ds}A_{ds}T_{ks}T_{es}{}^mC_{ks}{}^mC_e$ | 40 | 1047 |
| 785558 | 1763 | 1778 | 11328 | 11343 | ACATCTCCACATCAGT | $A_{ks}{}^mC_{ks}A_{ds}T_{ds}{}^mC_{ds}T_{ds}{}^mC_{ds}{}^mC_{ds}A_{ds}{}^mC_{ds}A_{es}T_{es}{}^mC_{es}A_{es}G_{ks}T_k$ | 24 | 632 |
| 785570 | N/A | N/A | 6539 | 6554 | CATTCCATATACACAC | $^mC_{ks}A_{ks}T_{ds}T_{ds}{}^mC_{ds}{}^mC_{ds}A_{ds}T_{ds}A_{ds}T_{ds}A_{ds}{}^mC_{es}{}^mC_{es}A_{es}{}^mC_{es}A_{ks}{}^mC_k$ | 21 | 1006 |
| 785571 | N/A | N/A | 6548 | 6563 | CCAATTTTGCATTCCA | $^mC_{ks}{}^mC_{ks}A_{ds}A_{ds}T_{ds}T_{ds}T_{ds}T_{ds}G_{ds}{}^mC_{ds}A_{es}T_{es}T_{es}{}^mC_{es}{}^mC_{ks}A_k$ | 48 | 1242 |
| 785609 | 1762 | 1777 | 11327 | 11342 | CATCTCCACATCAGTC | $^mC_{ks}A_{ks}T_{ds}{}^mC_{ds}T_{ds}{}^mC_{ds}{}^mC_{ds}A_{ds}{}^mC_{ds}A_{ds}T_{ds}{}^mC_{es}A_{ks}G_{es}T_{ks}{}^mC_k$ | 23 | 631 |
| 785610 | 1763 | 1778 | 11328 | 11343 | ACATCTCCACATCAGT | $A_{ks}{}^mC_{ks}A_{ds}T_{ds}{}^mC_{ds}T_{ds}{}^mC_{ds}{}^mC_{ds}A_{ds}{}^mC_{ds}A_{ks}T_{es}{}^mC_{ks}A_{es}G_{ks}T_k$ | 15 | 632 |
| 785611 | 1764 | 1779 | 11329 | 11344 | CACATCTCCACATCAG | $^mC_{ks}A_{ks}{}^mC_{ds}A_{ds}T_{ds}{}^mC_{ds}T_{ds}{}^mC_{ds}{}^mC_{ds}A_{ds}{}^mC_{ds}A_{ds}{}^mC_{ks}A_{es}T_{ks}{}^mC_{es}A_{ks}G_k$ | 17 | 633 |
| 785640 | N/A | N/A | 6539 | 6554 | CATTCCATATACACAC | $^mC_{ks}A_{ks}T_{ds}T_{ds}{}^mC_{ds}{}^mC_{ds}A_{ds}T_{ds}A_{ds}T_{ds}A_{ds}{}^mC_{ks}{}^mC_{es}A_{ks}{}^mC_{es}A_{ks}{}^mC_k$ | 17 | 1006 |
| 785641 | N/A | N/A | 6540 | 6555 | GCATTCCATATACACA | $G_{ks}{}^mC_{ks}A_{ds}T_{ds}T_{ds}{}^mC_{ds}{}^mC_{ds}A_{ds}T_{ds}A_{ds}T_{ks}A_{es}{}^mC_{ks}A_{es}{}^mC_{ks}A_k$ | 0 | 1003 |
| 785642 | N/A | N/A | 6547 | 6562 | CAATTTTGCATTCCAT | $^mC_{ks}A_{ks}A_{ds}T_{ds}T_{ds}T_{ds}T_{ds}G_{ds}{}^mC_{ds}A_{ds}T_{ks}T_{es}{}^mC_{ks}{}^mC_{es}A_{ks}T_k$ | 32 | 1241 |

TABLE 18-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785643 | N/A | N/A | 6548 | 6563 | CCAATTTTGCATTCCA | $^mC_{ks}{}^mC_{ks}A_{ds}A_{ds}T_{ds}T_{ds}T_{ds}T_{ds}G_{ds}{}^mC_{ds}A_{ks}T_{es}T_{ks}{}^mC_{es}{}^mC_{ks}A_k$ | 39 | 1242 |
| 785644 | N/A | N/A | 6549 | 6564 | TCCAATTTTGCATTCC | $T_{ks}{}^mC_{ks}{}^mC_{ds}A_{ds}A_{ds}T_{ds}T_{ds}T_{ds}T_{ds}G_{ds}{}^mC_{ks}A_{es}T_{ks}T_{es}{}^mC_{ks}{}^mC_k$ | 15 | 1047 |
| 785667 | 1763 | 1778 | 11328 | 11343 | ACATCTCCACATCAGT | $A_{ks}{}^mC_{ks}A_{ds}T_{ds}{}^mC_{ds}T_{ds}{}^mC_{ds}{}^mC_{ds}A_{ds}{}^mC_{ds}A_{ds}T_{es}{}^mC_{es}A_{es}G_{ks}T_k$ | 41 | 632 |
| 785679 | N/A | N/A | 6539 | 6554 | CATTCCATATACACAC | $^mC_{ks}A_{ks}T_{ds}T_{ds}{}^mC_{ds}{}^mC_{ds}A_{ds}T_{ds}A_{ds}T_{ds}A_{ds}{}^mC_{es}A_{es}{}^mC_{es}A_{ks}{}^mC_k$ | 21 | 1006 |
| 785680 | N/A | N/A | 6548 | 6563 | CCAATTTTGCATTCCA | $^mC_{ks}{}^mC_{ks}A_{ds}A_{ds}T_{ds}T_{ds}T_{ds}T_{ds}G_{ds}{}^mC_{ds}A_{ds}T_{es}T_{es}{}^mC_{es}{}^mC_{ks}A_k$ | 30 | 1242 |
| 785697 | 1763 | 1778 | 11328 | 11343 | ACATCTCCACATCAGT | $A_{ks}{}^mC_{ks}A_{ds}T_{ds}{}^mC_{ds}T_{ds}{}^mC_{ds}{}^mC_{ds}A_{ds}{}^mC_{ds}A_{ds}T_{ks}{}^mC_{ds}A_{ks}G_{ds}T_k$ | 28 | 632 |
| 785709 | N/A | N/A | 6539 | 6554 | CATTCCATATACACAC | $^mC_{ks}A_{ks}T_{ds}T_{ds}{}^mC_{ds}{}^mC_{ds}A_{ds}T_{ds}A_{ds}T_{ds}A_{ds}{}^mC_{ks}A_{ds}{}^mC_{ks}A_{ds}{}^mC_k$ | 25 | 1006 |
| 785710 | N/A | N/A | 6548 | 6563 | CCAATTTTGCATTCCA | $^mC_{ks}{}^mC_{ks}A_{ds}A_{ds}T_{ds}T_{ds}T_{ds}T_{ds}G_{ds}{}^mC_{ds}A_{ds}T_{ks}T_{ds}{}^mC_{ks}{}^mC_{ks}A_k$ | 42 | 1242 |
| 785738 | 1763 | 1778 | 11328 | 11343 | ACATCTCCACATCAGT | $A_{ks}{}^mC_{ks}A_{ds}T_{ds}{}^mC_{ds}T_{ds}{}^mC_{ds}{}^mC_{ds}A_{ds}{}^mC_{ds}A_{ds}T_{ks}{}^mC_{es}A_{ks}G_{es}T_k$ | 16 | 632 |
| 785739 | 1764 | 1779 | 11329 | 11344 | CACATCTCCACATCAG | $^mC_{ks}A_{ks}{}^mC_{ds}A_{ds}T_{ds}{}^mC_{ds}T_{ds}{}^mC_{ds}{}^mC_{ds}A_{ds}{}^mC_{ds}A_{ks}T_{es}{}^mC_{ks}A_{es}G_k$ | 22 | 633 |
| 785760 | N/A | N/A | 6539 | 6554 | CATTCCATATACACAC | $^mC_{ks}A_{ks}T_{ds}T_{ds}{}^mC_{ds}{}^mC_{ds}A_{ds}T_{ds}A_{ds}T_{ds}A_{ds}{}^mC_{ks}A_{es}{}^mC_{ks}A_{es}{}^mC_k$ | 54 | 1006 |
| 785761 | N/A | N/A | 6540 | 6555 | GCATTCCATATACACA | $G_{ks}{}^mC_{ks}A_{ds}T_{ds}T_{ds}{}^mC_{ds}{}^mC_{ds}A_{ds}T_{ds}A_{ds}T_{ds}A_{ks}{}^mC_{es}A_{ks}{}^mC_{es}A_k$ | 2 | 1003 |
| 785762 | N/A | N/A | 6548 | 6563 | CCAATTTTGCATTCCA | $^mC_{ks}{}^mC_{ks}A_{ds}A_{ds}T_{ds}T_{ds}T_{ds}T_{ds}G_{ds}{}^mC_{ds}A_{ds}T_{ks}T_{es}{}^mC_{ks}{}^mC_{es}A_k$ | 11 | 1242 |
| 785763 | N/A | N/A | 6549 | 6564 | TCCAATTTTGCATTCC | $T_{ks}{}^mC_{ks}{}^mC_{ds}A_{ds}A_{ds}T_{ds}T_{ds}T_{ds}T_{ds}G_{ds}{}^mC_{ds}A_{ks}T_{es}T_{ks}{}^mC_{es}{}^mC_k$ | 29 | 1047 |
| 785784 | 1764 | 1779 | 11329 | 11344 | CACATCTCCACATCAG | $^mC_{ks}A_{ks}{}^mC_{ks}A_{ds}T_{ds}{}^mC_{ds}T_{ds}{}^mC_{ds}{}^mC_{ds}A_{ds}{}^mC_{ds}A_{ks}T_{ds}{}^mC_{ks}A_{ds}G_k$ | 39 | 633 |
| 785796 | N/A | N/A | 6539 | 6554 | CATTCCATATACACAC | $^mC_{ks}A_{ks}T_{ks}T_{ds}{}^mC_{ds}{}^mC_{ds}A_{ds}T_{ds}A_{ds}T_{ds}A_{ds}{}^mC_{ks}A_{ds}{}^mC_{ks}A_{ds}{}^mC_k$ | 40 | 1006 |
| 785797 | N/A | N/A | 6540 | 6555 | GCATTCCATATACACA | $G_{ks}{}^mC_{ks}A_{ks}T_{ds}T_{ds}{}^mC_{ds}{}^mC_{ds}A_{ds}T_{ds}A_{ds}T_{ds}A_{ks}{}^mC_{ds}A_{ks}{}^mC_k$ | 0 | 1003 |
| 785798 | N/A | N/A | 6549 | 6564 | TCCAATTTTGCATTCC | $T_{ks}{}^mC_{ks}{}^mC_{ks}A_{ds}A_{ds}T_{ds}T_{ds}T_{ds}T_{ds}G_{ds}{}^mC_{ds}A_{ks}T_{ds}T_{ks}{}^mC_{ds}{}^mC_k$ | 32 | 1047 |

TABLE 18-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785826 | 1763 | 1778 | 11328 | 11343 | ACATCTCCACATCAGT | $A_{ks}{}^mC_{ks}A_{ks}T_{ds}{}^mC_{ds}T_{ds}{}^mC_{ds}{}^mC_{ds}A_{ds}{}^mC_{ds}A_{ds}T_{ks}{}^mC_{es}A_{ks}G_{es}T_k$ | 14 | 632 |
| 785827 | 1764 | 1779 | 11329 | 11344 | CACATCTCCACATCAG | ${}^mC_{ks}A_{ks}{}^mC_{ks}A_{ds}T_{ds}{}^mC_{ds}T_{ds}{}^mC_{ds}{}^mC_{ds}A_{ds}{}^mC_{ds}A_{ks}T_{es}{}^mC_{ks}A_{es}G_k$ | 43 | 633 |
| 785848 | N/A | N/A | 6539 | 6554 | CATTCCATATACACAC | ${}^mC_{ks}A_{ks}T_{ks}T_{ds}{}^mC_{ds}{}^mC_{ds}A_{ds}T_{ds}A_{ds}T_{ds}A_{ds}{}^mC_{ks}A_{es}{}^mC_{ks}A_{es}{}^mC_k$ | 32 | 1006 |
| 785849 | N/A | N/A | 6540 | 6555 | GCATTCCATATACACA | $G_{ks}{}^mC_{ks}A_{ks}T_{ds}T_{ds}{}^mC_{ds}{}^mC_{ds}A_{ds}T_{ds}A_{ds}T_{ds}A_{ks}{}^mC_{es}A_{ks}{}^mC_{es}A_k$ | 0 | 1003 |
| 785850 | N/A | N/A | 6548 | 6563 | CCAATTTTGCATTCCA | ${}^mC_{ks}{}^mC_{ks}A_{ks}A_{ds}T_{ds}T_{ds}T_{ds}T_{ds}G_{ds}{}^mC_{ds}A_{ds}T_{ks}T_{es}{}^mC_{ks}{}^mC_{es}A_k$ | 42 | 1242 |
| 785851 | N/A | N/A | 6549 | 6564 | TCCAATTTTGCATTCC | $T_{ks}{}^mC_{ks}{}^mC_{ks}A_{ds}A_{ds}T_{ds}T_{ds}T_{ds}T_{ds}G_{ds}{}^mC_{ds}A_{ks}T_{es}T_{ks}{}^mC_{es}{}^mC_k$ | 51 | 1047 |
| 785872 | 1764 | 1779 | 11329 | 11344 | CACATCTCCACATCAG | ${}^mC_{ks}A_{ks}{}^mC_{ks}A_{ds}T_{ds}{}^mC_{ds}T_{ds}{}^mC_{ds}{}^mC_{ds}A_{ds}{}^mC_{ds}A_{ds}T_{ks}{}^mC_{es}A_{ks}G_e$ | 38 | 633 |
| 785884 | N/A | N/A | 6539 | 6554 | CATTCCATATACACAC | ${}^mC_{ks}A_{ks}T_{ks}T_{ds}{}^mC_{ds}{}^mC_{ds}A_{ds}T_{ds}A_{ds}T_{ds}A_{ds}{}^mC_{ds}A_{ks}{}^mC_{es}A_{ks}{}^mC_e$ | 28 | 1006 |
| 785885 | N/A | N/A | 6540 | 6555 | GCATTCCATATACACA | $G_{ks}{}^mC_{ks}A_{ks}T_{ds}T_{ds}{}^mC_{ds}{}^mC_{ds}A_{ds}T_{ds}A_{ds}T_{ds}A_{ds}{}^mC_{ks}A_{es}{}^mC_{ks}A_e$ | 45 | 1003 |
| 785886 | N/A | N/A | 6549 | 6564 | TCCAATTTTGCATTCC | $T_{ks}{}^mC_{ks}{}^mC_{ks}A_{ds}A_{ds}T_{ds}T_{ds}T_{ds}T_{ds}G_{ds}{}^mC_{ds}A_{ds}T_{ks}T_{es}{}^mC_{ks}{}^mC_e$ | 14 | 1047 |
| 785914 | 1763 | 1778 | 11328 | 11343 | ACATCTCCACATCAGT | $A_{ks}{}^mC_{ks}A_{ks}T_{ds}{}^mC_{ds}T_{ds}{}^mC_{ds}{}^mC_{ds}A_{ds}{}^mC_{ds}A_{ds}T_{ds}{}^mC_{ks}A_{ks}G_{ks}T_e$ | 11 | 632 |
| 785915 | 1764 | 1779 | 11329 | 11344 | CACATCTCCACATCAG | ${}^mC_{ks}A_{ks}{}^mC_{ks}A_{ds}T_{ds}{}^mC_{ds}T_{ds}{}^mC_{ds}{}^mC_{ds}A_{ds}{}^mC_{ds}A_{ds}T_{ks}{}^mC_{ks}A_{ks}G_e$ | 25 | 633 |
| 785936 | N/A | N/A | 6539 | 6554 | CATTCCATATACACAC | ${}^mC_{ks}A_{ks}T_{ks}T_{ds}{}^mC_{ds}{}^mC_{ds}A_{ds}T_{ds}A_{ds}T_{ds}A_{ds}{}^mC_{ds}A_{ks}{}^mC_{ks}A_{ks}{}^mC_e$ | 39 | 1006 |
| 785937 | N/A | N/A | 6540 | 6555 | GCATTCCATATACACA | $G_{ks}{}^mC_{ks}A_{ks}T_{ds}T_{ds}{}^mC_{ds}{}^mC_{ds}A_{ds}T_{ds}A_{ds}T_{ds}A_{ds}{}^mC_{ks}A_{ks}{}^mC_{ks}A_e$ | 25 | 1003 |
| 785938 | N/A | N/A | 6548 | 6563 | CCAATTTTGCATTCCA | ${}^mC_{ks}{}^mC_{ks}A_{ks}A_{ds}T_{ds}T_{ds}T_{ds}T_{ds}G_{ds}{}^mC_{ds}A_{ds}T_{ds}T_{ks}{}^mC_{ks}{}^mC_{ks}A_e$ | 80 | 1242 |
| 785939 | N/A | N/A | 6549 | 6564 | TCCAATTTTGCATTCC | $T_{ks}{}^mC_{ks}{}^mC_{ks}A_{ds}A_{ds}T_{ds}T_{ds}T_{ds}T_{ds}G_{ds}{}^mC_{ds}A_{ds}T_{ks}T_{ks}{}^mC_{ks}{}^mC_e$ | 7 | 1047 |
| 786505 | N/A | N/A | 6546 | 6561 | AATTTTGCATTCCATA | $A_{ks}A_{ks}T_{ks}T_{ds}T_{ds}T_{ds}G_{ds}{}^mC_{ds}A_{ds}T_{ds}T_{ds}{}^mC_{ds}{}^mC_{ds}A_{ks}T_{ks}A_k$ | 41 | 1243 |
| 786506 | N/A | N/A | 6547 | 6562 | CAATTTTGCATTCCAT | ${}^mC_{ks}A_{ks}A_{ks}T_{ds}T_{ds}T_{ds}T_{ds}G_{ds}{}^mC_{ds}A_{ds}T_{ds}T_{ds}{}^mC_{ds}{}^mC_{ks}A_{ks}T_k$ | 52 | 1241 |

TABLE 18-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 786507 | N/A | N/A | 6548 | 6563 | CCAATTTTGCATTCCA | $^mC_{ks}{}^mC_{ks}A_{ks}A_{ds}T_{ds}T_{ds}T_{ds}T_{ds}G_{ds}{}^mC_{ds}A_{ds}T_{ds}T_{ds}{}^mC_{ks}{}^mC_{ks}A_k$ | 78 | 1242 |
| 786508 | N/A | N/A | 6550 | 6565 | TTCCAATTTTGCATTC | $T_{ks}T_{ks}{}^mC_{ks}{}^mC_{ds}A_{ds}A_{ds}T_{ds}T_{ds}T_{ds}T_{ds}G_{ds}{}^mC_{ds}A_{ds}T_{ks}T_{ks}{}^mC_k$ | 39 | 1244 |
| 786509 | N/A | N/A | 6551 | 6566 | ATTCCAATTTTGCATT | $A_{ks}T_{ks}T_{ks}{}^mC_{ds}{}^mC_{ds}A_{ds}A_{ds}T_{ds}T_{ds}T_{ds}T_{ds}G_{ds}{}^mC_{ds}A_{ks}T_{ks}T_k$ | 21 | 1245 |
| 786510 | N/A | N/A | 6553 | 6568 | TGATTCCAATTTTGCA | $T_{ks}G_{ks}A_{ks}T_{ds}T_{ds}{}^mC_{ds}{}^mC_{ds}A_{ds}A_{ds}T_{ds}T_{ds}T_{ds}T_{ds}G_{ks}{}^mC_{ks}A_k$ | 17 | 1246 |
| 786511 | N/A | N/A | 6555 | 6570 | CTTGATTCCAATTTTG | $^mC_{ks}T_{ks}T_{ks}G_{ds}A_{ds}T_{ds}T_{ds}{}^mC_{ds}{}^mC_{ds}A_{ds}A_{ds}T_{ds}T_{ds}T_{ks}T_{ks}G_k$ | 20 | 1247 |
| 786512 | N/A | N/A | 6557 | 6572 | CACTTGATTCCAATTT | $^mC_{ks}A_{ks}{}^mC_{ks}T_{ds}T_{ds}G_{ds}A_{ds}T_{ds}T_{ds}{}^mC_{ds}{}^mC_{ds}A_{ds}A_{ks}T_{ks}T_k$ | 36 | 1248 |

TABLE 19

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 665795 | 385 | 400 | 4710 | 4725 | GTTATCTCCGTCCTGG | $G_{ks}T_{ks}T_{ks}A_{ds}T_{ds}{}^mC_{ds}T_{ds}{}^mC_{ds}{}^mC_{ds}G_{ds}T_{ds}{}^mC_{ds}{}^mC_{ds}T_{ks}G_{ks}G_k$ | 31 | 113 |
| 728489 | 484 | 499 | 8377 | 8392 | AAGGGCACAGACGCAGG | $A_{ks}A_{ks}G_{ks}G_{ds}G_{ds}{}^mC_{ds}A_{ds}{}^mC_{ds}A_{ds}G_{ds}{}^mC_{ds}G_{ds}{}^mC_{ds}A_{ks}G_{ks}G_k$ | 0 | 1249 |
| 728695 | 1270 | 1285 | 10503 | 10518 | TGAGTCATGGGCTGAG | $T_{ks}G_{ks}A_{ks}G_{ds}T_{ds}{}^mC_{ds}A_{ds}T_{ds}G_{ds}G_{ds}G_{ds}{}^mC_{ds}T_{ds}G_{ks}A_{ks}G_k$ | 0 | 423 |
| 728696 | 1271 | 1286 | 10504 | 10519 | ATGAGTCATGGGCTGA | $A_{ks}T_{ks}G_{ks}A_{ds}G_{ds}T_{ds}{}^mC_{ds}A_{ds}T_{ds}G_{ds}G_{ds}G_{ds}{}^mC_{ds}T_{ks}G_{ks}A_k$ | 21 | 424 |
| 728708 | 1308 | 1323 | 10541 | 10556 | AGCTTGGTCTTGACCT | $A_{ks}G_{ks}{}^mC_{ks}T_{ds}T_{ds}G_{ds}G_{ds}T_{ds}{}^mC_{ds}T_{ds}T_{ds}G_{ds}A_{ds}{}^mC_{ks}{}^mC_{ks}T_k$ | 38 | 436 |
| 785345 | 383 | 398 | 4708 | 4723 | TATCTCCGTCCTGGCT | $T_{ks}A_{ds}T_{ds}{}^mC_{ds}T_{ds}{}^mC_{ds}{}^mC_{ds}G_{ds}T_{ds}{}^mC_{ds}{}^mC_{ds}T_{ks}G_{es}G_{ks}{}^mC_{es}T_k$ | 0 | 116 |
| 785346 | 385 | 400 | 4710 | 4725 | GTTATCTCCGTTCCTGG | $G_{ks}T_{ds}T_{ds}A_{ds}T_{ds}{}^mC_{ds}T_{ds}{}^mC_{ds}{}^mC_{ds}G_{ds}T_{ds}{}^mC_{ks}{}^mC_{es}T_{ks}G_{es}G_k$ | 0 | 113 |
| 785350 | 482 | 497 | 8375 | 8390 | GGGCACAGCGCCAGGTT | $G_{ks}G_{ds}G_{ds}{}^mC_{ds}A_{ds}{}^mC_{ds}A_{ds}G_{ds}{}^mC_{ds}G_{ds}{}^mC_{ds}A_{ks}G_{es}G_{ks}T_{es}T_k$ | 37 | 1250 |
| 785351 | 484 | 499 | 8377 | 8392 | AAGGGCACAGCGCAGG | $A_{ks}A_{ds}G_{ds}G_{ds}G_{ds}{}^mC_{ds}A_{ds}{}^mC_{ds}A_{ds}G_{ds}{}^mC_{ds}G_{ks}{}^mC_{es}A_{ks}G_{es}G_k$ | 0 | 1249 |

TABLE 19-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785355 | 1268 | 1283 | 10501 | 10516 | AGTCATGGGCTGAGGC | $A_{ks}G_{ds}T_{ds}{}^mC_{ds}A_{ds}T_{ds}G_{ds}G_{ds}G_{ds}{}^mC_{ds}T_{ds}G_{ds}A_{es}G_{ks}G_{es}{}^mC_k$ | 25 | 421 |
| 785356 | 1269 | 1284 | 10502 | 10517 | GAGTCATGGGCTGAGG | $G_{ks}A_{ds}G_{ds}T_{ds}{}^mC_{ds}A_{ds}T_{ds}G_{ds}G_{ds}G_{ds}{}^mC_{ds}T_{ks}G_{es}A_{ks}G_{es}G_k$ | 0 | 422 |
| 785357 | 1270 | 1285 | 10503 | 10518 | TGAGTCATGGGCTGAG | $T_{ks}G_{ds}A_{ds}G_{as}T_{as}{}^mC_{ds}A_{ds}T_{ds}G_{ds}G_{ds}G_{ds}{}^mC_{ks}T_{es}G_{ks}A_{es}G_k$ | 0 | 423 |
| 785358 | 1271 | 1286 | 10504 | 10519 | ATGAGTCATGGGCTGA | $A_{ks}T_{ds}G_{ds}A_{ds}G_{ds}T_{ds}{}^mC_{ds}A_{ds}T_{ds}G_{ds}G_{ds}G_{ks}{}^mC_{es}T_{ks}G_{es}A_k$ | 0 | 424 |
| 785405 | 482 | 497 | 8375 | 8390 | GGGCACAGCGCAGGTT | $G_{ks}G_{ds}G_{ds}{}^mC_{ds}A_{ds}{}^mC_{ds}A_{ds}G_{ds}{}^mC_{ds}G_{ds}{}^mC_{ks}A_{es}G_{ks}G_{es}T_{ks}T_e$ | 33 | 1250 |
| 785406 | 484 | 499 | 8377 | 8392 | AAGGGCACAGACGCAGG | $A_{ks}A_{ds}G_{ds}G_{ds}G_{ds}{}^mC_{ds}A_{ds}{}^mC_{ds}A_{ds}G_{ds}{}^mC_{ks}G_{es}{}^mC_{ks}A_{es}G_{ks}G_e$ | 0 | 1249 |
| 785410 | 1268 | 1283 | 10501 | 10516 | AGTCATGGGCGTGAGGC | $A_{ks}G_{ds}T_{ds}{}^mC_{ds}A_{ds}T_{ds}G_{ds}G_{ds}G_{ds}{}^mC_{ks}T_{ks}G_{es}A_{ks}G_{es}G_{ks}{}^mC_e$ | 17 | 421 |
| 785411 | 1269 | 1284 | 10502 | 10517 | GAGTCATGGGCTGAGG | $G_{ks}A_{ds}G_{ds}T_{ds}{}^mC_{ds}A_{ds}T_{ds}G_{ds}G_{ds}G_{ds}{}^mC_{ks}T_{es}G_{ks}A_{es}G_{ks}G_e$ | 0 | 422 |
| 785412 | 1270 | 1285 | 10503 | 10518 | TGAGTCATGGAGCTGAG | $T_{ks}G_{ds}A_{ds}G_{ds}T_{ds}{}^mC_{ds}A_{ds}T_{ds}G_{ds}G_{ds}G_{ks}{}^mC_{es}T_{ks}G_{es}A_{ks}G_e$ | 0 | 423 |
| 785413 | 1271 | 1286 | 10504 | 10519 | ATGAGTCATGGGCTGA | $A_{ks}T_{ds}G_{ds}A_{ds}G_{ds}T_{ds}{}^mC_{ds}A_{ds}T_{ds}G_{ds}G_{ks}G_{es}{}^mC_{ks}T_{es}G_{ks}A_e$ | 7 | 424 |
| 785457 | 385 | 400 | 4710 | 4725 | GTTATCTCCGTCCTGG | $G_{ks}T_{es}T_{ks}A_{ds}T_{ds}{}^mC_{ds}T_{ds}{}^mC_{ds}{}^mC_{ds}G_{ds}T_{ds}{}^mC_{ds}{}^mC_{es}T_{es}G_{ks}G_k$ | 13 | 113 |
| 785460 | 484 | 499 | 8377 | 8392 | AAGGGCACAGCGCAGG | $A_{ks}A_{es}G_{ks}G_{ds}G_{ds}{}^mC_{ds}A_{ds}{}^mC_{ds}A_{ds}G_{ds}{}^mC_{ds}G_{ds}{}^mC_{es}A_{es}G_{ks}G_k$ | 0 | 1249 |
| 785462 | 1270 | 1285 | 10503 | 10518 | TGAGTCATGGGCTGAG | $T_{ks}G_{es}A_{ks}G_{ds}T_{ds}{}^mC_{ds}A_{ds}T_{ds}G_{ds}G_{ds}G_{ds}{}^mC_{ds}T_{es}G_{es}A_{ks}G_k$ | 12 | 423 |
| 785463 | 1271 | 1286 | 10504 | 10519 | ATGAGTCATGGGCTGA | $A_{ks}T_{es}G_{ks}A_{ds}G_{ds}T_{ds}{}^mC_{ds}A_{ds}T_{ds}G_{ds}G_{ds}G_{ks}{}^mC_{es}T_{es}G_{ks}A_k$ | 0 | 424 |
| 785489 | 384 | 399 | 4709 | 4724 | TTATCTCCGTCCTGGC | $T_{ks}T_{ks}A_{ds}T_{ds}{}^mC_{ds}T_{ds}{}^mC_{ds}{}^mC_{ds}G_{ds}T_{ds}{}^mC_{ds}{}^mC_{ds}T_{ks}G_{es}G_{ks}{}^mC_e$ | 0 | 117 |
| 785490 | 385 | 400 | 4710 | 4725 | GTTATCTCCGTCCTGG | $G_{ks}T_{ks}T_{ds}A_{ds}T_{ds}{}^mC_{ds}T_{ds}{}^mC_{ds}{}^mC_{ds}G_{ds}T_{ds}{}^mC_{ds}{}^mC_{ks}T_{es}G_{ks}G_e$ | 0 | 113 |
| 785495 | 484 | 499 | 8377 | 8392 | AAGGGCACAGCGCAGG | $A_{ks}A_{ks}G_{ds}G_{ds}G_{ds}{}^mC_{ds}A_{ds}{}^mC_{ds}A_{ds}G_{ds}{}^mC_{ds}G_{ds}{}^mC_{ks}A_{es}G_{ks}G_e$ | 0 | 1249 |
| 785499 | 1269 | 1284 | 10502 | 10517 | GAGTCATGGGCTGAGG | $G_{ks}A_{ks}G_{ds}T_{ds}{}^mC_{ds}A_{ds}T_{ds}G_{ds}G_{ds}G_{ds}{}^mC_{ds}T_{ks}G_{es}A_{ks}G_{ks}G_e$ | 40 | 422 |

TABLE 19-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785500 | 1270 | 1285 | 10503 | 10518 | TGAGTCATGGGCTGAG | $T_{ks}G_{ks}A_{ds}G_{ds}T_{ds}{}^mC_{ds}A_{ds}T_{ds}G_{ds}G_{ds}G_{ds}{}^mC_{ds}T_{es}G_{es}A_{ks}G_e$ | 0 | 423 |
| 785501 | 1271 | 1286 | 10504 | 10519 | ATGAGTCATGGGCTGA | $A_{ks}T_{ks}G_{ds}A_{ds}G_{ds}T_{ds}{}^mC_{ds}A_{ds}T_{ds}G_{ds}G_{ds}G_{ds}{}^mC_{ks}T_{es}G_{ks}A_e$ | 0 | 424 |
| 785545 | 384 | 399 | 4709 | 4724 | TTATCTCCGTCCTGGC | $T_{ks}T_{ks}A_{ds}T_{ds}{}^mC_{ds}T_{ds}{}^mC_{ds}{}^mC_{ds}G_{ds}T_{ds}{}^mC_{es}{}^mC_{es}T_{es}G_{es}G_{ks}{}^mC_k$ | 0 | 117 |
| 785550 | 1269 | 1284 | 10502 | 10517 | GAGTCATGGGCTGAGG | $T_{ks}A_{ks}G_{ds}T_{ds}{}^mC_{ds}A_{ds}T_{ds}G_{ds}G_{ds}G_{ds}{}^mC_{es}T_{es}G_{es}A_{es}G_{ks}G_k$ | 5 | 422 |
| 785551 | 1270 | 1285 | 10503 | 10518 | TGAGTCATGGGCTGAG | $T_{ks}G_{ks}A_{ds}G_{ds}T_{ds}{}^mC_{ds}A_{ds}T_{ds}G_{ds}G_{ds}G_{es}{}^mC_{es}T_{es}G_{es}A_{ks}G_k$ | 15 | 423 |
| 785575 | 383 | 398 | 4708 | 4723 | TATCTCCGTCCTGGCT | $T_{ks}A_{ks}T_{ds}{}^mC_{ds}T_{ds}{}^mC_{ds}{}^mC_{ds}G_{ds}T_{ds}{}^mC_{ds}{}^mC_{ks}T_{es}G_{ks}G_{es}{}^mC_{ks}T_k$ | 6 | 116 |
| 785576 | 384 | 399 | 4709 | 4724 | TTATCTCCGTCCTGGC | $T_{ks}T_{ks}A_{ds}T_{ds}{}^mC_{ds}T_{ds}{}^mC_{ds}{}^mC_{ds}G_{ds}T_{ds}{}^mC_{ks}{}^mC_{es}T_{ks}G_{es}G_{ks}{}^mC_k$ | 0 | 117 |
| 785577 | 385 | 400 | 4710 | 4725 | GTTATCTCCGTCCTGG | $G_{ks}T_{ks}T_{ds}A_{ds}T_{ds}{}^mC_{ds}T_{ds}{}^mC_{ds}{}^mC_{ds}G_{ds}T_{ks}{}^mC_{es}{}^mC_{ks}T_{es}G_{ks}G_k$ | 0 | 113 |
| 785583 | 482 | 497 | 8375 | 8390 | GGGCACAGCGCAGGTT | $G_{ks}G_{ks}G_{ds}{}^mC_{ds}A_{ds}{}^mC_{ds}A_{ds}G_{ds}{}^mC_{ds}G_{ds}{}^mC_{ks}A_{es}G_{ks}G_{es}T_{ks}T_k$ | 61 | 1250 |
| 785584 | 484 | 499 | 8377 | 8392 | AAGGGCACAGCGCAGG | $A_{ks}A_{ks}G_{ds}G_{ds}G_{ds}{}^mC_{ds}A_{ds}{}^mC_{ds}A_{ds}G_{ds}{}^mC_{ks}G_{es}{}^mC_{ks}A_{es}G_{ks}G_k$ | 0 | 1249 |
| 785590 | 1268 | 1283 | 10501 | 10516 | AGTCATGGGCGTGAGGC | $A_{ks}G_{ks}T_{ds}{}^mC_{ds}A_{ds}T_{ds}G_{ds}G_{ds}G_{ds}{}^mC_{ds}T_{ks}G_{es}A_{ks}G_{es}G_{ks}{}^mC_k$ | 17 | 421 |
| 785591 | 1269 | 1284 | 10502 | 10517 | GAGTCATGGGCTGAGG | $G_{ks}A_{ks}G_{ds}T_{ds}{}^mC_{ds}A_{ds}T_{ds}G_{ds}G_{ds}G_{ds}{}^mC_{ks}T_{es}G_{ks}A_{es}G_{ks}G_k$ | 0 | 422 |
| 785592 | 1270 | 1285 | 10503 | 10518 | TGAGTCATGGGCTGAG | $T_{ks}G_{ks}A_{ds}G_{ds}T_{ds}{}^mC_{ds}A_{ds}T_{ds}G_{ds}G_{ds}G_{ks}{}^mC_{es}T_{ks}G_{es}A_{ks}G_k$ | 0 | 423 |
| 785593 | 1271 | 1286 | 10504 | 10519 | ATGAGTCATGGGCTGA | $A_{ks}T_{ks}G_{ds}A_{ds}G_{ds}T_{ds}{}^mC_{ds}A_{ds}T_{ds}G_{ds}G_{ds}G_{es}{}^mC_{ks}T_{es}G_{ks}A_k$ | 0 | 424 |
| 785654 | 384 | 399 | 4709 | 4724 | TTATCTCCGTCCTGGC | $T_{ks}T_{ks}A_{ds}T_{ds}{}^mC_{ds}T_{ds}{}^mC_{ds}{}^mC_{ds}G_{ds}T_{ds}{}^mC_{ds}{}^mC_{es}T_{es}G_{es}G_{ks}{}^mC_k$ | 5 | 117 |
| 785659 | 1269 | 1284 | 10502 | 10517 | GAGTCATGGGCTGAGG | $G_{ks}A_{ks}G_{ds}T_{ds}{}^mC_{ds}A_{ds}T_{ds}G_{ds}G_{ds}G_{ds}{}^mC_{ds}T_{es}G_{es}A_{es}G_{ks}G_k$ | 30 | 422 |
| 785660 | 1270 | 1285 | 10503 | 10518 | TGAGTCATGGAGCTGAG | $T_{ks}G_{ks}A_{ds}G_{ds}T_{ds}{}^mC_{ds}A_{ds}T_{ds}G_{ds}G_{ds}G_{ds}{}^mC_{es}T_{es}G_{es}A_{ks}G_k$ | 16 | 423 |
| 785684 | 384 | 399 | 4709 | 4724 | TTATCTCCGTCCTGGC | $T_{ks}T_{ks}A_{ds}T_{ds}{}^mC_{ds}T_{ds}{}^mC_{ds}{}^mC_{ds}G_{ds}T_{ds}{}^mC_{ds}{}^mC_{ks}T_{ds}G_{ks}G_{ds}{}^mC_k$ | 14 | 117 |

TABLE 19-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785689 | 1269 | 1284 | 10502 | 10517 | GAGTCATGGGCTGAGG | $G_{ks}A_{ks}G_{ds}T_{ds}{}^mC_{ds}A_{ds}T_{ds}G_{ds}G_{ds}G_{ds}{}^mC_{ds}T_{ks}G_{ds}A_{ks}G_{ds}G_k$ | 31 | 422 |
| 785690 | 1270 | 1285 | 10503 | 10518 | TGAGTCATGGGCTGAG | $T_{ks}G_{ks}A_{ds}G_{ds}T_{ds}{}^mC_{ds}A_{ds}T_{ds}G_{ds}G_{ds}G_{ds}{}^mC_{ks}T_{ds}G_{ks}A_{ds}G_k$ | 12 | 423 |
| 785714 | 384 | 399 | 4709 | 4724 | TTATCTCCGTCCTGGC | $T_{ks}T_{ks}A_{ds}T_{ds}{}^mC_{ds}T_{ds}{}^mC_{ds}{}^mC_{ds}G_{ds}T_{ds}{}^mC_{ds}{}^mC_{ks}T_{es}G_{ks}G_{es}{}^mC_k$ | 0 | 117 |
| 785715 | 385 | 400 | 4710 | 4725 | GTTATCTCCGTCCTGG | $G_{ks}T_{ds}T_{ds}A_{ds}T_{ds}{}^mC_{ds}T_{ds}{}^mC_{ds}{}^mC_{ds}G_{ds}T_{ds}{}^mC_{ks}{}^mC_{es}T_{ks}G_{es}G_k$ | 0 | 113 |
| 785720 | 484 | 499 | 8377 | 8392 | AAGGGCACAGCGCAGG | $A_{ks}A_{ks}G_{ds}G_{ds}G_{ds}{}^mC_{ds}A_{ds}{}^mC_{ds}A_{ds}G_{ds}{}^mC_{ds}G_{ks}{}^mC_{es}A_{ks}G_{es}G_k$ | 0 | 1249 |
| 785724 | 1269 | 1284 | 10502 | 10517 | GAGTCATGGGCTGAGG | $G_{ks}A_{ks}G_{ds}T_{ds}{}^mC_{ds}A_{ds}T_{ds}G_{ds}G_{ds}G_{ds}{}^mC_{ds}T_{ks}G_{es}A_{ks}G_{es}G_k$ | 15 | 422 |
| 785725 | 1270 | 1285 | 10503 | 10518 | TGAGTCATGGGCTGAG | $T_{ks}G_{ks}A_{ds}G_{ds}T_{ds}{}^mC_{ds}A_{ds}T_{ds}G_{ds}G_{ds}G_{ds}{}^mC_{ks}T_{es}G_{ks}A_{es}G_k$ | 0 | 423 |
| 785726 | 1271 | 1286 | 10504 | 10519 | ATGAGTCATGGGCTGA | $A_{ks}T_{ks}G_{ds}A_{ds}G_{ds}T_{ds}{}^mC_{ds}A_{ds}T_{ds}G_{ds}G_{ds}G_{ks}{}^mC_{es}T_{ks}G_{es}A_k$ | 0 | 424 |
| 785770 | 385 | 400 | 4710 | 4725 | GTTATCTCCGTTCCTGG | $G_{ks}T_{ks}T_{ks}A_{ds}T_{ds}{}^mC_{ds}T_{ds}{}^mC_{ds}{}^mC_{ds}G_{ds}T_{ds}{}^mC_{ks}{}^mC_{ds}T_{ks}G_{ds}G_k$ | 27 | 113 |
| 785773 | 484 | 499 | 8377 | 8392 | AAGGGCACAGCGCAGG | $A_{ks}A_{ks}G_{ks}G_{ds}G_{ds}{}^mC_{ds}A_{ds}{}^mC_{ds}A_{ds}G_{ds}{}^mC_{ds}G_{ks}{}^mC_{ds}A_{ks}G_{ds}G_k$ | 12 | 1249 |
| 785775 | 1270 | 1285 | 10503 | 10518 | TGAGTCATGGGCTGAG | $T_{ks}G_{ks}A_{ks}G_{ds}T_{ds}{}^mC_{ds}A_{ds}T_{ds}G_{ds}G_{ds}G_{ds}{}^mC_{ks}T_{ds}G_{ks}A_{ds}G_k$ | 3 | 423 |
| 785776 | 1271 | 1286 | 10504 | 10519 | ATGAGTCATGGGCTGA | $A_{ks}T_{ks}G_{ks}A_{ds}G_{ds}T_{ds}{}^mC_{ds}A_{ds}T_{ds}G_{ds}G_{ds}G_{ks}{}^mC_{ds}T_{ks}G_{ds}A_k$ | 0 | 424 |
| 785802 | 384 | 399 | 4709 | 4724 | TTATCTCCGTCCTGGC | $T_{ks}T_{ks}A_{ks}T_{ds}{}^mC_{ds}T_{ds}{}^mC_{ds}{}^mC_{ds}G_{ds}T_{ds}{}^mC_{ds}{}^mC_{ks}T_{es}G_{ks}G_{es}{}^mC_k$ | 0 | 117 |
| 785803 | 385 | 400 | 4710 | 4725 | GTTATCTCCGTTCCTGG | $G_{ks}T_{ks}T_{ks}A_{ds}T_{ds}{}^mC_{ds}T_{ds}{}^mC_{ds}{}^mC_{ds}G_{ds}T_{ds}{}^mC_{ks}{}^mC_{es}T_{ks}G_{es}G_k$ | 0 | 113 |
| 785808 | 484 | 499 | 8377 | 8392 | AAGGGCACAGCGCAGG | $A_{ks}A_{ks}G_{ks}G_{ds}G_{ds}{}^mC_{ds}A_{ds}{}^mC_{ds}A_{ds}G_{ds}{}^mC_{ds}G_{ks}{}^mC_{es}A_{ks}G_{es}G_k$ | 0 | 1249 |
| 785812 | 1269 | 1284 | 10502 | 10517 | GAGTCATGGGCTGAGG | $G_{ks}A_{ks}G_{ks}T_{ds}{}^mC_{ds}A_{ds}T_{ds}G_{ds}G_{ds}G_{ds}{}^mC_{ds}T_{ks}G_{es}A_{ks}G_{es}G_k$ | 0 | 422 |
| 785813 | 1270 | 1285 | 10503 | 10518 | TGAGTCATGGGCTGAG | $T_{ks}G_{ks}A_{ks}G_{ds}T_{ds}{}^mC_{ds}A_{ds}T_{ds}G_{ds}G_{ds}G_{ds}{}^mC_{ks}T_{es}G_{ks}A_{es}G_k$ | 0 | 423 |
| 785814 | 1271 | 1286 | 10504 | 10519 | ATGAGTCATGGGCTGA | $A_{ks}T_{ks}G_{ks}A_{ds}G_{ds}T_{ds}{}^mC_{ds}A_{ds}T_{ds}G_{ds}G_{ds}G_{ks}{}^mC_{es}T_{ks}G_{es}A_k$ | 0 | 424 |

TABLE 19-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785858 | 385 | 400 | 4710 | 4725 | GTTATCTCCGTTCCTGG | $G_{ks}T_{ks}T_{ks}A_{ds}T_{ds}{}^mC_{ds}T_{ds}{}^mC_{ds}{}^mC_{ds}G_{ds}G_{ds}T_{ds}{}^mC_{ds}{}^mC_{ks}T_{es}G_{ks}G_e$ | 0 | 113 |
| 785861 | 484 | 499 | 8377 | 8392 | AAGGGCACAGCGCAGG | $A_{ks}A_{ks}G_{ks}G_{ds}G_{ds}{}^mC_{ds}A_{ds}{}^mC_{ds}A_{ds}G_{ds}{}^mC_{ds}G_{ds}{}^mC_{ks}A_{es}G_{ks}G_e$ | 0 | 1249 |
| 785863 | 1270 | 1285 | 10503 | 10518 | TGAGTCATGGGCTGAG | $T_{ks}G_{ks}A_{ks}G_{ds}T_{ds}{}^mC_{ds}A_{ds}T_{ds}G_{ds}G_{ds}G_{ds}{}^mC_{ds}T_{ks}G_{es}A_{ks}G_e$ | 17 | 423 |
| 785864 | 1271 | 1286 | 10504 | 10519 | ATGAGTCATGGGCTGA | $A_{ks}T_{ks}G_{ks}A_{ds}G_{ds}T_{ds}{}^mC_{ds}A_{ds}T_{ds}G_{ds}G_{ds}G_{ds}{}^mC_{ks}T_{es}G_{ks}A_e$ | 9 | 424 |
| 785890 | 384 | 399 | 4709 | 4724 | TTATCTCCGTCCTGGC | $T_{ks}T_{ks}A_{ks}T_{ds}{}^mC_{ds}T_{ds}{}^mC_{ds}{}^mC_{ds}G_{ds}T_{ds}{}^mC_{ds}{}^mC_{ds}T_{ks}G_{ks}G_{ks}{}^mC_e$ | 0 | 117 |
| 785891 | 385 | 400 | 4710 | 4725 | GTTATCTCCGTCCTGG | $G_{ks}T_{ks}T_{ks}A_{ds}T_{ds}{}^mC_{ds}T_{ds}{}^mC_{ds}{}^mC_{ds}G_{ds}G_{ds}T_{ds}{}^mC_{ds}{}^mC_{ks}T_{ks}G_{ks}G_e$ | 33 | 113 |
| 785896 | 484 | 499 | 8377 | 8392 | AAGGGCACAGCGCAGG | $A_{ks}A_{ks}G_{ks}G_{ds}G_{ds}{}^mC_{ds}A_{ds}{}^mC_{ds}A_{ds}G_{ds}{}^mC_{ds}G_{ds}{}^mC_{ks}A_{es}G_{ks}G_e$ | 3 | 1249 |
| 785900 | 1269 | 1284 | 10502 | 10517 | GAGTCATGGGCTGAGG | $G_{ks}A_{ks}G_{ks}T_{ds}{}^mC_{ds}A_{ds}T_{ds}G_{ds}G_{ds}G_{ds}{}^mC_{ds}T_{ds}G_{ks}A_{ks}G_{ks}G_e$ | 0 | 422 |
| 785901 | 1270 | 1285 | 10503 | 10518 | TGAGTCATGGGCTGAG | $T_{ks}G_{ks}A_{ks}G_{ds}T_{ds}{}^mC_{ds}A_{ds}T_{ds}G_{ds}G_{ds}G_{ds}{}^mC_{ds}T_{ks}G_{ks}A_{ks}G_e$ | 11 | 423 |
| 785902 | 1271 | 1286 | 10504 | 10519 | ATGAGTCATGGGCTGA | $A_{ks}T_{ks}G_{ks}A_{ds}G_{ds}T_{ds}{}^mC_{ds}A_{ds}T_{ds}G_{ds}G_{ds}G_{ds}{}^mC_{ks}T_{ks}G_{ks}A_e$ | 20 | 424 |
| 785938 | N/A | N/A | 6548 | 6563 | CCAATTTTGCATTCCA | ${}^mC_{ks}{}^mC_{ks}A_{ks}A_{ds}T_{ds}T_{ds}T_{ds}T_{ds}G_{ds}{}^mC_{ds}A_{ds}T_{ds}T_{ks}{}^mC_{ks}{}^mC_{ks}A_e$ | 71 | 1242 |
| 786473 | 385 | 400 | 4710 | 4725 | GTTATCTCCGTCCTGG | $G_{ks}T_{ds}T_{ds}A_{ds}T_{ds}{}^mC_{ds}T_{ds}{}^mC_{ds}{}^mC_{ds}G_{ds}G_{ds}T_{ks}{}^mC_{es}{}^mC_{ks}T_{es}G_{ks}G_e$ | 0 | 113 |
| 786474 | 383 | 398 | 4708 | 4723 | TATCTCCGTCCTGGCT | $T_{ks}A_{ds}T_{ds}{}^mC_{ds}T_{ds}{}^mC_{ds}{}^mC_{ds}G_{ds}T_{ds}{}^mC_{ds}{}^mC_{ks}T_{es}G_{es}{}^mC_{ks}T_e$ | 0 | 116 |
| 786495 | 483 | 498 | 8376 | 8391 | AGGGCACAGCGCAGGT | $A_{ks}G_{ks}G_{ks}G_{ds}{}^mC_{ds}A_{ds}{}^mC_{ds}A_{ds}G_{ds}{}^mC_{ds}G_{ds}{}^mC_{ds}A_{ds}G_{ks}G_{ks}T_k$ | 2 | 1251 |
| 786496 | 485 | 500 | 8378 | 8393 | TAAGGGCACAGCGCAG | $T_{ks}A_{ks}A_{ks}G_{ds}G_{ds}G_{ds}{}^mC_{ds}A_{ds}{}^mC_{ds}A_{ds}G_{ds}{}^mC_{ds}G_{ds}{}^mC_{ks}A_{ks}G_k$ | 0 | 1252 |
| 786497 | 486 | 501 | 8379 | 8394 | TTAAGGGCACAGCGCA | $T_{ks}T_{ks}A_{ks}A_{ds}G_{ds}G_{ds}G_{ds}{}^mC_{ds}A_{ds}{}^mC_{ds}A_{ds}G_{ds}{}^mC_{ds}G_{ks}{}^mC_{ks}A_k$ | 0 | 1253 |

TABLE 20

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 665892 | 1227 | 1242 | 10460 | 10475 | CACTGACACAGGCGGA | $^mC_{ks}A_{ks}{}^mC_{ks}T_{ds}G_{ds}A_{ds}$ $^mC_{ds}A_{ds}{}^mC_{ds}A_{ds}G_{ds}$ $^mC_{ds}G_{ks}G_{ks}A_k$ | 1 | 387 |
| 665893 | 1228 | 1243 | 10461 | 10476 | GCACTGACACAGGCGG | $G_{ks}{}^mC_{ks}A_{ks}{}^mC_{ds}T_{ds}G_{ds}$ $A_{ds}{}^mC_{ds}A_{ds}{}^mC_{ds}A_{ds}G_{ds}$ $G_{ds}{}^mC_{ks}G_{ks}G_k$ | 14 | 39 |
| 728466 | 427 | 442 | 8320 | 8335 | GGTGTATTTCCCTGTC | $G_{ks}G_{ks}T_{ds}G_{ds}T_{ds}A_{ds}T_{ds}$ $T_{ds}T_{ds}{}^mC_{ds}{}^mC_{ds}{}^mC_{ds}T$ $_{ds}G_{ks}T_{ks}{}^mC_k$ | 10 | 1254 |
| 728489 | 484 | 499 | 8377 | 8392 | AAGGGCACAGCGCAGG | $A_{ks}A_{ks}G_{ks}G_{ds}G_{ds}{}^mC_{ds}$ $A_{ds}{}^mC_{ds}A_{ds}G_{ds}{}^mC_{ds}G_{ds}$ $^mC_{ds}A_{ks}G_{ks}G_k$ | 48 | 1249 |
| 728670 | 1230 | 1245 | 10463 | 10478 | TTGCACTGACACAGGC | $T_{ks}T_{ks}G_{ks}{}^mC_{ds}A_{ds}{}^mC_{ds}$ $T_{ds}G_{ds}A_{ds}{}^mC_{ds}A_{ds}{}^mC_{ds}$ $A_{ds}G_{ks}G_{ks}{}^mC_k$ | 18 | 398 |
| 728705 | 1303 | 1318 | 10536 | 10551 | GGTCTTGACCTCCCGC | $G_{ks}G_{ks}T_{ks}{}^mC_{ds}T_{ds}T_{ds}$ $G_{ds}A_{ds}{}^mC_{ds}{}^mC_{ds}T_{ds}{}^mC_{ds}$ $^mC_{ds}{}^mC_{ks}G_{ks}{}^mC_k$ | 33 | 433 |
| 728706 | 1306 | 1321 | 10539 | 10554 | CTTGGTCTTGACCTCC | $^mC_{ks}T_{ks}T_{ks}G_{ds}G_{ds}T_{ds}{}^m$ $C_{ds}T_{ds}T_{ds}G_{ds}A_{ds}{}^mC_{ds}{}^m$ $C_{ds}T_{ks}{}^mC_{ks}{}^mC_k$ | 41 | 434 |
| 728707 | 1307 | 1322 | 10540 | 10555 | GCTTGGTCTTGACCTC | $G_{ks}{}^mC_{ks}T_{ks}T_{ds}G_{ds}G_{ds}$ $T_{ds}{}^mC_{ds}T_{ds}T_{ds}G_{ds}A_{ds}{}^m$ $C_{ds}{}^mC_{ks}T_{ks}{}^mC_k$ | 43 | 435 |
| 728708 | 1308 | 1323 | 10541 | 10556 | AGCTTGGTCTTGACCT | $A_{ks}G_{ks}{}^mC_{ks}T_{ds}T_{ds}G_{ds}$ $G_{ds}T_{ds}{}^mC_{ds}T_{ds}T_{ds}G_{ds}$ $A_{ds}{}^mC_{ks}{}^mC_{ks}T_k$ | 14 | 436 |
| 729037 | 2216 | 2231 | 11781 | 11796 | GGTTCTTGGACTCTCA | $G_{ks}G_{ks}T_{ks}T_{ds}{}^mC_{ds}T_{ds}$ $T_{ds}G_{ds}G_{ds}A_{ds}{}^mC_{ds}T_{ds}{}^m$ $C_{ds}T_{ks}{}^mC_{ks}A_k$ | 68 | 706 |
| 785354 | 1228 | 1243 | 10461 | 10476 | GCACTGACACAGGCGG | $G_{ks}{}^mC_{ds}A_{ds}{}^mC_{ds}T_{ds}G_{ds}$ $A_{ds}{}^mC_{ds}A_{ds}{}^mC_{ds}A_{ds}G_{ks}$ $G_{es}{}^mC_{ks}G_{es}G_k$ | 0 | 39 |
| 785359 | 1301 | 1316 | 10534 | 10549 | TCTTGACCTCCCGCTG | $T_{ks}{}^mC_{ds}T_{ds}T_{ds}G_{ds}A_{ds}{}^m$ $C_{ds}{}^mC_{ds}T_{ds}{}^mC_{ds}{}^mC_{ds}{}^m$ $C_{ks}G_{es}{}^mC_{ks}T_{es}G_k$ | 46 | 391 |
| 785360 | 1303 | 1318 | 10536 | 10551 | GGTCTTGACCTCCCGC | $G_{ks}G_{ds}T_{ds}{}^mC_{ds}T_{ds}T_{ds}$ $G_{ds}A_{ds}{}^mC_{ds}{}^mC_{ds}T_{ds}{}^mC_{ks}$ $^mC_{es}{}^mC_{ks}G_{es}{}^mC_k$ | 37 | 433 |
| 785361 | 1306 | 1321 | 10539 | 10554 | CTTGGTCTTGACCTCC | $^mC_{ks}T_{ds}T_{ds}G_{ds}G_{ds}T_{ds}{}^m$ $C_{ds}T_{ds}T_{ds}G_{ds}A_{ds}{}^mC_{ks}{}^m$ $C_{es}T_{ks}{}^mC_{es}{}^mC_k$ | 0 | 434 |
| 785362 | 1307 | 1322 | 10540 | 10555 | GCTTGGTCTTGACCTC | $G_{ks}{}^mC_{ds}T_{ds}T_{ds}G_{ds}G_{ds}$ $T_{ds}{}^mC_{ds}T_{ds}T_{ds}G_{ds}A_{ks}{}^m$ $C_{es}{}^mC_{ks}T_{es}{}^mC_k$ | 18 | 435 |
| 785363 | 1308 | 1323 | 10541 | 10556 | AGCTTGGTCTTGACCT | $A_{ks}G_{ds}{}^mC_{ds}T_{ds}T_{ds}G_{ds}$ $G_{ds}T_{ds}{}^mC_{ds}T_{ds}T_{ds}G_{ks}$ $A_{es}{}^mC_{ks}{}^mC_{es}T_k$ | 0 | 436 |
| 785409 | 1228 | 1243 | 10461 | 10476 | GCACTGACACAGGCGG | $G_{ks}{}^mC_{ds}A_{ds}{}^mC_{ds}T_{ds}G_{ds}$ $A_{ds}{}^mC_{ds}A_{ds}{}^mC_{ds}A_{ks}G_{es}$ $G_{ks}{}^mC_{es}G_{ks}G_e$ | 0 | 39 |
| 785414 | 1301 | 1316 | 10534 | 10549 | TCTTGACCTCCCGCTG | $T_{ks}{}^mC_{ds}T_{ds}T_{ds}G_{ds}A_{ds}{}^m$ $C_{ds}{}^mC_{ds}T_{ds}{}^mC_{ds}{}^mC_{ks}$ $C_{es}G_{ks}{}^mC_{es}T_{ks}G_e$ | 40 | 391 |

TABLE 20-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785415 | 1303 | 1318 | 10536 | 10551 | GGTCTTGACCTCCCGC | $G_{ks}G_{ds}T_{ds}{}^mC_{ds}T_{ds}T_{ds}G_{ds}A_{ds}{}^mC_{ds}{}^mC_{ds}T_{ks}{}^mC_{es}{}^mC_{ks}{}^mC_{es}G_{ks}{}^mC_{e}$ | 35 | 433 |
| 785416 | 1306 | 1321 | 10539 | 10554 | CTTGGTCTTGACCTCC | ${}^mC_{ks}T_{ds}T_{ds}G_{ds}G_{ds}T_{ds}{}^mC_{ds}T_{ds}T_{ds}G_{ds}A_{ks}{}^mC_{es}{}^mC_{ks}T_{es}{}^mC_{ks}{}^mC_{e}$ | 0 | 434 |
| 785417 | 1307 | 1322 | 10540 | 10555 | GCTTGGTCTTGACCTC | $G_{ks}{}^mC_{ds}T_{ds}T_{ds}G_{ds}G_{ds}T_{ds}{}^mC_{ds}T_{ds}T_{ds}G_{ks}A_{es}{}^mC_{ks}{}^mC_{es}T_{ks}{}^mC_{e}$ | 17 | 435 |
| 785418 | 1308 | 1323 | 10541 | 10556 | AGCTTGGTCTTGACCT | $A_{ks}G_{ds}{}^mC_{ds}T_{ds}T_{ds}G_{ds}G_{ds}T_{ds}{}^mC_{ds}T_{ds}T_{ks}G_{es}A_{ks}{}^mC_{es}{}^mC_{ks}T_{e}$ | 14 | 436 |
| 785464 | 1303 | 1318 | 10536 | 10551 | GGTCTTGACCTCCCGC | $G_{ks}G_{es}T_{ks}{}^mC_{ds}T_{ds}T_{ds}G_{ds}A_{ds}{}^mC_{ds}{}^mC_{ds}T_{ds}{}^mC_{ds}{}^mC_{es}{}^mC_{es}G_{ks}{}^mC_{k}$ | 33 | 433 |
| 785465 | 1306 | 1321 | 10539 | 10554 | CTTGGTCTTGACCTCC | ${}^mC_{ks}T_{es}T_{ks}G_{ds}G_{ds}T_{ds}{}^mC_{ds}T_{ds}T_{ds}G_{ds}A_{ds}{}^mC_{ds}{}^mC_{es}T_{es}{}^mC_{ks}{}^mC_{k}$ | 36 | 434 |
| 785466 | 1307 | 1322 | 10540 | 10555 | GCTTGGTCTTGACCTC | $G_{ks}{}^mC_{es}T_{ks}T_{ds}G_{ds}G_{ds}T_{ds}{}^mC_{ds}T_{ds}T_{ds}G_{ds}A_{ds}{}^mC_{es}{}^mC_{es}T_{ks}{}^mC_{k}$ | 46 | 435 |
| 785467 | 1308 | 1323 | 10541 | 10556 | AGCTTGGTCTTGACCT | $A_{ks}G_{es}{}^mC_{ks}T_{ds}T_{ds}G_{ds}G_{ds}T_{ds}{}^mC_{ds}T_{ds}T_{ds}G_{ds}A_{es}{}^mC_{es}{}^mC_{ks}T_{k}$ | 38 | 436 |
| 785498 | 1229 | 1244 | 10462 | 10477 | TGCACTGACACAGGCG | $T_{ks}G_{ks}{}^mC_{ds}A_{ds}{}^mC_{ds}T_{ds}G_{ds}A_{ds}{}^mC_{ds}A_{ds}{}^mC_{ds}A_{ds}G_{ks}G_{es}{}^mC_{ks}G_{e}$ | 16 | 388 |
| 785502 | 1302 | 1317 | 10535 | 10550 | GTCTTGACCTCCCGCT | $G_{ks}T_{ks}{}^mC_{ds}T_{ds}T_{ds}G_{ds}A_{ds}{}^mC_{ds}{}^mC_{ds}T_{ds}{}^mC_{ds}{}^mC_{ds}{}^mC_{ks}G_{es}{}^mC_{ks}T_{e}$ | 65 | 432 |
| 785503 | 1303 | 1318 | 10536 | 10551 | GGTCTTGACCTCCCGC | $G_{ks}G_{ks}T_{ds}{}^mC_{ds}T_{ds}T_{ds}G_{ds}A_{ds}{}^mC_{ds}{}^mC_{ds}T_{ds}{}^mC_{ds}{}^mC_{ks}{}^mC_{es}G_{ks}{}^mC_{e}$ | 0 | 433 |
| 785504 | 1306 | 1321 | 10539 | 10554 | CTTGGTCTTGACCTCC | ${}^mC_{ks}T_{ks}T_{ds}G_{ds}G_{ds}T_{ds}{}^mC_{ds}T_{ds}T_{ds}G_{ds}A_{ds}{}^mC_{ds}{}^mC_{ks}T_{es}{}^mC_{ks}{}^mC_{e}$ | 39 | 434 |
| 785505 | 1307 | 1322 | 10540 | 10555 | GCTTGGTCTTGACCTC | $G_{ks}{}^mC_{ds}T_{ds}T_{ds}G_{ds}G_{ds}T_{ds}{}^mC_{ds}T_{ds}T_{ds}G_{ds}A_{ds}{}^mC_{ks}{}^mC_{es}T_{ks}{}^mC_{e}$ | 9 | 435 |
| 785506 | 1308 | 1323 | 10541 | 10556 | AGCTTGGTCTTGACCT | $A_{ks}G_{ks}{}^mC_{ds}T_{ds}T_{ds}G_{ds}G_{ds}T_{ds}{}^mC_{ds}T_{ds}T_{ds}G_{ds}A_{ks}{}^mC_{es}{}^mC_{ks}T_{e}$ | 0 | 436 |
| 785549 | 1229 | 1244 | 10462 | 10477 | TGCACTGACACAGGCG | $T_{ks}G_{ks}{}^mC_{ds}A_{ds}{}^mC_{ds}T_{ds}G_{ds}A_{ds}{}^mC_{ds}A_{ds}{}^mC_{es}A_{es}G_{es}G_{es}{}^mC_{ks}G_{k}$ | 0 | 388 |
| 785552 | 1302 | 1317 | 10535 | 10550 | GTCTTGACCTCCCGCT | $G_{ks}T_{ks}{}^mC_{ds}T_{ds}T_{ds}G_{ds}A_{ds}{}^mC_{ds}{}^mC_{ds}T_{ds}{}^mC_{es}{}^mC_{es}{}^mC_{es}G_{es}{}^mC_{ks}T_{k}$ | 34 | 432 |
| 785553 | 1306 | 1321 | 10539 | 10554 | CTTGGTCTTGACCTCC | ${}^mC_{ks}T_{ks}T_{ds}G_{ds}G_{ds}T_{ds}{}^mC_{ds}T_{ds}T_{ds}G_{ds}A_{es}{}^mC_{es}{}^mC_{es}T_{es}{}^mC_{ks}{}^mC_{k}$ | 20 | 434 |
| 785554 | 1307 | 1322 | 10540 | 10555 | GCTTGGTCTTGACCTC | $G_{ks}{}^mC_{ks}T_{ds}T_{ds}G_{ds}G_{ds}T_{ds}{}^mC_{ds}T_{ds}T_{ds}G_{es}A_{es}{}^mC_{es}{}^mC_{es}T_{ks}{}^mC_{k}$ | 19 | 435 |

TABLE 20-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785588 | 1228 | 1243 | 10461 | 10476 | GCACTGACACAGGCGG | $G_{ks}{}^mC_{ds}A_{ds}{}^mC_{ds}T_{ds}G_{ds}A_{ds}{}^mC_{ds}A_{ds}{}^mC_{ds}A_{ks}G_{es}G_{ks}{}^mC_{es}G_{ks}G_k$ | 0 | 39 |
| 785589 | 1229 | 1244 | 10462 | 10477 | TGCACTGACACAGGCG | $T_{ks}G_{ks}{}^mC_{ds}A_{ds}{}^mC_{ds}T_{ds}G_{ds}A_{ds}{}^mC_{ds}A_{ds}{}^mC_{ks}A_{es}G_{ks}G_{es}{}^mC_{ks}G_k$ | 0 | 388 |
| 785594 | 1301 | 1316 | 10534 | 10549 | TCTTGACCTCCCGCTG | $T_{ks}{}^mC_{ks}T_{ds}T_{ds}G_{ds}A_{ds}{}^mC_{ds}{}^mC_{ds}T_{ds}{}^mC_{ds}{}^mC_{ks}{}^mC_{es}G_{ks}{}^mC_{es}T_{ks}G_k$ | 19 | 391 |
| 785595 | 1302 | 1317 | 10535 | 10550 | GTCTTGACCTCCCGCT | $G_{ks}T_{ks}{}^mC_{ds}T_{ds}T_{ds}G_{ds}A_{ds}{}^mC_{ds}{}^mC_{ds}T_{ds}{}^mC_{ks}{}^mC_{es}{}^mC_{ks}G_{es}{}^mC_{ks}T_k$ | 26 | 432 |
| 785596 | 1303 | 1318 | 10536 | 10551 | GGTCTTGACCTCCCGC | $G_{ks}G_{ks}T_{ds}{}^mC_{ds}T_{ds}T_{ds}G_{ds}A_{ds}{}^mC_{ds}{}^mC_{ds}T_{ks}{}^mC_{es}{}^mC_{ks}{}^mC_{es}G_{ks}{}^mC_k$ | 44 | 433 |
| 785597 | 1306 | 1321 | 10539 | 10554 | CTTGGTCTTGACCTCC | ${}^mC_{ks}T_{ks}T_{ds}G_{ds}G_{ds}T_{ds}{}^mC_{ds}T_{ds}T_{ds}G_{ds}A_{ks}{}^mC_{es}{}^mC_{ks}T_{es}{}^mC_{ks}{}^mC_k$ | 0 | 434 |
| 785598 | 1307 | 1322 | 10540 | 10555 | GCTTGGTCTTGACCTC | $G_{ks}{}^mC_{ks}T_{ds}T_{ds}G_{ds}G_{ds}T_{ds}{}^mC_{ds}T_{ds}T_{ds}G_{ks}A_{es}{}^mC_{ks}{}^mC_{es}T_{ks}{}^mC_k$ | 21 | 435 |
| 785599 | 1308 | 1323 | 10541 | 10556 | AGCTTGGTCTTGACCT | $A_{ks}G_{ks}{}^mC_{ds}T_{ds}T_{ds}G_{ds}G_{ds}T_{ds}{}^mC_{ds}T_{ds}T_{ks}G_{es}A_{ks}{}^mC_{es}{}^mC_{ks}T_k$ | 0 | 436 |
| 785658 | 1229 | 1244 | 10462 | 10477 | TGCACTGACACAGGCG | $T_{ks}G_{ks}{}^mC_{ds}A_{ds}{}^mC_{ds}T_{ds}G_{ds}A_{ds}{}^mC_{ds}A_{ds}{}^mC_{ds}A_{es}G_{es}G_{es}{}^mC_{ks}G_k$ | 18 | 388 |
| 785661 | 1302 | 1317 | 10535 | 10550 | GTCTTGACCTCCCGCT | $G_{ks}T_{ks}{}^mC_{ds}T_{ds}T_{ds}G_{ds}A_{ds}{}^mC_{ds}{}^mC_{ds}T_{ds}{}^mC_{ds}{}^mC_{es}{}^mC_{es}G_{es}{}^mC_{ks}T_k$ | 54 | 432 |
| 785662 | 1306 | 1321 | 10539 | 10554 | CTTGGTCTTGACCTCC | ${}^mC_{ks}T_{ks}T_{ds}G_{ds}G_{ds}T_{ds}{}^mC_{ds}T_{ds}T_{ds}G_{ds}A_{ds}{}^mC_{es}{}^mC_{es}T_{es}{}^mC_{ks}{}^mC_k$ | 11 | 434 |
| 785663 | 1307 | 1322 | 10540 | 10555 | GCTTGGTCTTGACCTC | $G_{ks}{}^mC_{ks}T_{ds}T_{ds}G_{ds}G_{ds}T_{ds}{}^mC_{ds}T_{ds}T_{ds}G_{ds}A_{es}{}^mC_{es}{}^mC_{es}T_{ks}{}^mC_k$ | 10 | 435 |
| 785688 | 1229 | 1244 | 10462 | 10477 | TGCACTGACACAGGCG | $T_{ks}G_{ks}{}^mC_{ds}A_{ds}{}^mC_{ds}T_{ds}G_{ds}A_{ds}{}^mC_{ds}A_{ds}{}^mC_{ds}A_{ks}G_{ds}G_{ks}{}^mC_{ds}G_k$ | 0 | 388 |
| 785691 | 1302 | 1317 | 10535 | 10550 | GTCTTGACCTCCCGCT | $G_{ks}T_{ks}{}^mC_{ds}T_{ds}T_{ds}G_{ds}A_{ds}{}^mC_{ds}{}^mC_{ds}T_{ds}{}^mC_{ds}{}^mC_{ks}{}^mC_{ds}G_{ks}{}^mC_{ds}T_k$ | 46 | 432 |
| 785692 | 1306 | 1321 | 10539 | 10554 | CTTGGTCTTGACCTCC | ${}^mC_{ks}T_{ks}T_{ds}G_{ds}G_{ds}T_{ds}{}^mC_{ds}T_{ds}T_{ds}G_{ds}A_{ds}{}^mC_{ks}{}^mC_{ds}T_{ds}{}^mC_{ds}{}^mC_k$ | 13 | 434 |
| 785693 | 1307 | 1322 | 10540 | 10555 | GCTTGGTCTTGACCTC | $G_{ks}{}^mC_{ks}T_{ds}T_{ds}G_{ds}G_{ds}T_{ds}{}^mC_{ds}T_{ds}T_{ds}G_{ds}A_{ks}{}^mC_{ds}{}^mC_{ks}T_{ds}{}^mC_k$ | 11 | 435 |
| 785723 | 1229 | 1244 | 10462 | 10477 | TGCACTGACACAGGCG | $T_{ks}G_{ks}{}^mC_{ds}A_{ds}{}^mC_{ds}T_{ds}G_{ds}A_{ds}{}^mC_{ds}A_{ds}{}^mC_{ds}A_{ks}G_{es}G_{ks}{}^mC_{es}G_k$ | 0 | 388 |
| 785727 | 1302 | 1317 | 10535 | 10550 | GTCTTGACCTCCCGCT | $G_{ks}T_{ks}{}^mC_{ds}T_{ds}T_{ds}G_{ds}A_{ds}{}^mC_{ds}{}^mC_{ds}T_{ds}{}^mC_{ds}{}^mC_{ks}{}^mC_{es}G_{ks}{}^mC_{es}T_k$ | 40 | 432 |

TABLE 20-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785728 | 1303 | 1318 | 10536 | 10551 | GGTCTTGACCTCCCGC | $G_{ks}G_{ks}T_{ks}{}^mC_{ds}T_{ds}T_{ds}G_{ds}A_{ds}{}^mC_{ds}{}^mC_{ds}T_{ds}{}^mC_{ks}{}^mC_{es}{}^mC_{ks}G_{es}{}^mC_k$ | 7 | 433 |
| 785729 | 1306 | 1321 | 10539 | 10554 | CTTGGTCTTGACCTCC | ${}^mC_{ks}T_{ks}T_{ds}G_{ds}G_{ds}T_{ds}{}^mC_{ds}T_{ds}T_{ds}G_{ds}A_{ds}{}^mC_{ks}{}^mC_{es}T_{ks}{}^mC_{es}{}^mC_k$ | 3 | 434 |
| 785730 | 1307 | 1322 | 10540 | 10555 | GCTTGGTCTTGACCTC | $G_{ks}{}^mC_{ks}T_{ds}T_{ds}G_{ds}G_{ds}T_{ds}{}^mC_{ds}T_{ds}T_{ds}G_{ds}A_{ks}{}^mC_{es}{}^mC_{ks}T_{es}{}^mC_k$ | 33 | 435 |
| 785731 | 1308 | 1323 | 10541 | 10556 | AGCTTGGTCTTGACCT | $A_{ks}G_{ks}{}^mC_{ds}T_{ds}T_{ds}G_{ds}G_{ds}T_{ds}{}^mC_{ds}T_{ds}T_{ds}G_{ks}A_{es}{}^mC_{ks}{}^mC_{es}T_k$ | 8 | 436 |
| 785777 | 1303 | 1318 | 10536 | 10551 | GGTCTTGACCTCCCGC | $G_{ks}G_{ks}T_{ks}{}^mC_{ds}T_{ds}T_{ds}G_{ds}A_{ds}{}^mC_{ds}{}^mC_{ds}T_{ds}{}^mC_{ks}{}^mC_{ds}{}^mC_{ks}G_{ds}{}^mC_k$ | 4 | 433 |
| 785778 | 1306 | 1321 | 10539 | 10554 | CTTGGTCTTGACCTCC | ${}^mC_{ks}T_{ks}T_{ks}G_{ds}G_{ds}T_{ds}{}^mC_{ds}T_{ds}T_{ds}G_{ds}A_{ds}{}^mC_{ks}{}^mC_{ds}T_{ks}{}^mC_{ds}{}^mC_k$ | 19 | 434 |
| 785779 | 1307 | 1322 | 10540 | 10555 | GCTTGGTCTTGACCTC | $G_{ks}{}^mC_{ks}T_{ks}T_{ds}G_{ds}G_{ds}T_{ds}{}^mC_{ds}T_{ds}T_{ds}G_{ds}A_{ks}{}^mC_{ds}{}^mC_{ks}T_{ds}{}^mC_k$ | 30 | 435 |
| 785780 | 1308 | 1323 | 10541 | 10556 | AGCTTGGTCTTGACCT | $A_{ks}G_{ks}{}^mC_{ks}T_{ds}T_{ds}G_{ds}G_{ds}T_{ds}{}^mC_{ds}T_{ds}T_{ds}G_{ks}A_{ds}{}^mC_{ks}{}^mC_{ds}T_k$ | 12 | 436 |
| 785811 | 1229 | 1244 | 10462 | 10477 | TGCACTGACACAGGCG | $T_{ks}G_{ks}{}^mC_{ks}A_{ds}{}^mC_{ds}T_{ds}G_{ds}A_{ds}{}^mC_{ds}A_{ds}{}^mC_{ds}A_{ks}G_{es}G_{ks}{}^mC_{es}G_k$ | 0 | 388 |
| 785815 | 1302 | 1317 | 10535 | 10550 | GTCTTGACCTCCCGCT | $G_{ks}T_{ks}{}^mC_{ks}T_{ds}T_{ds}G_{ds}A_{ds}{}^mC_{ds}{}^mC_{ds}T_{ds}{}^mC_{ds}{}^mC_{ks}{}^mC_{es}G_{ks}{}^mC_{es}T_k$ | 23 | 432 |
| 785816 | 1303 | 1318 | 10536 | 10551 | GGTCTTGACCTCCCGC | $G_{ks}G_{ks}T_{ks}{}^mC_{ds}T_{ds}T_{ds}G_{ds}A_{ds}{}^mC_{ds}{}^mC_{ds}T_{ds}{}^mC_{ks}{}^mC_{es}{}^mC_{ks}G_{es}{}^mC_k$ | 29 | 433 |
| 785817 | 1306 | 1321 | 10539 | 10554 | CTTGGTCTTGACCTCC | ${}^mC_{ks}T_{ks}T_{ks}G_{ds}G_{ds}T_{ds}{}^mC_{ds}T_{ds}T_{ds}G_{ds}A_{ds}{}^mC_{ks}{}^mC_{es}T_{ks}{}^mC_{es}{}^mC_k$ | 1 | 434 |
| 785818 | 1307 | 1322 | 10540 | 10555 | GCTTGGTCTTGACCTC | $G_{ks}{}^mC_{ks}T_{ks}T_{ds}G_{ds}G_{ds}T_{ds}{}^mC_{ds}T_{ds}T_{ds}G_{ds}A_{ks}{}^mC_{es}{}^mC_{ks}T_{es}{}^mC_k$ | 0 | 435 |
| 785819 | 1308 | 1323 | 10541 | 10556 | AGCTTGGTCTTGACCT | $A_{ks}G_{ks}{}^mC_{ks}T_{ds}T_{ds}G_{ds}G_{ds}T_{ds}{}^mC_{ds}T_{ds}T_{ds}G_{ks}A_{es}{}^mC_{ks}{}^mC_{es}T_k$ | 3 | 436 |
| 785865 | 1303 | 1318 | 10536 | 10551 | GGTCTTGACCTCCCGC | $G_{ks}G_{ks}T_{ks}{}^mC_{ds}T_{ds}T_{ds}G_{ds}A_{ds}{}^mC_{ds}{}^mC_{ds}T_{ds}{}^mC_{ds}{}^mC_{ks}{}^mC_{es}G_{ks}{}^mC_e$ | 7 | 433 |
| 785866 | 1306 | 1321 | 10539 | 10554 | CTTGGTCTTGACCTCC | ${}^mC_{ks}T_{ks}T_{ks}G_{ds}G_{ds}T_{ds}{}^mC_{ds}T_{ds}T_{ds}G_{ds}A_{ds}{}^mC_{ds}{}^mC_{ks}T_{es}{}^mC_{ks}{}^mC_e$ | 15 | 434 |
| 785867 | 1307 | 1322 | 10540 | 10555 | GCTTGGTCTTGACCTC | $G_{ks}{}^mC_{ks}T_{ks}T_{ds}G_{ds}G_{ds}T_{ds}{}^mC_{ds}T_{ds}T_{ds}G_{ds}A_{ds}{}^mC_{ks}{}^mC_{es}T_{ks}{}^mC_e$ | 35 | 435 |
| 785868 | 1308 | 1323 | 10541 | 10556 | AGCTTGGTCTTGACCT | $A_{ks}G_{ks}{}^mC_{ks}T_{ds}T_{ds}G_{ds}G_{ds}T_{ds}{}^mC_{ds}T_{ds}T_{ds}G_{ds}A_{ks}{}^mC_{es}{}^mC_{ks}T_e$ | 26 | 436 |

TABLE 20-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785899 | 1229 | 1244 | 10462 | 10477 | TGCACTGACACAGGCG | $T_{ks}G_{ks}{}^mC_{ks}A_{ds}{}^mC_{ds}T_{ds}G_{ds}A_{ds}{}^mC_{ds}A_{ds}{}^mC_{ds}A_{ds}G_{ks}G_{ks}{}^mC_{ks}G_e$ | 0 | 388 |
| 785903 | 1302 | 1317 | 10535 | 10550 | GTCTTGACCTCCCGCT | $G_{ks}{}^mT_{ks}{}^mC_{ks}T_{ds}T_{ds}G_{ds}A_{ds}{}^mC_{ds}{}^mC_{ds}T_{ds}{}^mC_{ds}{}^mC_{ds}{}^mC_{ks}G_{ks}{}^mC_{ks}T_e$ | 51 | 432 |
| 785904 | 1303 | 1318 | 10536 | 10551 | GGTCTTGACCTCCCGC | $G_{ks}G_{ks}T_{ks}{}^mC_{ds}T_{ds}T_{ds}G_{ds}A_{ds}{}^mC_{ds}{}^mC_{ds}T_{ds}{}^mC_{ds}{}^mC_{ks}{}^mC_{ks}G_{ks}{}^mC_e$ | 22 | 433 |
| 785905 | 1306 | 1321 | 10539 | 10554 | CTTGGTCTTGACCTCC | ${}^mC_{ks}T_{ks}T_{ks}G_{ds}G_{ds}T_{ds}{}^mC_{ds}T_{ds}T_{ds}G_{ds}A_{ds}{}^mC_{ds}{}^mC_{ks}T_{ks}{}^mC_{ks}{}^mC_e$ | 6 | 434 |
| 785906 | 1307 | 1322 | 10540 | 10555 | GCTTGGTCTTGACCTC | $G_{ks}{}^mC_{ks}T_{ks}T_{ds}G_{ds}G_{ds}T_{ds}{}^mC_{ds}T_{ds}T_{ds}G_{ds}A_{ds}{}^mC_{ks}{}^mC_{ks}T_{ks}{}^mC_e$ | 29 | 435 |
| 785907 | 1308 | 1323 | 10541 | 10556 | AGCTTGGTCTTGACCT | $A_{ks}G_{ks}{}^mC_{ks}T_{ds}T_{ds}G_{ds}G_{ds}T_{ds}{}^mC_{ds}T_{ds}T_{ds}G_{ds}A_{ks}{}^mC_{ks}{}^mC_{ks}T_e$ | 10 | 436 |
| 785938 | N/A | N/A | 6548 | 6563 | CCAATTTTGCATTCCA | ${}^mC_{ks}{}^mC_{ks}A_{ks}A_{ds}T_{ds}T_{ds}T_{ds}T_{ds}G_{ds}{}^mC_{ds}A_{ds}T_{ds}T_{ks}{}^mC_{ks}{}^mC_{ks}A_e$ | 30 | 1242 |

TABLE 21

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 665908 | 1363 | 1378 | 10684 | 10699 | GGTCTGGCCCTTTTGG | $G_{ks}G_{ks}T_{ks}{}^mC_{ds}T_{ds}G_{ds}G_{ds}{}^mC_{ds}{}^mC_{ds}{}^mC_{ds}T_{ds}T_{ds}T_{ds}T_{ks}G_{ks}G_k$ | 16 | 393 |
| 728466 | 427 | 442 | 8320 | 8335 | GGTGTATTTCCCTGTC | $G_{ks}G_{ks}T_{ks}G_{ds}T_{ds}A_{ds}T_{ds}T_{ds}T_{ds}{}^mC_{ds}{}^mC_{ds}{}^mC_{ds}T_{ds}G_{ks}T_{ks}{}^mC_k$ | 50 | 1254 |
| 728670 | 1230 | 1245 | 10463 | 10478 | TTGCACTGACACAGGC | $T_{ks}T_{ks}G_{ks}{}^mC_{ds}A_{ds}{}^mC_{ds}T_{ds}G_{ds}A_{ds}{}^mC_{ds}A_{ds}{}^mC_{ds}A_{ds}G_{ks}G_{ks}{}^mC_k$ | 8 | 398 |
| 728707 | 1307 | 1322 | 10540 | 10555 | GCTTGGTCTTGACCTC | $G_{ks}{}^mC_{ks}T_{ks}T_{ds}G_{ds}G_{ds}T_{ds}{}^mC_{ds}T_{ds}T_{ds}G_{ds}A_{ds}{}^mC_{ds}{}^mC_{ks}T_{ks}{}^mC_k$ | 0 | 435 |
| 728708 | 1308 | 1323 | 10541 | 10556 | AGCTTGGTCTTGACCT | $A_{ks}G_{ks}{}^mC_{ks}T_{ds}T_{ds}G_{ds}G_{ds}T_{ds}{}^mC_{ds}T_{ds}T_{ds}G_{ds}A_{ks}{}^mC_{ks}{}^mC_{ks}T_k$ | 16 | 436 |
| 729037 | 2216 | 2231 | 11781 | 11796 | GGTTCTTGGACTCTCA | $G_{ks}G_{ks}T_{ks}T_{ds}{}^mC_{ds}T_{ds}T_{ds}G_{ds}G_{ds}A_{ds}{}^mC_{ds}T_{ds}{}^mC_{ds}T_{ks}{}^mC_{ks}A_k$ | 0 | 706 |
| 729038 | 2217 | 2232 | 11782 | 11797 | AGGTTCTTGGACTCTC | $A_{ks}G_{ks}G_{ks}T_{ds}T_{ds}{}^mC_{ds}T_{ds}T_{ds}G_{ds}G_{ds}A_{ds}{}^mC_{ds}T_{ds}{}^mC_{ks}T_{ks}{}^mC_k$ | 0 | 707 |
| 729039 | 2218 | 2233 | 11783 | 11798 | CAGGTTCTTGGACTCT | ${}^mC_{ks}A_{ks}G_{ks}G_{ds}T_{ds}T_{ds}{}^mC_{ds}T_{ds}T_{ds}G_{ds}G_{ds}A_{ds}{}^mC_{ds}T_{ks}{}^mC_{ks}T_k$ | 0 | 708 |

TABLE 21-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785364 | 1361 | 1376 | 10682 | 10697 | TCTGGCCCTTTTGGAA | $T_{ks}{}^mC_{ds}T_{ds}G_{ds}G_{ds}{}^mC_{ds}$ ${}^mC_{ds}{}^mC_{ds}T_{ds}T_{ds}T_{ds}T_{ks}$ $G_{es}G_{ks}A_{es}A_k$ | 0 | 454 |
| 785365 | 1363 | 1378 | 10684 | 10699 | GGTCTGGCCCTTTTGG | $G_{ks}G_{ds}T_{ds}{}^mC_{ds}T_{ds}G_{ds}$ $G_{ds}{}^mC_{ds}{}^mC_{ds}{}^mC_{ds}T_{ds}T_{ks}$ $T_{es}T_{ks}G_{es}G_k$ | 0 | 393 |
| 785378 | 2214 | 2229 | 11779 | 11794 | TTCTTGGACTCTCAAG | $T_{ks}T_{ds}{}^mC_{ds}T_{ds}T_{ds}G_{ds}$ $G_{ds}A_{ds}{}^mC_{ds}T_{ds}{}^mC_{ds}T_{ks}$ $C_{es}A_{ks}A_{es}G_k$ | 0 | 705 |
| 785379 | 2215 | 2230 | 11780 | 11795 | GTTCTTGGACTCTCAA | $G_{ks}T_{ds}T_{ds}{}^mC_{ds}T_{ds}T_{ds}$ $G_{ds}G_{ds}A_{ds}{}^mC_{ds}T_{ds}{}^mC_{ks}$ $T_{es}{}^mC_{ks}A_{es}A_k$ | 35 | 695 |
| 785380 | 2216 | 2231 | 11781 | 11796 | GGTTCTTGGACTCTCA | $G_{ks}G_{ds}T_{ds}T_{ds}{}^mC_{ds}T_{ds}$ $T_{ds}G_{ds}G_{ds}A_{ds}{}^mC_{ds}T_{ks}{}^m$ $C_{es}T_{ks}{}^mC_{es}A_k$ | 9 | 706 |
| 785381 | 2217 | 2232 | 11782 | 11797 | AGGTTCTTGGACTCTC | $A_{ks}G_{ds}G_{ds}T_{ds}T_{ds}{}^mC_{ds}$ $T_{ds}T_{ds}G_{ds}G_{ds}A_{ds}{}^mC_{ks}$ $T_{es}{}^mC_{ks}T_{es}{}^mC_k$ | 34 | 707 |
| 785382 | 2218 | 2233 | 11783 | 11798 | CAGGTTCTTGGACTCT | ${}^mC_{ks}A_{ds}G_{ds}G_{ds}T_{ds}T_{ds}{}^m$ $C_{ds}T_{ds}T_{ds}G_{ds}G_{ds}A_{ks}$ $C_{es}T_{ks}{}^mC_{es}T_k$ | 0 | 708 |
| 785419 | 1361 | 1376 | 10682 | 10697 | TCTGGCCCTTTTGGAA | $T_{ks}{}^mC_{ds}T_{ds}G_{ds}G_{ds}{}^mC_{ds}$ ${}^mC_{ds}{}^mC_{ds}T_{ds}T_{ds}T_{ks}T_{es}$ $G_{ks}G_{es}A_{ks}A_e$ | 0 | 454 |
| 785420 | 1363 | 1378 | 10684 | 10699 | GGTCTGGCCCTTTTGG | $G_{ks}G_{ds}T_{ds}{}^mC_{ds}T_{ds}G_{ds}$ $G_{ds}{}^mC_{ds}{}^mC_{ds}{}^mC_{ds}T_{ds}T_{ks}T_{es}$ $T_{ks}T_{es}G_{ks}G_e$ | 0 | 393 |
| 785433 | 2214 | 2229 | 11779 | 11794 | TTCTTGGACTCTCAAG | $T_{ks}T_{ds}{}^mC_{ds}T_{ds}T_{ds}G_{ds}$ $G_{ds}A_{ds}{}^mC_{ds}T_{ds}{}^mC_{ks}T_{es}$ $C_{ks}A_{es}A_{ks}G_e$ | 0 | 705 |
| 785434 | 2215 | 2230 | 11780 | 11795 | GTTCTTGGACTCTCAA | $G_{ks}T_{ds}T_{ds}{}^mC_{ds}T_{ds}T_{ds}$ $G_{ds}G_{ds}A_{ds}{}^mC_{ds}T_{ks}{}^mC_{es}$ $T_{ks}{}^mC_{es}A_{ks}A_e$ | 0 | 695 |
| 785435 | 2216 | 2231 | 11781 | 11796 | GGTTCTTGGACTCTCA | $G_{ks}G_{ds}T_{ds}T_{ds}{}^mC_{ds}T_{ds}$ $T_{ds}G_{ds}G_{ds}A_{ds}{}^mC_{ks}T_{es}{}^m$ $C_{ks}T_{es}{}^mC_{ks}A_e$ | 0 | 706 |
| 785436 | 2217 | 2232 | 11782 | 11797 | AGGTTCTTGGACTCTC | $A_{ks}G_{ds}G_{ds}T_{ds}T_{ds}{}^mC_{ds}$ $T_{ds}T_{ds}G_{ds}G_{ds}A_{ks}{}^mC_{es}$ $T_{ks}{}^mC_{es}T_{ks}{}^mC_e$ | 0 | 707 |
| 785437 | 2218 | 2233 | 11783 | 11798 | CAGGTTCTTGGACTCT | ${}^mC_{ks}A_{ds}G_{ds}G_{ds}T_{ds}T_{ds}{}^m$ $C_{ds}T_{ds}T_{ds}G_{ds}G_{ks}A_{es}{}^m$ $C_{ks}T_{es}{}^mC_{ks}T_e$ | 0 | 708 |
| 785468 | 1363 | 1378 | 10684 | 10699 | GGTCTGGCCCTTTTGG | $G_{ks}G_{es}T_{ks}{}^mC_{ds}T_{ds}G_{ds}$ $G_{ds}{}^mC_{ds}{}^mC_{ds}{}^mC_{ds}T_{ds}T_{ds}$ $T_{es}T_{es}G_{ks}G_k$ | 13 | 393 |
| 785475 | 2216 | 2231 | 11781 | 11796 | GGTTCTTGGACTCTCA | $G_{ks}G_{es}T_{ks}T_{ds}{}^mC_{ds}T_{ds}$ $T_{ds}G_{ds}G_{ds}A_{ds}{}^mC_{ds}T_{ds}{}^m$ $C_{es}T_{es}{}^mC_{ks}A_k$ | 60 | 706 |
| 785476 | 2217 | 2232 | 11782 | 11797 | AGGTTCTTGGACTCTC | $A_{ks}G_{es}G_{ks}T_{ds}T_{ds}{}^mC_{ds}$ $T_{ds}T_{ds}G_{ds}G_{ds}A_{ds}{}^mC_{ds}$ $T_{es}{}^mC_{es}T_{ks}{}^mC_k$ | 0 | 707 |
| 785477 | 2218 | 2233 | 11783 | 11798 | CAGGTTCTTGGACTCT | ${}^mC_{ks}A_{es}G_{ks}G_{ds}T_{ds}T_{ds}{}^m$ $C_{ds}T_{ds}T_{ds}G_{ds}G_{ds}A_{ds}{}^m$ $C_{es}T_{es}{}^mC_{ks}T_k$ | 48 | 708 |

TABLE 21-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785507 | 1362 | 1377 | 10683 | 10698 | GTCTGGCCCTTTTGGA | $G_{ks}T_{ks}{}^mC_{ds}T_{ds}G_{ds}G_{ds}{}^mC_{ds}{}^mC_{ds}{}^mC_{ds}T_{ds}T_{ds}T_{ds}T_{ks}G_{es}G_{ks}A_e$ | 0 | 455 |
| 785508 | 1363 | 1378 | 10684 | 10699 | GGTCTGGCCCTTTTGG | $G_{ks}G_{ks}T_{ds}{}^mC_{ds}T_{ds}G_{ds}G_{ds}{}^mC_{ds}{}^mC_{ds}{}^mC_{ds}T_{ds}T_{ds}T_{ds}T_{ks}T_{es}G_{ks}G_e$ | 0 | 393 |
| 785521 | 2215 | 2230 | 11780 | 11795 | GTTCTTGGACTCTCAA | $G_{ks}T_{ks}T_{ds}{}^mC_{ds}T_{ds}T_{ds}G_{ds}G_{ds}A_{ds}{}^mC_{ds}T_{ds}{}^mC_{ds}T_{ks}{}^mC_{es}A_{ks}A_e$ | 27 | 695 |
| 785522 | 2216 | 2231 | 11781 | 11796 | GGTTCTTGGACTCTCA | $G_{ks}G_{ks}T_{ds}T_{ds}{}^mC_{ds}T_{ds}T_{ds}G_{ds}G_{ds}A_{ds}{}^mC_{ds}T_{ds}{}^mC_{ks}T_{es}{}^mC_{ks}A_e$ | 51 | 706 |
| 785523 | 2217 | 2232 | 11782 | 11797 | AGGTTCTTGGACTCTC | $A_{ks}G_{ks}G_{ds}T_{ds}T_{ds}{}^mC_{ds}T_{ds}T_{ds}G_{ds}G_{ds}A_{ds}{}^mC_{ds}T_{ks}{}^mC_{es}T_{ks}{}^mC_e$ | 41 | 707 |
| 785524 | 2218 | 2233 | 11783 | 11798 | CAGGTTCTTGGACTCT | ${}^mC_{ks}A_{ks}G_{ds}G_{ds}T_{ds}T_{ds}{}^mC_{ds}T_{ds}T_{ds}G_{ds}G_{ds}A_{ds}{}^mC_{ks}T_{es}{}^mC_{ks}T_e$ | 28 | 708 |
| 785555 | 1362 | 1377 | 10683 | 10698 | GTCTGGCCCTTTTGGA | $G_{ks}T_{ks}{}^mC_{ds}T_{ds}G_{ds}G_{ds}{}^mC_{ds}{}^mC_{ds}{}^mC_{ds}T_{ds}T_{es}T_{es}T_{es}G_{es}G_{ks}A_k$ | 0 | 455 |
| 785562 | 2215 | 2230 | 11780 | 11795 | GTTCTTGGACTCTCAA | $G_{ks}T_{ks}T_{ds}{}^mC_{ds}T_{ds}T_{ds}G_{ds}G_{ds}A_{ds}{}^mC_{ds}T_{es}{}^mC_{es}T_{es}{}^mC_{es}A_{ks}A_k$ | 8 | 695 |
| 785563 | 2216 | 2231 | 11781 | 11796 | GGTTCTTGGACTCTCA | $G_{ks}G_{ks}T_{ds}T_{ds}{}^mC_{ds}T_{ds}T_{ds}G_{ds}G_{ds}A_{ds}{}^mC_{es}T_{es}{}^mC_{es}T_{es}{}^mC_{ks}A_k$ | 54 | 706 |
| 785564 | 2217 | 2232 | 11782 | 11797 | AGGTTCTTGGACTCTC | $A_{ks}G_{ks}G_{ds}T_{ds}T_{ds}{}^mC_{ds}T_{ds}T_{ds}G_{ds}G_{ds}A_{es}{}^mC_{es}T_{es}{}^mC_{es}T_{ks}{}^mC_k$ | 17 | 707 |
| 785600 | 1361 | 1376 | 10682 | 10697 | TCTGGCCCTTTTGGAA | $T_{ks}{}^mC_{ks}T_{ds}G_{ds}G_{ds}{}^mC_{ds}{}^mC_{ds}{}^mC_{ds}T_{ds}T_{ds}T_{ks}T_{es}G_{es}G_{es}A_{ks}A_k$ | 0 | 454 |
| 785601 | 1362 | 1377 | 10683 | 10698 | GTCTGGCCCTTTTGGA | $G_{ks}T_{ks}{}^mC_{ds}T_{ds}G_{ds}G_{ds}{}^mC_{ds}{}^mC_{ds}{}^mC_{ds}T_{ds}T_{ks}T_{es}T_{ks}G_{es}G_{ks}A_k$ | 0 | 455 |
| 785602 | 1363 | 1378 | 10684 | 10699 | GGTCTGGCCCTTTTGG | $G_{ks}G_{ks}T_{ds}{}^mC_{ds}T_{ds}G_{ds}G_{ds}{}^mC_{ds}{}^mC_{ds}{}^mC_{ds}T_{ds}T_{ks}T_{es}T_{ks}T_{es}G_{ks}G_k$ | 0 | 393 |
| 785621 | 2214 | 2229 | 11779 | 11794 | TTCTTGGACTCTCAAG | $T_{ks}T_{ks}{}^mC_{ds}T_{ds}T_{ds}G_{ds}G_{ds}A_{ds}{}^mC_{ds}T_{ds}{}^mC_{ks}T_{es}{}^mC_{ks}A_{es}A_{ks}G_k$ | 0 | 705 |
| 785622 | 2215 | 2230 | 11780 | 11795 | GTTCTTGGACTCTCAA | $G_{ks}T_{ks}T_{ds}{}^mC_{ds}T_{ds}T_{ds}G_{ds}G_{ds}A_{ds}{}^mC_{ds}T_{ks}{}^mC_{es}T_{ks}{}^mC_{es}A_{ks}A_k$ | 0 | 695 |
| 785623 | 2216 | 2231 | 11781 | 11796 | GGTTCTTGGACTCTCA | $G_{ks}G_{ks}T_{ds}T_{ds}{}^mC_{ds}T_{ds}T_{ds}G_{ds}G_{ds}A_{ds}{}^mC_{ks}T_{es}{}^mC_{ks}T_{es}{}^mC_{ks}A_k$ | 0 | 706 |
| 785624 | 2217 | 2232 | 11782 | 11797 | AGGTTCTTGGACTCTC | $A_{ks}G_{ks}G_{ds}T_{ds}T_{ds}{}^mC_{ds}T_{ds}T_{ds}G_{ds}G_{ds}A_{ks}{}^mC_{es}T_{ks}{}^mC_{es}T_{ks}{}^mC_k$ | 0 | 707 |
| 785625 | 2218 | 2233 | 11783 | 11798 | CAGGTTCTTGGACTCT | ${}^mC_{ks}A_{ks}G_{ds}G_{ds}T_{ds}T_{ds}{}^mC_{ds}T_{ds}T_{ds}G_{ds}G_{ds}A_{es}{}^mC_{ks}T_{es}{}^mC_{ks}T_k$ | 0 | 708 |

TABLE 21-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785664 | 1362 | 1377 | 10683 | 10698 | GTCTGGCCCTTTTGGA | G$_{ks}$T$_{ks}$$^m$C$_{ds}$T$_{ds}$G$_{ds}$G$_{ds}$$^m$C$_{ds}$$^m$C$_{ds}$$^m$C$_{ds}$T$_{ds}$T$_{ds}$T$_{es}$T$_{es}$G$_{es}$G$_{ks}$A$_k$ | 0 | 455 |
| 785671 | 2215 | 2230 | 11780 | 11795 | GTTCTTGGACTCTCAA | G$_{ks}$T$_{ks}$T$_{ds}$$^m$C$_{ds}$T$_{ds}$T$_{ds}$G$_{ds}$G$_{ds}$A$_{ds}$$^m$C$_{ds}$T$_{ds}$$^m$C$_{es}$T$_{es}$$^m$C$_{es}$A$_{ks}$A$_k$ | 22 | 695 |
| 785672 | 2216 | 2231 | 11781 | 11796 | GGTTCTTGGACTCTCA | G$_{ks}$G$_{ks}$T$_{ds}$T$_{ds}$$^m$C$_{ds}$T$_{ds}$T$_{ds}$G$_{ds}$G$_{ds}$A$_{ds}$$^m$C$_{ds}$T$_{es}$$^m$C$_{es}$T$_{es}$$^m$C$_{ks}$A$_k$ | 48 | 706 |
| 785673 | 2217 | 2232 | 11782 | 11797 | AGGTTCTTGGACTCTC | A$_{ks}$G$_{ks}$G$_{ds}$T$_{ds}$T$_{ds}$$^m$C$_{ds}$T$_{ds}$T$_{ds}$G$_{ds}$G$_{ds}$A$_{ds}$$^m$C$_{es}$T$_{es}$$^m$C$_{es}$T$_{ks}$$^m$C$_k$ | 0 | 707 |
| 785694 | 1362 | 1377 | 10683 | 10698 | GTCTGGCCCTTTTGGA | G$_{ks}$T$_{ks}$$^m$C$_{ds}$T$_{ds}$G$_{ds}$G$_{ds}$$^m$C$_{ds}$$^m$C$_{ds}$$^m$C$_{ds}$T$_{ds}$T$_{ds}$T$_{ks}$T$_{ds}$G$_{ks}$G$_{ds}$A$_k$ | 0 | 455 |
| 785701 | 2215 | 2230 | 11780 | 11795 | GTTCTTGGACTCTCAA | G$_{ks}$T$_{ks}$T$_{ds}$$^m$C$_{ds}$T$_{ds}$T$_{ds}$G$_{ds}$G$_{ds}$A$_{ds}$$^m$C$_{ds}$T$_{ds}$$^m$C$_{ks}$T$_{ds}$$^m$C$_{ks}$A$_{ds}$A$_k$ | 20 | 695 |
| 785702 | 2216 | 2231 | 11781 | 11796 | GGTTCTTGGACTCTCA | G$_{ks}$G$_{ks}$T$_{ds}$T$_{ds}$$^m$C$_{ds}$T$_{ds}$T$_{ds}$G$_{ds}$G$_{ds}$A$_{ds}$$^m$C$_{ds}$T$_{ks}$$^m$C$_{ds}$T$_{ks}$$^m$C$_{ds}$A$_k$ | 29 | 706 |
| 785703 | 2217 | 2232 | 11782 | 11797 | AGGTTCTTGGACTCTC | A$_{ks}$G$_{ks}$G$_{ds}$T$_{ds}$T$_{ds}$$^m$C$_{ds}$T$_{ds}$T$_{ds}$G$_{ds}$G$_{ds}$A$_{ds}$$^m$C$_{ks}$T$_{ds}$$^m$C$_{ks}$T$_{ds}$$^m$C$_k$ | 36 | 707 |
| 785732 | 1362 | 1377 | 10683 | 10698 | GTCTGGCCCTTTTGGA | G$_{ks}$T$_{ks}$$^m$C$_{ds}$T$_{ds}$G$_{ds}$G$_{ds}$$^m$C$_{ds}$$^m$C$_{ds}$$^m$C$_{ds}$T$_{ds}$T$_{ds}$T$_{ks}$T$_{es}$G$_{ks}$G$_{es}$A$_k$ | 0 | 455 |
| 785733 | 1363 | 1378 | 10684 | 10699 | GGTCTGGCCCTTTTGG | G$_{ks}$G$_{ks}$T$_{ds}$$^m$C$_{ds}$T$_{ds}$G$_{ds}$G$_{ds}$$^m$C$_{ds}$$^m$C$_{ds}$$^m$C$_{ds}$T$_{ds}$T$_{ks}$T$_{es}$T$_{ks}$G$_{es}$G$_k$ | 3 | 393 |
| 785746 | 2215 | 2230 | 11780 | 11795 | GTTCTTGGACTCTCAA | G$_{ks}$T$_{ks}$T$_{ds}$$^m$C$_{ds}$T$_{ds}$T$_{ds}$G$_{ds}$G$_{ds}$A$_{ds}$$^m$C$_{ds}$T$_{ds}$$^m$C$_{ks}$T$_{es}$$^m$C$_{ks}$A$_{es}$A$_k$ | 31 | 695 |
| 785747 | 2216 | 2231 | 11781 | 11796 | GGTTCTTGGACTCTCA | G$_{ks}$G$_{ks}$T$_{ds}$T$_{ds}$$^m$C$_{ds}$T$_{ds}$T$_{ds}$G$_{ds}$G$_{ds}$A$_{ds}$$^m$C$_{ds}$T$_{ks}$$^m$C$_{es}$T$_{ks}$$^m$C$_{es}$A$_k$ | 0 | 706 |
| 785748 | 2217 | 2232 | 11782 | 11797 | AGGTTCTTGGACTCTC | A$_{ks}$G$_{ks}$G$_{ds}$T$_{ds}$T$_{ds}$$^m$C$_{ds}$T$_{ds}$T$_{ds}$G$_{ds}$G$_{ds}$A$_{ds}$$^m$C$_{ks}$T$_{es}$$^m$C$_{ks}$T$_{es}$$^m$C$_k$ | 38 | 707 |
| 785749 | 2218 | 2233 | 11783 | 11798 | CAGGTTCTTGGACTCT | $^m$C$_{ks}$A$_{ks}$G$_{ds}$G$_{ds}$T$_{ds}$T$_{ds}$$^m$C$_{ds}$T$_{ds}$T$_{ds}$G$_{ds}$G$_{ds}$A$_{ks}$$^m$C$_{es}$T$_{ks}$$^m$C$_{es}$T$_k$ | 0 | 708 |
| 785781 | 1363 | 1378 | 10684 | 10699 | GGTCTGGCCCTTTTGG | G$_{ks}$G$_{ks}$T$_{ks}$$^m$C$_{ds}$T$_{ds}$G$_{ds}$G$_{ds}$$^m$C$_{ds}$$^m$C$_{ds}$$^m$C$_{ds}$T$_{ds}$T$_{ks}$T$_{ds}$T$_{ks}$G$_{ds}$G$_k$ | 0 | 393 |
| 785788 | 2216 | 2231 | 11781 | 11796 | GGTTCTTGGACTCTCA | G$_{ks}$G$_{ks}$T$_{ks}$T$_{ds}$$^m$C$_{ds}$T$_{ds}$T$_{ds}$G$_{ds}$G$_{ds}$A$_{ds}$$^m$C$_{ds}$T$_{ks}$$^m$C$_{ds}$T$_{ks}$$^m$C$_{ds}$A$_k$ | 28 | 706 |
| 785789 | 2217 | 2232 | 11782 | 11797 | AGGTTCTTGGACTCTC | A$_{ks}$G$_{ks}$G$_{ks}$T$_{ds}$T$_{ds}$$^m$C$_{ds}$T$_{ds}$T$_{ds}$G$_{ds}$G$_{ds}$A$_{ds}$$^m$C$_{ks}$T$_{ds}$$^m$C$_{ks}$T$_{ds}$$^m$C$_k$ | 0 | 707 |
| 785790 | 2218 | 2233 | 11783 | 11798 | CAGGTTCTTGGACTCT | $^m$C$_{ks}$A$_{ks}$G$_{ks}$G$_{ds}$T$_{ds}$T$_{ds}$$^m$C$_{ds}$T$_{ds}$T$_{ds}$G$_{ds}$G$_{ds}$A$_{ks}$$^m$C$_{ds}$T$_{ks}$$^m$C$_{ds}$T$_k$ | 0 | 708 |

TABLE 21-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785820 | 1362 | 1377 | 10683 | 10698 | GTCTGGCCCTTTTGGA | $G_{ks}T_{ks}{}^mC_{ks}T_{ds}G_{ds}G_{ds}{}^mC_{ds}{}^mC_{ds}{}^mC_{ds}T_{ds}T_{ds}T_{es}G_{ks}G_{es}A_k$ | 0 | 455 |
| 785821 | 1363 | 1378 | 10684 | 10699 | GGTCTGGCCCTTTTGG | $G_{ks}G_{ks}T_{ks}{}^mC_{ds}T_{ds}G_{ds}G_{ds}{}^mC_{ds}{}^mC_{ds}{}^mC_{ds}T_{ds}T_{ks}T_{es}T_{ks}G_{es}G_k$ | 2 | 393 |
| 785834 | 2215 | 2230 | 11780 | 11795 | GTTCTTGGACTCTCAA | $G_{ks}T_{ks}T_{ks}{}^mC_{ds}T_{ds}T_{ds}G_{ds}G_{ds}A_{ds}{}^mC_{ds}T_{ds}{}^mC_{ks}T_{es}{}^mC_{ks}A_{es}A_k$ | 0 | 695 |
| 785835 | 2216 | 2231 | 11781 | 11796 | GGTTCTTGGACTCTCA | $G_{ks}G_{ks}T_{ks}T_{ds}{}^mC_{ds}T_{ds}T_{ds}G_{ds}G_{ds}A_{ds}{}^mC_{ds}T_{ks}{}^mC_{es}T_{ks}{}^mC_{es}A_k$ | 25 | 706 |
| 785836 | 2217 | 2232 | 11782 | 11797 | AGGTTCTTGGACTCTC | $A_{ks}G_{ks}G_{ks}T_{ds}T_{ds}{}^mC_{ds}T_{ds}T_{ds}G_{ds}G_{ds}A_{ds}{}^mC_{ks}T_{es}{}^mC_{ks}T_{es}{}^mC_k$ | 8 | 707 |
| 785837 | 2218 | 2233 | 11783 | 11798 | CAGGTTCTTGGACTCT | ${}^mC_{ks}A_{ks}G_{ks}G_{ds}T_{ds}T_{ds}{}^mC_{ds}T_{ds}T_{ds}G_{ds}G_{ds}A_{ds}{}^mC_{es}T_{ks}{}^mC_{es}T_k$ | 0 | 708 |
| 785869 | 1363 | 1378 | 10684 | 10699 | GGTCTGGCCCTTTTGG | $G_{ks}G_{ks}T_{ks}{}^mC_{ds}T_{ds}G_{ds}G_{ds}{}^mC_{ds}{}^mC_{ds}{}^mC_{ds}T_{ds}T_{ds}T_{ks}T_{es}G_{ks}G_e$ | 17 | 393 |
| 785876 | 2216 | 2231 | 11781 | 11796 | GGTTCTTGGACTCTCA | $G_{ks}G_{ks}T_{ks}T_{ds}{}^mC_{ds}T_{ds}T_{ds}G_{ds}G_{ds}A_{ds}{}^mC_{ds}T_{ds}{}^mC_{ks}T_{es}{}^mC_{ks}A_e$ | 48 | 706 |
| 785877 | 2217 | 2232 | 11782 | 11797 | AGGTTCTTGGACTCTC | $A_{ks}G_{ks}G_{ks}T_{ds}T_{ds}{}^mC_{ds}T_{ds}T_{ds}G_{ds}G_{ds}A_{ds}{}^mC_{ds}T_{ks}{}^mC_{es}T_{ks}{}^mC_e$ | 0 | 707 |
| 785878 | 2218 | 2233 | 11783 | 11798 | CAGGTTCTTGGACTCT | ${}^mC_{ks}A_{ks}G_{ks}G_{ds}T_{ds}T_{ds}{}^mC_{ds}T_{ds}T_{ds}G_{ds}G_{ds}A_{ds}{}^mC_{ks}T_{es}{}^mC_{ks}T_e$ | 1 | 708 |
| 785908 | 1362 | 1377 | 10683 | 10698 | GTCTGGCCCTTTTGGA | $G_{ks}T_{ks}{}^mC_{ks}T_{ds}G_{ds}G_{ds}{}^mC_{ds}{}^mC_{ds}{}^mC_{ds}T_{ds}T_{ds}T_{ds}T_{ks}G_{ks}G_{ks}A_e$ | 0 | 455 |
| 785909 | 1363 | 1378 | 10684 | 10699 | GGTCTGGCCCTTTTGG | $G_{ks}G_{ks}T_{ks}{}^mC_{ds}T_{ds}G_{ds}G_{ds}{}^mC_{ds}{}^mC_{ds}{}^mC_{ds}T_{ds}T_{ds}T_{ks}T_{ks}G_{ks}G_e$ | 0 | 393 |
| 785922 | 2215 | 2230 | 11780 | 11795 | GTTCTTGGACTCTCAA | $G_{ks}T_{ks}T_{ks}{}^mC_{ds}T_{ds}T_{ds}G_{ds}G_{ds}A_{ds}{}^mC_{ds}T_{ds}{}^mC_{ds}T_{ks}{}^mC_{ks}A_{ks}A_e$ | 37 | 695 |
| 785923 | 2216 | 2231 | 11781 | 11796 | GGTTCTTGGACTCTCA | $G_{ks}G_{ks}T_{ks}T_{ds}{}^mC_{ds}T_{ds}T_{ds}G_{ds}G_{ds}A_{ds}{}^mC_{ds}T_{ds}{}^mC_{ks}T_{ks}{}^mC_{ks}A_e$ | 0 | 706 |
| 785924 | 2217 | 2232 | 11782 | 11797 | AGGTTCTTGGACTCTC | $A_{ks}G_{ks}G_{ks}T_{ds}T_{ds}{}^mC_{ds}T_{ds}T_{ds}G_{ds}G_{ds}A_{ds}{}^mC_{ds}T_{ks}{}^mC_{ks}T_{ks}{}^mC_e$ | 19 | 707 |
| 785925 | 2218 | 2233 | 11783 | 11798 | CAGGTTCTTGGACTCT | ${}^mC_{ks}A_{ks}G_{ks}G_{ds}T_{ds}T_{ds}{}^mC_{ds}T_{ds}T_{ds}G_{ds}G_{ds}A_{ds}{}^mC_{ks}T_{ks}{}^mC_{ks}T_e$ | 0 | 708 |
| 785938 | N/A | N/A | 6548 | 6563 | CCAATTTTGCATTCCA | ${}^mC_{ks}{}^mC_{ks}A_{ks}A_{ds}T_{ds}T_{ds}T_{ds}T_{ds}G_{ds}{}^mC_{ds}A_{ds}T_{ds}T_{ks}{}^mC_{ks}{}^mC_{kse}$ | 71 | 1242 |

TABLE 22

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 728708 | 1308 | 1323 | 10541 | 10556 | AGCTTGGTCTTGACCT | $A_{ks}G_{ks}{}^mC_{ks}T_{ds}T_{ds}G_{ds}$ $G_{ds}T_{ds}{}^mC_{ds}T_{ds}T_{ds}G_{ds}$ $A_{ds}{}^mC_{ks}{}^mC_{ks}T_k$ | 12 | 436 |
| 728898 | 1769 | 1784 | 11334 | 11349 | GCTGTCACATCTCCAC | $G_{ks}{}^mC_{ks}T_{ks}G_{ds}T_{ds}{}^mC_{ds}$ $A_{ds}{}^mC_{ds}A_{ds}T_{ds}{}^mC_{ds}T_{ds}$ ${}^mC_{ds}{}^mC_{ks}A_{ks}{}^mC_k$ | 33 | 637 |
| 729049 | 2230 | 2245 | 11795 | 11810 | TTATTTCTGCTCCAGG | $T_{ks}T_{ks}A_{ks}T_{ds}T_{ds}T_{ds}{}^mC_{ds}$ $T_{ds}G_{ds}{}^mC_{ds}T_{ds}{}^mC_{ds}{}^m$ ${}^mC_{ds}A_{ks}G_{ks}G_k$ | 55 | 718 |
| 729589 | N/A | N/A | 9259 | 9274 | CCTTCTGCAGGGAGTC | ${}^mC_{ks}{}^mC_{ks}T_{ks}T_{ds}{}^mC_{ds}T_{ds}$ $G_{ds}{}^mC_{ds}A_{ds}G_{ds}G_{ds}G_{ds}$ $A_{ds}G_{ks}T_{ks}{}^mC_k$ | 0 | 1184 |
| 785372 | 1767 | 1782 | 11332 | 11347 | TGTCACATCTCCACAT | $T_{ks}G_{ds}T_{ds}{}^mC_{ds}A_{ds}{}^mC_{ds}$ $A_{ds}T_{ds}{}^mC_{ds}T_{ds}{}^mC_{ds}{}^mC_{ks}$ $A_{es}{}^mC_{ks}A_{es}T_k$ | 16 | 635 |
| 785373 | 1769 | 1784 | 11334 | 11349 | GCTGTCACATCTCCAC | $G_{ks}{}^mC_{ds}T_{ds}G_{ds}T_{ds}{}^mC_{ds}$ $A_{ds}{}^mC_{ds}A_{ds}T_{ds}{}^mC_{ds}T_{ks}$ ${}^mC_{es}{}^mC_{ks}A_{es}{}^mC_k$ | 17 | 637 |
| 785383 | 2228 | 2243 | 11793 | 11808 | ATTTCTGCTCCAGGTT | $A_{ks}T_{ds}T_{ds}T_{ds}{}^mC_{ds}T_{ds}G_{ds}$ ${}^mC_{ds}T_{ds}{}^mC_{ds}{}^mC_{ds}A_{ks}$ $G_{es}G_{ks}T_{es}T_k$ | 39 | 696 |
| 785384 | 2230 | 2245 | 11795 | 11810 | TTATTTCTGCTCCAGG | $T_{ks}T_{ds}A_{ds}T_{ds}T_{ds}T_{ds}{}^mC_{ds}$ $T_{ds}G_{ds}{}^mC_{ds}T_{ds}{}^mC_{ks}{}^m$ ${}^mC_{es}A_{ks}G_{es}G_k$ | 0 | 718 |
| 785400 | N/A | N/A | 9257 | 9272 | TTCTGCAGGGAGTCAG | $T_{ks}T_{ds}{}^mC_{ds}T_{ds}G_{ds}{}^mC_{ds}$ $A_{ds}G_{ds}G_{ds}G_{ds}A_{ds}G_{ks}T_{es}$ ${}^mC_{ks}A_{es}G_k$ | 4 | 1255 |
| 785401 | N/A | N/A | 9259 | 9274 | CCTTCTGCAGGGAGTC | ${}^mC_{ks}{}^mC_{ds}T_{ds}T_{ds}{}^mC_{ds}T_{ds}$ $G_{ds}{}^mC_{ds}A_{ds}G_{ds}G_{ds}G_{ks}$ $A_{es}G_{ks}T_{es}{}^mC_k$ | 0 | 1184 |
| 785427 | 1767 | 1782 | 11332 | 11347 | TGTCACATCTCCACAT | $T_{ks}G_{ds}T_{ds}{}^mC_{ds}A_{ds}{}^mC_{ds}$ $A_{ds}T_{ds}{}^mC_{ds}T_{ds}{}^mC_{ks}{}^mC_{es}$ $A_{ks}{}^mC_{es}A_{ks}T_e$ | 0 | 635 |
| 785428 | 1769 | 1784 | 11334 | 11349 | GCTGTCACATCTCCAC | $G_{ks}{}^mC_{ds}T_{ds}G_{ds}T_{ds}{}^mC_{ds}$ $A_{ds}{}^mC_{ds}A_{ds}T_{ds}{}^mC_{ks}T_{es}$ ${}^mC_{ks}{}^mC_{es}A_{ks}{}^mC_e$ | 0 | 637 |
| 785438 | 2228 | 2243 | 11793 | 11808 | ATTTCTGCTCCAGGTT | $A_{ks}T_{ds}T_{ds}T_{ds}{}^mC_{ds}T_{ds}G_{ds}$ ${}^mC_{ds}T_{ds}{}^mC_{ds}{}^mC_{ks}A_{es}$ $G_{ks}G_{es}T_{ks}T_e$ | 13 | 696 |
| 785439 | 2230 | 2245 | 11795 | 11810 | TTATTTCTGCTCCAGG | $T_{ks}T_{ds}A_{ds}T_{ds}T_{ds}T_{ds}{}^mC_{ds}$ $T_{ds}G_{ds}{}^mC_{ds}T_{ks}{}^mC_{es}{}^m$ ${}^mC_{ks}A_{es}G_{ks}G_e$ | 0 | 718 |
| 785455 | N/A | N/A | 9257 | 9272 | TTCTGCAGGGAGTCAG | $T_{ks}T_{ds}{}^mC_{ds}T_{ds}G_{ds}{}^mC_{ds}$ $A_{ds}G_{ds}G_{ds}G_{ds}A_{ks}G_{es}T_{ks}$ ${}^mC_{es}A_{ks}G_e$ | 0 | 1255 |
| 785456 | N/A | N/A | 9259 | 9274 | CCTTCTGCAGGGAGTC | ${}^mC_{ks}{}^mC_{ds}T_{ds}T_{ds}{}^mC_{ds}T_{ds}$ $G_{ds}{}^mC_{ds}A_{ds}G_{ds}G_{ks}G_{es}$ $A_{ks}G_{es}T_{ks}{}^mC_e$ | 0 | 1184 |
| 785472 | 1769 | 1784 | 11334 | 11349 | GCTGTCACATCTCCAC | $G_{ks}{}^mC_{es}T_{ks}G_{ds}T_{ds}{}^mC_{ds}$ $A_{ds}{}^mC_{ds}A_{ds}T_{ds}{}^mC_{ds}T_{ds}$ ${}^mC_{es}{}^mC_{es}A_{ks}{}^mC_k$ | 0 | 637 |
| 785478 | 2230 | 2245 | 11795 | 11810 | TTATTTCTGCTCCAGG | $T_{ks}T_{es}A_{ks}T_{ds}T_{ds}T_{ds}{}^mC_{ds}$ $T_{ds}G_{ds}{}^mC_{ds}T_{ds}{}^mC_{ds}{}^m$ ${}^mC_{es}A_{ks}G_{ks}G_k$ | 56 | 718 |

TABLE 22-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785488 | N/A | N/A | 9259 | 9274 | CCTTCTGCAG GGAGTC | $^mC_{ks}{}^mC_{es}T_{ks}T_{ds}{}^mC_{ds}T_{ds}$ $G_{ds}{}^mC_{ds}A_{ds}G_{ds}G_{ds}G_{ds}$ $A_{es}G_{es}T_{ks}{}^mC_k$ | 14 | 1184 |
| 785515 | 1768 | 1783 | 11333 | 11348 | CTGTCACATC TCCACA | $^mC_{ks}T_{ks}G_{ds}T_{ds}{}^mC_{ds}A_{ds}$ $^mC_{ds}A_{ds}T_{ds}{}^mC_{ds}T_{ds}{}^mC_{ds}$ $^mC_{ks}A_{es}{}^mC_{ks}A_e$ | 19 | 636 |
| 785516 | 1769 | 1784 | 11334 | 11349 | GCTGTCACAT CTCCAC | $G_{ks}{}^mC_{ks}T_{ds}G_{ds}T_{ds}{}^mC_{ds}$ $A_{ds}{}^mC_{ds}A_{ds}T_{ds}{}^mC_{ds}T_{ds}$ $^mC_{ks}{}^mC_{es}A_{ks}{}^mC_e$ | 8 | 637 |
| 785525 | 2229 | 2244 | 11794 | 11809 | TATTTCTGCTC CAGGT | $T_{ks}A_{ds}T_{ds}T_{ds}T_{ds}{}^mC_{ds}T_{ds}$ $G_{ds}{}^mC_{ds}T_{ds}{}^mC_{ds}{}^mC_{ds}$ $A_{ks}G_{es}G_{ks}T_e$ | 49 | 717 |
| 785526 | 2230 | 2245 | 11795 | 11810 | TTATTTCTGCT CCAGG | $T_{ks}T_{ks}A_{ds}T_{ds}T_{ds}T_{ds}{}^mC_{ds}$ $T_{ds}G_{ds}{}^mC_{ds}T_{ds}{}^mC_{ds}{}^m$ $^mC_{ks}A_{es}G_{ks}G_e$ | 26 | 718 |
| 785543 | N/A | N/A | 9258 | 9273 | CTTCTGCAGG GAGTCA | $^mC_{ks}T_{ks}T_{ds}{}^mC_{ds}T_{ds}G_{ds}$ $^mC_{ds}A_{ds}G_{ds}G_{ds}G_{ds}A_{ds}$ $G_{ks}T_{es}{}^mC_{ks}A_e$ | 8 | 1256 |
| 785544 | N/A | N/A | 9259 | 9274 | CCTTCTGCAG GGAGTC | $^mC_{ks}{}^mC_{ks}T_{ds}T_{ds}{}^mC_{ds}T_{ds}$ $G_{ds}{}^mC_{ds}A_{ds}G_{ds}G_{ds}G_{ds}$ $A_{ks}G_{es}T_{ks}{}^mC_e$ | 0 | 1184 |
| 785559 | 1768 | 1783 | 11333 | 11348 | CTGTCACATC TCCACA | $^mC_{ks}T_{ks}G_{ds}T_{ds}{}^mC_{ds}A_{ds}$ $^mC_{ds}A_{ds}T_{ds}{}^mC_{ds}T_{es}{}^mC_{es}$ $^mC_{es}A_{es}{}^mC_{ks}A_k$ | 11 | 636 |
| 785565 | 2229 | 2244 | 11794 | 11809 | TATTTCTGCTC CAGGT | $T_{ks}A_{ds}T_{ds}T_{ds}T_{ds}{}^mC_{ds}T_{ds}$ $G_{ds}{}^mC_{ds}T_{ds}{}^mC_{es}{}^mC_{es}$ $A_{es}G_{es}G_{ks}T_k$ | 43 | 717 |
| 785574 | N/A | N/A | 9258 | 9273 | CTTCTGCAGG GAGTCA | $^mC_{ks}T_{ks}T_{ds}{}^mC_{ds}T_{ds}G_{ds}$ $^mC_{ds}A_{ds}G_{ds}G_{ds}G_{es}A_{es}$ $G_{es}T_{es}{}^mC_{ks}A_k$ | 0 | 1256 |
| 785612 | 1767 | 1782 | 11332 | 11347 | TGTCACATCT CCACAT | $T_{ks}G_{ks}T_{ds}{}^mC_{ds}A_{ds}{}^mC_{ds}$ $A_{ds}T_{ds}{}^mC_{ds}T_{ds}{}^mC_{ks}{}^mC_{es}$ $A_{ks}{}^mC_{es}A_{ks}T_k$ | 0 | 635 |
| 785613 | 1768 | 1783 | 11333 | 11348 | CTGTCACATC TCCACA | $^mC_{ks}T_{ks}G_{ds}T_{ds}{}^mC_{ds}A_{ds}$ $^mC_{ds}A_{ds}T_{ds}{}^mC_{ds}T_{ks}{}^mC_{es}$ $^mC_{ks}A_{es}{}^mC_{ks}A_k$ | 0 | 636 |
| 785614 | 1769 | 1784 | 11334 | 11349 | GCTGTCACAT CTCCAC | $G_{ks}{}^mC_{ks}T_{ds}G_{ds}T_{ds}{}^mC_{ds}$ $A_{ds}{}^mC_{ds}A_{ds}T_{ds}{}^mC_{ks}T_{es}$ $^mC_{ks}{}^mC_{es}A_{ks}{}^mC_k$ | 29 | 637 |
| 785626 | 2228 | 2243 | 11793 | 11808 | ATTTCTGCTCC AGGTT | $A_{ks}T_{ds}T_{ds}T_{ds}{}^mC_{ds}T_{ds}G_{ds}$ $^mC_{ds}T_{ds}{}^mC_{ds}{}^mC_{ks}A_{es}$ $G_{ks}G_{es}T_{ks}T_k$ | 6 | 696 |
| 785627 | 2229 | 2244 | 11794 | 11809 | TATTTCTGCTC CAGGT | $T_{ks}A_{ds}T_{ds}T_{ds}T_{ds}{}^mC_{ds}T_{ds}$ $G_{ds}{}^mC_{ds}T_{ds}{}^mC_{ks}{}^mC_{es}$ $A_{ks}G_{es}G_{ks}T_k$ | 0 | 717 |
| 785628 | 2230 | 2245 | 11795 | 11810 | TTATTTCTGCT CCAGG | $T_{ks}T_{ks}A_{ds}T_{ds}T_{ds}T_{ds}{}^mC_{ds}$ $T_{ds}G_{ds}{}^mC_{ds}T_{ks}{}^mC_{es}$ $^mC_{ks}A_{es}G_{ks}G_k$ | 0 | 718 |
| 785651 | N/A | N/A | 9257 | 9272 | TTCTGCAGGG AGTCAG | $T_{ks}T_{ks}{}^mC_{ds}T_{ds}G_{ds}{}^mC_{ds}$ $A_{ds}G_{ds}G_{ds}G_{ds}A_{ks}G_{es}T_{ks}$ $^mC_{es}A_{ks}G_k$ | 0 | 1255 |
| 785652 | N/A | N/A | 9258 | 9273 | CTTCTGCAGG GAGTCA | $^mC_{ks}T_{ks}T_{ds}{}^mC_{ds}T_{ds}G_{ds}$ $^mC_{ds}A_{ds}G_{ds}G_{ds}G_{ks}A_{es}$ $G_{ks}T_{es}{}^mC_{ks}A_k$ | 0 | 1256 |

TABLE 22-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785653 | N/A | N/A | 9259 | 9274 | CCTTCTGCAGGGAGTC | $^mC_{ks}{}^mC_{ks}T_{ds}T_{ds}{}^mC_{ds}T_{ds}G_{ds}{}^mC_{ds}A_{ds}G_{ds}G_{ks}G_{es}A_{ks}G_{es}T_{ks}{}^mC_k$ | 0 | 1184 |
| 785668 | 1768 | 1783 | 11333 | 11348 | CTGTCACATCTCCACA | $^mC_{ks}T_{ks}G_{ds}T_{ds}{}^mC_{ds}A_{ds}{}^mC_{ds}A_{ds}T_{ds}{}^mC_{ds}T_{ds}{}^mC_{es}{}^mC_{es}A_{es}{}^mC_{ks}A_k$ | 10 | 636 |
| 785674 | 2229 | 2244 | 11794 | 11809 | TATTTCTGCTCCAGGT | $T_{ks}A_{ds}T_{ds}T_{ds}{}^mC_{ds}T_{ds}G_{ds}{}^mC_{ds}T_{ds}{}^mC_{ds}{}^mC_{es}A_{es}G_{es}G_{ks}T_k$ | 44 | 717 |
| 785683 | N/A | N/A | 9258 | 9273 | CTTCTGCAGGGAGTCA | $^mC_{ks}T_{ks}T_{ds}{}^mC_{ds}T_{ds}G_{ds}{}^mC_{cis}A_{ds}G_{ds}G_{ds}G_{ds}A_{es}G_{es}T_{es}{}^mC_{ks}A_k$ | 0 | 1256 |
| 785698 | 1768 | 1783 | 11333 | 11348 | CTGTCACATCTCCACA | $^mC_{ks}T_{ks}G_{ds}T_{ds}{}^mC_{ds}A_{ds}{}^mC_{ds}A_{ds}T_{ds}{}^mC_{ds}T_{ds}{}^mC_{ks}{}^mC_{ds}A_{ks}{}^mC_{ds}A_k$ | 6 | 636 |
| 785704 | 2229 | 2244 | 11794 | 11809 | TATTTCTGCTCCAGGT | $T_{ks}A_{ds}T_{ds}T_{ds}{}^mC_{ds}T_{ds}G_{ds}{}^mC_{ds}T_{ds}{}^mC_{ds}{}^mC_{ks}A_{ds}G_{ks}G_{ds}T_k$ | 27 | 717 |
| 785713 | N/A | N/A | 9258 | 9273 | CTTCTGCAGGGAGTCA | $^mC_{ks}T_{ks}T_{ds}{}^mC_{ds}T_{ds}G_{ds}{}^mC_{ds}A_{ds}G_{ds}G_{ds}G_{ds}A_{ks}G_{ds}T_{ks}{}^mC_{ds}A_k$ | 0 | 1256 |
| 785740 | 1768 | 1783 | 11333 | 11348 | CTGTCACATCTCCACA | $^mC_{ks}T_{ks}G_{ds}T_{ds}{}^mC_{ds}A_{ds}{}^mC_{ds}A_{ds}T_{ds}{}^mC_{ds}T_{ds}{}^mC_{ks}{}^mC_{es}A_{ks}{}^mC_{es}A_k$ | 23 | 636 |
| 785741 | 1769 | 1784 | 11334 | 11349 | GCTGTCACATCTCCAC | $G_{ks}{}^mC_{ks}T_{ds}G_{ds}T_{ds}{}^mC_{ds}A_{ds}{}^mC_{ds}A_{ds}T_{ds}{}^mC_{ds}T_{ks}{}^mC_{es}{}^mC_{ks}A_{es}{}^mC_k$ | 5 | 637 |
| 785750 | 2229 | 2244 | 11794 | 11809 | TATTTCTGCTCCAGGT | $T_{ks}A_{ds}T_{ds}T_{ds}{}^mC_{ds}T_{ds}G_{ds}{}^mC_{ds}T_{ds}{}^mC_{ds}{}^mC_{ks}A_{es}G_{ks}G_{es}T_k$ | 5 | 717 |
| 785751 | 2230 | 2245 | 11795 | 11810 | TTATTTCTGCTCCAGG | $T_{ks}T_{ds}A_{ds}T_{ds}T_{ds}T_{ds}{}^mC_{ds}T_{ds}G_{ds}{}^mC_{ds}T_{ds}{}^mC_{ks}{}^mC_{es}A_{ks}G_{es}G_k$ | 9 | 718 |
| 785768 | N/A | N/A | 9258 | 9273 | CTTCTGCAGGGAGTCA | $^mC_{ks}T_{ks}T_{ds}{}^mC_{ds}T_{ds}G_{ds}{}^mC_{ds}A_{ds}G_{ds}G_{ds}G_{ds}A_{ks}G_{es}T_{ks}{}^mC_{es}A_k$ | 0 | 1256 |
| 785769 | N/A | N/A | 9259 | 9274 | CCTTCTGCAGGGAGTC | $^mC_{ks}{}^mC_{ks}T_{ds}T_{ds}{}^mC_{ds}T_{ds}G_{ds}{}^mC_{ds}A_{ds}G_{ds}G_{ds}G_{ks}A_{es}G_{ks}T_{es}{}^mC_k$ | 0 | 1184 |
| 785785 | 1769 | 1784 | 11334 | 11349 | GCTGTCACATCTCCAC | $G_{ks}{}^mC_{ks}T_{ks}G_{ds}T_{ds}{}^mC_{ds}A_{ds}{}^mC_{ds}A_{ds}T_{ds}{}^mC_{ds}T_{ks}{}^mC_{ds}{}^mC_{ds}A_{ds}{}^mC_k$ | 35 | 637 |
| 785791 | 2230 | 2245 | 11795 | 11810 | TTATTTCTGCTCCAGG | $T_{ks}T_{ks}A_{ks}T_{ds}T_{ds}T_{ds}{}^mC_{ds}T_{ds}G_{ds}{}^mC_{ds}T_{ds}{}^mC_{ks}{}^mC_{ds}A_{ks}G_{ds}G_k$ | 57 | 718 |
| 785801 | N/A | N/A | 9259 | 9274 | CCTTCTGCAGGGAGTC | $^mC_{ks}{}^mC_{ks}T_{ks}{}^mC_{ds}T_{ds}{}^mC_{ds}T_{ds}G_{ds}{}^mC_{ds}A_{ds}G_{ds}G_{ds}G_{ks}A_{ds}G_{ks}T_{ds}{}^mC_k$ | 0 | 1184 |
| 785828 | 1768 | 1783 | 11333 | 11348 | CTGTCACATCTCCACA | $^mC_{ks}T_{ks}G_{ks}T_{ds}{}^mC_{ds}A_{ds}{}^mC_{ds}A_{ds}T_{ds}{}^mC_{ds}T_{ds}{}^mC_{ks}{}^mC_{es}A_{ks}{}^mC_{es}A_k$ | 0 | 636 |
| 785829 | 1769 | 1784 | 11334 | 11349 | GCTGTCACATCTCCAC | $G_{ks}{}^mC_{ks}T_{ks}G_{ds}T_{ds}{}^mC_{ds}A_{ds}{}^mC_{ds}A_{ds}T_{ds}{}^mC_{ds}T_{ks}{}^mC_{es}{}^mC_{ks}A_{es}{}^mC_k$ | 0 | 637 |

TABLE 22-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785838 | 2229 | 2244 | 11794 | 11809 | TATTTCTGCTCCAGGT | $T_{ks}A_{ks}T_{ks}T_{ds}T_{ds}{}^mC_{ds}T_{ds}G_{ds}{}^mC_{ds}T_{ds}{}^mC_{ds}{}^mC_{ks}A_{es}G_{ks}G_{es}T_k$ | 24 | 717 |
| 785839 | 2230 | 2245 | 11795 | 11810 | TTATTTCTGCTCCAGG | $T_{ks}T_{ks}A_{ks}T_{ds}T_{ds}T_{ds}{}^mC_{ds}T_{ds}G_{ds}{}^mC_{ds}T_{ds}{}^mC_{ks}{}^mC_{es}A_{ks}G_{es}G_k$ | 23 | 718 |
| 785856 | N/A | N/A | 9258 | 9273 | CTTCTGCAGGGAGTCA | ${}^mC_{ks}T_{ks}T_{ks}{}^mC_{ds}T_{ds}G_{ds}{}^mC_{ds}A_{ds}G_{ds}G_{ds}G_{ds}A_{ks}G_{es}T_{ks}{}^mC_{es}A_k$ | 0 | 1256 |
| 785857 | N/A | N/A | 9259 | 9274 | CCTTCTGCAGGGAGTC | ${}^mC_{ks}{}^mC_{ks}T_{ks}T_{ds}{}^mC_{ds}T_{ds}G_{ds}{}^mC_{ds}A_{ds}G_{ds}G_{ds}G_{ds}G_{ks}A_{es}G_{ks}T_{es}{}^mC_k$ | 0 | 1184 |
| 785873 | 1769 | 1784 | 11334 | 11349 | GCTGTCACATCTCCAC | $G_{ks}{}^mC_{ks}T_{ks}G_{ds}T_{ds}{}^mC_{ds}A_{ds}{}^mC_{ds}A_{ds}T_{ds}{}^mC_{ds}T_{ds}{}^mC_{ks}{}^mC_{es}A_{ks}{}^mC_e$ | 3 | 637 |
| 785879 | 2230 | 2245 | 11795 | 11810 | TTATTTCTGCTCCAGG | $T_{ks}T_{ks}A_{ks}T_{ds}T_{ds}T_{ds}{}^mC_{ds}T_{ds}G_{ds}{}^mC_{ds}T_{ds}{}^mC_{ds}{}^mC_{ks}A_{es}G_{ks}G_e$ | 43 | 718 |
| 785889 | N/A | N/A | 9259 | 9274 | CCTTCTGCAGGGAGTC | ${}^mC_{ks}{}^mC_{ks}T_{ks}T_{ds}{}^mC_{ds}T_{ds}G_{ds}{}^mC_{ds}A_{ds}G_{ds}G_{ds}G_{ds}A_{ks}G_{es}T_{ks}{}^mC_e$ | 1 | 1184 |
| 785916 | 1768 | 1783 | 11333 | 11348 | CTGTCACATCTCCACA | ${}^mC_{ks}T_{ks}G_{ks}T_{ds}{}^mC_{ds}A_{ds}{}^mC_{ds}A_{ds}T_{ds}{}^mC_{ds}T_{ds}{}^mC_{ds}{}^mC_{ks}A_{ks}{}^mC_{ks}A_e$ | 28 | 636 |
| 785917 | 1769 | 1784 | 11334 | 11349 | GCTGTCACATCTCCAC | $G_{ks}{}^mC_{ks}T_{ks}G_{ds}T_{ds}{}^mC_{ds}A_{ds}{}^mC_{ds}A_{ds}T_{ds}{}^mC_{ds}T_{ds}{}^mC_{ks}{}^mC_{ks}A_{ks}{}^mC_e$ | 23 | 637 |
| 785926 | 2229 | 2244 | 11794 | 11809 | TATTTCTGCTCCAGGT | $T_{ks}A_{ks}T_{ks}T_{ds}T_{ds}{}^mC_{ds}T_{ds}G_{ds}{}^mC_{ds}T_{ds}{}^mC_{ds}{}^mC_{ds}A_{ks}G_{ks}T_e$ | 45 | 717 |
| 785927 | 2230 | 2245 | 11795 | 11810 | TTATTTCTGCTCCAGG | $T_{ks}T_{ks}A_{ks}T_{ds}T_{ds}T_{ds}{}^mC_{ds}T_{ds}G_{ds}{}^mC_{ds}T_{ds}{}^mC_{ds}{}^mC_{ks}A_{ks}G_{ks}G_e$ | 28 | 718 |
| 785938 | N/A | N/A | 6548 | 6563 | CCAATTTTGCATTCCA | ${}^mC_{ks}{}^mC_{ks}A_{ks}A_{ds}T_{ds}T_{ds}T_{ds}T_{ds}G_{ds}{}^mC_{ds}A_{ds}T_{ds}T_{ks}{}^mC_{ks}{}^mC_{ks}A_e$ | 75 | 1242 |
| 785944 | N/A | N/A | 9258 | 9273 | CTTCTGCAGGGAGTCA | ${}^mC_{ks}T_{ks}T_{ks}{}^mC_{ds}T_{ds}G_{ds}{}^mC_{ds}A_{ds}G_{ds}G_{ds}G_{ds}A_{ds}G_{ks}T_{ks}{}^mC_{ks}A_e$ | 0 | 1256 |
| 785945 | N/A | N/A | 9259 | 9274 | CCTTCTGCAGGGAGTC | ${}^mC_{ks}{}^mC_{ks}T_{ks}T_{ks}{}^mC_{ds}T_{ds}G_{ds}{}^mC_{ds}A_{ds}G_{ds}G_{ds}G_{ds}A_{ks}G_{ks}T_{ks}{}^mC_e$ | 0 | 1184 |
| 786513 | N/A | N/A | 9250 | 9265 | GGGAGTCAGACCTACC | $G_{ks}G_{ks}G_{ks}A_{ds}G_{ds}T_{ds}{}^mC_{ds}A_{ds}G_{ds}A_{ds}{}^mC_{ds}{}^mC_{ds}T_{ds}A_{ks}{}^mC_{ks}{}^mC_k$ | 0 | 1257 |
| 786514 | N/A | N/A | 9252 | 9267 | CAGGGAGTCAGACCTA | ${}^mC_{ks}A_{ks}G_{ks}G_{ds}G_{ds}A_{ds}G_{ds}T_{ds}{}^mC_{ds}A_{ds}G_{ds}A_{ds}{}^mC_{ds}{}^mC_{ks}T_{ks}A_k$ | 0 | 1258 |
| 786515 | N/A | N/A | 9254 | 9269 | TGCAGGGAGTCAGACC | $T_{ks}G_{ks}{}^mC_{ks}A_{ds}G_{ds}G_{ds}G_{ds}A_{ds}G_{ds}T_{ds}{}^mC_{ds}A_{ds}G_{ks}A_{ks}{}^mC_{ks}{}^mC_k$ | 0 | 1259 |
| 786516 | N/A | N/A | 9256 | 9271 | TCTGCAGGGAGTCAGA | $T_{ks}{}^mC_{ks}T_{ks}G_{ds}{}^mC_{ds}A_{ds}G_{ds}G_{ds}G_{ds}A_{ds}G_{ds}T_{ds}{}^mC_{ds}A_{ks}G_{ks}A_k$ | 0 | 1260 |

TABLE 22-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 786517 | N/A | N/A | 9257 | 9272 | TTCTGCAGGGAGTCAG | $T_{ks}T_{ks}{}^mC_{ks}T_{ds}G_{ds}{}^mC_{ds}A_{ds}G_{ds}G_{ds}G_{ds}A_{ds}G_{ds}T_{ds}{}^mC_{ks}A_{ks}G_k$ | 0 | 1255 |
| 786518 | N/A | N/A | 9258 | 9273 | CTTCTGCAGGGAGTCA | ${}^mC_{ks}T_{ks}T_{ks}{}^mC_{ds}T_{ds}G_{ds}{}^mC_{ds}A_{ds}G_{ds}G_{ds}G_{ds}A_{ds}G_{ds}T_{ks}{}^mC_{ks}A_k$ | 0 | 1256 |
| 786519 | N/A | N/A | 9260 | 9275 | GCCTTCTGCAGGGAGT | $G_{ks}{}^mC_{ks}{}^mC_{ks}T_{ds}T_{ds}{}^mC_{ds}T_{ds}G_{ds}{}^mC_{ds}A_{ds}G_{ds}G_{ds}G_{ds}A_{ks}G_{ks}T_k$ | 0 | 1261 |
| 786520 | N/A | N/A | 9261 | 9276 | TGCCTTCTGCAGGGAG | $T_{ks}G_{ks}{}^mC_{ks}{}^mC_{ds}T_{ds}T_{ds}{}^mC_{ds}T_{ds}G_{ds}{}^mC_{ds}A_{ds}G_{ds}G_{ds}G_{ks}A_{ks}G_k$ | 0 | 1262 |
| 786521 | N/A | N/A | 9262 | 9277 | TTGCCTTCTGCAGGGA | $T_{ks}T_{ks}G_{ks}{}^mC_{ds}{}^mC_{ds}T_{ds}T_{ds}{}^mC_{ds}T_{ds}G_{ds}{}^mC_{ds}A_{ds}G_{ds}G_{ds}G_{ks}A_k$ | 0 | 1263 |
| 786522 | N/A | N/A | 9264 | 9279 | ATTTGCCTTCTGCAGG | $A_{ks}T_{ks}T_{ks}T_{ds}G_{ds}{}^mC_{ds}{}^mC_{ds}T_{ds}T_{ds}{}^mC_{ds}T_{ds}G_{ds}{}^mC_{ds}A_{ks}G_{ks}G_k$ | 0 | 1264 |
| 786523 | N/A | N/A | 9266 | 9281 | TCATTTGCCTTCTGCA | $T_{ks}{}^mC_{ks}A_{ks}T_{ds}T_{ds}T_{ds}G_{ds}{}^mC_{ds}{}^mC_{ds}T_{ds}T_{ds}{}^mC_{ds}T_{ds}G_{ks}{}^mC_{ks}A_k$ | 6 | 1265 |

TABLE 23

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 728466 | 427 | 442 | 8320 | 8335 | GGTGTATTTCCCTGTC | $G_{ks}G_{ks}T_{ks}G_{ds}T_{ds}A_{ds}T_{ds}T_{ds}T_{ds}{}^mC_{ds}{}^mC_{ds}{}^mC_{ds}T_{ds}G_{ks}T_{ks}{}^mC_k$ | 37 | 1254 |
| 728708 | 1308 | 1323 | 10541 | 10556 | AGCTTGGTCTTGACCT | $A_{ks}G_{ks}{}^mC_{ks}T_{ds}T_{ds}G_{ds}G_{ds}T_{ds}{}^mC_{ds}T_{ds}T_{ds}G_{ds}A_{ds}{}^mC_{ks}{}^mC_{ks}T_k$ | 37 | 436 |
| 728998 | 2119 | 2134 | 11684 | 11699 | AGGAAGTGAGTCTCAA | $A_{ks}G_{ks}G_{ks}A_{ds}A_{ds}G_{ds}T_{ds}G_{ds}A_{ds}G_{ds}T_{ds}{}^mC_{ds}T_{ds}{}^mC_{ks}A_{ks}A_k$ | 42 | 208 |
| 729018 | 2172 | 2187 | 11737 | 11752 | TCTGATATGATACCTA | $T_{ks}{}^mC_{ks}T_{ks}G_{ds}A_{ds}T_{ds}A_{ds}T_{ds}G_{ds}A_{ds}T_{ds}A_{ds}{}^mC_{ds}{}^mC_{ks}T_{ks}A_k$ | 63 | 228 |
| 729454 | N/A | N/A | 5170 | 5185 | AGGAGTGAGACGAGCA | $A_{ks}G_{ks}G_{ks}A_{ds}G_{ds}T_{ds}G_{ds}A_{ds}G_{ds}A_{ds}{}^mC_{ds}G_{ds}A_{ds}G_{ks}{}^mC_{ks}A_k$ | 56 | 995 |
| 785376 | 2117 | 2132 | 11682 | 11697 | GAAGTGAGTCTCAAAC | $G_{ks}A_{ds}A_{ds}G_{ds}T_{ds}G_{ds}A_{ds}G_{ds}T_{ds}{}^mC_{ds}T_{ds}{}^mC_{ks}A_{es}A_{ks}A_{es}{}^mC_k$ | 44 | 207 |
| 785377 | 2119 | 2134 | 11684 | 11699 | AGGAAGTGAGTCTCAA | $A_{ks}G_{ds}G_{ds}A_{ds}A_{ds}G_{ds}T_{ds}G_{ds}A_{ds}G_{ds}T_{ds}{}^mC_{ks}T_{es}{}^mC_{ks}A_{es}A_k$ | 11 | 208 |
| 785387 | N/A | N/A | 5168 | 5183 | GAGTGAGACGAGCAAA | $G_{ks}A_{ds}G_{ds}T_{ds}G_{ds}A_{ds}G_{ds}A_{ds}{}^mC_{ds}G_{ds}A_{ds}G_{ks}{}^mC_{es}A_{ks}A_{es}A_k$ | 18 | 1266 |

TABLE 23-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785388 | N/A | N/A | 5170 | 5185 | AGGAGTGAGACGAGCA | $A_{ks}G_{ds}G_{ds}A_{ds}G_{ds}T_{ds}G_{ds}A_{ds}G_{ds}A_{ds}{}^mC_{ds}G_{ks}A_{es}G_{ks}{}^mC_{es}A_{k}$ | 37 | 995 |
| 785431 | 2117 | 2132 | 11682 | 11697 | GAAGTGAGTCTCAAAC | $G_{ks}A_{ds}A_{ds}G_{ds}T_{ds}G_{ds}A_{ds}G_{ds}T_{ds}{}^mC_{ds}T_{ks}{}^mC_{es}A_{ks}A_{es}A_{ks}{}^mC_{e}$ | 11 | 207 |
| 785432 | 2119 | 2134 | 11684 | 11699 | AGGAAGTGAGTCTCAA | $A_{ks}G_{ds}G_{ds}A_{ds}A_{ds}G_{ds}T_{ds}G_{ds}A_{ds}G_{ds}T_{ks}{}^mC_{es}T_{ks}{}^mC_{es}A_{ks}A_{e}$ | 23 | 208 |
| 785442 | N/A | N/A | 5168 | 5183 | GAGTGAGACGAGCAAA | $G_{ks}A_{ds}G_{ds}T_{ds}G_{ds}A_{ds}G_{ds}A_{ds}{}^mC_{ds}G_{ds}A_{ks}G_{es}{}^mC_{ks}A_{es}A_{ks}A_{e}$ | 6 | 1266 |
| 785443 | N/A | N/A | 5170 | 5185 | AGGAGTGAGACGAGCA | $A_{ks}G_{ds}G_{ds}A_{ds}G_{ds}T_{ds}G_{ds}A_{ds}G_{ds}A_{ds}{}^mC_{ks}G_{es}A_{ks}G_{es}{}^mC_{ks}A_{e}$ | 0 | 995 |
| 785474 | 2119 | 2134 | 11684 | 11699 | AGGAAGTGAGTCTCAA | $A_{ks}G_{es}G_{ks}A_{ds}A_{ds}G_{ds}T_{ds}G_{ds}A_{ds}G_{ds}T_{ds}{}^mC_{ds}T_{es}{}^mC_{es}A_{ks}A_{k}{}^mC_{es}A_{ks}A_{k}$ | 43 | 208 |
| 785480 | N/A | N/A | 5170 | 5185 | AGGAGTGAGACGAGCA | $A_{ks}G_{es}G_{ks}A_{ds}G_{ds}T_{ds}G_{ds}A_{ds}G_{ds}A_{ds}{}^mC_{ds}G_{ds}A_{es}G_{es}{}^mC_{ks}A_{k}$ | 22 | 995 |
| 785519 | 2118 | 2133 | 11683 | 11698 | GGAAGTGAGTCTCAAA | $G_{ks}G_{ks}A_{ds}A_{ds}G_{ds}T_{ds}G_{ds}A_{ds}G_{ds}T_{ds}{}^mC_{ds}T_{ds}{}^mC_{ks}A_{es}A_{ks}A_{e}$ | 55 | 1267 |
| 785520 | 2119 | 2134 | 11684 | 11699 | AGGAAGTGAGTCTCAA | $A_{ks}G_{ks}G_{ds}A_{ds}A_{ds}G_{ds}T_{ds}G_{ds}A_{ds}G_{ds}T_{ds}{}^mC_{ds}T_{ks}{}^mC_{es}A_{ks}A_{e}$ | 39 | 208 |
| 785529 | N/A | N/A | 5169 | 5184 | GGAGTGAGACGAGCAA | $G_{ks}G_{ks}A_{ds}G_{ds}T_{ds}G_{ds}A_{ds}G_{ds}A_{ds}{}^mC_{ds}G_{ds}A_{ds}G_{ks}{}^mC_{es}A_{ks}A_{e}$ | 33 | 1268 |
| 785530 | N/A | N/A | 5170 | 5185 | AGGAGTGAGACGAGCA | $A_{ks}G_{ks}G_{ds}A_{ds}G_{ds}T_{ds}G_{ds}A_{ds}G_{ds}A_{ds}{}^mC_{ds}G_{ds}A_{ks}G_{es}{}^mC_{ks}A_{e}$ | 28 | 995 |
| 785561 | 2118 | 2133 | 11683 | 11698 | GGAAGTGAGTCTCAAA | $G_{ks}G_{ks}A_{ds}A_{ds}G_{ds}T_{ds}G_{ds}A_{ds}G_{ds}T_{ds}{}^mC_{es}T_{es}{}^mC_{es}A_{es}A_{ks}A_{k}$ | 34 | 1267 |
| 785567 | N/A | N/A | 5169 | 5184 | GGAGTGAGACGAGCAA | $G_{ks}G_{ks}A_{ds}G_{ds}T_{ds}G_{ds}A_{ds}G_{ds}A_{ds}{}^mC_{ds}G_{ds}A_{es}G_{es}{}^mC_{es}A_{ks}A_{k}$ | 17 | 1268 |
| 785618 | 2117 | 2132 | 11682 | 11697 | GAAGTGAGTCTCAAAC | $G_{ks}A_{ks}A_{ds}G_{ds}T_{ds}G_{ds}A_{ds}G_{ds}T_{ds}{}^mC_{ds}T_{ks}{}^mC_{es}A_{ks}A_{es}A_{ks}{}^mC_{k}$ | 27 | 207 |
| 785619 | 2118 | 2133 | 11683 | 11698 | GGAAGTGAGTCTCAAA | $G_{ks}G_{ks}A_{ds}A_{ds}G_{ds}T_{ds}G_{ds}A_{ds}G_{ds}T_{ds}{}^mC_{ks}T_{es}{}^mC_{ks}A_{es}A_{ks}A_{k}$ | 36 | 1267 |
| 785620 | 2119 | 2134 | 11684 | 11699 | AGGAAGTGAGTCTCAA | $a_{ks}G_{ks}G_{ds}A_{ds}A_{ds}G_{ds}T_{ds}G_{ds}A_{ds}G_{ds}T_{ks}{}^mC_{es}T_{ks}{}^mC_{es}A_{ks}A_{k}$ | 20 | 208 |
| 785632 | N/A | N/A | 5168 | 5183 | GAGTGAGACGAGCAAA | $G_{ks}A_{ks}G_{ds}T_{ds}G_{ds}A_{ds}G_{ds}A_{ds}{}^mC_{ds}G_{ds}A_{ks}G_{es}{}^mC_{ks}A_{es}A_{ks}A_{k}$ | 17 | 1266 |
| 785633 | N/A | N/A | 5169 | 5184 | GGAGTGAGACGAGCAA | $G_{ks}G_{ks}A_{ds}G_{ds}T_{ds}G_{ds}A_{ds}G_{ds}A_{ds}{}^mC_{ds}G_{ds}A_{es}G_{ks}{}^mC_{es}A_{ks}A_{k}$ | 38 | 1268 |

TABLE 23-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785634 | N/A | N/A | 5170 | 5185 | AGGAGTGAGACGAGCA | $A_{ks}G_{ks}G_{ds}A_{ds}G_{ds}T_{ds}G_{ds}A_{ds}G_{ds}A_{ds}{}^mC_{ks}G_{es}A_{ks}G_{es}{}^mC_{ks}A_{k}$ | 35 | 995 |
| 785670 | 2118 | 2133 | 11683 | 11698 | GGAAGTGAGTCTCAAA | $G_{ks}G_{ks}A_{ds}A_{ds}G_{ds}T_{ds}G_{ds}A_{ds}G_{ds}T_{ds}{}^mC_{ds}T_{es}{}^mC_{es}A_{es}A_{ks}A_{k}$ | 32 | 1267 |
| 785676 | N/A | N/A | 5169 | 5184 | GGAGTGAGACGAGCAA | $G_{ks}G_{ks}A_{ds}G_{ds}T_{ds}G_{ds}A_{ds}G_{ds}A_{ds}{}^mC_{ds}G_{ds}A_{es}G_{es}{}^mC_{es}A_{ks}A_{k}$ | 25 | 1268 |
| 785700 | 2118 | 2133 | 11683 | 11698 | GGAAGTGAGTCTCAAA | $G_{ks}G_{ks}A_{ds}A_{ds}G_{ds}T_{ds}G_{ds}A_{ds}G_{ds}T_{ds}{}^mC_{ds}T_{ks}{}^mC_{ds}A_{ks}A_{ds}A_{k}$ | 12 | 1267 |
| 785706 | N/A | N/A | 5169 | 5184 | GGAGTGAGACGAGCAA | $G_{ks}G_{ks}A_{ds}G_{ds}T_{ds}G_{ds}A_{ds}G_{ds}A_{ds}{}^mC_{ds}G_{ds}A_{ks}G_{ds}{}^mC_{ks}A_{ds}A_{k}$ | 16 | 1268 |
| 785744 | 2118 | 2133 | 11683 | 11698 | GGAAGTGAGTCTCAAA | $G_{ks}g_{ks}A_{ds}A_{ds}G_{ds}T_{ds}G_{ds}A_{ds}G_{ds}T_{ds}{}^mC_{ds}T_{ks}{}^mC_{es}A_{ks}A_{es}A_{k}$ | 25 | 1267 |
| 785745 | 2119 | 2134 | 11684 | 11699 | AGGAAGTGAGTCTCAA | $A_{ks}G_{ks}G_{ds}A_{ds}A_{ds}G_{ds}T_{ds}G_{ds}A_{ds}G_{ds}T_{ds}{}^mC_{ks}T_{es}{}^mC_{es}A_{es}A_{k}$ | 42 | 208 |
| 785754 | N/A | N/A | 5169 | 5184 | GGAGTGAGACGAGCAA | $G_{ks}G_{ks}A_{ds}G_{ds}T_{ds}G_{ds}A_{ds}G_{ds}A_{ds}{}^mC_{ds}G_{ds}A_{ks}G_{es}{}^mC_{es}A_{es}A_{k}$ | 27 | 1268 |
| 785755 | N/A | N/A | 5170 | 5185 | AGGAGTGAGACGAGCA | $A_{ks}G_{ks}G_{ds}A_{ds}G_{ds}T_{ds}G_{ds}A_{ds}G_{ds}A_{ds}{}^mC_{ds}G_{ks}A_{es}G_{ks}{}^mC_{es}A_{k}$ | 36 | 995 |
| 785787 | 2119 | 2134 | 11684 | 11699 | AGGAAGTGAGTCTCAA | $A_{ks}G_{ks}G_{ks}A_{ds}A_{ds}G_{ds}T_{ds}G_{ds}A_{ds}G_{ds}T_{ds}{}^mC_{ks}T_{ds}{}^mC_{ks}A_{ds}A_{k}$ | 40 | 208 |
| 785793 | N/A | N/A | 5170 | 5185 | AGGAGTGAGACGAGCA | $A_{ks}G_{ks}G_{ks}A_{ds}G_{ds}T_{ds}G_{ds}A_{ds}G_{ds}A_{ds}{}^mC_{ds}G_{ks}A_{ds}G_{ks}{}^mC_{ds}A_{k}$ | 37 | 995 |
| 785832 | 2118 | 2133 | 11683 | 11698 | GGAAGTGAGTCTCAAA | $G_{ks}G_{ks}A_{ks}A_{ds}G_{ds}T_{ds}G_{ds}A_{ds}G_{ds}T_{ds}{}^mC_{ds}T_{ks}{}^mC_{es}A_{ks}A_{es}A_{k}$ | 45 | 1267 |
| 785833 | 2119 | 2134 | 11684 | 11699 | AGGAAGTGAGTCTCAA | $A_{ks}G_{ks}G_{ks}A_{ds}A_{ds}G_{ds}T_{ds}G_{ds}A_{ds}G_{ds}T_{ds}{}^mC_{ks}T_{es}{}^mC_{es}A_{es}A_{k}$ | 24 | 208 |
| 785842 | N/A | N/A | 5169 | 5184 | GGAGTGAGACGAGCAA | $G_{ks}G_{ks}A_{ks}G_{ds}T_{ds}G_{ds}A_{ds}G_{ds}A_{ds}{}^mC_{ds}G_{ds}A_{ks}G_{es}{}^mC_{ks}A_{es}A_{k}$ | 5 | 1268 |
| 785843 | N/A | N/A | 5170 | 5185 | AGGAGTGAGACGAGCA | $A_{ks}G_{ks}G_{ks}A_{ds}G_{ds}T_{ds}G_{ds}A_{ds}G_{ds}A_{ds}{}^mC_{ds}G_{ks}A_{es}G_{ks}{}^mC_{es}A_{k}$ | 24 | 995 |
| 785875 | 2119 | 2134 | 11684 | 11699 | AGGAAGTGAGTCTCAA | $A_{ks}G_{ks}G_{ks}A_{ds}A_{ds}G_{ds}T_{ds}G_{ds}A_{ds}G_{ds}T_{ds}{}^mC_{ds}T_{ks}{}^mC_{es}A_{ks}A_{e}$ | 21 | 208 |
| 785881 | N/A | N/A | 5170 | 5185 | AGGAGTGAGACGAGCA | $A_{ks}G_{ks}G_{ks}A_{ds}G_{ds}T_{ds}G_{ds}A_{ds}G_{ds}A_{ds}{}^mC_{ds}G_{ds}A_{ks}G_{es}{}^mC_{ks}A_{e}$ | 42 | 995 |
| 785920 | 2118 | 2133 | 11683 | 11698 | GGAAGTGAGTCTCAAA | $G_{ks}G_{ks}A_{ks}A_{ds}G_{ds}T_{ds}G_{ds}A_{ds}G_{ds}T_{ds}{}^mC_{ds}T_{ds}{}^mC_{ks}A_{ks}A_{ks}A_{e}$ | 49 | 1267 |

TABLE 23-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 785921 | 2119 | 2134 | 11684 | 11699 | AGGAAGTGAGTCTCAA | $A_{ks}G_{ks}G_{ks}A_{ds}A_{ds}G_{ds}T_{ds}G_{ds}A_{ds}G_{ds}T_{ds}{}^mC_{ds}T_{ks}{}^mC_{ks}A_{ks}A_e$ | 47 | 208 |
| 785930 | N/A | N/A | 5169 | 5184 | GGAGTGAGACGAGCAA | $G_{ks}G_{ks}A_{ks}G_{ds}T_{ds}A_{ds}G_{ds}A_{ds}{}^mC_{ds}G_{ds}A_{ds}G_{ks}{}^mC_{ks}A_{ks}A_e$ | 33 | 1268 |
| 785931 | N/A | N/A | 5170 | 5185 | AGGAGTGAGACGAGCA | $A_{ks}G_{ks}G_{ks}A_{ds}G_{ds}T_{ds}G_{ds}A_{ds}A_{ds}{}^mC_{ds}G_{ds}A_{ks}G_{ks}{}^mC_{ks}A_e$ | 37 | 995 |
| 785938 | N/A | N/A | 6548 | 6563 | CCAATTTTGCATTCCA | ${}^mC_{ks}{}^mC_{ks}A_{ks}A_{ds}T_{ds}T_{ds}T_{ds}T_{ds}G_{ds}{}^mC_{ds}A_{ds}T_{ds}T_{ks}{}^mC_{ks}{}^mC_{ks}A_e$ | 10 | 1242 |
| 786501 | 2118 | 2133 | 11683 | 11698 | GGAAGTGAGTCTCAAA | $G_{ks}G_{ks}A_{ks}A_{ds}G_{ds}T_{ds}G_{ds}A_{ds}G_{ds}T_{ds}{}^mC_{ds}T_{ds}{}^mC_{ds}A_{ks}A_{ks}A_k$ | 51 | 1267 |
| 786502 | 2120 | 2135 | 11685 | 11700 | GAGGAAGTGAGTCTCA | $G_{ks}A_{ks}G_{ks}G_{ds}A_{ds}A_{ds}G_{ds}T_{ds}G_{ds}A_{ds}G_{ds}T_{ds}{}^mC_{ds}T_{ks}{}^mC_{ks}A_k$ | 0 | 1269 |
| 786503 | 2171 | 2186 | 11736 | 11751 | CTGATATGATACCTAA | ${}^mC_{ks}T_{ks}G_{ks}A_{ds}T_{ds}A_{ds}T_{ds}G_{ds}A_{ds}T_{ds}A_{ds}{}^mC_{ds}{}^mC_{ds}T_{ks}A_{ks}A_k$ | 59 | 1270 |
| 786504 | 2173 | 2188 | 11738 | 11753 | ATCTGATATGATACCT | $A_{ks}T_{ks}{}^mC_{ks}T_{ds}G_{ds}A_{ds}T_{ds}A_{ds}T_{ds}G_{ds}A_{ds}T_{ds}A_{ds}{}^mC_{ks}{}^mC_{ks}T_k$ | 36 | 1271 |
| 786524 | N/A | N/A | 5141 | 5156 | ACGAGTTATGGGAAGG | $A_{ks}{}^mC_{ks}G_{ks}A_{ds}G_{ds}T_{ds}T_{ds}A_{ds}T_{ds}G_{ds}G_{ds}G_{ds}A_{ds}A_{ks}G_{ks}G_k$ | 74 | 1272 |
| 786525 | N/A | N/A | 5143 | 5158 | GGACGAGTTATGGGAA | $G_{ks}G_{ks}A_{ks}{}^mC_{ds}G_{ds}A_{ds}G_{ds}T_{ds}T_{ds}A_{ds}T_{ds}G_{ds}G_{ds}G_{ks}A_{ks}A_k$ | 37 | 1273 |
| 786526 | N/A | N/A | 5145 | 5160 | TAGGACGAGTTATGGG | $T_{ks}A_{ks}G_{ks}G_{ds}A_{ds}{}^mC_{ds}G_{ds}A_{ds}G_{ds}T_{ds}T_{ds}A_{ds}T_{ds}G_{ks}G_{ks}G_k$ | 25 | 1274 |
| 786527 | N/A | N/A | 5147 | 5162 | AGTAGGACGAGTTATG | $A_{ks}G_{ks}T_{ks}A_{ds}G_{ds}G_{ds}A_{ds}{}^mC_{ds}G_{ds}A_{ds}G_{ds}T_{ds}T_{ds}A_{ks}T_{ks}G_k$ | 0 | 1275 |
| 786528 | N/A | N/A | 5149 | 5164 | TGAGTAGGACGAGTTA | $T_{ks}G_{ks}A_{ks}G_{ds}T_{ds}A_{ds}G_{ds}G_{ds}A_{ds}{}^mC_{ds}G_{ds}A_{ds}G_{ds}T_{ks}T_{ks}A_k$ | 18 | 1276 |
| 786529 | N/A | N/A | 5151 | 5166 | GGTGAGTAGGACGAGT | $G_{ks}G_{ks}T_{ks}G_{ds}A_{ds}G_{ds}T_{ds}A_{ds}G_{ds}G_{ds}A_{ds}{}^mC_{ds}G_{ds}A_{ks}G_{ks}T_k$ | 48 | 1277 |
| 786530 | N/A | N/A | 5153 | 5 168 | AGGGTGAGTAGGACGA | $A_{ks}G_{ks}G_{ks}G_{ds}T_{ds}G_{ds}A_{ds}G_{ds}T_{ds}A_{ds}G_{ds}G_{ds}A_{ds}{}^mC_{ks}G_{ks}A_k$ | 19 | 1278 |
| 786531 | N/A | N/A | 5155 | 5170 | AAAGGGTGAGTAGGAC | $A_{ks}A_{ks}A_{ks}G_{ds}G_{ds}G_{ds}T_{ds}G_{ds}A_{ds}G_{ds}T_{ds}A_{ds}G_{ds}G_{ks}A_{ks}{}^mC_k$ | 24 | 1279 |
| 786532 | N/A | N/A | 5157 | 5172 | GCAAAGGGTGAGTAGG | $G_{ks}{}^mC_{ks}A_{ks}A_{ds}A_{ds}G_{ds}G_{ds}G_{ds}T_{ds}G_{ds}A_{ds}G_{ds}T_{ds}A_{ks}G_{ks}G_k$ | 24 | 1280 |
| 786533 | N/A | N/A | 5159 | 5174 | GAGCAAAGGGTGAGTA | $G_{ks}A_{ks}G_{ks}{}^mC_{ds}A_{ds}A_{ds}A_{ds}G_{ds}G_{ds}G_{ds}T_{ds}G_{ds}A_{ds}G_{ks}T_{ks}A_k$ | 0 | 1281 |

TABLE 23-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | (% Inhibition) | SEQ ID NO |
|---|---|---|---|---|---|---|---|---|
| 786534 | N/A | N/A | 5161 | 5176 | ACGAGCAAAGGGTGAG | $A_{ks}{}^mC_{ks}G_{ks}A_{ds}G_{ds}{}^mC_{ds}A_{ds}A_{ds}A_{ds}G_{ds}G_{ds}G_{ds}T_{ds}G_{ks}A_{ks}G_k$ | 47 | 1282 |
| 786535 | N/A | N/A | 5163 | 5178 | AGACGAGCAAAGGGTG | $A_{ks}G_{ks}A_{ks}{}^mC_{ds}G_{ds}A_{ds}G_{ds}{}^mC_{ds}A_{ds}A_{ds}A_{ds}G_{ds}G_{ds}G_{ks}T_{ks}G_k$ | 35 | 1283 |
| 786536 | N/A | N/A | 5164 | 5179 | GAGACGAGCAAAGGGT | $G_{ks}A_{ks}G_{ks}A_{ds}{}^mC_{ds}G_{ds}A_{ds}G_{ds}{}^mC_{ds}A_{ds}A_{ds}A_{ds}G_{ds}G_{ks}G_{ks}T_k$ | 40 | 1284 |
| 786537 | N/A | N/A | 5165 | 5180 | TGAGACGAGCAAAGGG | $T_{ks}G_{ks}A_{ks}G_{ds}A_{ds}{}^mC_{ds}G_{ds}A_{ds}G_{ds}{}^mC_{ds}A_{ds}A_{ds}A_{ds}G_{ks}G_{ks}G_k$ | 22 | 1285 |
| 786538 | N/A | N/A | 5166 | 5181 | GTGAGACGAGCAAAGG | $G_{ks}T_{ks}G_{ks}A_{ds}G_{ds}A_{ds}{}^mC_{ds}G_{ds}A_{ds}G_{ds}{}^mC_{ds}A_{ds}A_{ds}A_{ks}G_{ks}G_k$ | 49 | 1286 |
| 786539 | N/A | N/A | 5167 | 5182 | AGTGAGACGAGCAAAG | $A_{ks}G_{ks}T_{ks}G_{ds}A_{ds}G_{ds}A_{ds}{}^mC_{ds}G_{ds}A_{ds}G_{ds}{}^mC_{ds}A_{ds}A_{ks}A_{ks}G_k$ | 16 | 1287 |
| 786540 | N/A | N/A | 5168 | 5183 | GAGTGAGACGAGCAAA | $G_{ks}A_{ks}G_{ks}T_{ds}G_{ds}A_{ds}G_{ds}A_{ds}{}^mC_{ds}G_{ds}A_{ds}G_{ds}{}^mC_{ds}A_{ks}A_{ks}A_k$ | 27 | 1266 |
| 786541 | N/A | N/A | 5169 | 5184 | GGAGTGAGACGAGCAA | $G_{ks}G_{ks}A_{ks}G_{ds}T_{ds}G_{ds}A_{ds}G_{ds}A_{ds}{}^mC_{ds}G_{ds}A_{ds}G_{ds}{}^mC_{ks}A_{ks}A_k$ | 37 | 1268 |
| 786542 | N/A | N/A | 5171 | 5186 | TAGGAGTGAGACGAGC | $T_{ks}A_{ks}G_{ks}G_{ds}A_{ds}G_{ds}T_{ds}G_{ds}A_{ds}G_{ds}A_{ds}{}^mC_{ds}G_{ds}A_{ks}G_{ks}{}^mC_k$ | 1 | 1288 |
| 786543 | N/A | N/A | 5172 | 5187 | ATAGGAGTGAGACGAG | $A_{ks}T_{ks}A_{ks}G_{ds}G_{ds}A_{ds}G_{ds}T_{ds}G_{ds}A_{ds}G_{ds}A_{ds}{}^mC_{ds}G_{ks}A_{ks}G_k$ | 16 | 1289 |
| 786544 | N/A | N/A | 5173 | 5188 | AATAGGAGTGAGACGA | $A_{ks}A_{ks}T_{ks}A_{ds}G_{ds}G_{ds}A_{ds}G_{ds}T_{ds}G_{ds}A_{ds}G_{ds}A_{ds}{}^mC_{ks}G_{ks}A_k$ | 25 | 1290 |
| 786545 | N/A | N/A | 5174 | 5189 | TAATAGGAGTGAGACG | $T_{ks}A_{ks}A_{ks}T_{ds}A_{ds}G_{ds}G_{ds}A_{ds}G_{ds}T_{ds}G_{ds}A_{ds}G_{ds}A_{ks}{}^mC_{ks}G_k$ | 12 | 1291 |
| 786546 | N/A | N/A | 5175 | 5190 | GTAATAGGAGTGAGAC | $G_{ks}T_{ks}A_{ks}A_{ds}T_{ds}A_{ds}G_{ds}G_{ds}A_{ds}G_{ds}T_{ds}G_{ds}A_{ds}G_{ks}A_{ks}{}^mC_k$ | 11 | 1292 |
| 786547 | N/A | N/A | 5177 | 5192 | GAGTAATAGGAGTGAG | $G_{ks}A_{ks}G_{ks}T_{ds}A_{ds}A_{ds}T_{ds}A_{ds}G_{ds}G_{ds}A_{ds}G_{ds}T_{ds}G_{ks}A_{ks}G_k$ | 33 | 1293 |
| 786548 | N/A | N/A | 5179 | 5194 | ATGAGTAATAGGAGTG | $A_{ks}T_{ks}G_{ks}A_{ds}G_{ds}T_{ds}A_{ds}A_{ds}T_{ds}A_{ds}G_{ds}G_{ds}A_{ds}G_{ks}T_{ks}G_k$ | 56 | 1294 |
| 786549 | N/A | N/A | 5181 | 5196 | TCATGAGTAATAGGAG | $T_{ks}{}^mC_{ks}A_{ks}T_{ds}G_{ds}A_{ds}G_{ds}T_{ds}A_{ds}A_{ds}T_{ds}A_{ds}G_{ds}G_{ks}A_{ks}G_k$ | 11 | 1295 |
| 786550 | N/A | N/A | 5183 | 5198 | CCTCATGAGTAATAGG | ${}^mC_{ks}{}^mC_{ks}T_{ks}{}^mC_{ds}A_{ds}T_{ds}G_{ds}A_{ds}G_{ds}T_{ds}A_{ds}A_{ds}T_{ds}A_{ks}G_{ks}G_k$ | 0 | 1296 |

TABLE 24

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 665892 | 1227 | 1242 | 10460 | 10475 | CACTGACACAGGCGGA | $^mC_{ks}A_{ks}{}^mC_{ks}T_{ds}G_{ds}A_{ds}{}^mC_{ds}A_{ds}{}^mC_{ds}A_{ds}G_{ds}G_{ds}{}^mC_{ds}G_{ks}G_{ks}A_k$ | 0 | 387 |
| 665893 | 1228 | 1243 | 10461 | 10476 | GCACTGACACAGGCGG | $G_{ks}{}^mC_{ks}A_{ks}{}^mC_{ds}T_{ds}G_{ds}A_{ds}{}^mC_{ds}A_{ds}{}^mC_{ds}A_{ds}G_{ds}G_{ds}{}^mC_{ks}G_{ks}G_k$ | 0 | 39 |
| 728466 | 427 | 442 | 8320 | 8335 | GGTGTATTTCCCTGTC | $G_{ks}G_{ks}T_{ks}G_{ds}T_{ds}A_{ds}T_{ds}T_{ds}T_{ds}{}^mC_{ds}{}^mC_{ds}{}^mC_{ds}T_{ds}G_{ks}T_{ks}{}^mC_k$ | 27 | 1254 |
| 728489 | 484 | 499 | 8277 | 8392 | AAGGGCACAGCGCAGG | $A_{ks}A_{ks}G_{ks}G_{ds}G_{ds}{}^mC_{ds}A_{ds}{}^mC_{ds}A_{ds}G_{ds}{}^mC_{ds}G_{ds}{}^mC_{ds}A_{ks}G_{ks}G_k$ | 42 | 1249 |
| 728670 | 1230 | 1245 | 10463 | 10478 | TTGCACTGACACAGGC | $T_{ks}T_{ks}G_{ks}{}^mC_{ds}A_{ds}{}^mC_{ds}T_{ds}G_{ds}A_{ds}{}^mC_{ds}A_{ds}{}^mC_{ds}A_{ds}G_{ks}G_{ks}{}^mC_k$ | 21 | 398 |
| 728707 | 1307 | 1322 | 10540 | 10555 | GCTTGGTCTTGACCTC | $G_{ks}{}^mC_{ks}T_{ks}T_{ds}G_{ds}G_{ds}T_{ds}{}^mC_{ds}T_{ds}T_{ds}G_{ds}A_{ds}{}^mC_{ds}{}^mC_{ks}T_{ks}{}^mC_k$ | 52 | 435 |
| 728708 | 1308 | 1323 | 10541 | 10556 | AGCTTGGTCTTGACCT | $A_{ks}G_{ks}{}^mC_{ks}T_{ds}T_{ds}G_{ds}G_{ds}T_{ds}{}^mC_{ds}T_{ds}T_{ds}G_{ds}A_{ds}{}^mC_{ks}{}^mC_{ks}T_k$ | 40 | 436 |
| 728958 | 1979 | 1994 | 11544 | 11559 | CCTATACAGCTAGGCC | $^mC_{ks}{}^mC_{ks}T_{ks}A_{ds}T_{ds}A_{ds}{}^mC_{ds}A_{ds}G_{ds}{}^mC_{ds}T_{ds}A_{ds}G_{ds}G_{ks}{}^mC_{ks}{}^mC_k$ | 0 | 168 |
| 729037 | 2216 | 2231 | 11781 | 11796 | GGTTCTTGGACTCTCA | $G_{ks}G_{ks}T_{ks}T_{ds}{}^mC_{ds}T_{ds}T_{ds}G_{ds}G_{ds}A_{ds}{}^mC_{ds}T_{ds}{}^mC_{ds}T_{ks}{}^mC_{ks}A_k$ | 68 | 706 |
| 729494 | N/A | N/A | 6958 | 6973 | GAATTTGTGACTGTA | $G_{ks}A_{ks}A_{ds}T_{ds}T_{ds}T_{ds}G_{ds}T_{ds}G_{ds}A_{ds}{}^mC_{ds}T_{ds}G_{ks}T_{ks}A_k$ | 57 | 1065 |
| 729495 | N/A | N/A | 6981 | 6996 | ACCATTCTATGCCTTT | $A_{ks}{}^mC_{ks}{}^mC_{ks}A_{ds}T_{ds}T_{ds}{}^mC_{ds}T_{ds}A_{ds}T_{ds}G_{ds}{}^mC_{ds}{}^mC_{ds}T_{ks}T_{ks}T_k$ | 70 | 1066 |
| 785352 | 1225 | 1240 | 10458 | 10473 | CTGACACAGGCGGATG | $^mC_{ks}T_{ds}G_{ds}A_{ds}{}^mC_{ds}A_{ds}{}^mC_{ds}A_{ds}G_{ds}G_{ds}{}^mC_{ds}G_{ks}G_{es}A_{ks}T_{es}G_k$ | 0 | 1297 |
| 785353 | 1227 | 1242 | 10460 | 10475 | CACTGACACAGGCGGA | $^mC_{ks}A_{ds}{}^mC_{ds}T_{ds}G_{ds}A_{ds}{}^mC_{ds}A_{ds}{}^mC_{ds}A_{ds}G_{ds}G_{ds}{}^mC_{es}G_{ks}G_{es}A_k$ | 0 | 387 |
| 785396 | N/A | N/A | 6979 | 6994 | CATTCTATGCCTTTTA | $^mC_{ks}A_{ds}T_{ds}T_{ds}{}^mC_{ds}T_{ds}A_{ds}T_{ds}G_{ds}{}^mC_{ds}{}^mC_{ds}T_{ks}T_{es}T_{ks}T_{es}A_k$ | 37 | 1298 |
| 785397 | N/A | N/A | 6981 | 6996 | ACCATTCTATGCCTTT | $A_{ks}{}^mC_{ds}{}^mC_{ds}A_{ds}T_{ds}T_{ds}{}^mC_{ds}T_{ds}A_{ds}T_{ds}G_{ks}{}^mC_{es}{}^mC_{ks}T_{es}T_{ks}T_k$ | 0 | 1066 |
| 785407 | 1225 | 1240 | 10458 | 10473 | CTGACACAGGCGGATG | $^mC_{ks}T_{ds}G_{ds}A_{ds}{}^mC_{ds}A_{ds}{}^mC_{ds}A_{ds}G_{ds}G_{ds}{}^mC_{ks}G_{es}G_{ks}A_{es}T_{ks}G_e$ | 0 | 1297 |
| 785408 | 1227 | 1242 | 10460 | 10475 | CACTGACACAGGCGGA | $^mC_{ks}A_{ds}{}^mC_{ds}T_{ds}G_{ds}A_{ds}{}^mC_{ds}A_{ds}{}^mC_{ds}A_{ds}G_{ks}G_{es}{}^mC_{ks}G_{es}G_{ks}A_e$ | 0 | 387 |
| 785451 | N/A | N/A | 6979 | 6994 | CATTCTATGCCTTTTA | $^mC_{ks}A_{ds}T_{ds}T_{ds}{}^mC_{ds}T_{ds}A_{ds}T_{ds}G_{ds}{}^mC_{ds}{}^mC_{ks}T_{es}T_{ks}T_{es}T_{ks}A_e$ | 13 | 1298 |
| 785452 | N/A | N/A | 6981 | 6996 | ACCATTCTATGCCTTT | $A_{ks}{}^mC_{ds}{}^mC_{ds}A_{ds}T_{ds}T_{ds}{}^mC_{ds}T_{ds}A_{ds}T_{ds}G_{ks}{}^mC_{es}{}^mC_{ks}T_{es}T_{ks}T_e$ | 10 | 1066 |
| 785461 | 1227 | 1242 | 10460 | 10475 | CACTGACACAGGCGGA | $^mC_{ks}A_{es}{}^mC_{ks}T_{ds}G_{ds}A_{ds}{}^mC_{ds}A_{ds}{}^mC_{ds}A_{ds}G_{ds}G_{ds}{}^mC_{es}G_{ks}G_{es}A_k$ | 0 | 387 |
| 785486 | N/A | N/A | 6981 | 6996 | ACCATTCTATGCCTTT | $A_{ks}{}^mC_{es}{}^mC_{ks}A_{ds}T_{ds}T_{ds}{}^mC_{ds}T_{ds}A_{ds}T_{ds}G_{ds}{}^mC_{ds}{}^mC_{es}T_{es}T_{ks}T_k$ | 51 | 1066 |
| 785496 | 1226 | 1242 | 10459 | 10474 | ACTGACACAGGCGGAT | $A_{ks}{}^mC_{ks}T_{ds}G_{ds}A_{ds}{}^mC_{ds}A_{ds}{}^mC_{ds}A_{ds}G_{ds}G_{ds}{}^mC_{ds}G_{es}G_{ks}A_{ks}T_e$ | 0 | 397 |
| 785497 | 1227 | 1242 | 10460 | 10475 | CACTGACACAGGCGGA | $^mC_{ks}A_{ks}{}^mC_{ds}T_{ds}G_{ds}A_{ds}{}^mC_{ds}A_{ds}{}^mC_{ds}A_{ds}G_{ds}G_{ds}{}^mC_{es}G_{es}G_{ks}A_e$ | 0 | 387 |
| 785539 | N/A | N/A | 6980 | 6995 | CCATTCTATGCCTTTT | $^mC_{ks}{}^mC_{ks}A_{ds}T_{ds}T_{ds}{}^mC_{ds}T_{ds}A_{ds}T_{ds}G_{ds}{}^mC_{ds}{}^mC_{ds}T_{ks}T_{es}T_{ks}T_e$ | 61 | 1299 |

TABLE 24-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 785504 | N/A | N/A | 6981 | 6996 | ACCATTCTATGCCTTT | $A_{ks}{}^mC_{ks}{}^mC_{ds}A_{ds}T_{ds}T_{ds}{}^mC_{ds}T_{ds}A_{ds}T_{ds}G_{ds}{}^mC_{ds}{}^mC_{ks}T_{es}T_{ks}T_{e}$ | 51 | 1066 |
| 785548 | 1226 | 1241 | 10459 | 10474 | ACTGACACAGGCGGAT | $A_{ks}{}^mC_{ks}T_{ds}G_{ds}A_{ds}{}^mC_{ds}A_{ds}{}^mC_{ds}A_{ds}G_{ds}G_{es}{}^mC_{es}G_{es}G_{es}A_{ks}T_{k}$ | 0 | 397 |
| 785572 | N/A | N/A | 6980 | 6995 | CCATTCTATGCCTTTT | ${}^mC_{ks}{}^mC_{ks}A_{ds}T_{ds}T_{ds}{}^mC_{ds}T_{ds}A_{ds}T_{ds}G_{ds}{}^mC_{es}{}^mC_{es}T_{es}T_{es}T_{ks}T_{k}$ | 17 | 1299 |
| 785585 | 1225 | 1240 | 10458 | 10473 | CTGACACAGGCGGATG | ${}^mC_{ks}T_{ks}G_{ds}A_{ds}{}^mC_{ds}A_{ds}{}^mC_{ds}A_{ds}G_{ds}G_{ds}{}^mC_{ks}G_{es}G_{ks}A_{es}T_{ks}G_{k}$ | 0 | 1297 |
| 785586 | 1226 | 1241 | 10459 | 10474 | ACTGACACAGGCGGAT | $A_{ks}{}^mC_{ks}T_{ds}G_{ds}A_{ds}{}^mC_{ds}A_{ds}{}^mC_{ds}A_{ds}G_{ds}G_{ks}{}^mC_{es}G_{es}G_{es}A_{ks}T_{k}$ | 0 | 397 |
| 785587 | 1227 | 1242 | 10460 | 10475 | CACTGACACAGGCGGA | ${}^mC_{ks}A_{ks}{}^mC_{ds}T_{ds}G_{ds}A_{ds}{}^mC_{ds}A_{ds}{}^mC_{ds}A_{ds}G_{ds}G_{ks}{}^mC_{ks}G_{es}G_{ks}A_{k}$ | 0 | 387 |
| 785645 | N/A | N/A | 6979 | 6994 | CATTCTATGCCTTTTA | ${}^mC_{ks}A_{ks}T_{ds}T_{ds}{}^mC_{ds}T_{ds}A_{ds}T_{ds}G_{ds}{}^mC_{ds}{}^mC_{ks}T_{es}T_{ks}T_{es}T_{ks}A_{k}$ | 56 | 1298 |
| 785646 | N/A | N/A | 6980 | 6995 | CCATTCTATGCCTTTT | ${}^mC_{ks}{}^mC_{ks}A_{ds}T_{ds}T_{ds}{}^mC_{ds}T_{ds}A_{ds}T_{ds}G_{ds}{}^mC_{ks}{}^mC_{es}T_{ks}T_{es}T_{ks}T_{k}$ | 3 | 1299 |
| 785647 | N/A | N/A | 6981 | 6996 | ACCATTCTATGCCTTT | $A_{ks}{}^mC_{ks}{}^mC_{ds}A_{ds}T_{ds}T_{ds}{}^mC_{ds}T_{ds}A_{ds}T_{ds}G_{ks}{}^mC_{es}{}^mC_{ks}T_{es}T_{ks}T_{k}$ | 0 | 1066 |
| 785657 | 1226 | 1241 | 10459 | 10474 | ACTGACACAGGCGGAT | $A_{ks}{}^mC_{ks}T_{ds}G_{ds}A_{ds}{}^mC_{ds}A_{ds}{}^mC_{ds}A_{ds}G_{ds}G_{ds}{}^mC_{es}G_{es}G_{es}A_{ks}T_{k}$ | 0 | 397 |
| 785681 | N/A | N/A | 6980 | 6995 | CCATTCTATGCCTTTT | ${}^mC_{ks}{}^mC_{ks}A_{ds}T_{ds}T_{ds}{}^mC_{ds}T_{ds}A_{ds}T_{ds}G_{ds}{}^mC_{ds}{}^mC_{es}T_{es}T_{es}T_{ks}T_{k}$ | 50 | 1299 |
| 785687 | 1226 | 1241 | 10459 | 10474 | ACTGACACAGGCGGAT | $A_{ks}{}^mC_{ks}T_{ds}G_{ds}A_{ds}{}^mC_{ds}A_{ds}{}^mC_{ds}A_{ds}G_{ds}G_{ds}{}^mC_{ks}G_{ds}G_{ks}A_{ds}T_{k}$ | 6 | 397 |
| 785711 | N/A | N/A | 6980 | 6995 | CCATTCTATGCCTTTT | ${}^mC_{ks}{}^mC_{ks}A_{ds}T_{ds}T_{ds}{}^mC_{ds}T_{ds}A_{ds}T_{ds}G_{ds}{}^mC_{ds}{}^mC_{ks}T_{ds}T_{ks}T_{ds}T_{k}$ | 46 | 1299 |
| 785721 | 1226 | 1241 | 10459 | 10474 | ACTGACACAGGCGGAT | $A_{ks}{}^mC_{ks}T_{ds}G_{ds}A_{ds}{}^mC_{ds}A_{ds}{}^mC_{ds}A_{ds}G_{ds}G_{ds}{}^mC_{ks}G_{es}G_{ks}A_{es}T_{k}$ | 0 | 397 |
| 785722 | 1227 | 1242 | 10460 | 10475 | CACTGACACAGGCGGA | ${}^mC_{ks}A_{ks}{}^mC_{ds}T_{ds}G_{ds}A_{ds}{}^mC_{ds}A_{ds}{}^mC_{ds}A_{ds}G_{ds}G_{ks}{}^mC_{es}G_{ks}G_{es}A_{k}$ | 0 | 387 |
| 785764 | N/A | N/A | 6980 | 6995 | CCATTCTATGCCTTTT | ${}^mC_{ks}{}^mC_{ks}A_{ds}T_{ds}T_{ds}{}^mC_{ds}T_{ds}A_{ds}T_{ds}G_{ds}{}^mC_{ds}{}^mC_{ks}T_{es}T_{ks}T_{es}T_{k}$ | 62 | 1299 |
| 785765 | N/A | N/A | 6981 | 6996 | ACCATTCTATGCCTTT | $A_{ks}{}^mC_{ks}{}^mC_{ds}A_{ds}T_{ds}T_{ds}{}^mC_{ds}T_{ds}A_{ds}T_{ds}G_{ds}{}^mC_{ks}{}^mC_{es}T_{ks}T_{es}T_{k}$ | 40 | 1066 |
| 785774 | 1227 | 1242 | 10460 | 10475 | CACTGACACAGGCGGA | ${}^mC_{ks}A_{ks}{}^mC_{ks}T_{ds}G_{ds}A_{ds}{}^mC_{ds}A_{ds}{}^mC_{ds}A_{ds}G_{ds}G_{ks}{}^mC_{ds}G_{ks}G_{ds}A_{k}$ | 0 | 387 |
| 785799 | N/A | N/A | 6981 | 6996 | ACCATTCTATGCCTTT | $A_{ks}{}^mC_{ks}{}^mC_{ks}A_{ds}T_{ds}T_{ds}{}^mC_{ds}T_{ds}A_{ds}T_{ds}G_{ds}{}^mC_{ks}{}^mC_{ds}T_{ks}T_{ds}T_{k}$ | 11 | 1066 |
| 785809 | 1226 | 1241 | 10459 | 10474 | ACTGACACAGGCGGAT | $A_{ks}{}^mC_{ks}T_{ks}G_{ds}A_{ds}{}^mC_{ds}A_{ds}{}^mC_{ds}A_{ds}G_{ds}G_{ds}{}^mC_{ks}G_{es}G_{ks}A_{es}T_{k}$ | 0 | 397 |
| 785810 | 1227 | 1242 | 10460 | 10475 | CACTGACACAGGCGGA | ${}^mC_{ks}A_{ks}{}^mC_{ks}T_{ds}G_{ds}A_{ds}{}^mC_{ds}A_{ds}{}^mC_{ds}A_{ds}G_{ds}G_{ks}{}^mC_{ks}G_{es}G_{es}A_{k}$ | 0 | 387 |
| 785852 | N/A | N/A | 6980 | 6995 | CCATTCTATGCCTTTT | ${}^mC_{ks}{}^mC_{ks}A_{ks}T_{ds}T_{ds}{}^mC_{ds}T_{ds}A_{ds}T_{ds}G_{ds}{}^mC_{ds}{}^mC_{ks}T_{es}T_{ks}T_{es}T_{k}$ | 44 | 1299 |
| 785853 | N/A | N/A | 6981 | 6996 | ACCATTCTATGCCTTT | $A_{ks}{}^mC_{ks}{}^mC_{ks}A_{ds}T_{ds}T_{ds}{}^mC_{ds}T_{ds}A_{ds}T_{ds}G_{ds}{}^mC_{ks}{}^mC_{es}T_{ks}T_{es}T_{k}$ | 15 | 1066 |
| 785862 | 1227 | 1242 | 10460 | 10475 | CACTGACACAGGCGGA | ${}^mC_{ks}A_{ks}{}^mC_{ks}T_{ds}G_{ds}A_{ds}{}^mC_{ds}A_{ds}{}^mC_{ds}A_{ds}G_{ds}G_{ds}{}^mC_{ks}G_{es}G_{ks}A_{e}$ | 0 | 387 |

TABLE 24-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 785887 | N/A | N/A | 6981 | 6996 | ACCATTCTATGCCTTT | $A_{ks}{}^mC_{ks}{}^mC_{ks}A_{ds}T_{ds}T_{ds}{}^mC_{ds}T_{ds}A_{ds}T_{ds}G_{ds}{}^mC_{ds}{}^mC_{ks}T_{es}T_{ks}T_e$ | 49 | 1066 |
| 785897 | 1226 | 1241 | 10459 | 10474 | ACTGACACAGGCGGAT | $A_{ks}{}^mC_{ks}T_{ks}G_{ds}A_{ds}{}^mC_{ds}A_{ds}{}^mC_{ds}A_{ds}G_{ds}G_{ds}{}^mC_{ds}G_{ks}G_{ks}A_{ks}T_e$ | 0 | 397 |
| 785898 | 1227 | 1242 | 10460 | 10475 | CACTGACACAGGCGGA | ${}^mC_{ks}A_{ks}{}^mC_{ks}T_{ds}G_{ds}A_{ds}{}^mC_{ds}A_{ds}{}^mC_{ds}A_{ds}G_{ds}G_{ds}{}^mC_{ks}G_{ks}G_{ks}A_e$ | 0 | 387 |
| 785938 | N/A | N/A | 6548 | 6563 | CCAATTTTGCATTCCA | ${}^mC_{ks}{}^mC_{ks}A_{ks}A_{ds}T_{ds}T_{ds}T_{ds}T_{ds}G_{ds}{}^mC_{ds}A_{ds}T_{ds}T_{ks}{}^mC_{ks}{}^mC_{ks}A_e$ | 0 | 1242 |
| 785940 | N/A | N/A | 6980 | 6995 | CCATTCTATGCCTTTT | ${}^mC_{ks}{}^mC_{ks}A_{ks}T_{ds}T_{ds}{}^mC_{ds}T_{ds}A_{ds}T_{ds}G_{ds}{}^mC_{ds}{}^mC_{ds}T_{ks}T_{ks}T_{ks}T_e$ | 58 | 1299 |
| 785941 | N/A | N/A | 6981 | 6996 | ACCATTCTATGCCTTT | $A_{ks}{}^mC_{ks}{}^mC_{ks}A_{ds}T_{ds}T_{ds}{}^mC_{ds}T_{ds}A_{ds}T_{ds}G_{ds}{}^mC_{ds}{}^mC_{ks}T_{ks}T_{ks}T_e$ | 59 | 1066 |
| 786551 | N/A | N/A | 6979 | 6994 | CATTCTATGCCTTTTA | ${}^mC_{ks}A_{ks}T_{ks}T_{ds}{}^mC_{ds}T_{ds}A_{ds}T_{ds}G_{ds}{}^mC_{ds}{}^mC_{ds}T_{ds}T_{ds}T_{ks}T_{ks}A_k$ | 24 | 1298 |
| 786552 | N/A | N/A | 6980 | 6995 | CCATTCTATGCCTTTT | ${}^mC_{ks}{}^mC_{ks}A_{ks}T_{ds}T_{ds}{}^mC_{ds}T_{ds}A_{ds}T_{ds}G_{ds}{}^mC_{ds}{}^mC_{ds}T_{ks}T_{ks}T_{ks}T_k$ | 43 | 1299 |
| 785663 | N/A | N/A | 6982 | 6997 | AACCATTCTATGCCTT | $A_{ks}A_{ks}{}^mC_{ks}{}^mC_{ds}A_{ds}T_{ds}T_{ds}{}^mC_{ds}T_{ds}A_{ds}T_{ds}G_{ds}{}^mC_{ds}{}^mC_{ks}T_{ks}T_k$ | 33 | 1300 |
| 786554 | N/A | N/A | 6983 | 6998 | AAACCATTCTATGCCT | $A_{ks}A_{ks}A_{ks}{}^mC_{ds}{}^mC_{ds}A_{ds}T_{ds}T_{ds}{}^mC_{ds}T_{ds}A_{ds}T_{ds}G_{ds}{}^mC_{ks}{}^mC_{ks}T_k$ | 0 | 1301 |
| 786555 | N/A | N/A | 6984 | 6999 | TAAACCATTCTATGCC | $T_{ks}A_{ks}A_{ks}A_{ds}{}^mC_{ds}{}^mC_{ds}A_{ds}T_{ds}T_{ds}{}^mC_{ds}T_{ds}A_{ds}T_{ds}G_{ks}{}^mC_{ks}{}^mC_k$ | 9 | 1302 |
| 786556 | N/A | N/A | 6985 | 7000 | CTAAACCATTCTATGC | ${}^mC_{ks}T_{ks}A_{ks}A_{ds}A_{ds}{}^mC_{ds}{}^mC_{ds}A_{ds}T_{ds}T_{ds}{}^mC_{ds}T_{ds}A_{ds}T_{ks}G_{ks}{}^mC_k$ | 0 | 1303 |
| 786557 | N/A | N/A | 6987 | 7002 | CTCTAAACCATTCTAT | ${}^mC_{ks}T_{ks}{}^mC_{ks}T_{ds}A_{ds}A_{ds}A_{ds}{}^mC_{ds}{}^mC_{ds}A_{ds}T_{ds}T_{ds}{}^mC_{ds}T_{ks}A_{ks}T_k$ | 0 | 1304 |
| 786558 | N/A | N/A | 6989 | 7004 | TGCTCTAAACCATTCT | $T_{ks}G_{ks}{}^mC_{ks}T_{ds}{}^mC_{ds}T_{ds}A_{ds}A_{ds}A_{ds}{}^mC_{ds}{}^mC_{ds}A_{ds}T_{ds}T_{ks}{}^mC_{ks}T_k$ | 0 | 1305 |
| 786559 | N/A | N/A | 6991 | 7006 | TTTGCTCTAAACCATT | $T_{ks}T_{ks}T_{ks}G_{ds}{}^mC_{ds}T_{ds}{}^mC_{ds}T_{ds}A_{ds}A_{ds}A_{ds}{}^mC_{ds}{}^mC_{ds}A_{ks}T_{ks}T_k$ | 2 | 1306 |
| 786560 | N/A | N/A | 6994 | 7009 | CTTTTTGCTCTAAACC | ${}^mC_{ks}T_{ks}T_{ks}T_{ds}T_{ds}T_{ds}G_{ds}{}^mC_{ds}T_{ds}{}^mC_{ds}T_{ds}A_{ds}A_{ds}A_{ks}{}^mC_{ks}{}^mC_k$ | 0 | 1307 |
| 786561 | N/A | N/A | 6997 | 7012 | AGACTTTTGCTCTAA | $A_{ks}G_{ks}A_{ks}{}^mC_{ds}T_{ds}T_{ds}T_{ds}T_{ds}G_{ds}{}^mC_{ds}T_{ds}{}^mC_{ds}T_{ks}A_{ks}A_k$ | 0 | 1308 |
| 786587 | N/A | N/A | 6948 | 6963 | ACTGTATTACCTATAC | $A_{ks}{}^mC_{ks}T_{ks}G_{ds}T_{ds}A_{ds}T_{ds}T_{ds}A_{ds}{}^mC_{ds}{}^mC_{ds}T_{ds}A_{ds}T_{ks}A_{ks}{}^mC_k$ | 22 | 1309 |
| 786588 | N/A | N/A | 6949 | 6964 | GACTGTATTACCTATA | $G_{ks}A_{ks}{}^mC_{ks}T_{ds}G_{ds}T_{ds}A_{ds}T_{ds}T_{ds}A_{ds}{}^mC_{ds}{}^mC_{ds}T_{ds}A_{ks}T_{ks}A_k$ | 41 | 1310 |
| 786589 | N/A | N/A | 6950 | 6965 | TGACTGTATTACCTAT | $T_{ks}G_{ks}A_{ks}{}^mC_{ds}T_{ds}G_{ds}T_{ds}A_{ds}T_{ds}T_{ds}A_{ds}{}^mC_{ds}{}^mC_{ds}T_{ks}A_{ks}T_k$ | 18 | 1311 |
| 786590 | N/A | N/A | 6951 | 6966 | GTGACTGTATTACCTA | $G_{ks}T_{ks}G_{ks}A_{ds}{}^mC_{ds}T_{ds}G_{ds}T_{ds}A_{ds}T_{ds}T_{ds}A_{ds}{}^mC_{ds}{}^mC_{ks}T_{ks}A_k$ | 62 | 1312 |
| 786591 | N/A | N/A | 6952 | 6967 | TGTGACTGTATTACCT | $T_{ks}G_{ks}T_{ks}G_{ds}A_{ds}{}^mC_{ds}T_{ds}G_{ds}T_{ds}A_{ds}T_{ds}T_{ds}A_{ds}{}^mC_{ks}{}^mC_{ks}T_k$ | 81 | 1313 |
| 786592 | N/A | N/A | 6953 | 6968 | TTGTGACTGTATTACC | $T_{ks}T_{ks}G_{ks}T_{ds}G_{ds}A_{ds}{}^mC_{ds}T_{ds}G_{ds}T_{ds}A_{ds}T_{ds}T_{ds}A_{ks}{}^mC_{ks}{}^mC_k$ | 56 | 1314 |
| 786593 | N/A | N/A | 6954 | 6969 | TTTGTGACTGTATTAC | $T_{ks}T_{ks}T_{ks}G_{ds}T_{ds}G_{ds}A_{ds}{}^mC_{ds}T_{ds}G_{ds}T_{ds}A_{ds}T_{ds}T_{ks}A_{ks}{}^mC_k$ | 50 | 1315 |

TABLE 24-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 786594 | N/A | N/A | 6955 | 6970 | TTTTGTGACTGTATTA | $T_{ks}T_{ks}T_{ks}T_{ds}G_{ds}T_{ds}G_{ds}A_{ds}{}^mC_{ds}T_{ds}G_{ds}T_{ds}A_{ds}T_{ks}T_{ks}A_k$ | 2 | 1316 |
| 786595 | N/A | N/A | 6956 | 6971 | ATTTTGTGACTGTATT | $A_{ks}T_{ks}T_{ks}T_{ds}T_{ds}G_{ds}T_{ds}G_{ds}A_{ds}{}^mC_{ds}T_{ds}G_{ds}T_{ds}A_{ks}T_{ks}T_k$ | 4 | 1317 |
| 786596 | N/A | N/A | 6957 | 6972 | AATTTTGTGACTGTAT | $A_{ks}A_{ks}T_{ks}T_{ds}T_{ds}T_{ds}G_{ds}T_{ds}G_{ds}A_{ds}{}^mC_{ds}T_{ds}G_{ds}T_{ks}A_{ks}T_k$ | 0 | 1318 |
| 786597 | N/A | N/A | 6959 | 6974 | TGAATTTTGTGACTGT | $T_{ks}GksA_{ks}A_{ds}T_{ds}T_{ds}T_{ds}T_{ds}G_{ds}T_{ds}G_{ds}A_{ds}{}^mC_{ds}T_{ks}G_{ks}T_k$ | 64 | 1319 |
| 786598 | N/A | N/A | 6960 | 6975 | TTGAATTTTGTGACTG | $T_{ks}T_{ks}G_{ks}A_{ds}A_{ds}T_{ds}T_{ds}T_{ds}T_{ds}G_{ds}T_{ds}G_{ds}A_{ds}{}^mC_{ks}T_{ks}G_k$ | 45 | 1320 |
| 786599 | N/A | N/A | 6961 | 6976 | GTTGAATTTTGTGACT | $G_{ks}T_{ks}T_{ks}G_{ds}A_{ds}A_{ds}T_{ds}T_{ds}T_{ds}G_{ds}T_{ds}G_{ds}A_{ks}{}^mC_{ks}T_k$ | 0 | 1321 |
| 786600 | N/A | N/A | 6962 | 6977 | TGTTGAATTTTGTGAC | $T_{ks}G_{ks}T_{ks}T_{ds}G_{ds}A_{ds}A_{ds}T_{ds}T_{ds}T_{ds}T_{ds}G_{ds}T_{ds}GksA_{ks}{}^mC_k$ | 26 | 1322 |

TABLE 25

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 728466 | 427 | 442 | 8320 | 8335 | GGTGTATTTCCCTGTC | $G_{ks}G_{ks}T_{ks}G_{ds}T_{ds}A_{ds}T_{ds}T_{ds}T_{ds}{}^mC_{ds}{}^mC_{ds}{}^mC_{ds}T_{ds}G_{ks}T_{ks}{}^mC_k$ | 12 | 1254 |
| 728489 | 484 | 499 | 8377 | 8392 | AAGGGCACAGCGCAGG | $A_{ks}A_{ks}G_{ds}G_{ds}G_{ds}{}^mC_{ds}A_{ds}{}^mC_{ds}A_{ds}G_{ds}{}^mC_{ds}G_{ds}{}^mC_{ds}A_{ks}G_{ks}G_k$ | 0 | 1249 |
| 728670 | 1230 | 1245 | 10463 | 10478 | TTGCACTGACACAGGC | $T_{ks}T_{ks}G_{ks}{}^mC_{ds}A_{ds}{}^mC_{ds}T_{ds}G_{ds}A_{ds}{}^mC_{ds}A_{ds}{}^mC_{ds}A_{ds}G_{ks}G_{ks}{}^mC_k$ | 6 | 398 |
| 728708 | 1308 | 1323 | 10541 | 10556 | AGCTTGGTCTTGACCT | $A_{ks}G_{ks}{}^mC_{ks}T_{ds}T_{ds}G_{ds}G_{ds}T_{ds}{}^mC_{ds}T_{ds}T_{ds}G_{ds}A_{ds}{}^mC_{ks}{}^mC_{ks}T_k$ | 11 | 436 |
| 729513 | N/A | N/A | 7316 | 7331 | CCCAATGCAACATCCA | ${}^mC_{ks}{}^mC_{ks}{}^mC_{ks}A_{ds}A_{ds}T_{ds}G_{ds}{}^mC_{ds}A_{ds}A_{ds}{}^mC_{ds}A_{ds}T_{ds}{}^mC_{ks}{}^mC_{ks}A_k$ | 12 | 1097 |
| 785349 | 427 | 442 | 8320 | 8335 | GGTGTATTTCCCTGTC | $G_{ks}G_{ds}T_{ds}G_{ds}T_{ds}A_{ds}T_{ds}T_{ds}T_{ds}{}^mC_{ds}{}^mC_{ds}{}^mC_{ks}T_{es}GksT_{es}{}^mC_k$ | 0 | 1254 |
| 785398 | N/A | N/A | 7314 | 7329 | CAATGCAACATCCATC | ${}^mC_{ks}A_{ds}A_{ds}T_{ds}G_{ds}{}^mC_{ds}A_{ds}A_{ds}{}^mC_{ds}A_{ds}T_{ds}{}^mC_{ks}{}^mC_{es}A_{ks}T_{es}{}^mC_k$ | 0 | 1323 |
| 785399 | N/A | N/A | 7316 | 7331 | CCCAATGCAACATCCA | ${}^mC_{ks}{}^mC_{ds}{}^mC_{ds}A_{ds}A_{ds}T_{ds}G_{ds}{}^mC_{ds}A_{ds}A_{ds}{}^mC_{ds}A_{ds}T_{ks}{}^mC_{es}{}^mC_{es}A_k$ | 0 | 1097 |
| 785404 | 427 | 442 | 8320 | 8335 | GGTGTATTTCCCTGTC | $G_{ks}G_{ds}T_{ds}G_{ds}T_{ds}A_{ds}T_{ds}T_{ds}T_{ds}{}^mC_{ds}{}^mC_{ks}{}^mC_{es}T_{ks}G_{es}T_{ks}{}^mC_e$ | 0 | 1254 |
| 785453 | N/A | N/A | 7314 | 7329 | CAATGCAACATCCATC | ${}^mC_{ks}A_{ds}A_{ds}T_{ds}G_{ds}{}^mC_{ds}A_{ds}A_{ds}{}^mC_{ds}A_{ds}Tks{}^mC_{es}{}^mC_{ks}A_{es}T_{ks}{}^mC_e$ | 0 | 1323 |
| 785454 | N/A | N/A | 7316 | 7331 | CCCAATGCAACATCCA | ${}^mC_{ks}{}^mC_{ds}{}^mC_{ds}A_{ds}A_{ds}T_{ds}G_{ds}{}^mC_{ds}A_{ds}A_{ds}{}^mC_{ks}A_{es}T_{ks}{}^mC_{es}{}^mC_{ks}A_e$ | 0 | 1097 |
| 785459 | 427 | 442 | 8320 | 8335 | GGTGTATTTCCCTGTC | $GksG_{es}T_{ks}G_{ds}T_{ds}A_{ds}T_{ds}T_{ds}T_{ds}{}^mC_{ds}{}^mC_{ds}{}^mC_{ds}T_{es}G_{es}T_{ks}{}^mC_k$ | 5 | 1254 |

TABLE 25-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 785487 | N/A | N/A | 7316 | 7331 | CCCAATGCAACATCCA | $^mC_{ks}{}^mC_{es}{}^mC_{ks}A_{ds}A_{ds}T_{ds}G_{ds}{}^mC_{ds}A_{ds}A_{ds}{}^mC_{ds}A_{ds}T_{es}{}^mC_{es}{}^mC_{ks}A_k$ | 0 | 1097 |
| 785493 | 426 | 441 | 8319 | 8334 | GTGTATTTCCCTGTCT | $G_{ks}T_{ks}G_{ds}T_{ds}A_{ds}T_{ds}T_{ds}T_{ds}{}^mC_{ds}{}^mC_{ds}{}^mC_{ds}T_{ds}G_{ks}T_{es}{}^mC_{ks}T_e$ | 0 | 1324 |
| 785494 | 427 | 442 | 8320 | 8335 | GGTGTATTTCCCTGTC | $G_{ks}G_{ks}T_{ds}G_{ds}T_{ds}A_{ds}T_{ds}T_{ds}T_{ds}{}^mC_{ds}{}^mC_{ds}{}^mC_{ds}T_{ks}G_{ks}T_{ks}{}^mC_e$ | 21 | 1254 |
| 785541 | N/A | N/A | 7315 | 7330 | CCAATGCAACATCCAT | $^mC_{ks}{}^mC_{ks}A_{ds}A_{ds}T_{ds}G_{ds}{}^mC_{ds}A_{ds}A_{ds}{}^mC_{ds}A_{ds}T_{ds}{}^mC_{ks}{}^mC_{es}A_{ks}T_e$ | 0 | 1325 |
| 785542 | N/A | N/A | 7316 | 7331 | CCCAATGCAACATCCA | $^mC_{ks}{}^mC_{ks}{}^mC_{ds}A_{ds}A_{ds}T_{ds}G_{ds}{}^mC_{ds}A_{ds}A_{ds}{}^mC_{ds}A_{ds}T_{ks}{}^mC_{es}{}^mC_{ks}A_e$ | 0 | 1097 |
| 785547 | 426 | 441 | 8319 | 8334 | GTGTATTTCCCTGTCT | $G_{ks}T_{ks}G_{ds}T_{ds}A_{ds}T_{ds}T_{ds}T_{ds}{}^mC_{ds}{}^mC_{ds}{}^mCesT_{es}G_{es}T_{es}{}^mC_{ks}T_k$ | 0 | 1324 |
| 785573 | N/A | N/A | 7315 | 7330 | CCAATGCAACATCCAT | $^mC_{ks}{}^mC_{ks}A_{ds}A_{ds}T_{ds}G_{ds}{}^mC_{ds}A_{ds}A_{ds}{}^mC_{ds}A_{es}T_{es}{}^mC_{es}{}^mC_{es}A_{ks}T_k$ | 0 | 1325 |
| 785581 | 426 | 441 | 8319 | 8334 | GTGTATTTCCCTGTCT | $G_{ks}T_{ks}G_{ds}T_{ds}A_{ds}T_{ds}T_{ds}T_{ds}{}^mC_{ds}{}^mC_{ds}{}^mC_{ks}T_{es}G_{ks}T_{es}{}^mC_{ks}T_k$ | 0 | 1324 |
| 785582 | 427 | 442 | 8320 | 8335 | GGTGTATTTCCCTGTC | $G_{ks}G_{ks}T_{ds}G_{ds}T_{ds}A_{ds}T_{ds}T_{ds}T_{ds}{}^mC_{ds}{}^mC_{ks}{}^mC_{es}T_{ks}G_{es}G_{ks}{}^mC_k$ | 0 | 1254 |
| 785648 | N/A | N/A | 7314 | 7329 | CAATGCAACATCCATC | $^mC_{ks}A_{ks}A_{ds}T_{ds}G_{ds}{}^mC_{ds}A_{ds}A_{ds}{}^mC_{ds}A_{ds}T_{ks}{}^mC_{es}{}^mC_{ks}A_{es}T_{ks}{}^mC_k$ | 0 | 1323 |
| 785649 | N/A | N/A | 7315 | 7330 | CCAATGCAACATCCAT | $^mC_{ks}{}^mC_{ks}A_{ds}A_{ds}T_{ds}G_{ds}{}^mC_{ds}A_{ds}A_{ds}{}^mC_{ds}A_{ks}T_{es}{}^mC_{ks}{}^mC_{es}A_{ks}T_k$ | 0 | 1325 |
| 785650 | N/A | N/A | 7316 | 7331 | CCCAATGCAACATCCA | $^mC_{ks}{}^mC_{ks}{}^mC_{ds}A_{ds}A_{ds}T_{ds}G_{ds}{}^mC_{ds}A_{ds}A_{ds}{}^mC_{ks}A_{es}T_{ks}{}^mC_{es}{}^mC_{ks}A_k$ | 0 | 1097 |
| 785656 | 426 | 441 | 8319 | 8334 | GTGTATTTCCCTGTCT | $G_{ks}T_{ks}G_{ds}T_{ds}A_{ds}T_{ds}T_{ds}T_{ds}{}^mC_{ds}{}^mC_{ds}{}^mC_{ds}T_{es}G_{es}T_{es}{}^mC_{ks}T_k$ | 16 | 1324 |
| 785682 | N/A | N/A | 7315 | 7330 | CCAATGCAACATCCAT | $^mC_{ks}{}^mC_{ks}A_{ds}A_{ds}T_{ds}G_{ds}{}^mC_{ds}A_{ds}A_{ds}{}^mC_{ds}A_{ds}T_{es}{}^mC_{es}{}^mC_{es}A_{ks}T_k$ | 0 | 1325 |
| 785686 | 426 | 441 | 8319 | 8334 | GTGTATTTCCCTGTCT | $G_{ks}T_{ks}G_{ds}T_{ds}A_{ds}T_{ds}T_{ds}T_{ds}{}^mC_{ds}{}^mC_{ds}{}^mC_{ds}TksG_{ds}T_{ks}{}^mC_{ds}T_k$ | 0 | 1324 |
| 785712 | N/A | N/A | 7315 | 7330 | CCAATGCAACATCCAT | $^mC_{ks}{}^mC_{ks}A_{ds}A_{ds}T_{ds}G_{ds}{}^mC_{ds}A_{ds}A_{ds}{}^mC_{ds}A_{ds}T_{ks}{}^mC_{ds}{}^mC_{ks}A_{ds}T_k$ | 0 | 1325 |
| 785718 | 426 | 441 | 8319 | 8334 | GTGTATTTCCCTGTCT | $G_{ks}T_{ks}G_{ds}T_{ds}A_{ds}T_{ds}T_{ds}T_{ds}{}^mC_{ds}{}^mC_{ds}{}^mC_{ds}TksG_{es}T_{ks}{}^mC_{es}T_k$ | 0 | 1324 |
| 785719 | 427 | 442 | 8320 | 8335 | GGTGTATTTCCCTGTC | $G_{ks}G_{ks}T_{ds}G_{ds}T_{ds}A_{ds}T_{ds}T_{ds}T_{ds}{}^mC_{ds}{}^mC_{ds}{}^mC_{ks}T_{es}G_{ks}T_{es}{}^mC_k$ | 26 | 1254 |
| 785766 | N/A | N/A | 7315 | 7330 | CCAATGCAACATCCAT | $^mC_{ks}{}^mC_{ks}A_{ds}A_{ds}T_{ds}G_{ds}{}^mC_{ds}A_{ds}A_{ds}{}^mC_{ds}A_{ds}T_{ks}{}^mC_{es}{}^mC_{ks}A_{es}T_k$ | 0 | 1325 |
| 785767 | N/A | N/A | 7316 | 7331 | CCCAATGCAACATCCA | $^mC_{ks}{}^mC_{ks}{}^mC_{ds}A_{ds}A_{ds}T_{ds}G_{ds}{}^mC_{ds}A_{ds}A_{ds}{}^mC_{ds}A_{ks}T_{es}{}^mC_{ks}{}^mC_{es}A_k$ | 0 | 1097 |
| 785772 | 427 | 442 | 8320 | 8335 | GGTGTATTTCCCTGTC | $G_{ks}G_{ks}T_{ks}G_{ds}T_{ds}A_{ds}T_{ds}T_{ds}T_{ds}{}^mC_{ds}{}^mC_{ds}{}^mC_{ks}T_{ds}G_{ks}T_{ds}{}^mC_k$ | 1 | 1254 |

TABLE 25-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 785800 | N/A | N/A | 7316 | 7331 | CCCAATGCAACATCCA | $^mC_{ks}{}^mC_{ks}{}^mC_{ks}A_{ds}A_{ds}T_{ds}G_{ds}{}^mC_{ds}A_{ds}A_{ds}{}^mC_{ds}A_{ks}T_{ds}{}^mC_{ks}{}^mC_{ds}A_k$ | 0 | 1097 |
| 785806 | 426 | 441 | 8319 | 8334 | GTGTATTTCCCTGTCT | $G_{ks}T_{ks}G_{ks}T_{ds}A_{ds}T_{ds}T_{ds}T_{ds}{}^mC_{ds}{}^mC_{ds}{}^mC_{ds}T_{ks}G_{es}T_{ks}{}^mC_{es}T_k$ | 0 | 1324 |
| 785807 | 427 | 442 | 8320 | 8335 | GGTGTATTTCCCTGTC | $G_{ks}G_{ks}T_{ks}G_{ds}T_{ds}A_{ds}T_{ds}T_{ds}T_{ds}{}^mC_{ds}{}^mC_{ds}{}^mC_{ks}T_{es}G_{ks}T_{es}{}^mC_k$ | 0 | 1254 |
| 785854 | N/A | N/A | 7315 | 7330 | CCAATGCAACATCCAT | $^mC_{ks}{}^mC_{ks}A_{ds}A_{ds}T_{ds}G_{ds}{}^mC_{ds}A_{ds}A_{ds}{}^mC_{ds}A_{ds}T_{ks}{}^mC_{es}{}^mC_{ks}A_{es}T_k$ | 0 | 1325 |
| 785855 | N/A | N/A | 7316 | 7331 | CCCAATGCAACATCCA | $^mC_{ks}{}^mC_{ks}{}^mC_{ks}A_{ds}A_{ds}T_{ds}G_{ds}{}^mC_{ds}A_{ds}A_{ds}{}^mC_{ds}A_{ks}T_{es}{}^mC_{ks}{}^mC_{es}A_k$ | 0 | 1097 |
| 785860 | 427 | 442 | 8320 | 8335 | GGTGTATTTCCCTGTC | $G_{ks}G_{ks}T_{ks}G_{ds}T_{ds}A_{ds}T_{ds}T_{ds}T_{ds}{}^mC_{ds}{}^mC_{ds}{}^mC_{ks}T_{ks}G_{es}T_{ks}{}^mC_e$ | 0 | 1254 |
| 785888 | N/A | N/A | 7316 | 7331 | CCCAATGCAACATCCA | $^mC_{ks}{}^mC_{ks}{}^mC_{ks}A_{ds}A_{ds}T_{ds}G_{ds}{}^mC_{ds}A_{ds}A_{ds}{}^mC_{ds}A_{ds}T_{ks}{}^mC_{es}{}^mC_{ks}A_e$ | 0 | 1097 |
| 785894 | 426 | 441 | 8319 | 8334 | GTGTATTTCCCTGTCT | $G_{ks}T_{ks}G_{ks}T_{ds}A_{ds}T_{ds}T_{ds}T_{ds}{}^mC_{ds}{}^mC_{ds}{}^mC_{ds}T_{ds}G_{ks}T_{ks}{}^mC_{ks}T_e$ | 30 | 1324 |
| 785895 | 427 | 442 | 8320 | 8335 | GGTGTATTTCCCTGTC | $G_{ks}G_{ks}T_{ks}G_{ds}T_{ds}A_{ds}T_{ds}T_{ds}T_{ds}{}^mC_{ds}{}^mC_{ds}{}^mC_{ds}T_{ks}G_{ks}T_{ks}{}^mC_e$ | 0 | 1254 |
| 785938 | N/A | N/A | 6548 | 6563 | CCAATTTTGCATTCCA | $^mC_{ks}{}^mC_{ks}A_{ds}A_{ds}T_{ds}T_{ds}T_{ds}T_{ds}G_{ds}{}^mC_{ds}A_{ds}T_{ds}T_{ks}{}^mC_{ks}{}^mC_{ks}A_e$ | 61 | 1242 |
| 785942 | N/A | N/A | 7315 | 7330 | CCAATGCAACATCCAT | $^mC_{ks}{}^mC_{ks}A_{ds}A_{ds}T_{ds}G_{ds}{}^mC_{ds}A_{ds}A_{ds}{}^mC_{ds}A_{ds}T_{ds}{}^mC_{ks}{}^mC_{ks}A_{ks}T_e$ | 16 | 1325 |
| 785943 | N/A | N/A | 7316 | 7331 | CCCAATGCAACATCCA | $^mC_{ks}{}^mC_{ks}{}^mC_{ks}A_{ds}A_{ds}T_{ds}G_{ds}{}^mC_{ds}A_{ds}A_{ds}{}^mC_{ds}A_{ds}T_{ks}{}^mC_{ks}{}^mC_{ks}A_e$ | 0 | 1097 |
| 786494 | 428 | 443 | 8321 | 8336 | CGGTGTATTTCCCTGT | $^mC_{ks}G_{ks}G_{ks}T_{ds}G_{ds}T_{ds}A_{ds}T_{ds}T_{ds}T_{ds}{}^mC_{ds}{}^mC_{ds}{}^mC_{ds}T_{ks}G_{ks}T_k$ | 0 | 1326 |
| 786562 | N/A | N/A | 7307 | 7322 | ACATCCATCAATGAGG | $A_{ks}{}^mC_{ks}A_{ks}T_{ds}{}^mC_{ds}{}^mC_{ds}A_{ds}T_{ds}{}^mC_{ds}A_{ds}A_{ds}T_{ds}G_{ds}A_{ks}G_{ks}G_k$ | 0 | 1327 |
| 786563 | N/A | N/A | 7309 | 7324 | CAACATCCATCAATGA | $^mC_{ks}A_{ks}A_{ks}{}^mC_{ds}A_{ds}T_{ds}{}^mC_{ds}{}^mC_{ds}A_{ds}T_{ds}{}^mC_{ds}A_{ds}A_{ds}T_{ks}G_{ks}A_k$ | 0 | 1328 |
| 786564 | N/A | N/A | 7311 | 7326 | TGCAACATCCATCAAT | $T_{ks}G_{ks}{}^mC_{ks}A_{ds}A_{ds}{}^mC_{ds}A_{ds}T_{ds}{}^mC_{ds}{}^mC_{ds}A_{ds}T_{ds}{}^mC_{ds}A_{ks}A_{ks}T_k$ | 0 | 1329 |
| 786565 | N/A | N/A | 7312 | 7327 | ATGCAACATCCATCAA | $A_{ks}T_{ks}G_{ks}{}^mC_{ds}A_{ds}A_{ds}{}^mC_{ds}A_{ds}T_{ds}{}^mC_{ds}{}^mC_{ds}A_{ds}T_{ds}{}^mC_{ks}A_{ks}A_k$ | 0 | 1330 |
| 786566 | N/A | N/A | 7313 | 7328 | AATGCAACATCCATCA | $A_{ks}A_{ks}T_{ks}G_{ds}{}^mC_{ds}A_{ds}A_{ds}{}^mC_{ds}A_{ds}T_{ds}{}^mC_{ds}{}^mC_{ds}A_{ds}T_{ks}{}^mC_{ks}A_k$ | 0 | 1331 |
| 786567 | N/A | N/A | 7314 | 7329 | CAATGCAACATCCATC | $^mC_{ks}A_{ks}A_{ks}T_{ds}G_{ds}{}^mC_{ds}A_{ds}A_{ds}{}^mC_{ds}A_{ds}T_{ds}{}^mC_{ds}{}^mC_{ds}A_{ks}T_{ks}{}^mC_k$ | 0 | 1323 |
| 786568 | N/A | N/A | 7315 | 7330 | CCAATGCAACATCCAT | $^mC_{ks}{}^mC_{ks}A_{ks}A_{ds}T_{ds}G_{ds}{}^mC_{ds}A_{ds}A_{ds}{}^mC_{ds}A_{ds}T_{ds}{}^mC_{ds}{}^mC_{ks}A_{ks}T_k$ | 0 | 1325 |
| 786569 | N/A | N/A | 7317 | 7332 | ACCCAATGCAACATCC | $A_{ks}{}^mC_{ks}{}^mC_{ks}{}^mC_{ks}A_{ds}A_{ds}T_{ds}G_{ds}{}^mC_{ds}A_{ds}A_{ds}{}^mC_{ds}A_{ds}T_{ks}{}^mC_{ks}{}^mC_k$ | 33 | 1332 |

TABLE 25-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 786570 | N/A | N/A | 7318 | 7333 | TACCCAATGCAACATC | $T_{ks}A_{ks}{}^mC_{ks}{}^mC_{ds}{}^mC_{ds}A_{ds}A_{ds}T_{ds}$ $G_{ds}{}^mC_{ds}A_{ds}A_{ds}{}^mC_{ds}A_{ks}T_{ks}{}^mT_k$ | 0 | 1333 |
| 786571 | N/A | N/A | 7319 | 7334 | ATACCCAATGCAACAT | $A_{ks}T_{ks}A_{ks}{}^mC_{ds}{}^mC_{ds}{}^mC_{ds}A_{ds}A_{ds}$ $T_{ds}G_{ds}{}^mC_{ds}A_{ds}A_{ds}{}^mC_{ks}A_{ks}T_k$ | 1 | 1334 |

TABLE 26

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 665892 | 1227 | 1242 | 10460 | 10475 | CACTGACACAGGCGGA | $mC_{ks}A_{ks}mC_{ks}T_{ds}G_{ds}A_{ds}mC_{ds}$ $A_{ds}{}^mC_{ds}A_{ds}G_{ds}G_{ds}{}^mC_{ds}G_{ks}G_{ks}A_k$ | 0 | 387 |
| 665893 | 128 | 1243 | 10461 | 10476 | GCACTGACACAGGCGG | $G_{ks}{}^mC_{ks}A_{ks}{}^mC_{ds}T_{ds}G_{ds}A_{ds}{}^m$ $C_{ds}A_{ds}{}^mC_{ds}A_{ds}G_{ds}G_{ds}{}^mC_{ks}G_{ks}G_k$ | 0 | 39 |
| 666168 | N/A | N/A | 5286 | 5301 | ATCACCACTGTGTACC | $A_{ks}T_{ks}{}^mC_{ks}A_{ds}{}^mC_{ds}{}^mC_{ds}A_{ds}{}^m$ $C_{ds}T_{ds}G_{ds}T_{ds}G_{ds}T_{ds}A_{ks}{}^mC_{ks}{}^mC_k$ | 11 | 927 |
| 728458 | 392 | 407 | 4717 | 4732 | AGATGGTGTTATCTCC | $A_{ks}G_{ks}A_{ks}T_{ds}G_{ds}G_{ds}T_{ds}G_{ds}$ $T_{ds}T_{ds}A_{ds}T_{ds}{}^mC_{ds}T_{ks}{}^mC_{ks}{}^mC_k$ | 0 | 123 |
| 728466 | 427 | 442 | 8320 | 8335 | GGTGTATTTCCCTGTC | $G_{ks}G_{ks}T_{ks}G_{ds}T_{ds}A_{ds}T_{ds}T_{ds}$ $T_{ds}{}^mC_{ds}{}^mC_{ds}{}^mC_{ds}T_{ds}G_{ks}T_{ks}{}^mC_k$ | 37 | 1254 |
| 728489 | 484 | 499 | 8377 | 8392 | AAGGGCACAGCGCAGG | $A_{ks}A_{ks}G_{ds}G_{ds}G_{ds}{}^mC_{ds}A_{ds}{}^mC_{ds}$ $A_{ds}G_{ds}{}^mC_{ds}G_{ds}{}^mC_{ds}A_{ks}G_{ks}G_k$ | 2 | 1249 |
| 728670 | 1230 | 1245 | 10463 | 10478 | TTGCACTGACACAGGC | $T_{ks}T_{ks}G_{ks}{}^mC_{ds}A_{ds}{}^mC_{ds}T_{ds}G_{ds}$ $A_{ds}{}^mC_{ds}A_{ds}{}^mC_{ds}A_{ds}G_{ks}G_{ks}{}^mC_k$ | 0 | 398 |
| 728707 | 1307 | 1322 | 10540 | 10555 | GCTTGGTCTTGACCTC | $G_{ks}{}^mC_{ks}T_{ks}T_{ds}G_{ds}G_{ds}T_{ds}{}^mC_{ds}$ $T_{ds}T_{ds}G_{ds}A_{ds}{}^mC_{ds}{}^mC_{ks}T_{ks}{}^mC_k$ | 0 | 435 |
| 728708 | 1308 | 1322 | 10541 | 10556 | AGCTTGGTCTTGACCT | $A_{ks}G_{ks}{}^mC_{ks}T_{ds}T_{ds}G_{ds}G_{ds}T_{ds}{}^m$ $C_{ds}T_{ds}T_{ds}G_{ds}A_{ds}{}^mC_{ks}{}^mC_{ks}T_k$ | 41 | 436 |
| 728958 | 1979 | 1994 | 11544 | 11559 | CCTATACAGCTAGGCC | $^mC_{ks}{}^mC_{ks}T_{ks}A_{ds}T_{ds}A_{ds}{}^mC_{ds}A_{ds}$ $G_{ds}{}^mC_{ds}T_{ds}A_{ds}G_{ds}G_{ks}{}^mC_{ks}{}^mC_k$ | 0 | 168 |
| 728996 | 2114 | 2129 | 11679 | 11694 | GTGAGTCTCAAACCAG | $G_{ks}T_{ks}G_{ks}A_{ds}G_{ds}T_{ds}{}^mC_{ds}T_{ds}{}^m$ $C_{ds}A_{ds}A_{ds}A_{ds}{}^mC_{ds}{}^mC_{ks}A_{ks}G_k$ | 9 | 206 |
| 729037 | 2216 | 2231 | 11781 | 11796 | GGTTCTTGGACTCTCA | $G_{ks}G_{ks}T_{ks}T_{ds}{}^mC_{ds}T_{ds}T_{ds}G_{ds}$ $G_{ds}A_{ds}{}^mC_{ds}T_{ds}{}^mC_{ds}T_{ks}{}^mC_{ks}A_k$ | 47 | 706 |
| 785347 | 390 | 405 | 4715 | 4730 | ATGGTGTTATCTCCGT | $A_{ks}T_{ds}G_{ds}G_{ds}T_{ds}G_{ds}T_{ds}T_{ds}$ $A_{ds}T_{ds}{}^mC_{ds}T_{ks}{}^mC_{es}{}^mC_{ks}G_{es}T_k$ | 0 | 122 |
| 785348 | 392 | 107 | 4717 | 4732 | AGATGGTGTTATCTCC | $A_{ks}G_{ds}A_{ds}T_{ds}G_{ds}G_{ds}T_{ds}G_{ds}T_{ds}$ $T_{ds}A_{ds}T_{ks}{}^mC_{es}T_{ks}{}^mC_{es}{}^mC_k$ | 0 | 123 |
| 785374 | 2112 | 2127 | 11677 | 11692 | GAGTCTCAAACCAGGG | $G_{ks}A_{ds}G_{ds}T_{ds}{}^mC_{ds}T_{ds}{}^mC_{ds}A_{ds}$ $A_{ds}A_{ds}{}^mC_{ds}{}^mC_{ks}A_{es}G_{ks}G_{es}G_k$ | 0 | 205 |
| 785375 | 2114 | 2129 | 11679 | 11694 | GTGAGTCTCAAACCAG | $G_{ks}T_{ds}G_{ds}A_{ds}G_{ds}T_{ds}{}^mC_{ds}T_{ds}{}^m$ $C_{ds}A_{ds}A_{ds}A_{ks}{}^mC_{es}{}^mC_{ks}A_{es}G_k$ | 0 | 206 |
| 785390 | N/A | N/A | 5284 | 5299 | CACCACTGTGTACCCC | $^mC_{ks}A_{ds}{}^mC_{ds}{}^mC_{ds}A_{ds}{}^mC_{ds}T_{ds}G_{ds}$ $T_{ds}G_{ds}T_{ds}A_{ks}{}^mC_{es}{}^mC_{ks}{}^mC_{es}{}^mC_k$ | 0 | 938 |
| 785391 | N/A | N/A | 5286 | 5301 | ATCACCACTGTGTACC | $A_{ks}T_{ds}{}^mC_{ds}A_{ds}{}^mC_{ds}{}^mC_{ds}A_{ds}{}^m$ $C_{ds}T_{ds}G_{ds}T_{ds}G_{ks}T_{es}A_{ks}{}^mC_{es}{}^mC_k$ | 0 | 927 |

TABLE 26-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 785402 | 390 | 405 | 4715 | 4730 | ATGGTGTTATCTCCGT | $A_{ks}T_{ds}G_{ds}G_{ds}T_{ds}G_{ds}T_{ds}T_{ds}A_{ds}T_{ds}{}^mC_{ks}T_{es}{}^mC_{ks}{}^mC_{es}G_{ks}T_e$ | 0 | 122 |
| 785403 | 392 | 407 | 4717 | 4732 | AGATGGTGTTATCTCC | $A_{ks}G_{ds}A_{ds}T_{ds}G_{ds}G_{ds}T_{ds}G_{ds}T_{ds}T_{ds}A_{ks}T_{es}{}^mC_{ks}T_{es}{}^mC_{ks}{}^mC_e$ | 0 | 123 |
| 785429 | 2112 | 2127 | 11677 | 11692 | GAGTCTCAAACCAGGG | $G_{ks}A_{ds}G_{ds}T_{ds}{}^mC_{ds}T_{ds}{}^mC_{ds}A_{ds}A_{ds}A_{ds}{}^mC_{ks}{}^mC_{es}A_{ks}G_{es}G_{ks}G_e$ | 6 | 205 |
| 785430 | 2114 | 2129 | 11679 | 11694 | GTGAGTCTCAAACCAG | $G_{ks}T_{ds}G_{ds}A_{ds}G_{ds}T_{ds}{}^mC_{ds}T_{ds}{}^mC_{ds}A_{ds}A_{ks}A_{es}{}^mC_{ks}{}^mC_{es}A_{ks}G_e$ | 0 | 206 |
| 785445 | N/A | N/A | 5284 | 5299 | CACCACTGTGTACCCC | ${}^mC_{ks}A_{ds}{}^mC_{ds}{}^mC_{ds}A_{ds}{}^mC_{ds}T_{ds}G_{ds}T_{ds}G_{ds}T_{ks}A_{es}{}^mC_{ks}{}^mC_{es}{}^mC_{ks}{}^mC_e$ | 0 | 938 |
| 785446 | N/A | N/A | 5286 | 5301 | ATCACCACTGTGTACC | $A_{ks}T_{ds}{}^mC_{ds}A_{ds}{}^mC_{ds}{}^mC_{ds}A_{ds}{}^mC_{ds}T_{ds}G_{ds}T_{ks}G_{es}T_{ks}A_{es}{}^mC_{ks}{}^mC_e$ | 0 | 927 |
| 785458 | 392 | 407 | 4717 | 4732 | AGATGGTGTTATCTCC | $A_{ks}G_{es}A_{ks}T_{ds}G_{ds}G_{ds}T_{ds}G_{ds}T_{ds}T_{ds}A_{ds}T_{ds}{}^mC_{es}T_{es}{}^mC_{ks}{}^mC_k$ | 0 | 123 |
| 785473 | 2114 | 2129 | 11679 | 11694 | GTGAGTCTCAAACCAG | $G_{ks}T_{es}G_{ks}A_{ds}G_{ds}T_{ds}{}^mC_{ds}T_{ds}{}^mC_{ds}A_{ds}A_{ds}A_{ds}{}^mC_{es}{}^mC_{es}A_{ks}G_k$ | 22 | 206 |
| 785482 | N/A | N/A | 5286 | 5301 | ATCACCACTGTGTACC | $A_{ks}T_{es}{}^mC_{ks}A_{ds}{}^mC_{ds}{}^mC_{ds}A_{ds}{}^mC_{ds}T_{ds}G_{ds}T_{ds}G_{ds}T_{es}A_{ks}{}^mC_{ks}{}^mC_k$ | 0 | 927 |
| 785491 | 391 | 406 | 4716 | 4731 | GATGGTGTTATCTCCG | $G_{ks}A_{ds}T_{ds}G_{ds}G_{ds}T_{ds}G_{ds}T_{ds}T_{ds}A_{ds}T_{ds}{}^mC_{ds}T_{ks}{}^mC_{es}{}^mC_{ks}G_e$ | 0 | 1335 |
| 785492 | 392 | 407 | 4717 | 4732 | AGATGGTGTTATCTCC | $A_{ks}G_{ks}A_{ds}T_{ds}G_{ds}G_{ds}T_{ds}G_{ds}T_{ds}T_{ds}A_{ds}T_{ds}{}^mC_{ks}T_{es}{}^mC_{ks}{}^mC_e$ | 0 | 123 |
| 785517 | 2113 | 2128 | 11678 | 11693 | TGAGTCTCAAACCAGG | $T_{ks}G_{ks}A_{ds}G_{ds}T_{ds}{}^mC_{ds}T_{ds}{}^mC_{ds}A_{ds}A_{ds}A_{ds}{}^mC_{ds}{}^mC_{ks}A_{es}G_{ks}G_e$ | 7 | 1336 |
| 785518 | 2114 | 2129 | 11679 | 11694 | GTGAGTCTCAAACCAG | $G_{ks}T_{ks}G_{ds}A_{ds}G_{ds}T_{ds}{}^mC_{ds}T_{ds}{}^mC_{ds}A_{ds}A_{ds}A_{ds}{}^mC_{ks}{}^mC_{es}A_{ks}G_e$ | 31 | 206 |
| 785533 | N/A | N/A | 5285 | 5300 | TCACCACTGTGTACCC | $T_{ks}{}^mC_{ks}A_{ds}{}^mC_{ds}{}^mC_{ds}A_{ds}{}^mC_{ds}T_{ds}G_{ds}T_{ds}G_{ds}T_{ds}A_{ks}{}^mC_{es}{}^mC_{ks}{}^mC_e$ | 0 | 939 |
| 785534 | N/A | N/A | 5286 | 5301 | ATCACCACTGTGTACC | $A_{ks}T_{ks}{}^mC_{ds}A_{ds}{}^mC_{ds}{}^mC_{ds}A_{ds}{}^mC_{ds}T_{ds}G_{ds}T_{ds}G_{ds}T_{ks}A_{es}{}^mC_{ks}{}^mC_e$ | 0 | 927 |
| 785546 | 391 | 406 | 4716 | 4731 | GATGGTGTTATCTCCG | $G_{ks}A_{ks}T_{ds}G_{ds}G_{ds}T_{ds}G_{ds}T_{ds}T_{ds}A_{ds}T_{es}{}^mC_{es}T_{es}{}^mC_{ks}G_k$ | 0 | 1335 |
| 785560 | 2113 | 2128 | 11678 | 11693 | TGAGTCTCAAACCAGG | $T_{ks}G_{ks}A_{ds}G_{ds}T_{ds}{}^mC_{ds}T_{ds}{}^mC_{ds}A_{ds}A_{ds}A_{es}{}^mC_{es}{}^mC_{es}A_{ks}G_{ks}G_e$ | 0 | 1336 |
| 785569 | N/A | N/A | 5285 | 5300 | TCACCACTGTGTACCC | $T_{ks}{}^mC_{ks}A_{ds}{}^mC_{ds}{}^mC_{ds}A_{ds}{}^mC_{ds}T_{ds}G_{ds}T_{ds}G_{es}T_{es}A_{es}{}^mC_{es}{}^mC_{ks}{}^mC_k$ | 0 | 939 |
| 785578 | 390 | 405 | 4715 | 4730 | ATGGTGTTATCTCCGT | $A_{ks}T_{ks}G_{ds}G_{ds}T_{ds}G_{ds}T_{ds}T_{ds}A_{ds}T_{ds}{}^mC_{ks}T_{es}{}^mC_{ks}{}^mC_{es}G_{ks}T_k$ | 0 | 122 |
| 785579 | 391 | 406 | 4716 | 4731 | GATGGTGTTATCTCCG | $G_{ks}A_{ks}T_{ds}G_{ds}G_{ds}T_{ds}G_{ds}T_{ds}T_{ds}dA_{ds}T_{ks}{}^mC_{es}T_{ks}{}^mC_{es}{}^mC_{ks}G_e$ | 0 | 1335 |
| 785580 | 392 | 407 | 4717 | 4732 | AGATGGTGTTATCTCC | $A_{ks}G_{ks}A_{ds}T_{ds}G_{ds}G_{ds}T_{ds}G_{ds}T_{ds}T_{ds}A_{ks}T_{es}{}^mC_{ks}T_{es}{}^mC_{ks}{}^mC_k$ | 0 | 123 |
| 785615 | 2112 | 2127 | 11677 | 11692 | GAGTCTCAAACCAGGG | $G_{ks}A_{ds}G_{ds}T_{ds}{}^mC_{ds}T_{ds}{}^mC_{ds}A_{ds}A_{ds}A_{ds}{}^mC_{ks}{}^mC_{es}A_{ks}G_{ks}G_k$ | 0 | 205 |
| 785616 | 2113 | 2128 | 11678 | 11693 | TGAGTCTCAAACCAGG | $T_{ks}G_{ks}A_{ds}G_{ds}T_{ds}{}^mC_{ks}T_{ds}{}^mC_{ds}A_{ds}A_{ds}A_{ks}{}^mC_{ks}{}^mC_{es}A_{ks}G_{ks}G_k$ | 0 | 1336 |
| 785617 | 2114 | 2129 | 11679 | 11694 | GTGAGTCTCAAACCAG | $G_{ks}T_{ds}G_{ds}A_{ds}G_{ds}T_{ds}{}^mC_{ds}T_{ds}{}^mC_{ds}A_{ds}A_{ks}A_{es}{}^mC_{ks}{}^mC_{es}A_{ks}G_k$ | 9 | 206 |

TABLE 26-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 785637 | N/A | N/A | 5284 | 5299 | CACCACTGTGTACCCC | $^mC_{ks}A_{ks}{}^mC_{ds}{}^mC_{ds}A_{ds}{}^mC_{ds}T_{ds}G_{ds}T_{ds}G_{ds}T_{ks}A_{es}{}^mC_{ks}{}^mC_{es}{}^mC_{ks}{}^mC$ | 0 | 938 |
| 785638 | N/A | N/A | 5285 | 5300 | TCACCACTGTGTACCC | $T_{ks}{}^mC_{ks}A_{ds}{}^mC_{ds}{}^mC_{ds}A_{ds}{}^mC_{ds}T_{ds}G_{ds}T_{ds}G_{ks}T_{es}A_{ks}{}^mC_{es}{}^mC_{ks}{}^mC$ | 0 | 939 |
| 785639 | N/A | N/A | 5286 | 5301 | ATCACCACTGTGTACC | $A_{ks}T_{ks}{}^mC_{ds}A_{ds}{}^mC_{ds}{}^mC_{ds}A_{ds}{}^mC_{ds}T_{ds}G_{ds}T_{ds}G_{ds}T_{ks}A_{es}{}^mC_{ks}{}^mC$ | 0 | 927 |
| 785655 | 391 | 406 | 4716 | 4731 | GATGGTGTTATCTCCG | $G_{ks}A_{ks}T_{ds}G_{ds}G_{ds}T_{ds}G_{ds}T_{ds}T_{ds}A_{ds}T_{ds}{}^mC_{es}T_{es}{}^mC_{es}{}^mC_{ks}G_k$ | 0 | 1335 |
| 785669 | 2113 | 2128 | 11678 | 11693 | TGAGTCTCAAACCAGG | $T_{ks}G_{ks}A_{ds}G_{ds}T_{ds}{}^mC_{ds}T_{ds}{}^mC_{ds}A_{ds}A_{ds}A_{ds}{}^mC_{es}{}^mC_{es}A_{es}G_{ks}G_k$ | 0 | 1336 |
| 785678 | N/A | N/A | 5285 | 5300 | TCACCACTGTGTACCC | $T_{ks}{}^mC_{ks}A_{ds}{}^mC_{ds}{}^mC_{ds}A_{ds}{}^mC_{ds}T_{ds}G_{ds}T_{ds}G_{ds}T_{es}A_{es}{}^mC_{es}{}^mC_{ks}{}^mC_k$ | 0 | 939 |
| 785685 | 391 | 406 | 4716 | 4731 | GATGGTGTTATCTCCG | $G_{ks}A_{ks}T_{ds}G_{ds}G_{ds}T_{ds}G_{ds}T_{ds}T_{ds}A_{ds}T_{ds}{}^mC_{ks}T_{es}{}^mC_{ks}{}^mC_{ds}G_k$ | 0 | 1335 |
| 785699 | 2113 | 2128 | 11678 | 11693 | TGAGTCTCAAACCAGG | $T_{ks}G_{ks}A_{ds}G_{ds}T_{ds}{}^mC_{ds}T_{ds}{}^mC_{ds}A_{ds}A_{ds}A_{ds}{}^mC_{ks}{}^mC_{ds}A_{ks}G_{ds}G_k$ | 0 | 1336 |
| 785708 | N/A | N/A | 5285 | 5300 | TCACCACTGTGTACCC | $T_{ks}{}^mC_{ks}A_{ds}{}^mC_{ds}{}^mC_{ds}A_{ds}{}^mC_{ds}T_{ds}G_{ds}T_{ds}G_{ds}T_{ks}A_{ds}{}^mC_{ks}{}^mC_{ds}{}^mC_k$ | 0 | 939 |
| 785716 | 391 | 406 | 4716 | 4731 | GATGGTGTTATCTCCG | $G_{ks}A_{ks}T_{ds}G_{ds}G_{ds}T_{ds}G_{ds}T_{ds}T_{ds}A_{ds}T_{ds}{}^mC_{ks}T_{es}{}^mC_{ks}{}^mC_{es}G_k$ | 0 | 1335 |
| 785717 | 392 | 407 | 4717 | 4732 | AGATGGTGTTATCTCC | $A_{ks}G_{ks}A_{ds}T_{ds}G_{ds}G_{ds}T_{ds}G_{ds}T_{ds}T_{ds}A_{ds}T_{ks}{}^mC_{es}T_{ks}{}^mC_{es}{}^mC_k$ | 0 | 123 |
| 785742 | 2113 | 2128 | 11678 | 11693 | TGAGTCTCAAACCAGG | $T_{ks}G_{ks}A_{ds}G_{ds}T_{ds}{}^mC_{ds}T_{ds}{}^mC_{ds}A_{ds}A_{ds}A_{ds}{}^mC_{es}{}^mC_{es}A_{ks}G_{es}G_k$ | 0 | 1336 |
| 785743 | 2114 | 2129 | 11679 | 11694 | GTGAGTCTCAAACCAG | $G_{ks}T_{ks}G_{ds}A_{ds}G_{ds}T_{ds}{}^mC_{ds}T_{ds}{}^mC_{ds}A_{ds}A_{ds}A_{ks}{}^mC_{es}{}^mC_{ks}A_{es}G_k$ | 0 | 206 |
| 785758 | N/A | N/A | 5285 | 5300 | TCACCACTGTGTACCC | $T_{ks}{}^mC_{ks}A_{ds}{}^mC_{ds}{}^mC_{ds}A_{ds}{}^mC_{ds}T_{ds}G_{ds}T_{ds}G_{ds}T_{ks}A_{es}{}^mC_{ks}{}^mC_{es}{}^mC_k$ | 0 | 939 |
| 785759 | N/A | N/A | 5286 | 5301 | ATCACCACTGTGTACC | $A_{ks}T_{ks}{}^mC_{ds}A_{ds}{}^mC_{ds}{}^mC_{ds}A_{ds}{}^mC_{ds}T_{ds}G_{ds}T_{ds}G_{ks}T_{es}A_{ks}{}^mC_{es}{}^mC_k$ | 0 | 927 |
| 785771 | 392 | 407 | 4717 | 4732 | AGATGGTGTTATCTCC | $A_{ks}G_{ks}A_{ds}T_{ds}G_{ds}G_{ds}T_{ds}G_{ds}T_{ds}T_{ds}A_{ds}T_{ks}{}^mC_{ds}T_{ks}{}^mC_{ds}{}^mC_k$ | 0 | 123 |
| 785786 | 2114 | 2129 | 11679 | 11694 | GTGAGTCTCAAACCAG | $G_{ks}T_{ks}G_{ks}A_{ds}G_{ds}T_{ds}{}^mC_{ds}T_{ds}{}^mC_{ds}A_{ds}A_{ds}A_{ks}{}^mC_{ds}{}^mC_{ks}A_{ds}G_k$ | 0 | 206 |
| 785795 | N/A | N/A | 5286 | 5301 | ATCACCACTGTGTACC | $A_{ks}T_{ks}{}^mC_{ks}A_{ds}{}^mC_{ds}{}^mC_{ds}A_{ds}{}^mC_{ds}T_{ds}G_{ds}G_{ds}T_{ks}A_{ks}{}^mC_{ds}{}^mC_k$ | 0 | 927 |
| 785804 | 391 | 406 | 4716 | 4731 | GATGGTGTTATCTCCG | $G_{ks}A_{ks}T_{ds}G_{ds}G_{ds}T_{ds}G_{ds}T_{ds}T_{ds}A_{ds}T_{ds}{}^mC_{ks}T_{es}{}^mC_{ks}{}^mC_{es}G_k$ | 0 | 1335 |
| 785805 | 392 | 407 | 4717 | 4732 | AGATGGTGTTATCTCC | $A_{ks}G_{ks}A_{ds}T_{ds}G_{ds}G_{ds}T_{ds}G_{ds}T_{ds}T_{ds}A_{ds}T_{ks}{}^mC_{es}T_{ks}{}^mC_{es}{}^mC_k$ | 0 | 123 |
| 785830 | 2113 | 2128 | 11678 | 11693 | TGAGTCTCAAACCAGG | $T_{ks}G_{ks}A_{ds}G_{ds}T_{ds}{}^mC_{ds}T_{ds}{}^mC_{ds}A_{ds}A_{ds}A_{ds}{}^mC_{ks}{}^mC_{es}A_{ks}G_{es}G_k$ | 0 | 1336 |
| 785831 | 2114 | 2129 | 11679 | 11694 | GTGAGTCTCAAACCAG | $G_{ks}T_{ks}G_{ks}A_{ds}G_{ds}T_{ds}{}^mC_{ds}T_{ds}{}^mC_{ds}A_{ds}A_{ds}A_{ks}{}^mC_{es}{}^mC_{ks}A_{es}G_k$ | 0 | 206 |
| 785846 | N/A | N/A | 5285 | 5300 | TCACCACTGTGTACCC | $T_{ks}{}^mC_{ks}A_{ks}{}^mC_{ds}{}^mC_{ds}A_{ds}d{}^mC_{ds}T_{ds}G_{ds}T_{ds}G_{ks}T_{ks}A_{es}{}^mC_{ks}{}^mC_k$ | 0 | 939 |
| 785847 | N/A | N/A | 5286 | 5301 | ATCACCACTGTGTACC | $A_{ks}T_{ks}{}^mC_{ks}A_{ds}{}^mC_{ds}{}^mC_{ds}A_{ds}{}^mC_{ds}T_{ds}G_{ds}T_{ds}G_{ks}T_{es}Ak_{ds}{}^mC_{es}{}^mC_k$ | 0 | 927 |

TABLE 26-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 785859 | 392 | 407 | 4717 | 4732 | AGATGGTGTTATCTCC | $A_{ks}G_{ks}A_{ks}T_{ds}G_{ds}G_{ds}T_{ds}G_{ds}T_{ds}T_{ds}A_{ds}T_{ds}{}^mC_{ks}Tes{}^mC_{ks}{}^mC_e$ | 8 | 123 |
| 785874 | 2114 | 2129 | 11679 | 11694 | GTGAGTCTCAAACCAG | $G_{ks}T_{ks}GksA_{ds}G_{ds}T_{ds}{}^mC_{ds}T_{ds}{}^mC_{ds}A_{ds}A_{ds}A_{ds}{}^mC_{ks}{}^mC_{es}A_{ks}G_e$ | 0 | 206 |
| 785883 | N/A | N/A | 5286 | 5301 | ATCACCACTGTGTACC | $A_{ks}T_{ks}{}^mC_{ks}A_{ds}{}^mC_{ds}{}^mC_{ds}A_{ds}{}^mC_{ds}T_{ds}G_{ds}T_{ds}G_{ds}T_{ks}A_{es}{}^mC_{ks}{}^mC_e$ | 0 | 927 |
| 785892 | 391 | 406 | 4716 | 4731 | GATGGTGTTATCTCCG | $G_{ks}A_{ks}gT_{ks}G_{ds}G_{ds}T_{ds}G_{ds}T_{ds}T_{ds}A_{ds}T_{ds}{}^mC_{ds}T_{ks}{}^mC_{ks}{}^mC_{ks}G_e$ | 0 | 1335 |
| 785893 | 392 | 407 | 4717 | 4732 | AGATGGTGTTATCTCC | $A_{ks}G_{ks}A_{ks}T_{ds}G_{ds}G_{ds}T_{ds}G_{ds}T_{ds}T_{ds}A_{ds}T_{ds}{}^mC_{ks}T_{ks}{}^mC_{ks}{}^mC_e$ | 0 | 123 |
| 785918 | 2113 | 2128 | 11678 | 11693 | TGAGTCTCAAACCAGG | $T_{ks}G_{ks}A_{ks}G_{ds}T_{ds}{}^mC_{ds}T_{ds}{}^mC_{ds}A_{ds}A_{ds}A_{ds}{}^mC_{ds}{}^mC_{ds}A_{ks}G_{ks}G_e$ | 0 | 1336 |
| 785919 | 2114 | 2129 | 11679 | 11694 | GTGAGTCTCAAACCAG | $G_{ks}T_{ks}G_{ks}A_{ds}G_{ds}T_{ds}{}^mC_{ds}T_{ds}{}^mC_{ds}A_{ds}A_{ds}A_{ds}{}^mC_{ks}{}^mC_{ks}A_{ks}G_e$ | 44 | 206 |
| 785934 | N/A | N/A | 5285 | 5300 | TCACCACTGTGTACCC | $T_{ks}{}^mC_{ks}A_{ks}{}^mC_{ds}{}^mC_{ds}A_{ds}{}^mC_{ds}T_{ds}G_{ds}T_{ds}G_{ds}T_{ds}A_{ks}{}^mC_{ks}{}^mC_{ks}{}^mC_e$ | 21 | 939 |
| 785935 | N/A | N/A | 5286 | 5301 | ATCACCACTGTGTACC | $A_{ks}T_{ks}{}^mC_{ks}A_{ds}{}^mC_{ds}{}^mC_{ds}A_{ds}{}^mC_{ds}T_{ds}G_{ds}T_{ds}G_{ds}T_{ks}A_{ks}{}^mC_{ks}{}^mC_e$ | 19 | 927 |
| 785938 | N/A | N/A | 6548 | 6563 | CCAATTTTGCATTCCA | ${}^mC_{ks}{}^mC_{ks}A_{ks}A_{ds}T_{ds}T_{ds}T_{ds}T_{ds}G_{ds}{}^mC_{ds}A_{ds}T_{ds}T_{ks}{}^mC_{ks}{}^mC_{ks}A_e$ | 68 | 1242 |
| 786493 | 393 | 408 | 4718 | 4733 | AAGATGGTGTTATCTC | $A_{ks}A_{ks}G_{ks}A_{ds}T_{ds}G_{ds}G_{ds}T_{ds}G_{ds}T_{ds}T_{ds}A_{ds}T_{ds}{}^mC_{ks}T_{ks}{}^mC_k$ | 0 | 1337 |
| 786499 | 2113 | 2128 | 11678 | 11693 | TGAGTCTCAAACCAGG | $T_{ks}G_{ks}A_{ks}G_{ds}T_{ds}{}^mC_{ds}T_{ds}{}^mC_{ds}A_{ds}A_{ds}A_{ds}{}^mC_{ds}{}^mC_{ds}A_{ks}G_{ks}G_k$ | 16 | 1336 |
| 786500 | 2115 | 2130 | 11680 | 11695 | AGTGAGTCTCAAACCA | $A_{ks}G_{ks}T_{ks}G_{ds}A_{ds}G_{ds}T_{ds}{}^mC_{ds}T_{ds}{}^mC_{ds}A_{ds}A_{ds}A_{ds}{}^mC_{ks}{}^mC_{ks}A_k$ | 0 | 1338 |

TABLE 27

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 728806 | 1560 | 1575 | 11125 | 11140 | CGGTCTTTGAGGTCTGCks | ${}^mC_{ks}G_{ks}G_{ks}T_{ds}{}^mC_{ds}T_{ds}T_{ds}T_{ds}G_{ds}A_{ds}G_{ds}G_{ds}T_{ds}{}^mC_{ks}T_{ks}G_k$ | 32 | 539 |
| 729205 | N/A | N/A | 5283 | 5298 | ACCACTGTGTACCCCA | $A_{ks}{}^mC_{ks}{}^mC_{ks}A_{ds}{}^mC_{ds}T_{ds}G_{ds}T_{ds}G_{ds}T_{ds}A_{ds}{}^mC_{ds}{}^mC_{ds}{}^mC_{ks}{}^mC_{ks}A_k$ | 75 | 937 |
| 729433 | N/A | N/A | 4367 | 4382 | TTGTCTAGTGTCATGG | $T_{ks}T_{ks}G_{ks}T_{ds}{}^mC_{ds}T_{ds}A_{ds}G_{ds}T_{ds}G_{ds}T_{ds}{}^mC_{ds}A_{ds}T_{ks}G_{ks}G_k$ | 60 | 974 |
| 785368 | 1558 | 1573 | 11123 | 11138 | GTCTTTGAGGTCTGGG | $G_{ks}T_{ds}{}^mC_{ds}T_{ds}T_{ds}T_{ds}G_{ds}A_{ds}G_{ds}G_{ds}T_{ds}{}^mC_{ks}T_{es}G_{ks}G_{es}G_k$ | 0 | 537 |
| 785369 | 1560 | 1575 | 11125 | 11140 | CGGTCTTTGAGGTCTG | ${}^mC_{ks}G_{ds}G_{ds}T_{ds}{}^mC_{ds}T_{ds}T_{ds}T_{ds}G_{ds}ad_{ds}G_{ds}G_{ks}T_{es}{}^mC_{ks}T_{es}G_k$ | 68 | 539 |
| 785385 | N/A | N/A | 4365 | 4380 | GTCTAGTGTCATGGAA | $G_{ks}T_{ds}{}^mC_{ds}T_{ds}A_{ds}G_{ds}T_{ds}G_{ds}T_{ds}{}^mC_{ds}A_{ds}T_{ks}G_{ks}G_{ks}A_{es}A_k$ | 42 | 1339 |
| 785386 | N/A | N/A | 4367 | 4382 | TTGTCTAGTGTCATGG | $T_{ks}T_{ds}G_{ds}T_{ds}{}^mC_{ds}T_{ds}A_{ds}G_{ds}T_{ds}G_{ds}T_{ds}{}^mC_{ks}A_{es}T_{ks}G_{es}G_k$ | 44 | 974 |

TABLE 27-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 785389 | N/A | N/A | 5283 | 5298 | ACCACTGTGTACCCCA | $A_{ks}{}^mC_{ds}{}^mC_{ds}ad_{ds}{}^mC_{ds}T_{ds}G_{ds}T_{ds}$ $G_{ds}T_{ds}A_{ds}{}^mC_{ks}{}^mC_{es}{}^mC_{ks}{}^mC_{es}A_k$ | 43 | 937 |
| 785423 | 1558 | 1573 | 11123 | 11138 | GTCTTTGAGGTCTGGG | $G_{ks}T_{ds}{}^mC_{ds}T_{ds}T_{ds}T_{ds}G_{ds}A_{ds}$ $G_{ds}G_{ds}T_{ks}{}^mC_{es}T_{ks}G_{es}G_{ks}G_e$ | 33 | 537 |
| 785424 | 1560 | 1575 | 11125 | 11140 | CGGTCTTTGAGGTCTG | ${}^mC_{ds}G_{ds}G_{ds}T_{ds}{}^mC_{ds}T_{ds}T_{ds}T_{ds}$ $G_{ds}A_{ds}G_{ks}G_{es}T_{ks}{}^mC_{es}T_{ks}G_e$ | 40 | 539 |
| 785440 | N/A | N/A | 4365 | 4380 | GTCTAGTGTCATGGAA | $G_{ks}T_{ds}{}^mC_{ds}T_{ds}A_{ds}G_{ds}T_{ds}G_{ds}$ $T_{ds}{}^mC_{ds}A_{ks}T_{es}G_{ks}G_{es}A_{ks}A_e$ | 35 | 1339 |
| 785441 | N/A | N/A | 4367 | 4382 | TTGTCTAGTGTCATGG | $T_{ks}T_{ds}G_{ds}T_{ds}{}^mC_{ds}T_{ds}A_{ds}G_{ds}$ $T_{ds}G_{ds}T_{ks}{}^mC_{es}A_{ks}T_{es}G_{ks}G_e$ | 8 | 974 |
| 785444 | N/A | N/A | 5283 | 5298 | ACCACTGTGTACCCCA | $A_{ks}{}^mC_{ds}{}^mC_{ds}A_{ds}{}^mC_{ds}T_{ds}G_{ds}T_{ds}$ $G_{ds}T_{ds}A_{ks}{}^mC_{es}{}^mC_{ks}{}^mC_{es}{}^mC_{ks}A_e$ | 40 | 937 |
| 785470 | 1560 | 1575 | 11125 | 11140 | CGGTCTTTGAGGTCTG | ${}^mC_{ks}G_{es}G_{ks}td_{ds}{}^mC_{ds}T_{ds}T_{ds}T_{ds}$ $G_{ds}A_{ds}G_{ds}G_{ds}T_{es}{}^mC_{es}T_{ks}G_k$ | 49 | 539 |
| 785479 | N/A | N/A | 4367 | 4382 | TTGTCTAGTGTCATGG | $T_{ks}T_{es}G_{ks}T_{ds}{}^mC_{ds}T_{ds}A_{ds}G_{ds}T_{ds}$ $G_{ds}T_{ds}{}^mC_{ds}A_{es}T_{es}G_{ks}G_k$ | 55 | 974 |
| 785481 | N/A | N/A | 5283 | 5298 | ACCACTGTGTACCCCA | $A_{ks}{}^mC_{es}{}^mC_{ks}A_{ds}{}^mC_{ds}G_{ds}T_{ds}$ $G_{ds}T_{ds}A_{ds}{}^mC_{ds}{}^mC_{es}{}^mC_{es}{}^mC_{ks}A_k$ | 63 | 937 |
| 785511 | 1559 | 1574 | 11124 | 11139 | GGTCTTTGAGGTCTGG | $G_{ks}G_{ks}T_{ds}{}^mC_{ds}T_{ds}T_{ds}T_{ds}G_{ds}A_{ds}$ $G_{ds}G_{ds}T_{ks}{}^mC_{es}T_{es}G_{ks}G_e$ | 67 | 538 |
| 785512 | 1560 | 1575 | 11125 | 11140 | CGGTCTTTGAGGTCTG | ${}^mC_{ks}G_{ks}G_{ds}T_{ds}{}^mC_{ds}T_{ds}T_{ds}T_{ds}$ $G_{ds}ad_{ds}G_{ds}G_{ds}T_{ks}{}^mC_{es}T_{ks}G_e$ | 43 | 539 |
| 785527 | N/A | N/A | 4366 | 4381 | TGTCTAGTGTCATGGA | $T_{ks}G_{ks}T_{ds}{}^mC_{ds}T_{ds}A_{ds}G_{ds}T_{ds}$ $G_{ds}T_{ds}T_{ds}{}^mC_{ds}A_{ks}T_{ks}G_{es}G_{ks}A_e$ | 44 | 1340 |
| 785528 | N/A | N/A | 4367 | 4382 | TTGTCTAGTGTCATGG | $T_{ks}T_{ks}G_{ds}T_{ds}{}^mC_{ds}T_{ds}A_{ds}G_{ds}$ $T_{ds}G_{ds}T_{ds}{}^mC_{ds}A_{ks}T_{es}G_{ks}G_e$ | 38 | 974 |
| 785531 | N/A | N/A | 5282 | 5297 | CCACTGTGTACCCCAT | ${}^mC_{ks}{}^mC_{ks}A_{ds}{}^mC_{ds}T_{ds}G_{ds}T_{ds}G_{ds}$ $T_{ds}A_{ds}{}^mC_{ds}{}^mC_{ds}{}^mC_{ks}{}^mC_{es}A_{ks}T_e$ | 19 | 936 |
| 785532 | N/A | N/A | 5283 | 5298 | ACCACTGTGTACCCCA | $A_{ks}{}^mC_{ks}{}^mC_{ds}A_{ds}{}^mC_{ds}T_{ds}G_{ds}T_{ds}$ $G_{ds}T_{ds}A_{ds}{}^mC_{ds}{}^mC_{ks}{}^mC_{es}{}^mC_{ks}A_e$ | 66 | 937 |
| 785557 | 1559 | 1574 | 11124 | 11139 | GGTCTTTGAGGTCTGG | $G_{ks}G_{ks}T_{ds}{}^mC_{ds}T_{ds}T_{ds}T_{ds}G_{ds}$ $A_{ds}G_{ds}G_{es}T_{es}{}^mC_{es}T_{es}G_{ks}G_k$ | 56 | 538 |
| 785566 | N/A | N/A | 4366 | 4381 | TGTCTAGTGTCATGGA | $T_{ks}G_{ks}T_{ds}{}^mC_{ds}T_{ds}A_{ds}G_{ds}T_{ds}$ $G_{ds}td_{ds}{}^mC_{es}A_{es}T_{es}G_{es}G_{ks}A_k$ | 54 | 1340 |
| 785568 | N/A | N/A | 5282 | 5297 | CCACTGTGTACCCCAT | ${}^mC_{ks}{}^mC_{ks}A_{ds}{}^mC_{ds}T_{ds}G_{ds}T_{ds}G_{ds}$ $T_{ds}A_{ds}{}^mC_{es}{}^mC_{es}{}^mC_{es}{}^mC_{es}A_{ks}T_k$ | 44 | 936 |
| 785606 | 1558 | 1573 | 11123 | 11138 | GTCTTTGAGGTCTGGG | $G_{ks}T_{ks}{}^mC_{ds}T_{ds}T_{ds}T_{ds}G_{ds}A_{ds}$ $G_{ds}G_{ds}T_{ks}{}^mC_{es}T_{ks}G_{es}G_{ks}G_k$ | 34 | 537 |
| 785607 | 1559 | 1574 | 11124 | 11139 | GGTCTTTGAGGTCTGG | $G_{ks}G_{ks}T_{ds}{}^mC_{ds}T_{ds}T_{ds}T_{ds}G_{ds}A_{ds}$ $G_{ds}G_{ks}T_{es}{}^mC_{es}T_{es}G_{ks}G_k$ | 52 | 538 |
| 785608 | 1560 | 1575 | 11125 | 11140 | CGGTCTTTGAGGTCTG | ${}^mC_{ks}G_{ks}G_{ds}T_{ds}{}^mC_{ds}T_{ds}T_{ds}T_{ds}$ $G_{ds}A_{ds}G_{ks}G_{es}T_{ks}{}^mC_{es}T_{ks}G_k$ | 33 | 539 |
| 785629 | N/A | N/A | 4365 | 4380 | GTCTAGTGTCATGGAA | $G_{ks}T_{ks}{}^mC_{ds}T_{ds}A_{ds}G_{ds}T_{ds}G_{ds}$ $T_{ds}{}^mC_{ds}A_{ks}T_{es}G_{ks}G_{es}A_{ks}A_k$ | 9 | 1339 |
| 785630 | N/A | N/A | 4366 | 4381 | TGTCTAGTGTCATGGA | $T_{ks}G_{ks}T_{ds}{}^mC_{ds}T_{ds}A_{ds}G_{ds}T_{ds}$ $G_{ds}T_{ds}{}^mC_{ds}A_{es}T_{ks}G_{es}G_{ks}A_k$ | 10 | 1340 |
| 785631 | N/A | N/A | 4367 | 4382 | TTGTCTAGTGTCATGG | $T_{ks}T_{ks}G_{ds}T_{ds}{}^mC_{ds}T_{ds}A_{ds}G_{ds}T_{ds}$ $G_{ds}T_{ks}{}^mC_{es}A_{ks}T_{es}G_{ks}G_k$ | 0 | 974 |

TABLE 27-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 785635 | N/A | N/A | 5282 | 5297 | CCACTGTGTACCCAT | $^mC_{ks}{}^mC_{ks}A_{ds}{}^mC_{ds}T_{ds}G_{ds}T_{ds}G_{ds}T_{ds}A_{ds}{}^mC_{ks}{}^mC_{es}{}^mC_{ks}{}^mC_{es}A_{ks}T_k$ | 0 | 936 |
| 785636 | N/A | N/A | 5283 | 5298 | ACCACTGTGTACCCCA | $A_{ks}{}^mC_{ks}{}^mC_{ds}A_{ds}{}^mC_{ds}T_{ds}G_{ds}T_{ds}G_{ds}T_{ds}A_{ks}{}^mC_{es}{}^mC_{ks}{}^mC_{es}{}^mC_{ks}A_k$ | 15 | 937 |
| 785666 | 1559 | 1574 | 11124 | 11139 | GGTCTTTGAGGTCTGG | $G_{ks}G_{ks}T_{ds}{}^mC_{ds}T_{ds}T_{ds}T_{ds}G_{ds}A_{ds}G_{ds}G_{ds}T_{es}{}^mC_{es}T_{es}G_{ks}G_k$ | 74 | 538 |
| 785675 | N/A | N/A | 4366 | 4381 | TGTCTAGTGTCATGGA | $T_{ks}G_{ks}T_{ds}{}^mC_{ds}T_{ds}A_{ds}G_{ds}T_{ds}G_{ds}T_{ds}{}^mC_{ds}A_{es}T_{es}G_{es}G_{ks}A_k$ | 60 | 1340 |
| 755677 | N/A | N/A | 5282 | 5297 | CCACTGTGTACCCAT | $^mC_{ks}{}^mC_{ks}A_{ds}{}^mC_{ds}T_{ds}G_{ds}T_{ds}G_{ds}T_{ds}A_{ds}{}^mC_{ds}{}^mC_{es}{}^mC_{es}{}^mC_{es}A_{ks}T_k$ | 64 | 936 |
| 785696 | 1559 | 1574 | 11124 | 11139 | GGTCTTTGAGGTCTGG | $G_{ks}G_{ks}T_{ds}{}^mC_{ds}T_{ds}T_{ds}T_{ds}G_{ds}A_{ds}G_{ds}G_{ds}T_{ks}{}^mC_{ds}T_{ks}G_{ds}G_k$ | 56 | 538 |
| 785705 | N/A | N/A | 4366 | 4381 | TGTCTAGTGTCATGGA | $T_{ks}G_{ks}T_{ds}{}^mC_{ds}T_{ds}A_{ds}dG_{ds}T_{ds}G_{ds}T_{ds}{}^mC_{ds}A_{ks}T_{ds}G_{ks}dsA_k$ | 40 | 1340 |
| 785707 | N/A | N/A | 5282 | 5297 | CCACTGTGTACCCAT | $^mC_{ks}{}^mC_{ks}A_{ds}{}^mC_{ds}T_{ds}G_{ds}T_{ds}G_{ds}T_{ds}A_{ds}{}^mC_{ds}{}^mC_{ks}{}^mC_{ds}{}^mC_{ks}A_{ds}T_k$ | 54 | 936 |
| 785736 | 1559 | 1574 | 11124 | 11139 | GGTCTTTGAGGTCTGG | $G_{ks}G_{ks}T_{ds}{}^mC_{ds}T_{ds}T_{ds}T_{ds}G_{ds}A_{ds}G_{ds}G_{ds}T_{ks}{}^mC_{es}T_{ks}G_{es}G_k$ | 54 | 538 |
| 785737 | 1560 | 1575 | 11125 | 11140 | CGGTCTTTGAGGTCTG | $^mC_kG_{ks}G_{ds}T_{ds}{}^mC_{ds}T_{ds}T_{ds}T_{ds}G_{ds}A_{ds}G_{ds}G_{ks}T_{es}{}^mC_{ks}T_{es}G_k$ | 44 | 539 |
| 785752 | N/A | N/A | 4366 | 4381 | TGTCTAGTGTCATGGA | $T_{ks}G_{ks}T_{ds}{}^mC_{ds}T_{ds}A_{ds}G_{ds}T_{ds}G_{ds}T_{ds}{}^mC_{ds}A_{ks}T_{es}G_{ks}G_{es}A_k$ | 44 | 1340 |
| 785753 | N/A | N/A | 4367 | 4382 | TTGTCTAGTGTCATGG | $T_{ks}T_{ks}G_{ds}T_{ds}{}^mC_{ds}T_{ds}A_{ds}G_{ds}T_{ds}G_{ds}T_{ds}{}^mC_{ks}A_{es}T_{ks}G_{es}G_k$ | 24 | 974 |
| 785756 | N/A | N/A | 5282 | 5297 | CCACTGTGTACCCAT | $^mC_{ks}{}^mC_{ks}A_{ds}{}^mC_{ds}T_{ds}G_{ds}T_{ds}G_{ds}T_{ds}A_{ds}{}^mC_{ds}{}^mC_{ks}{}^mC_{es}{}^mC_{ks}A_{es}T_k$ | 42 | 936 |
| 785757 | N/A | N/A | 5283 | 5298 | ACCACTGTGTACCCCA | $A_{ks}{}^mC_{ks}{}^mC_{ds}A_{ds}{}^mC_{ds}T_{ds}G_{ds}T_{ds}G_{ds}T_{ds}A_{ds}{}^mC_{ks}{}^mC_{es}{}^mC_{ks}{}^mC_{es}A_k$ | 17 | 937 |
| 785783 | 1560 | 1575 | 11125 | 11140 | CGGTCTTTGAGGTCTG | $^mC_{ks}G_{ks}G_{ks}T_{ds}{}^mC_{ds}T_{ds}T_{ds}T_{ds}G_{ds}A_{ds}G_{ds}G_{ks}T_{ds}{}^mC_{ks}T_{ds}G_k$ | 57 | 539 |
| 785792 | N/A | N/A | 4367 | 4382 | TTGTCTAGTGTCATGG | $T_{ks}T_{ks}G_{ks}T_{ds}{}^mC_{ds}T_{ds}A_{ds}G_{ds}T_{ds}G_{ds}T_{ds}{}^mC_{ks}A_{ks}T_{ks}G_{ds}G_k$ | 36 | 974 |
| 785794 | N/A | N/A | 5283 | 5298 | ACCACTGTGTACCCCA | $A_{ks}{}^mC_{ks}{}^mC_{ks}A_{ds}{}^mC_{ds}T_{ds}G_{ds}T_{ds}G_{ds}T_{ds}A_{ds}A_{ds}{}^mC_{ks}{}^mC_{ds}{}^mC_{ks}{}^mC_{ds}A_k$ | 40 | 937 |
| 785824 | 1559 | 1574 | 11124 | 11139 | GGTCTTTGAGGTCTGG | $G_{ks}G_{ks}T_{ks}{}^mC_{ds}T_{ds}T_{ds}T_{ds}G_{ds}A_{ds}G_{ds}G_{ds}T_{ks}{}^mC_{es}T_{ks}G_{es}G_k$ | 46 | 538 |
| 785825 | 1560 | 1575 | 11125 | 11140 | CGGTCTTTGAGGTCTG | $^mC_{ks}G_{ks}G_{ks}T_{ds}{}^mC_{ds}T_{ds}T_{ds}T_{ds}G_{ds}A_{ds}G_{ds}G_{ks}T_{es}{}^mC_{ks}T_{es}G_k$ | 56 | 539 |
| 785840 | N/A | N/A | 4366 | 4381 | TGTCTAGTGTCATGGA | $T_{ks}G_{ks}T_{ks}{}^mC_{ds}T_{ds}A_{ds}G_{ds}T_{ds}G_{ds}T_{ds}{}^mC_{ds}A_{ks}T_{es}G_{ks}G_{es}A_k$ | 57 | 1340 |
| 785841 | N/A | N/A | 4367 | 4382 | TTGTCTAGTGTCATGG | $T_{ks}T_{ks}G_{ks}T_{ds}{}^mC_{ds}T_{ds}A_{ds}G_{ds}T_{ds}G_{ds}T_{ds}{}^mC_{ks}A_{es}T_{ks}G_{es}G_k$ | 16 | 974 |
| 785844 | N/A | N/A | 5282 | 5297 | CCACTGTGTACCCAT | $^mC_{ks}{}^mC_{ks}A_{ds}{}^mC_{ds}T_{ds}G_{ds}T_{ds}G_{ds}T_{ds}A_{ds}{}^mC_{ds}{}^mC_{ks}{}^mC_{es}{}^mC_{ks}A_{es}T_k$ | 10 | 936 |
| 785845 | N/A | N/A | 5283 | 5298 | ACCACTGTGTACCCCA | $A_{ks}{}^mC_{ks}{}^mC_{ks}A_{ds}{}^mC_{ds}T_{ds}G_{ds}T_{ds}G_{ds}T_{ds}A_{ds}{}^mC_{ks}{}^mC_{es}{}^mC_{ks}{}^mC_{es}A_k$ | 6 | 937 |
| 785871 | 1560 | 1575 | 11125 | 11140 | CGGTCTTTGAGGTCTG | $^mC_{ks}G_{ks}G_{ks}T_{ds}{}^mC_{ds}T_{ds}T_{ds}T_{ds}G_{ds}A_{ds}G_{ds}G_{ds}T_{ks}{}^mC_{es}T_{ks}G_e$ | 38 | 539 |

TABLE 27-continued

Inhibition of IRF5 mRNA by modified oligonucleotides targeting SEQ ID NO: 1 and 2

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry Notation | % Inhibition | SEQ ID NO |
|---|---|---|---|---|---|---|---|---|
| 785880 | N/A | N/A | 4367 | 4382 | TTGTCTAGTGTCATGG | $T_{ks}T_{ks}G_{ks}T_{ds}{}^mC_{ds}T_{ds}A_{ds}G_{ds}T_{ds}G_{ds}T_{ds}{}^mC_{ds}A_{ks}T_{es}G_{ks}G_e$ | 39 | 974 |
| 785882 | N/A | N/A | 5283 | 5298 | ACCACTGTGTACCCCA | $A_{ks}{}^mC_{ks}{}^mC_{ks}A_{ds}{}^mC_{ds}T_{ds}G_{ds}T_{ds}G_{ds}T_{ds}A_{ds}{}^mC_{ds}{}^mC_{ks}{}^mC_{es}{}^mC_{ks}A_e$ | 39 | 937 |
| 785912 | 1559 | 1574 | 11124 | 11139 | GGTCTTTGAGGTCTGG | $G_{ks}G_{ks}T_{ks}{}^mC_{ds}T_{ds}T_{ds}T_{ds}G_{ds}A_{ds}G_{ds}G_{ds}T_{ds}{}^mC_{ks}T_{ks}G_{ks}G_e$ | 33 | 538 |
| 785913 | 1560 | 1575 | 11125 | 11140 | CGGTCTTTGAGGTCTG | ${}^mC_{ks}G_{ks}G_{ks}T_{ds}{}^mC_{ds}T_{ds}T_{ds}T_{ds}G_{ds}A_{ds}G_{ds}G_{ds}T_{ks}{}^mC_{ks}T_{ks}G_e$ | 32 | 539 |
| 785928 | N/A | N/A | 4366 | 4381 | TGTCTAGTGTCATGGA | $T_{ks}G_{ks}T_{ks}{}^mC_{ds}T_{ds}A_{ds}G_{ds}T_{ds}G_{ds}T_{ds}T_{ds}{}^mC_{ds}A_{ds}T_{ks}G_{ks}G_{ks}A_e$ | 39 | 1340 |
| 785929 | N/A | N/A | 4367 | 4382 | TTGTCTAGTGTCATGG | $T_{ks}T_{ks}G_{ks}T_{ds}{}^mC_{ds}T_{ds}A_{ds}G_{ds}T_{ds}G_{ds}T_{ds}T_{ds}{}^mC_{ds}A_{ks}T_{ks}G_{ks}G_e$ | 20 | 974 |
| 785935 | N/A | N/A | 5282 | 5297 | CCACTGTGTACCCCAT | ${}^mC_{ks}{}^mC_{ks}A_{ks}{}^mC_{ds}T_{ds}G_{ds}T_{ds}G_{ds}T_{ds}A_{ds}{}^mC_{ds}{}^mC_{ds}{}^mC_{ds}{}^mC_{ks}A_{ks}T_e$ | 57 | 936 |
| 785933 | N/A | N/A | 5283 | 5298 | ACCACTGTGTACCCCA | $A_{ks}{}^mC_{ks}{}^mC_{ks}A_{ds}{}^mC_{ds}T_{ds}G_{ds}T_{ds}G_{ds}T_{ds}A_{ds}{}^mC_{ds}{}^mC_{ks}{}^mC_{ks}{}^mC_{ks}A_e$ | 47 | 937 |
| 785938 | N/A | N/A | 6548 | 6563 | CCAATTTTGCATTCCA | ${}^mC_{ks}{}^mC_{ks}A_{ks}A_{ds}T_{ds}T_{ds}T_{ds}T_{ds}G_{ds}{}^mC_{ds}A_{ds}T_{ds}T_{ks}{}^mC_{ks}{}^mC_{ks}A_e$ | 75 | 1242 |
| 786572 | N/A | N/A | 4358 | 4373 | GTCATGGAATTTTGTG | $G_{ks}T_{ks}{}^mC_{ks}A_{ds}T_{ds}G_{ds}G_{ds}A_{ds}A_{ds}T_{ds}T_{ds}T_{ds}T_{ks}G_{ks}T_{ks}G_k$ | 54 | 1341 |
| 786573 | N/A | N/A | 4360 | 4375 | GTGTCATGGAATTTTG | $G_{ks}T_{ks}G_{ks}T_{ds}{}^mC_{ds}A_{ds}T_{ds}G_{ds}G_{ds}A_{ds}A_{ds}T_{ds}T_{ks}T_{ks}T_{ks}G_k$ | 58 | 1342 |
| 786574 | N/A | N/A | 4362 | 4377 | TAGTGTCATGGAATTT | $T_{ks}A_{ks}G_{ks}T_{ds}G_{ds}T_{ds}{}^mC_{ds}A_{ds}T_{ds}G_{ds}G_{ds}A_{ds}A_{ds}T_{ks}T_{ks}T_k$ | 38 | 1343 |
| 786575 | N/A | N/A | 4363 | 4378 | CTAGTGTCATGGAATT | ${}^mC_{ks}T_{ks}A_{ks}G_{ds}T_{ds}G_{ds}T_{ds}{}^mC_{ds}A_{ds}T_{ds}G_{ds}G_{ds}A_{ds}A_{ks}T_{ks}T_k$ | 34 | 1344 |
| 786576 | N/A | N/A | 4364 | 4379 | TCTAGTGTCATGGAAT | $T_{ks}{}^mC_{ks}T_{ks}A_{ds}G_{ds}T_{ds}G_{ds}T_{ds}{}^mC_{ds}A_{ds}T_{ds}G_{ds}G_{ds}A_{ks}A_{ks}T_k$ | 14 | 1345 |
| 76577 | N/A | N/A | 4365 | 4380 | GTCTAGTGTCATGGAA | $G_{ks}T_{ks}{}^mC_{ks}T_{ds}A_{ds}G_{ds}T_{ds}G_{ds}T_{ds}{}^mC_{ds}A_{ds}T_{ds}G_{ds}G_{ks}A_{ks}A_k$ | 38 | 1339 |
| 786578 | N/A | N/A | 4366 | 4381 | TGTCTAGTGTCATGGA | $T_{ks}G_{ks}T_{ks}{}^mC_{ds}T_{ds}A_{ds}G_{ds}T_{ds}G_{ds}T_{ds}{}^mC_{ds}A_{ds}T_{ds}G_{ks}G_{ks}A_k$ | 61 | 1340 |
| 786579 | N/A | N/A | 4368 | 4383 | CTTGTCTAGTGTCATG | ${}^mC_{ks}T_{ks}T_{ks}G_{ds}T_{ds}{}^mC_{ds}T_{ds}A_{ds}G_{ds}T_{ds}G_{ds}T_{ds}{}^mC_{ds}A_{ks}T_{ks}G_k$ | 58 | 1346 |
| 786580 | N/A | N/A | 4369 | 4384 | TCTTGTCTAGTGTCAT | $T_{ks}{}^mC_{ks}T_{ks}T_{ds}G_{ds}T_{ds}{}^mC_{ds}T_{ds}A_{ds}G_{ds}T_{ds}G_{ds}T_{ds}{}^mC_{ks}A_{ks}T_k$ | 0 | 1347 |
| 786581 | N/A | N/A | 4370 | 4385 | TTCTTGTCTAGTGTCA | $T_{ks}T_{ks}{}^mC_{ks}T_{ds}T_{ds}G_{ds}T_{ds}{}^mC_{ds}T_{ds}A_{ds}G_{ds}T_{ds}G_{ds}T_{ks}{}^mC_{ks}A_k$ | 49 | 1348 |
| 786582 | N/A | N/A | 4371 | 4386 | TTTCTTGTCTAGTGTC | $T_{ks}T_{ks}T_{ks}{}^mC_{ds}T_{ds}T_{ds}G_{ds}T_{ds}{}^mC_{ds}T_{ds}A_{ds}G_{ds}T_{ds}G_{ks}T_{ks}{}^mC_k$ | 53 | 1349 |
| 786583 | N/A | N/A | 4372 | 4387 | CTTTCTTGTCTAGTGT | ${}^mC_{ks}T_{ks}T_{ks}T_{ds}{}^mC_{ds}T_{ds}T_{ds}G_{ds}T_{ds}{}^mC_{ds}T_{ds}A_{ds}G_{ds}T_{ks}G_{ks}T_k$ | 48 | 1350 |
| 786584 | N/A | N/A | 4374 | 4389 | AGCTTTCTTGTCTAGT | $A_{ks}G_{ks}{}^mC_{ks}T_{ds}T_{ds}T_{ds}{}^mC_{ds}T_{ds}T_{ds}G_{ds}T_{ds}{}^mC_{ds}T_{ds}A_{ks}G_{ks}T_k$ | 20 | 1351 |
| 786585 | N/A | N/A | 4376 | 4391 | TCAGCTTTCTTGTCTA | $T_{ks}{}^mC_{ks}A_{ks}G_{ds}{}^mC_{ds}T_{ds}T_{ds}T_{ds}{}^mC_{ds}T_{ds}T_{ds}G_{ds}T_{ds}{}^mC_{ks}T_{ks}A_k$ | 15 | 1352 |
| 786586 | N/A | N/A | 4378 | 4393 | CATCAGCTTTCTTGTC | ${}^mC_{ks}A_{ks}T_{ks}{}^mC_{ds}A_{ds}G_{ds}{}^mC_{ds}T_{ds}T_{ds}T_{ds}{}^mC_{ds}T_{ds}T_{ds}G_{ks}T_{ks}{}^mC_k$ | 28 | 1353 |

Example 3: Dose-Dependent Inhibition of Human IRF5 by cEt Gapmers

Modified oligonucleotides described in the studies above exhibiting significant in vitro inhibition of IRF5 RNA were selected and tested at various doses in THP-1 cells, as well as in KARPAS-229 cells. The modified oligonucleotides were tested in a series of experiments that had similar culture conditions. The results for each experiment are presented in separate tables shown below.

Assay in THP-1 Cells

Cultured THP-1 cells at a density of 30,000 cells per well were transfected using electroporation with modified oligonucleotides diluted to different concentrations as specified in the Tables below. After a treatment period of approximately 24 hours, IRF5 RNA levels were measured as previously described using the human IRF5 primer-probe set HTS4167. IRF5 RNA levels were adjusted according to total RNA content, as measured by RIBOGREEN®. Results are presented in the tables below as percent inhibition of IRF5, relative to untreated control cells. The half maximal inhibitory concentration (IC$_{50}$) of each modified oligonucleotide is also presented. IC$_{50}$ was calculated using a linear regression on a log/linear plot of the data in excel.

TABLE 28

Multi-dose assay of modified oligonucleotides in THP-1 cells

| Compound No. | % Inhibition | | | | IC$_{50}$ (μM) |
|---|---|---|---|---|---|
| | 185.19 nM | 555.56 nM | 1666.67 nM | 5000.00 nM | |
| 665795 | 36 | 57 | 76 | 85 | 0.4 |
| 665892 | 40 | 59 | 74 | 82 | 0.3 |
| 665893 | 26 | 53 | 74 | 83 | 0.6 |
| 665908 | 19 | 45 | 57 | 73 | 1.1 |
| 665933 | 30 | 38 | 66 | 79 | 0.8 |
| 728408 | 19 | 32 | 55 | 82 | 1.1 |
| 728458 | 29 | 45 | 58 | 80 | 0.8 |
| 728498 | 24 | 31 | 61 | 81 | 1.0 |
| 728670 | 58 | 51 | 70 | 79 | 0.1 |
| 728673 | 25 | 32 | 51 | 84 | 1.1 |
| 728695 | 23 | 54 | 72 | 80 | 0.6 |
| 728696 | 38 | 62 | 73 | 89 | 0.3 |
| 728705 | 39 | 57 | 71 | 82 | 0.4 |
| 728706 | 35 | 55 | 72 | 92 | 0.4 |
| 728707 | 50 | 64 | 74 | 85 | 0.2 |
| 728708 | 53 | 69 | 86 | 88 | 0.1 |
| 728806 | 33 | 47 | 74 | 87 | 0.5 |

TABLE 29

Multi-dose assay of modified oligonucleotides in THP-1 cells

| Compound No. | % Inhibition | | | | IC$_{50}$ (μM) |
|---|---|---|---|---|---|
| | 185.19 nM | 555.5556 nM | 185.19 nM | 5000.0 nM | |
| 665893 | 25 | 50 | 64 | 81 | 0.7 |
| 665933 | 18 | 30 | 67 | 69 | 1.2 |
| 728739 | 14 | 26 | 55 | 58 | 2.2 |
| 728741 | 13 | 35 | 65 | 82 | 1.0 |
| 728759 | 40 | 49 | 49 | 68 | 0.8 |
| 728778 | 10 | 32 | 46 | 79 | 1.5 |
| 728793 | 10 | 21 | 39 | 68 | 2.4 |
| 728800 | 23 | 39 | 62 | 68 | 1.1 |
| 728802 | 20 | 35 | 34 | 65 | 2.5 |
| 728887 | 8 | 34 | 60 | 72 | 1.4 |
| 728891 | 43 | 23 | 50 | 74 | 1.2 |
| 728893 | 9 | 28 | 45 | 74 | 1.7 |

TABLE 29-continued

Multi-dose assay of modified oligonucleotides in THP-1 cells

| Compound No. | % Inhibition | | | | IC$_{50}$ (μM) |
|---|---|---|---|---|---|
| | 185.19 nM | 555.5556 nM | 185.19 nM | 5000.0 nM | |
| 728894 | 20 | 42 | 68 | 85 | 0.8 |
| 728898 | 16 | 41 | 69 | 86 | 0.8 |
| 728899 | 10 | 34 | 65 | 79 | 1.1 |
| 728905 | 21 | 31 | 57 | 77 | 1.2 |
| 728944 | 15 | 21 | 71 | 79 | 1.1 |
| 728954 | 7 | 21 | 60 | 82 | 1.3 |
| 728970 | 30 | 50 | 78 | 85 | 0.5 |

TABLE 30

Multi-dose assay of modified oligonucleotides in THP-1 cells

| Compound No. | % Inhibition | | | | IC$_{50}$ (μM) |
|---|---|---|---|---|---|
| | 185.19 nM | 555.56 nM | 1666.67 nM | 5000.00 nM | |
| 665893 | 38 | 59 | 72 | 83 | 0.4 |
| 665933 | 13 | 39 | 52 | 71 | 1.4 |
| 666168 | 29 | 30 | 60 | 82 | 0.9 |
| 728958 | 30 | 43 | 68 | 83 | 0.7 |
| 728969 | 30 | 55 | 81 | 89 | 0.5 |
| 728996 | 36 | 57 | 73 | 84 | 0.4 |
| 728998 | 27 | 56 | 73 | 85 | 0.5 |
| 729018 | 33 | 52 | 69 | 85 | 0.5 |
| 729037 | 58 | 64 | 86 | 94 | 0.1 |
| 729038 | 41 | 65 | 89 | 92 | 0.3 |
| 729039 | 40 | 50 | 77 | 90 | 0.39 |
| 729049 | 35 | 57 | 76 | 85 | 0.4 |
| 729050 | 21 | 52 | 75 | 90 | 0.6 |
| 729205 | 23 | 42 | 73 | 84 | 0.7 |
| 729206 | 11 | 40 | 54 | 73 | 1.3 |
| 729433 | 25 | 41 | 65 | 86 | 0.8 |
| 729453 | 16 | 43 | 61 | 80 | 1.0 |
| 729454 | 31 | 40 | 69 | 87 | 0.7 |
| 729456 | 11 | 38 | 63 | 80 | 1.1 |

TABLE 31

Multi-dose assay of modified oligonucleotides in THP-1 cells

| Compound No. | % Inhibition | | | | IC$_{50}$ (μM) |
|---|---|---|---|---|---|
| | 185.19 nM | 555.56 nM | 1666.67 nM | 5000.00 nM | |
| 665893 | 24 | 53 | 74 | 86 | 0.6 |
| 665933 | 13 | 36 | 58 | 71 | 1.3 |
| 666178 | 29 | 46 | 65 | 82 | 0.7 |
| 666208 | 0 | 24 | 50 | 73 | 1.8 |
| 729201 | 18 | 35 | 49 | 73 | 1.4 |
| 729207 | 12 | 34 | 60 | 84 | 1.1 |
| 729213 | 19 | 47 | 70 | 85 | 0.7 |
| 729221 | 5 | 31 | 53 | 73 | 1.5 |
| 729243 | 5 | 34 | 54 | 77 | 1.4 |
| 729447 | 0 | 0 | 10 | 53 | >5.0 |
| 729460 | 18 | 31 | 63 | 81 | 1.1 |
| 729475 | 22 | 39 | 57 | 80 | 1.0 |
| 729476 | 42 | 63 | 85 | 91 | 0.3 |
| 729494 | 27 | 42 | 67 | 80 | 0.8 |
| 729495 | 16 | 57 | 74 | 86 | 0.6 |
| 729497 | 0 | 35 | 48 | 72 | 1.7 |
| 729513 | 18 | 41 | 67 | 89 | 0.8 |
| 729589 | 14 | 47 | 70 | 85 | 0.8 |
| 729659 | 3 | 32 | 60 | 85 | 1.2 |

Assay in KARPAS-229 Cells

Cultured KARPAS-229 cells at a density of 10,000 cells per well were treated using free uptake with modified oligonucleotides diluted to different concentrations as specified in the Tables below. After a treatment period of approximately 24 hours, IRF5 mRNA levels were measured as previously described using the Human IRF5 primer-probe set RTS4524. IRF5 mRNA levels were adjusted according to total RNA content, as measured by RIBOGREEN®. Results are presented in the tables below as percent inhibition of IRF5, relative to untreated control cells.

The half maximal inhibitory concentration ($IC_{50}$) of each modified oligonucleotide is also presented. $IC_{50}$ was calculated using a linear regression on a log/linear plot of the data in excel. 'N.D.' indicates that the % inhibition is not defined for that dosage with the modified oligonucleotide.

TABLE 32

Multi-dose assay of modified oligonucleotides in KARPAS-229 cells

| Com- | % Inhibition | | | | |
|---|---|---|---|---|---|
| pound No. | 444.44 nM | 1333.33 nM | 4000.00 nM | 12000.00 nM | $IC_{50}$ (µM) |
| 728466 | 32 | 38 | 56 | 69 | 2.6 |
| 729037 | 52 | 65 | 79 | 86 | 0.3 |
| 729476 | 38 | 66 | 78 | 83 | 0.7 |
| 785350 | 23 | 40 | 62 | 87 | 2.0 |
| 785475 | 31 | 44 | 66 | 81 | 1.6 |
| 785477 | 34 | 48 | 62 | 74 | 1.6 |
| 785478 | 53 | 69 | 80 | 86 | 0.3 |
| 785485 | 42 | 68 | 78 | 82 | 0.5 |
| 785502 | 38 | 47 | 69 | 78 | 1.2 |
| 785522 | 39 | 59 | 73 | 84 | 0.8 |
| 785537 | 47 | 66 | 75 | 82 | 0.4 |
| 785563 | 25 | 51 | 64 | 77 | 1.8 |
| 785583 | 15 | 32 | 66 | 76 | 2.7 |
| 785661 | 22 | 32 | 41 | 58 | 7.0 |
| 785672 | 46 | 64 | 73 | 84 | 0.5 |
| 785791 | 42 | 62 | 67 | 79 | 0.7 |
| 785876 | 41 | 56 | 67 | 81 | 0.9 |
| 785938 | 61 | 79 | 84 | 88 | 0.1 |
| 786507 | 51 | 74 | 83 | 89 | 0.3 |

TABLE 33

Multi-dose assay of modified oligonucleotides in KARPAS-229 cells

| Com- | % Inhibition | | | | |
|---|---|---|---|---|---|
| pound No. | 444.44 nM | 1333.33 nM | 4000.00 nM | 12000.00 nM | $IC_{50}$ (µM) |
| 729018 | 59 | 68 | 78 | 83 | 0.1 |
| 729049 | 51 | 66 | 77 | 84 | 0.3 |
| 729454 | 12 | 41 | 58 | 70 | 3.0 |
| 729495 | 44 | 60 | 74 | 86 | 0.7 |
| 785519 | 6 | 12 | 49 | 65 | 5.5 |
| 785525 | 40 | 53 | 71 | 79 | 1.0 |
| 785674 | 57 | 71 | 77 | 83 | 0.1 |
| 785764 | 29 | N.D | 61 | 81 | 1.8 |
| 785920 | 21 | 13 | 71 | 76 | 2.9 |
| 785926 | 46 | 52 | 67 | 74 | 0.8 |
| 785938 | 54 | 75 | 87 | 91 | 0.2 |
| 786501 | 27 | 39 | 68 | 79 | 1.9 |
| 786503 | 42 | 45 | 76 | 77 | 1.0 |
| 786524 | 50 | 54 | 73 | 81 | 0.6 |
| 786538 | 60 | 49 | 74 | 77 | 0.3 |
| 786548 | 15 | 46 | 52 | 70 | 3.0 |
| 786590 | 9 | 39 | 70 | 81 | 2.3 |
| 786591 | 38 | 44 | 66 | 78 | 1.4 |
| 786597 | 32 | 59 | 70 | 81 | 1.1 |

TABLE 34

Multi-dose assay of modified oligonucleotides in KARPAS-229 cells

| Com- | % Inhibition | | | | |
|---|---|---|---|---|---|
| pound No. | 444.44 nM | 1333.33 nM | 4000.00 nM | 12000.00 nM | $IC_{50}$ (µM) |
| 728466 | 25 | 56 | 50 | 67 | 2.4 |
| 728708 | 33 | 41 | 46 | 55 | 6.1 |
| 729037 | 54 | 72 | 75 | 82 | 0.2 |
| 729205 | 16 | 41 | 57 | 65 | 3.3 |
| 729433 | 37 | N.D. | 70 | 84 | 1.1 |
| 729494 | 41 | 66 | 67 | 78 | 0.7 |
| 785369 | 31 | 29 | 46 | 57 | 6.5 |
| 785481 | 28 | 45 | 62 | 77 | 1.9 |
| 785511 | 39 | 43 | 63 | 72 | 1.6 |
| 785532 | 26 | 38 | 56 | 70 | 2.7 |
| 785539 | 37 | 45 | 62 | 73 | 1.6 |
| 785666 | 22 | 58 | 69 | 79 | 1.5 |
| 785675 | 33 | 50 | 57 | 70 | 1.9 |
| 785677 | 14 | 39 | 55 | 71 | 3.1 |
| 785919 | 23 | 39 | 50 | 59 | 4.4 |
| 785938 | 62 | 82 | 87 | 88 | <0.4 |
| 785940 | 31 | 44 | 70 | 78 | 1.6 |
| 785941 | 33 | 56 | 61 | 75 | 1.3 |
| 786578 | 0 | 42 | 65 | 74 | 3.3 |

Example 4: Tolerability of Modified Oligonucleotides Targeting Human IRF5 in CD-1 Mice CD-1 mice are a multipurpose mouse model frequently utilized for safety and efficacy testing. The mice were treated with modified oligonucleotides selected from studies described above and evaluated for changes in the levels of various plasma chemistry markers.

Study 1

Treatment

Groups of 6- to 8-week-old male CD-1 mice were injected subcutaneously once a week for seven weeks (for a total of 7 treatments) with 50 mg/kg of modified oligonucleotides. One group of male CD-1 mice was injected with PBS. Mice were euthanized 48 hours following the final administration.

Plasma Chemistry Markers

To evaluate the effect of modified oligonucleotides on liver function, plasma levels of blood urea nitrogen (BUN), albumin, alanine aminotransferase (ALT), aspartate aminotransferase (AST), and total bilirubin (TBIL) were measured using an automated clinical chemistry analyzer (Hitachi Olympus AU400c, Melville, N.Y.). The results are presented in the Table below. Modified oligonucleotides that caused changes in the levels of any of the liver or kidney function markers outside the expected range for modified oligonucleotides were excluded in further studies.

TABLE 35

Plasma chemistry markers in male CD-1 mice

| Compound No. | BUN (mg/dL) | Albumin (g/dL) | AST (IU/L) | ALT (IU/L) | TBIL (mg/dL) |
|---|---|---|---|---|---|
| PBS | 25 | 3.5 | 57 | 45 | 0.2 |
| 665795 | 27 | 3.2 | 237 | 541 | 0.3 |
| 665892 | 35 | 3.3 | 212 | 245 | 0.2 |
| 665893 | 25 | 3.5 | 210 | 290 | 0.2 |
| 665908 | 29 | 4.1 | 4665 | 6042 | 0.5 |
| 665933 | 31 | 3.8 | 767 | 1353 | 0.3 |
| 666168 | 26 | 3.4 | 3931 | 3855 | 0.7 |
| 666178 | 30 | 2.9 | 16490 | 14669 | 6.4 |

TABLE 35-continued

Plasma chemistry markers in male CD-1 mice

| Compound No. | BUN (mg/dL) | Albumin (g/dL) | AST (IU/L) | ALT (IU/L) | TBIL (mg/dL) |
|---|---|---|---|---|---|
| 728458 | 32 | 3.7 | 821 | 1311 | 0.2 |
| 728706 | 28 | 3.7 | 2893 | 3673 | 0.8 |
| 728708 | 24 | 3.9 | 1770 | 3270 | 0.2 |
| 728759 | 22 | 3.7 | 860 | 599 | 0.2 |
| 728806 | 38 | 3.8 | 2503 | 2422 | 0.4 |
| 728958 | 23 | 3.0 | 214 | 158 | 0.2 |
| 728969 | 22 | 3.5 | 70 | 59 | 0.2 |
| 728970 | 20 | 3.6 | 157 | 140 | 0.2 |
| 728998 | 24 | 3.5 | 583 | 865 | 0.2 |
| 729018 | 19 | 3.2 | 86 | 66 | 0.2 |
| 729049 | 21 | 3.7 | 425 | 771 | 0.2 |
| 729050 | 22 | 3.5 | 193 | 246 | 0.2 |
| 729213 | 25 | 3.1 | 344 | 411 | 0.2 |
| 729433 | 26 | 3.7 | 802 | 791 | 0.2 |
| 729454 | 25 | 3.6 | 3958 | 4541 | 0.5 |
| 729476 | 77 | 2.7 | 1660 | 2046 | 0.7 |
| 729494 | 20 | 3.2 | 157 | 149 | 0.2 |
| 729495 | 57 | 3.2 | 240 | 254 | 0.1 |
| 729513 | 23 | 4.8 | 1558 | 2743 | 0.4 |

Body and Organ Weights

Body weights of CD-1 mice were measured at days 1 and 44, and the average body weight for each group is presented in the Table below. Heart, kidney, spleen, liver and thymus weights were measured at the end of the study and are presented in the Table below. Modified oligonucleotides that caused any changes in organ weights outside the expected range for modified oligonucleotides were excluded from further studies.

TABLE 36

Body and organ weights (in grams)

| Compound No. | Body Weight (g) Day 1 | Body Weight (g) Day 44 | Heart (g) | Kidney (g) | Spleen (g) | Liver (g) | Thymus (g) |
|---|---|---|---|---|---|---|---|
| PBS | 34 | 37 | 0.2 | 0.7 | 0.1 | 2.2 | 0.05 |
| 665795 | 34 | 40 | 0.2 | 0.7 | 0.2 | 2.6 | 0.03 |
| 665892 | 34 | 38 | 0.2 | 0.8 | 0.2 | 2.9 | 0.02 |
| 665893 | 34 | 39 | 0.2 | 0.8 | 0.2 | 2.6 | 0.02 |
| 665908 | 34 | 35 | 0.2 | 0.6 | 0.2 | 3.5 | 0.02 |
| 665933 | 34 | 39 | 0.2 | 0.7 | 0.1 | 3.1 | 0.02 |
| 666168 | 34 | 31 | 0.2 | 0.4 | 0.2 | 2.3 | 0.01 |
| 666178 | 33 | 28 | 0.1 | 0.6 | 0.1 | 1.8 | 0.02 |
| 728458 | 34 | 37 | 0.2 | 0.8 | 0.2 | 3.3 | 0.05 |
| 728706 | 34 | 31 | 0.2 | 0.6 | 0.1 | 2.3 | 0.01 |
| 728708 | 33 | 36 | 0.2 | 0.7 | 0.2 | 3.0 | 0.03 |
| 728759 | 33 | 39 | 0.2 | 0.7 | 0.1 | 3.5 | 0.04 |
| 728806 | 33 | 33 | 0.1 | 0.6 | 0.1 | 3.0 | 0.02 |
| 728958 | 34 | 39 | 0.2 | 0.8 | 0.2 | 2.8 | 0.03 |
| 728969 | 34 | 38 | 0.2 | 0.6 | 0.1 | 2.2 | 0.05 |
| 728970 | 32 | 37 | 0.2 | 0.6 | 0.1 | 2.3 | 0.04 |
| 728998 | 34 | 41 | 0.2 | 0.7 | 0.2 | 3.2 | 0.05 |
| 729018 | 34 | 37 | 0.2 | 0.7 | 0.1 | 2.2 | 0.04 |
| 729049 | 34 | 36 | 0.2 | 0.6 | 0.2 | 2.6 | 0.02 |
| 729050 | 34 | 36 | 0.2 | 0.6 | 0.1 | 2.4 | 0.04 |
| 729213 | 33 | 35 | 0.2 | 0.7 | 0.1 | 2.0 | 0.01 |
| 729433 | 32 | 32 | 0.1 | 0.6 | 0.1 | 2.7 | 0.02 |
| 729454 | 32 | 36 | 0.2 | 0.6 | 0.1 | 3.2 | 0.02 |
| 729476 | 33 | 32 | 0.2 | 0.5 | 0.1 | 2.2 | 0.04 |
| 729494 | 33 | 40 | 0.2 | 0.7 | 0.2 | 2.5 | 0.02 |
| 729495 | 32 | 26 | 0.1 | 0.5 | 0.04 | 1.4 | 0.01 |
| 729513 | 33 | 30 | 0.2 | 0.5 | 0.1 | 2.8 | 0.01 |

Study 2

Treatment

Groups of 6- to 7-week-old male CD-1 mice (obtained from Charles River) were injected subcutaneously once a week for four weeks (for a total of 5 treatments) with 50 mg/kg of modified oligonucleotides. One group of male CD-1 mice was injected with PBS. Mice were euthanized 48 hours following the final administration.

Plasma Chemistry Markers

To evaluate the effect of modified oligonucleotides on liver function, plasma levels of blood urea nitrogen (BUN), albumin, alanine aminotransferase (ALT), aspartate aminotransferase (AST), and total bilirubin (TBIL) were measured using an automated clinical chemistry analyzer (Hitachi Olympus AU400c, Melville, N.Y.). The results are presented in the Table below. Modified oligonucleotides that caused changes in the levels of any of the liver or kidney function markers outside the expected range for modified oligonucleotides were excluded in further studies.

TABLE 37

Plasma chemistry markers in male CD-1 mice

| Compound No. | BUN (mg/dL) | Albumin (g/dL) | AST (IU/L) | ALT (IU/L) | TBIL (mg/dL) |
|---|---|---|---|---|---|
| PBS | 19 | 2.6 | 91 | 132 | 0.3 |
| 785478 | 19 | 2.6 | 175 | 228 | 0.2 |
| 785502 | 23 | 2.5 | 479 | 639 | 0.5 |
| 785525 | 19 | 2.4 | 197 | 265 | 0.2 |
| 785532 | 15 | 2.2 | 471 | 591 | 0.3 |
| 785537 | 17 | 2.6 | 420 | 335 | 0.3 |
| 785539 | 17 | 2.4 | 143 | 145 | 0.2 |
| 785674 | 18 | 2.8 | 118 | 101 | 0.2 |
| 785675 | 19 | 2.7 | 85 | 62 | 0.2 |
| 785677 | 18 | 2.9 | 311 | 526 | 0.2 |
| 785920 | 20 | 3.0 | 875 | 1356 | 0.3 |
| 785926 | 24 | 3.3 | 197 | 232 | 0.2 |
| 785940 | 19 | 2.4 | 1201 | 754 | 0.2 |
| 786524 | 18 | 2.8 | 175 | 208 | 0.2 |
| 786538 | 18 | 2.9 | 569 | 1514 | 0.2 |

Body and Organ Weights

Body weights of CD-1 mice were measured at days 1 and 28, and the average body weight for each group is presented in the Table below. Kidney, spleen, and liver weights were measured at the end of the study and are presented in the Table below. Modified oligonucleotides that caused any changes in organ weights outside the expected range for modified oligonucleotides were excluded from further studies.

TABLE 38

Body and organ weights (in grams)

| Compound No. | Body Weight (g) Day 1 | Body Weight (g) Day 28 | Kidney (g) | Spleen (g) | Liver (g) |
|---|---|---|---|---|---|
| PBS | 29 | 38 | 0.6 | 0.1 | 1.9 |
| 785478 | 30 | 39 | 0.7 | 0.2 | 2.3 |
| 785502 | 29 | 35 | 0.6 | 0.2 | 1.6 |
| 785525 | 29 | 37 | 0.6 | 0.2 | 2.2 |
| 785532 | 28 | 33 | 0.6 | 0.4 | 2.7 |
| 785537 | 30 | 36 | 0.6 | 0.2 | 2.0 |
| 785539 | 30 | 41 | 0.6 | 0.2 | 2.4 |
| 785674 | 30 | 40 | 0.8 | 0.2 | 2.3 |
| 785675 | 30 | 39 | 0.7 | 0.2 | 2.5 |
| 785677 | 28 | 37 | 0.6 | 0.3 | 2.2 |
| 785920 | 29 | 39 | 0.7 | 0.4 | 3.4 |
| 785926 | 29 | 36 | 0.6 | 0.2 | 1.8 |
| 785940 | 29 | 30 | 0.6 | 0.1 | 1.8 |
| 786524 | 30 | 39 | 0.6 | 0.2 | 2.4 |
| 786538 | 30 | 38 | 0.6 | 0.2 | 3.3 |

Study 3
Treatment

Groups of 6- to 7-week-old male CD-1 mice (obtained from Charles River) were injected subcutaneously once a week for six weeks (for a total of 7 treatments) with 50 mg/kg of modified oligonucleotides. One group of male CD-1 mice was injected with PBS. Mice were euthanized 48 hours following the final administration.

Plasma Chemistry Markers

To evaluate the effect of modified oligonucleotides on liver function, plasma levels of blood urea nitrogen (BUN), albumin, alanine aminotransferase (ALT), aspartate aminotransferase (AST), and total bilirubin (TBIL) were measured using an automated clinical chemistry analyzer (Hitachi Olympus AU400c, Melville, N.Y.). The results are presented in the Table below. Modified oligonucleotides that caused changes in the levels of any of the liver or kidney function markers outside the expected range for modified oligonucleotides were excluded in further studies.

TABLE 39

Plasma chemistry markers in male CD-1 mice

| Compound No. | BUN (mg/dL) | Albumin (g/dL) | AST (IU/L) | ALT (IU/L) | TBIL (mg/dL) |
|---|---|---|---|---|---|
| PBS | 25 | 2.5 | 69 | 60 | 0.2 |
| 729049 | 22 | 2.7 | 214 | 322 | 0.2 |
| 785478 | 20 | 2.5 | 166 | 237 | 0.1 |
| 785525 | 21 | 2.6 | 172 | 134 | 0.2 |
| 785539 | 18 | 2.6 | 96 | 64 | 0.2 |
| 785674 | 22 | 2.4 | 129 | 83 | 0.1 |
| 785675 | 23 | 2.4 | 98 | 100 | 0.1 |
| 785764 | 19 | 2.5 | 89 | 49 | 0.2 |
| 786503 | 20 | 2.4 | 74 | 47 | 0.1 |
| 786524 | 20 | 2.6 | 136 | 145 | 0.1 |
| 786548 | 22 | 2.3 | 132 | 125 | 0.1 |
| 786597 | 21 | 2.4 | 127 | 69 | 0.2 |

Body and Organ Weights

Body weights of CD-1 mice were measured at days 1 and 43, and the average body weight for each group is presented in the Table below. Kidney, spleen, and liver weights were measured at the end of the study and are presented in the Table below. Modified oligonucleotides that caused any changes in organ weights outside the expected range for modified oligonucleotides were excluded from further studies.

TABLE 40

Body and organ weights (in grams)

| Compound No. | Body Weight (g) Day 1 | Body Weight (g) Day 43 | Kidney (g) | Spleen (g) | Liver (g) |
|---|---|---|---|---|---|
| PBS | 28 | 41 | 0.7 | 0.1 | 2.1 |
| 729049 | 30 | 39 | 0.7 | 0.2 | 2.2 |
| 785478 | 29 | 39 | 0.7 | 0.2 | 2.4 |
| 785525 | 28 | 39 | 0.7 | 0.3 | 2.2 |
| 785539 | 28 | 45 | 0.7 | 0.2 | 2.6 |
| 785674 | 28 | 37 | 0.6 | 0.3 | 2.1 |
| 785675 | 29 | 41 | 0.7 | 0.2 | 2.7 |
| 785764 | 28 | 43 | 0.7 | 0.3 | 2.5 |
| 786503 | 29 | 41 | 0.7 | 0.2 | 2.4 |
| 786524 | 29 | 41 | 0.6 | 0.2 | 2.5 |
| 786548 | 27 | 41 | 0.6 | 0.2 | 2.4 |
| 786597 | 30 | 41 | 0.6 | 0.2 | 2.5 |

Study 4

CD-1 mice were treated with modified oligonucleotides selected from studies described above and evaluated for changes in the levels of various plasma chemistry markers.

Treatment

Groups of 6-week-old male CD-1 mice (obtained from Charles River) were injected subcutaneously once a week for four weeks (for a total of 5 treatments) with 50 mg/kg of modified oligonucleotides. One group of male CD-1 mice was injected with PBS. Mice were euthanized 48 hours following the final administration.

Plasma Chemistry Markers

To evaluate the effect of modified oligonucleotides on liver function, plasma levels of blood urea nitrogen (BUN), albumin, alanine aminotransferase (ALT), aspartate aminotransferase (AST), and total bilirubin (TBIL) were measured using an automated clinical chemistry analyzer (Hitachi Olympus AU400c, Melville, N.Y.). The results are presented in the Table below. Modified oligonucleotides that caused changes in the levels of any of the liver or kidney function markers outside the expected range for modified oligonucleotides were excluded in further studies.

TABLE 41

Plasma chemistry markers in male CD-1 mice

| Compound No. | BUN (mg/dL) | Albumin (g/dL) | AST (IU/L) | ALT (IU/L) | TBIL (mg/dL) |
|---|---|---|---|---|---|
| PBS | 23 | 2.7 | 80 | 59 | 0.2 |
| 728466 | 25 | 3.0 | 463 | 868 | 0.3 |
| 729049 | 24 | 2.6 | 246 | 253 | 0.2 |
| 729205 | 22 | 2.4 | 649 | 1130 | 0.6 |
| 729433 | 23 | 2.4 | 660 | 579 | 0.5 |
| 785485 | 25 | 2.6 | 559 | 701 | 0.3 |
| 785666 | 21 | 2.5 | 273 | 321 | 0.3 |
| 785764 | 21 | 2.6 | 78 | 46 | 0.2 |
| 785791 | 30 | 3.1 | 754 | 937 | 0.3 |
| 785938 | 24 | 2.7 | 402 | 348 | 0.4 |
| 786501 | 23 | 3.2 | 733 | 1258 | 0.4 |
| 786503 | 21 | 2.7 | 86 | 44 | 0.3 |
| 786548 | 22 | 2.6 | 135 | 142 | 0.2 |
| 786578 | 19 | 1.5 | 664 | 439 | 0.4 |
| 786597 | 20 | 2.4 | 136 | 70 | 0.2 |

Body and Organ Weights

Body weights of CD-1 mice were measured at days 1 and 43, and the average body weight for each group is presented in the Table below. Kidney, spleen, and liver weights were measured at the end of the study and are presented in the Table below. Modified oligonucleotides that caused any changes in organ weights outside the expected range for modified oligonucleotides were excluded from further studies.

TABLE 42

Body and organ weights (in grams)

| Compound No. | Body Weight (g) Day 1 | Body Weight (g) Day 43 | Kidney (g) | Spleen (g) | Liver (g) |
|---|---|---|---|---|---|
| PBS | 26 | 33 | 0.6 | 0.1 | 1.9 |
| 728466 | 27 | 33 | 0.4 | 0.2 | 2.4 |
| 729049 | 26 | 35 | 0.6 | 0.2 | 2.2 |
| 729205 | 24 | 33 | 0.5 | 0.3 | 3.0 |
| 729433 | 25 | 29 | 0.4 | 0.1 | 1.9 |
| 785485 | 25 | 28 | 0.4 | 0.2 | 1.4 |
| 785666 | 26 | 33 | 0.4 | 0.2 | 2.2 |
| 785764 | 25 | 38 | 0.7 | 0.2 | 2.3 |
| 785791 | 27 | 33 | 0.6 | 0.1 | 1.9 |
| 785938 | 28 | 31 | 0.4 | 0.3 | 1.6 |
| 786501 | 27 | 38 | 0.6 | 0.5 | 3.7 |
| 786503 | 26 | 35 | 0.6 | 0.2 | 2.1 |
| 786548 | 26 | 38 | 0.6 | 0.1 | 2.2 |

TABLE 42-continued

Body and organ weights (in grams)

| Compound No. | Body Weight (g) Day 1 | Body Weight (g) Day 43 | Kidney (g) | Spleen (g) | Liver (g) |
|---|---|---|---|---|---|
| 786578 | 27 | 37 | 0.6 | 0.2 | 1.7 |
| 786597 | 28 | 40 | 0.6 | 0.3 | 2.5 |

Study 5

CD-1 mice were treated with modified oligonucleotides selected from studies described above and evaluated for changes in the levels of various plasma chemistry markers.

Treatment

Groups of 6- to 7-week-old male CD-1 mice (obtained from Charles River) were injected subcutaneously once a week for six weeks (for a total of 7 treatments) with 50 mg/kg of modified oligonucleotides. One group of male CD-1 mice was injected with PBS. Mice were euthanized 48 hours following the final administration.

Plasma Chemistry Markers

To evaluate the effect of modified oligonucleotides on liver function, plasma levels of blood urea nitrogen (BUN), albumin, alanine aminotransferase (ALT), aspartate aminotransferase (AST), and total bilirubin (TBIL) were measured using an automated clinical chemistry analyzer (Hitachi Olympus AU400c, Melville, N.Y.). The results are presented in the Table below. Modified oligonucleotides that caused changes in the levels of any of the liver or kidney function markers outside the expected range for modified oligonucleotides were excluded in further studies.

TABLE 43

Plasma chemistry markers in male CD-1 mice

| Compound No. | BUN (mg/dL) | Albumin (g/dL) | AST (IU/L) | ALT (IU/L) | TBIL (mg/dL) |
|---|---|---|---|---|---|
| PBS | 29 | 3.0 | 57 | 42 | 0.2 |
| 665892 | 27 | 3.1 | 275 | 265 | 0.2 |
| 665893 | 25 | 3.2 | 1718 | 2229 | 2.9 |
| 728958 | 26 | 2.6 | 88 | 57 | 0.1 |
| 728969 | 27 | 3.4 | 149 | 142 | 0.2 |
| 728970 | 33 | 3.5 | 1142 | 631 | 0.4 |
| 729018 | 23 | 2.9 | 187 | 101 | 0.2 |
| 729050 | 26 | 3.1 | 141 | 119 | 0.2 |
| 729494 | 26 | 2.9 | 178 | 53 | 0.2 |

Body and Organ Weights

Body weights of CD-1 mice were measured at days 1 and 43, and the average body weight for each group is presented in the Table below. Kidney, spleen, and liver weights were measured at the end of the study and are presented in the Table below. Modified oligonucleotides that caused any changes in organ weights outside the expected range for modified oligonucleotides were excluded from further studies.

TABLE 44

Body and organ weights (in grams)

| Compound No. | Body Weight (g) Day 1 | Body Weight (g) Day 43 | Kidney (g) | Spleen (g) | Liver (g) |
|---|---|---|---|---|---|
| PBS | 29 | 37 | 0.6 | 0.1 | 1.8 |
| 665892 | 31 | 36 | 0.6 | 0.2 | 2.3 |
| 665893 | 30 | 35 | 0.6 | 0.2 | 2.4 |
| 728958 | 31 | 38 | 0.7 | 0.2 | 2.0 |
| 728969 | 30 | 37 | 0.6 | 0.2 | 2.3 |
| 728970 | 29 | 37 | 0.5 | 0.2 | 2.7 |
| 729018 | 31 | 41 | 0.8 | 0.3 | 2.4 |
| 729050 | 29 | 35 | 0.6 | 0.2 | 2.1 |
| 729494 | 29 | 37 | 0.6 | 0.2 | 2.2 |

Example 5: Tolerability of Modified Oligonucleotides Targeting Human IRF5 in Sprague-Dawley Rats Sprague-Dawley rats are a multipurpose model used for safety and efficacy evaluations. The rats were treated with Ionis modified oligonucleotides from the studies described in the Examples above and evaluated for changes in the levels of various plasma chemistry markers.

Study 1

Treatment

Male Sprague-Dawley rats were maintained on a 12-hour light/dark cycle and fed ad libitum with Purina normal rat chow. Groups of 4 Sprague-Dawley rats each were weekly injected subcutaneously with 50 mg/kg of Ionis oligonucleotide for 6 weeks (total 7 doses). Forty-eight hours after the last dose, rats were euthanized and organs, urine and plasma were harvested for further analysis.

Plasma Chemistry Markers

To evaluate the effect of Ionis oligonucleotides on hepatic function, plasma levels of transaminases were measured using an automated clinical chemistry analyzer (Hitachi Olympus AU400c, Melville, N.Y.). Plasma levels of ALT (alanine transaminase) and AST (aspartate transaminase) were measured and the results are presented in the Table below expressed in IU/L. Plasma levels of total bilirubin (TBIL), creatinine, albumin, and Blood Urea Nitrogen (BUN) were also measured using the same clinical chemistry analyzer and the results are also presented in the Table below. Ionis modified oligonucleotides that caused changes in the levels of any markers of liver function outside the expected range for modified oligonucleotides were excluded in further studies.

TABLE 45

Plasma chemistry markers in Sprague-Dawley rats

| Compound No. | ALT (IU/L) | AST (IU/L) | BUN (mg/dL) | Albumin (g/dL) | Creatinine (mg/dL) | TBIL (mg/dL) |
|---|---|---|---|---|---|---|
| PBS | 57 | 83 | 16 | 4.9 | 0.4 | 0.2 |
| 665892 | 216 | 319 | 25 | 4.6 | 0.5 | 0.2 |
| 665893 | 365 | 472 | 31 | 4.0 | 0.6 | 0.3 |
| 728958 | 90 | 118 | 26 | 3.3 | 0.5 | 0.1 |
| 728969 | 154 | 175 | 24 | 3.4 | 0.5 | 0.2 |
| 728970 | 309 | 274 | 34 | 3.1 | 0.6 | 0.2 |
| 729018 | 70 | 98 | 23 | 3.3 | 0.5 | 0.1 |
| 729050 | 118 | 115 | 86 | 1.6 | 1.1 | 0.1 |
| 729494 | 60 | 97 | 43 | 1.6 | 0.5 | 0.1 |

Hematology Assays

Blood obtained from mouse groups at week 6 were sent to IDEXX BioResearch for measurement of blood cell counts. Counts taken include red blood cell (RBC) count, white blood cell (WBC) count, hemoglobin (HGB), hematocrit (HCT), and individual white blood cell counts, such as that of monocytes (MON), neutrophils (NEU), lymphocytes (LYM), and platelets (PLT). The results are presented in the tables below. Ionis oligonucleotides that caused changes in the blood cell count outside the expected range for modified oligonucleotides were excluded in further studies.

TABLE 46

Blood Cell Count in Sprague-Dawley Rats

| Compound No. | WBC | RBC | HGB | HCT |
|---|---|---|---|---|
| PBS | 15 | 9 | 17 | 54 |
| 665892 | 11 | 9 | 16 | 51 |
| 665893 | 13 | 9 | 17 | 54 |
| 728958 | 18 | 8 | 14 | 45 |
| 728969 | 10 | 8 | 15 | 49 |
| 728970 | 14 | 8 | 15 | 49 |
| 729018 | 8 | 8 | 15 | 48 |
| 729050 | 16 | 8 | 13 | 44 |
| 729494 | 17 | 4 | 7 | 24 |

TABLE 47

Blood Cell Count in Sprague-Dawley Rats

| Compound No. | NEU | LYM | MON | PLT |
|---|---|---|---|---|
| PBS | 14 | 81 | 3.6 | 720 |
| 665892 | 15 | 80 | 4.6 | 620 |
| 665893 | 13 | 80 | 5.9 | 647 |
| 728958 | 14 | 82 | 4.1 | 944 |
| 728969 | 12 | 83 | 4.8 | 857 |
| 728970 | 12 | 79 | 8.6 | 837 |
| 729018 | 10 | 85 | 4.4 | 801 |
| 729050 | 13 | 75 | 10.1 | 324 |
| 729494 | 13 | 77 | 9.5 | 777 |

Kidney Function

To evaluate the effect of Ionis oligonucleotides on kidney function, urinary levels of total protein and creatinine were measured using an automated clinical chemistry analyzer (Hitachi Olympus AU400c, Melville, N.Y.). The ratios of total protein to creatinine (P/C ratio) are presented in the Table below. Ionis oligonucleotides that caused changes in the levels of the ratio outside the expected range for modified oligonucleotides were excluded in further studies.

TABLE 48

Total protein to creatinine ratio in Sprague-Dawley rats

| Compound No. | P/C Ratio |
|---|---|
| PBS | 0.7 |
| 665892 | 5.6 |
| 665893 | 5.9 |
| 728958 | 5.3 |
| 728969 | 4.1 |
| 728970 | 6.0 |
| 729018 | 4.3 |
| 729050 | 8.2 |
| 729494 | 17.2 |

Organ Weights

Liver, heart, spleen and kidney weights were measured at the end of the study and are presented in the Table below. Ionis oligonucleotides that caused any changes in organ weights outside the expected range for modified oligonucleotides were excluded from further studies.

TABLE 49

Organ weights (g)

| Compound No. | Liver (g) | Kidney (g) | Spleen (g) |
|---|---|---|---|
| PBS | 17 | 3.7 | 0.8 |
| 665892 | 16 | 3.1 | 1.4 |
| 665893 | 14 | 3.1 | 1.0 |
| 728958 | 17 | 3.2 | 1.6 |
| 728969 | 15 | 3.8 | 1.5 |
| 728970 | 12 | 3.3 | 1.5 |
| 729018 | 15 | 3.1 | 1.7 |
| 729050 | 13 | 3.8 | 1.4 |
| 729494 | 15 | 4.1 | 2.0 |

Study 2
Treatment

Male Sprague-Dawley rats were maintained on a 12-hour light/dark cycle and fed ad libitum with Purina normal rat chow. Groups of 4 Sprague-Dawley rats each were weekly injected subcutaneously with 50 mg/kg of Ionis oligonucleotide for 6 weeks (total 7 doses). Forty-eight hours after the last dose, the rats were euthanized; and organs, urine and plasma were harvested for further analysis.

Plasma Chemistry Markers

To evaluate the effect of Ionis oligonucleotides on hepatic function, plasma levels of transaminases were measured using an automated clinical chemistry analyzer (Hitachi Olympus AU400c, Melville, N.Y.). Plasma levels of ALT (alanine transaminase) and AST (aspartate transaminase) were measured and the results are presented in the Table below expressed in IU/L. Plasma levels of total bilirubin (TBIL), albumin, and blood urea nitrogen (BUN) were also measured using the same clinical chemistry analyzer and the results are also presented in the Table below. Ionis modified oligonucleotides that caused changes in the levels of any markers of liver function outside the expected range for modified oligonucleotides were excluded in further studies.

TABLE 50

Plasma chemistry markers in Sprague-Dawley rats

| Compound No. | ALT (IU/L) | AST (IU/L) | BUN (mg/dL) | Albumin (g/dL) | TBIL (mg/dL) |
|---|---|---|---|---|---|
| PBS | 41 | 73 | 18 | 3.4 | 0.2 |
| 729049 | 70 | 121 | 154 | 1.4 | 0.1 |
| 785478 | 68 | 112 | 41 | 1.7 | 0.1 |
| 785525 | 78 | 118 | 20 | 3.3 | 0.1 |
| 785539 | 60 | 128 | 55 | 2.4 | 0.1 |
| 785674 | 64 | 131 | 22 | 3.2 | 0.1 |
| 785675 | 123 | 139 | 18 | 3.4 | 0.2 |
| 785764 | 65 | 95 | 60 | 1.7 | 0.2 |
| 786503 | 33 | 72 | 17 | 2.9 | 0.1 |
| 786524 | 64 | 105 | 21 | 3.1 | 0.2 |
| 786548 | 34 | 67 | 20 | 3.2 | 0.1 |
| 786597 | 40 | 66 | 19 | 2.8 | 0.1 |

Hematology Assays

Blood obtained from mouse groups at week 6 were sent to IDEXX BioResearch for measurement of blood cell counts. Counts taken include red blood cell (RBC) count, white blood cell (WBC) count, hemoglobin (HGB), hematocrit (HCT), and individual white blood cell counts, such as that of monocytes (MON), neutrophils (NEU), lymphocytes (LYM), and platelets (PLT). The results are presented in the tables below. Ionis oligonucleotides that caused changes in the blood cell count outside the expected range for modified oligonucleotides were excluded in further studies.

TABLE 51

Blood cell count in Sprague-Dawley Rats

| Compound No. | WBC | RBC | HGB | HCT |
|---|---|---|---|---|
| PBS | 14 | 8 | 16 | 50 |
| 729049 | 30 | 5 | 9 | 27 |
| 785478 | 45 | 7 | 12 | 37 |
| 785525 | 18 | 8 | 14 | 44 |
| 785539 | 32 | 4 | 8 | 25 |
| 785674 | 34 | 8 | 14 | 43 |
| 785675 | 16 | 9 | 15 | 47 |
| 785764 | 22 | 6 | 10 | 33 |
| 786503 | 20 | 7 | 14 | 39 |
| 786524 | 16 | 8 | 14 | 44 |
| 786548 | 18 | 8 | 14 | 43 |
| 786597 | 28 | 4 | 7 | 24 |

TABLE 52

Blood cell count in Sprague-Dawley Rats

| Compound No. | NEU | LYM | MON | PLT |
|---|---|---|---|---|
| PBS | 10 | 84 | 5.5 | 904 |
| 729049 | 47 | 45 | 3.8 | 1418 |
| 785478 | 11 | 89 | 1.0 | 383 |
| 785525 | 13 | 77 | 8.6 | 881 |
| 785539 | 34 | 57 | 9.0 | 734 |
| 785674 | 12 | 79 | 7.0 | 731 |
| 785675 | 9 | 81 | 9.2 | 783 |
| 785764 | 17 | 76 | 6.8 | 1231 |
| 786503 | 10 | 81 | 7.5 | 650 |
| 786524 | 6 | 87 | 6.6 | 731 |
| 786548 | 4 | 87 | 6.6 | 653 |
| 786597 | 15 | 77 | 6.9 | 965 |

Kidney Function

To evaluate the effect of Ionis oligonucleotides on kidney function, urinary levels of total protein and creatinine were measured using an automated clinical chemistry analyzer (Hitachi Olympus AU400c, Melville, N.Y.). The ratios of total protein to creatinine (P/C ratio) are presented in the Table below. Ionis oligonucleotides that caused changes in the levels of the ratio outside the expected range for modified oligonucleotides were excluded in further studies.

TABLE 53

Total protein to creatinine ratio in Sprague-Dawley rats

| Compound No. | P/C Ratio |
|---|---|
| PBS | 0.8 |
| 729049 | 11.1 |
| 785478 | 15.0 |
| 785525 | 7.4 |
| 785539 | 51.1 |
| 785674 | 4.4 |
| 785675 | 2.1 |
| 785764 | 20.8 |
| 786503 | 2.5 |
| 786524 | 1.7 |
| 786548 | 2.5 |
| 786597 | 14.4 |

Organ Weights

Liver, heart, spleen and kidney weights were measured at the end of the study, and are presented in the Table below. Ionis oligonucleotides that caused any changes in organ weights outside the expected range for modified oligonucleotides were excluded from further studies.

TABLE 54

Organ weights (g)

| Compound No. | Liver | Kidney | Spleen |
|---|---|---|---|
| PBS | 19 | 3.3 | 1.0 |
| 729049 | 19 | 3.5 | 1.1 |
| 785478 | 19 | 4.2 | 2.3 |
| 785525 | 18 | 3.4 | 1.5 |
| 785539 | 18 | 4.3 | 2.3 |
| 785674 | 17 | 2.7 | 1.6 |
| 785675 | 13 | 2.8 | 1.4 |
| 785764 | 18 | 4.5 | 2.7 |
| 786503 | 16 | 2.8 | 1.8 |
| 786524 | 14 | 3.2 | 1.8 |
| 786548 | 13 | 2.6 | 1.4 |
| 786597 | 16 | 3.6 | 2.4 |

Example 6: Effect of Modified Oligonucleotides on Human IRF5 Expression in a KARPAS-229 Xenograft Model in NOD Scid Mice Male, 14-15 week old NOD Scid mice (Jackson Laboratory) were inoculated with human non-Hodgkin's Large Cell Lymphoma KARPAS-229 cells and treated with modified oligonucleotides described in the tables above or with PBS. Effects of the modified oligonucleotides on IRF5 RNA expression in the tumors and tolerability in the mice were evaluated.

Treatment

The mice were inoculated with 2 million of KARPAS-229 cells in 1:1 matrigel+KARPAS-299 suspension subcutaneously in the flank for tumor development. Modified oligonucleotide treatment started when the mean tumor size reached approximately 100 mm$^3$. The mice were subcutaneously injected with modified oligonucleotide at a concentration of 250 mg/kg/week for two weeks, for a total of eight doses. An additional control group was similarly treated with PBS for 8 doses. On day 12 after start of treatment, the mice were sacrificed, and IRF5 levels in tumor were measured.

RNA Analysis

Primer probe set HTS4167 was used to measure human IRF5 RNA levels. Results are presented as percent change of RNA, relative to PBS control, normalized to both human GAPDH and human beta-actin or ACTB. As presented in the Table below, treatment with Ionis modified oligonucleotides resulted in significant reduction of IRF5 RNA in comparison to the PBS control. '0' indicates that the oligonucleotides did not inhibit RNA expression.

TABLE 55

Modified oligonucleotide mediated
inhibition of human IRF5 RNA
expression in KARPAS-229 model

| Compound No. | % Inhibition Normalized to GAPDH | % Inhibition Normalized to ACTB |
|---|---|---|
| PBS | 0 | 0 |
| 728969 | 14 | 18 |
| 729018 | 34 | 47 |
| 729049 | 43 | 54 |
| 785478 | 34 | 33 |
| 785525 | 32 | 43 |
| 785674 | 0 | 26 |
| 785675 | 0 | 13 |
| 785764 | 0 | 7 |
| 786503 | 0 | 29 |
| 786524 | 31 | 43 |
| 786597 | 45 | 55 |

Plasma Chemistries

In addition, plasma levels of ALT (alanine transaminase) and AST (aspartate transaminase) were measured using an automated clinical chemistry analyzer (Hitachi Olympus AU400c, Melville, N.Y.) and the results are presented in the Table below expressed in IU/L. Plasma levels of bilirubin, albumin, and BUN were also measured using the same clinical chemistry analyzer and the results are also presented in the Table below. N/A refers to groups where data is not available, usually due to death of animal.

TABLE 56

Plasma chemistry markers in xenograft model

| Compound No. | ALT (U/L) | AST (U/L) | BUN (mg/dL) | Albumin (g/dL) | Bilirubin (mg/dL) |
|---|---|---|---|---|---|
| PBS | 28 | 80 | 24 | 2. | 0.2 |
| 728969 | 81 | 114 | 28 | 2.7 | 0.2 |
| 729018 | 317 | 257 | 22 | 2.5 | 0.2 |
| 729049 | 3640 | 2555 | 22 | 2.7 | 1.2 |
| 785478 | 4243 | 2610 | 20 | 2.8 | 1.1 |
| 785525 | 3989 | 3936 | 21 | 2.7 | 5.2 |
| 785674 | 1289 | 939 | 20 | 2.6 | 0.2 |
| 785675 | 411 | 368 | 18 | 2.5 | 0.1 |
| 785764 | 462 | 736 | 11 | 3.1 | 10.5 |
| 786503 | 630 | 717 | 24 | 2.5 | 0.2 |
| 786524 | 5094 | 3564 | 32 | 2.5 | 8.9 |
| 786597 | 2705 | 2479 | 24 | 2.4 | 10.7 |

Example 7: Effect of Antisense Inhibition of Human IRF5 in Transgenic Mouse Model A transgenic mouse model was developed in-house using the Fosmid ABC10-44445800E12 (NCBI Clone DB ID:6338898). The clone was digested at SpeI and FspI restriction sites to produce a region containing the human IRF5 gene with 12,002 bp upstream and 5159 bp downstream of the IRF5 gene included. The gene fragment was introduced into fertilized eggs from C57BL/6 mice by pronuclear injection to produce four founder lines. Line C57BL/6-Tg(IRF5)F20.11 was used in the experiments described herein. Human IRF5 RNA expression is found in the lung, spleen, kidney, and peritoneal exudate cells (PEC) in this model. The efficacy of Ionis oligonucleotides was evaluated in this model.

Treatment

Transgenic mice were maintained on a 12-hour light/dark cycle and were fed ad libitum normal Purina mouse chow. Animals were acclimated for at least 7 days in the research facility before initiation of the experiment. Modified oligonucleotides were prepared in PBS and sterilized by filtering through a 0.2 micron filter.

The transgenic mice were divided into groups of 4 mice each for modified oligonucleotide treatment. Groups received subcutaneous injections of Ionis oligonucleotide at a dose of either 35 mg/kg once a week or 70 mg/kg once a week for three weeks (4 treatments). One group of four mice received subcutaneous injections of PBS once a week for three weeks (4 treatments). The PBS-injected group served as the control group to which oligonucleotide-treated groups were compared.

RNA Analysis

On day 23, RNA was extracted from PECs, lung and spleen for real-time RTPCR analysis of IRF5 RNA expression. Primer probe set HTS4167 was used to measure human IRF5 RNA levels. Results are presented as percent change of RNA, relative to PBS control, normalized to mouse GAPDH.

As presented in the Tables below, treatment with Ionis modified oligonucleotides resulted in significant reduction of IRF5 RNA in comparison to the PBS control. '0' indicates that the oligonucleotides did not inhibit RNA expression.

TABLE 57

Modified oligonucleotide mediated inhibition
(%) of human IRF5 in transgenic model
(data normalized to mouse GAPDH)

| Dose (mg/kg) | Compound No. | PEC | Lung | Spleen |
|---|---|---|---|---|
| 35 | PBS | 0 | 0 | 0 |
|  | 728958 | 75 | 20 | 44 |
|  | 729018 | 53 | 27 | 30 |
|  | 785525 | 2 | 20 | 54 |
|  | 785674 | 30 | 7 | 27 |
|  | 785675 | 57 | 12 | 36 |
|  | 786503 | 53 | 29 | 55 |
|  | 786524 | 64 | 27 | 9 |
|  | 786548 | 35 | 2 | 10 |
| 70 | 728958 | 23 | 0 | 23 |
|  | 729018 | 72 | 19 | 58 |
|  | 785525 | 45 | 32 | 49 |
|  | 785674 | 76 | 12 | 49 |
|  | 785675 | 47 | 37 | 63 |
|  | 786503 | 61 | 23 | 47 |
|  | 786524 | 81 | 30 | 0 |
|  | 786548 | 75 | 14 | 52 |

Example 8: Effect of Modified Oligonucleotides Targeting Human IRF5 in Cynomolgus Monkeys Cynomolgus monkeys were treated with Ionis modified oligonucleotides selected from studies described in the Examples above. Modified oligonucleotide tolerability was evaluated.

Treatment

Prior to the study, the monkeys were kept in quarantine during which the animals were observed daily for general health. The monkeys were 2-4 years old and weighed 2-4 kg. Nine groups of 4 randomly assigned male cynomolgus monkeys each were injected subcutaneously with Ionis oligonucleotide or saline in a clock-wise rotation between four different sites on the back. Following loading doses on days 1, 4 and 7, the monkeys were dosed once per week (on days 14, 21, 28, 35, 42, 49, 56, 63, 70, 77 and 84) with 35 mg/kg of Ionis oligonucleotide. A control group of 4 cynomolgus monkeys was injected with 0.9% saline in a similar manner and served as the control group.

During the study period, the monkeys were observed twice daily for signs of illness or distress. Any animal experiencing more than momentary or slight pain or distress due to the treatment, injury or illness was treated by the veterinary staff with approved analgesics or agents to relieve the pain after consultation with the Study Director. Any animal in poor health or in a possible moribund condition was identified for further monitoring and possible euthanasia. Scheduled euthanasia of the animals was conducted on day 86 approximately 48 hours after the last dose by exsanguination while under deep anesthesia. The protocols described in the Example were approved by the Institutional Animal Care and Use Committee (IACUC).

Body and Organ Weight Measurements

To evaluate the effect of Ionis oligonucleotides on the overall health of the animals, body and organ weights were measured. Terminal body weight was measured prior to necropsy. Organ weights were measured as well, and all weight measurements are presented in the Table below. The results indicate that effect of treatment with modified oligonucleotides on body and organ weights was within the expected range for modified oligonucleotides. Specifically, treatment with ION 729018 was well tolerated in terms of the body and organ weights of the monkeys.

TABLE 58

Body and organ weights (g)

| Compound No. | Body Weight (g) Day 86 | Heart | kidney | spleen | testes | thymus | liver |
|---|---|---|---|---|---|---|---|
| Saline | 2828 | 12 | 14 | 2 | 2 | 3 | 59 |
| 728958 | 2791 | 10 | 17 | 3 | 1 | 3 | 72 |
| 729018 | 2726 | 11 | 14 | 4 | 1 | 3 | 66 |
| 785525 | 3017 | 12 | 17 | 5 | 1 | 4 | 78 |
| 785674 | 2618 | 10 | 15 | 4 | 1 | 2 | 63 |
| 785675 | 2793 | 11 | 16 | 3 | 2 | 3 | 63 |
| 786503 | 2926 | 10 | 17 | 4 | 1 | 3 | 73 |
| 786524 | 2917 | 11 | 16 | 5 | 1 | 4 | 67 |
| 786548 | 2668 | 9 | 16 | 4 | 1 | 3 | 66 |

Kidney and Liver Function

To evaluate the effect of Ionis oligonucleotides on hepatic and kidney function, blood samples were collected from all the study groups on day 86. The monkeys were fasted overnight prior to blood collection. Blood was collected in tubes without anticoagulant for serum separation. The tubes were kept at room temperature for a minimum of 90 minutes and then centrifuged at 3000 rpm for 10 minutes to obtain serum. Levels of various liver function markers were measured using a Toshiba 200FR NEO chemistry analyzer (Toshiba Co., Japan). Plasma levels of blood urea nitrogen (BUN), creatinine (CREA), total protein (TP), albumin (ALB), alanine aminotransferase (ALT), aspartate aminotransferase (AST), and total bilirubin (TBIL) were measured and the results are presented in the Table below. The results indicate that modified oligonucleotides had no effect on liver or kidney function outside the expected range for modified oligonucleotides. Specifically, treatment with ION 729018 was well tolerated in terms of the liver and kidney function in monkeys.

TABLE 59

Liver and kidney function markers in cynomolgus monkey plasma

| Compound No. | BUN (mg/dL) | CREA (mg/dL) | TP (g/dL) | ALB (g/dL) | ALT (IU/L) | AST (IU/L) | TBIL (mg/dL) |
|---|---|---|---|---|---|---|---|
| Saline | 24 | 0.8 | 7.1 | 4.2 | 44 | 75 | 0.3 |
| 728958 | 26 | 0.8 | 7.0 | 4.2 | 55 | 99 | 0.2 |
| 729018 | 23 | 0.9 | 7.0 | 4.0 | 73 | 95 | 03 |
| 785525 | 24 | 1.0 | 7.0 | 4.0 | 44 | 102 | 0.2 |
| 785674 | 26 | 0.9 | 7.1 | 3.8 | 53 | 110 | 0.2 |
| 785675 | 25 | 0.8 | 6.8 | 4.0 | 57 | 96 | 0.3 |
| 786503 | 28 | 0.9 | 6.7 | 3.9 | 58 | 108 | 0.2 |
| 786524 | 27 | 0.9 | 7.6 | 3.7 | 58 | 93 | 0.2 |
| 786548 | 27 | 0.9 | 7.0 | 4.0 | 58 | 102 | 0.3 |

Pro-Inflammatory Proteins Analysis

To evaluate any inflammatory effect of Ionis oligonucleotides in cynomolgus monkeys, blood samples were taken for analysis. The monkeys were fasted overnight prior to blood collection. On day 84 (pre-dose and 24 hours post-dose), approximately 0.8 mL of blood was collected from each animal and put into tubes without anticoagulant for serum separation. The tubes were kept at room temperature for a minimum of 90 min and then centrifuged at 3,000 rpm for 10 min at room temperature to obtain serum. Complement C3 were measured using a Toshiba 120 FR NEO chemistry analyzer (Toshiba Co., Japan). The results indicate that treatment with ION 729018 did not cause any inflammation in monkeys. Another marker of inflammation, C-Reactive Protein (CRP) was tested on day 86.

TABLE 60

Pro-inflammatory protein analysis in cynomolgus monkeys

| | Complement C3 (mg/dL) | | |
|---|---|---|---|
| Compound No. | Day 84 (pre-dose) | Day 84 (24 hr post-dose) | CRP (mg/L) day 86 |
| Saline | 106 | 104 | 0.1 |
| 728958 | 96 | 91 | 0.1 |
| 729018 | 93 | 84 | 0.1 |
| 785525 | 90 | 88 | 0.2 |
| 785674 | 79 | 71 | 0.1 |
| 785675 | 82 | 83 | 0.1 |
| 786503 | 93 | 101 | 0.1 |
| 786524 | 86 | 78 | 0.6 |
| 786548 | 87 | 92 | 1.2 |

Hematology

To evaluate any effect of Ionis oligonucleotides in cynomolgus monkeys on hematologic parameters, blood samples of approximately 0.5 mL of blood was collected from each of the available study animals on day 86. The samples were collected in tubes containing $K_2$-EDTA. Samples were analyzed for red blood cell (RBC) count, Hemoglobin (HGB), Hematocrit (HCT), platelet count (PLT), white blood cells (WBC) count, individual white blood cell counts, such as that of monocytes (MON), neutrophils (NEU), and lymphocytes (LYM) using an ADVIA2120i hematology analyzer (Siemens, USA).

The data indicate the oligonucleotides did not cause any changes in hematologic parameters outside the expected range for modified oligonucleotides at this dose. Specifically, treatment with ION 729018 was well tolerated in terms of the hematologic parameters of the monkeys.

TABLE 61

Blood cell counts in cynomolgus monkeys

| Compound No. | RBC (×10$^6$/μL) | HGB (g/dL) | HCT (%) | PLT (10$^3$/μL) |
|---|---|---|---|---|
| Saline | 5.6 | 13.0 | 43 | 312 |
| 728958 | 5.7 | 12.7 | 43 | 442 |
| 729018 | 6.1 | 13.4 | 44 | 334 |
| 785525 | 5.4 | 12.2 | 41 | 459 |
| 785674 | 5.6 | 13.1 | 43 | 405 |
| 785675 | 5.9 | 13.5 | 45 | 342 |
| 786503 | 5.6 | 12.5 | 43 | 378 |
| 786524 | 5.8 | 12.6 | 44 | 252 |
| 786548 | 5.9 | 13.3 | 45 | 390 |

TABLE 62

Blood cell counts in cynomolgus monkeys

| Compound No. | WBC (×10$^3$/μL) | NEU (%) | LYM (%) | MON (%) |
|---|---|---|---|---|
| Saline | 11 | 4 | 7 | 0.3 |
| 728958 | 10 | 4 | 6 | 0.3 |
| 729018 | 9 | 4 | 5 | 0.2 |
| 785525 | 12 | 4 | 7 | 0.3 |
| 785674 | 16 | 8 | 7 | 0.4 |
| 785675 | 9 | 1 | 7 | 0.3 |
| 786503 | 16 | 4 | 11 | 0.3 |
| 786524 | 9 | 4 | 4 | 0.3 |
| 786548 | 10 | 3 | 6 | 0.2 |

Coagulation

To evaluate effect of Ionis modified oligonucleotides on coagulation in cynomolgus monkeys, blood samples of approximately 0.9 mL were collected from each of the available study animals on day 86. The samples were collected in tubes containing 3.2% sodium citrate. Coagulation parameters tested include Activated partial thromboplastin time (APTT), prothrombin time (PT) and Fibrinogen (FIB).

The data indicate the modified oligonucleotides did not cause any changes in coagulation parameters outside the expected range for modified oligonucleotides at this dose. Specifically, treatment with ION 729018 was well tolerated in terms of the coagulation parameters of the monkeys.

TABLE 63

Coagulation Parameters in cynomolgus monkeys

| Compound No. | PT (sec) | FIB (mg/dL) | APTT (sec) |
|---|---|---|---|
| Saline | 10 | 195 | 18 |
| 728958 | 10 | 249 | 19 |
| 729018 | 10 | 219 | 18 |
| 785525 | 10 | 208 | 20 |
| 785674 | 9 | 238 | 19 |
| 785675 | 9 | 216 | 19 |
| 786503 | 10 | 226 | 18 |
| 786524 | 10 | 235 | 18 |
| 786548 | 10 | 302 | 16 |

Pharmacokinetic Analysis

Accumulation of modified oligonucleotides in the liver and kidney were measured in tissues collected at necropsy. 729018 showed tissue accumulation profiles in the kidney and liver that were typical for this class of compound.

TABLE 64

Mean tissue concentration on Day 86 following 12-weeks subcutaneous administration

| Organ | Compound No. | Mean Concentration (μg/g) |
|---|---|---|
| Kidney Cortex | 728958 | 2078 |
| | 729018 | 1472 |
| | 785525 | 1702 |
| | 785674 | 2169 |
| | 785675 | 1444 |
| | 786503 | 1180 |
| | 786524 | 1679 |
| | 786548 | 1513 |
| Liver | 728958 | 657 |
| | 729018 | 763 |
| | 785525 | 732 |
| | 785674 | 773 |
| | 785675 | 753 |
| | 786503 | 496 |
| | 786524 | 409 |
| | 786548 | 392 |

Example 9: Measurement of Viscosity of Modified Oligonucleotides Targeting Human IRF5

The viscosity of select modified oligonucleotides from the studies described above was measured with the aim of screening out modified oligonucleotides which have a viscosity of more than 40 centipoise (cP). Modified oligonucleotides having a viscosity greater than 40 cP would have less than optimal viscosity.

Oligonucleotides (32-38 mg) were weighed into a glass vial; approximately 100 μL of water was added, and the modified oligonucleotide was dissolved into solution by heating the vial to 55° C. Part (75 μL) of the pre-heated sample was pipetted to a micro-viscometer (PAC Cambridge Viscosity Viscometer). The temperature of the micro-viscometer was set to 25° C. and the viscosity of the sample was measured. The entire 75 uL of sample was them combined with the remaining portion of the sample was diluted appropriately for UV reading at 260 nM (Cary UV instrument). The data below indicates that all the modified oligonucleotides solutions are optimal in their viscosity under the criterion stated above.

TABLE 65

Viscosity of modified oligonucleotides

| Compound No. | Concentration by weight (mg/mL) | Concentration by UV (mg/mL) | Viscocity (cP) |
|---|---|---|---|
| 728958 | 300 | 201 | 17 |
| 729018 | 350 | 262 | 24 |
| 785524 | 350 | 277 | 14 |
| 785674 | 350 | 280 | 16 |
| 786503 | 300 | 218 | 40 |
| 786548 | 270 | 214 | 17 |
| 785675 | 250 | 209 | 6 |
| 786524 | 250 | 208 | 36 |

Example 10: Confirmation of Dose-Dependent Inhibition of Human IRF5 Gapmers

Modified oligonucleotides described in the studies above exhibiting significant in vitro inhibition of IRF5 mRNA were selected and tested at various doses in human A-431 cells and SH-SY5Y cells.

Study 1

Cultured A-431 cells at a density of 11,000 cells per well were treated using free uptake with modified oligonucleotides diluted to different concentrations as specified in the Tables below. After a treatment period of approximately 48 hours, IRF5 mRNA levels were measured using the Human IRF5 primer-probe set RTS37490 ((forward sequence CCACCTCAGCCCTACAAGA, designated herein as SEQ ID NO: 17; reverse sequence TCAGGCTTGGCAACATCC; designated herein as SEQ ID NO: 18; probe sequence CCTGCTCCCACAGACTCCCAG, designated herein as SEQ ID NO: 19). IRF5 mRNA levels were normalized to human GAPDH measured by primer-probe set RTS104. Results are presented in the tables below as percent inhibition of IRF5, relative to untreated control cells.

The half maximal inhibitory concentration ($IC_{50}$) of each modified oligonucleotide is also presented. $IC_{50}$ was calculated using a linear regression on a log/linear plot of the data in excel.

TABLE 66

Multi-dose assay of modified oligonucleotides in A-431 cells

| Compound No. | % Inhibition | | | | | $IC_{50}$ (μM) |
|---|---|---|---|---|---|---|
| | 23.44 nM | 93.75 nM | 375.00 nM | 1500.00 nM | 6000.00 nM | |
| 728958 | 0 | 16 | 36 | 57 | 71 | 1.07 |
| 729018 | 31 | 72 | 93 | 98 | 99 | 005 |
| 785525 | 32 | 68 | 88 | 95 | 97 | 0.05 |
| 785675 | 7 | 27 | 57 | 80 | 90 | 0.28 |
| 786503 | 29 | 70 | 93 | 98 | 99 | 0.05 |

Study 2

Cultured SH-SY5Y cells at a density of 45,000 cells per well were treated using electroporation with modified oligonucleotides diluted to different concentrations as specified in the Tables below. After a treatment period of approximately 24 hours, IRF5 mRNA levels were measured using the Human IRF5 primer-probe set RTS37490. IRF5 mRNA levels were normalized to human GAPDH measured by primer-probe set RTS104. Results are presented in the tables below as percent inhibition of IRF5, relative to untreated control cells.

The half maximal inhibitory concentration ($IC_{50}$) of each modified oligonucleotide is also presented. $IC_{50}$ was calculated using a linear regression on a log/linear plot of the data in excel.

TABLE 67

Multi-dose assay of modified oligonucleotides in SH-SY5Y cells

| Compound No. | % Inhibition | | | | | $IC_{50}$ (μM) |
|---|---|---|---|---|---|---|
| | 23.44 nM | 93.75 nM | 375.00 nM | 1500.00 nM | 6000.00 nM | |
| 728958 | 0 | 0 | 23 | 47 | 64 | 1.07 |
| 729018 | 8 | 19 | 46 | 66 | 80 | 005 |
| 785525 | 8 | 15 | 36 | 68 | 80 | 0.05 |
| 785675 | 0 | 0 | 17 | 42 | 65 | 0.28 |
| 786503 | 22 | 15 | 32 | 64 | 80 | 0.05 |

Example 11: Evaluation of Proinflammatory Effects in hPBMC Assay

Human IRF5 modified oligonucleotides were tested for potential immunostimulatory properties in an in vitro human peripheral blood mononuclear cell (PBMC) activation assay. Human PBMCs were isolated from fresh whole blood donated by healthy donors (with informed consent at US HealthWorks clinic, Carlsbad). The blood was collected into 8 mL Vacutainer CPT tubes that contained sodium citrate anticoagulant and Ficoll density media with polyester gel barrier separating those liquids. Following centrifugation of CPT tubes at 1215 rpm in Beckman Allegra 6R centrifuge, red blood cells and granulocytes were separated from plasma and PBMCs by polyester gel barrier. PBMCs accumulated at the interface between Ficoll and plasma, just above the polymer gel layer. Purified PBMCs were washed with PBS ($Ca^{++}$, $Mg^{++}$ free), and resuspended in RPMI culture medium (RPMI containing 10% FBS and penicillin and streptomycin). Only PBMC preps with viability >80% were used for the assay. The average viability of the PBMC used in these assays was 86.6%.

For cultures, PBMC were plated at $5\times10^5$ cells/well in sterile, 96-round bottomed polypropylene plates. Cells were treated with increasing concentrations of modified oligonucleotides targeting human IRF5 (as indicated in tables below) and incubated for 24 hours at 37° C. and 5% $CO_2$. ION No. 353512 (3-14-3 MOE gapmer, TCCCATTTCAGGAGACCTGG, designated herein as SEQ ID NO: 35) is an internal standard known to be a high responder for IL-6 release in the assay. ION No. 104838 (5-10-5 MOE gapmer, GCTGATTAGAGAGAGGTCCC, designated herein as SEQ ID NO: 36) is an internal standard known to be a non-responder in the assay (a negative control). After a 24-hour incubation, plates were centrifuged at 330 g for 5 min; supernatants were collected for MSD human Proinflammatory Panel 1_V-plex (custom 4-plex) cytokine assay. Multiplex MSD cytokine assay was conducted following the manufacturer's instructions to measure levels of IL-6, IL-10, and TNF-α in the supernatant. Electrochemiluminescence was measured using Sector Imager 2400 (Meso Scale Discovery) and data analyzed using MSD Discovery Workbench® software.

Levels of IL-6, IL-10 and TNF-α measured are presented in the Tables below. Many of the oligonucleotides tested were deemed tolerable. ION No. 729018 consistently elicited similar or less cytokine production than the negative control oligonucleotide.

TABLE 68

IL-6 levels following treatment of human PBMCs with modified oligonucleotides

| Concentration (uM) | Compound No. | | | | | | | | |
|---|---|---|---|---|---|---|---|---|---|
| | 728958 | 729018 | 785525 | 785674 | 785675 | 786503 | 786524 | 786548 | 353512 | 104838 |
| 0 | 172 | 162 | 144 | 148 | 219 | 193 | 198 | 194 | 213 | 205 |
| 0.0128 | 212 | 180 | 211 | 201 | 245 | 159 | 189 | 247 | 198 | 211 |

TABLE 68-continued

IL-6 levels following treatment of human PBMCs with modified oligonucleotides

| Concentration (uM) | Compound No. | | | | | | | | |
|---|---|---|---|---|---|---|---|---|---|
| | 728958 | 729018 | 785525 | 785674 | 785675 | 786503 | 786524 | 786548 | 353512 | 104838 |
| 0.064 | 228 | 201 | 211 | 211 | 217 | 207 | 204 | 184 | 206 | 307 |
| 0.32 | 264 | 183 | 301 | 298 | 292 | 246 | 212 | 297 | 381 | 339 |
| 1.6 | 216 | 208 | 355 | 391 | 376 | 271 | 208 | 273 | 332 | 258 |
| 8.0 | 254 | 243 | 370 | 353 | 436 | 341 | 242 | 290 | 472 | 297 |
| 40.0 | 326 | 276 | 456 | 417 | 491 | 342 | 217 | 282 | 470 | 332 |
| 200.0 | 2709 | 286 | 745 | 502 | 738 | 446 | 286 | 452 | 632 | 524 |

TABLE 69

IL-10 levels following treatment of human PBMCs with modified oligonucleotides

| Concentration (uM) | Compound No. | | | | | | | | |
|---|---|---|---|---|---|---|---|---|---|
| | 728958 | 729018 | 785525 | 785674 | 785675 | 786503 | 786524 | 786548 | 353512 | 104838 |
| 0 | 7 | 12 | 6 | 8 | 10 | 9 | 9 | 9 | 8 | 7 |
| 0.0128 | 7 | 8 | 10 | 8 | 10 | 7 | 8 | 8 | 13 | 6 |
| 0.064 | 27 | 36 | 9 | 12 | 13 | 10 | 8 | 9 | 43 | 12 |
| 0.32 | 13 | 15 | 20 | 28 | 37 | 25 | 9 | 14 | 66 | 24 |
| 1.6 | 10 | 24 | 40 | 47 | 55 | 31 | 13 | 18 | 52 | 24 |
| 8.0 | 14 | 26 | 29 | 43 | 60 | 34 | 18 | 20 | 28 | 21 |
| 40.0 | 9 | 17 | 11 | 20 | 27 | 15 | 21 | 13 | 11 | 11 |
| 200.0 | 13 | 5 | 7 | 9 | 9 | 8 | 15 | 5 | 8 | 6 |

TABLE 70

TNF-a levels following treatment of human PBMCs with modified oligonucleotides

| Concentration (uM) | Compound No. | | | | | | | | |
|---|---|---|---|---|---|---|---|---|---|
| | 728958 | 729018 | 785525 | 785674 | 785675 | 786503 | 786524 | 786548 | 353512 | 104838 |
| 0 | 11 | 10 | 9 | 9 | 11 | 10 | 10 | 11 | 12 | 12 |
| 0.0128 | 9 | 10 | 11 | 12 | 12 | 14 | 10 | 11 | 11 | 11 |
| 0.064 | 15 | 22 | 10 | 10 | 10 | 10 | 9 | 10 | 14 | 12 |
| 0.32 | 16 | 11 | 13 | 12 | 13 | 11 | 8 | 11 | 17 | 14 |
| 1.6 | 11 | 13 | 19 | 16 | 17 | 15 | 10 | 13 | 22 | 15 |
| 8.0 | 13 | 14 | 25 | 20 | 25 | 20 | 12 | 15 | 35 | 20 |
| 40.0 | 22 | 20 | 40 | 32 | 35 | 26 | 16 | 19 | 41 | 28 |
| 200.0 | 92 | 28 | 115 | 50 | 63 | 36 | 24 | 29 | 89 | 55 |

Example 12: Dose-Dependent Inhibition of Human IRF5 in A-431 Cells by Modified Oligonucleotides Modified oligonucleotides described in the studies above exhibiting significant in vitro inhibition of IRF5 RNA were selected and tested at various doses in Human A-431 cells. Cultured A-431 cells at a density of 10,000 cells per well were treated using free uptake with modified oligonucleotides diluted to different concentrations as specified in the Tables below. After a treatment period of approximately 48 hours, IRF5 mRNA levels were measured as previously described using the Human IRF5 primer-probe set RTS4524. IRF5 mRNA levels were adjusted according to total RNA content, as measured by RIBOGREEN®. Results are presented in the tables below as percent inhibition of IRF5, relative to untreated control cells. The half maximal inhibitory concentration (IC$_{50}$) of each modified oligonucleotide is also presented.

TABLE 71

Multi-dose assay of modified oligonucleotides in A-431 cells

| | % Inhibition | | | | | | | |
|---|---|---|---|---|---|---|---|---|
| Compound No. | 4.57 nM | 13.72 nM | 41.152 nM | 123.457 nM | 370.37 nM | 1111.111 nM | 3333.33 nM | 10000.0 nM | IC$_{50}$ (μM) |
| 729018 | 0 | 11 | 41 | 64 | 77 | 83 | 86 | 88 | 0.1 |
| 786503 | 0 | 2 | 26 | 57 | 71 | 82 | 88 | 89 | 0.1 |
| 786524 | 0 | 10 | 28 | 53 | 78 | 85 | 88 | 89 | 0.1 |

Example 13: Design and Dose-Dependent Inhibition of Modified Oligonucleotides Targeting Human IRF5

Modified oligonucleotides with additional chemistry modifications were designed overlapping the active sites of 729018, 786503, and 785675, which were selected based on studies above. The newly designed oligonucleotides were tested for in vitro inhibition of human IRF5 mRNA in human A-431 cells. Several different chemistry modifications were tested, which are specified in the Chemistry Notation column of the tables below, wherein the notation "d" refers to a 2'-deoxyribose sugar, the notation "s" refers to a phosphorothioate internucleoside linkage, the notation "k" refers to a cEt modified sugar, the notation "y" refers to a 2'-o-methyl ribose sugar, the notation "MOP" refers to a methoxypropyl phosphonate internucleoside linkage, and the notation "$^m$C" refers to a 5-methyl cytosine. In some instances, the thymine was replaced by uracil.

Cultured A-431 cells at a density of 10,000 cells per well were treated using free uptake with modified oligonucleotides diluted to different concentrations as specified in the Tables below. After a treatment period of approximately 72 hours, IRF5 mRNA levels were measured using the Human IRF5 primer-probe set RTS4524. IRF5 RNA levels were adjusted according to total RNA content, as measured by RIBOGREEN®. Results are presented as percent inhibition of IRF5 relative to untreated control cells. As used herein, a value of '0' indicates that treatment with the modified oligonucleotide did not inhibit IRF5 mRNA levels.

The half maximal inhibitory concentration ($IC_{50}$) of each modified oligonucleotide is also presented. $IC_{50}$ was calculated using a linear regression on a log/linear plot of the data in excel. Data below shows that 729018 shows significant activity against human IRF5 compared to all other modified oligonucleotides tested.

TABLE 72

List of modified oligonucleotid+HD +HD es+L +L  designed for dose-dependent inhibition study

| Compound No. | SEQ ID NO: 2 Start Site | Sequence (5' to 3') | Chemistry Notation | SEQ ID NO |
|---|---|---|---|---|
| 785675 | 4366 | TGTCTAGTGTCATGGA | $T_{ks}GksT_{ds}{}^mC_{ds}T_{ds}A_{ds}G_{ds}T_{ds}G_{ds}T_{ds}{}^mC_{ds}A_{es}T_{es}G_{es}GksA_k$ | 1340 |
| 1073764 | 4366 | TGTCTAGTGTCATGGA | $T_{ks}GksT_{ds}{}^mC_{ks}T_{ds}A_{ds}G_{ds}T_{ds}G_{ds}T_{ds}{}^mC_{ds}A_{es}T_{es}G_{es}GksA_k$ | 1340 |
| 1073765 | 4366 | TGTCTAGTGTCATGGA | $T_{ks}GksT_{ds}{}^mC_{ds}TksA_{ds}G_{ds}T_{ds}G_{ds}T_{ds}{}^mC_{ds}A_{es}T_{es}G_{es}GksA_k$ | 1340 |
| 1073766 | 4366 | TGTCTAGTGTCATGGA | $T_{ks}GksT_{ds}{}^mC_{dMOP}T_{ds}A_{ds}G_{ds}T_{ds}G_{ds}T_{ds}{}^mC_{ds}A_{es}T_{es}G_{es}GksA_k$ | 1340 |
| 1073767 | 4366 | TGTCTAGTGTCATGGA | $T_{ks}GksT_{ds}{}^mC_{ds}T_{dMOP}A_{ds}G_{ds}T_{ds}G_{ds}T_{ds}{}^mC_{ds}A_{es}T_{es}G_{es}GksA_k$ | 1340 |
| 1073768 | 4366 | TGTCTAGTGTCATGGA | $T_{ks}GksT_{ds}C_{ys}T_{ds}A_{ds}G_{ds}T_{ds}G_{ds}T_{ds}{}^mC_{ds}A_{es}T_{es}G_{es}GksA_k$ | 1340 |
| 7073769 | 4366 | TGTCUAGTGTCATGGA | $T_{ks}GksT_{ds}{}^mC_{ds}U_{ys}A_{ds}G_{ds}T_{ds}G_{ds}T_{ds}{}^mC_{ds}A_{es}T_{es}G_{es}GksA_k$ | 1356 |
| 786503 | 11736 | CTGATATGATACCTAA | ${}^mC_{ks}T_{ks}GksA_{ds}T_{ds}A_{ds}T_{ds}G_{ds}A_{ds}T_{ds}A_{ds}{}^mC_{ds}{}^mC_{ds}T_{ks}A_{ks}A_k$ | 1270 |
| 1072783 | 11736 | CTGATATGATACCTAA | ${}^mC_{ks}T_{ks}GksA_{ds}T_{ks}A_{ds}T_{ds}G_{ds}A_{ds}T_{ds}A_{ds}{}^mC_{ds}{}^mC_{ds}T_{ks}A_{ks}A_k$ | 1270 |
| 1072784 | 11736 | CTGATATGATACCTAA | ${}^mC_{ks}T_{ks}GksA_{ds}T_{ds}A_{ks}T_{ds}G_{ds}A_{ds}T_{ds}A_{ds}{}^mC_{ds}{}^mC_{ds}T_{ks}A_{ks}A_k$ | 1270 |
| 1072785 | 11736 | CTGATATGATACCTAA | ${}^mC_{ks}T_{ks}GksA_{ds}T_{dMOP}A_{ds}T_{ds}G_{ds}A_{ds}T_{ds}A_{ds}{}^mC_{ds}{}^mC_{ds}T_{ks}A_{ks}A_k$ | 1270 |
| 1072786 | 11736 | CTGATATGATACCTAA | ${}^mC_{ks}T_{ks}GksA_{ds}T_{ds}A_{dMOP}T_{ds}G_{ds}A_{ds}T_{ds}A_{ds}{}^mC_{ds}{}^mC_{ds}T_{ks}A_{ks}A_k$ | 1270 |
| 1072788 | 11736 | CTGATATGATACCTAA | ${}^mC_{ks}T_{ks}GksA_{ds}T_{ds}A_{ys}T_{ds}G_{ds}A_{ds}T_{ds}A_{ds}{}^mC_{ds}{}^mC_{ds}T_{ks}A_{ks}A_k$ | 1270 |
| 1072787 | 11736 | CTGAUATGATACCTAA | ${}^mC_{ks}T_{ks}GksA_{ds}U_{ys}A_{ds}T_{ds}G_{ds}A_{ds}T_{ds}A_{ds}{}^mC_{ds}{}^mC_{ds}T_{ks}A_{ks}A_k$ | 1355 |
| 729018 | 11737 | TCTGATATGATACCTA | $T_{ks}{}^mC_{ks}T_{ks}G_{ds}A_{ds}T_{ds}A_{ds}T_{ds}G_{ds}A_{ds}T_{ds}A_{ds}{}^mC_{ds}{}^mC_{ks}T_{ks}A_k$ | 228 |
| 1072777 | 11737 | TCTGATATGATACCTA | $T_{ks}{}^mC_{ks}T_{ks}G_{ds}A_{ks}T_{ds}A_{ds}T_{ds}G_{ds}A_{ds}T_{ds}A_{ds}{}^mC_{ds}{}^mC_{ks}T_{ks}A_k$ | 228 |
| 1072778 | 11737 | TCTGATATGATACCTA | $T_{ks}{}^mC_{ks}T_{ks}G_{ds}A_{ds}T_{ks}A_{ds}T_{ds}G_{ds}A_{ds}T_{ds}A_{ds}{}^mC_{ds}{}^mC_{ks}T_{ks}A_k$ | 228 |
| 1072779 | 11737 | TCTGATATGATACCTA | $T_{ks}{}^mC_{ks}T_{ks}G_{ds}A_{dMOP}T_{ds}A_{ds}T_{ds}G_{ds}A_{ds}T_{ds}A_{ds}{}^mC_{ds}{}^mC_{ks}T_{ks}A_k$ | 228 |
| 1072780 | 11737 | TCTGATATGATACCTA | $T_{ks}{}^mC_{ks}T_{ks}G_{ds}A_{ds}T_{dMOP}A_{ds}T_{ds}G_{ds}A_{ds}T_{ds}A_{ds}{}^mC_{ds}{}^mC_{ks}T_{ks}A_k$ | 228 |
| 1072781 | 11737 | TCTGATATGATACCTA | $T_{ks}{}^mC_{ks}T_{ks}G_{ds}A_{ys}T_{ds}A_{ds}T_{ds}G_{ds}A_{ds}T_{ds}A_{ds}{}^mC_{ds}{}^mC_{ks}T_{ks}A_k$ | 228 |
| 1072782 | 11737 | TCTGAUATGATACCTA | $T_{ks}{}^mC_{ks}T_{ks}G_{ds}A_{ds}U_{ys}A_{ds}T_{ds}G_{ds}A_{ds}T_{ds}A_{ds}{}^mC_{ds}{}^mC_{ks}T_{ks}A_k$ | 1354 |

TABLE 73

Multi-dose assay of modified oligonucleotides in A-431 cells

| Compound No. | % Inhibition | | | | | |
|---|---|---|---|---|---|---|
| | 4.12 nM | 12.25 nM | 37.04 nM | 111.11 nM | 333.33 nM | 1000 nM |
| 729018 | 8 | 27 | 54 | 78 | 89 | 92 |
| 1072777 | 0 | 7 | 43 | 65 | 81 | 85 |
| 1072778 | 4 | 8 | 36 | 54 | 69 | 74 |
| 1072779 | 10 | 14 | 43 | 66 | 80 | 87 |
| 1072780 | 10 | 6 | 38 | 56 | 71 | 77 |
| 1072781 | 1 | 8 | 35 | 57 | 77 | 81 |
| 1072782 | 0 | 12 | 35 | 58 | 79 | 83 |
| 786503 | 13 | 29 | 54 | 80 | 88 | 90 |
| 1072783 | 20 | 29 | 38 | 64 | 83 | 83 |
| 1072784 | 18 | 23 | 41 | 63 | 80 | 75 |
| 1072785 | 11 | 22 | 29 | 56 | 76 | 78 |
| 1072786 | 0 | 15 | 25 | 54 | 71 | 71 |
| 1072787 | 6 | 23 | 41 | 64 | 82 | 82 |
| 1072788 | 1 | 14 | 31 | 56 | 74 | 79 |
| 785675 | 0 | 0 | 24 | 44 | 59 | 69 |
| 785675 | 4 | 2 | 28 | 44 | 60 | 74 |
| 1073764 | 0 | 5 | 6 | 24 | 23 | 41 |
| 1073765 | 0 | 0 | 9 | 17 | 13 | 29 |
| 1073766 | 0 | 15 | 10 | 39 | 58 | 75 |
| 1073767 | 2 | 11 | 4 | 8 | 18 | 32 |
| 1073768 | 0 | 11 | 5 | 15 | 25 | 33 |
| 1073769 | 0 | 7 | 10 | 26 | 46 | 62 |

What is claimed:

1. A compound comprising a modified oligonucleotide consisting of 16 to 30 linked nucleosides, wherein the modified oligonucleotide has a nucleobase sequence comprising a 16 nucleobase portion that is at least 80% complementary to an equal length portion of nucleobases 11737-11752 of SEQ ID NO: 2; and wherein the modified oligonucleotide comprises at least one modification selected from at least one modified internucleoside linkage, at least one modified sugar, and at least one modified nucleobase that is a 5-methylcytosine.

2. A compound comprising a modified oligonucleotide consisting of 16 to 30 linked nucleosides, wherein the modified oligonucleotide has a nucleobase sequence comprising a 16 nucleobase portion that is at least 80% complementary to an equal length portion of nucleobases 11737-11752 of SEQ ID NO: 2; and wherein the modified oligonucleotide comprises:
  a gap segment consisting of linked deoxynucleosides;
  a 5' wing segment consisting of linked nucleosides; and
  a 3' wing segment consisting of linked nucleosides;
wherein the gap segment is positioned immediately adjacent to and between the 5' wing segment and the 3' wing segment and wherein each nucleoside of each wing segment comprises a modified sugar.

3. A compound having the nucleotide sequence of SEQ ID NO: 228 and the following formula:

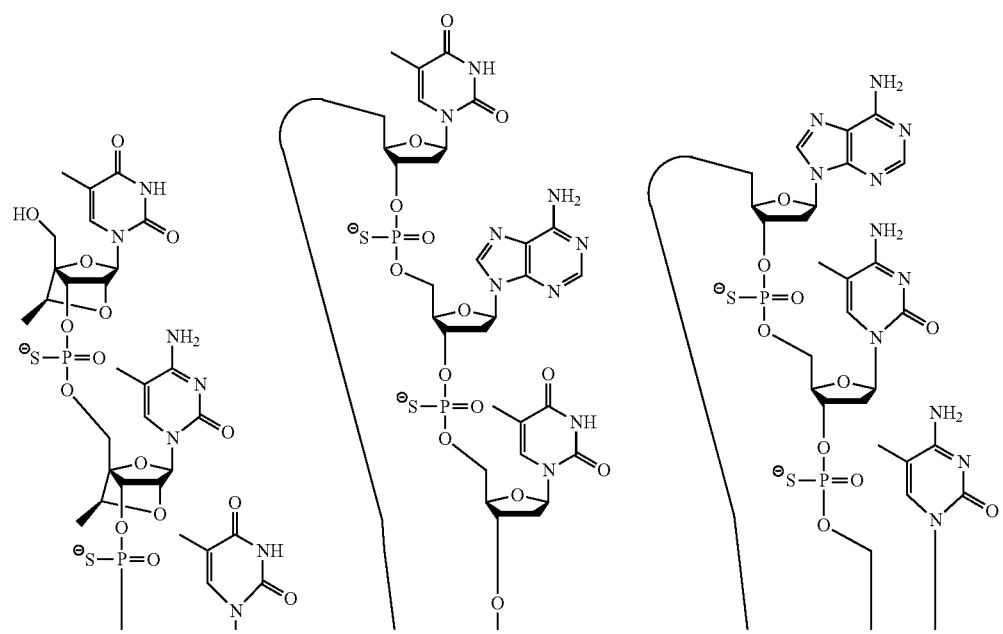

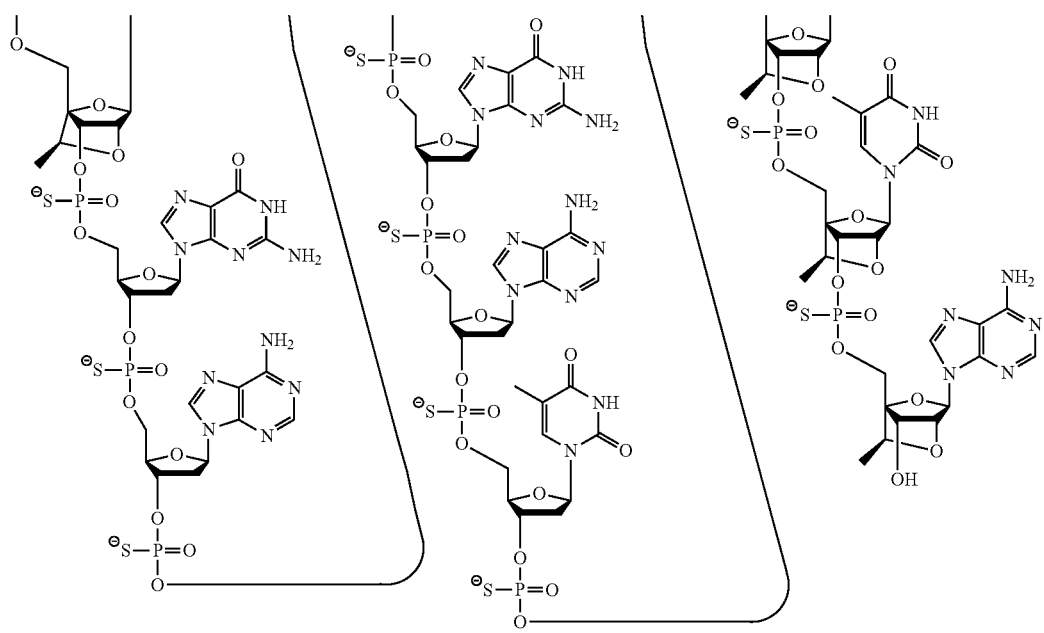

or a salt thereof.

4. A compound having the nucleotide sequence of SEQ ID NO: 228 and the following formula:

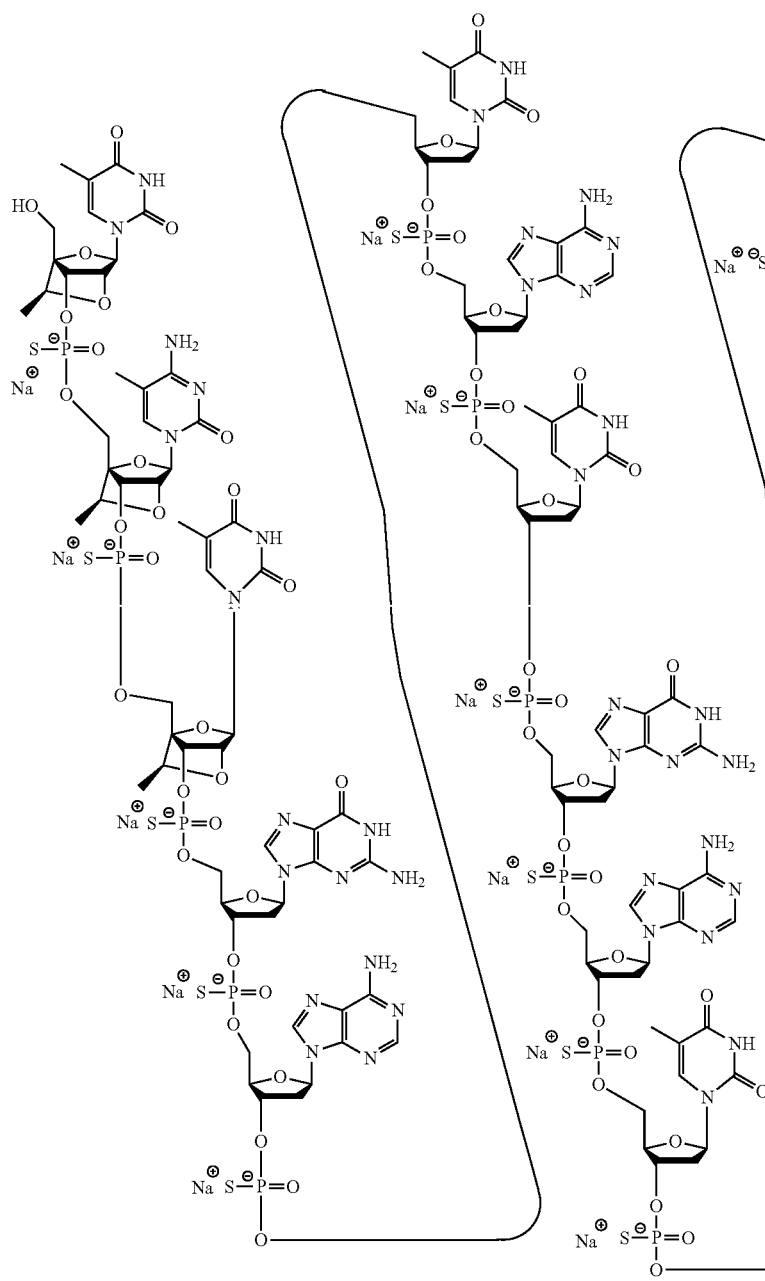
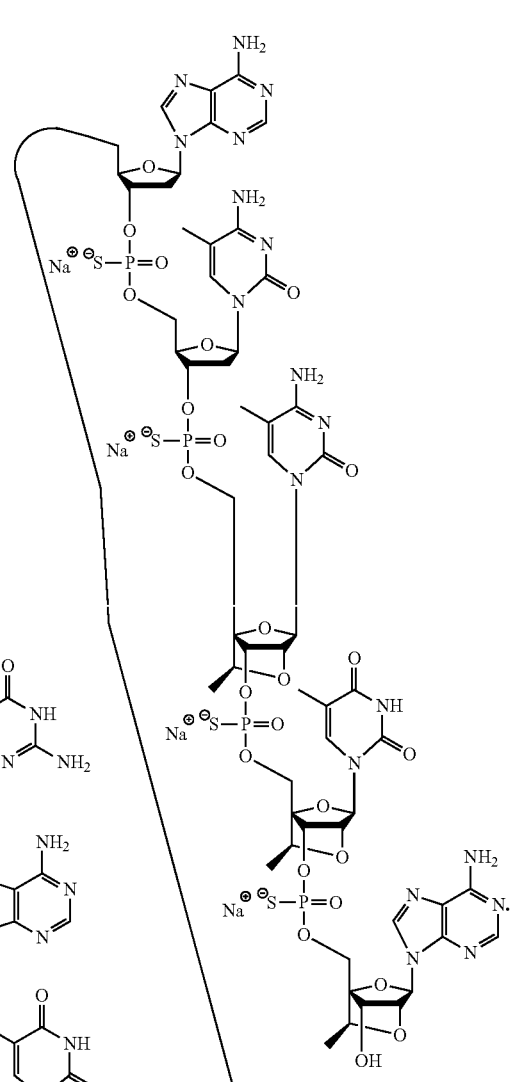

5. A composition comprising the compound of claim 3 and a pharmaceutically acceptable carrier.

6. A method of treating, preventing, or ameliorating a disease associated with IRF5 in an individual in need thereof, comprising administering to the individual the compound of claim 3, thereby treating, preventing, or ameliorating the disease.

7. A method of administering the compound of claim 3 to an individual in need thereof, wherein the individual has a disease associated with IRF5.

8. The method of claim 7, wherein the disease is an inflammatory bowel disease.

9. The method of claim 8, wherein the inflammatory bowel disease is ulcerative colitis.

10. The method of claim 8, wherein the inflammatory bowel disease is Crohn's disease.

11. The method of claim 6, wherein administering the compound inhibits or reduces inflammation in the gastrointestinal tract, diarrhea, pain, fatigue, abdominal cramping, blood in the stool, intestinal inflammation, disruption of the epithelial barrier of the gastrointestinal tract, dysbiosis, increased bowel frequency, tenesmus or painful spasms of the anal sphincter, constipation, or unintended weight loss in the individual.

12. The compound of claim 2, wherein:

the gap segment consists of ten linked deoxynucleotides;

the 5' wing segment consists of three linked nucleosides;

the 3' wing segment consists of three linked nucleosides; and the modified sugar is a cEt sugar.

13. The compound of claim 12, wherein each internucleoside linkage of the modified oligonucleotide is a phosphorothioate linkage.

14. The compound of claim 12, wherein each cytosine of the modified oligonucleotide is a 5-methylcytosine.

15. An oligomeric compound comprising a modified oligonucleotide according to the following formula: $T_{ks}{}^m C_{ks} T_{ks} G_{ds} A_{ds} T_{ds} A_{ds} T_{ds} G_{ds} A_{ds} T_{ds} A_{ds} {}^m C_{ds} {}^m C_{ks} T_{ks} A_k$, wherein A=an adenine nucleobase,
$^m$C=a 5-methyl cytosine nucleobase,
G=a guanine nucleobase,
T=a thymine nucleobase,
d=2'-deoxyribose sugar,
k=a cEt modified sugar, and
s=a phosphorothioate internucleoside linkage.

16. The compound of claim 3, wherein the salt is a potassium salt or a sodium salt.

\* \* \* \* \*